US012799119B2

(12) United States Patent
Kasibhatla et al.

(10) Patent No.: US 12,799,119 B2
(45) Date of Patent: Nov. 17, 2026

(54) IMIDAZOPYRIDAZINE AND IMIDAZOPYRAZINE COMPOUNDS AS INHIBITORS OF CDK7

(71) Applicant: THE TRANSLATIONAL GENOMICS RESEARCH INSTITUTE, Phoenix, AZ (US)

(72) Inventors: Srinivas Rao Kasibhatla, San Diego, CA (US); Sunil Sharma, Phoenix, AZ (US); Mohan Kaadige, Scottsdale, AZ (US); Alexis Weston, Phoenix, AZ (US); Srikanta Dana, Phoenix, AZ (US); Trason Thode, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 594 days.

(21) Appl. No.: 18/245,715

(22) PCT Filed: Sep. 17, 2021

(86) PCT No.: PCT/US2021/050936
§ 371 (c)(1),
(2) Date: Mar. 16, 2023

(87) PCT Pub. No.: WO2022/061155
PCT Pub. Date: Mar. 24, 2022

(65) Prior Publication Data

US 2023/0348475 A1 Nov. 2, 2023

Related U.S. Application Data

(60) Provisional application No. 63/079,951, filed on Sep. 17, 2020, provisional application No. 63/079,954, filed on Sep. 17, 2020.

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
None
See application file for complete search history.

(56) References Cited

U.S. PATENT DOCUMENTS

2008/0045536 A1* 2/2008 Vaccaro .................. A61P 31/18
544/236

FOREIGN PATENT DOCUMENTS

| | | |
|---|---|---|
| WO | WO 2004026310 A1 | 4/2004 |
| WO | WO 2007058873 A2 | 5/2007 |
| WO | WO 2008057512 A2 | 5/2008 |
| WO | WO 2019057825 A1 | 3/2019 |
| WO | WO 2020186196 A1 | 9/2020 |

OTHER PUBLICATIONS

Nekardová et al., "Structural Basis of the Interaction of Cyclin-Dependent Kinase 2 with Roscovitine and Its Analogues Having Bioisosteric Central Heterocycles," *Chemphyschem 18*(7):785-795, Apr. 5, 2017 [Published online Apr. 5, 2017]. (12 pages).
Pevarello et al., "Cyclin-dependent kinase inhibitors: a survey of the recent patent literature," *Expert Opin. Ther. Patents 15*(6):675-703, 2005 [Published online Jun. 14, 2005]. (29 pages).
Riazanski et al., "TRPC6 channel translocation into phagosomal membrane augments phagosomal function," *PNAS 112*(42):E6486-E6495, Nov. 24, 2015 [Published online Nov. 10, 2015]. (10 pages).

* cited by examiner

*Primary Examiner* — Kortney L. Klinkel
(74) *Attorney, Agent, or Firm* — Seed Intellectual Property Law Group LLP

(57) ABSTRACT

Compounds having activity as anti-cancer agents are provided. The compounds have the following structure (I) or a pharmaceutically acceptable salt, stereoisomer or tautomer, thereof, wherein X, Y, $R^1$, $R^2$, $R^3$ $R^4$, $R^5$ and L are as defined herein. This disclosure provides methods associated with preparation and use of such compounds, pharmaceutical compositions comprising such compounds, and methods for treating a CDK7-dependent disease (e.g., cancer).

(I)

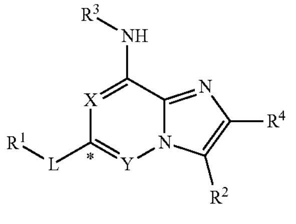

21 Claims, No Drawings

IMIDAZOPYRIDAZINE AND IMIDAZOPYRAZINE COMPOUNDS AS INHIBITORS OF CDK7

BACKGROUND

Technical Field

The present disclosure is directed to novel compounds having activity as inhibitors of CDK7 and methods for their preparation and use as therapeutic or prophylactic agents, for example for treatment of cancer (e.g., solid tumors and hematological cancers).

Description of the Related Art

Cancer is a group of diseases involving abnormal cell growth with a potential to spread to various parts of the body. Hundreds of types of cancers affect humans, and millions of people have been diagnosed and millions more are being diagnosed every year. The most common types of cancers include lung cancer, breast cancers, prostate cancers, colorectal cancers, among others. Treatment for cancers includes surgery, radiation therapy, chemotherapy, immunotherapy, hormone therapy, and stem cell replacement. Treatment options can be invasive and have a variety of undesirable side effects.

Accordingly, while the scientific community has made progress in this field, there remains a need in the art for improved compounds and methods for treatment of cancer. The present disclosure fulfills this need and provides further related advantages.

BRIEF SUMMARY

In brief, embodiments of the present disclosure provide compounds, including pharmaceutically acceptable salts, stereoisomers, tautomers, isotopic forms or prodrugs thereof. Methods for use of such compounds for treatment of various diseases or conditions, such as cancers provided.

One embodiment provides a compound having the following structure (I):

(I)

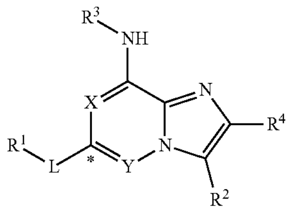

or a stereoisomer, tautomer, prodrug or pharmaceutically acceptable salt thereof, wherein X, Y, $R^1$, $R^2$, $R^3$, $R^4$, $R^5$ and L are as defined herein. Another embodiment provides pharmaceutical compositions comprising one or more compounds of structure (I) and a pharmaceutically acceptable carrier or excipient.

Other embodiments of the present disclosure provide a method for treatment of a disease (e.g., CDK7-dependent disease), the method comprising administering an effective amount of a compound of structure (I) or pharmaceutical composition comprising a compound of structure (I) to a subject in need thereof. These and other aspects of the disclosure will be apparent upon reference to the following detailed description.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word “comprise” and variations thereof, such as, “comprises” and “comprising” are to be construed in an open, inclusive sense, that is, as “including, but not limited to”.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms “about” and “approximately” mean±20%, ±10%, ±5% or ±1% of the indicated range, value, or structure, unless otherwise indicated. It should be understood that the terms “a” and “an” as used herein refer to “one or more” of the enumerated components. The use of the alternative (e.g., “or”) should be understood to mean either one, both, or any combination thereof the alternatives.

Reference throughout this specification to “one embodiment” or “an embodiment” means that a particular feature, structure or characteristic described in connection with the embodiment is included in at least one embodiment of the present disclosure. Thus, the appearances of the phrases “in one embodiment” or “in an embodiment” in various places throughout this specification are not necessarily all referring to the same embodiment. Furthermore, the particular features, structures, or characteristics may be combined in any suitable manner in one or more embodiments. Unless defined otherwise, all technical and scientific terms used herein have the same meaning as is commonly understood by one of skill in the art to which this disclosure belongs. As used in the specification and claims, the singular form “a”, “an” and “the” include plural references unless the context clearly dictates otherwise.

DEFINITIONS

“Amino” refers to the —$NH_2$ radical.

“Carboxy” or “carboxyl” refers to the —$CO_2H$ radical.

“Cyano” refers to the —CN radical.

“Hydroxy” or “hydroxyl” refers to the —OH radical.

“Oxo” refers to the =O substituent.

“Nitro” refers to the —$NO_2$ radical.

“Thiol” refers to the —SH substituent.

“Thioxo” refers to the =S substituent.

“Alkyl” refers to a saturated, straight or branched hydrocarbon chain radical consisting solely of carbon and hydrogen atoms, having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. Unless stated otherwise specifically in the specification, an alkyl group is optionally substituted.

"Alkenyl" refers to an unsaturated, straight or branched hydrocarbon chain radical consisting solely of carbon and hydrogen atoms, which contains one or more carbon-carbon double bonds, having from two to twelve carbon atoms ($C_2$-$C_{12}$ alkenyl), two to eight carbon atoms ($C_2$-$C_8$ alkenyl) or two to six carbon atoms ($C_2$-$C_6$ alkenyl), or any value within these ranges, and which is attached to the rest of the molecule by a single bond, e.g., ethenyl, prop-1-enyl, but-1-enyl, pent-1-enyl, penta-1,4-dienyl, and the like.

The number of carbons referred to relates to the carbon backbone and carbon branching, but does not include carbon atoms belonging to any substituents. Unless stated otherwise specifically in the specification, an alkenyl group is optionally substituted.

"Alkoxy" refers to a radical of the formula —$OR_a$ where $R_a$ is an alkyl radical as defined above containing one to twelve carbon atoms ($C_1$-$C_{12}$ alkoxy), one to eight carbon atoms ($C_1$-$C_8$ alkoxy) or one to six carbon atoms ($C_1$-$C_6$ alkoxy), or any value within these ranges. Unless stated otherwise specifically in the specification, an alkoxy group is optionally substituted.

"Alkylamino" refers to a radical of the formula —$NR_aR_b$ where $R_a$ is alkyl as defined above and Rb is H or alkyl as defined above. Unless stated otherwise specifically in the specification, an alkylamino group is optionally substituted.

"Aromatic ring" refers to a cyclic planar portion of a molecule (i.e., a radical) with a ring of resonance bonds that exhibits increased stability relative to other connective arrangements with the same sets of atoms. Generally, aromatic rings contains a set of covalently bound co-planar atoms and comprises a number of π-electrons (for example, alternating double and single bonds) that is even but not a multiple of 4 (i.e., 4π+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system (i.e., a ring system wherein each ring atom is carbon) radical comprising 6 to 18 carbon ring atoms and at least one aromatic ring. For purposes of embodiments of this disclosure, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Arylalkyl" refers to a radical of the formula —$R_bR_f$ where $R_b$ is an alkylene chain as defined above and $R_f$ is an aryl radical as defined above. Unless stated otherwise specifically in the specification, an alkylaryl group is optionally substituted.

"Cycloalkyl" refers to a stable non-aromatic monocyclic or polycyclic carbocyclic radical, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure that becomes part of the fused heterocyclyl ring or the fused heteroaryl ring is replaced with a nitrogen atom.

"Halo" or "halogen" refers to bromo (Br), chloro (Cl), fluoro (F) or iodo (I).

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,2,3,4-tetrahydroquinolinyl, and 1,1-dioxo-thiomorpholinyl. Unless stated otherwise specifically in the specification, a heterocyclyl group is optionally substituted.

"Hydroxyalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted.

"Heteroaryl" refers to a 5- to 18-membered, for example 5- to 6-membered, ring system radical comprising one to thirteen ring carbon atoms, one to six ring heteroatoms selected from the group consisting of nitrogen, oxygen and sulfur, and at least one aromatic ring. Heteroaryl radicals may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo [1,2-a]pyridinyl, carbazolyl, cinnolinyl, dibenzofuranyl, dibenzothiophenyl, furanyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Haloalkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heterocyclylalkyl" refers to a radical of the formula —$R_bR_c$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group is optionally substituted.

The term "substituted" as used herein means any of the above groups wherein at least one hydrogen atom (e.g., 1, 2, 3 or all hydrogen atoms) is replaced by a bond to a non-hydrogen substituent. Examples of non-hydrogen substituents include, but are not limited to: amino, carboxyl, cyano, hydroxyl, halo, nitro, oxo, thiol, thioxo, alkyl, alkenyl, alkylcarbonyl, alkoxy, aryl, cyanoalkyl, cycloalkyl, haloalkyl, heterocyclyl, heterocyclylalkyl, heteroaryl, heteroarylalkyl and/or hydroxylalkyl substituents, each of which may also be optionally substituted with one or more of the above substituents.

In some embodiments, the optional substituents are selected from the group consisting of amino, carboxyl, cyano, halo, hydroxyl, $C_{1-6}$ alkyl, $C_{1-6}$ alkylamino, $C_{1-6}$ haloalkyl, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

It is understood that each choice for $R^1$, $R^2$, $R^3$, $R^4$, $R^5$ and L is optionally substituted as described above unless specifically stated otherwise, and provided that all valences are satisfied by the substitution. Specifically, each choice for $R^1$, $R^2$, $R^3$, $R^4$, $R^5$ and L is optionally substituted unless specifically stated otherwise, and provided such substitution results in a stable molecule (e.g., groups such as H and halo are not optionally substituted).

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. "Therapeutic benefit" means eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The terms "antagonist" and "inhibitor" are used interchangeably, and they refer to a compound having the ability to inhibit a biological function of a target protein, whether by inhibiting the activity or expression of the protein, such as CDK7. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

Prodrugs of the disclosed compounds are included in various embodiments. "Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" includes any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

Embodiments disclosed herein are also meant to encompass all pharmaceutically acceptable compounds of structure (I) being isotopically-labelled by having one or more atoms replaced by an atom having a different atomic mass or mass number (i.e., an "isotopic form" of a compound of structure (I)). Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$ $^{13}N$, $^{15}N$, $^{15}O$, $^{17}O$ $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically labeled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence are preferred in some circumstances.

Substitution with positron emitting isotopes, such as C, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the disclosure. As used herein, the term "solvate" refers to an aggregate that comprises one or more molecules of a compound of the disclosure with one or more molecules of solvent. In some embodiments, the solvent is water, in which case the solvate is a hydrate. Alternatively, in other embodiments, the solvent is an organic solvent. Thus, the compounds of structure (I) may exist as a hydrate, including a monohydrate, dihydrate, hemihydrate, sesquihydrate, trihydrate, tetrahydrate and the like, as well as the corresponding solvated forms. In some aspects, the compound of the disclosure is a true solvate, while in other cases, the compound of the disclosure merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the disclosure (i.e., compounds of structure (I) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also included.

The present disclosure includes all manner of rotamers and conformationally restricted states of a compound of the disclosure.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. Unless otherwise indicated, stereoisomers include racemers, enantiomers and diastereomers.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

As detailed above, the present disclosure provides compounds showing significant activity as CDK7 inhibitors. Accordingly, one embodiment provides a compound having the following structure (I):

(I)

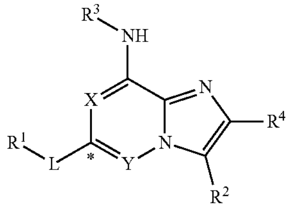

or a pharmaceutically acceptable salt, stereoisomer or prodrug thereof, wherein:

X and Y are each independently N or $CR_5$, wherein one of X and Y is N, and the other of X and Y is $CR_5$;

$R^1$ is $C_3$-$C_8$ heterocyclyl, $C_1$-$C_6$ alkyl or C(O)O—$C_{1-6}$ alkyl, each of which is optionally substituted with one or more substituents;

$R^2$ is halo, —$CF_3$, $C_3$-$C_5$ cycloalkyl or $C_1$-$C_6$ alkyl, each of which optionally substituted with one or more substituents;

$R^3$ is $C_6$-$C_{10}$ aryl or $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H, $C_{1-6}$ alkyl or amino, and ~ represents a covalent bond to the carbon with an *; and n is 0, 1, 2, or 3.

Another embodiment provides a compound having structure (Ia):

(Ia)

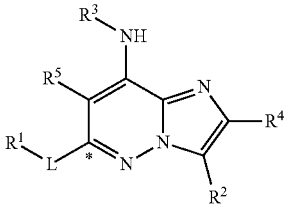

or a pharmaceutically acceptable salt, stereoisomer or prodrug thereof, wherein:

$R^1$ is $C_3$-$C_8$ heterocyclyl, $C_1$-$C_6$ alkyl or C(O)O—$C_{1-6}$ alkyl, each of which is optionally substituted with one or more substituents;

$R^2$ is halo, —$CF_3$, $C_3$-$C_8$ cycloalkyl or $C_1$-$C_6$ alkyl, each of which optionally substituted with one or more substituents;

$R^3$ is $C_6$-$C_{10}$ aryl or $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H, $C_1$-6 alkyl or amino, and ~ represents a covalent bond to the carbon with an *; and n is 0, 1, 2, or 3.

In some embodiments, the substituents are selected from the group consisting of amino, carboxyl, cyano, halo, hydroxyl, $C_{1-6}$ alkyl, $C_{1-6}$ alkylamino, $C_{1-6}$ haloalkyl, —C(O)$CF_3$, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

One embodiment provides a compound having the following structure (Ia):

(Ia)

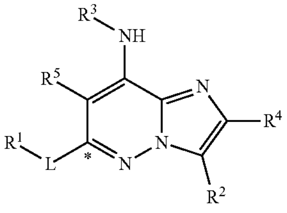

or a pharmaceutically acceptable salt, stereoisomer or prodrug thereof, wherein:

$R^1$ is $C_3$-$C_8$ heterocyclyl or $C_1$-$C_6$ alkyl, each of which is optionally substituted with one or more substituents;

$R^2$ is halo, $C_3$-$C_5$ cycloalkyl or $C_1$-$C_6$ alkyl, each of which optionally substituted with one or more substituents;

$R^3$ is $C_6$-$C_{10}$ aryl or $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H or $C_{1-6}$ alkyl, and ~ represents a covalent bond to the carbon with an *; and n is 0, 1, 2, or 3.

In some embodiments, the substituents are selected from the group consisting of amino, carboxyl, cyano, halo, hydroxyl, $C_{1-6}$ alkyl, $C_{1-6}$ alkylamino, $C_{1-6}$ haloalkyl, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

One embodiment provides a compound having structure (Ib):

(Ib)

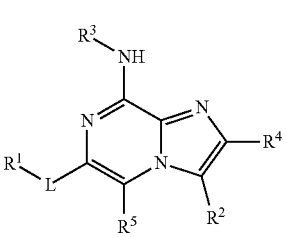

or a pharmaceutically acceptable salt, stereoisomer or prodrug thereof, wherein:

$R^1$ is $C_3$-$C_8$ heterocyclyl, $C_1$-$C_6$ alkyl or C(O)O—$C_{1-6}$ alkyl, each of which is optionally substituted with one or more substituents;

$R^2$ is halo, —$CF_3$, $C_3$-$C_5$ cycloalkyl or $C_1$-$C_6$ alkyl, each of which optionally substituted with one or more substituents;

$R^3$ is $C_6$-$C_{10}$ aryl or $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H, $C_{1-6}$ alkyl or amino, and ~ represents a covalent bond to the carbon with an *; and n is 0, 1, 2, or 3.

In some embodiments, the substituents are selected from the group consisting of amino, carboxyl, cyano, halo, hydroxyl, $C_{1-6}$ alkyl, $C_{1-6}$ alkylamino, $C_{1-6}$ haloalkyl, —C(O)$CF_3$, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

One embodiment provides a compound having structure (Ib):

(Ib)

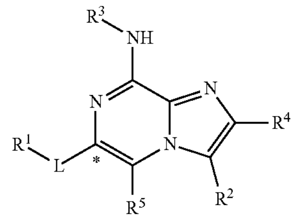

or a pharmaceutically acceptable salt, stereoisomer or prodrug thereof, wherein:

$R^1$ is $C_3$-$C_8$ heterocyclyl or $C_1$-$C_6$ alkyl, each of which is optionally substituted with one or more substituents;

$R^2$ is halo, $C_3$-$C_8$ cycloalkyl or $C_1$-$C_6$ alkyl, each of which optionally substituted with one or more substituents;

$R^3$ is $C_6$-$C_{10}$ aryl or $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H or $C_{1-6}$ alkyl, and ~ represents a covalent bond to the carbon with an *; and n is 0, 1, 2, or 3.

In some embodiments, the substituents are selected from the group consisting of amino, carboxyl, cyano, halo, hydroxyl, $C_{1-6}$ alkyl, $C_{1-6}$ alkylamino, $C_{1-6}$ haloalkyl, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

In yet other embodiments, L is —$(CHR^6)_n$—$NR^6$~. In some specific embodiments, L is —$C(R^6)_2$~. In other embodiments L is —$(CHR^6)_n$—O~. In still other embodiments, L is —$(CHR^6)_n$—S~.

In a specific embodiment, $R^6$ is at each occurrence H.

In one embodiment, n is 0. In yet other embodiments, n is 1. In some specific embodiments, n is 2. In other embodiments, n is 3.

In a specific embodiment, $R^1$ is $C_3$-$C_8$ heterocyclyl. In some embodiments, $R^1$ is unsubstituted. In yet other embodiments, $R^1$ is substituted with one or more substituents. In still other embodiments, the substituents are selected from $C_{1-6}$ alkyl, $C_{1-6}$ haloalkyl, hydroxyl, halogen and —CN.

In a specific embodiment, the substituent is methyl.

In some embodiments, $R^1$ has one of the following structures:

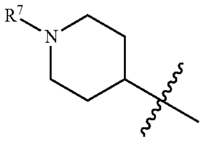 ; 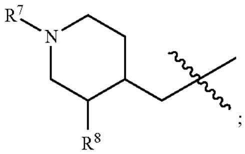 ;

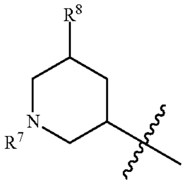 ; 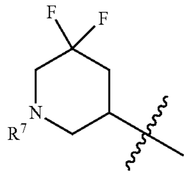 ;

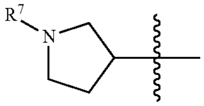 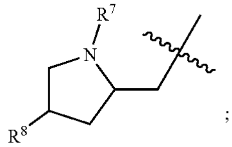 ;

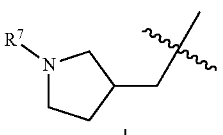 ; 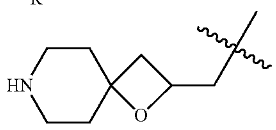 ;

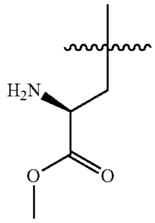 or 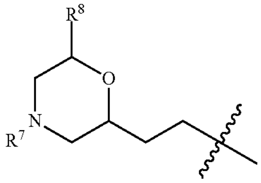 ;

wherein: $R^7$ is H, —$CH_2CH_2OH$, —C(O)$CF_3$, or $C_{1-3}$ alkyl; and $R^8$ is H, OH, CN or F.

In other embodiments, $R^1$ has one of the following structures:

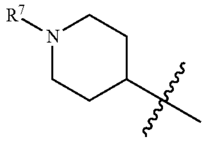 ; 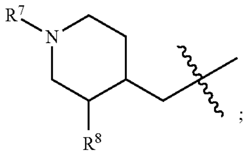 ;

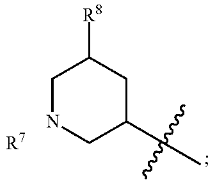 ; 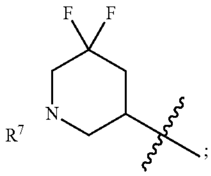 ;

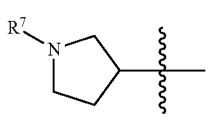 ; 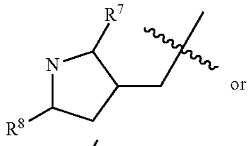 or

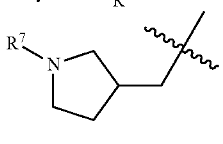 ;

where $R^7$ is H, or $C_{1-3}$ alkyl; and $R^8$ is H, OH, CN or F.

In a specific embodiment, $R^2$ is halo. In yet other embodiments, $R^2$ is $C_3$-$C_8$ cycloalkyl optionally substituted with one or substituents. In one embodiment, $R_2$ is $CF_3$. In still other embodiments, $R^2$ is $C_1$-$C_6$ alkyl optionally substituted with one or substituents. In yet other embodiments, $R^2$ is unsubstituted. In a specific embodiment, $R^2$ is cyclopropyl. In some other embodiments, $R^2$ is isopropyl.

In a specific embodiment, $R^3$ is $C_6$-$C_{10}$ aryl. In yet other embodiments, $R^3$ is $C_7$-$C_{12}$ arylalkyl. In still other embodiments, $R^3$ is unsubstituted. In yet other embodiments, $R^3$ is substituted with one or more substituents. In some embodiments, the substituents are selected from cyano, halo, $C_{1-6}$ alkyl, $C_{1-6}$ alkylamino, $C_{1-6}$ alkoxy, $C_{1-6}$ haloalkoxy and $C_6$-$C_{10}$ heteroaryl. In yet other embodiments, the substituents are selected from cyano, chloro, fluoro, methoxy, ethoxy, isopropoxy, difluoromethyl, dimethylamino and imidazolyl.

In some embodiments, $R^3$ has one of the following structures:

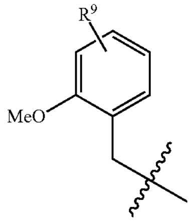 ;
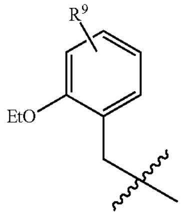 ;
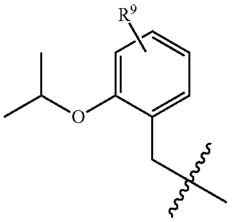 ;
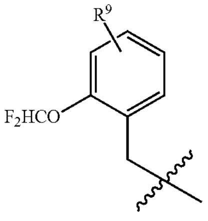 ;
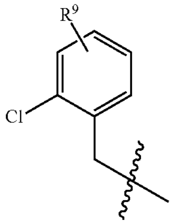 ;
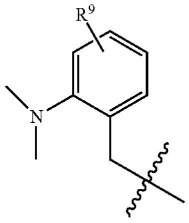 ;
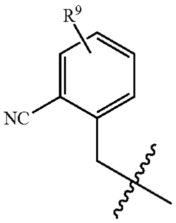 ;
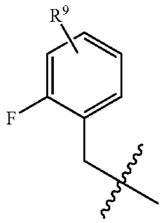 ;
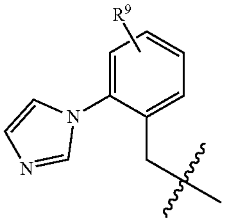 ;
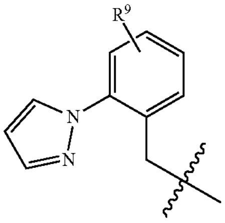 ;

-continued

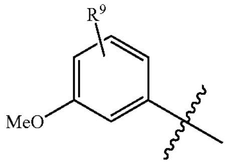 ;
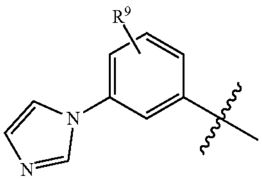 ;
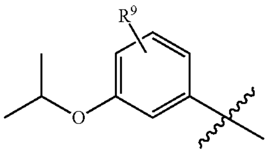 ;
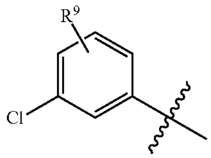 ;
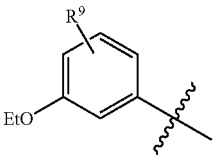 ;
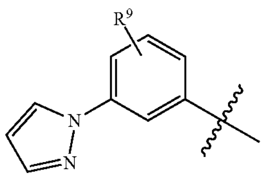 ;
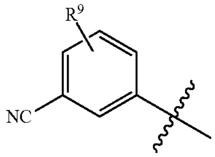 ;
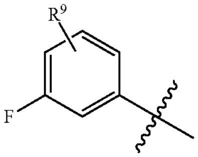 ;
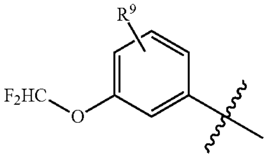 ;
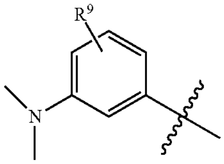 ;
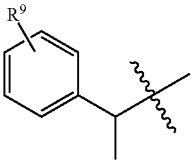 ;
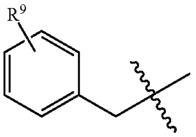 ;
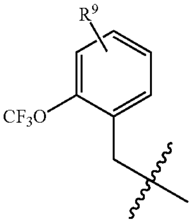 ;
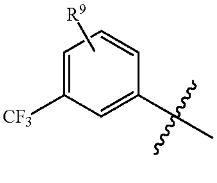 ;
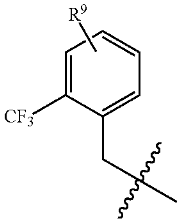 ;
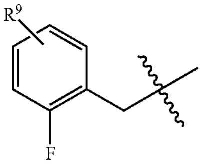 ;
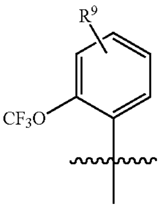 ;
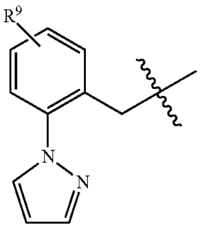 or -continued
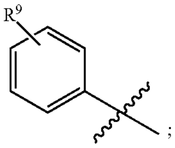
wherein $R^9$ is H, F, $C_1$, Me, CN, $CF_3$, $-OC_{1-6}$ alkyl, or $OCF_3$.
In other embodiments, $R^3$ has one of the following structures:
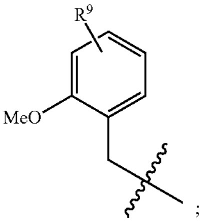
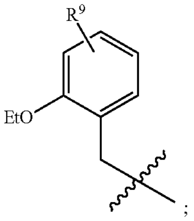
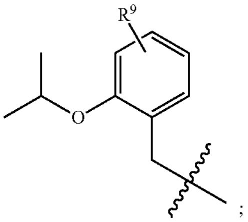
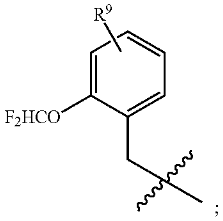
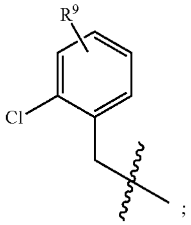
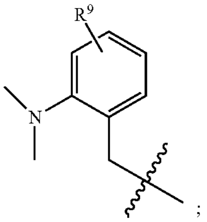
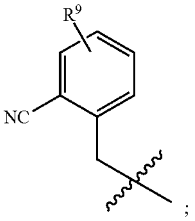
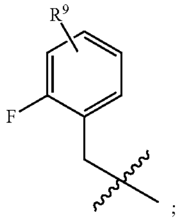
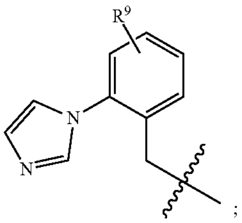
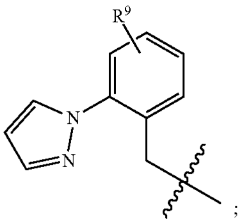
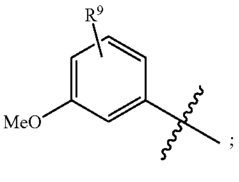
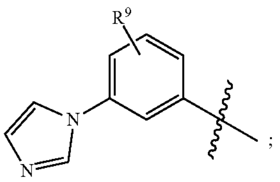
-continued
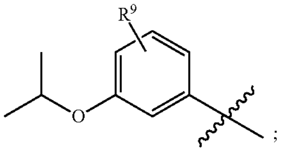
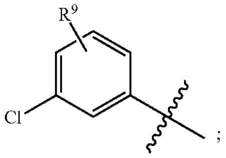
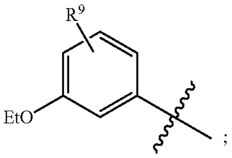
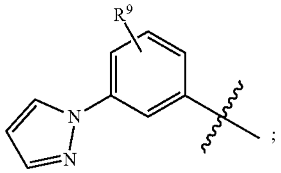
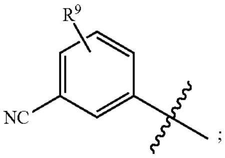
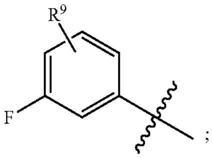
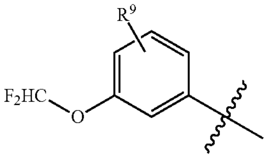
or
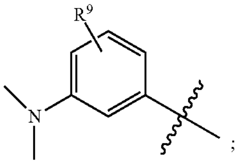
wherein $R^9$ is H, F, $C_1$, Me, or CN.
In a specific embodiment, $R^4$ is H.
In yet other embodiments, $R^5$ is H.
In one embodiment, a compound is selected having one of the following structures:
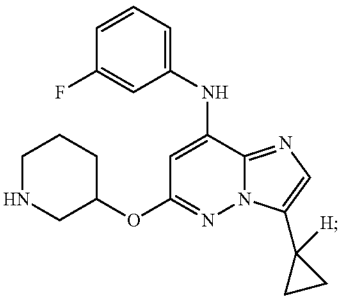
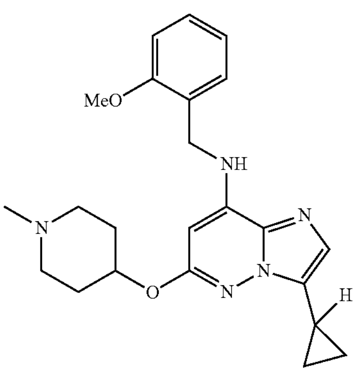
or -continued

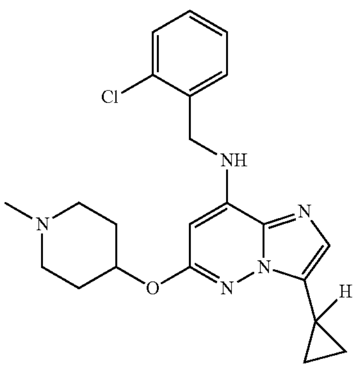

or a pharmaceutically acceptable salt, stereoisomer or prodrug thereof.

In another embodiment, a compound is selected from any one of the compounds listed in Tables 1-5, or a pharmaceutically acceptable salt, stereoisomer or prodrug thereof.

Representative compounds of structure (I), as well as structure (Ia)-(Ib) as applicable, include any one of the compounds listed in Tables 1-5 below, as well as a pharmaceutically acceptable salt, stereoisomer or prodrug thereof. To this end, representative compounds are identified herein by their respective "Compound Number", which is sometimes abbreviated as "Compound No." or "Cpd. No." or "No."

TABLE 1

| Representative Compounds | |
|---|---|
| Cpd. No. | Structure |
| 1 | 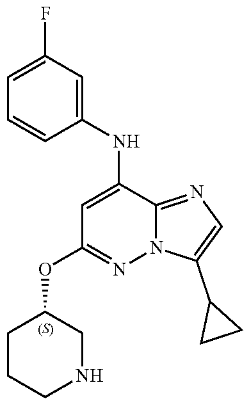 |

TABLE 1-continued

| Representative Compounds | |
|---|---|
| Cpd. No. | Structure |
| 2 | 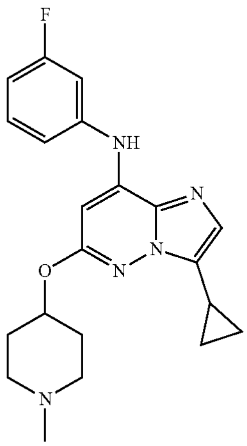 [SMILES: CN1CCC(Oc2cc(Nc3cccc(F)c3)c3ncc(C4CC4)n3n2)CC1] |
| 3 | 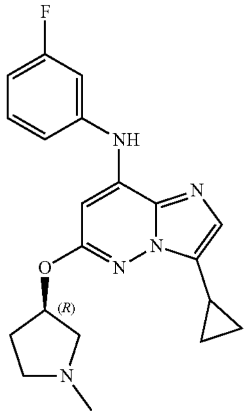 |
| 4 | 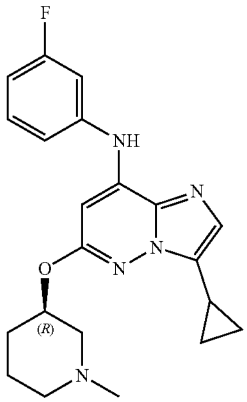 |

TABLE 1-continued
| Representative Compounds | |
|---|---|
| Cpd. No. | Structure |
| 5 | 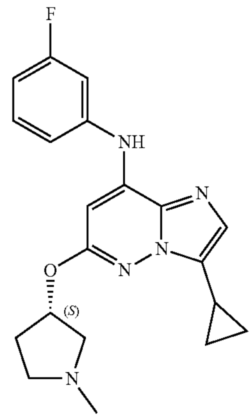 |
| 6 | 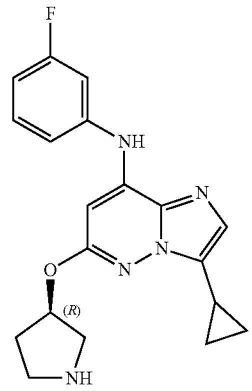 |
| 7 | 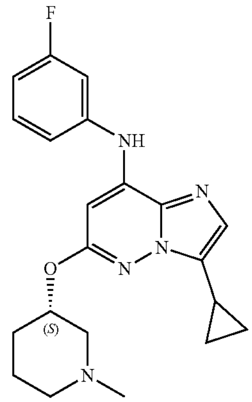 |
| 8 | 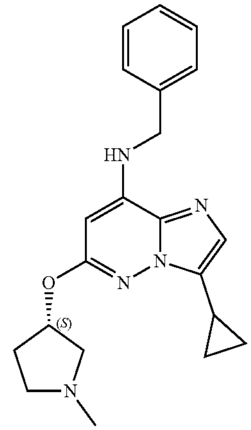 |
| 9 | 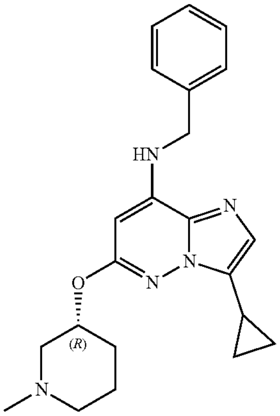 |
| 10 | 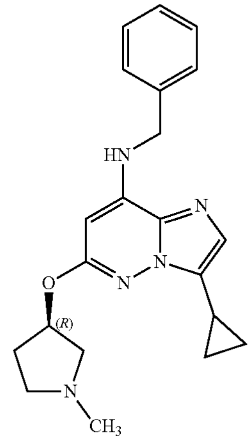 |

TABLE 1-continued
| Representative Compounds | |
|---|---|
| Cpd. No. | Structure |
| 11 | 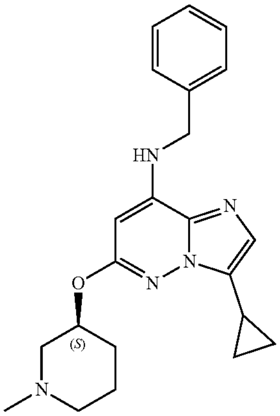 |
| 12 | 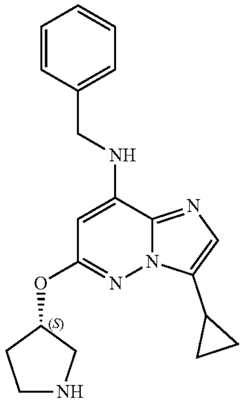 |
| 13 | 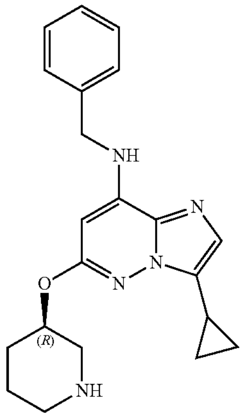 |
TABLE 1-continued
| Representative Compounds | |
|---|---|
| Cpd. No. | Structure |
| 14 | 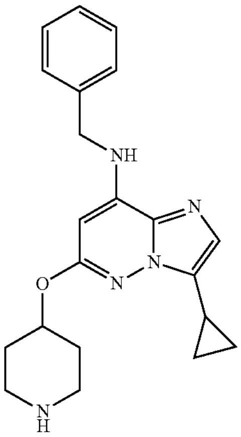 [SMILES: c1ccc(CNc2cc(OC3CCNCC3)nn3c(C4CC4)cnc23)cc1] |
| 15 | 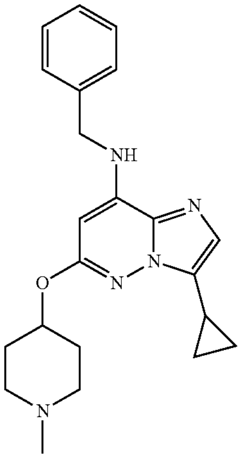 [SMILES: CN1CCC(Oc2cc(NCc3ccccc3)c3ncc(C4CC4)n3n2)CC1] |
| 16 | 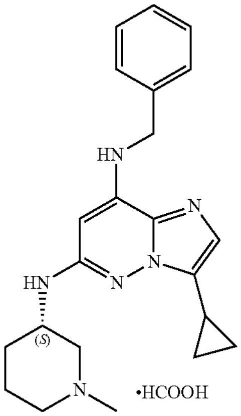 •HCOOH |

TABLE 1-continued
| Representative Compounds | |
|---|---|
| Cpd. No. | Structure |
| 17 | 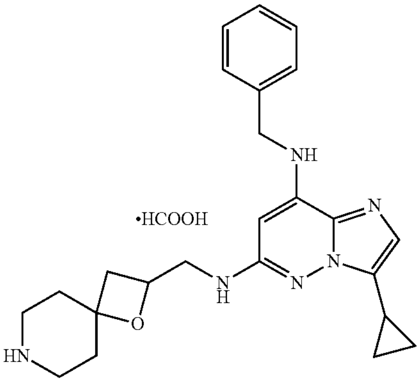 [SMILES: c1ccc(CNc2cc(NCC3CC4(CCNCC4)O3)nn3c(C4CC4)cnc23)cc1 ; "·HCOOH"] |
| 18 | 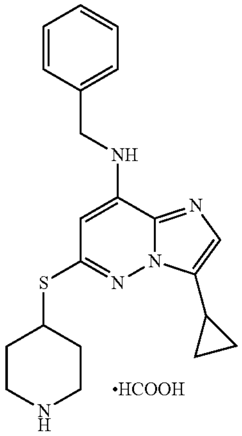 |
| 19 | 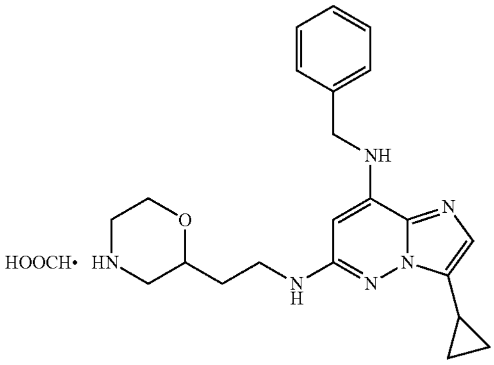 [SMILES: c1ccc(CNc2cc(NCCC3CNCCO3)nn3c(C4CC4)cnc23)cc1] |
TABLE 1-continued
| Representative Compounds | |
|---|---|
| Cpd. No. | Structure |
| 20 | 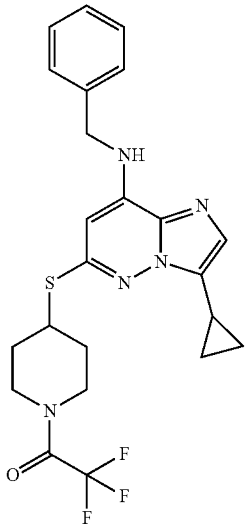 [SMILES: O=C(N1CCC(Sc2cc(NCc3ccccc3)c3ncc(C4CC4)n3n2)CC1)C(F)(F)F] |
| 21 | 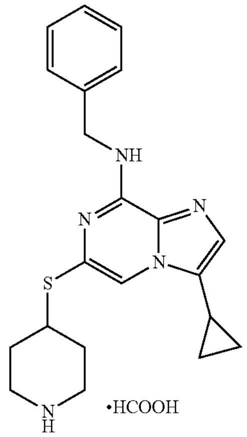 |
| 22 | 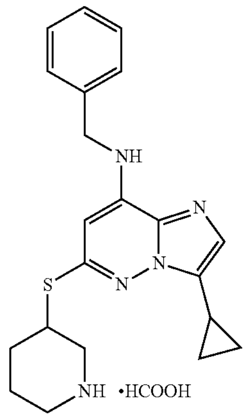 |

TABLE 1-continued
| Representative Compounds | |
|---|---|
| Cpd. No. | Structure |
| 23 | 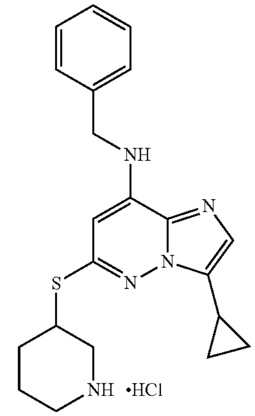 [SMILES: c1ccc(CNc2cc(SC3CCCNC3)nn3c(C4CC4)cnc23)cc1 ; Cl] |
| 24 | 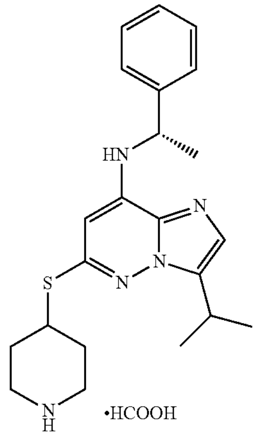 [SMILES: CC(C)c1cnc2c(N[C@@H](C)c3ccccc3)cc(SC3CCNCC3)nn12 ; "·HCOOH"] |
| 25 | 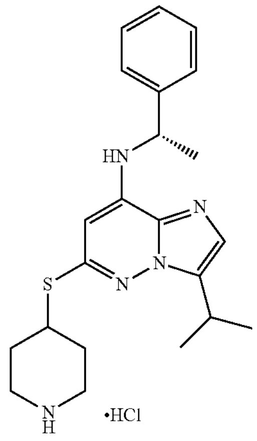 [SMILES: CC(C)c1cnc2c(N[C@@H](C)c3ccccc3)cc(SC3CCNCC3)nn12 ; Cl] |
TABLE 1-continued
| Representative Compounds | |
|---|---|
| Cpd. No. | Structure |
| 26 | 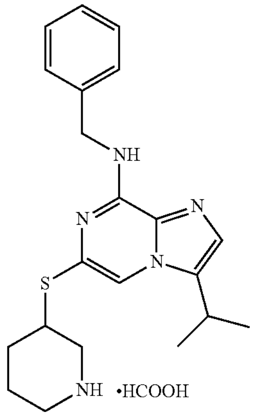 |
| 27 | 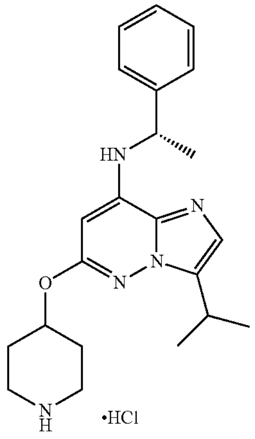 [SMILES: CC(C)c1cnc2c(N[C@@H](C)c3ccccc3)cc(OC3CCNCC3)nn12 ; Cl] |
| 28 | 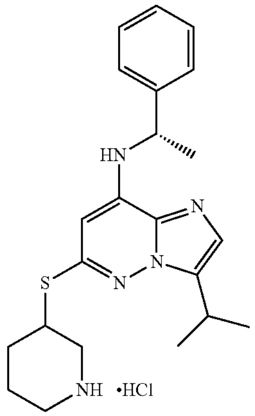 [SMILES: CC(C)c1cnc2c(N[C@@H](C)c3ccccc3)cc(SC3CCCNC3)nn12 ; Cl] |

TABLE 1-continued
Representative Compounds
| Cpd. No. | Structure |
|---|---|
| 29 | 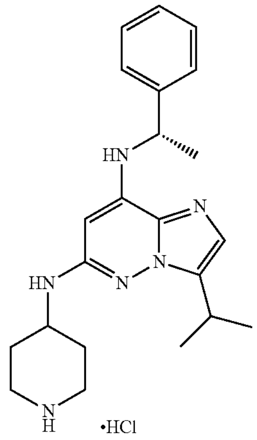 [SMILES: CC(C)c1cnc2c(N[C@@H](C)c3ccccc3)cc(NC3CCNCC3)nn12 ; Cl] |
| 30 | 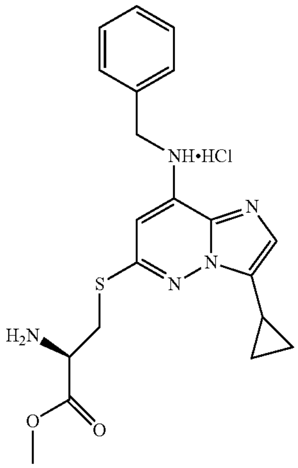 |
| 31 | 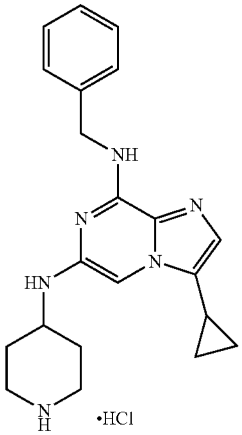 [SMILES: c1ccc(CNc2nc(NC3CCNCC3)cn3c(C4CC4)cnc23)cc1 ; Cl] |
| 32 | 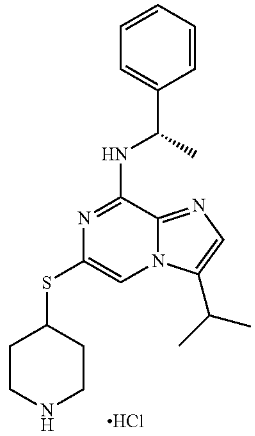 [SMILES: CC(C)c1cnc2c(N[C@@H](C)c3ccccc3)nc(SC3CCNCC3)cn12 ; Cl] |
| 33 | 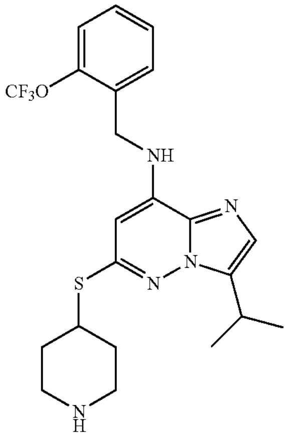 |
| 33a | 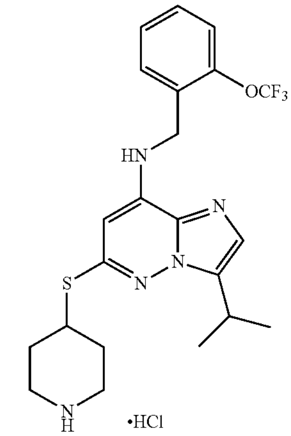 [SMILES: CC(C)c1cnc2c(NCc3ccccc3OC(F)(F)F)cc(SC3CCNCC3)nn12 ; Cl] |

TABLE 1-continued
| Representative Compounds | |
|---|---|
| Cpd. No. | Structure |
| 33b | 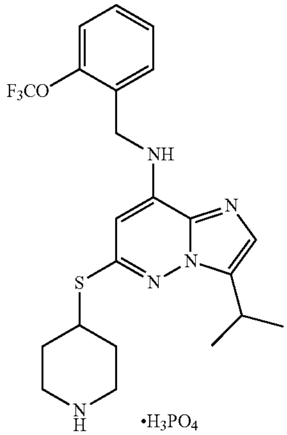 •$H_3PO_4$ |
| 33c | 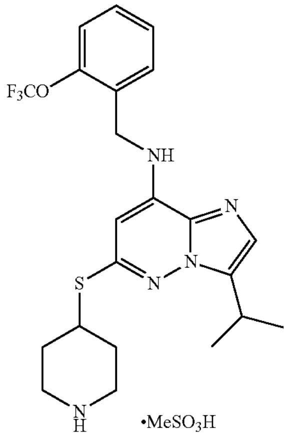 [SMILES: "·MeSO3H" ; CC(C)c1cnc2c(NCc3ccccc3OC(F)(F)F)cc(SC3CCNCC3)nn12] •$MeSO_3H$ |
| 33d | 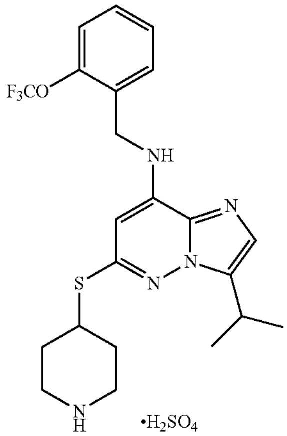 •$H_2SO_4$ |
| 33e | 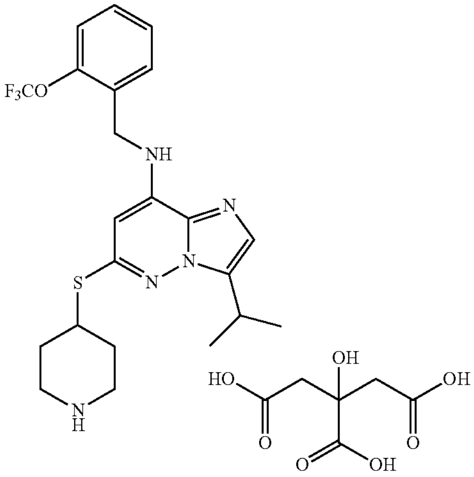 |
| 34 | 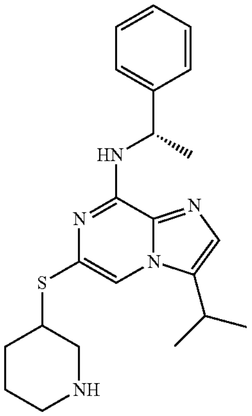 [SMILES: CC(C)c1cnc2c(N[C@@H](C)c3ccccc3)nc(SC3CCCNC3)cn12] |
| 35 | 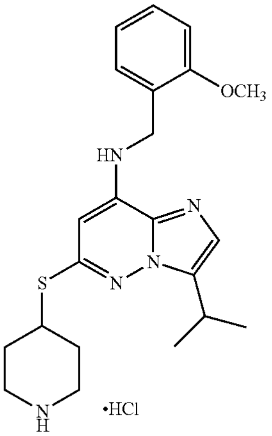 [SMILES: COc1ccccc1CNc1cc(SC2CCNCC2)nn2c(C(C)C)cnc12 ; Cl] •HCl |

TABLE 1-continued
| Representative Compounds | |
|---|---|
| Cpd. No. | Structure |
| 36 | 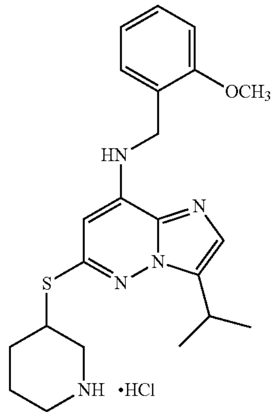 [SMILES: COc1ccccc1CNc1cc(SC2CCCNC2)nn2c(C(C)C)cnc12 ; Cl] |
| 37 | 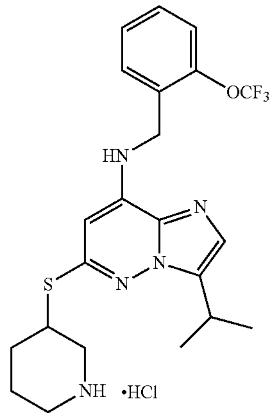 [SMILES: CC(C)c1cnc2c(NCc3ccccc3OC(F)(F)F)cc(SC3CCCNC3)nn12 ; Cl] |
| 38 | 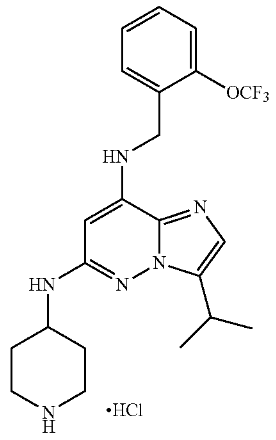 [SMILES: CC(C)c1cnc2c(NCc3ccccc3OC(F)(F)F)cc(NC3CCNCC3)nn12 ; Cl] |
| 39 | 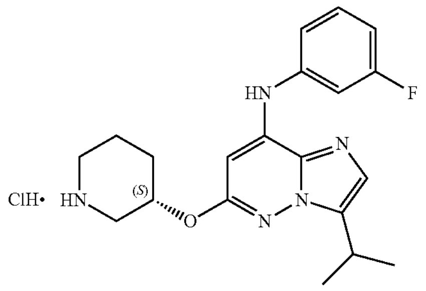 |
| 40 | 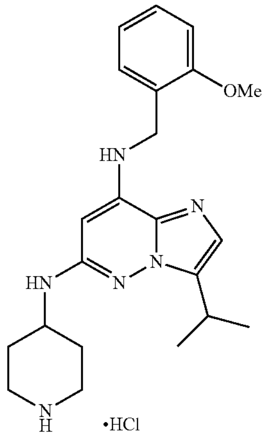 [SMILES: COc1ccccc1CNc1cc(NC2CCNCC2)nn2c(C(C)C)cnc12 ; Cl] |
| 41 | 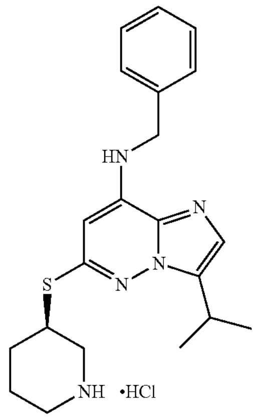 [SMILES: CC(C)c1cnc2c(NCc3ccccc3)cc(S[C@@H]3CCCNC3)nn12 ; Cl] |

TABLE 1-continued
| Representative Compounds | |
|---|---|
| Cpd. No. | Structure |
| 42 | 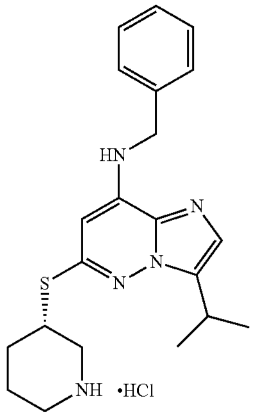 [SMILES: CC(C)c1cnc2c(NCc3ccccc3)cc(S[C@H]3CCCNC3)nn12 ; Cl] |
| 43 | 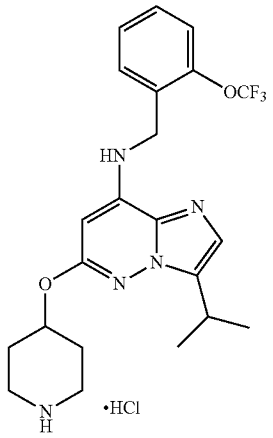 [SMILES: CC(C)c1cnc2c(NCc3ccccc3OC(F)(F)F)cc(OC3CCNCC3)nn12 ; Cl] |
| 44 | 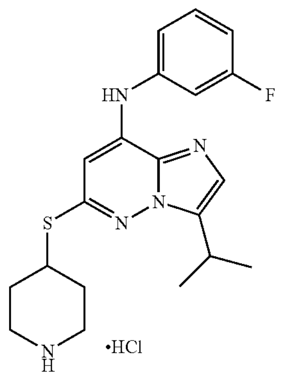 [SMILES: CC(C)c1cnc2c(Nc3cccc(F)c3)cc(SC3CCNCC3)nn12 ; Cl] |
TABLE 1-continued
| Representative Compounds | |
|---|---|
| Cpd. No. | Structure |
| 45 | 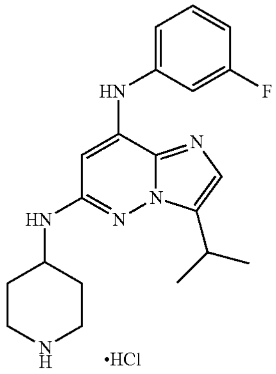 [SMILES: CC(C)c1cnc2c(Nc3cccc(F)c3)cc(NC3CCNCC3)nn12 ; Cl] |
| 46 | 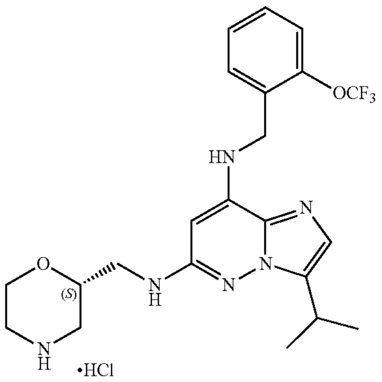 |
| 47 | 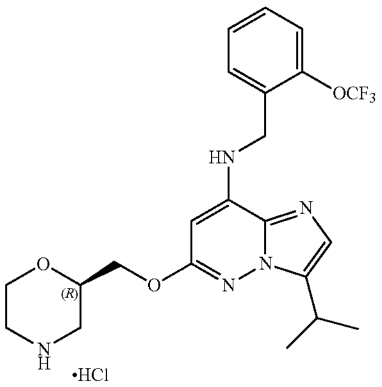 |
| 48 | 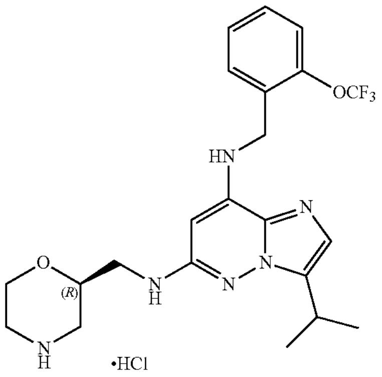 |

TABLE 1-continued
| Representative Compounds | |
|---|---|
| Cpd. No. | Structure |
| 49 | 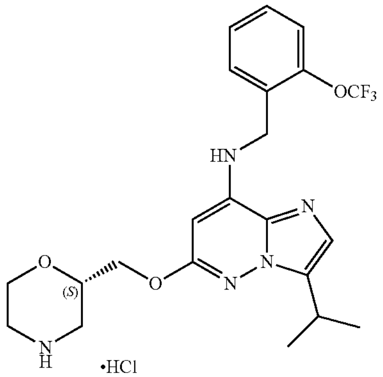 •HCl |
| 50 | 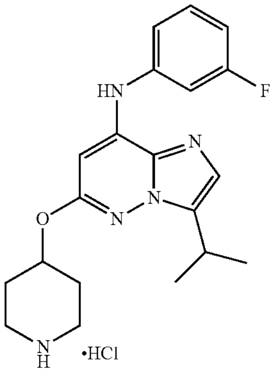 [SMILES: CC(C)c1cnc2c(Nc3cccc(F)c3)cc(OC3CCNCC3)nn12 ; Cl] •HCl |
| 51 | 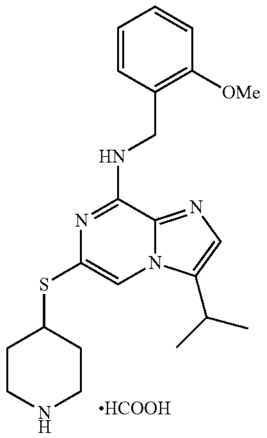 •HCOOH |
TABLE 1-continued
| Representative Compounds | |
|---|---|
| Cpd. No. | Structure |
| 52 | 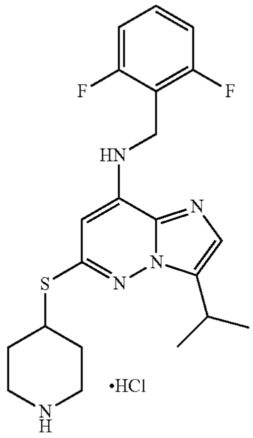 [SMILES: CC(C)c1cnc2c(NCc3c(F)cccc3F)cc(SC3CCNCC3)nn12 ; Cl] •HCl |
| 53 | 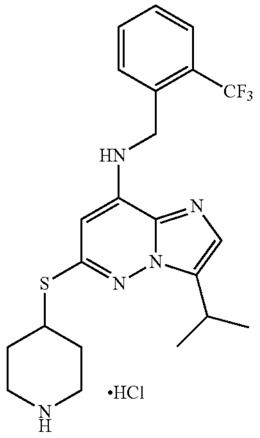 [SMILES: CC(C)c1cnc2c(NCc3ccccc3C(F)(F)F)cc(SC3CCNCC3)nn12 ; Cl] •HCl |
| 54 | 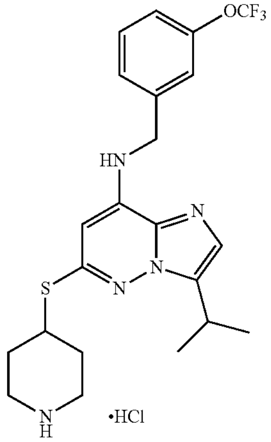 [SMILES: CC(C)c1cnc2c(NCc3cccc(OC(F)(F)F)c3)cc(SC3CCNCC3)nn12 ; Cl] •HCl |

TABLE 1-continued
| Representative Compounds | |
|---|---|
| Cpd. No. | Structure |
| 55 | 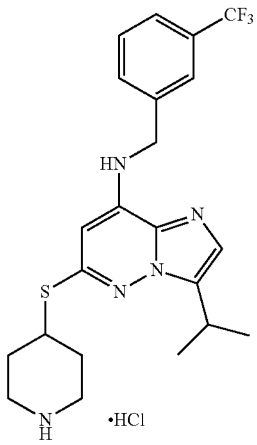 [SMILES: CC(C)c1cnc2c(NCc3cccc(C(F)(F)F)c3)cc(SC3CCNCC3)nn12 ; Cl] |
| 56 | 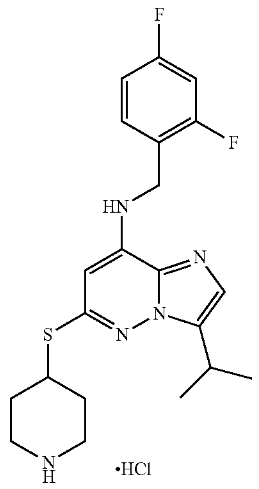 [SMILES: CC(C)c1cnc2c(NCc3ccc(F)cc3F)cc(SC3CCNCC3)nn12 ; Cl] |
| 57 | 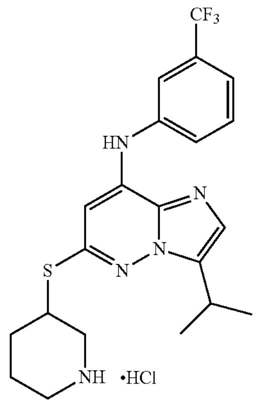 [SMILES: CC(C)c1cnc2c(Nc3cccc(C(F)(F)F)c3)cc(SC3CCCNC3)nn12 ; Cl] |
| 58 | 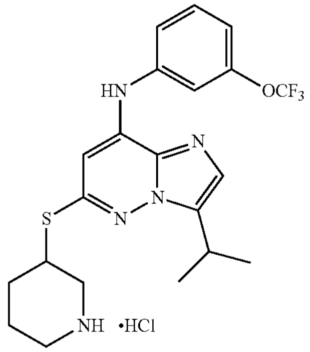 [SMILES: CC(C)c1cnc2c(Nc3cccc(OC(F)(F)F)c3)cc(SC3CCCNC3)nn12 ; Cl] |
| 59 | 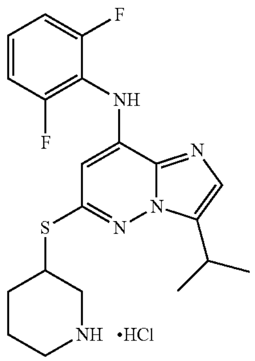 [SMILES: CC(C)c1cnc2c(Nc3c(F)cccc3F)cc(SC3CCCNC3)nn12 ; Cl] |
| 60 | 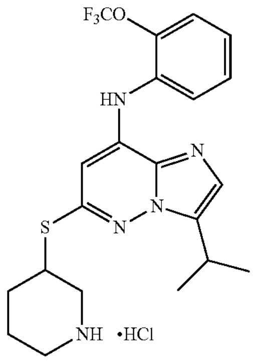 [SMILES: CC(C)c1cnc2c(Nc3ccccc3OC(F)(F)F)cc(SC3CCCNC3)nn12 ; Cl] |
| 61 | 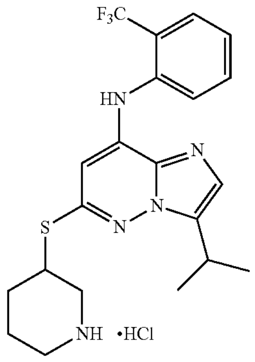 [SMILES: CC(C)c1cnc2c(Nc3ccccc3C(F)(F)F)cc(SC3CCCNC3)nn12 ; Cl] |

TABLE 1-continued
| Representative Compounds | |
|---|---|
| Cpd. No. | Structure |
| 62 | 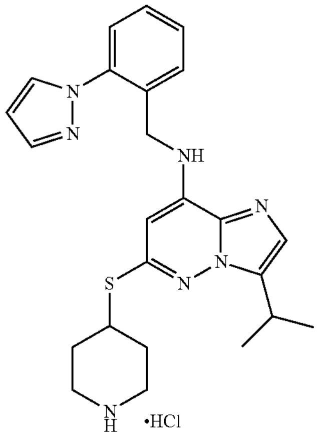 [SMILES: CC(C)c1cnc2c(NCc3ccccc3-n3cccn3)cc(SC3CCNCC3)nn12 ; Cl] |
| 63 | 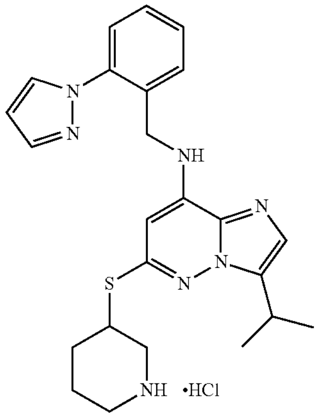 [SMILES: CC(C)c1cnc2c(NCc3ccccc3-n3cccn3)cc(SC3CCCNC3)nn12 ; Cl] |
| 64 | 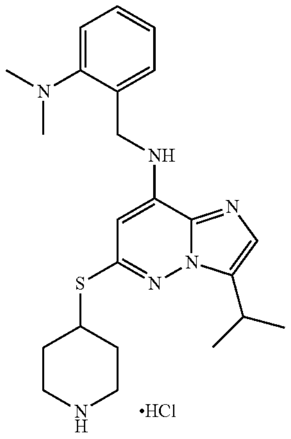 [SMILES: CC(C)c1cnc2c(NCc3ccccc3N(C)C)cc(SC3CCNCC3)nn12 ; Cl] |
| 65 | 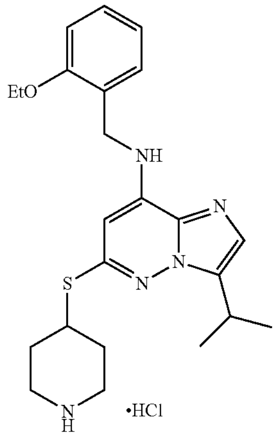 [SMILES: CCOc1ccccc1CNc1cc(SC2CCNCC2)nn2c(C(C)C)cnc12 ; Cl] |
| 66 | 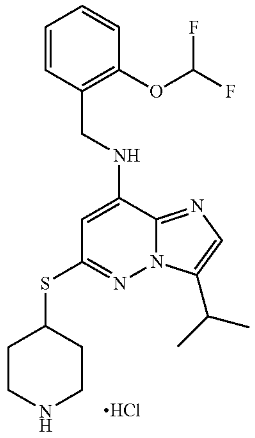 [SMILES: CC(C)c1cnc2c(NCc3ccccc3OC(F)F)cc(SC3CCNCC3)nn12 ; Cl] |
| 67 | 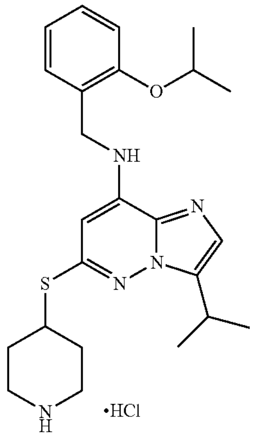 [SMILES: CC(C)Oc1ccccc1CNc1cc(SC2CCNCC2)nn2c(C(C)C)cnc12 ; Cl] |

TABLE 1-continued
| Representative Compounds | |
|---|---|
| Cpd. No. | Structure |
| 68 | 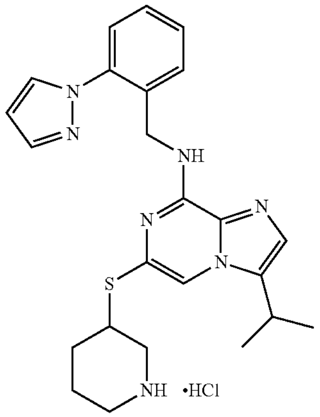 [SMILES: CC(C)c1cnc2c(NCc3ccccc3-n3cccn3)nc(SC3CCCNC3)cn12 ; Cl] •HCl |
| 69 | 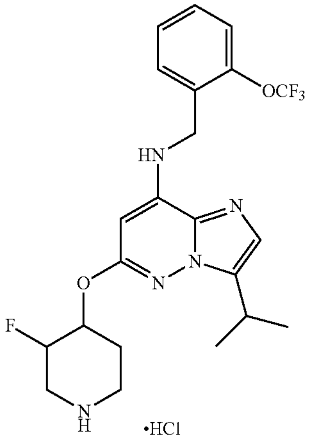 [SMILES: CC(C)c1cnc2c(NCc3ccccc3OC(F)(F)F)cc(OC3CCNCC3F)nn12 ; Cl] •HCl |
| 70 | 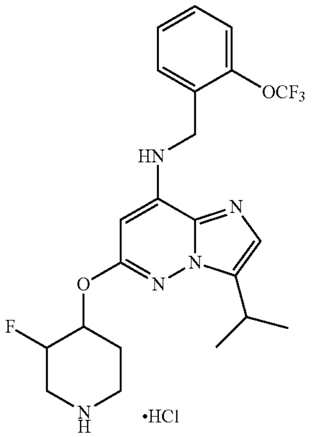 [SMILES: CC(C)c1cnc2c(NCc3ccccc3OC(F)(F)F)cc(OC3CCNCC3F)nn12 ; Cl] •HCl |
| 71 | 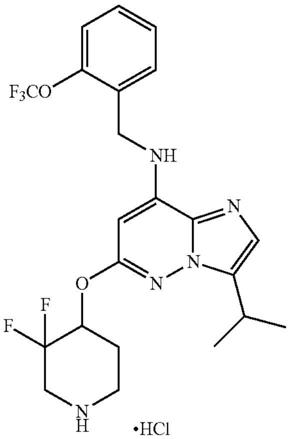 [SMILES: CC(C)c1cnc2c(NCc3ccccc3OC(F)(F)F)cc(OC3CCNCC3(F)F)nn12 ; Cl] •HCl |
| 72 | 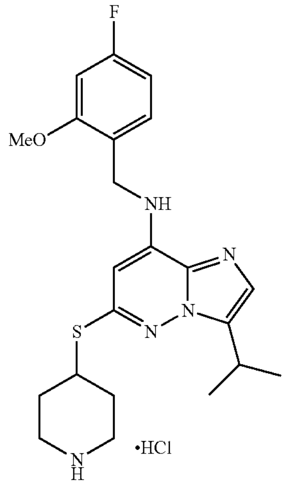 [SMILES: COc1cc(F)ccc1CNc1cc(SC2CCNCC2)nn2c(C(C)C)cnc12 ; Cl] •HCl |
| 73 | 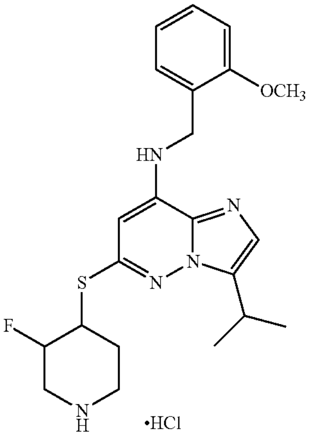 [SMILES: COc1ccccc1CNc1cc(SC2CCNCC2F)nn2c(C(C)C)cnc12 ; Cl] •HCl |

TABLE 1-continued
| Cpd. No. | Structure |
| --- | --- |
| 74 | 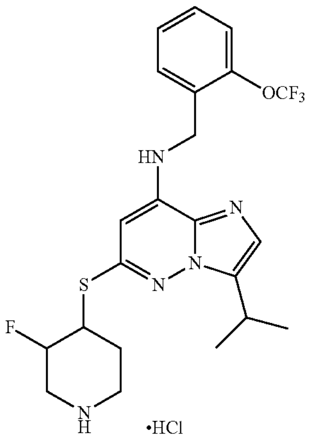 [SMILES: CC(C)c1cnc2c(NCc3ccccc3OC(F)(F)F)cc(SC3CCNCC3F)nn12 ; Cl] |
| 75 | 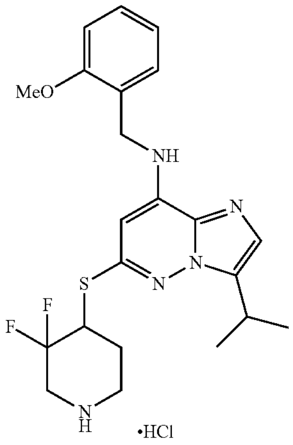 [SMILES: COc1ccccc1CNc1cc(SC2CCNCC2(F)F)nn2c(C(C)C)cnc12 ; Cl] |
| 76 | 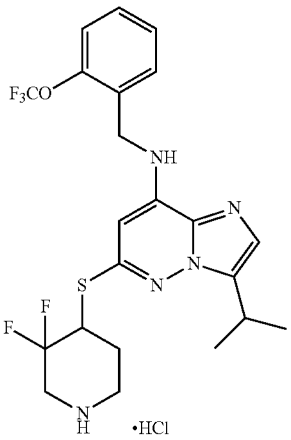 [SMILES: CC(C)c1cnc2c(NCc3ccccc3OC(F)(F)F)cc(SC3CCNCC3(F)F)nn12 ; Cl] |
| 77 | 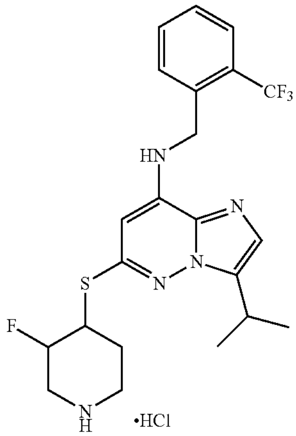 [SMILES: CC(C)c1cnc2c(NCc3ccccc3C(F)(F)F)cc(SC3CCNCC3F)nn12 ; Cl] |
| 78 | 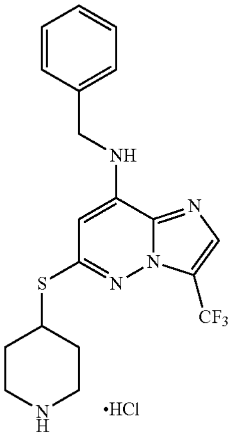 [SMILES: FC(F)(F)c1cnc2c(NCc3ccccc3)cc(SC3CCNCC3)nn12 ; Cl] |
| 79 | 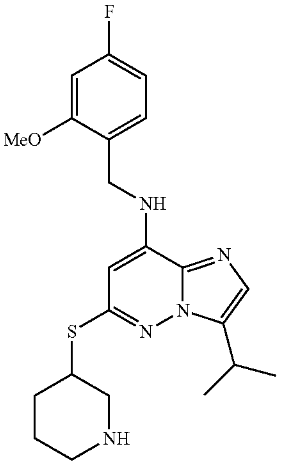 [SMILES: COc1cc(F)ccc1CNc1cc(SC2CCCNC2)nn2c(C(C)C)cnc12] |
Representative Compounds TABLE 1-continued
| Representative Compounds | |
|---|---|
| Cpd. No. | Structure |
| 80 | 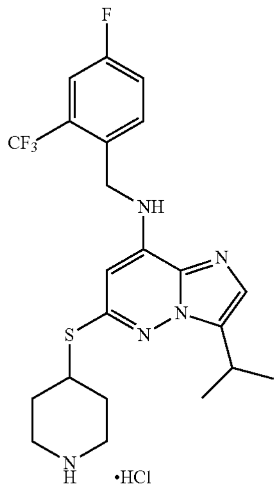 [SMILES: CC(C)c1cnc2c(NCc3ccc(F)cc3C(F)(F)F)cc(SC3CCNCC3)nn12 ; Cl] |
| 81 | 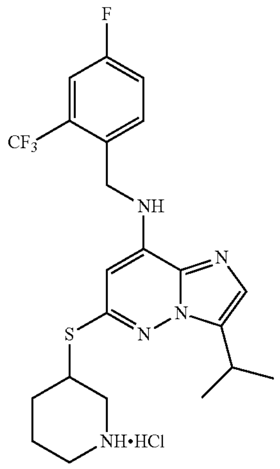 |
| 82 | 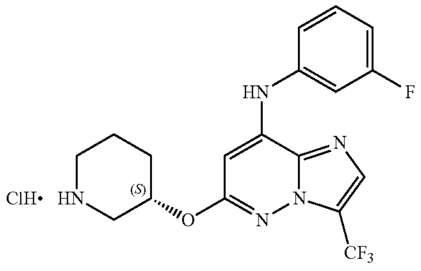 |
TABLE 2
| Representative compounds of structure (Ia) | |
|---|---|
| No. | Structure |
| I-1 | 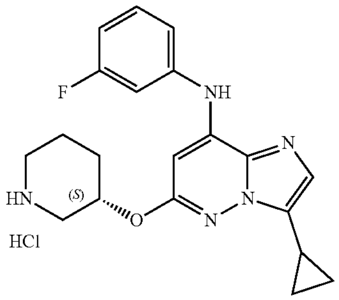 |
| I-2 | 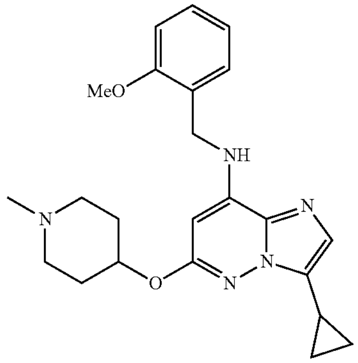 [SMILES: COc1ccccc1CNc1cc(OC2CCN(C)CC2)nn2c(C3CC3)cnc12] |
| I-3 | 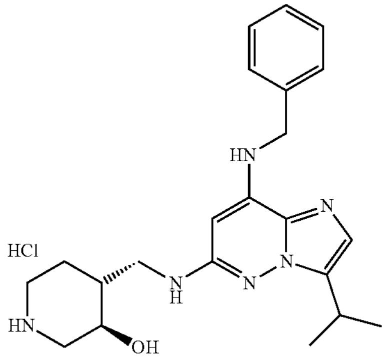 |
| I-4 | 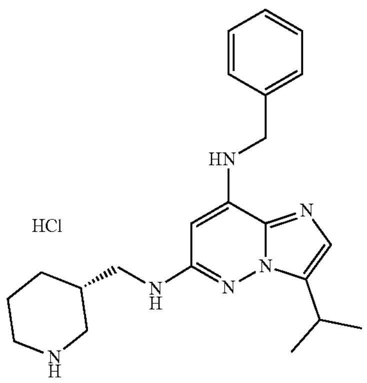 [SMILES: CC(C)c1cnc2c(NCc3ccccc3)cc(NC[C@H]3CCCNC3)nn12 ; Cl] |

TABLE 2-continued
| Representative compounds of structure (Ia) | |
|---|---|
| No. | Structure |
| I-5 | 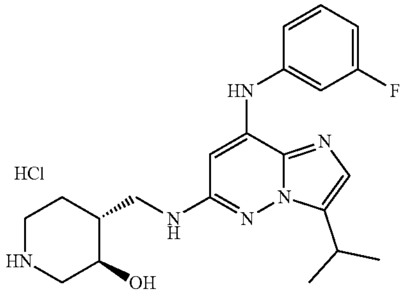 [SMILES: Cl ; CC(C)c1cnc2c(Nc3cccc(F)c3)cc(NC[C@H]3CCNC[C@@H]3O)nn12] |
| I-6 | 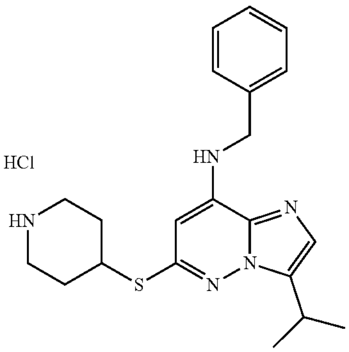 [SMILES: Cl ; CC(C)c1cnc2c(NCc3ccccc3)cc(SC3CCNCC3)nn12] |
| I-7 | 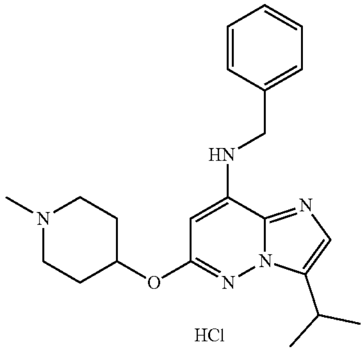 [SMILES: CC(C)c1cnc2c(NCc3ccccc3)cc(OC3CCN(C)CC3)nn12 ; Cl] |
| I-8 | 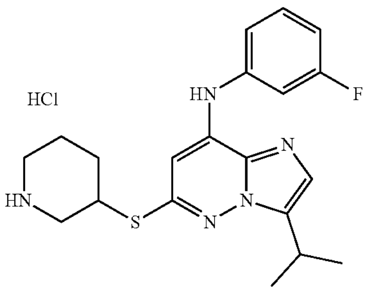 [SMILES: CC(C)c1cnc2c(Nc3cccc(F)c3)cc(SC3CCCNC3)nn12 ; Cl] |
TABLE 3
| Representative compounds of structure (Ib) | |
|---|---|
| No. | Structure |
| Ib-1 | 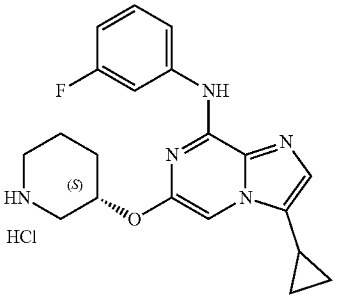 |
| Ib-2 | 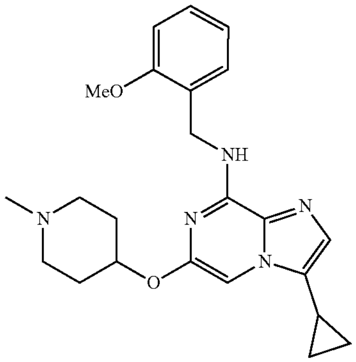 [SMILES: COc1ccccc1CNc1nc(OC2CCN(C)CC2)cn2c(C3CC3)cnc12] |
| Ib-3 | 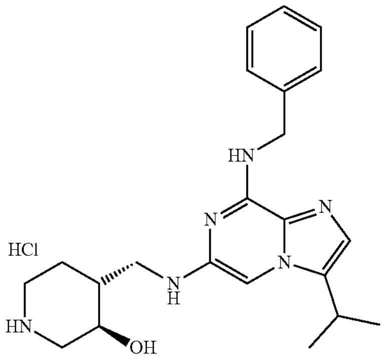 |
| Ib-4 | 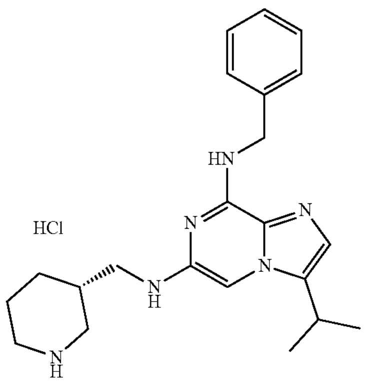 [SMILES: CC(C)c1cnc2c(NCc3ccccc3)nc(NC[C@H]3CCCNC3)cn12 ; Cl] |

TABLE 3-continued

| Representative compounds of structure (Ib) | |
|---|---|
| No. | Structure |
| Ib-5 | 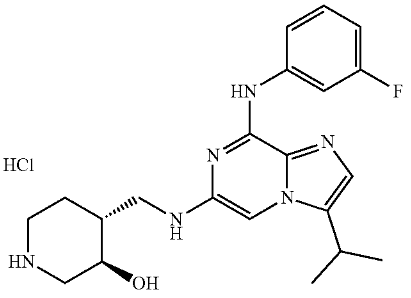 [SMILES: Cl ; CC(C)c1cnc2c(Nc3cccc(F)c3)nc(NC[C@H]3CCNC[C@@H]3O)cn12] HCl |
| Ib-6 | 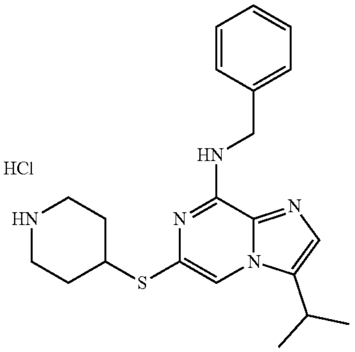 [SMILES: Cl ; CC(C)c1cnc2c(NCc3ccccc3)nc(SC3CCNCC3)cn12] HCl |
| Ib-7 | 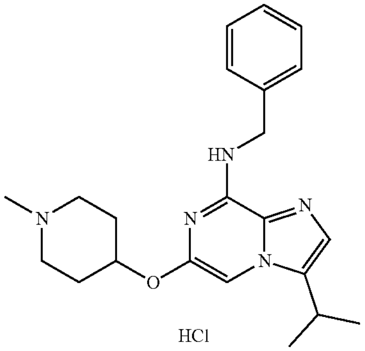 [SMILES: CC(C)c1cnc2c(NCc3ccccc3)nc(OC3CCN(C)CC3)cn12 ; Cl] HCl |
| Ib-8 | 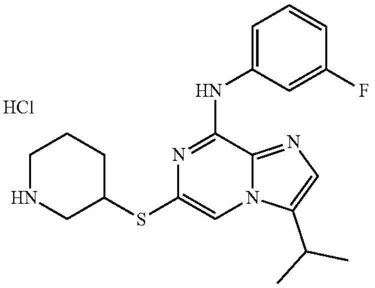 [SMILES: Cl ; CC(C)c1cnc2c(Nc3cccc(F)c3)nc(SC3CCCNC3)cn12] HCl |

Just as examples, which are not intended to limit the scope of the present invention, additional embodiments of the compound of structure (Ia) are also provided as represented in Table 4, which describe the substitutions for the variables $R^1$, $R^2$ and $R^3$:

TABLE 4

| Additional embodiments of structure (1a) | | |
|---|---|---|
| ~NH-$R_3$ | ~L-$R_1$ | ~$R_2$ |
| 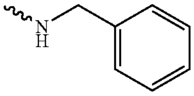 | 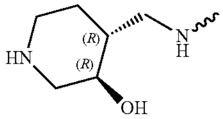 | 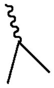 |
| 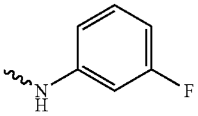 | 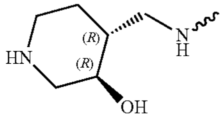 | 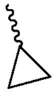 |
| 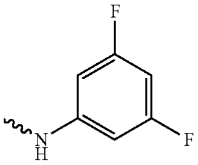 | 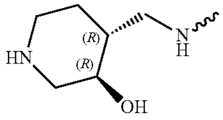 | 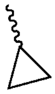 |
| 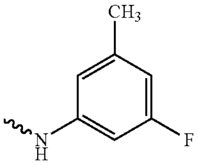 | 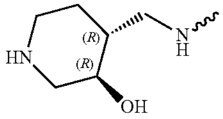 | 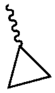 |

TABLE 4-continued
| Additional embodiments of structure (1a) | | |
|---|---|---|
| ~NH-$R_3$ | ~L-$R_1$ | ~$R_2$ |
| 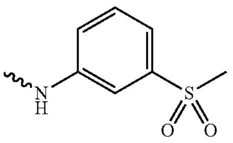 | 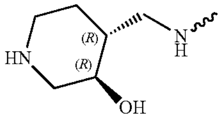 | 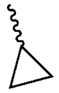 |
| 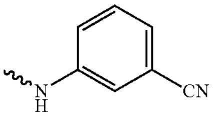 | 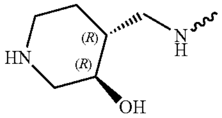 | 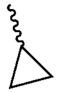 |
| 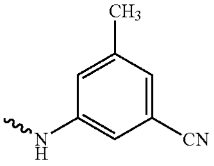 | 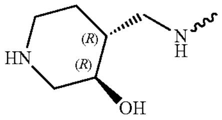 | 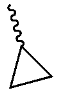 |
| 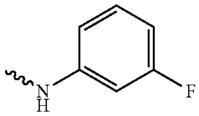 | 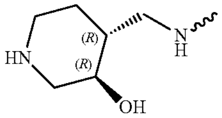 | 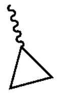 |
| 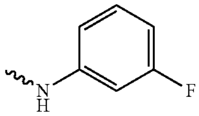 | 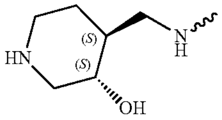 | 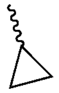 |
| 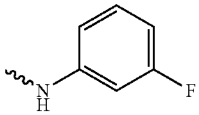 | 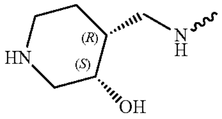 | 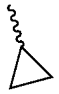 |
| 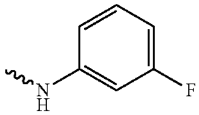 | 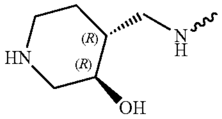 | 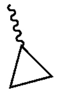 |
| 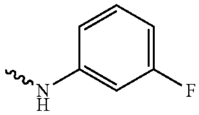 | 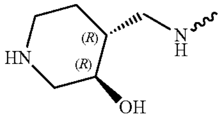 | 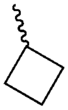 |
| 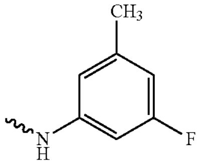 | 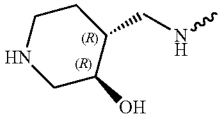 | 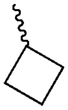 |
| 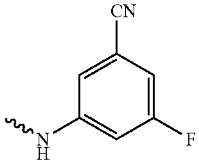 | 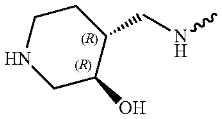 | 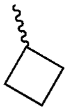 |

TABLE 4-continued
Additional embodiments of structure (1a)
| ~NH-$R_3$ | ~L-$R_1$ | ~$R_2$ |
|---|---|---|
| 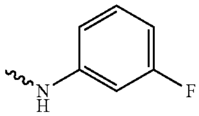 | 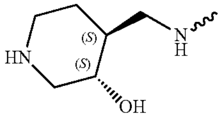 | 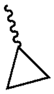 |
| 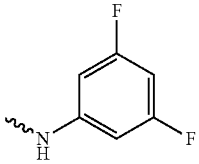 | 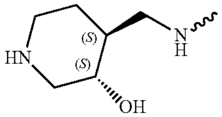 | 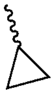 |
| 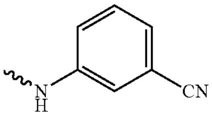 | 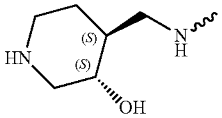 | 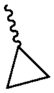 |
| 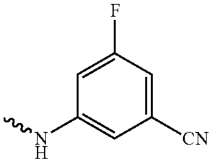 | 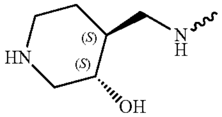 | 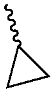 |
| 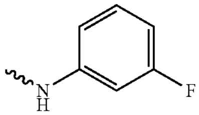 | 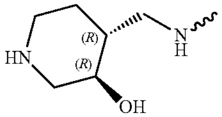 | 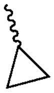 |
| 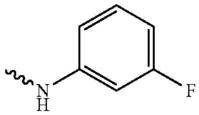 | 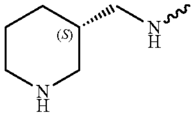 | 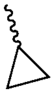 |
| 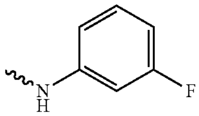 | 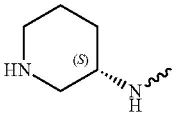 | 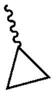 |
| 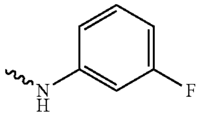 | 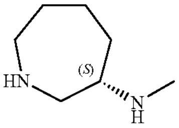 | 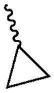 |
| 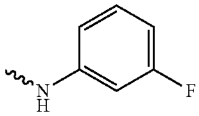 | 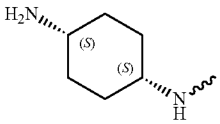 | 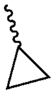 |
| 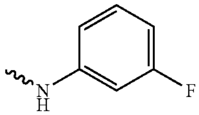 | 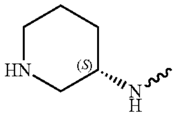 | 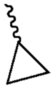 |
| 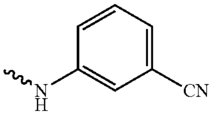 | 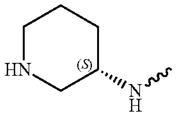 | 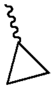 |

TABLE 4-continued
| Additional embodiments of structure (1a) | | |
|---|---|---|
| ~NH-$R_3$ | ~L-$R_1$ | ~$R_2$ |
| 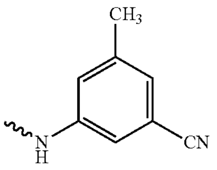 | 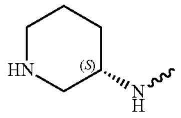 | 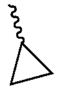 |
| 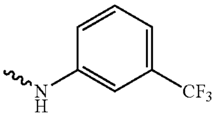 | 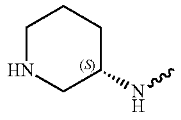 | 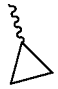 |
| 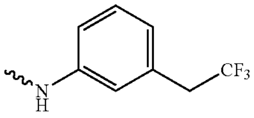 | 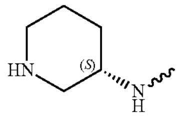 | 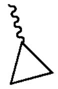 |
| 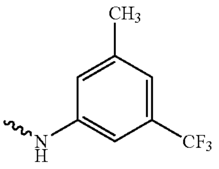 | 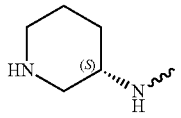 | 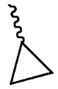 |
| 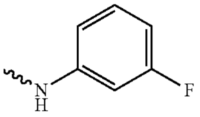 | 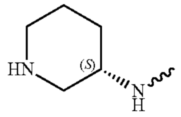 | 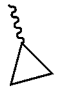 |
| 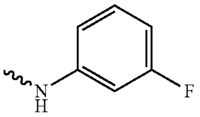 | 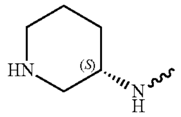 | 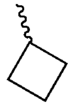 |
| 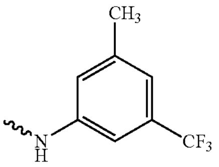 | 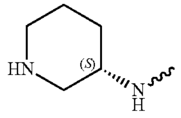 | 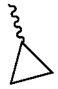 |
| 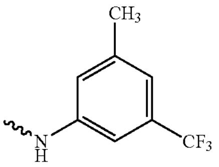 | 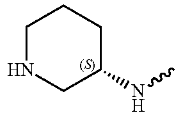 | 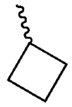 |
| 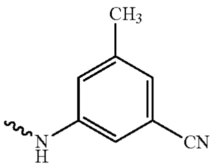 | 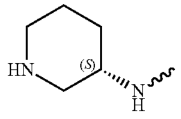 | 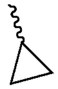 |

TABLE 4-continued
| Additional embodiments of structure (1a) | | |
|---|---|---|
| ~NH-$R_3$ | ~L-$R_1$ | ~$R_2$ |
| 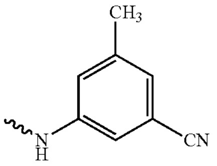 | 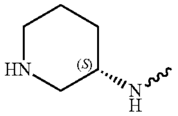 | 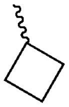 |
| 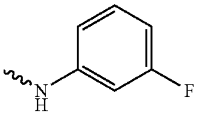 | 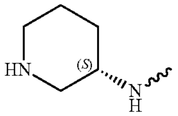 | 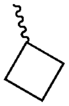 |
| 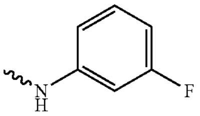 | 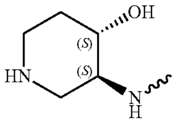 | 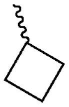 |
| 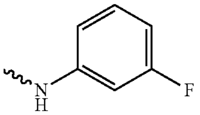 | 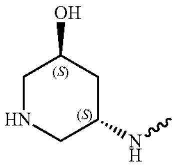 | 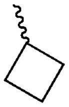 |
| 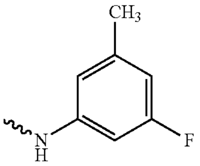 | 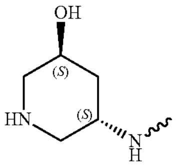 | 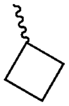 |
| 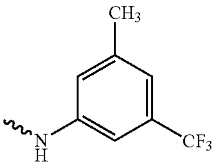 | 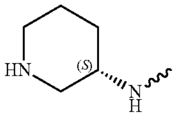 | 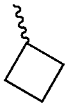 |
| 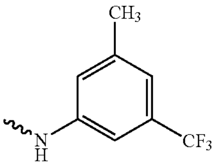 | 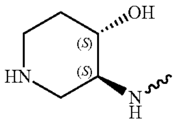 | 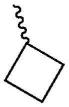 |
| 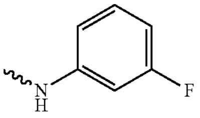 | 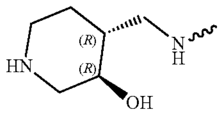 | 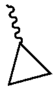 |
| 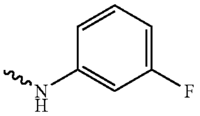 | 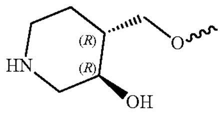 | 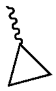 |
| 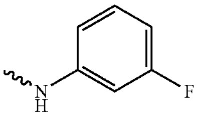 | 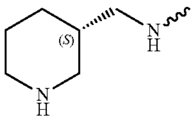 | 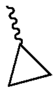 |

TABLE 4-continued
| Additional embodiments of structure (1a) | | |
|---|---|---|
| ~NH-$R_3$ | ~L-$R_1$ | ~$R_2$ |
| 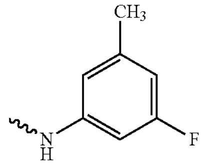 | 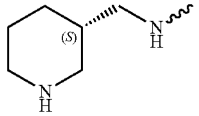 | 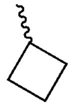 |
| 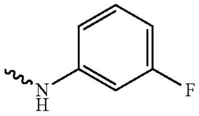 | 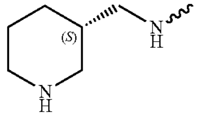 | 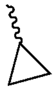 |
| 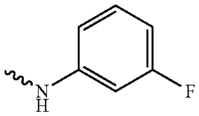 | 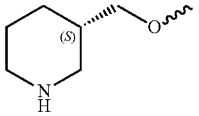 | 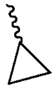 |
| 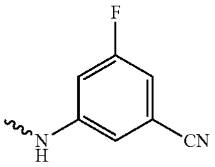 | 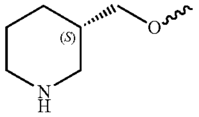 | 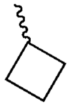 |
| 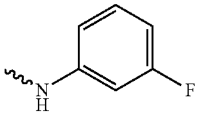 | 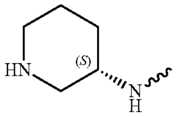 | 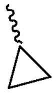 |
| 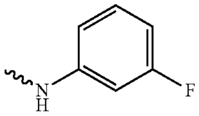 | 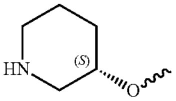 | 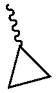 |
| 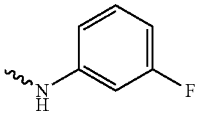 | 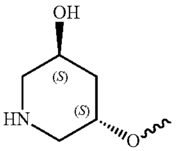 | 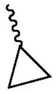 |
| 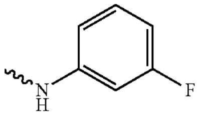 | 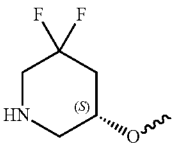 | 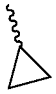 |
| 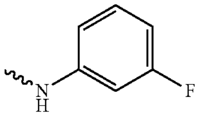 | 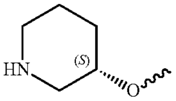 | 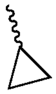 |
| 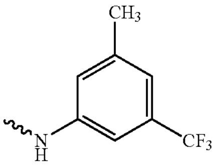 | 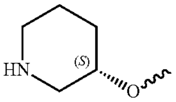 | 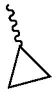 |

TABLE 4-continued

| Additional embodiments of structure (1a) | | |
|---|---|---|
| ~NH-$R_3$ | ~L-$R_1$ | ~$R_2$ |
| 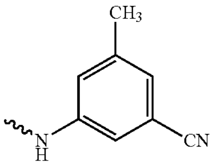 | 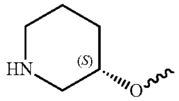 | 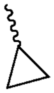 |
| 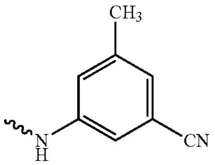 | 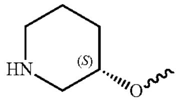 | 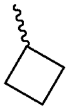 |
| 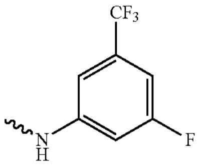 | 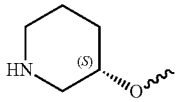 | 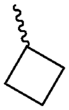 |
| 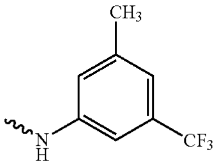 | 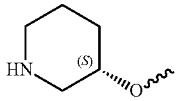 | 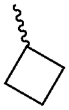 |
| 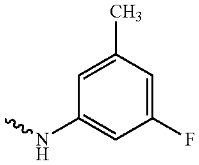 | 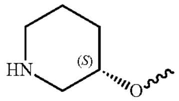 | 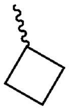 |
| 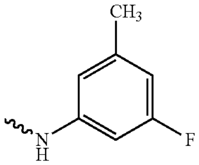 | 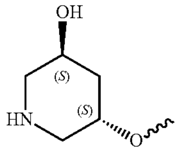 | 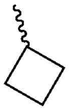 |

Just as examples, which are not intended to limit the scope of the present invention, additional embodiments of the compound of structure (Ib) are also provided as represented in Table 5, which describe the substitutions for the variables $R^1$, $R^2$ and $R^3$:

TABLE 5

| Additional embodiments of structure (1b) | | |
|---|---|---|
| ~NH-$R_3$ | ~L-$R_1$ | ~$R_2$ |
| 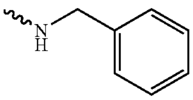 | 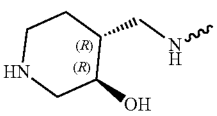 | 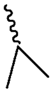 |

TABLE 5-continued

| Additional embodiments of structure (1b) | | |
|---|---|---|
| ~NH-$R_3$ | ~L-$R_1$ | ~$R_2$ |
| 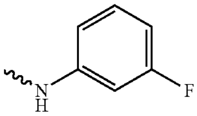 | 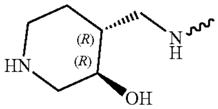 | 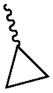 |
| 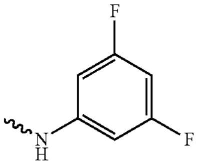 | 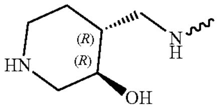 | 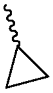 |

TABLE 5-continued
| Additional embodiments of structure (1b) | | |
|---|---|---|
| ~NH-$R_3$ | ~L-$R_1$ | ~$R_2$ |
| 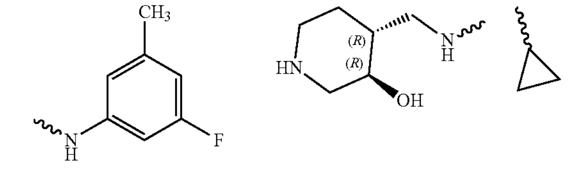 | | |
| 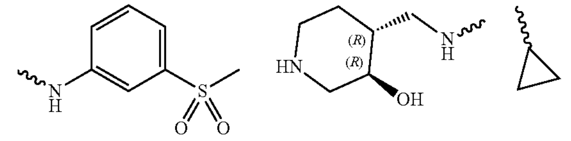 | | |
| 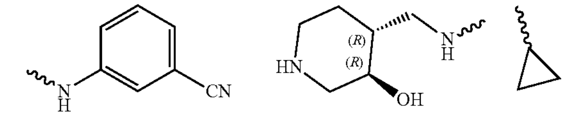 | | |
| 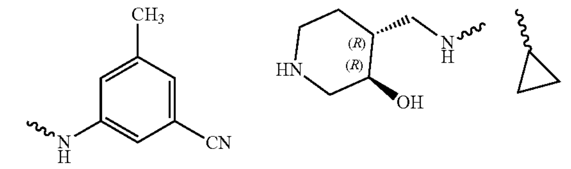 | | |
| 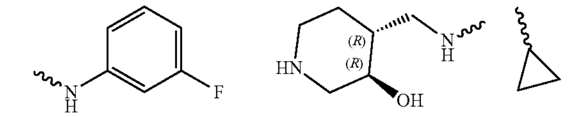 | | |
| 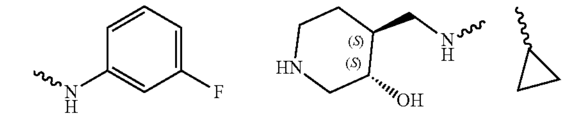 | | |
| 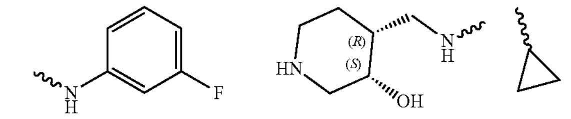 | | |
| 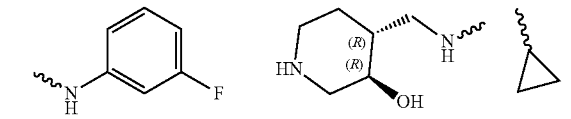 | | |
| 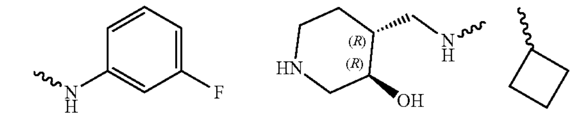 | | |
| 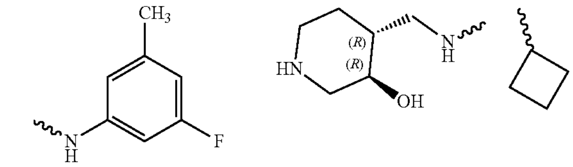 | | |
TABLE 5-continued
| Additional embodiments of structure (1b) | | |
|---|---|---|
| ~NH-$R_3$ | ~L-$R_1$ | ~$R_2$ |
| 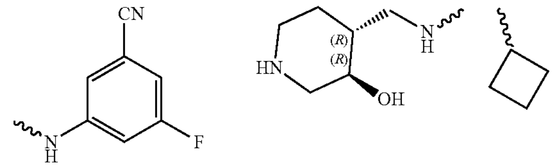 | | |
| 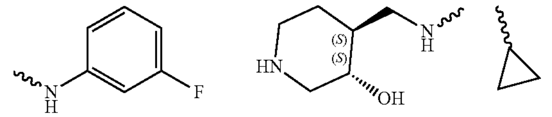 | | |
| 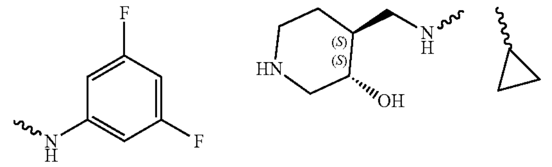 | | |
| 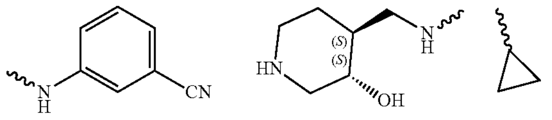 | | |
| 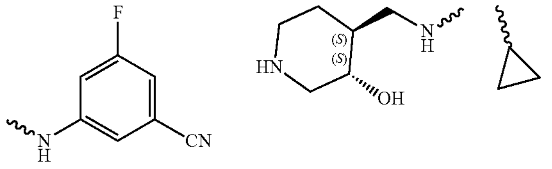 | | |
| 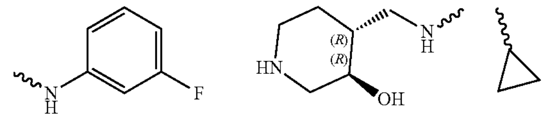 | | |
| 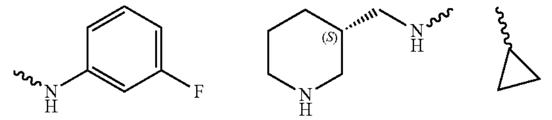 | | |
| 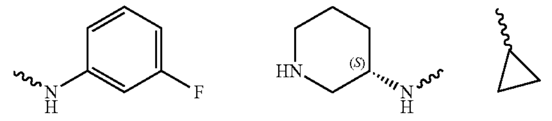 | | |
| 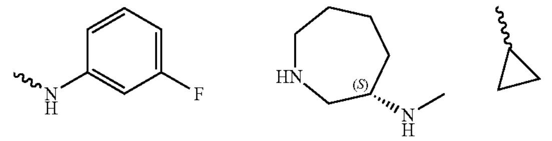 | | |
| 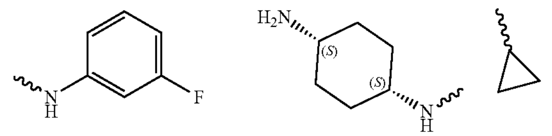 | | |

TABLE 5-continued

| Additional embodiments of structure (1b) | | |
|---|---|---|
| ~NH-$R_3$ | ~L-$R_1$ | ~$R_2$ |
| 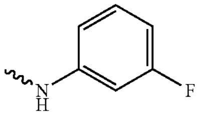 | 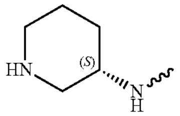 | 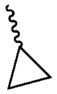 |
| 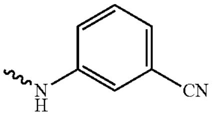 | 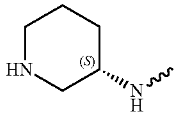 | 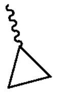 |
| 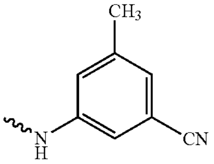 | 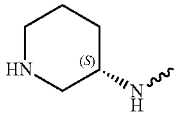 | 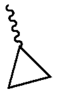 |
| 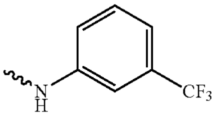 | 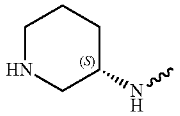 | 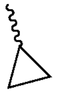 |
| 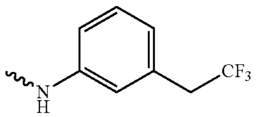 | 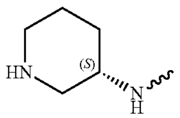 | 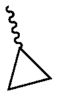 |
| 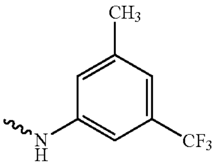 | 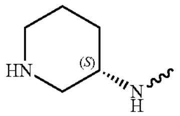 | 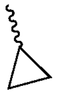 |
| 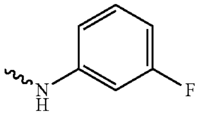 | 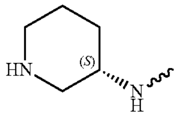 | 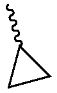 |
| 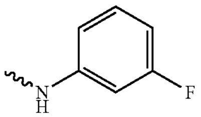 | 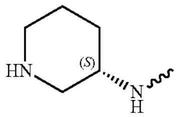 | 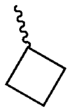 |
| 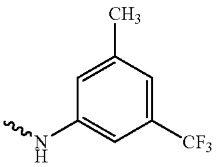 | 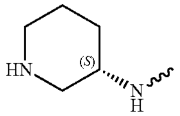 | 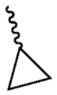 |
| 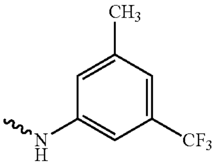 | 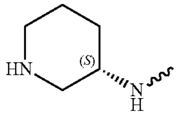 | 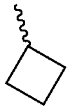 |

TABLE 5-continued

| Additional embodiments of structure (1b) | | |
|---|---|---|
| ~NH-$R_3$ | ~L-$R_1$ | ~$R_2$ |
| 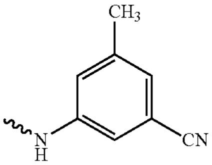 | 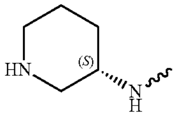 | 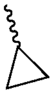 |
| 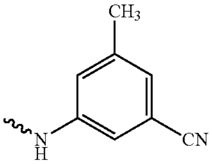 | 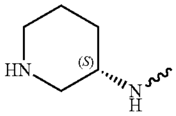 | 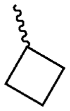 |
| 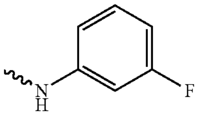 | 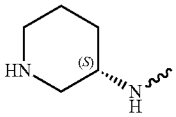 | 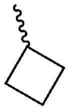 |

Pharmaceutical Compositions

Other embodiments are directed to pharmaceutical compositions. The pharmaceutical composition comprises any one (or more) of the foregoing compounds of structure (I) (or pharmaceutically acceptable salt thereof) and a pharmaceutically acceptable carrier or excipient. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent. Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound of structure (I) is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound of structure (I) is provided in the form of a rapid release formulation, in the form of an extended release formulation, or in the form of an intermediate release formulation. In yet other embodiments, the compound of structure (I) is administered topically.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the disclosure is administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, a compound of the disclosure is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the disclosure and another agent are administered together about once per day to about 6 times per day. In another embodiment the administration of a compound of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the disclosure may continue as long as necessary. In some embodiments, a compound of the disclosure is administered for more than 1, 2, 3, 4, 5, 6, 7, 14, or 28 days. In some embodiments, a compound of the disclosure is administered for less than 28, 14, 7, 6, 5, 4, 3, 2, or 1 day. In some embodiments, a compound of the disclosure is administered chronically on an ongoing basis, e.g., for the treatment of chronic effects.

In some embodiments, the compounds of the disclosure are administered in dosages. It is known in the art that due to intersubject variability in compound pharmacokinetics, individualization of dosing regimen is necessary for optimal therapy. Dosing for a compound of the disclosure may be found by routine experimentation in light of the instant disclosure.

In some embodiments, the compounds of structure (I) are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds of structure (I) are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds of structure (I) are formulated for other parenteral injections, appropriate formulations include aqueous or non-aqueous solutions. In specific embodiments, such solutions include physiologically compatible buffers and/or excipients.

In another embodiment, compounds of structure (I) are formulated for oral administration. Compounds of structure (I) are formulated by combining the active compounds with, e.g., pharmaceutically acceptable carriers or excipients. In various embodiments, the compounds of structure (I) are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds of structure (I), optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating.

In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds of structure (I) are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds of structure (I) are formulated for buccal or sublingual administration. Formulations suitable for buccal or sublingual administration include, by way of example only, tablets, lozenges, or gels. In still other embodiments, the compounds of structure (I) are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions of structure (I) include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds of structure (I) are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), as an active ingredient. The active ingredient is in free-acid or free-base form, or in a pharmaceutically acceptable salt form. In addition, the methods and pharmaceutical compositions of structure (I) include the use of N-oxides, crystalline forms (also known as polymorphs), as well as active metabolites of these compounds having the same type of activity. All tautomers of the compounds of structure (I) are included within the scope of the compounds presented herein. Additionally, the compounds of structure (I) encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Accordingly, one embodiment provides a pharmaceutically acceptable salt of any one of the compounds of structure (I) described herein. In more specific embodiments, the pharmaceutically acceptable salt is an acid addition salt (e.g., a trifluoroacetic acid salt or a hydrochloric acid salt).

Methods for the preparation of compositions comprising the compounds of structure (I)include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions of structure (I) include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term “solubilizing agent” generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds of structure (I) are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of the compound of structure (I) provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.00010% w/w, w/v, or v/v.

In some embodiments, the concentration of the compound of structure (I) provided in the pharmaceutical compositions is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds of structure (I), optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound of structure (I). Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods of Treatment and Administration

Embodiments of the present disclosure provide a method for treating CDK7-dependent diseases (e.g., cancer). One embodiment provides a method for treating a CDK7-dependent disease, the method comprising administering an effective amount of a compound of structure (I) (or pharmaceutically acceptable salt thereof) or a pharmaceutical composition comprising a compound of structure (I) as disclosed in any one of the embodiments herein to a subject in need thereof. Another embodiment provides a method of modulating CDK7 comprising contacting a cell with an effective amount of the compound of structure (I) or the pharmaceutical composition of the compound of structure (I) and any of its embodiments.

In some more specific embodiments, the CDK7-dependent disease is cancer. For example, in some embodiments, the cancer is a breast cancer. In some embodiments, the cancer is triple negative breast cancer (TNBC). In some embodiments, the cancer is pancreatic cancer. In some embodiments, the cancer is a sarcoma.

In some embodiments, the method of administering relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In some more specific embodiments, the cancer is neuroblastoma, medulloblastoma, Ewing sarcoma, chordoma or combinations thereof. In some embodiments, the cancer is neuroblastoma. In some other embodiments, the cancer is medulloblastoma. In still other embodiments, the cancer is Ewing sarcoma. In certain embodiments, the cancer is chordoma.

In some embodiments, the cancer is a gastric. In some embodiments, the cancer is ovarian. In some embodiments, the cancer is glioblastoma. In some embodiments, the cancer is DIPG. In some embodiments, the cancer is pancreatic. In some embodiments, the cancer is colon cancer. In some embodiments, the cancer is small cell lung cancer (SCLC). In some embodiments, the cancer is AML. In some embodiments, the cancer comprises solid tumors. In some specific embodiments, the cancer is brain cancer. In some embodiments, the cancer comprises a cancer addicted to oncogenic super-enhancers that drive expression of oncogenes such as MYC.

Further therapeutic agents that can be combined with a compound of the disclosure are found in Goodman and Gilman's "The Pharmacological Basis of Therapeutics" Thirteenth Edition edited by Brunton, Hilal-Dandan and Knollmann or the Physician's Desk Reference, both of which are incorporated herein by reference in their entirety.

The compounds of structure (I) can be used in combination with the agents disclosed herein or other suitable agents, depending on the condition being treated. Hence, in some embodiments the one or more compounds of structure (I) will be co-administered with other agents as described above. When used in combination therapy, the compounds of structure (I) are administered with the second agent simultaneously or separately. This administration in combination can include simultaneous administration of the two agents in the same dosage form, simultaneous administration in separate dosage forms, and separate administration. That is, a compound of structure (I) and any of the agents described above can be formulated together in the same dosage form and administered simultaneously. Alternatively, a compound of structure (I) and any of the agents described above can be simultaneously administered, wherein both the agents are present in separate formulations. In another alternative, a compound of structure (I) can be administered just followed by and any of the agents described above, or vice versa. In some embodiments of the separate administration protocol, a compound of structure (I) and any of the agents described above are administered a few minutes apart, or a few hours apart, or a few days apart.

The compounds of structure (I) include novel compounds as inhibitors of cyclin-dependent kinase (CDK7). CDK7 is a unique kinase that has the ability to regulate both cell-cycle progression and RNA polymerase-dependent transcription and is member of CDK family kinases including CDK1, 2, 4, 5, 6, 8, and 9 which regulates the cell cycle function and phosphorylation.

The present disclosure also provides methods for single or combination therapies in which an agent known to modulate other pathways, or other components of the same pathway, or even overlapping sets of target enzymes are used in combination with a compound of structure (I), or a stereoisomer, tautomer, prodrug, or pharmaceutically acceptable salt thereof. In one aspect, such therapy includes but is not limited to the combination of one or more compounds of structure (I) with chemotherapeutic agents, therapeutic antibodies, and radiation treatment, to provide a synergistic or additive therapeutic effect.

In various embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitors (suich as irinotecan, etoposide, or asdoxorubicin), taxanes (such as anti-microtubule agents including paclitaxel and docetaxel), anti-metabolite agents (such as 5-FU or such as gemcitabine), alkylating agents (such as cisplatin or such as cyclophosphamide), or a taxane.

In other embodiments, the additional therapeutic agent is a checkpoint inhibitor.

A "checkpoint inhibitor" is an agent which acts on surface proteins which are members of either the TNF receptor or B7 superfamilies, including agents which bind to negative co-stimulatory molecules selected from CTLA-4, PD-1, TIM-3, BTLA, VISTA, LAG-3, and/or their respective ligands, including PD-L1.

In some embodiments, the additional therapeutic agent is selected from chemotherapeutic drugs, radiation therapy, HDAC inhibitors, PARP inhibitors, or checkpoint inhibitors.

In some specific embodiments, the additional therapeutic agent is gemcitabine, cisplatin, 5-fluorouracil, nutlin, panobinostat, olaparib, or combinations thereof. In some more specific embodiments, the additional therapeutic agent is Gemcitabine. In some embodiments, the additional therapeutic agent is cisplatin. In some embodiments, the additional therapeutic agent is 5-fluorouracil. In some embodiments, the additional therapeutic agent is nutlin. In some embodiments, the additional therapeutic agent is abraxane. In some embodiments, the additional therapeutic agent is panobinostat. In some embodiments, the additional therapeutic agent is olaparib. In some embodiments, the additional therapeutic agent is radiation.

In some embodiments, the additional therapeutic agent is selected from the group consisting of gemcitabine, cisplatin, 5-fluorouracil, nutlin, panobinostat, olaparib, checkpoint inhibitors and combinations thereof.

In some embodiments, the additional therapeutic agent is an epidermal growth factor receptor (EGFR) inhibitor, such as Erlotinib or such as Afatinib. In some embodiments, the additional therapeutic agent is Iressa. In some embodiments, the additional therapeutic agent is a monoclonal antibody such as cetuximab (Erbitux) or panitumumab (Vectibix). In some embodiments the GFR inhibitor is a dual or pan-HER inhibitor. In other embodiments, the additional therapeutic agent is a phosphatidylinositol-3kinase (PI3K) inhibitor, such as GDC0941, MLN1117, BYL719 (Alpelisib) or BKM120 (Buparlisib). GDC0941 refers to 2-(1H-indazol-4-yl)-6-(4-methanesulfonyl-piperazin-1-ylmethyl)-4-morpholin-4-yl-thieno[3,2-d]pyrimidine or a salt thereof (e.g., bismesylate salt).

In still different embodiments, the additional therapeutic agent is an insulin-like growth factor receptor (IGF1R) inhibitor. For example, in some embodiments the insulin-like growth factor receptor (IGF1R) inhibitor is NVP-AEW541. In other embodiments, the additional therapeutic agent is IGOSI-906 (Linsitinib), BMS-754807, or in other embodiments the additional therapeutic agent is a neutralizing monoclonal antibodies specific to IGF1R such as AMG-479 (ganitumab), CP-751,871 (figitumumab), IMC-A12 (cixutumumab), MK-0646 (dalotuzumab), and R-1507 (robatumumab).

In some other embodiments, the additional therapeutic agent is a Janus kinase (JAK) inhibitor. In some embodiments, the additional therapueitc agent is CYT387, GLPG0634, Baricitinib, Lestaurtinib, momelotinib, Pacritinib, Ruxolitinib or TG101348.

In some other embodiments, the additional therapeutic agent is an MET kinase inhibitor, such as Crizotinib, tivantinib, AMG337, cabozantinib, foretinib. In other embodiments, the additional therapueitc agent is a neutralizing monoclonal antibody to MET such as onartuzumab.

In more embodiments, the additional therapeutic agent is a SRC family non-receptor tyrosine kinase inhibitor. For example in some embodiments, the additional therapeutic agent is an inhibitor of the subfamily of SRC family non-receptor tyrosine kinases. Exemplary inhibitors in this respect include Dasatinib. Other examples in this regard include Ponatinib, saracatinib, and bosutinib In yet different embodiments, the additional therapeutic agent is a mitogen-activated protein kinase (MEK) inhibitor. In some of these embodiments, the mitogen-activated protein kinase (MEK) inhibitor is trametinib, selumetinib, cobimetinib, PD0325901, or RO5126766. In other embodiments, the MEK inhibitor is GSK-1120212, also known as trametinib.

In yet different embodiments, the additional therapeutic agent is an extracellular-signal-regulated kinase (ERK)

inhibitor. In some of these embodiments, the mitogen-activated protein kinase (MEK) inhibitor is SCH722984 or GDC-0994.

The exact method for administering the compound of structure (I) and the additional therapeutic agent will be apparent to one of ordinary skill in the art. In some exemplary embodiments, the compound of structure (I) and the additional therapeutic agent are co-administered. In other embodiments, the compound of structure (I) and the additional therapeutic agent are separately administered.

In some embodiments, the compound of structure (I) and the additional therapeutic agent are administered with the second agent simultaneously or separately. This administration in combination can include simultaneous administration of the two agents in the same dosage form, simultaneous administration in separate dosage forms, and separate administration. That is, the compound of structure (I) and any of the additional therapeutic agents described herein can be formulated together in the same dosage form and administered simultaneously. Alternatively, the compound of structure (I) and any of the additional therapeutic agents described herein can be simultaneously administered, wherein both the agents are present in separate formulations. In another alternative, the compound of structure (I) can be administered just followed by and any of the additional therapeutic agents described herein, or vice versa. In some embodiments of the separate administration protocol, the compound of structure (I) and any of the additional therapeutic agents described herein are administered a few minutes apart, or a few hours apart, or a few days apart.

In other embodiments, the additional therapeutic agent is a protein kinase inhibitor, such as Staurosporine or Midostaurin. In other embodiments, the protein kinase inhibitor is Afatinib, Axitinib, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, or Vemurafenib.

In still more embodiments, the additional therapeutic agent is a topoisomerase inhibitor. In some of these embodiments, the topoisomerase inhibitor is Irinotecan. In some more embodiments, the additional therapeutic agent is a taxane. Exemplary taxanes include Taxol and Docetaxel.

In addition to the above additional therapeutic agent, other chemotherapeutics are presently known in the art and can be used in combination with the compounds of structure (I). In some embodiments, the chemotherapeutic agent is selected from the group consisting of mitotic inhibitors, alkylating agents, anti-metabolites, intercalating antibiotics, growth factor inhibitors, cell cycle inhibitors, enzymes, topoisomeRASe inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents.

Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO). Where desired, the compounds or pharmaceutical composition of structure (I) can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds of structure (I) or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of structure (I) in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term includes exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. The radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of structure (I) can render abnormal cells more sensitive to treatment with radiation for purposes of killing and/or inhibiting the growth of such cells. Accordingly, this disclosure further relates to a method for sensitizing abnormal cells in a mammal to treatment with radiation which comprises administering to the mammal an amount of a compound of structure (I) or a stereoisomer, tautomer, prodrug, or pharmaceutically acceptable salt thereof, which amount is effective is sensitizing abnormal cells to treatment with radiation. The amount of the compound of structure (I) in this method can be determined according to the means for ascertaining effective amounts of such compounds described herein.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

The examples and preparations provided below further illustrate and exemplify the compounds of structure (I) and methods of preparing such compounds. It is understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers are obtained by methods known to those skilled in the art.

Methods of Preparation

Compounds of structure (Ia) can be prepared according to methods known in the art and according to methods disclosed herein. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)).

General Reaction Scheme 1A

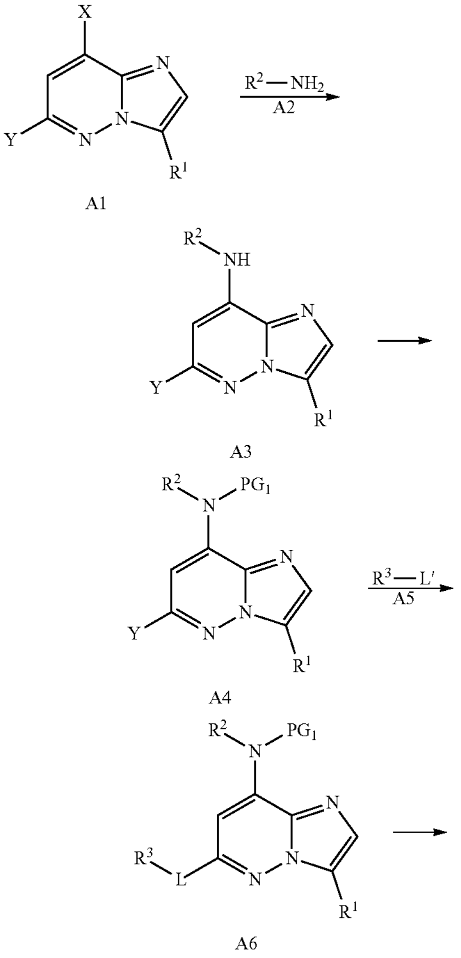

-continued

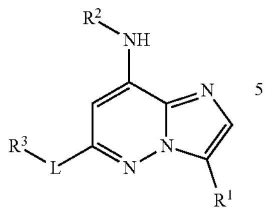

Structure (Ia)

General Reaction Scheme 1A provides an exemplary method for preparation of compounds of structure (Ia). $R^1$, $R^2$, $R^3$, and L in General Reaction Scheme 1 are as defined herein. X and Y are reactive moieties selected to facilitate the desired reactions (e.g., halo). L' is selected such that a desired L moiety results from the reaction between A5 and A4. Compounds of structure A1, A2 and A5 are purchased or prepared according to methods known in the art; or as described herein. Reaction of A1 with A2 under appropriate coupling conditions (e.g., use of base; or use of base in combination with heat and/or microwave irradiation) yields the product of the coupling reaction between A1 and A2. A3 is then reacted under suitable conditions (e.g., $(Boc)_2O$, base) to introduce a protecting group ($PG_1$) on compound A3 to provide product A4. $PG_1$ can be selected (and, alternatively, modified if necessary) based on compatibility with other synthetic steps (e.g., the conditions required to couple A4 and A5 to form A6) in view of the entire reaction scheme. $PG_1$ may include, but is not limited to, Boc, benzyl, DMB, or Cbz. Reaction of A4 with A5 under appropriate coupling conditions (e.g., use of base; or use of base in combination with heat and microwave irradiation; or Buchwald-Hartwig coupling conditions, such as, $Pd_2(dba)_3$, (rac)-BINAP and base in toluene while heating) yields the product of the coupling reaction between A4 and A5, A6. A6 is then reacted under suitable protecting group removal conditions (e.g., DCM and TFA; or HCl and dioxane) to afford a compound of structure (Ia).

Compounds of structure (Ib) can be prepared according to methods known in the art and according to methods disclosed herein. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)).

General Reaction Scheme 1B

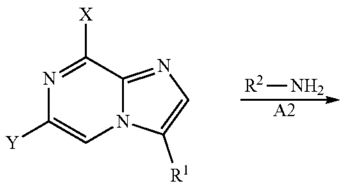

A1′

-continued

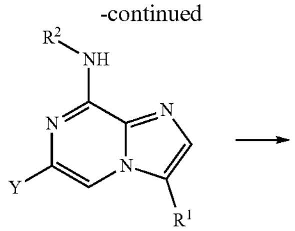

A3′

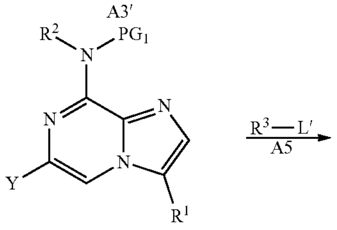

A4′

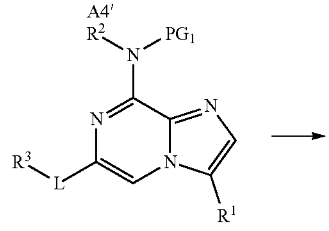

A6′

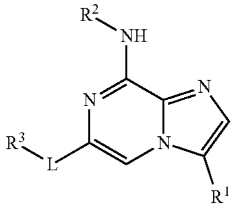

Structure (Ib)

General Reaction Scheme 1B provides an exemplary method for preparation of compounds of structure (Ib). $R^1$, $R^2$, $R^3$, and L in General Reaction Scheme 1 are as defined herein. X and Y are reactive moieties selected to facilitate the desired reactions (e.g., halo). L' is selected such that a desired L moiety results from the reaction between A5 and A4. Compounds of structure A1, A2 and A5 are purchased or prepared according to methods known in the art; or as described herein. Reaction of A1 with A2 under appropriate coupling conditions (e.g., use of base; or use of base in combination with heat and/or microwave irradiation) yields the product of the coupling reaction between A1 and A2. A3 is then reacted under suitable conditions (e.g., $(Boc)_{20}$, base) to introduce a protecting group ($PG_1$) on compound A3 to provide product A4. $PG_1$ can be selected (and, alternatively, modified if necessary) based on compatibility with other synthetic steps (e.g., the conditions required to couple A4 and A5 to form A6) in view of the entire reaction scheme. $PG_1$ may include, but is not limited to, Boc, benzyl, DMB, or Cbz. Reaction of A4 with A5 under appropriate coupling conditions (e.g., use of base; or use of base in combination with heat and microwave irradiation; or Buchwald-Hartwig coupling conditions, such as, $Pd_2(dba)_3$, (rac)-BINAP and base in toluene while heating) yields the product of the coupling reaction between A4 and A5, A6. A6 is then reacted under suitable protecting group removal conditions (e.g., DCM and TFA; or HCl and dioxane) to afford a compound of structure (Ib).

It should be noted that various alternative strategies for preparation of compounds of structure (Ia) or (Ib) are available to those of ordinary skill in the art. For example, other compounds of structure (Ia) or (Ib) can be prepared according to analogous methods using the appropriate starting material. It will also be appreciated by those skilled in the art that in the processes for preparing the compounds of structure (Ia) or (Ib), the functional groups of intermediate compounds may need to be protected by suitable protecting groups. Such functional groups include, but are not limited to, hydroxy, amino, mercapto and carboxylic acid.

Suitable protecting groups for hydroxy include, but are not limited to, trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl ("Boc"), benzyloxycarbonyl, and the like. Protecting groups are optionally added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the disclosure.

The examples and preparations provided below further illustrate and exemplify the compounds of structure (I) and methods of preparing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes. Other compounds of structure (I) exemplified in Tables 1-2 were prepared according to analogous procedures, routine in the art. For examples below which result in a compound of structure (Ia) or (Ib), Scheme IA or IB, as described above, was generally used, unless otherwise noted.

Example 1

Synthesis of 8-bromo-6-chloro-3-isopropylimidazo[1,2-b]pyridazine

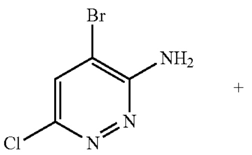

-continued

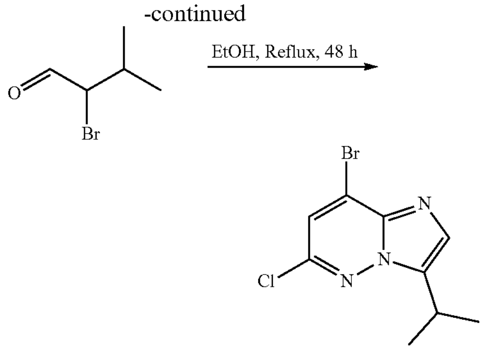

A mixture of 2-bromo-3-methylbutanal (5 gm, 30.03 mmol, 5 eqv) and 4-bromo-6-chloropyridazin-3-amine (1.263 gm, 6.06 mmol, 1 eqv)) in ethanol (25 mL) was refluxed for 48 h. The reaction mixture was cooled to room temperature. Saturated sodium bicarbonate solution was added to the reaction mixture and extracted with DCM (3×50 ml). Combined organic layer was washed with brine solution (2×50 mL), dried over anhydrous $Na_2SO_4$, and evaporated under reduced pressure to afford the oily residue as crude compound. Further purification of oily residue by combiflash on silica column (0-20% EtOAc gradient in Hexane) afforded the desired product 8-bromo-6-chloro-3-isopropylimidazo[1,2-b]pyridazine as pale brown solid. Yield: 1.293 (78%). $R_f$=0.32 (4:1 Hexane/EtOAc). $^1H$ NMR (500 MHz, $CDCl_3$, 298 K, TMS): δ=7.61 (s, 1H), 7.32 (s, 1H), 3.44 (hept, J=6.8 Hz, 1H), 1.41 (d, J=6.8 Hz, 6H).

Example 2

Synthesis of N-benzyl-6-chloro-3-isopropylimidazo[1,2-b]pyridazin-8-amine

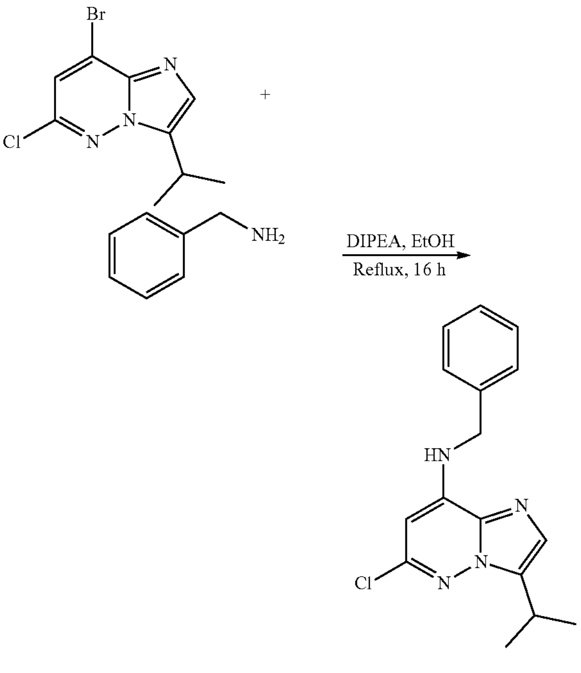

A mixture of 8-bromo-6-chloro-3-isopropylimidazo[1,2-b]pyridazine (1.1 g, 4.00 mmol, 1 eqv), benzylamine (0.644 g, 0.657 μL, 6.00 mmol, 1.5 eqv), and DIPEA (1.4 mL, 8.00 mmol) in ethanol (25 mL) was heated to reflux for 16 h. The reaction mixture was allowed to cool to room temperature and then diluted with 0.5 N HCl and EtOAc. The aqueous layer was separated and extracted with EtOAc (2×). The combined extracts were washed with water, brine, dried over $Na_2SO_4$, filtered, and evaporated. The residue was purified by combiflash on silica column (EtOAc/hexane, gradient 0-20% EtOAc) to afford N-benzyl-6-chloro-3-isopropylimidazo[1,2-b]pyridazin-8-amine as a white solid. Yield: 1.15 gm (95%). $R_f$=0.34 (3:1 Hexane/EtOAc). $^1H$ NMR (500 MHz, $CDCl_3$, 298 K, TMS): δ=8.73 (s, 1H), 7.40-7.26 (m, 6H), 6.15 (s, 1H), 4.58 (d, J=5.8 Hz, 2H), 3.43 (hept, J=6.9 Hz, 1H), 1.39 (d, J=7.0 Hz, 6H).

Example 3

Synthesis of tert-butyl benzyl (6-chloro-3-isopropylimidazo[1,2-]pyridazin-8-yl) carbamate

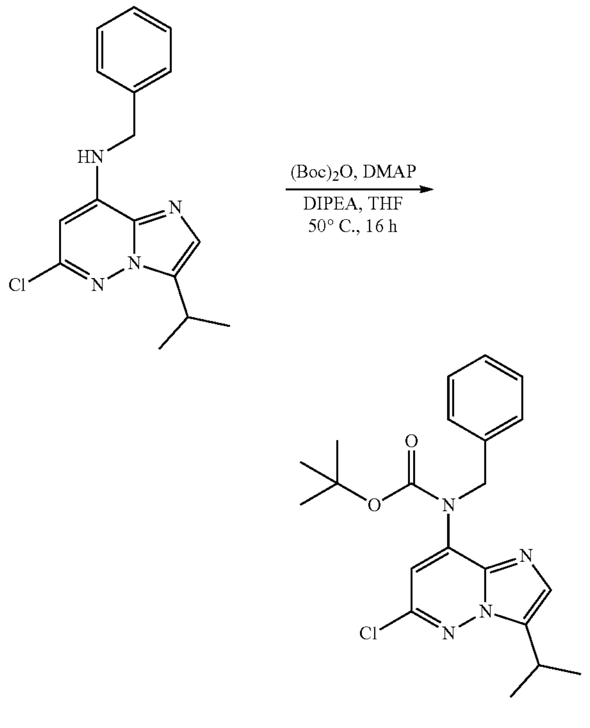

N-benzyl-6-chloro-3-isopropylimidazo[1,2-b]pyridazin-8-amine (0.85 gm, 2.83 mmol, 1 eqv), $(Boc)_2O$ (6.17 g, 28.3 mmol, 10 eqv), DMAP (35 mg, 0.28 mmol, 0.1 eqv) and DIPEA (4.92 mL, 28.3 mmol, 10 eqv) in THE (15 mL) were stirred for 16 h at 50 °C. The reaction mixture was allowed to cool to room temperature. EtOAc (150 mL) was added, and the organic layer was washed with water (2×100 mL) and saturated aqueous $NaHCO_3$(100 mL) and dried over $Na_2SO_4$, filtered, and evaporated. The residue was purified by combiflash on silica column (EtOAc/hexane, gradient 0-20% EtOAc) to afford tert-butyl benzyl (6-chloro-3-isopropylimidazo[1,2-]pyridazin-8-yl) carbamate as a yellow oil. Yield: 1.08 gm (95%). $R_f$=0.53 (4:1 Hexane/EtOAc). $^1H$ NMR (500 MHz, $CDCl_3$, 298 K, TMS): δ=7.50 (s, 1H), 7.28-7.25 (m, 2H), 7.23-7.18 (m, 3H), 7.06 (s, 1H), 5.48 (s, 2H), 3.43 (hept, J=7.0 Hz, 1H), 1.45 (s, 9H), 1.40 (d, J=7.0 Hz, 6H).

Example 4

Synthesis of tert-butyl (3R)-3-{[(8-{benzyl[(tert-butoxy)carbonyl]amino}-3-(propan-2-yl)imidazo[1,2-b]pyridazin-6-yl)amino]methyl}piperidine-1-carboxylate

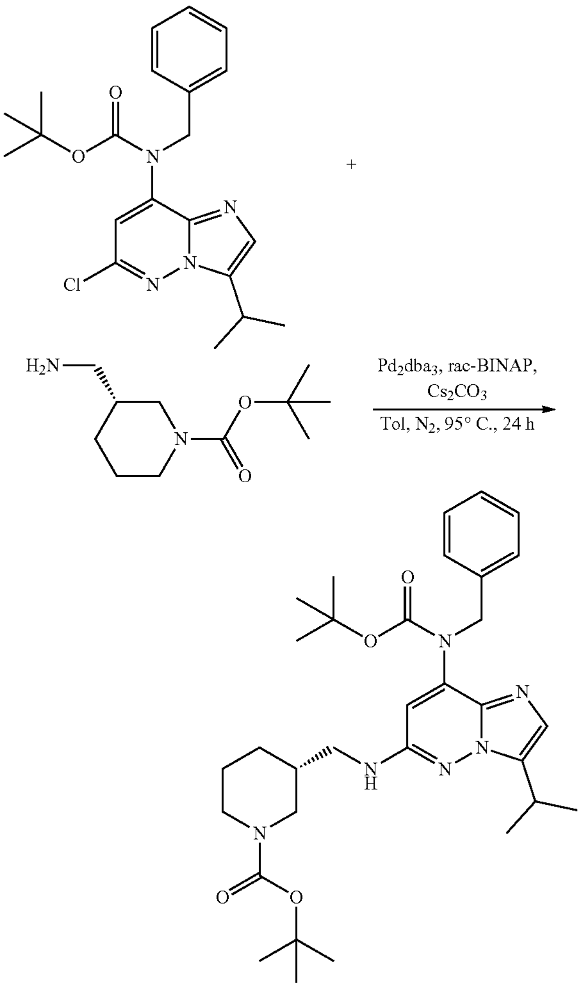

To a stirred solution of Tris(dibenzylideneacetone)dipalladium (23 mg, 5 mol %) and rac-BINAP (31 mg, 10 mol %) in toluene (5 mL), tert-butyl benzyl (6-chloro-3-isopropylimidazo[1,2-]pyridazin-8-yl) carbamate (200 mg, 0.5 mmol, 1 eq), (R)-tert-butyl 3-(aminomethyl)piperidine-1-carboxylate (160 mg, 0.75 mmol, 1.5 eq) and $Cs_2CO_3$ (325 mg, 1.0 mmol, 2 eq) were added at room temperature. The reaction mixture was flush with nitrogen for 5 minutes and heated at 95 °C for 8 h. The reaction mixture cooled to RT and further added Tris(dibenzylideneacetone)dipalladium (23 mg, 5 mol %) and rac-BINAP (31 mg, 10 mol %) in toluene (5 mL), (R)-tert-butyl 3-(aminomethyl)piperidine-1-carboxylate (160 mg, 0.75 mmol, 1.5 eq) and $Cs_2CO_3$ (325 mg, 1.0 mmol, 2 eq) to the reaction mixture. Again, the reaction mixture was flush with nitrogen for 5 minutes and stirred at 95 °C for another 16 h. The reaction mixture was diluted with ethyl acetate and filtered with celite. The organic phase was washed with water (3×), brine, dried over $Na_2SO_4$ and concentrated in vacuo. The residue was purified by combiflash on silica column (EtOAc/hexane, gradient 0-30% EtOAc) to afford tert-butyl (3R)-3-{[(8-{benzyl[(tert-butoxy)carbonyl]amino}-3-(propan-2-yl)imidazo[1,2-b]pyridazin-6-yl)amino]methyl}piperidine-1-carboxylate as a yellow oil. Yield: 115 mg (40%). $R_f$=0.4 (2:1 Hexane/EtOAc). $^1$H NMR (500 MHz, $CDCl_3$, 298 K, TMS): δ=7.28-7.19 (m, 6H), 6.35 (s, 1H), 5.30 (d, J=5.0 Hz, 2H), 4.44-4.26 (br. m, 1H), 3.81-3.79 (m, 1H), 3.70 (br. s, 1H), 3.34-3.26 (m, 2H), 3.17 (br. s, 1H), 3.03 (br. s, 1H), 2.85 (dd, J=12.8, 8.6 Hz, 1H), 1.91-1.81 (m, 2H), 1.68 (s, 1H), 1.65 (br. s, 1H), 1.44 (s, 9H), 1.43 (s, 9H), 1.36 (dd, J=6.8, 3.0 Hz, 6H).

Example 5

Synthesis of N8-benzyl-3-isopropyl-N6-(((S)-piperidin-3-yl)methyl)imidazo[1,2-b]pyridazine-6,8-diamine hydrochloride

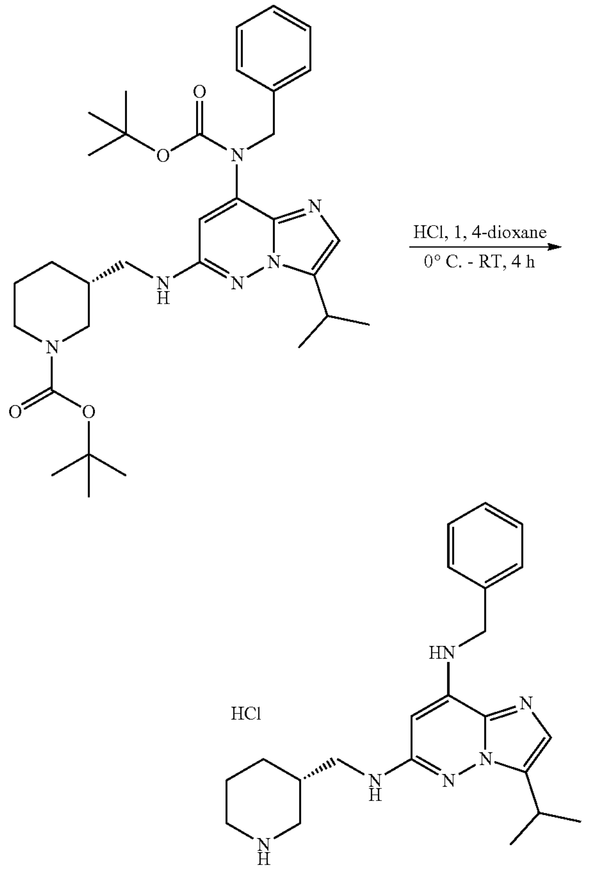

A solution of tert-butyl (3R)-3-{[(8-{benzyl[(tert-butoxy)carbonyl]amino}-3-(propan-2-yl)imidazo[1,2-b]pyridazin-6-yl)amino]methyl}piperidine-1-carboxylate (75 mg, 0.14 mmol, 1eq) in 1,4-dioxane (2 mL) at 0 °C was added 4M HCl in 1,4-dioxane (1 mL) drop-wise and stirred at room temperature for 4 h. After completion of reaction by TLC, the reaction mixture was subjected to rotary evaporator for removal of volatiles. The obtained residue was triturated with ether (3x30 mL), EtOAc/Hex (1:1-30 mL), EtOAc (20 mL) and then normal phase (silica-gel 100-200 mesh) column chromatography [gradient elution with 5-10% MeOH/$CHCl_3$] afforded N8-benzyl-3-isopropyl-N6-(((S)-piperidin-3-yl)methyl)imidazo[1,2-b]pyridazine-6,8-diamine hydrochloride as an off white solid. Yield: 25 mg (46%). $R_f$=0.31 (4:1 $CHCl_3$/MeOH). $^1$H NMR (500 MHz, DMSO-$d_6$, 298 K, TMS): δ=8.89 (s, 1H), 8.59 (s, 1H), 7.41 (t, J=6.4 Hz, 1H), 7.34-7.31 (m, 4H), 7.26-7.21 (m, 1H), 7.01 (s, 1H), 6.38 (t, J=5.8 Hz, 1H), 5.35 (s, 1H), 4.42 (d, J=6.4 Hz, 2H), 3.21-3.14 (m, 4H), 3.03-2.98 (m, 1H), 2.72 (t, J=11.4 Hz, 1H), 2.56 (t, J=12.0 Hz, 1H), 2.09-200 (br. m, 1H), 1.78-1.74 (m, 2H), 1.63-1.53 (m, 1H), 1.30 (dd, J=6.8, 4.2 Hz, 6H), 1.24-1.17 (m, 2H).

Example 6

Synthesis of tert-butyl (3R,4R)-4-{[(8-{benzyl[(tert-butoxy)carbonyl]amino}-3-(propan-2-yl)imidazo[1,2-b]pyridazin-6-yl)amino]methyl}-3-hydroxypiperidine-1-carboxylate

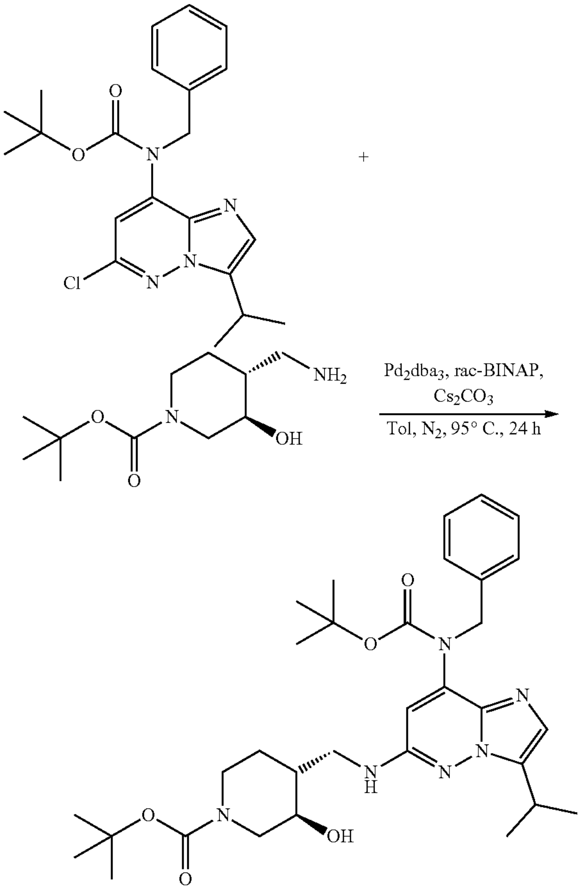

To a stirred solution of Tris(dibenzylideneacetone)dipalladium (23 mg, 5 mol %) and rac-BINAP (31 mg, 10 mol %) in toluene (5 mL), tert-butyl benzyl (6-chloro-3-isopropylimidazo[1,2-]pyridazin-8-yl) carbamate (200 mg, 0.5 mmol, 1 eq), (3R,4R)-tert-butyl 4-(aminomethyl)-3-hydroxypiperidine-1-carboxylate (138 mg, 0.6 mmol, 1.2 eq) and $Cs_2CO_3$ (325 mg, 1.0 mmol, 2 eq) were added at room temperature. The reaction mixture was flush with nitrogen for 5 minutes and heated at 95 °C for 8 h. The reaction mixture cooled to RT and further Tris(dibenzylideneacetone)dipalladium (23 mg, 5 mol %) and rac-BINAP (31 mg, 10 mol %) in toluene (5 mL), tert-butyl benzyl (6-chloro-3-isopropylimidazo[1,2-]pyridazin-8-yl) carbamate (200 mg, 0.5 mmol, 1 eq), and $Cs_2CO_3$ (325 mg, 1.0 mmol, 2 eq) were added to the reaction mixture. Again, the reaction mixture was flush with nitrogen for 5 minutes and stirred at 95 °C for another 16 h. The reaction mixture was diluted with ethyl acetate and filtered with celite. The organic phase was washed with water (3×), brine, dried over $Na_2SO_4$ and concentrated in vacuo. The residue was purified by combi-flash on silica column (EtOAc/hexane, gradient 0-40% EtOAc) to afford tert-butyl (3R,4R)-4-{[(8-{benzyl[(tert-butoxy)carbonyl]amino}-3-(propan-2-yl)imidazo[1,2-b]pyridazin-6-yl)amino]methyl}-3-hydroxypiperidine-1-carboxylate as a white crystalline solid. Yield: 151 mg (53%). $R_f$=0.36 (1.5:1 Hexane/EtOAc). $^1H$ NMR (500 MHz, $CDCl_3$, 298 K, TMS): δ=7.28-7.25 (m, 4H), 7.22-7.20 (m, 3H), 6.42 (s, 1H), 5.33 (s, 2H), 4.70 (s, 1H), 4.22 (s, 2H), 3.83 (s, 1H), 3.35 (s, 1H), 3.26 (hept, J=6.8 Hz, 1H), 3.12 (d, J=13.4 Hz, 1H), 2.65 (s, 1H), 2.53 (s, 1H), 1.63-1.55 (m, 4H), 1.43 (s, 18H), 1.39-1.36 (m, 6H).

Example 7

Synthesis of (3R,4R)-4-((8-(benzylamino)-3-isopropylimidazo[1,2-b]pyridazin-6-ylamino)methyl)piperidin-3-ol hydrochloride

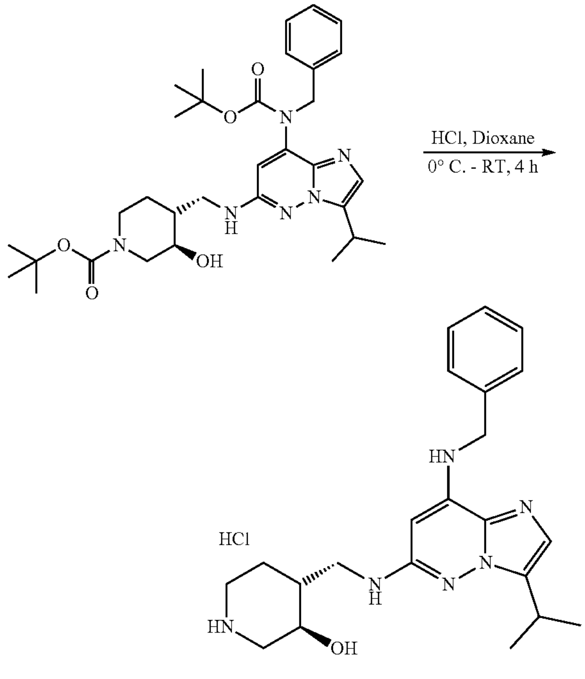

To A solution of tert-butyl (3R,4R)-4-{[(8-{benzyl[(tert-butoxy)carbonyl]amino}-3-(propan-2-yl)imidazo[1,2-b]pyridazin-6-yl)amino]methyl}-3-hydroxypiperidine-1-carboxylate (135 mg, 0.313 mmol, 1eq) in 1,4-dioxane (2 mL) at 0 °C was added 4M Dioxane·HCl (1 mL) drop-wise and stirred at room temperature for 4 h. After completion of reaction by TLC, the reaction mixture was subjected to rotary evaporator for removal of volatiles. The obtained residue was triturated with ether (3×30 mL), EtOAc/Hex (1:1-30 mL), EtOAc (20 mL) to afford the compound (3R,4R)-4-((8-(benzylamino)-3-isopropylimidazo[1,2-b]pyridazin-6-ylamino)methyl)piperidin-3-ol hydrochloride as an off white solid. Yield: 75 mg (77%). $R_f$=0.20 (4:1 $CHCl_3$/MeOH). $^1H$ NMR (500 MHz, DMSO-$d_6$, 298 K, TMS): δ=14.73 (br. s, 1H), 8.99 (s, 2H), 8.49 (s, 1H), 7.83 (s, 1H), 7.41-7.36 (m, 4H), 7.29 (t, J=7.0 Hz, 1H), 7.08 (t, J=5.4 Hz, 1H), 5.95 (s, 1H), 5.44 (s, 1H), 4.48 (d, J=5.8 Hz, 2H), 3.64-3.60 (m, 1H), 3.57-3.52 (m, 1H), 3.27 (hept, J=6.8 Hz, 1H), 3.20-3.14 (m, 2H), 3.10-3.0 (m, 1H), 2.78-2.71 (m, 1H), 2.66-2.56 (m, 1H), 1.94-1.90 (m, 1H), 1.76-1.69 (m, 1H), 1.45-1.36 (m, 1H), 1.32 (d, J=6.8 Hz, 6H).

Example 8

Synthetic Scheme for tert-butyl (6-chloro-3-cyclopropylimidazo[1,2-b]pyridazin-8-yl)(3-fluorophenyl) carbamate

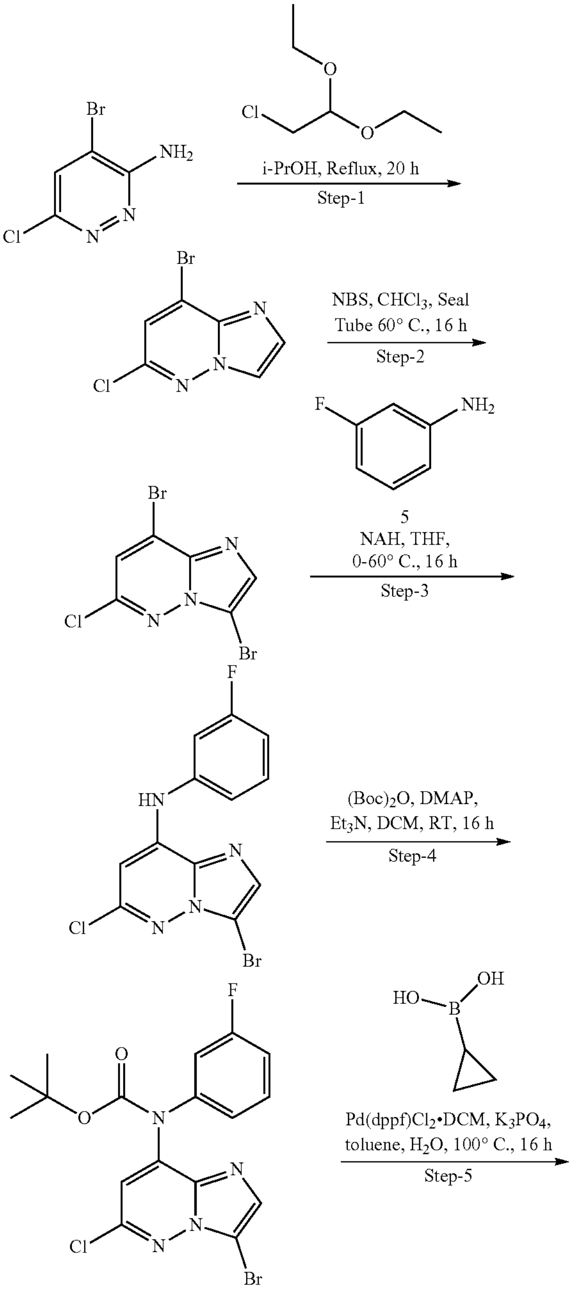

-continued

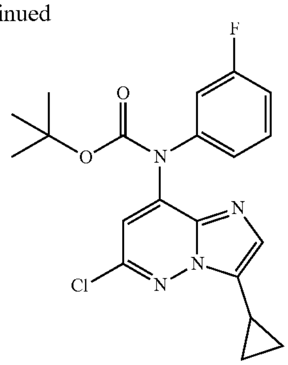

Synthesis of 8-bromo-6-chloroimidazo[1,2-b]pyridazine

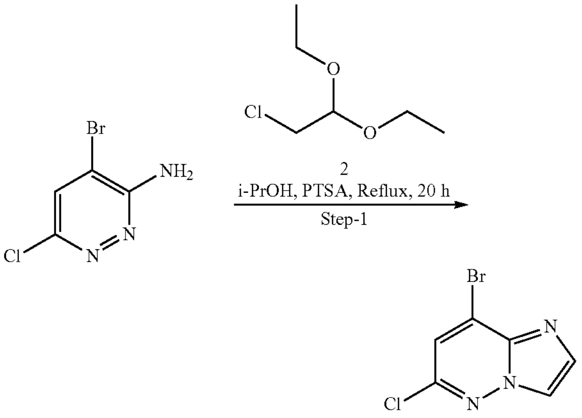

A mixture of 2-chloro-1,1-diethoxyethane (2.68 g, 21.634 mmol, 1.5 eq.), 4-bromo-6-chloropyridazin-3-amine (3 g, 14.423 mmol, 1 eq.) and p-TSA (3.72 g, 21.634 mmol, 1.5 eq.) in i-PrOH (80 mL) was heated at temperature for 20 h. After this time, reaction mixture was cooled to room temperature, the solution was concentrated under reduced pressure. The resulting mixture was treated with saturated aqueous $NaHCO_3$ solution (300 mL), extracted with EtOAc (3×100 mL). Combined organic layer was washed with brine solution (2×100 mL), dried over anhydrous $Na_2SO_4$, filtered and concentrated under reduced pressure. Obtained crude compound was purified by combiflash on silica column (0-50% EtOAc gradient in Hexane) afforded the desired product 8-bromo-6-chloroimidazo[1,2-b]pyridazine as yellow solid (1.4 g, 42% yield). $R_f$=0.5 (1:1 Hexane/EtOAc). $^1$H NMR (400 MHz, DMSO): δ=8.00 (d, J=1.2 Hz, 1H), 7.84 (d, J=1.2 Hz, 1H), 7.40 (s, 1H).

Synthesis of 3,8-dibromo-6-chloroimidazo[1,2-b]pyridazine

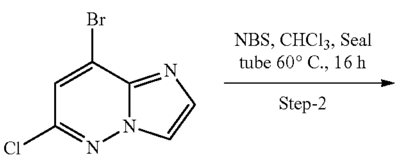

-continued

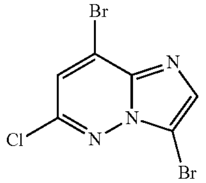

N-Bromosuccinimide (0.4 g, 1.508 mmol, 1.5 eq.) was added to a solution of 8-bromo-6-chloroimidazo[1,2-b]pyridazine (4.50 g 19.4 mmol, 1 eq.) in $CHCl_3$ (5 mL) at 0 °C. The mixture was heated to 60 °C for 16 h. After this time, the mixture was partitioned between saturated aqueous $NaHCO_3$(20 mL) and DCM (30 mL). Organic layer was separated and aqueous layer was extracted with DCM (30 mL). The combined organic layer was dried over $Na_2SO_4$, filtered and concentrated under reduced pressure. The residue was purified by combiflash on silica column (EtOAc/hexane, gradient 0-20% EtOAc) to afford 3,8-dibromo-6-chloroimidazo[1,2-b]pyridazine as a yellow solid (0.38 g, 82% yield). $R_f$=0.5 (7:3 Hexane/EtOAc). $^1$H NMR (400 MHz, DMSO): δ=8.45 (s, 1H), 7.94 (s, 1H).

Synthesis of 3-bromo-6-chloro-N-(3-fluorophenyl)imidazo[1,2-b]pyridazin-8-amine

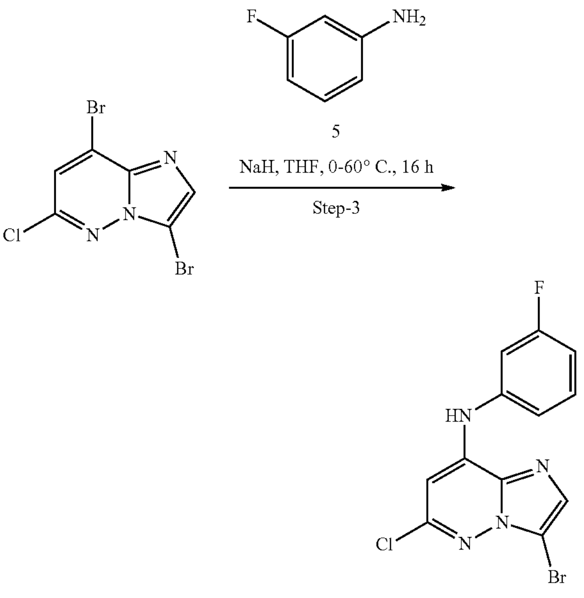

To a solution of 3-fluoroaniline (0.15 g, 1.360 mmol, 1.2 eq.), and in anhydrous THF (5 mL) was added NaH (60% in mineral oil, 0.04 g, 1.699 mmol, 1.5 eq.) at 0 °C. The mixture was allowed to stir at RT for 10 min, then 3,8-dibromo-6-chloroimidazo[1,2-b]pyridazine (0.35 g, 1.133 mmol, 1 eq.) was added and heated to 60 °C for 16 h. After this time, reaction was quenched with ice cold water (6 mL) and product was extracted with EtOAc (2×30 mL). Combine organic layer was dried over $Na_2SO_4$, filtered and concentrated under reduced pressure. Obtained crude compound was purified by combiflash on silica column (EtOAc/hexane, gradient 0-50% EtOAc) to afford 3-bromo-6-chloro-N-(3-fluorophenyl)imidazo[1,2-b]pyridazin-8-amine as a yellow solid (0.18 g, 47% yield). $R_f$=0.3 (1:1 Hexane/

EtOAc). $^1$H NMR (400 MHz, DMSO): δ=10.13 (s, 1H), 7.81 (s, 1H), 7.47 (d, J=6.8 Hz, 1H), 7.32-7.29 (m, 2H), 7.02 (t, J=5.2 Hz, 1H), 6.55 (s, 1H).

Synthesis of tert-butyl (3-bromo-6-chloroimidazo[1,2-b]pyridazin-8-yl)(3-fluorophenyl)carbamate

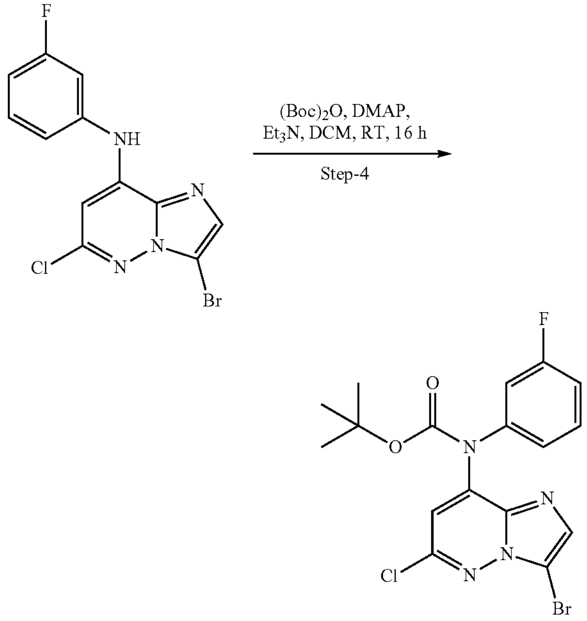

To a stirred solution of 3-bromo-6-chloro-N-(3-fluorophenyl)imidazo[1,2-b]pyridazin-8-amine (0.18 g, 0.529 mmol, 1 eq.) in DCM (5 mL) was added $Et_3N$ (0.15 mL, 1.058 mmol, 2 eq.), $(Boc)_2O$ (0.16 mL, 0.688 mmol, 1.3 eq.) and DMAP (0.052 g, 0.029 mmol, 0.1 eq.) and stirred for 16 h at room temperature. The reaction mixture was diluted with water and extracted with DCM (2×10 mL). The combined organic layer was washed with brine solution (20 mL), dried over $Na_2SO_4$ concentrated under reduced pressure. The residue was purified by combiflash on silica column (EtOAc/hexane, gradient 0-40% EtOAc) to get tert-butyl (3-bromo-6-chloroimidazo[1,2-b]pyridazin-8-yl)(3-fluorophenyl)carbamate as a yellow gum (0.18 g, 85% yield). $R_f$=0.5 (6:4 Hexane/EtOAc). LCMS (m/z): 443.0 (M+H)$^+$. $^1$H NMR (400 MHz,): δ=7.68 (s, 1H), 7.30 (d, J=2.0 Hz, 1H), 7.06-6.99 (m, 4H), 1.45 (s, 9H).

Synthesis of tert-butyl (6-chloro-3-cyclopropylimidazo[1,2-b]pyridazin-8-yl)(3-fluorophenyl)carbamate

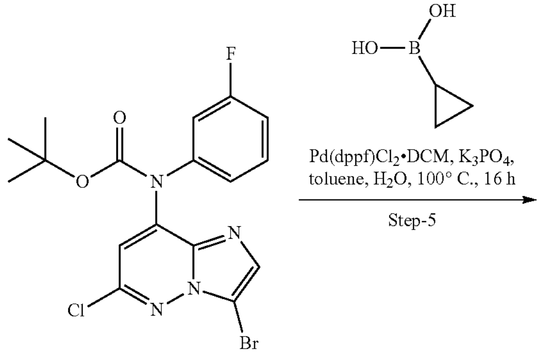

-continued

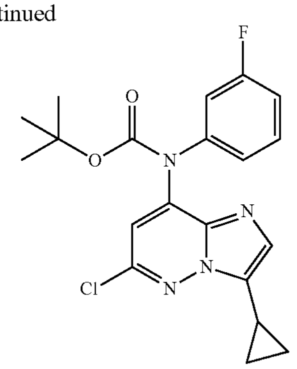

To the stirred solution of tert-butyl (3-bromo-6-chloroimidazo[1,2-b]pyridazin-8-yl)(3-fluorophenyl)carbamate (0.18 g, 0.447 mmol, 1eq.) in toluene:water (3:1; 5 mL) was added cyclopropylboronic acid (0.1 mL, 0.670 mmol, 1.5 eq.) and $K_3PO_4$ (0.19 g, 0.895 mmol, 2 eq.) and degassed for 10 min later added $Pd(dppf)Cl_2DCM$ (2 mg, 0.0447 mmol, 0.1 eq.) and degassed for 10 min, then reaction mas was stirred at 100 °C for 16 h. After completion of reaction by TLC, diluted with ice cold water (20 mL) and extracted with ethyl acetate (3×20 mL). The combined organic layer was washed with brine solution (20 mL), dried over sodium sulfate and concentrated under reduced pressure to provide crude. The residue was purified by combiflash on silica column (EtOAc/hexane, gradient 20-30% EtOAc) to afford tert-butyl (6-chloro-3-cyclopropylimidazo[1,2-b]pyridazin-8-yl)(3-fluorophenyl)carbamate (9) as yellow solid (0.025 g, 19% yield). $R_f$=0.5 (7:3 Hexane/EtOAc). LCMS (m/z): 403.0 (M+H)$^+$. $^1$HNMR (400 MHz, $CDCl_3$-$d_6$) δ7.35 (s, 1H), 7.31 (d, J=6.4 Hz, 1H), 7.11-7.07 (m, 1H), 7.05 (t, J=2.4 Hz, 1H), 7.00-7.696 (m, 1H), 6.93 (s, 1H), 2.15-2.16 (m, 1H), 1.46 (s, 9H), 1.14-1.09 (m, 2H), 0.86-0.82 (m, 2H).

Example 9

Synthetic Scheme for tert-butyl (6-chloro-3-cyclopropylimidazo[1,2-b]pyridazin-8-yl)(3-fluorophenyl)carbamate

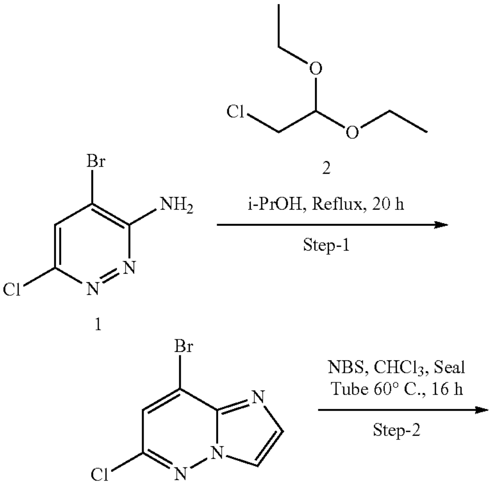

2

1

3

-continued

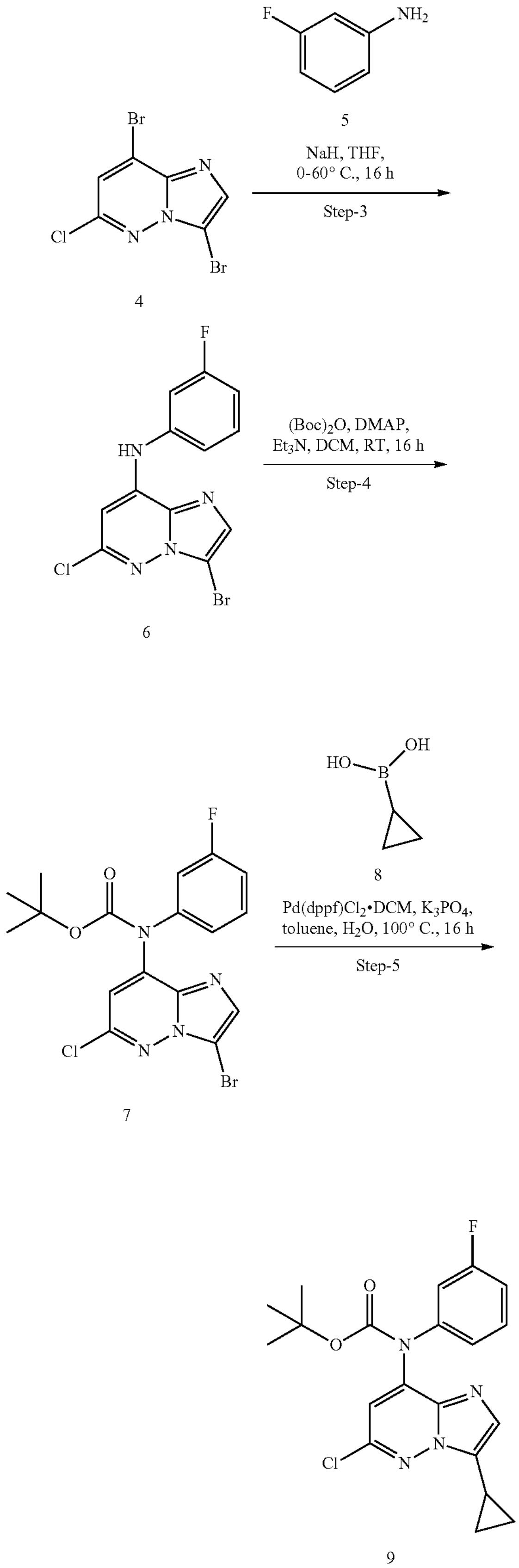

Synthesis of 8-bromo-6-chloroimidazo[1,2-b]pyridazine

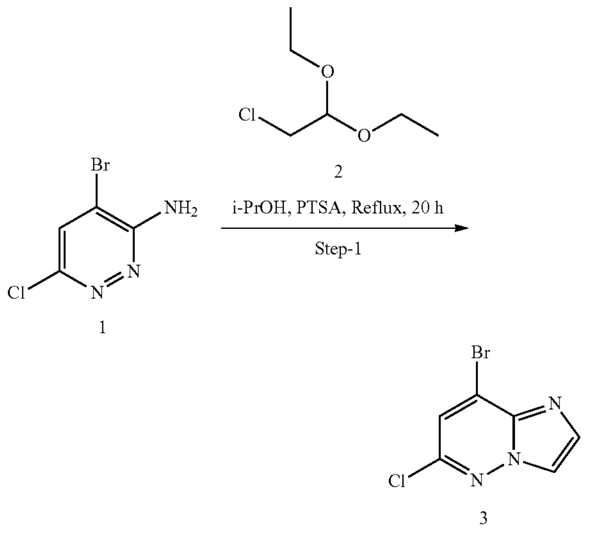

A mixture of 2-chloro-1,1-diethoxyethane (2.68 g, 21.634 mmol, 1.5 eq.), 4-bromo-6-chloropyridazin-3-amine (3 g, 14.423 mmol, 1 eq.) and p-TSA (3.72 g, 21.634 mmol, 1.5 eq.) in i-PrOH (80 mL) was heated at temperature for 20 h. After this time, reaction mixture was cooled to room temperature, the solution was concentrated under reduced pressure. The resulting mixture was treated with saturated aqueous $NaHCO_3$ solution (300 mL), extracted with EtOAc (3×100 mL). Combined organic layer was washed with brine solution (2×100 mL), dried over anhydrous $Na_2SO_4$, filtered and concentrated under reduced pressure. Obtained crude compound was purified by combiflash on silica column (0-50% EtOAc gradient in Hexane) afforded the desired product 8-bromo-6-chloroimidazo[1,2-b]pyridazine as yellow solid (1.4 g, 42% yield). $R_f$=0.5 (1:1 Hexane/EtOAc). $^1$H NMR (400 MHz, DMSO): δ=8.00 (d, J=1.2 Hz, 1H), 7.84 (d, J=1.2 Hz, 1H), 7.40 (s, 1H).

Synthesis of 3,8-dibromo-6-chloroimidazo[1,2-b]pyridazine

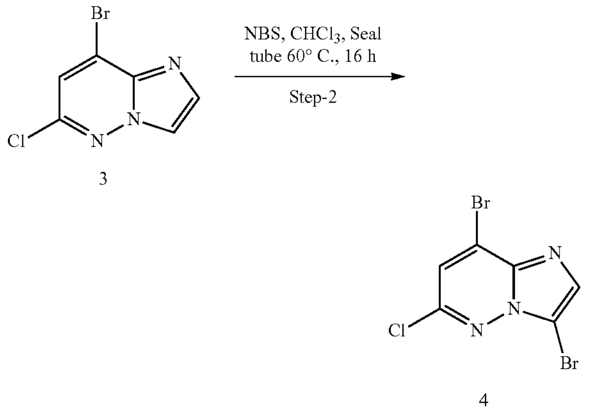

N-Bromosuccinimide (0.4 g, 1.508 mmol, 1.5 eq.) was added to a solution of 8-bromo-6-chloroimidazo[1,2-b]pyridazine (4.50 g 19.4 mmol, 1 eq.) in $CHCl_3$ (5 mL) at 0 °C. The mixture was heated to 60 °C for 16 h. After this time, the mixture was partitioned between saturated aqueous $NaHCO_3$(20 mL) and DCM (30 mL). Organic layer was separated and aqueous layer was extracted with DCM (30 mL). The combined organic layer was dried over $Na_2SO_4$, filtered and concentrated under reduced pressure. The residue was purified by combiflash on silica column (EtOAc/hexane, gradient 0-20% EtOAc) to afford 3,8-dibromo-6-chloroimidazo[1,2-b]pyridazine as a yellow solid (0.38 g, 82% yield). $R_f$=0.5 (7:3 Hexane/EtOAc). $^1$H NMR (400 MHz, DMSO): δ=8.45 (s, 1H), 7.94 (s, 1H).

Synthesis of 3-bromo-6-chloro-N-(3-fluorophenyl)imidazo[1,2-b]pyridazin-8-amine

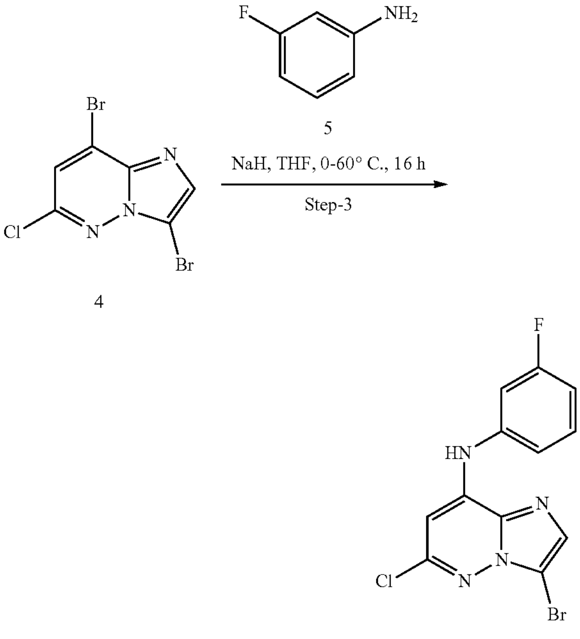 [SMILES: Nc1cccc(F)c1 ; Clc1cc(Br)c2ncc(Br)n2n1 ; Fc1cccc(Nc2cc(Cl)nn3c(Br)cnc23)c1]

5

4

6

To a solution of 3-fluoroaniline (0.15 g, 1.360 mmol, 1.2 eq.), and in anhydrous THF (5 mL) was added NaH (60% in mineral oil, 0.04 g, 1.699 mmol, 1.5 eq.) at 0 °C. The mixture was allowed to stir at RT for 10 min, then 3,8-dibromo-6-chloroimidazo[1,2-b]pyridazine (0.35 g, 1.133 mmol, 1 eq.) was added and heated to 60 °C for 16 h. After this time, reaction was quenched with ice cold water (6 mL) and product was extracted with EtOAc (2×30 mL). Combine organic layer was dried over $Na_2SO_4$, filtered and concentrated under reduced pressure. Obtained crude compound was purified by combiflash on silica column (EtOAc/hexane, gradient 0-50% EtOAc) to afford 3-bromo-6-chloro-N-(3-fluorophenyl)imidazo[1,2-b]pyridazin-8-amine as a yellow solid (0.18 g, 47% yield). $R_f$=0.3 (1:1 Hexane/EtOAc). $^1$H NMR (400 MHz, DMSO): δ=10.13 (s, 1H), 7.81 (s, 1H), 7.47 (d, J=6.8 Hz, 1H), 7.32-7.29 (m, 2H), 7.02 (t, J=5.2 Hz, 1H), 6.55 (s, 1H).

Synthesis of tert-butyl (3-bromo-6-chloroimidazo[1,2-b]pyridazin-8-yl)(3-fluorophenyl)carbamate

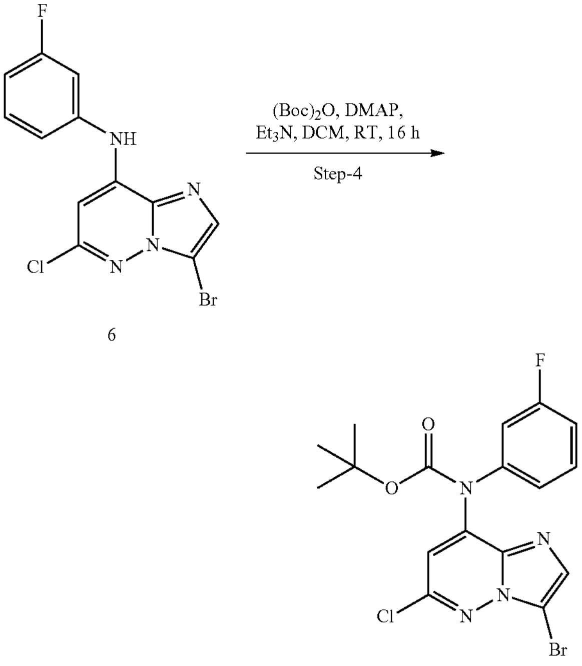 [SMILES: Fc1cccc(Nc2cc(Cl)nn3c(Br)cnc23)c1 ; CC(C)(C)OC(=O)N(c1cccc(F)c1)c1cc(Cl)nn2c(Br)cnc12]

6

7

To a stirred solution of 3-bromo-6-chloro-N-(3-fluorophenyl)imidazo[1,2-b]pyridazin-8-amine (0.18 g, 0.529 mmol, 1 eq.) in DCM (5 mL) was added $Et_3N$ (0.15 mL, 1.058 mmol, 2 eq.), $(Boc)_2O$ (0.16 mL, 0.688 mmol, 1.3 eq.) and DMAP (0.052 g, 0.029 mmol, 0.1 eq.) and stirred for 16 h at room temperature. The reaction mixture was diluted with water and extracted with DCM (2×10 mL). The combined organic layer was washed with brine solution (20 mL), dried over $Na_2SO_4$ concentrated under reduced pressure. The residue was purified by combiflash on silica column (EtOAc/hexane, gradient 0-40% EtOAc) to get tert-butyl (3-bromo-6-chloroimidazo[1,2-b]pyridazin-8-yl)(3-fluorophenyl)carbamate as a yellow gum (0.18 g, 85% yield). $R_f$=0.5 (6:4 Hexane/EtOAc). LCMS (m/z): 443.0 $(M+H)^+$. $^1$H NMR (400 MHz,): δ=7.68 (s, 1H), 7.30 (d, J=2.0 Hz, 1H), 7.06-6.99 (m, 4H), 1.45 (s, 9H).

Synthesis of tert-butyl (6-chloro-3-cyclopropylimidazo[1,2-b]pyridazin-8-yl)(3-fluorophenyl)carbamate

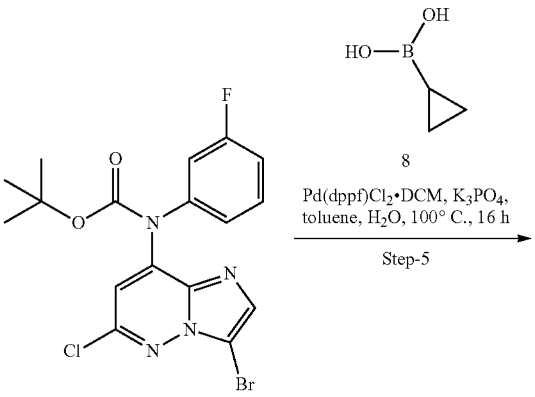

8

7

-continued

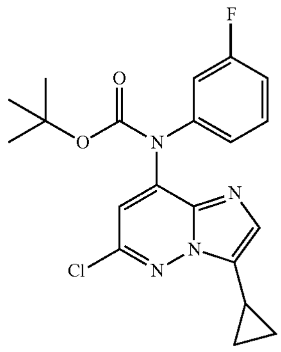

9

To the stirred solution of tert-butyl (3-bromo-6-chloroimidazo[1,2-b]pyridazin-8-yl)(3-fluorophenyl)carbamate (0.18 g, 0.447 mmol, 1eq.) in toluene:water (3:1; 5 mL) was added cyclopropylboronic acid (0.1 mL, 0.670 mmol, 1.5 eq.) and $K_3PO_4$ (0.19 g, 0.895 mmol, 2 eq.) and degassed for 10 min later added Pd(dppf)$Cl_2$DCM (2 mg, 0.0447 mmol, 0.1 eq.) and degassed for 10 min, then reaction mas was stirred at 100 °C for 16 h. After completion of reaction by TLC, diluted with ice cold water (20 mL) and extracted with ethyl acetate (3×20 mL). The combined organic layer was washed with brine solution (20 mL), dried over sodium sulfate and concentrated under reduced pressure to provide crude. The residue was purified by combiflash on silica column (EtOAc/hexane, gradient 20-30% EtOAc) to afford tert-butyl (6-chloro-3-cyclopropylimidazo[1,2-b]pyridazin-8-yl)(3-fluorophenyl)carbamate (9) as yellow solid (0.025 g, 19% yield). $R_f$=0.5 (7:3 Hexane/EtOAc). LCMS (m/z): 403.0 $(M+H)^+$. $^1$HNMR (400 MHz, $CDCl_3$-$d_6$) δ 7.35 (s, 1H), 7.31 (d, J=6.4 Hz, 1H), 7.11-7.07 (m, 1H), 7.05 (t, J=2.4 Hz, 1H), 7.00-7.696 (m, 1H), 6.93 (s, 1H), 2.15-2.16 (m, 1H), 1.46 (s, 9H), 1.14-1.09 (m, 2H), 0.86-0.82 (m, 2H).

Example 10

Synthetic Scheme for Ltg-Target

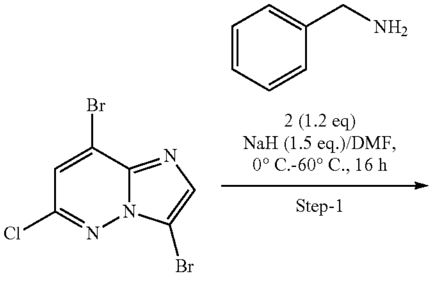

1

-continued

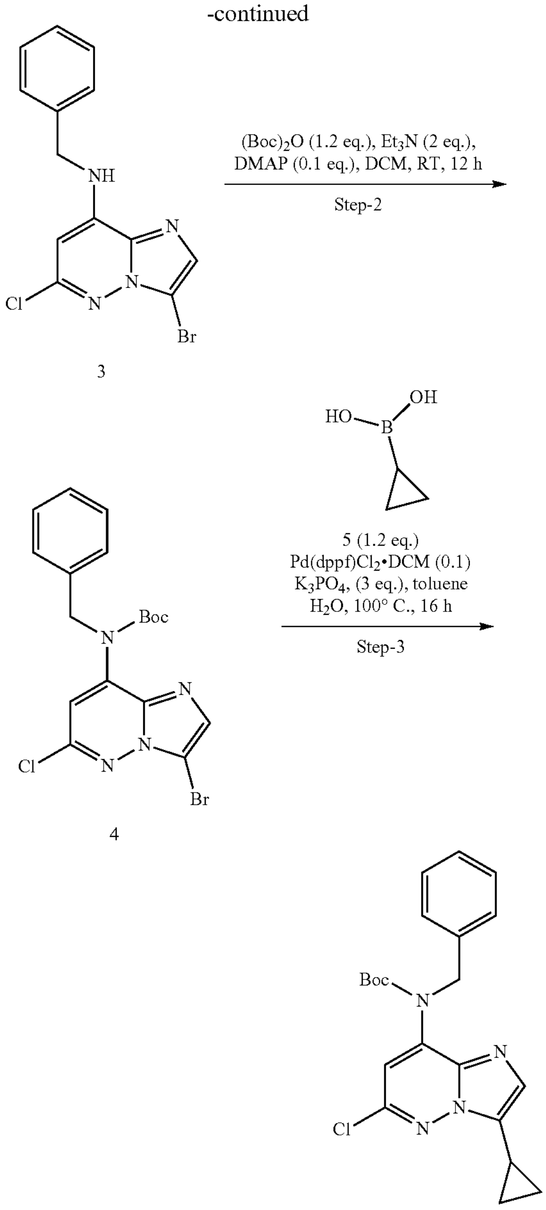

3

4

6

Synthesis of N-benzyl-3-bromo-6-chloroimidazo[1,2-b]pyridazin-8-amine

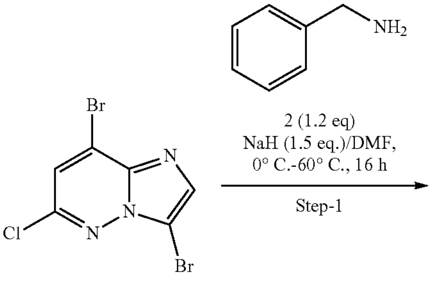

1

-continued

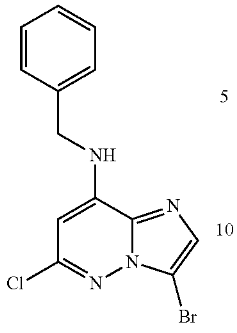

3

To the stirred solution of phenylmethanamine (2) (7.74 g, 72.26 mmol, 1.5 eq) in DMF (75 mL) at 0 °C was added NaH (1.73 g, 72.26 mmol, 1.5 eq), stirred for 15 min later added 3,8-dibromo-6-chloroimidazo[1,2-b]pyridazine (1) (15 g, 48.17 mmol, 1 eq) and stirred at room temperature for 16 h. After completion of reaction by TLC, diluted with ice cold water (100 mL) and extracted with ethyl acetate (3×100 mL). The combined organic layers were washed with brine solution (40 mL), dried over sodium sulfate and concentrated to provide crude. The crude material was purified by silica column chromatography [with a gradient elution of 15-20% of EtOAc/Hexane] to afford N-benzyl-3-bromo-6-chloroimidazo[1,2-b]pyridazin-8-amine (3) as off-white solid (8.5 g, 52%). TLC system: EtOAc/hexane (15:85), $R_f$ value: ~0.3; LCMS (m/z): 336 $(M+H)^+$; $^1H$ NMR (400 MHz, DMSO-$d_6$) δ 8.68 (brs, 1H), 7.69 (s, 1H), 7.38-7.23 (m, 5H), 6.22 (s, 1H), 4.57 (s, 2H).

Synthesis of tert-butyl benzyl(3-bromo-6-chloroimidazo[1,2-b]pyridazin-8-yl)carbamate

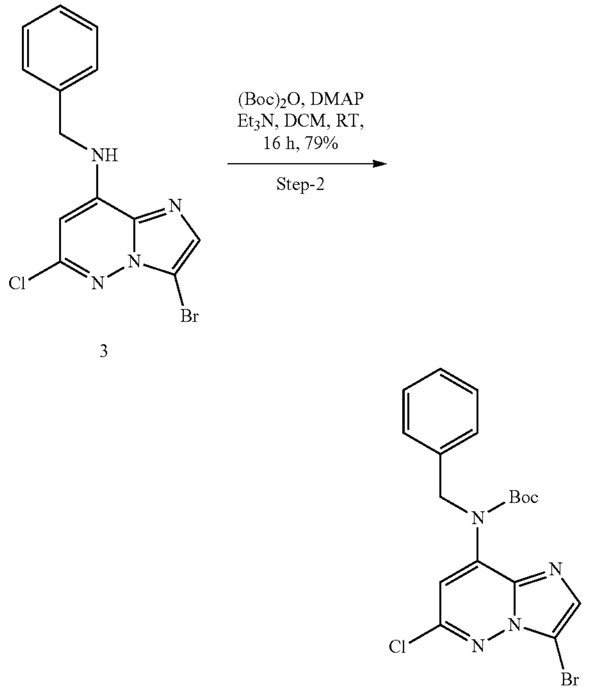

3

4

To a stirred solution of N-benzyl-3-bromo-6-chloroimidazo[1,2-b]pyridazin-8-amine (3) (5 g, 14.88 mmol, 1eq) in DCM (40 mL) at room temperature was added $Et_3N$ (4.17 mL, 29.76 mmol, 2 eq), $Boc_2O$ (5.12 mL, 22.32 mmol, 1.5 eq) and DMAP (0.181 g, 1.48 mmol, 0.1 eq). The reaction mixture was stirred at room temperature for 16 h. After completion of conversion by TLC, diluted with water and extracted with DCM (2×150 mL). The combined organic layers were washed with brine solution (100 mL), dried over sodium sulfate and concentrated to provide crude. The crude material was purified by silica column chromatography [with a gradient elution of 5-10% of EtOAc/Hexane] to afford tert-butyl benzyl(3-bromo-6-chloroimidazo[1,2-b]pyridazin-8-yl)carbamate (4) as an pale yellow (6 g, 92%). TLC system: EtOAc/hexane (10:90), $R_f$-value:–0.6; LCMS (m/z): 436 $(M+H)^+$; $^1$HNMR (400 MHz, DMSO-$d_6$) δ 7.96 (d, J=4.0 Hz, 1H), 7.51 (s, 1H), 7.25-7.18 (m, 5H), 5.25 (s, 2H), 1.34 (m, 9H).

Synthesis of tert-butyl benzyl(6-chloro-3-cyclopropylimidazo[1,2-b]pyridazin-8-yl)carbamate

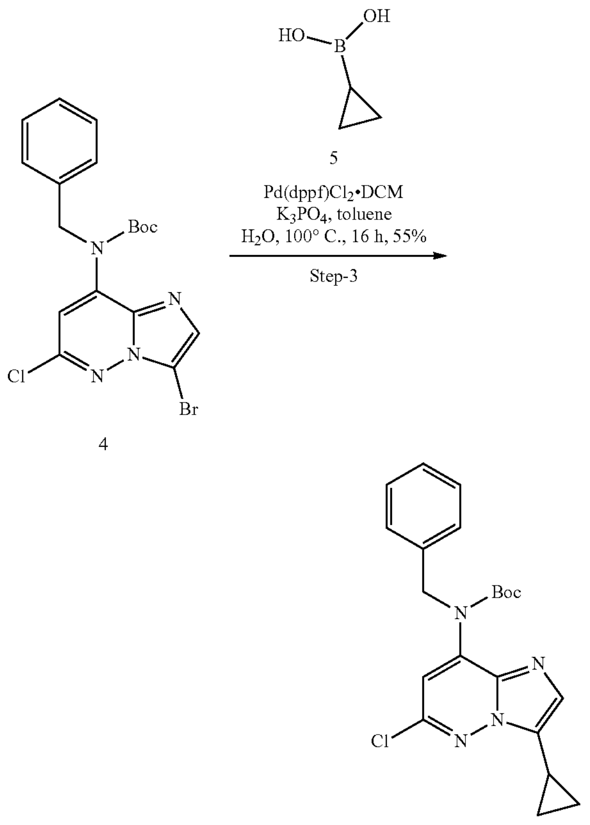

5

4

6

To the stirred solution of tert-butyl benzyl(3-bromo-6-chloroimidazo[1,2-b]pyridazin-8-yl)carbamate (4) (2 g, 4.58 mmol, 1eq) in toluene: water (3:1; 23 mL) was added cyclopropyl boronic acid (5) (0.47 g, 5.50 mmol, 1.2) and $K_3PO_4$ (2.91 g, 13.76 mmol, 3 eq) and degassed for 10 min later added Pd(dppf)$Cl_2$DCM (0.37 g, 0.45 mmol, 0.1 eq) and stirred at 100 °C for 16 h. After completion of reaction by TLC, diluted with ice cold water (100 mL) and extracted with ethyl acetate (3×100 mL). The combined organic layers were washed with brine solution (60 mL), dried over sodium sulfate and concentrated to provide crude. The crude material was purified by silica phase column chromatography [with a gradient elution of 15-20% of EtOAc/Hexane] to afford tert-butyl benzyl(6-chloro-3-cyclopropylimidazo[1,2-b]pyridazin-8-yl)carbamate (6) as yellow (130 mg, 7%). TLC system: EtOAc/hexane (10:90), $R_f$ value: ~0.4; LCMS (m/z): 398.0 $(M+H)^+$; $^1$HNMR (400 MHz, DMSO-$d_6$) δ 7.55 (s, 1H), 7.34 (s, 1H), 7.28-7.17 (m, 5H), 5.30 (s, 2H), 2.15-2.08 (m, 1H), 1.35 (s, 9H), 1.05-1.00 (m, 2H), 0.82-0.78 (m, 2H).

Synthesis of 2-bromo-3-methylbutanal

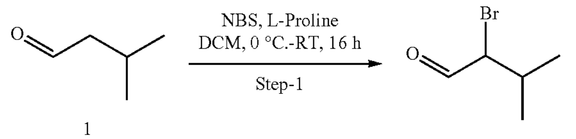

1

2

To a stirred solution of 3-Methylbutyraldehyde (10 g, 116.3 mmol, 1 eq.) in DCM (100 mL) was added N-bromosuccinimide (24.8 g, 139.3 mmol, 1.3 eq.) and L-proline (1.34 g, 11.6 mmol, 0.1 eq.) at 0 °C and the mixture was warmed to room temperature stirred for 16 h. Progress of reaction was monitored by TLC (9:1 Hexane/EtOAc). After completion of reaction n-Pentane (500 mL) was added precipitate formed was filtered through celite bed. The filtrate was washed with water (3×200 mL) and brine (200 mL). Finally, organic layer was dried over sodium sulfate, filtered and concentrated under reduced pressure (maintained bath temperature below 30 °C) to give the 2-bromo-3-methylbutanal (7.5 g, 39%) as a reddish-brown oily liquid. $^1$HNMR (400 MHz, DMSO-$d_6$): δ 9.40 (d, J=3.6 Hz, 1H), 4.06-4.03 (m, 1H), 2.26-2.15 (m, 1H), 1.07-1.04 (m, 6H).

Example 11

Synthesis of tert-butyl 3-mercaptopiperidine-1-carboxylate

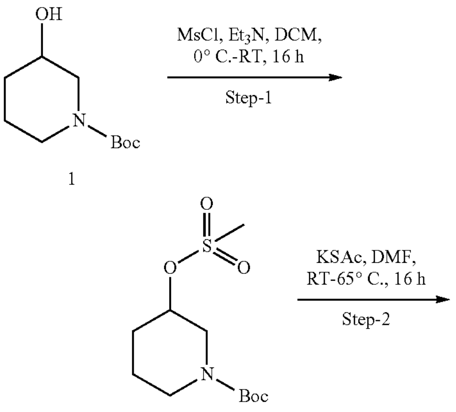

1

2

-continued

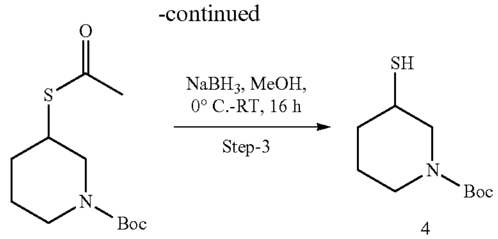

3

4

Synthesis of tert-butyl 3-((methylsulfonyl)oxy)piperidine-1-carboxylate (2)

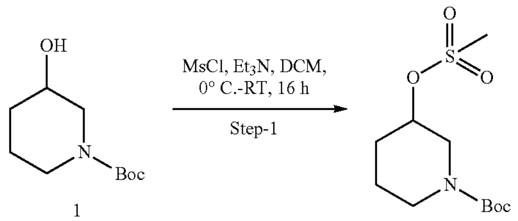

1

2

To a stirred solution of tert-butyl 3-hydroxypiperidine-1-carboxylate (10 g, 49.75 mmol, 1 eq.) in DCM (100 mL) was added triethylamine (8.37 mL, 59.61 mmol, 1.2 eq.) followed by methanesulfonyl chloride (4.61 mL, 59.61 mmol, 1.2 eq.) at 0 °C. The reaction mixture was allowed to room temperature and stirred for 16 h. Progress of reaction was monitored by TLC, after completion of reaction, diluted with ice-cold water (500 mL) and extracted with DCM (3×500 mL). The combined organic layer was washed with brine solution (200 mL), dried over sodium sulfate and concentrated under reduced pressure to get the crude of tert-butyl 3-((methylsulfonyl)oxy)piperidine-1-carboxylate (2) as brown oil (12 g, quantitative) which was carried to next step without any further purification. TLC system: EtOAc/hexane (1:1), $R_f$=0.4; $KMnO_4$ stain +ve.

Synthesis of tert-butyl 3-(acetylthio)piperidine-1-carboxylate

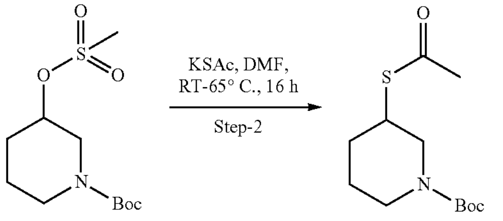

2

3

To a stirred solution of tert-butyl 3-((methylsulfonyl)oxy)piperidine-1-carboxylate (12 g, 43.01 mmol, 1 eq.) in DMF (120 mL) was added potassium thioacetate (7.27 g, 63.65 mmol, 1.48 eq.) at room temperature. Reaction mixture was heated at 65 °C for 16 h. The progress of reaction was monitored by TLC. After completion of reaction, it was cooled and poured into crushed ice water (1000 mL), extracted with diethyl ether (3×500 mL). The combined organic layer was washed with brine solution (200 mL), dried over sodium sulfate and evaporated under reduced pressure to get the crude compound. The crude compound was purified by silica phase column chromatography [with a gradient elution of 0-5% of EtOAc/Hexane] to afford the title compound tert-butyl 3-(acetylthio)piperidine-1-carboxylate as brown oil (6 g, 53.9%). TLC system: EtOAc/hexane (1:4), $R_f$=0.4. $^1$H-NMR (400 MHz, $CDCl_3$): δ 3.79 (m, 1H), 3.57-3.49 (m, 2H), 3.24-3.21 (m, 2H), 2.32 (s, 3H), 2.00-1.98 (m, 1H), 1.69-1.56 (m, 3H), 1.46 (s, 9H).

Synthesis of tert-butyl 3-mercaptopiperidine-1-carboxylate

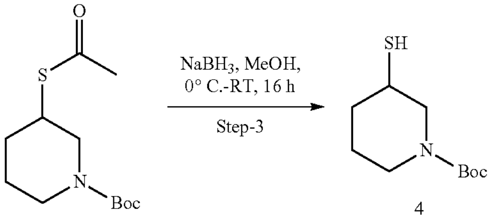

3

4

To a stirred solution of tert-butyl 3-(acetylthio) piperidine-1-carboxylate (6 g, 23.16 mmol, 1 eq.) in methanol (80 mL) was added sodium borohydride (6.13 g, 162.16 mmol, 7 eq.) portion wise at 0 °C. Reaction mixture was allowed to room temperature and stirred for 16 h. After complete conversion by TLC, reaction mixture was concentrated under reduced pressure. Obtained residue was carefully dissolved in water and acidified with citric acid (pH=6). Then the product was extracted with dichloromethane (2×100 mL), the extracts combined, dried over sodium sulfate, filtered and the filtrate evaporated in vacuum obtained crude. The crude compound was purified by silica phase column chromatography [with a gradient elution of 0-2% of EtOAc/Hexane] to afford the title compound the tert-butyl 3-mercaptopiperidine-1-carboxylate (4) as brown oil (2.8 g, 55.7%). TLC system: EtOAc/hexane (1:4), $R_f$=0.4, $KMnO_4$ stain +ve. $^1$H-NMR (400 MHz, DMSO-$d_6$): δ 3.93 (b, 1H), 3.69 (d, J=12.4 Hz, 1H), 2.84-2.51 (m, 4H), 1.99 (m, 1H), 1.65 (m, 1H), 1.40 (m, 2H), 1.40 (s, 9H).

Example 12

Synthesis of tert-butyl 4-mercaptopiperidine-1-carboxylate

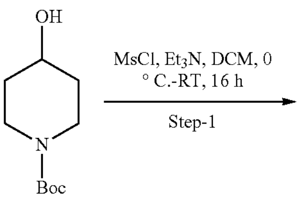

1

-continued

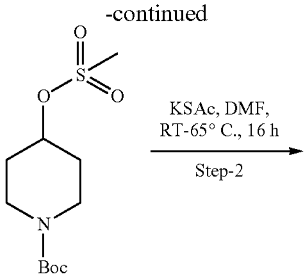

2

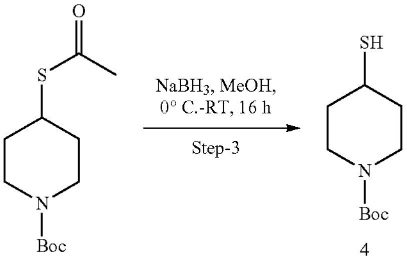

3

4

Synthesis of tert-butyl 4-((methylsulfonyl)oxy)piperidine-1-carboxylate (2)

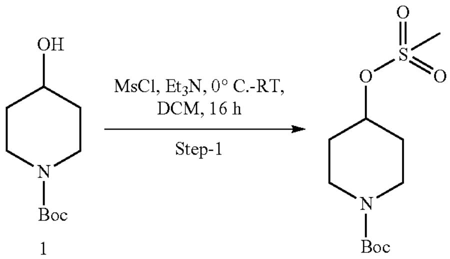

1

2

To a solution of tert-butyl 4-hydroxypiperidine-1-carboxylate (10 g, 49.75 mmol, 1 eq.) in DCM (100 mL) was added triethylamine (8.37 mL, 59.61 mmol, 1.2 eq.) followed by methanesulfonyl chloride (4.61 mL, 59.61 mmol, 1.2 eq.) at 0 °C. Reaction mixture was allowed to come to room temperature and stirred for 16 h. After completion of reaction by TLC, reaction mixture was diluted with ice cold water (500 mL) and product was extracted with DCM (3×500 mL). The combined organic layer was washed with brine solution (200 mL), dried over sodium sulfate and concentrated under reduced pressure to get the crude of tert-butyl 4-((methylsulfonyl)oxy)piperidine-1-carboxylate (2) as brown oil, (12 g, quantitative) which was carried to next step without any further purification. TLC system: EtOAc/hexane (1:1), $R_f$=0.4 ($KMnO_4$ stain +ve). $^1$H-NMR (400 MHz, DMSO-$d_6$) δ 4.91-4.85 (m, 1H), 3.72-3.70 (m, 2H), 3.35-3.27 (m, 2H), 3.04 (s, 3H), 1.99-1.93 (m, 2H), 1.85-1.77 (m, 2H), 1.48 (s, 9H).

Synthesis of tert-butyl 4-(acetylthio)piperidine-1-carboxylate

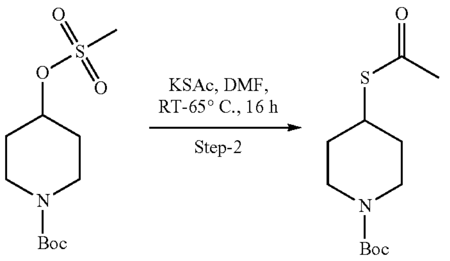

2 3

To a stirred solution of tert-butyl 4-((methylsulfonyl)oxy) piperidine-1-carboxylate (12 g, 43.01 mmol, 1eq.) in DMF (120 mL) was added potassium thioacetate (7.27 g, 63.65 mmol, 1.48 eq.) at room temperature. Reaction mixture was heated at 65 °C for 16 h. After complete conversion by TLC, reaction mixture was cooled, poured into crushed ice water (500 mL), extracted with diethyl ether (3×500 mL). The combined organic layer was washed with brine solution (2×500 mL), dried over sodium sulfate and evaporated under reduced pressure. The crude compound was purified by silica phase column chromatography [with a gradient elution of 0-5% of EtOAc/Hexane] to afford the title compound tert-butyl 4-(acetylthio)piperidine-1-carboxylate as brown oil, (8 g, 71.87% yield). TLC system: EtOAc/hexane (1:4), $R_f$=0.4. $^1$H-NMR (400 MHz, DMSO-$d_6$): δ 3.73-3.70 (m, 2H), 3.58-3.51 (m, 1H), 3.02 (bs, 2H), 2.32 (s, 3H), 1.80-1.85 (m, 2H), 1.44-1.43 (m, 2H), 1.39 (s, 9H).

Synthesis of tert-butyl 4-mercaptopiperidine-1-carboxylate

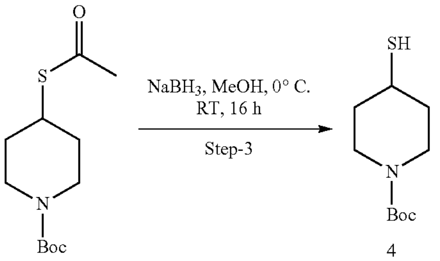

3 4

To a stirred solution of tert-butyl 4-(acetylthio)piperidine-1-carboxylate (8 g, 30.88 mmol, 1eq.) in methanol (80 mL) was added sodium borohydride (8.17 g, 21.62 mmol, 7 eq.) portion wise at 0 °C. Reaction mixture was allowed to room temperature and stirred for 16 h. After complete conversion by TLC, reaction mixture was concentrated under reduced pressure. The residue was carefully dissolved in water and acidified with citric acid (pH=6). The product was extracted with dichloromethane (2×100 mL), the extracts combined, dried over sodium sulfate, filtered and the filtrate evaporated in vacuum obtained the tert-butyl 4-mercaptopiperidine-1-carboxylate as a brown oil (6 g, 89%). TLC system: EtOAc/hexane (1:4), $R_f$value: ~0.4, $KMnO_4$ stain +ve. $^1$HNMR (400 MHz, DMSO-$d_6$) δ 3.81-3.77 (m, 2H), 2.93-2.83 (m, 3H), 2.65 (d, J=7.2 Hz, 1H) 1.88-1.85 (m, 2H), 1.30-1.32 (m, 2H), 1.38 (s, 9H).

Example 13

Synthetic Scheme for (S)-3-methyl-N-(1-phenylethyl)-6-(piperidin-4-yloxy)imidazo[1,2-b]pyridazin-8-amine hydrochloride

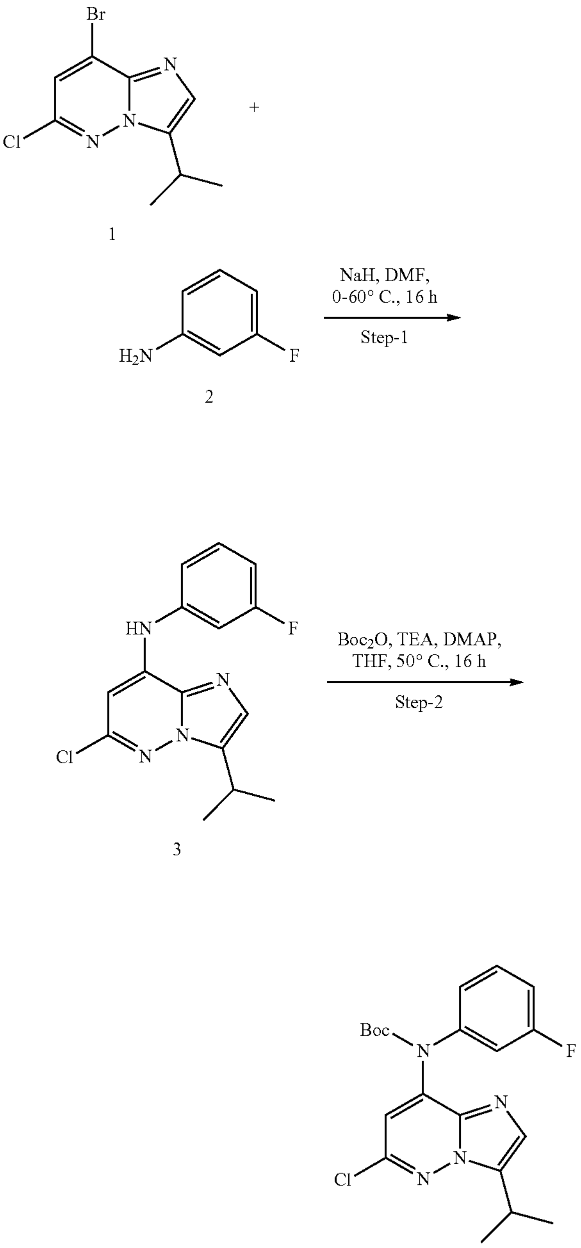

1 2 3 4

Synthesis of 6-chloro-N-(3-fluorophenyl)-3-isopropylimidazo[1,2-b]pyridazin-8-amine

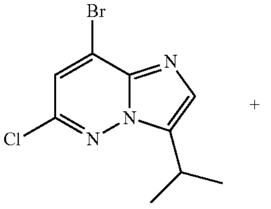

1

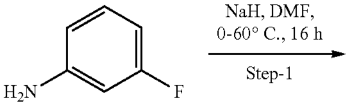

2

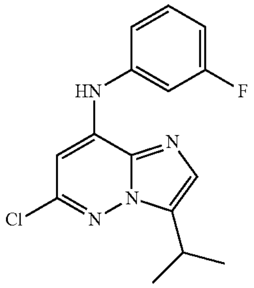

3

To a solution of 3-fluoroaniline (0.29 g, 1.360 mmol, 1.2 eq.), in anhydrous DMF (5 mL) was added NaH (60% in mineral oil, 0.132 g, 3.295 mmol, 1.5 eq.) at 0 °C. The mixture was allowed to stir at RT for 15 min, then 8-bromo-6-chloro-3-isopropylimidazo[1,2-b]pyridazine (0.6 g, 2.197 mmol, 1 eq.) was added and heated to 60 °C for 16 h. After this time, reaction was quenched with ice cold water (6 mL) and product was extracted with EtOAc (2x30 mL). Combine organic layer was dried over $Na_2SO_4$, filtered and concentrated under reduced pressure. Obtained crude compound was purified by combiflash on silica column (EtOAc/hexane, gradient 0-50% EtOAc) to afford 6-chloro-N-(3-fluorophenyl)-3-isopropylimidazo[1,2-b]pyridazin-8-amine as a yellow gum (0.395 g, 58% yield). $R_f$=0.5 (7:3 Hexane/EtOAc). $^1$H NMR (400 MHz, DMSO): δ 9.98 (s, 1H), 7.48-7.44 (m, 2H), 7.34-7.28 (m, 2H), 7.04-7.01 (m, 1H), 6.54 (d, J=5.6 Hz, 1H), 3.37-3.29 (m, 1H), 1.36-1.29 (m, 6H).

Synthesis of tert-butyl (6-chloro-3-isopropylimidazo[1,2-b]pyridazin-8-yl)(3-fluorophenyl)carbamate

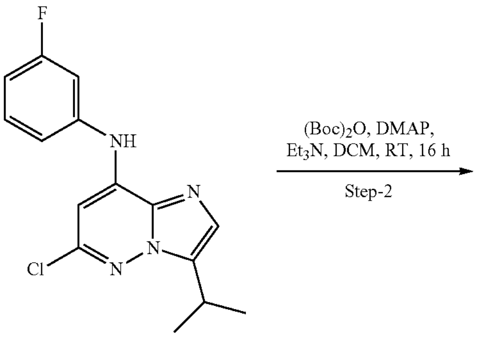

3

-continued

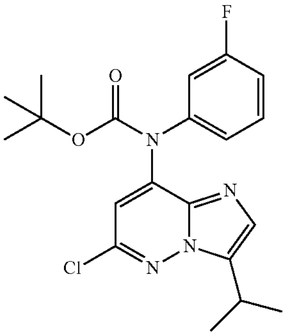

4

To a stirred solution of 6-chloro-N-(3-fluorophenyl)-3-isopropylimidazo[1,2-b]pyridazin-8-amine (0.35 g, 1.151 mmol, 1 eq.) in THE (5 mL) was added DIPEA (2.0 mL, 11.51 mmol, 10 eq.), $(Boc)_2O$ (2.6 mL, 11.51 mmol, 10 eq.) and DMAP (0.014 g, 0.115 mmol, 0.1 eq.) and stirred for 16 h at room temperature. The reaction mixture was concentered under reduced pressure. The obtained crude was diluted with water and extracted with EtOAc (2x10 mL). The combined organic layer was washed with brine solution (20 mL), dried over $Na_2SO_4$ concentrated under reduced pressure. The residue was purified by combiflash on silica column (EtOAc/hexane, gradient 0-40% EtOAc) to get tert-butyl (6-chloro-3-isopropylimidazo[1,2-b]pyridazin-8-yl)(3-fluorophenyl)carbamate as a yellow gum (0.35 g, 75% yield). $R_f$=0.8 (7:3 Hexane/EtOAc). $^1$H NMR (400 MHz): δ 7.22-7.61 (m, 1H), 7.44-7.34 (m, 1H), 7.31-7.25 (m, 1H), 7.19-6.98 (m, 3H), 3.64-3.58 (m, 1H), 1.35 (s, 9H).

Example 14

Synthetic Scheme for tert-butyl (6-chloro-3-isopropylimidazo[1,2-b]pyridazin-8-yl)(2-(trifluoromethoxy)benzyl)carbamate

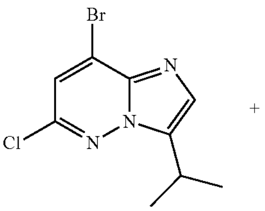

1

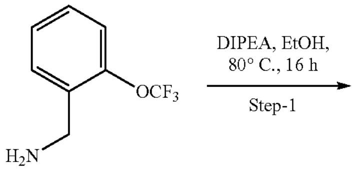

2

-continued

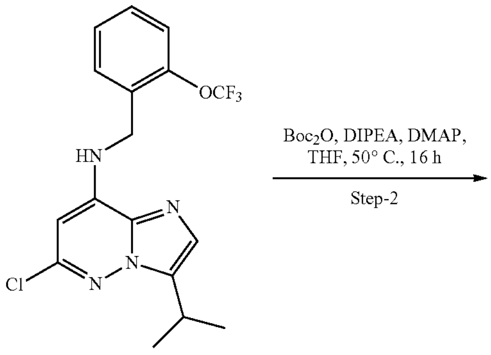

3

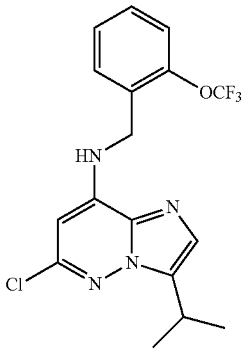

3

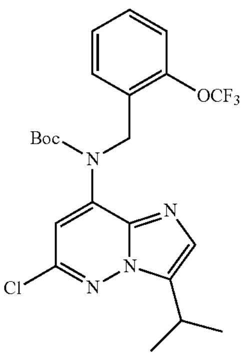

4

Synthesis of 6-chloro-3-isopropyl-N-(2-(trifluoromethoxy)benzyl)imidazo[1,2-b]pyridazin-8-amine

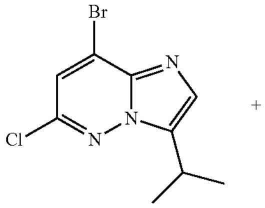

1

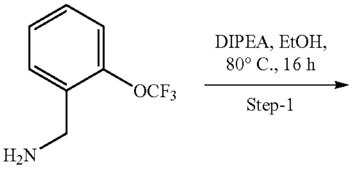

2

To a stirred solution of 8-bromo-6-chloro-3-isopropylimidazo[1,2-b]pyridazine (1.0 g, 3.66 mmol, 1 eq.) and (2-(trifluoromethoxy)phenyl)methanamine (1.05 g, 5.49 mmol, 1.5 eq.) in EtOH (15 mL) was added DIPEA (1.2 mL, 7.32 mmol, 2 eq.) and stirred for 16 h at 80 °C. Progress of reaction was monitored by TLC, after completion of reaction, volatiles were concentered under reduced pressure to get crude compound. The obtained crude was diluted with water and aqueous layer was extracted with EtOAc (2×100 mL). The combined organic layer was washed with brine solution (100 mL), dried over $Na_2SO_4$ concentrated under reduced pressure. Crude compound was purified by column chromatography using EtOAc: hexane as eluting system to afford 6-chloro-3-isopropyl-N-(2-(trifluoromethoxy)benzyl)imidazo[1,2-b]pyridazin-8-amine as a yellow gum (0.90 g, 63% yield). $R_f$=0.6 (8:2 Hexane/EtOAc). LCMS (m/z): 385.0 $(M+H)^+$. $^1H$ NMR (400 MHz, $CDCl_3$): δ 7.46-7.26 (m, 5H), 6.92 (bs, 1H), 6.00 (d, J=6.8 Hz, 1H), 4.64 (d, J=6.4 Hz, 2H), 3.45-3.40 (m, 1H), 1.42-1.38 (d, J=8 Hz, 6H).

Synthesis of tert-butyl (6-chloro-3-isopropylimidazo[1,2-b]pyridazin-8-yl)(2-(trifluoromethoxy)benzyl)carbamate

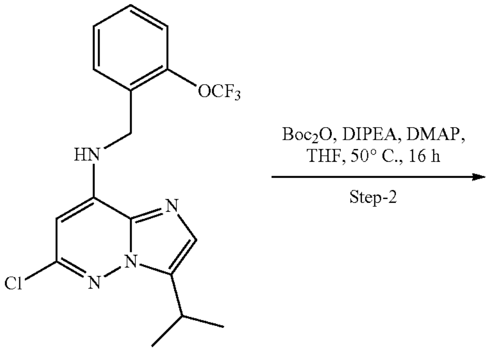

3

-continued

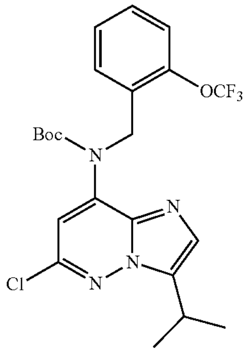

4

To a stirred solution of 6-chloro-3-isopropyl-N-(2-(trifluoromethoxy)benzyl)imidazo[1,2-b]pyridazin-8-amine (0.90 g, 2.34 mmol, 1 eq.) in THF (10 mL) was added DIPEA (4.07 mL, 23.4 mmol, 10 eq.), $(Boc)_2O$ (5.3 mL, 23.4 mmol, 10 eq.) and DMAP (0.028 g, 0.23 mmol, 0.1 eq.) and stirred for 16 h at 50 °C. Progress of reaction was monitored by TLC. After completion of reaction, the reaction mixture was concentered under reduced pressure. The obtained crude was diluted with water and extracted with EtOAc (2×100 mL). The combined organic layer was washed with brine solution (100 mL), dried over $Na_2SO_4$ concentrated under reduced pressure to get crude compound. Crude compound was purified by column chromatography using (0-20%) EtOAc: hexane as eluting system to afford tert-butyl (6-chloro-3-isopropylimidazo[1,2-b]pyridazin-8-yl)(2-(trifluoromethoxy)benzyl)carbamate as a yellow gum (0.850 g, 75% yield). $R_f$=0.6 (8:2 Hexane/EtOAc). LCMS (m/z): 485.1 $(M+H)^+$. $^1H$ NMR (400 MHz, DMSO-$d_6$): δ 7.52-7.50 (d, J=6.4 Hz 1H), 7.43-7.40 (m, 1H), 7.26-7.16 (m, 3H), 7.08-7.07 (d, J=6.8 Hz 1H), 5.56 (s, 2H), 3.48-3.39 (m, 1H). 1.49-1.38 (m, 15H).

Synthetic Synthesis of tert-butyl (6-chloro-3-isopropylimidazo[1,2-b]pyridazin-8-yl)(3-(trifluoromethyl)benzyl)carbamate

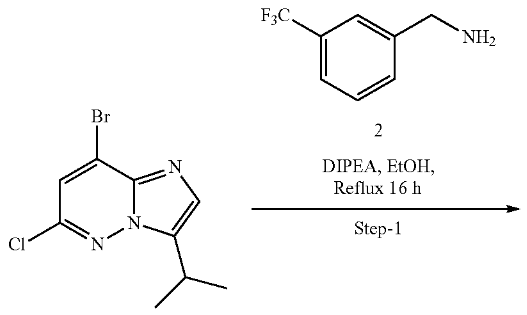

1

-continued

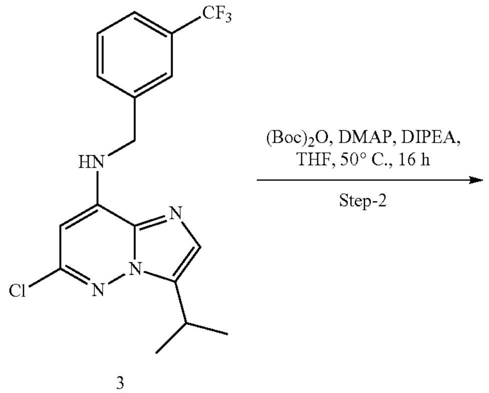

3

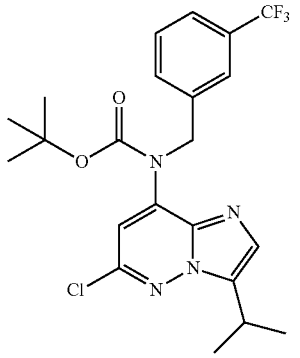

4

Synthesis of 6-chloro-3-isopropyl-N-(3-(trifluoromethyl)benzyl)imidazo[1,2-b]pyridazin-8-amine

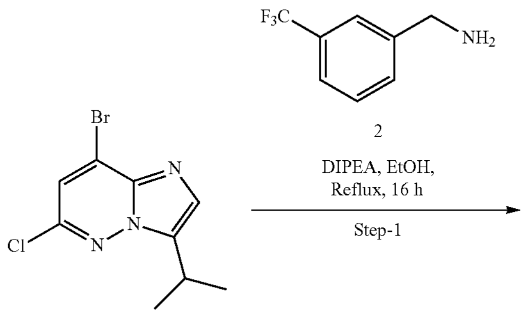

1

-continued

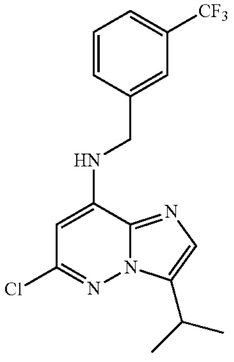

3

-continued

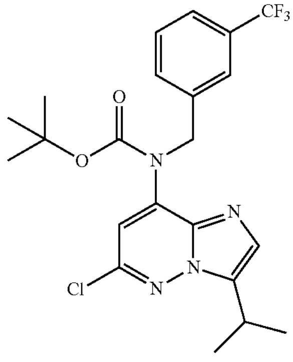

4

A mixture of 8-bromo-6-chloro-3-isopropylimidazo[1,2-b]pyridazine (1.0 g, 3.65 mmol, 1 eq.), (3-(trifluoromethyl)phenyl)methanamine (1.27 g, 7.299 mmol, 2 eq.), and DIPEA (1.9 mL, 10.947 mmol) in EtOH (10 mL) was heated to reflux for 16 h. The reaction mixture was allowed to cool to room temperature and then concentered under reduce pressure the obtained crude material was diluted with water and EtOAc. The aqueous layer was separated and extracted with EtOAc (2×50 mL). The combined extracts were washed with water, brine, dried over $Na_2SO_4$, filtered, and evaporated. The residue was purified by combiflash on silica column (EtOAc/hexane, gradient 0-30% EtOAc) to 6-chloro-3-isopropyl-N-(3-(trifluoromethyl)benzyl)imidazo[1,2-b]pyridazin-8-amine (3) as a yellow gum (1 g, 75% yield). $R_f$=0.3 (2:8 Hexane/EtOAc). $^1$H NMR (400 MHz, DMSO-$d_6$): δ 8.21 (s, 2H), 7.90 (s, 1H), 7.78 (t, J=8.0 Hz, 2H), 7.67 (t, J=7.6 Hz, 1H), 4.16 (s, 2H), 3.65-3.59 (m, 1H), 1.31-1.24 (m, 6H).

Synthesis of tert-butyl (6-chloro-3-isopropylimidazo[1,2-b]pyridazin-8-yl)(3-(trifluoromethyl)benzyl)carbamate

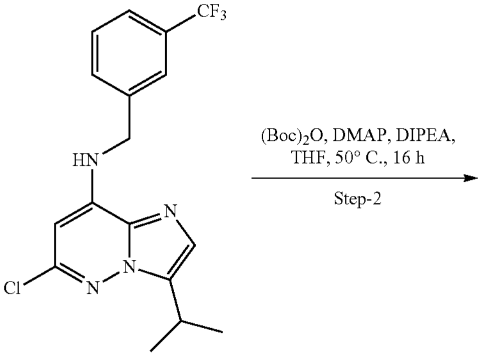

3

A stirred solution of 6-chloro-3-isopropyl-N-(3-(trifluoromethyl)benzyl)imidazo[1,2-b]pyridazin-8-amine (3) (1 g, 2.717 mmol, 1 eq.), $(Boc)_2O$ (6.2 mL, 27.17 mmol, 10 eq.), DMAP (26 mg, 0.271 mmol, 0.1 eq.) and DIPEA (4.7 mL, 27.17 mmol, 10 eq.) in THF (10 mL) were stirred for 16 h at 50 °C. The reaction mixture was allowed to cool to room temperature. EtOAc (150 mL) was added, and the organic layer was washed with water (2×100 mL) and saturated aqueous $NaHCO_3$(100 mL) and dried over $Na_2SO_4$, filtered, and evaporated. The residue was purified by combiflash on silica column (EtOAc/hexane, gradient 0-20% EtOAc) to afford tert-butyl (6-chloro-3-isopropylimidazo[1,2-b]pyridazin-8-yl)(3-(trifluoromethyl)benzyl)carbamate (4) as a yellow gum (1.0 g, 79% yield). $R_f$=0.5 (2:8 Hexane/EtOAc). $^1$H-NMR (400 MHz, DMSO-$d_6$): δ 7.68-7.42 (m, 6H), 4.21 (d, J=6.0 Hz, 2H), 3.39-3.34 (m, 1H), 1.39-1.32 (m, 15H).

Example 15

Synthetic Scheme for Synthesis of tert-butyl benzyl (6-chloro-3-isopropylimidazo[1,2-b]pyridazin-8-yl)carbamate

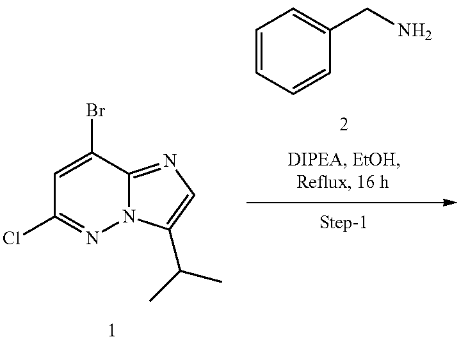

1

-continued

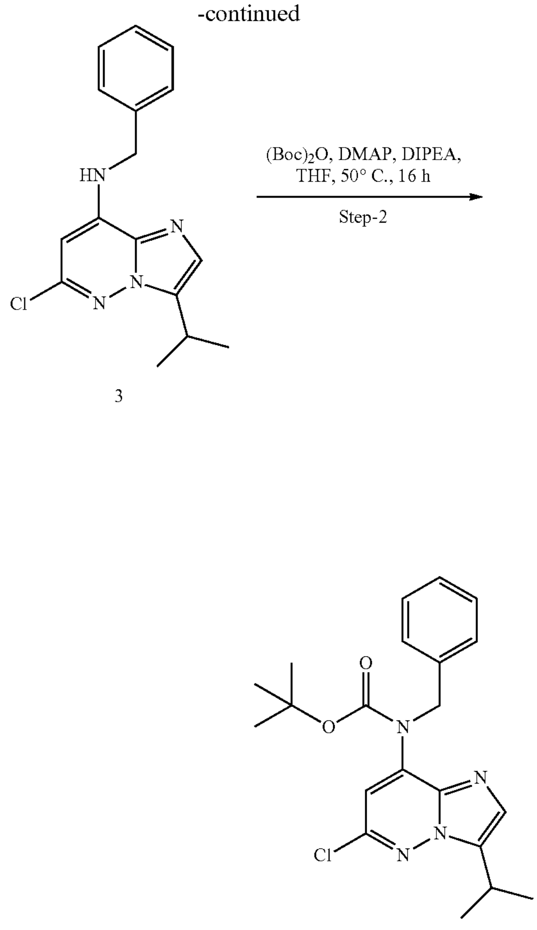

3

4

Synthesis of N-benzyl-6-chloro-3-isopropylimidazo [1,2-b]pyridazin-8-amine

A mixture of 8-bromo-6-chloro-3-isopropylimidazo[1,2-b]pyridazine (1) (8.0 g, 29.304 mmol, 1 eq.), phenylmethanamine (4.8 mL, 43.956 mmol, 1.5 eq.), and DIPEA (40.8 mL, 234.43 mmol, 10 eq.) in EtOH (80 mL) was heated to reflux for 16 h. The reaction mixture was allowed to cool to room temperature and then concentered under reduce pressure the obtained crude material was diluted with water and EtOAc. The aqueous layer was separated and extracted with EtOAc (2×50 mL). The combined extracts were washed with water, brine, dried over $Na_2SO_4$, filtered, and evaporated. The residue was purified by combiflash on silica column (EtOAc/hexane, gradient 0-30% EtOAc) to N-benzyl-6-chloro-3-isopropylimidazo[1,2-b]pyridazin-8-amine (3) as a yellow gum (8.7 g, 98% yield). $R_f$=0.5 (3:7 Hexane/EtOAc). $^1$H NMR (400 MHz, DMSO-$d_6$): δ 8.48 (s, 1H), 7.37-7.22 (s, 5H), 6.06 (s, 1H), 4.55 (s, 2H), 3.27-3.20 (m, 1H), 1.30 (d, J=5.2 Hz, 6H).

Synthesis of tert-butyl benzyl(6-chloro-3-isopropylimidazo[1,2-b]pyridazin-8-yl)carbamate

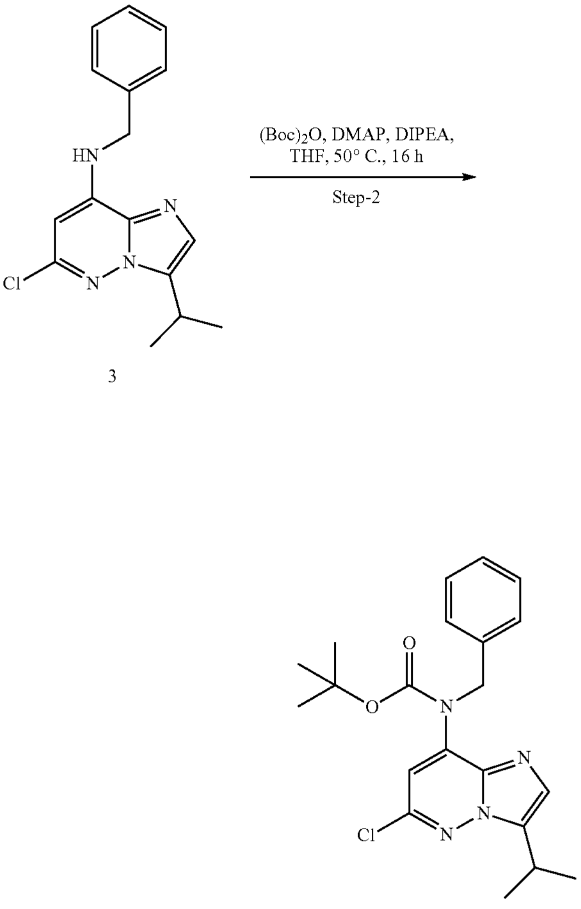

3

4

To a stirred solution of N-benzyl-6-chloro-3-isopropylimidazo[1,2-b]pyridazin-8-amine (3) (8.5 g, 28.33 mmol, 1 eq.), $(Boc)_2O$ (58.7 mL, 283.3 mmol, 10 eq.), DMAP (0.283 mg, 2.83 mmol, 0.1 eq.) and DIPEA (50.0 mL, 283.3 mmol, 10 eq.) in THF (85 mL) was stirred for 16 h at 50 °C. The reaction mixture was allowed to cool to room temperature. EtOAc (200 mL) was added, and the organic layer was washed with water (2×100 mL) and saturated aqueous $NaHCO_3$(100 mL) and dried over $Na_2SO_4$, filtered, and evaporated. The residue was purified by comb flash on silica column (EtOAc/hexane, gradient 0-20% EtOAc) to afford tert-butyl benzyl(6-chloro-3-isopropylimidazo[1,2-b]pyridazin-8-yl)carbamate (4) as a yellow solid (8.5 g, 75% yield). $R_f$=0.7 (2:8 Hexane/EtOAc). $^1$H NMR (400 MHz, DMSO-$d_6$): δ 7.66 (d, J=3.2 Hz, 1H), 7.50-7.42 ((d, J=3.2 Hz, 1H)), 7.28-7.19 (m, 5H), 5.31 (s, 2H), 3.39-3.34 (m, 1H), 1.35-1.32 (m, 15H).

Example 16

Synthetic Scheme for tert-butyl (6-chloro-3-isopropylimidazo[1,2-b]pyridazin-8-yl)(2-methoxybenzyl) carbamate

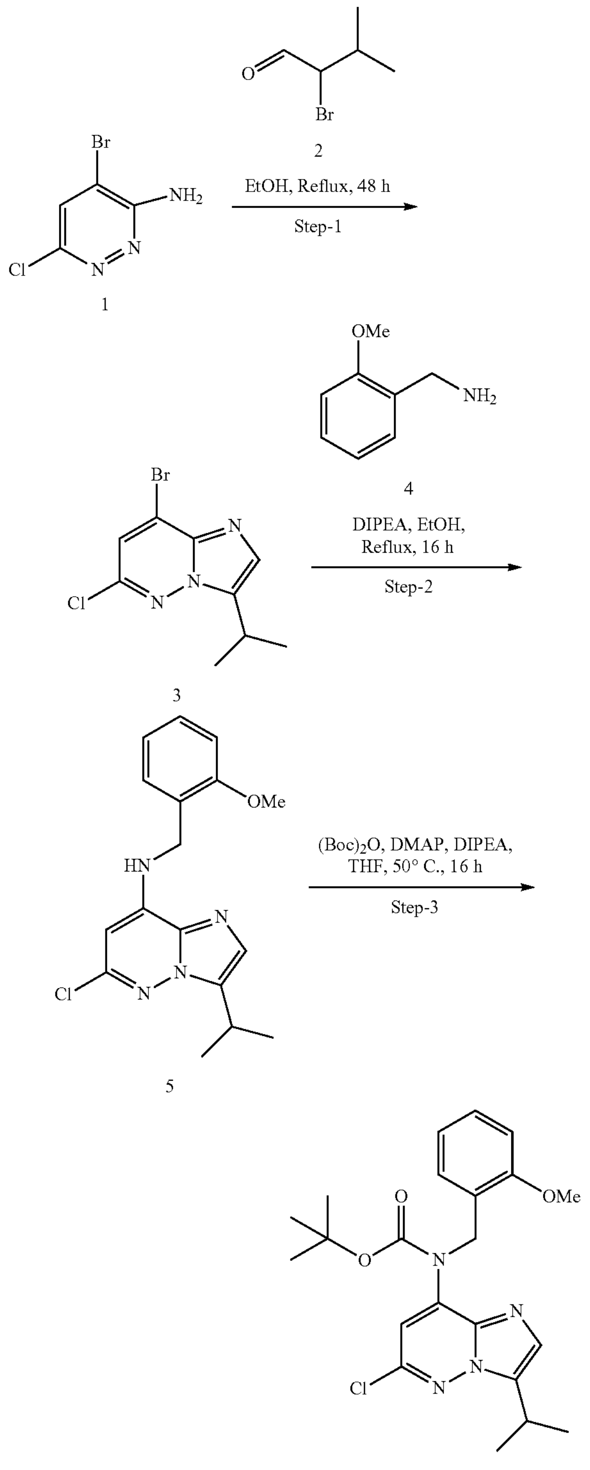

1 2 3 4 5 6

Synthesis of 8-bromo-6-chloro-3-isopropylimidazo[1,2-b]pyridazine

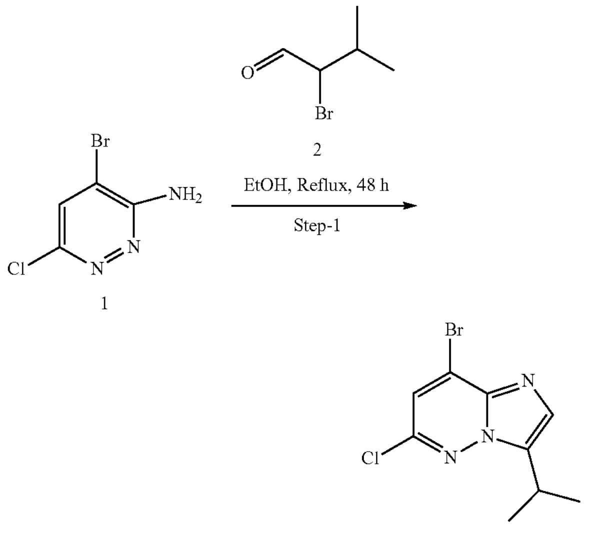

1 2 3

A mixture of 2-bromo-3-methylbutanal (16.0 g, 96.618 mmol, 5 eq.) and 4-bromo-6-chloropyridazin-3-amine (4 g, 19.323 mmol, 1 eq.) in ethanol (80 mL) was refluxed for 48 h. The reaction mixture was cooled to room temperature. Saturated sodium bicarbonate solution was added to the reaction mixture and extracted with DCM (3×50 ml). Combined organic layer was washed with brine solution (2×50 mL), dried over anhydrous $Na_2SO_4$, and evaporated under reduced pressure to afford the oily residue as crude compound. Further purification of oily residue by combiflash on silica column (0-20% EtOAc gradient in Hexane) afforded the desired product 8-bromo-6-chloro-3-isopropylimidazo[1,2-b]pyridazine as pale brown solid. Yield: 3.8 g (78%). $R_f$=0.4 (30:70 Hexane/EtOAc). 1H NMR (400 MHz DMSO-$d_6$): δ 7.87 (s, 1H), 7.73 (s, 1H), 3.67-3.61 (hept, J=6.8 Hz, 1H), 1.34 (t, J=6.8 Hz, 6H).

Synthesis of 6-chloro-3-isopropyl-N-(2-methoxybenzyl)imidazo[1,2-b]pyridazin-8-amine

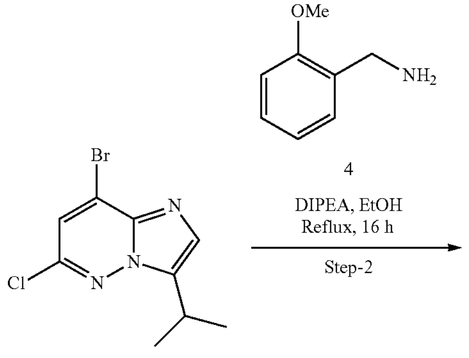

4 3

-continued

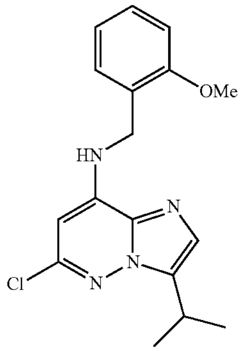

5

-continued

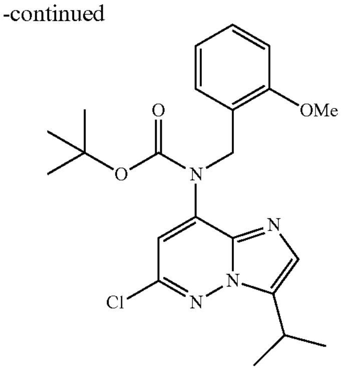

6

A mixture of 8-bromo-6-chloro-3-isopropylimidazo[1,2-b]pyridazine (3) (1.0 g, 3.663 mmol, 1 eq.), (2-methoxyphenyl)methanamine (0.91 g, 5.494 mmol, 1.5 eqv), and DIPEA (1.3 mL, 7.326 mmol) in EtOH (10 mL) was heated to reflux for 16 h. The reaction mixture was allowed to cool to room temperature and then concentered under reduce pressure the obtained crude material was diluted with water and EtOAc. The aqueous layer was separated and extracted with EtOAc (2×50 mL). The combined extracts were washed with water, brine, dried over $Na_2SO_4$, filtered, and evaporated. The residue was purified by combiflash on silica column (EtOAc/hexane, gradient 0-20% EtOAc) to 6-chloro-3-isopropyl-N-(2-methoxybenzyl)imidazo[1,2-b]pyridazin-8-amine (5) as a white solid. Yield: 0.9 gm (75%). $R_f$=0.5 (1:1 Hexane/EtOAc). $^1$H NMR (400 MHz, DMSO-$d_6$): δ 8.21 (s, 1H), 7.26 (t, J=6.8 Hz, 1H), 7.19 (d, J=6.4 Hz, 1H), 7.33 (d, J=3.6 Hz, 1H), 7.05 (t, J=4.8 Hz, 1H), 6.90 (t, J=7.6 Hz, 1H), 6.02 (s, 1H), 4.50 (s, 2H), 3.87 (s, 3H), 3.29-3.24 (m, 1H), 1.32 (t, J=5.2 Hz, 6H).

Synthesis of tert-butyl (6-chloro-3-isopropylimidazo[1,2-b]pyridazin-8-yl)(2-methoxybenzyl)carbamate

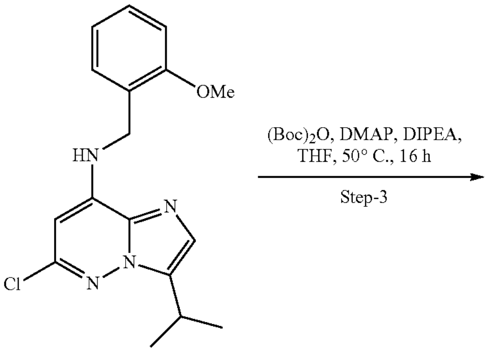

5

6-chloro-3-isopropyl-N-(2-methoxybenzyl)imidazo[1,2-b]pyridazin-8-amine (5) (0.9 g, 3.913 mmol, 1 eq.), $(Boc)_2O$ (8.9 mL, 39.13 mmol, 10 eq.), DMAP (48 mg, 0.391 mmol, 0.1 eq.) and DIPEA (6.8 mL, 39.13 mmol, 10 eq.) in THF (15 mL) were stirred for 16 h at 50 °C. The reaction mixture was allowed to cool to room temperature. EtOAc (150 mL) was added, and the organic layer was washed with water (2×100 mL) and saturated aqueous $NaHCO_3$(100 mL) and dried over $Na_2SO_4$, filtered, and evaporated. The residue was purified by combiflash on silica column (EtOAc/hexane, gradient 0-20% EtOAc) to afford tert-butyl (6-chloro-3-isopropylimidazo[1,2-b]pyridazin-8-yl)(2-methoxybenzyl)carbamate (6) as a yellow gum (1.0 g, 62% yield). $R_f$=0.53 (4:1 Hexane/EtOAc). $^1$H NMR (400 MHz, DMSO-$d_6$): δ 7.91 (t, J=3.6 Hz, 1H), 7.33 (d, J=3.6 Hz, 1H), 7.27 (d, J=7.2 Hz, 1H), 7.19 (t, J=6.8 Hz, 1H), 5.32 (s, 2H), 3.57 (s, 3H), 3.39-3.34 (m, 1H), 1.39 (s, 9H). 1.38-1.32 (m, 6H).

Example 17

Synthetic Scheme for (S)-3-cyclopropyl-N-(3-fluorophenyl)-6-(piperidin-3-yloxy)imidazo[1,2-b]pyridazin-8-amine

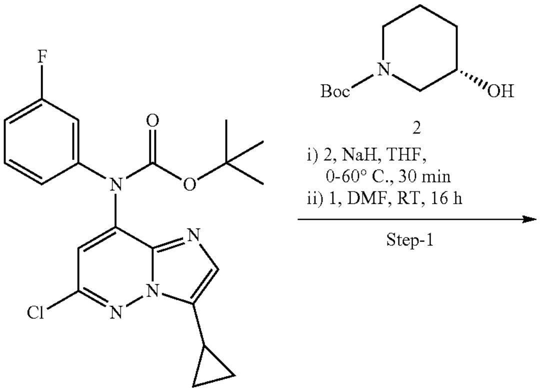

-continued

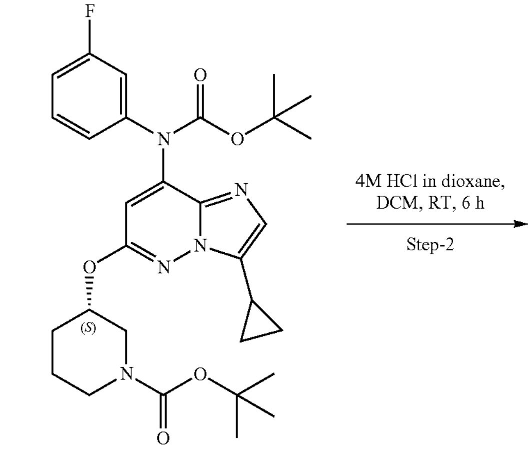

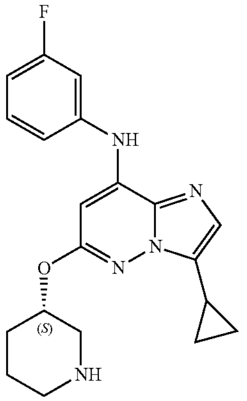

1

Synthesis of tert-butyl (S)-3-((8-((tert-butoxycarbonyl)(3-fluorophenyl)amino)-3-cyclopropylimidazo[1,2-b]pyridazin-6-yl)oxy)piperidine-1-carboxylate

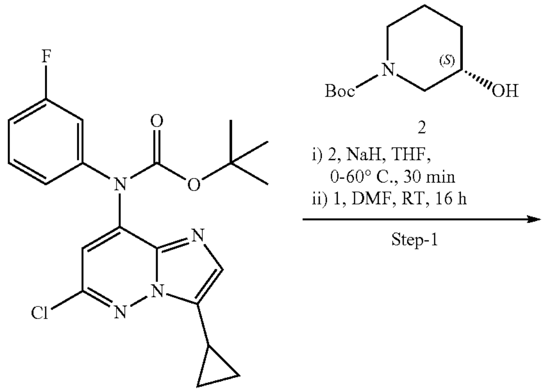

-continued

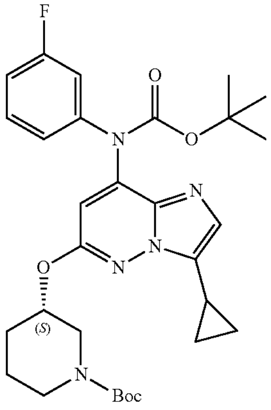

To a solution of tert-butyl (S)-3-hydroxypiperidine-1-carboxylate (0.3 g, 1.492 mmol, 3 eq.) in THF (4 mL) at 0 °C was added NaH (60% in mineral oil, 0.058 g, 1.492 mmol, 3 eq.) and heated to 60 °C, stirred for 30 min. Volatiles were evaporated, obtained sodium salt was dissolved in DMF (2 mL) and added a solution of tert-butyl tert-butyl (6-chloro-3-cyclopropylimidazo[1,2-b]pyridazin-8-yl)(3-fluorophenyl)carbamate (1) (450 mg, 1.05 mmol, 1 eq.) in DMF (4 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (S)-3-((8-((tert-butoxycarbonyl)(3-fluorophenyl)amino)-3-cyclopropylimidazo[1,2-b]pyridazin-6-yl)oxy)piperidine-1-carboxylate as a light yellow liquid (0.44 g, quantitative) which was carried to next step without any further purification, $R_f$=0.4 (2:8 Hexane/EtOAc). Note: Observed Cpd-1 de-boc as a major in TLC & LCMS. LCMS (m/z): 468.43 $(M+H)^+$ −100.

Synthesis of (S)-3-cyclopropyl-N-(3-fluorophenyl)-6-(piperidin-3-yloxy)imidazo[1,2-b]pyridazin-8-amine

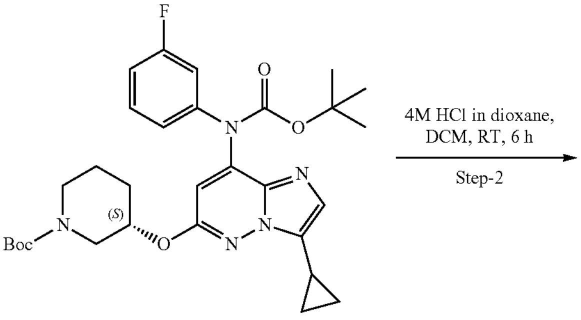

-continued

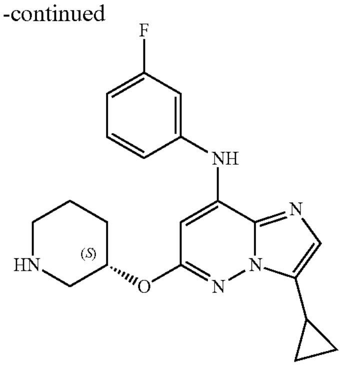

1

To a solution of tert-butyl (S)-3-((8-((tert-butoxycarbonyl)(3-fluorophenyl)amino)-3-cyclopropylimidazo[1,2-b]pyridazin-6-yl)oxy)piperidine-1-carboxylate (0.23 g, 0.404 mmol, 1 eq.) in DCM (10 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (S)-3-cyclopropyl-N-(3-fluorophenyl)-6-(piperidin-3-yloxy)imidazo[1,2-b]pyridazin-8-amine (1) as an off white solid (18 mg, 12% yield). $R_f$=0.2 (9:1 DCM/MeOH). LCMS (m/z): 368.09 $(M+H)^+$. $^1$H NMR (400 MHz, DMSO-$d_6$): δ 9.44 (s, 1H), 7.42 (q, J=7.8 Hz, 1H), 7.30-7.17 (m, 3H), 6.94 (td, J=8.5, 2.6 Hz, 1H), 6.10 (s, 1H), 4.88 (tt, J=7.5, 3.7 Hz, 1H), 3.21-3.17 (m, 1H), 2.76 (d, J=13.2 Hz, 1H), 2.72-2.60 (m, 1H), 2.62-2.53 (m, 1H), 2.08 (ddt, J=14.5, 11.4, 5.7 Hz, 2H), 1.74-1.55 (m, 2H), 1.62 (dt, J=13.3, 8.4 Hz, 1H), 1.02-0.93 (m, 2H), 0.87-0.78 (m, 2H). Note: $^1$H-NMR observed formate salt at δ 8.32 ppm.

Example 18

Synthetic Scheme for 3-cyclopropyl-n-(3-fluorophenyl)-6-((1-methylpiperidin-4-yl)oxy)imidazo[1,2-b]pyridazin-8-amine

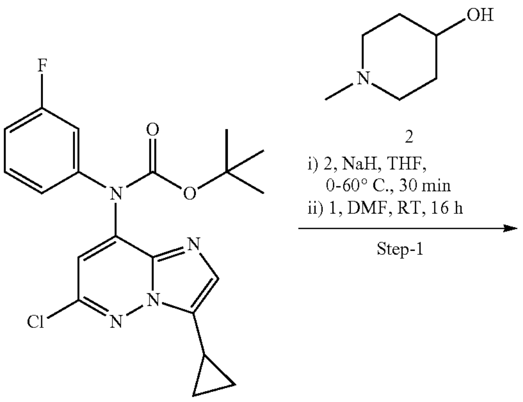

-continued

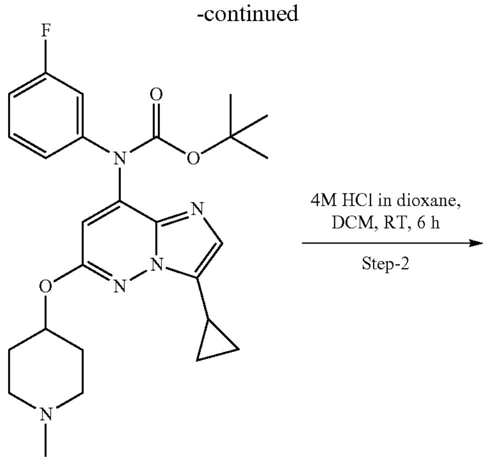

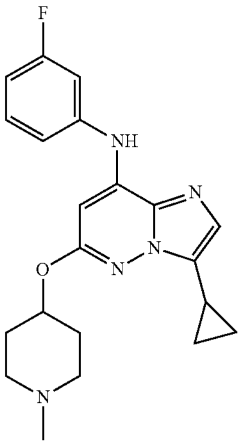

2

Synthesis of tert-butyl (3-cyclopropyl-6-((1-methylpiperidin-4-yl)oxy)imidazo[1,2-b]pyridazin-8-yl)(3-fluorophenyl)carbamate

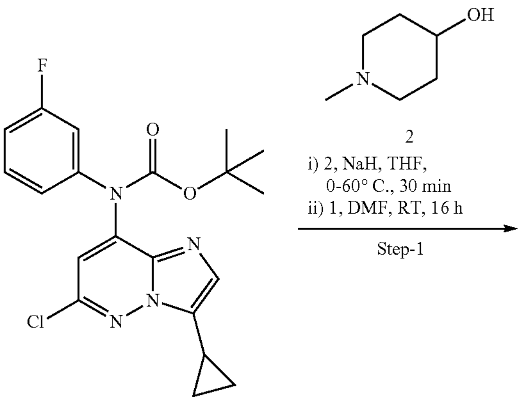

-continued

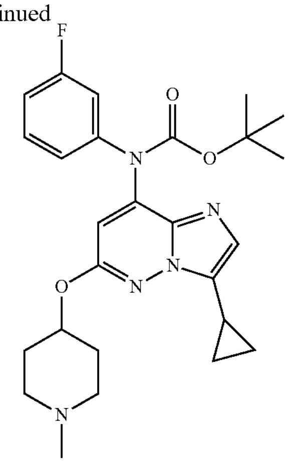

To a solution of 1-methylpiperidin-4-ol (2) (0.21 g, 1.861 mmol, 3 eq.) in THF (2 mL) at 0 °C was added NaH (60% in mineral oil, 0.074 g, 1.861 mmol, 3 eq.) and heated to 60 °C, stirred for 30 min. Volatiles were evaporated, obtained sodium salt was dissolved in DMF (2 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (3-cyclopropyl-6-((1-methylpiperidin-4-yl)oxy)imidazo[1,2-b]pyridazin-8-yl)(3-fluorophenyl)carbamate (3) as a yellow liquid (0.42 g, quantitative) which was carried to next step without any further purification, $R_f$=0.4 (4:6 Hexane/EtOAc). Note: Observed Cpd-1 de-boc as a major in TLC & LCMS. LCMS (m/z): 382.1 $(M+H)^+$ −100.

Synthesis of 3-cyclopropyl-N-(3-fluorophenyl)-6-((1-methylpiperidin-4-yl)oxy)imidazo[1,2-b]pyridazin-8-amine

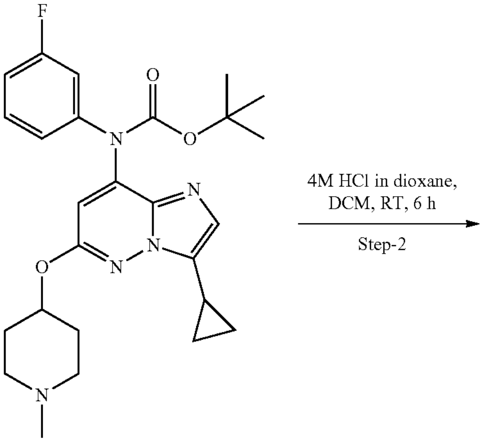

-continued

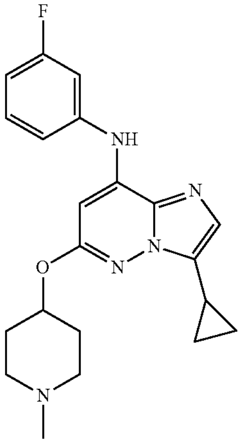

2

To a solution of tert-butyl (3-cyclopropyl-6-((1-methylpiperidin-4-yl)oxy)imidazo[1,2-b]pyridazin-8-yl)(3-fluorophenyl)carbamate (3) (0.22 g, 0.457 mmol, 1 eq.) in DCM (10 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford 3-cyclopropyl-N-(3-fluorophenyl)-6-((1-methylpiperidin-4-yl)oxy)imidazo[1,2-b]pyridazin-8-amine (2) as an off white solid (0.04 g, 23% yield). $R_f$=0.3 (9:1 DCM/MeOH). LCMS (m/z): 382.19 $(M+H)^+$. $^1$H NMR (400 MHz, DMSO-$d_6$): δ 9.42 (s, 1H), 7.42 (q, J=7.8 Hz, 1H), 7.30-7.17 (m, 3H), 6.94 (td, J=8.5, 2.5 Hz, 1H), 6.08 (s, 1H), 4.90 (dd, J=8.4, 4.3 Hz, 1H), 2.69-2.56 (m, 2H), 2.32 (p, J=1.9 Hz, 1H), 2.16 (s, 3H), 2.12-1.99 (m, 2H), 1.73-1.67 (m, 4H), 1.01-0.92 (m, 2H), 0.87-0.79 (m, 2H).

Example 19

Synthetic Scheme for (R)-3-cyclopropyl-N-(3-fluorophenyl)-6-((1-methylpyrrolidin-3-yl)oxy)imidazo[1,2-b]pyridazin-8-amine

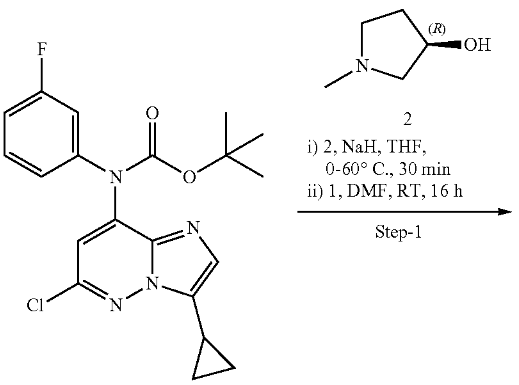

-continued

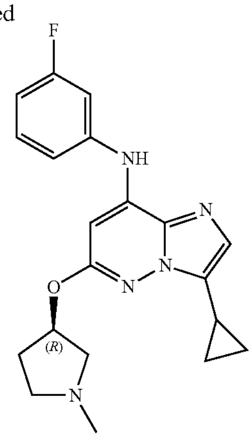

3

Synthesis of (R)-3-cyclopropyl-N-(3-fluorophenyl)-6-((1-methylpyrrolidin-3-yl)oxy)imidazo[1,2-b]pyridazin-8-amine

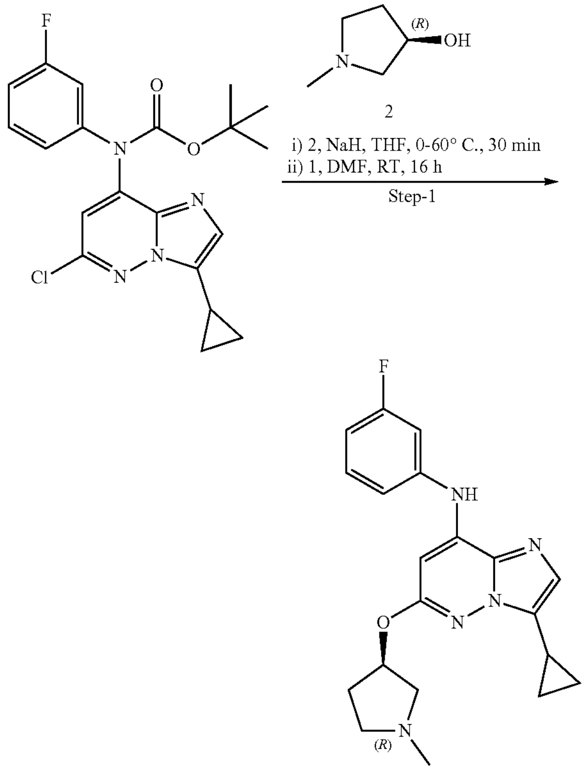

To a solution of (R)-1-methylpyrrolidin-3-ol (2) (0.188 g, 1.859 mmol, 3 eq.) in THF (2 mL) at 0 °C was added NaH (60% in mineral oil, 0.074 g, 1.859 mmol, 3 eq.) and heated to 60 °C, stirred for 30 min. Volatiles were evaporated, obtained sodium salt was dissolved in DMF (4 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure and obtained crude compound was purified by Prep-HPLC to afford (R)-3-cyclopropyl-N-(3-fluorophenyl)-6-((1-methylpyrrolidin-3-yl)oxy)imidazo[1,2-b]pyridazin-8-amine (3) as an off white solid (0.021 g, 9% yield). $R_f$=0.2 (8:2 Hexane/EtOAc). LCMS (m/z): 368.2 $(M+H)^+$. $^1$H NMR (400 MHz, DMSO-$d_6$) δ 9.43 (s, 1H), 7.41 (q, J=7.7 Hz, 1H), 7.30-7.18 (m, 3H), 6.93 (td, J=8.5, 2.6 Hz, 1H), 6.09 (s, 1H), 5.26 (tt, J=6.3, 3.1 Hz, 1H), 2.80 (dd, J=10.6, 6.2 Hz, 1H), 2.64 (dd, J=11.0, 3.2 Hz, 2H), 2.38-2.25 (m, 2H), 2.24 (s, 3H), 2.10 (tt, J=8.3, 5.2 Hz, 1H), 1.90-1.78 (m, 1H), 0.97 (dt, J=8.6, 3.2 Hz, 2H), 0.84 (tt, J=4.9, 2.1 Hz, 2H).

Example 20

Synthetic Scheme for (R)-3-cyclopropyl-N-(3-fluorophenyl)-6-((1-methylpiperidin-3-yl)oxy)imidazo[1,2-b]pyridazin-8-amine

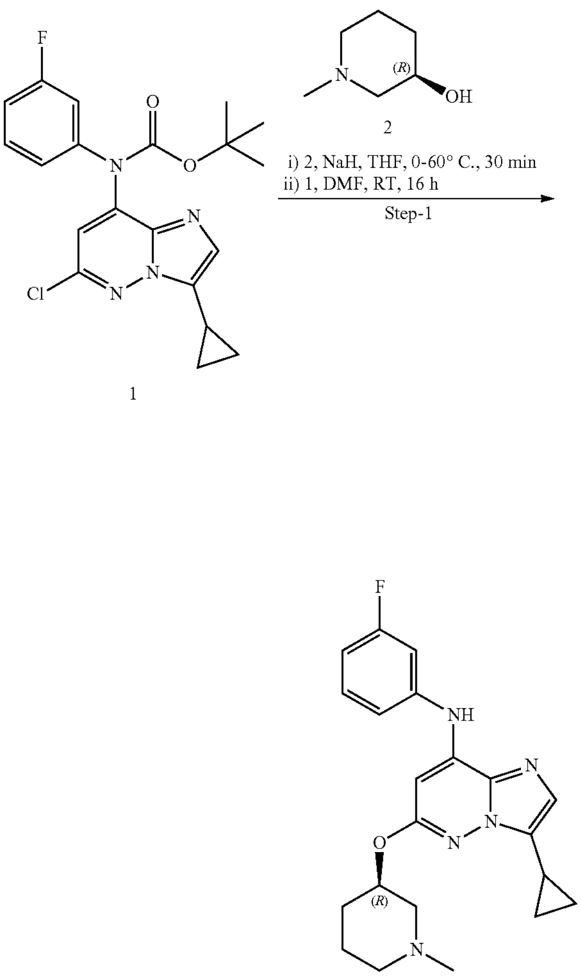

Synthesis of (R)-3-cyclopropyl-N-(3-fluorophenyl)-6-((1-methylpiperidin-3-yl)oxy)imidazo[1,2-b]pyridazin-8-amine

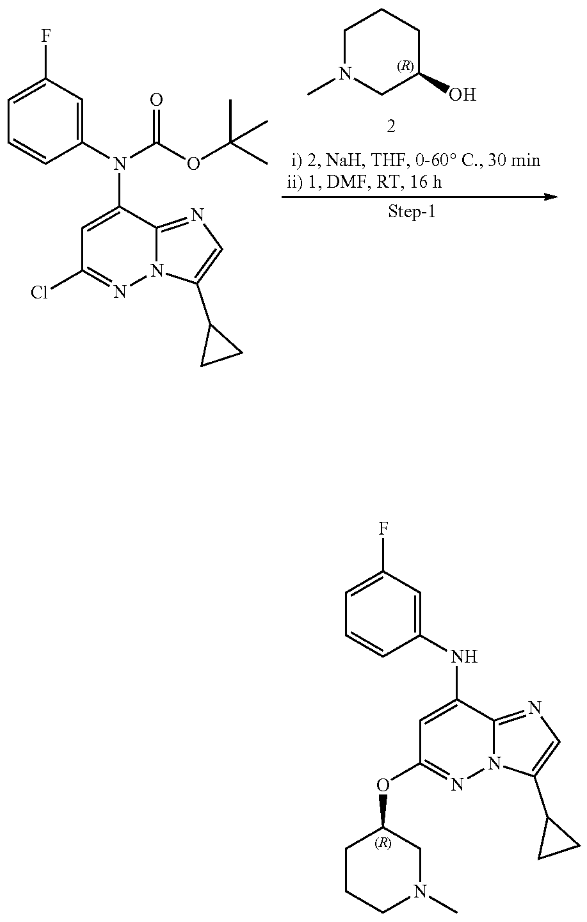

4

To a solution of (R)-1-methylpiperidin-3-ol (2) (0.214 g, 1.865 mmol, 3 eq.) in THF (2 mL) at 0 °C was added NaH (60% in mineral oil, 0.074 g, 1.859 mmol, 3 eq.) and heated to 60 °C, stirred for 30 min. Volatiles were evaporated, obtained sodium salt was dissolved in DMF (4 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure and obtained crude compound was purified by Prep-HPLC to afford (R)-3-cyclopropyl-N-(3-fluorophenyl)-6-((1-methylpiperidin-3-yl)oxy)imidazo[1,2-b]pyridazin-8-amine (4) as an off white solid (45 mg, 9% yield). $R_f$=0.3 (9:1 DCM/MeOH). LCMS (m/z): 368.2 $(M+H)^+$. $^1H$ NMR (400 MHz, DMSO-$d_6$): δ 9.43 (s, 1H), 7.41 (q, J=7.7 Hz, 1H), 7.30-7.18 (m, 3H), 6.94 (td, J=8.5, 2.5 Hz, 1H), 6.06 (s, 1H), 4.97 (tt, J=8.0, 3.9 Hz, 1H), 2.94-2.85 (m, 1H), 2.21-2.17 (m, 1H), 2.17 (s, 3H), 2.08 (tt, J=8.6, 5.3 Hz, 2H), 2.00-1.92 (m, 1H), 1.76-1.67 (m, 1H), 1.59-1.40 (m, 3H), 0.97 (dt, J=9.0, 3.0 Hz, 2H), 0.87-0.79 (m, 2H).

Example 21

Synthetic Scheme for (S)-3-cyclopropyl-N-(3-fluorophenyl)-6-((1-methylpyrrolidin-3-yl)oxy)imidazo[1,2-b]pyridazin-8-amine

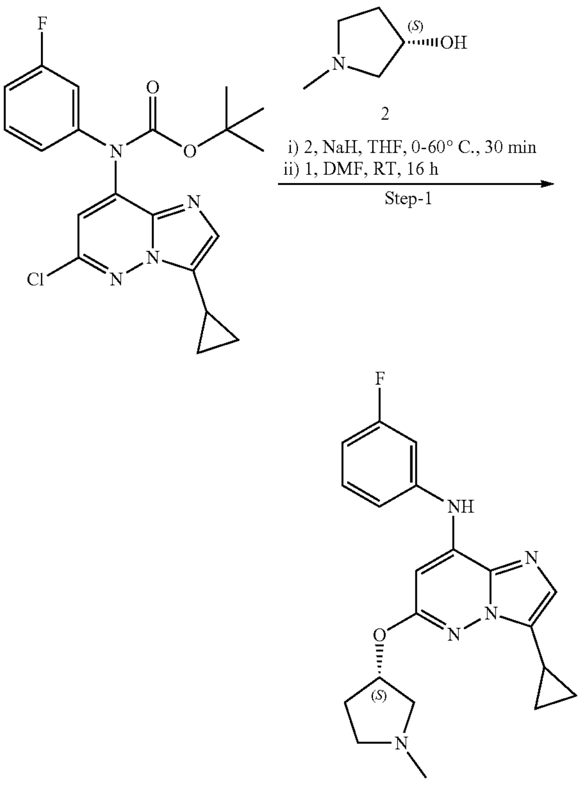

5

Synthesis of (S)-3-cyclopropyl-N-(3-fluorophenyl)-6-((1-methylpyrrolidin-3-yl)oxy)imidazo[1,2-b]pyridazin-8-amine

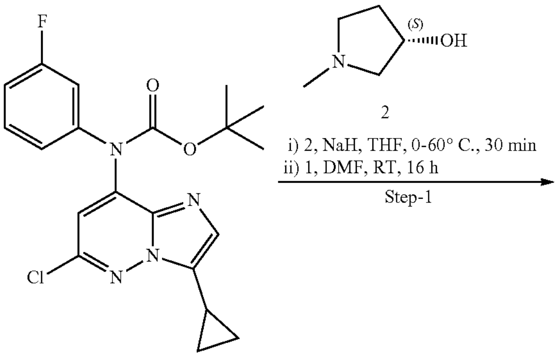

-continued

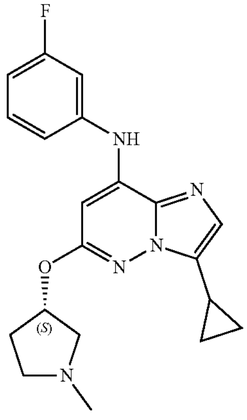

5

To a solution of (S)-1-methylpyrrolidin-3-ol (2) (0.188 g, 1.859 mmol, 3 eq.) in THF (5 mL) at 0 °C was added NaH (60% in mineral oil, 0.074 g, 1.865 mmol, 3 eq.) and heated to 60 °C, stirred for 30 min. Volatiles were evaporated, obtained sodium salt was dissolved in DMF (2 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (3 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure and obtained crude compound was purified by Prep-HPLC to afford (S)-3-cyclopropyl-N-(3-fluorophenyl)-6-((1-methylpyrrolidin-3-yl)oxy)imidazo[1,2-b]pyridazin-8-amine (5) as an off white solid (45 mg, 19% yield). $R_f$=0.2 (9:1 MeOH/DCM). LCMS (m/z): 368.2 $(M+H)^+$. $^1$H NMR (400 MHz, DMSO-$d_6$) δ 9.45 (s, 1H), 7.47-7.37 (m, 1H), 7.31-7.19 (m, 3H), 6.94 (td, J=8.6, 2.5 Hz, 1H), 6.10 (s, 1H), 5.28 (dp, J=9.1, 3.0 Hz, 1H), 2.85 (dd, J=10.8, 6.2 Hz, 1H), 2.74-2.66 (m, 2H), 2.44-2.28 (m, 5H), 2.11 (tt, J=8.4, 5.2 Hz, 1H), 1.86 (ddd, J=13.6, 9.8, 4.7 Hz, 1H), 0.99 (dq, J=8.6, 3.8, 3.1 Hz, 2H), 0.85 (tt, J=4.9, 2.0 Hz, 2H).

Example 22

Synthetic Scheme for (R)-3-cyclopropyl-N-(3-fluorophenyl)-6-(pyrrolidin-3-yloxy)imidazo[1,2-b]pyridazin-8-amine

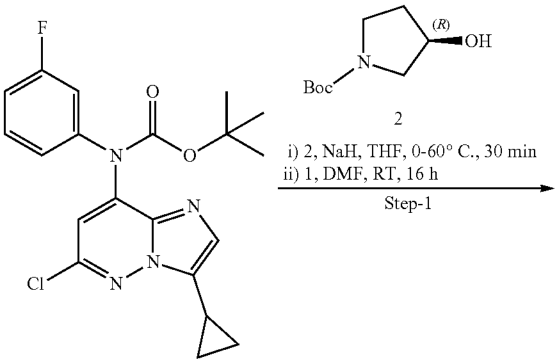

-continued

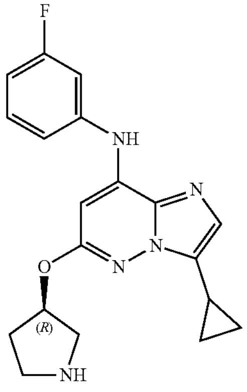

6

Synthesis of (R)-3-cyclopropyl-N-(3-fluorophenyl)-6-(pyrrolidin-3-yloxy)imidazo[1,2-b]pyridazin-8-amine

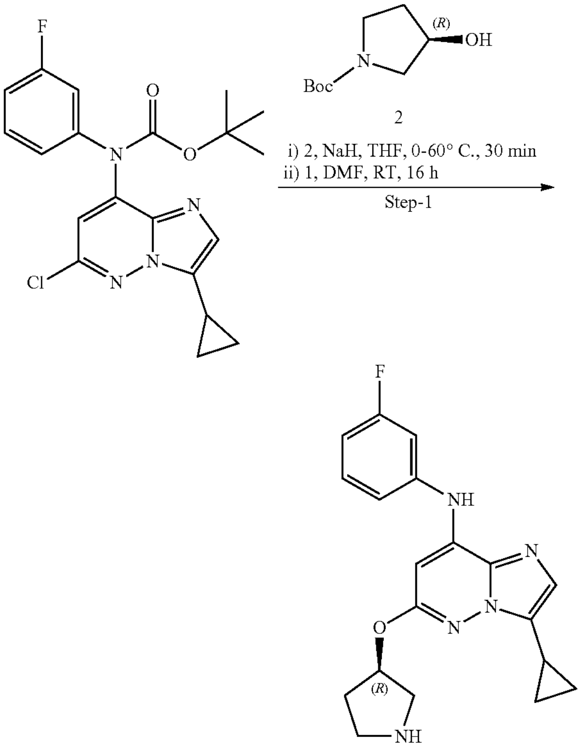

6

To a solution of tert-butyl (R)-3-hydroxypyrrolidine-1-carboxylate (2) (0.348 g, 1.865 mmol, 3 eq.) in THF (2 mL) at 0 °C was added NaH (60% in mineral oil, 0.074 g, 1.865 mmol, 3 eq.) and heated to 60 °C, stirred for 30 min. Volatiles were evaporated, obtained sodium salt was dissolved in DMF (2 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure and obtained crude compound was purified by Prep-HPLC to afford (R)-3-cyclopropyl-N-(3-fluorophenyl)-6-(pyrrolidin-3-yloxy)imidazo[1,2-b]pyridazin-8-amine (6) as an off white solid (14 mg, 6% yield). $R_f$=0.2 (9:1 MeOH/DCM). LCMS (m/z): 354.24 $(M+H)^+$. $^1H$ NMR (400 MHz, DMSO-$d_6$): δ 9.47 (s, 1H), 7.47-7.37 (m, 1H), 7.29-7.19 (m, 3H), 6.94 (ddd, J=10.3, 8.1, 2.5 Hz, 1H), 6.08 (s, 1H), 5.35 (p, J=3.1 Hz, 1H), 3.25 (dd, J=12.6, 5.4 Hz, 2H), 3.04 (d, J=14.0 Hz, 1H), 3.02-2.91 (m, 2H), 2.11 (dq, J=11.3, 4.4, 3.4 Hz, 2H), 1.98-1.90 (m, 1H), 1.03-0.94 (m, 2H), 0.89-0.81 (m, 2H).

Example 23

Synthetic Scheme for (S)-3-cyclopropyl-N-(3-fluorophenyl)-6-((1-methylpiperidin-3-yl)oxy)imidazo[1,2-b]pyridazin-8-amine

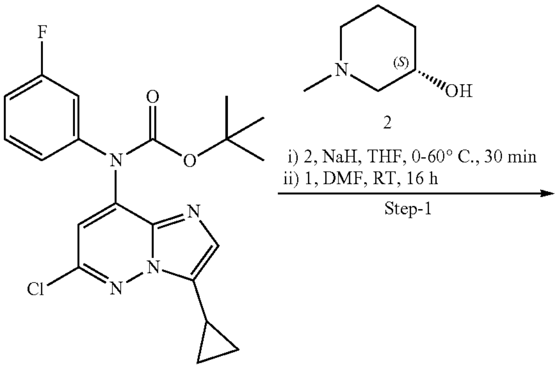

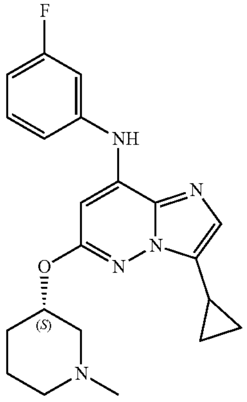

7

Synthesis of (S)-3-cyclopropyl-N-(3-fluorophenyl)-6-((1-methylpiperidin-3-yl)oxy)imidazo[1,2-b]pyridazin-8-amine

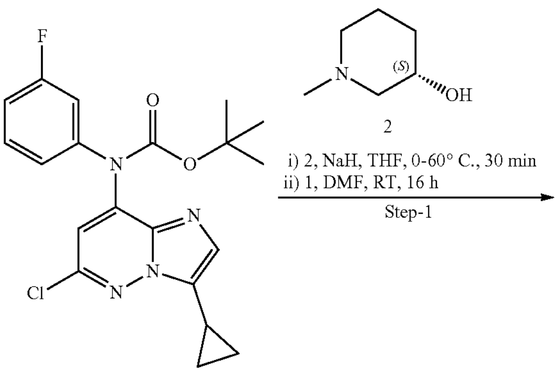

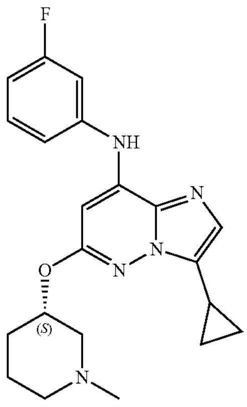

7

To a solution of (S)-1-methylpiperidin-3-ol (2) (0.214 g, 1.865 mmol, 3 eq.) in THF (2 mL) at 0 °C was added NaH (60% in mineral oil, 0.074 g, 1.859 mmol, 3 eq.) and heated to 60 °C, stirred for 30 min. Volatiles were evaporated, obtained sodium salt was dissolved in DMF (2 mL) and added a solution of tert-butyl tert-butyl (6-chloro-3-cyclopropylimidazo[1,2-b]pyridazin-8-yl)(3-fluorophenyl)carbamate (1) (0.25 g, 0.621 mmol, 1 eq.) in DMF (1 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure and obtained crude compound was purified by Prep-HPLC to afford (S)-3-cyclopropyl-N-(3-fluorophenyl)-6-((1-methylpiperidin-3-yl)oxy)imidazo[1,2-b]pyridazin-8-amine (7) as an off white solid (5 mg, 5% yield). $R_f$=0.3 (9:1 DCM/MeOH). LCMS (m/z): 382.06 $(M+H)^+$. $^1H$ NMR (400 MHz, DMSO-$d_6$): δ 9.43 (s, 1H), 7.41 (q, J=7.7 Hz, 1H), 7.30-7.18 (m, 3H), 6.94 (td, J=8.5, 2.5 Hz, 1H), 6.06 (s, 1H), 4.97 (tt, J=7.9, 3.9 Hz, 1H), 3.16 (s, 1H), 2.93-2.86 (m, 1H), 2.16 (s, 3H), 2.15-2.06 (m, 2H), 2.04 (d, J=7.3 Hz, 1H), 1.96 (d, J=11.5 Hz, 1H), 1.71 (dd, J=11.1, 6.9 Hz, 1H), 1.58-1.41 (m, 2H), 1.02-0.93 (m, 2H), 0.87-0.79 (m, 2H).

Example 24

Synthetic Scheme for (S)—N-benzyl-3-cyclopropyl-6-((1-methylpyrrolidin-3-yl)oxy)imidazo[1,2-b]pyridazin-8-amine

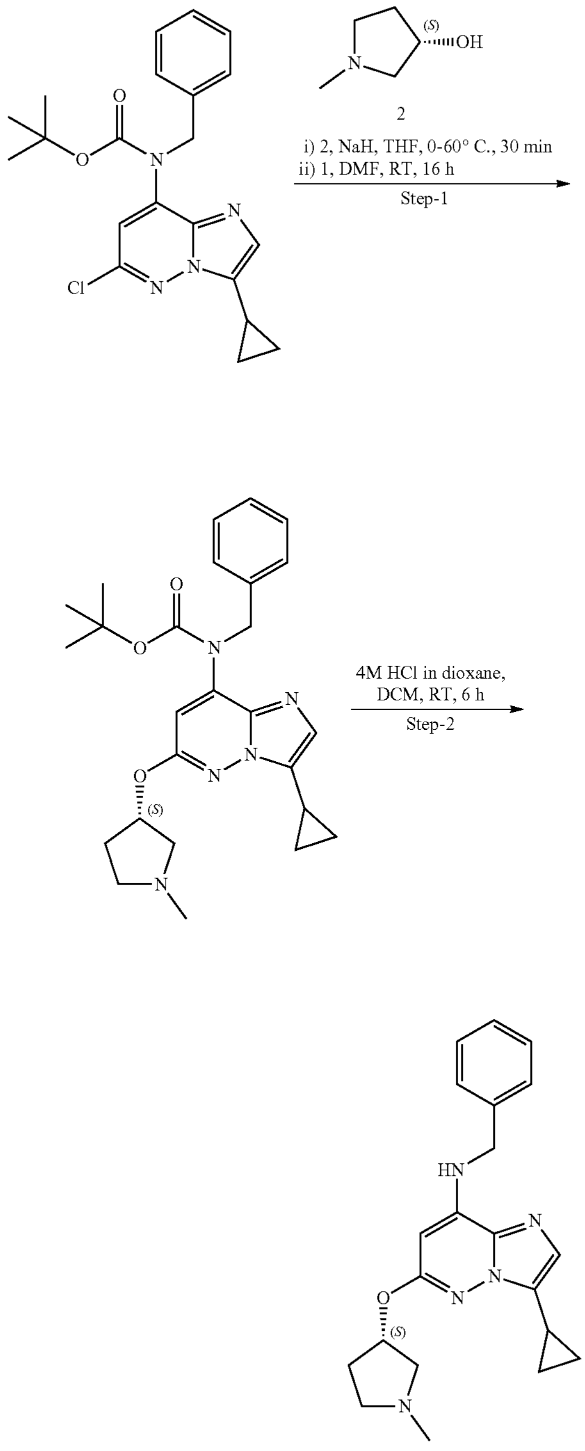

8

Synthesis of tert-butyl (S)-benzyl(3-cyclopropyl-6-((1-methylpyrrolidin-3-yl)oxy)imidazo[1,2-b]pyridazin-8-yl)carbamate (3)

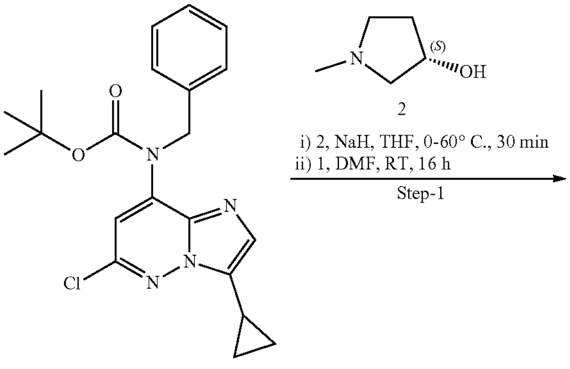

1

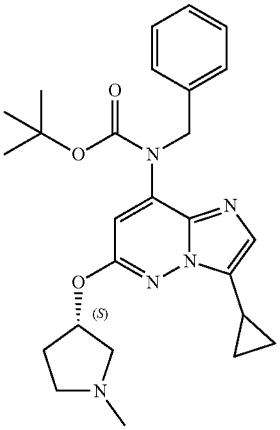

3

To a solution of tert-butyl (S)-1-methylpyrrolidin-3-ol (2) (0.152 g, 1.507 mmol, 3 eq.) in THF (5 mL) at 0 °C was added NaH (60% in mineral oil, 0.058 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (3 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (S)-benzyl(3-cyclopropyl-6-((1-methylpyrrolidin-3-yl)oxy)imidazo[1,2-b]pyridazin-8-yl)carbamate (3) as a pale yellow liquid (0.44 g, quantitative) which was carried to next step without any further purification, $R_f$=0.2 (9:1 DCM/MeOH). Note: Observed Cpd-1 de-boc as a major in TLC & LCMS. LCMS (m/z): 464.10 $(M+H)^+$.

Synthesis of (S)—N-benzyl-3-cyclopropyl-6-((1-methylpyrrolidin-3-yl)oxy)imidazo[1,2-b]pyridazin-8-amine

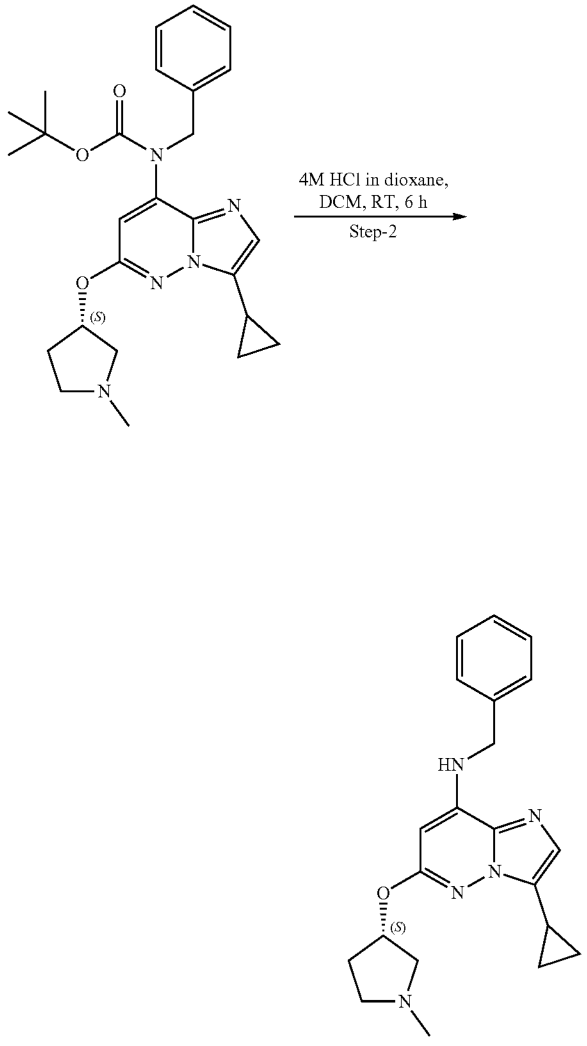

8

To a solution of tert-butyl (S)-3-((8-((tert-butoxycarbonyl)(3-fluorophenyl)amino)-3-cyclopropylimidazo[1,2-b]pyridazin-6-yl)oxy)piperidine-1-carboxylate (3) (0.22 g, 0.461 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC as an eluent afford (S)—N-benzyl-3-cyclopropyl-6-((1-methylpyrrolidin-3-yl)oxy)imidazo[1,2-b]pyridazin-8-amine (8) as an off white solid (28 mg, 23% yield). $R_f$=0.2 (9:1 DCM/MeOH). LCMS (m/z): 364.29 $(M+H)^+$. $^1H$ NMR (400 MHz, DMSO-$d_6$) δ 7.86 (t, J=6.4 Hz, 1H), 7.39-7.27 (m, 4H), 7.27-7.18 (m, 1H), 7.08 (s, 1H), 5.43 (s, 1H), 5.19 (dp, J=9.0, 3.0 Hz, 1H), 4.47 (d, J=6.4 Hz, 2H), 2.77 (dd, J=10.6, 6.1 Hz, 1H), 2.69-2.53 (m, 2H), 2.37-2.30 (m, 1H), 2.30-2.24 (m, 1H), 2.23 (s, 3H), 2.04 (tt, J=8.4, 5.2 Hz, 1H), 1.83-1.71 (m, 1H), 0.99-0.89 (m, 2H), 0.80 (tq, J=4.9, 2.0 Hz, 2H). Note: $^1H$-NMR observed formate salt at δ 8.32 ppm.

Example 25

Synthetic Scheme for (R)—N-benzyl-3-cyclopropyl-6-((1-methylpiperidin-3-yl)oxy)imidazo[1,2-b]pyridazin-8-amine

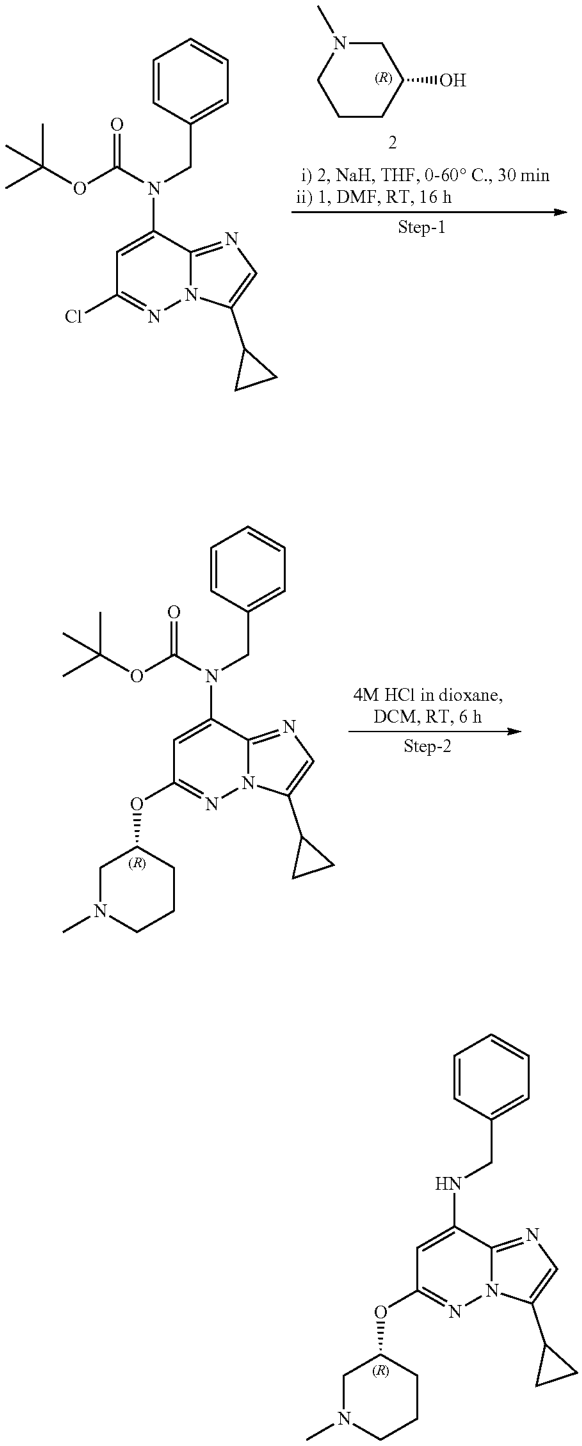

9

Synthesis of tert-butyl (R)-benzyl(3-cyclopropyl-6-((1-methylpiperidin-3-yl)oxy)imidazo[1,2-b]pyridazin-8-yl)carbamate Synthesis of (R)—N-benzyl-3-cyclopropyl-6-((1-methylpiperidin-3-yl)oxy)imidazo[1,2-b]pyridazin-8-amine

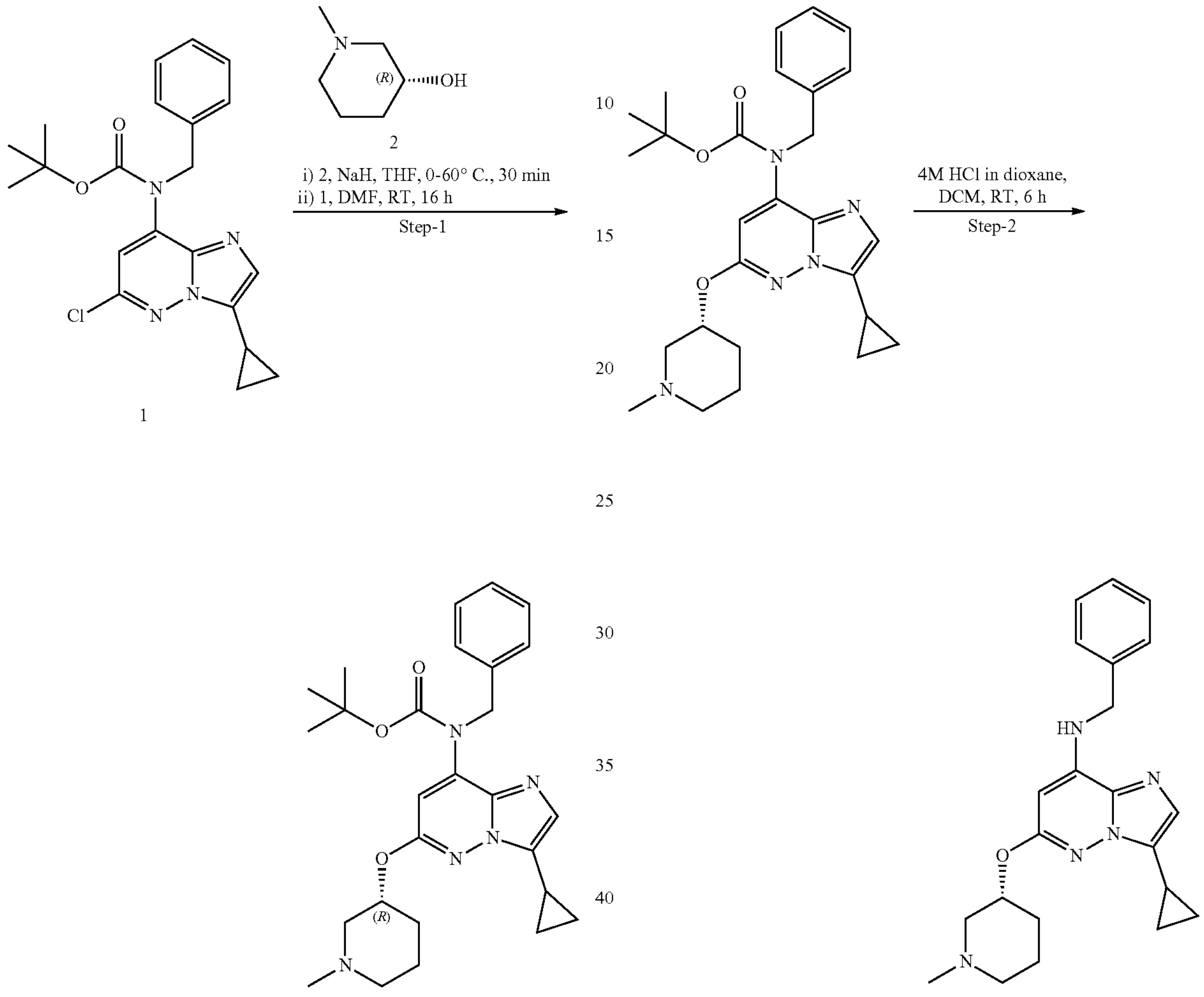

1 2 3 9

To a solution of (R)-1-methylpiperidin-3-ol (2) (0.173 g, 1.507 mmol, 3 eq.) in THE (3 mL) at 0 °C was added NaH (60% in mineral oil, 0.058 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (1 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (R)-benzyl(3-cyclopropyl-6-((1-methylpiperidin-3-yl)oxy)imidazo[1,2-b]pyridazin-8-yl)carbamate (3) as a pale yellow liquid (0.44 g, quantitative) which was carried to next step without any further purification, $R_f$=0.2 (9:1 DCM/MeOH). Note: Observed Cpd-1 de-boc as a major in TLC & LCMS. LCMS (m/z): 478.09 $(M+H)^+$.

To a solution of tert-butyl (R)-benzyl(3-cyclopropyl-6-((1-methylpiperidin-3-yl)oxy)imidazo[1,2-b]pyridazin-8-yl)carbamate (3) (0.44 g, 0.923 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (R)—N-benzyl-3-cyclopropyl-6-((1-methylpiperidin-3-yl)oxy)imidazo[1,2-b]pyridazin-8-amine (9) as an off white solid (53 mg, 15% yield). $R_f$=0.2 (9:1 DCM/MeOH). LCMS (m/z): 378.17 $(M+H)^+$. $^1H$ NMR (400 MHz, DMSO-$d_6$): δ 7.87 (t, J=6.4 Hz, 1H), 7.39-7.28 (m, 4H), 7.28-7.20 (m, 1H), 7.10 (s, 1H), 5.44 (s, 1H), 4.93 (dt, J=8.1, 4.1 Hz, 1H), 4.49 (d, J=6.4 Hz, 2H), 2.91 (dd, J=11.1, 3.6 Hz, 1H), 2.63-2.52 (m, 1H), 2.19 (s, 3H), 2.13-1.98 (m, 3H), 1.93 (t, J=8.9 Hz, 1H), 1.76-1.66 (m, 1H), 1.58-1.37 (m, 2H) 0.99-0.90 (m, 2H), 0.84-0.76 (m, 2H).

Example 26

Synthetic Scheme for (R)—N-benzyl-3-cyclopropyl-6-((1-methylpyrrolidin-3-yl)oxy)imidazo[1,2-b]pyridazin-8-amine

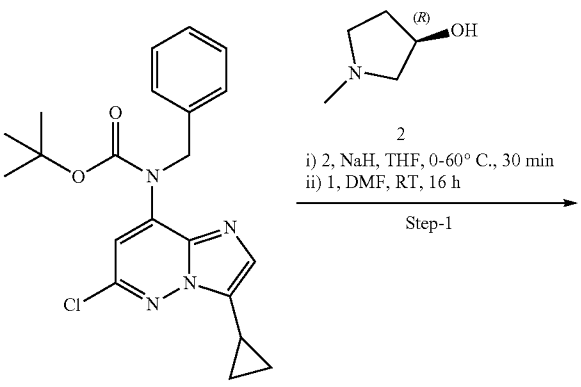

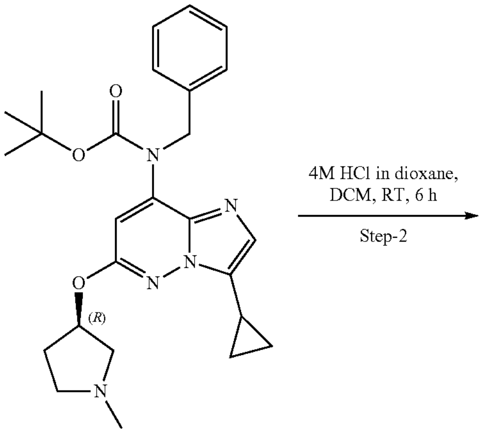

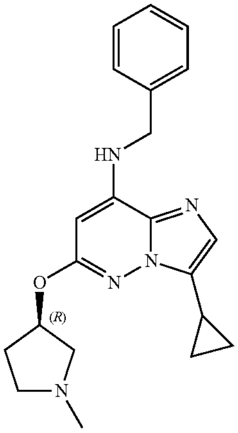

10

Synthesis of tert-butyl (R)-benzyl(3-cyclopropyl-6-((1-methylpyrrolidin-3-yl)oxy)imidazo[1,2-b]pyridazin-8-yl)carbamate (3)

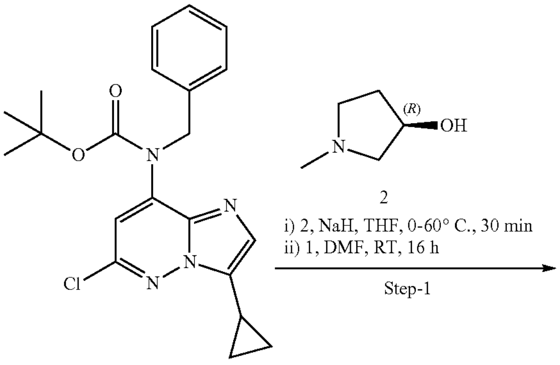

1

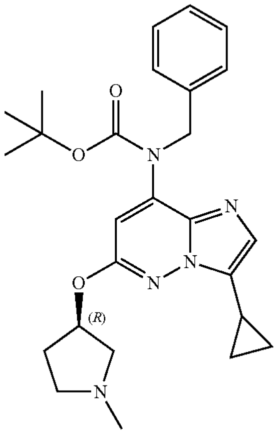

3

To a solution of tert-butyl (R)-1-methylpyrrolidin-3-ol (2) (0.152 g, 1.507 mmol, 3 eq.) in THE (5 mL) at 0 °C was added NaH (60% in mineral oil, 0.058 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (3 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (R)-benzyl(3-cyclopropyl-6-((1-methylpyrrolidin-3-yl)oxy)imidazo[1,2-b]pyridazin-8-yl)carbamate (3) as a pale yellow liquid (0.44 g, quantitative) which was carried to next step without any further purification, $R_f$=0.2 (9:1 DCM/MeOH). Note: Observed Cpd-1 de-boc as a major in TLC & LCMS. LCMS (m/z): 464.12 $(M+H)^+$.

Synthesis of (R)—N-benzyl-3-cyclopropyl-6-((1-methylpyrrolidin-3-yl)oxy)imidazo[1,2-b]pyridazin-8-amine

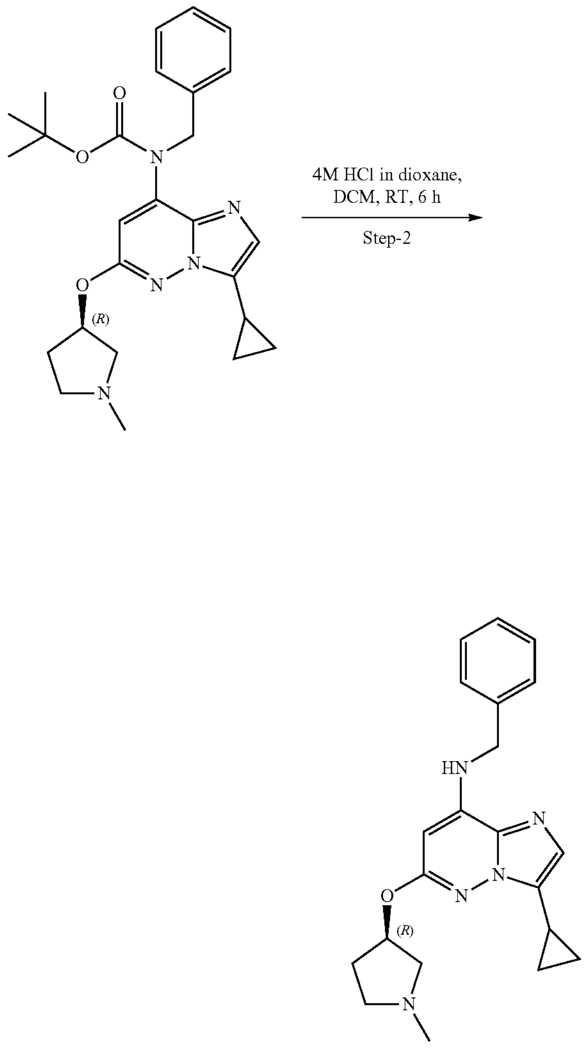

10

To a solution of tert-butyl (R)-benzyl(3-cyclopropyl-6-((1-methylpyrrolidin-3-yl)oxy)imidazo[1,2-b]pyridazin-8-yl)carbamate (3) (0.22 g, 0.461 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (R)—N-benzyl-3-cyclopropyl-6-((1-methylpyrrolidin-3-yl)oxy)imidazo[1,2-b]pyridazin-8-amine (10) as an off white solid (35 mg, 13% yield). $R_f$=0.2 (9:1 DCM/MeOH). LCMS (m/z): 364.2 $(M+H)^+$. $^1H$ NMR (400 MHz, DMSO) δ 7.86 (t, J=6.3 Hz, 1H), 7.34-7.28 (m, 4H), 7.21 (t, J=6.9 Hz, 1H), 7.07 (s, 1H), 5.42 (s, 1H), 5.20-5.15 (m, 1H), 4.46 (d, J=6.2 Hz, 2H), 2.74 (dd, J=10.5, 6.2 Hz, 1H), 2.61-2.54 (m, 2H), 2.30-2.25 (m, 2H), 2.20 (s, 3H), 1.79-1.72 (m, 1H), 1.22 (s, 1H), 0.93 (dd, J=8.4, 2.4 Hz, 2H), 0.78 (dd, J=4.9, 2.2 Hz, 2H).

Example 27

Synthetic Scheme for (S)—N-benzyl-3-cyclopropyl-6-((1-methylpiperidin-3-yl)oxy)imidazo[1,2-b]pyridazin-8-amine

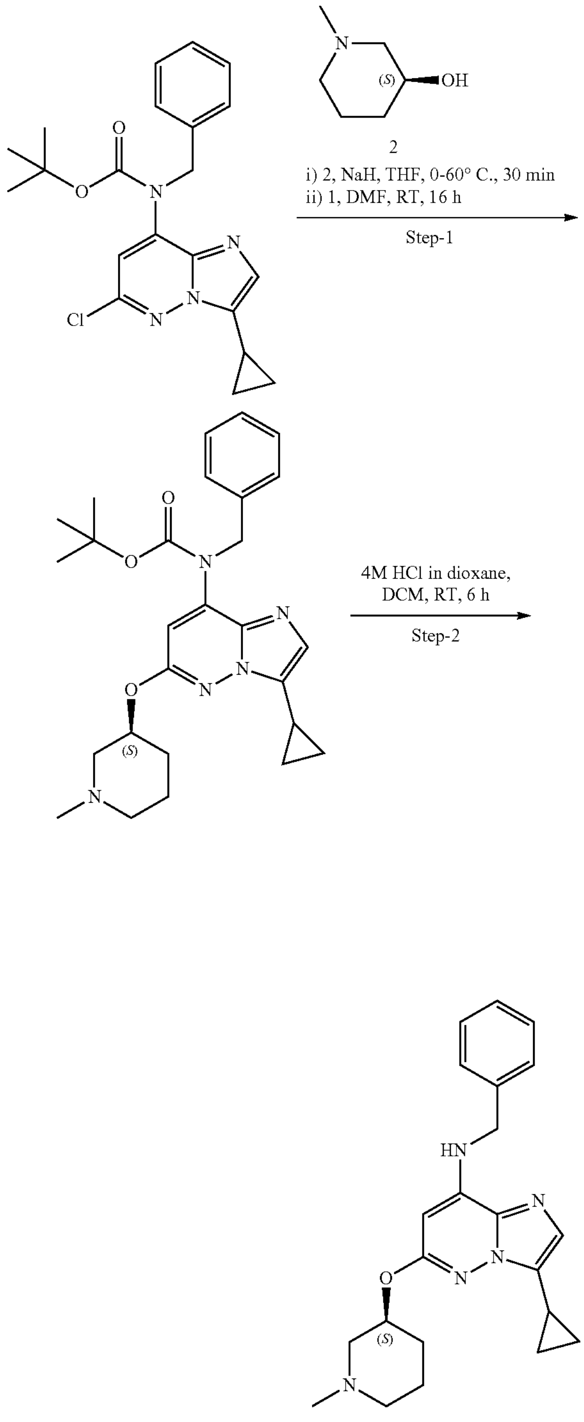

11

Synthesis of tert-butyl (S)-benzyl(3-cyclopropyl-6-((1-methylpiperidin-3-yl)oxy)imidazo[1,2-b]pyridazin-8-yl)carbamate (3)

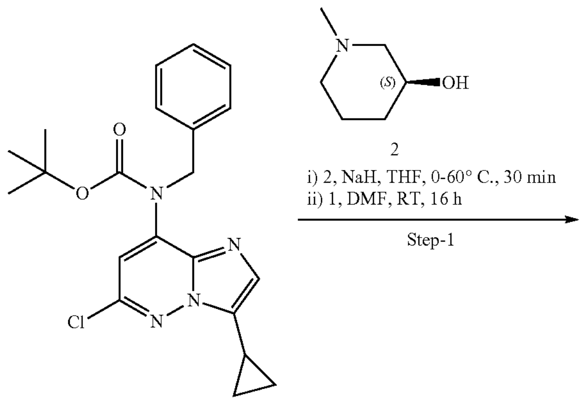

1

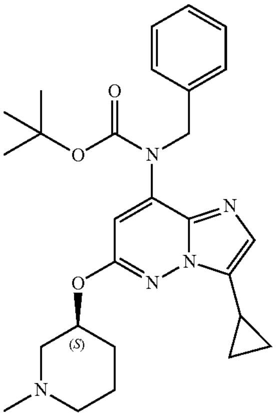

3

To a solution of (S)-1-methylpiperidin-3-ol (2) (0.173 g, 1.507 mmol, 3 eq.) in THE (3 mL) at 0 °C was added NaH (60% in mineral oil, 0.058 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (S)-benzyl(3-cyclopropyl-6-((1-methylpiperidin-3-yl)oxy)imidazo[1,2-b]pyridazin-8-yl)carbamate (3) as a pale yellow liquid (0.44 g, quantitative) which was carried to next step without any further purification, $R_f$=0.2 (9:1 DCM/MeOH). Note: Observed Cpd-1 de-boc as a major in TLC & LCMS. LCMS (m/z): 478.08 $(M+H)^+$.

Synthesis of (S)—N-benzyl-3-cyclopropyl-6-((1-methylpiperidin-3-yl)oxy)imidazo[1,2-b]pyridazin-8-amine

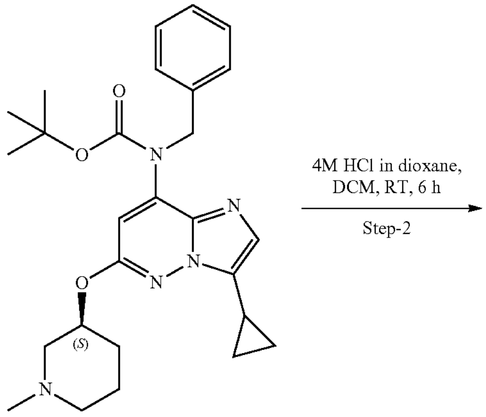

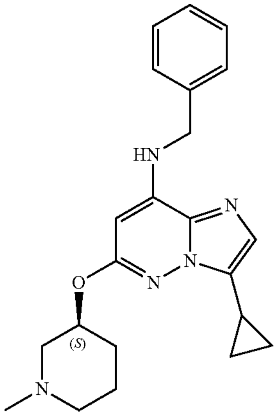

11

To a solution of tert-butyl (S)-benzyl(3-cyclopropyl-6-((1-methylpiperidin-3-yl)oxy)imidazo[1,2-b]pyridazin-8-yl)carbamate (3) (0.44 g, 0.461 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (S)—N-benzyl-3-cyclopropyl-6-((1-methylpiperidin-3-yl)oxy)imidazo[1,2-b]pyridazin-8-amine (11) as an off white solid (17 mg, 9% yield). $R_f$=0.2 (9:1 DCM/MeOH). LCMS (m/z): 378.18 $(M+H)^+$. $^1H$ NMR (400 MHz, DMSO-$d_6$): δ 7.86 (t, J=6.4 Hz, 1H), 7.38-7.27 (m, 4H), 7.27-7.19 (m, 1H), 7.09 (s, 1H), 5.42 (s, 1H), 4.90 (tt, J=8.0, 3.9 Hz, 1H), 4.48 (d, J=6.4 Hz, 2H), 2.90-2.82 (m, 1H), 2.49-2.41 (m, 1H), 2.14 (s, 3H), 2.12-1.95 (m, 3H), 1.92 (dd, J=12.3, 5.3 Hz, 1H), 1.73-1.64 (m, 1H), 1.48 (ttd, J=12.7, 9.7, 3.6 Hz, 1H), 1.39 (d, J=10.2 Hz, 1H), 0.98-0.89 (m, 2H), 0.83-0.75 (m, 2H).

Example 28

Synthetic Scheme for (S)—N-benzyl-3-cyclopropyl-6-(pyrrolidin-3-yloxy)imidazo[1,2-b]pyridazin-8-amine

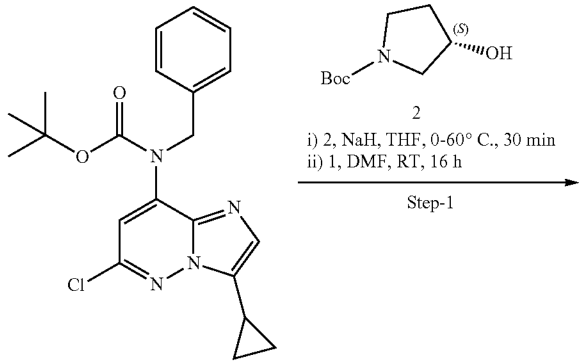

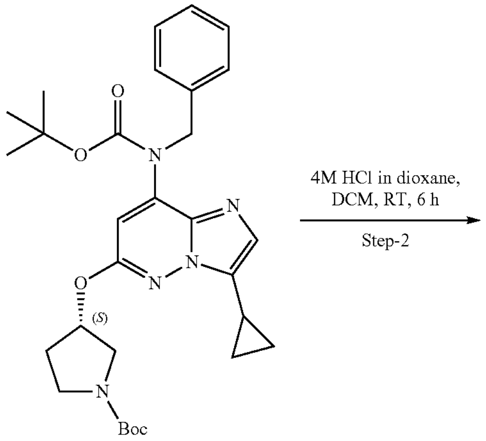

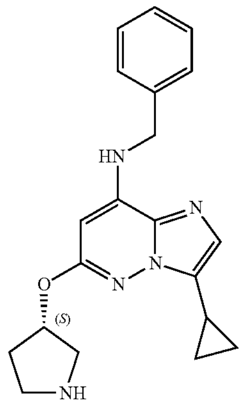

12

Synthesis of tert-butyl (S)-3-((8-(benzyl(tert-butoxycarbonyl)amino)-3-cyclopropylimidazo[1,2-b]pyridazin-6-yl)oxy)pyrrolidine-1-carboxylate (3)

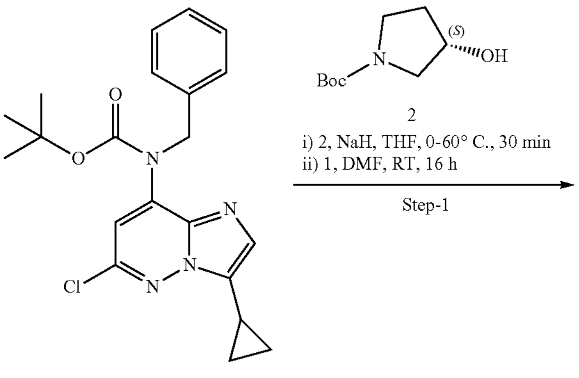

1

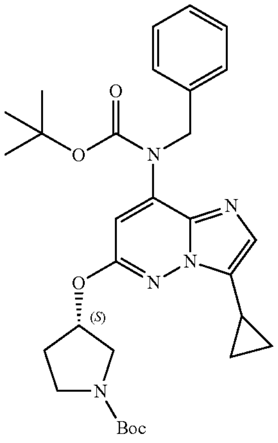

3

To a solution of tert-butyl (S)-3-hydroxypyrrolidine-1-carboxylate (2) (0.28 g, 1.506 mmol, 3 eq.) in THE (3 mL) at 0 °C was added NaH (60% in mineral oil, 0.060 g, 1.506 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (4 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to tert-butyl (S)-3-((8-(benzyl(tert-butoxycarbonyl)amino)-3-cyclopropylimidazo[1,2-b]pyridazin-6-yl)oxy)pyrrolidine-1-carboxylate (3) as a pale yellow liquid (0.23 g, quantitative) which was carried to next step without any further purification, $R_f$=0.2 (9:1 DCM/MeOH). Note: Observed Cpd-1 de-boc as a major in TLC & LCMS. LCMS (m/z): 550.22 $(M+H)^+$.

Synthesis of (S)—N-benzyl-3-cyclopropyl-6-(pyrrolidin-3-yloxy)imidazo[1,2-b]pyridazin-8-amine

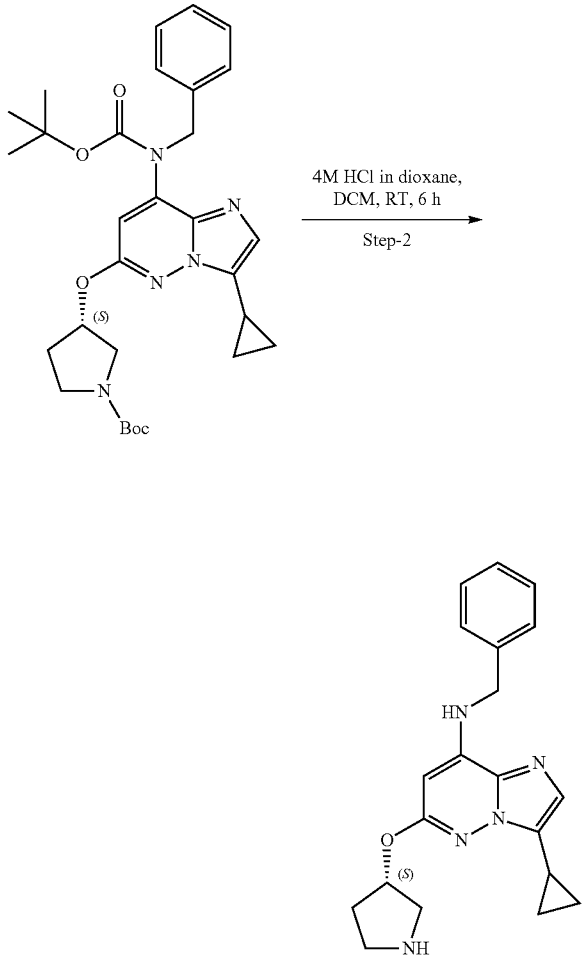

12

To a solution of tert-butyl (S)-3-((8-(benzyl(tert-butoxycarbonyl)amino)-3-cyclopropylimidazo[1,2-b]pyridazin-6-yl)oxy)pyrrolidine-1-carboxylate (3) (0.23 g, 0.418 mmol, 1 eq.) in DCM (6 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (S)—N-benzyl-3-cyclopropyl-6-(pyrrolidin-3-yloxy)imidazo[1,2-b]pyridazin-8-amine (12) as an off white solid (4 mg, 3% yield). $R_f$=0.2 (9:1 DCM/MeOH). LCMS (m/z): 350.20 $(M+H)^+$. $^1H$ NMR (400 MHz, DMSO-$d_6$) δ 7.85 (t, J=6.4 Hz, 1H), 7.31 (q, J=7.4 Hz, 4H), 7.26-7.17 (m, 1H), 7.08 (s, 1H), 5.41 (s, 1H), 5.22 (dq, J=6.3, 2.9 Hz, 1H), 4.47 (d, J=6.4 Hz, 2H), 3.14 (dd, J=12.6, 5.6 Hz, 1H), 2.91-2.85 (m, 3H), 2.83-2.77 (m, 1H), 2.08-1.97 (m, 2H), 1.80 (dt, J=9.4, 5.5 Hz, 1H), 0.98-0.89 (m, 2H), 0.88-0.76 (m, 2H).

Example 29

Synthetic Scheme for (R)—N-benzyl-3-cyclopropyl-6-(piperidin-3-yloxy)imidazo[1,2-b]pyridazin-8-amine

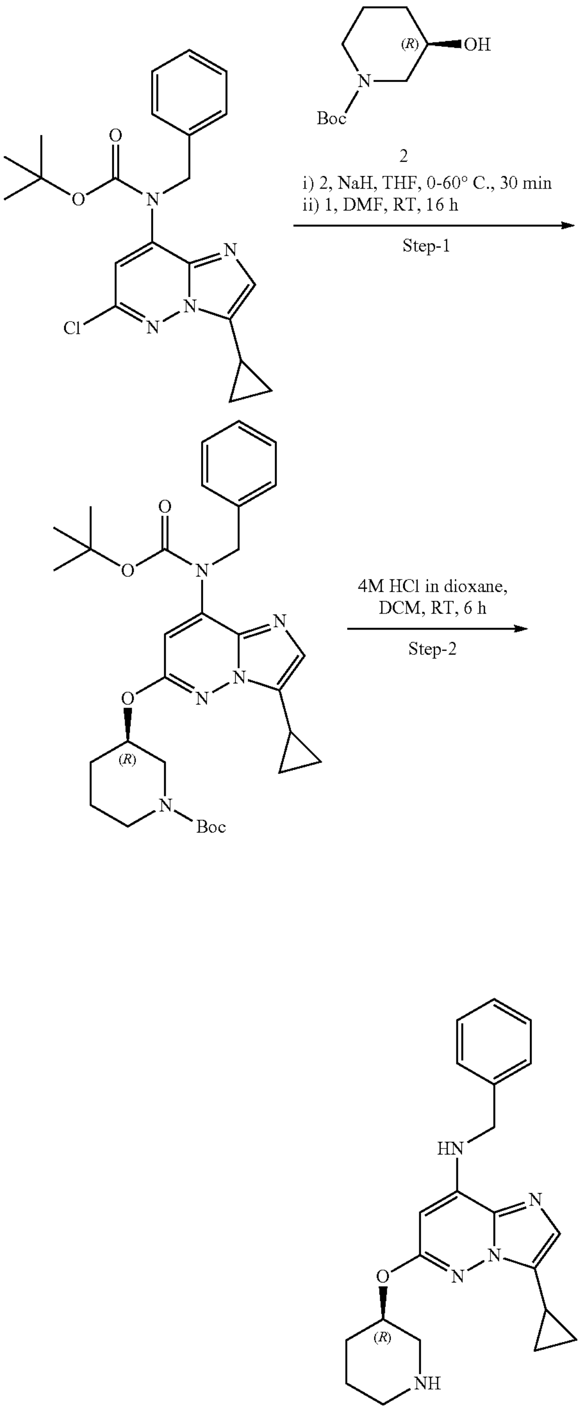

13

Synthesis of tert-butyl (R)-3-((8-(benzyl(tert-butoxycarbonyl)amino)-3-cyclopropylimidazo[1,2-b]pyridazin-6-yl)oxy)piperidine-1-carboxylate (3)

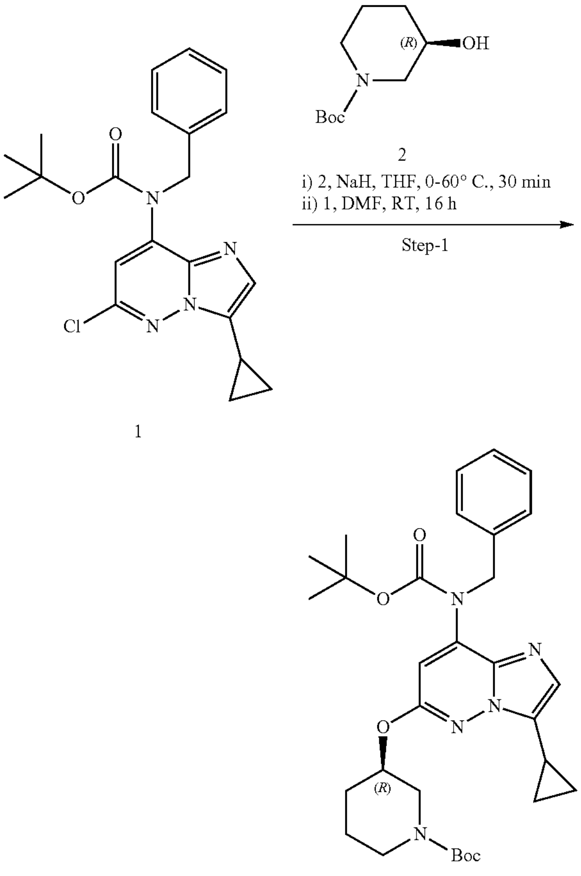

1

2

3

To a solution of tert-butyl (R)-3-hydroxypiperidine-1-carboxylate (2) (0.302 g, 1.507 mmol, 3 eq.) in THE (2 mL) at 0 °C was added NaH (60% in mineral oil, 0.060 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (R)-3-((8-(benzyl(tert-butoxycarbonyl)amino)-3-cyclopropylimidazo[1,2-b]pyridazin-6-yl)oxy)piperidine-1-carboxylate (3) as a pale yellow liquid (0.24 g, quantitative) which was carried to next step without any further purification, $R_f$=0.2 (9:1 DCM/MeOH). Note: Observed Cpd-1 de-boc as a major in TLC & LCMS. LCMS (m/z): 564.25 $(M+H)^+$.

Synthesis of (R)—N-benzyl-3-cyclopropyl-6-(piperidin-3-yloxy)imidazo[1,2-b]pyridazin-8-amine

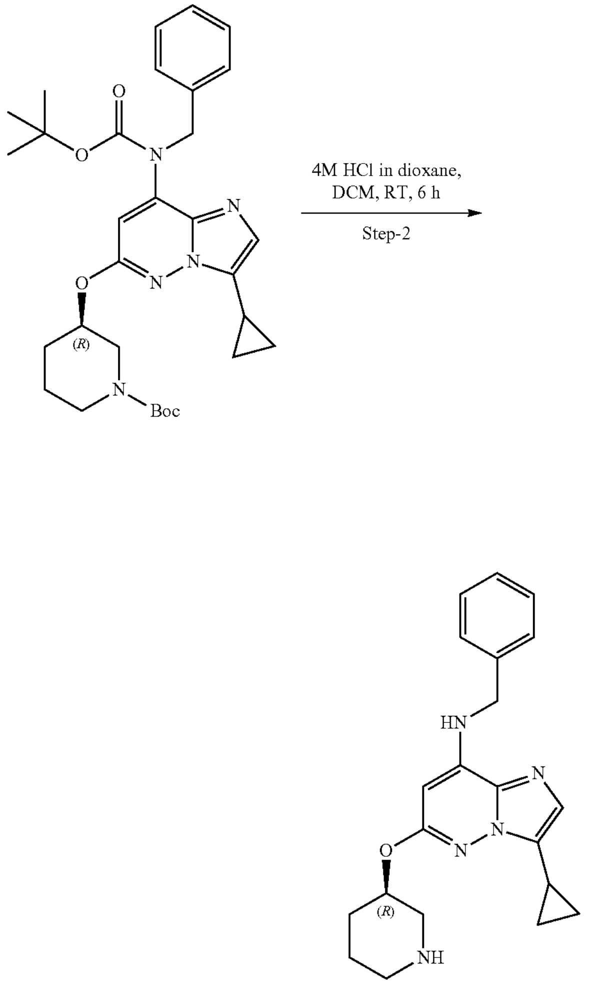

13

To a solution of tert-butyl (R)-3-((8-(benzyl(tert-butoxycarbonyl)amino)-3-cyclopropylimidazo[1,2-b]pyridazin-6-yl)oxy)piperidine-1-carboxylate (3) (0.24 g, 0.426 mmol, 1 eq.) in DCM (6 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC to afford (R)—N-benzyl-3-cyclopropyl-6-((1-methylpiperidin-3-yl)oxy)imidazo[1,2-b]pyridazin-8-amine (13) as an off white solid (17 mg, 3% yield). $R_f$=0.2 (9:1 DCM/MeOH). LCMS (m/z): 364.04 $(M+H)^+$. $^1H$ NMR (400 MHz, DMSO-$d_6$): δ 7.82 (t, J=6.4 Hz, 1H), 7.37-7.26 (m, 3H), 7.22 (t, J=6.7 Hz, 1H), 7.07 (s, 1H), 5.42 (s, 1H), 4.75 (tt, J=8.4, 4.0 Hz, 1H), 4.47 (d, J=6.4 Hz, 2H), 3.13 (dd, J=12.5, 3.8 Hz, 1H), 2.73 (dd, J=12.4, 4.5 Hz, 1H), 2.47-2.38 (m, 1H), 2.10-1.93 (m, 3H), 1.62 (dd, J=11.0, 6.7 Hz, 1H), 1.44 (ddd, J=20.0, 12.3, 6.3 Hz, 2H), 1.26-1.17 (m, 2H), 0.93 (dt, J=8.8, 3.0 Hz, 2H), 0.78 (dt, J=5.3, 2.8 Hz, 2H).

Example 30

Synthetic Scheme for N-benzyl-3-cyclopropyl-6-(piperidin-4-yloxy)imidazo[1,2-b]pyridazin-8-amine

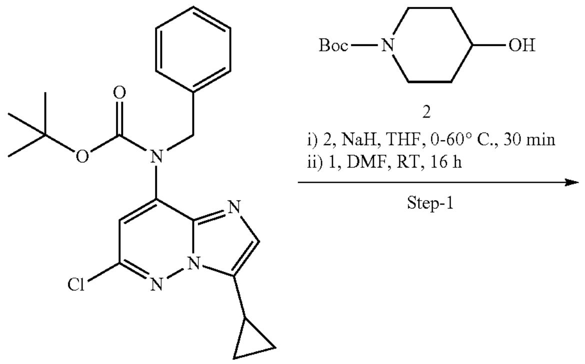

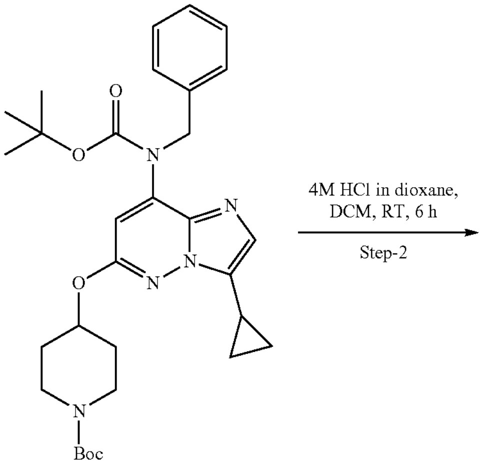

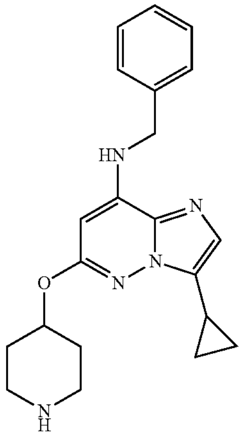

14

Synthesis of tert-butyl 4-((8-(benzyl(tert-butoxycarbonyl)amino)-3-cyclopropylimidazo[1,2-b]pyridazin-6-yl)oxy)piperidine-1-carboxylate

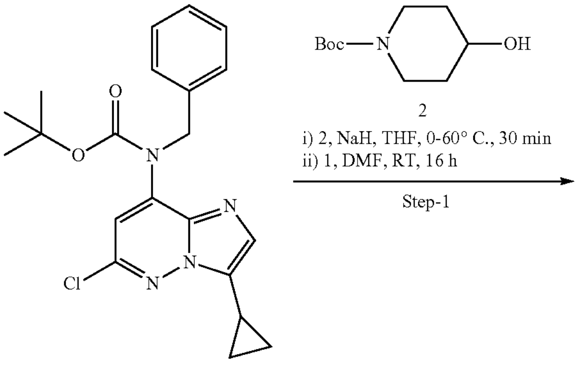

1

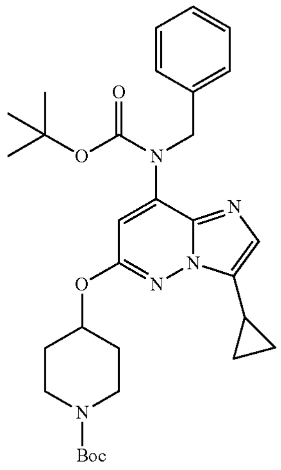

3

To a solution of tert-butyl 4-hydroxypiperidine-1-carboxylate (2) (0.302 g, 1.507 mmol, 3 eq.) in THF (4 mL) at 0 °C was added NaH (60% in mineral oil, 0.060 g, 1.507 mmol, 3 eq.) and heated to 60 °C, stirred for 30 min. Volatiles were evaporated, obtained sodium salt was dissolved in DMF (2 mL) and added a solution of tert-butyl benzyl(6-chloro-3-cyclopropylimidazo[1,2-b]pyridazin-8-yl)carbamate (1) (0.2 g, 0.502 mmol, 1 eq.) in DMF (2 mL) at 0 °C. The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl 4-((8-(benzyl(tert-butoxycarbonyl)amino)-3-cyclopropylimidazo[1,2-b]pyridazin-6-yl)oxy)piperidine-1-carboxylate (3) as a pale yellow liquid (0.22 g, quantitative) which was carried to next step without any further purification, $R_f$=0.2 (9:1 DCM/MeOH). Note: Observed Cpd-1 de-boc as a major in TLC & LCMS. LCMS (m/z): 464.36 $(M+H)^+$.

Synthesis of N-benzyl-3-cyclopropyl-6-(piperidin-4-yloxy)imidazo[1,2-b]pyridazin-8-amine

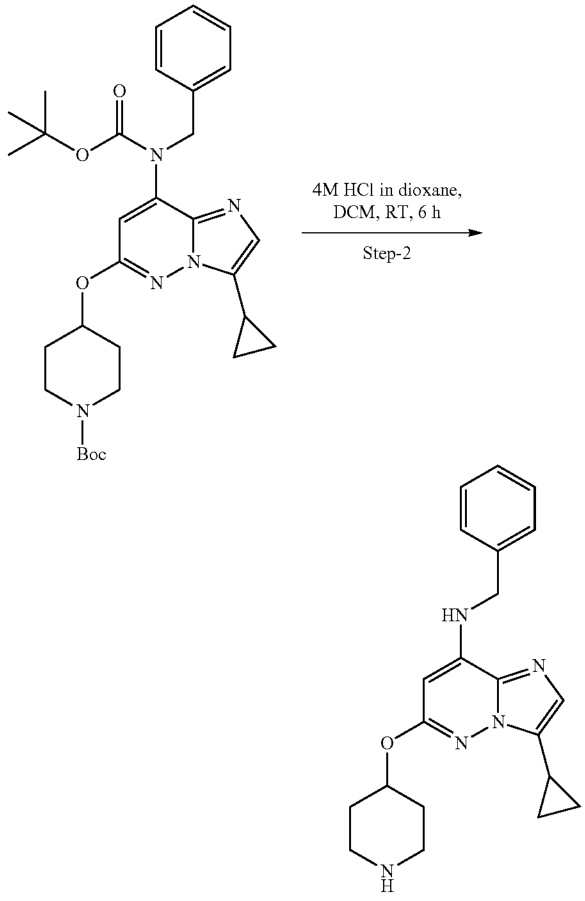

14

To a solution of tert-butyl 4-((8-(benzyl(tert-butoxycarbonyl)amino)-3-cyclopropylimidazo[1,2-b]pyridazin-6-yl)oxy)piperidine-1-carboxylate (3) (0.22 g, 0.390 mmol, 1 eq.) in DCM (6 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC to afford (R)—N-benzyl-3-cyclopropyl-6-((1-methylpiperidin-3-yl)oxy)imidazo[1,2-b]pyridazin-8-amine (14) as an off white solid (15 mg, 11% yield). $R_f$=0.2 (9:1 DCM/MeOH). LCMS (m/z): 364.1 $(M+H)^+$. $^1H$ NMR (400 MHz, DMSO-$d_6$): δ 7.84 (t, J=6.5 Hz, 1H), 7.38-7.27 (m, 4H), 7.22 (t, J=6.8 Hz, 1H), 7.07 (s, 1H), 5.45 (s, 1H), 4.91 (dt, J=9.1, 4.7 Hz, 1H), 4.47 (d, J=6.4 Hz, 2H), 3.00 (dd, J=11.7, 5.5 Hz, 2H), 2.75-2.62 (m, 3H), 2.02 (ddd, J=13.5, 6.9, 4.1 Hz, 3H), 1.57 (dtd, J=13.1, 9.4, 3.7 Hz, 2H), 0.92 (dt, J=8.5, 3.1 Hz, 2H), 0.82-0.73 (m, 2H).

Example 31

| No. | Structure | IUPAC name | Yield | LCMS | $^1H$-NMR |
|---|---|---|---|---|---|
| 15 | 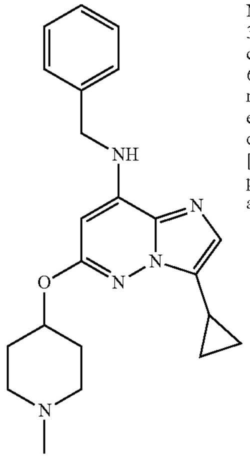 | N-benzyl-3-cyclopropyl-6-((1-methylpiperidin-4-yl)oxy)imidazo[1,2-b]pyridazin-8-amine | 8 mg. | 378.26 $(M + H)^+$. | $^1H$ NMR (400 MHz, DMSO-$d_6$,): δ 7.81 (t, J = 6 Hz, 1H), 7.34-7.28 (m, 4H), 7.23-7.19 (m, 1H), 7.07 (s, 1H), 5.43 (s, 1H), 4.81-4.77 (m, 1H), 4.47 (d, J = 6.4 Hz, 2H), 2.60-2.58 (m, 2H), 2.17-2.02 (m, 5H), 2.01-1.96 (m, 3H), 1.66-1.58 (m, 2H), 0.94-0.89 (m, 2H), 0.79-0.75 (m, 2H). |

Example 32

Synthetic Scheme for (S)—N8-benzyl-3-cyclopropyl-N6-(1-methylpiperidin-3-yl)imidazo[1,2-b]pyridazine-6,8-diamine

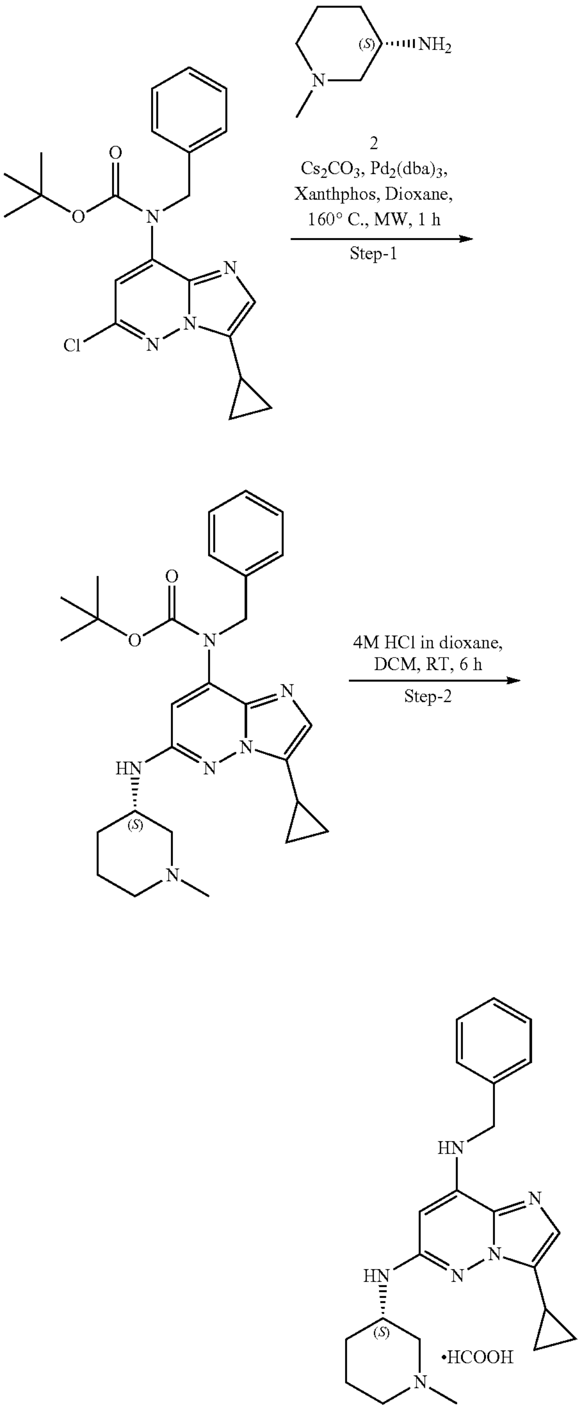

16

Synthesis of tert-butyl (S)-benzyl(3-cyclopropyl-6-((1-methylpiperidin-3-yl)amino)imidazo[1,2-b]pyridazin-8-yl)carbamate

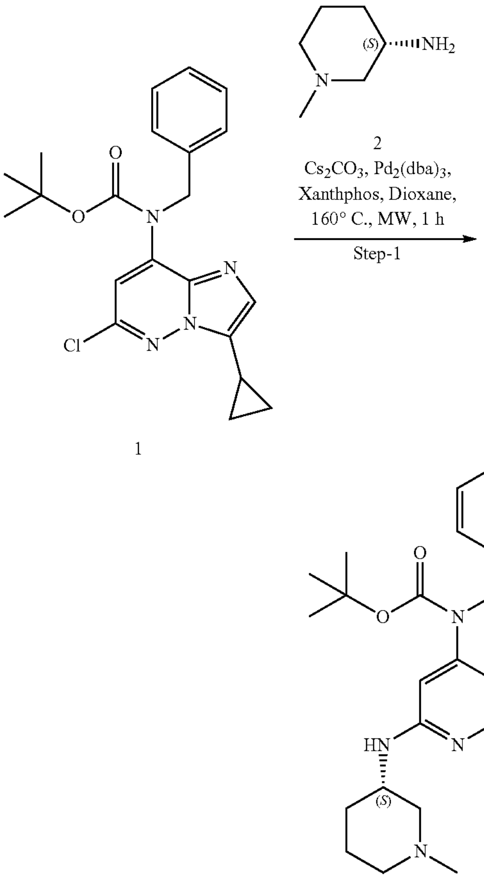

1

3

Under an atmosphere of argon 1,4,-dioxane (4 mL) was added to tert-butyl benzyl(6-chloro-3-cyclopropylimidazo[1,2-b]pyridazin-8-yl)carbamate (1) (0.2 g, 0.502 mmol, 1 eq.), $Cs_2CO_3$ (0.5 g, 1.507 mmol, 3 eq.), (S)-3-Amino-1-methyl-piperidine (2) (0.172 g, 1.507 mmol, 3 eq.) and xantphos (0.029 g, 0.1 mmol) at room temperature. The reaction mixture was degas with argon for 10 min and added Tris(dibenzylideneacetone)dipalladium (0.046 g, 10 mol %) again degas with argon for 10 min and heated to 160 °C for 1 h in Microwave. The reaction mixture was diluted with ethyl acetate and filtered with celite. The organic phase was washed with water (3×20 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl (S)-benzyl(3-cyclopropyl-6-((1-methylpiperidin-3-yl)amino)imidazo[1,2-b]pyridazin-8-yl)carbamate (3) as a pale yellow liquid (0.1 g, quantitative) which was carried to next step without any further purification, $R_f$=0.2 (2:8 hexane/ethyl acetate). Note: Observed Cpd-1 de-boc as a major in TLC & LCMS. LCMS (m/z): 478.14 $(M+H)^+$.

Synthesis of (S)—N8-benzyl-3-cyclopropyl-N6-(1-methylpiperidin-3-yl)imidazo[1,2-b]pyridazine-6,8-diamine

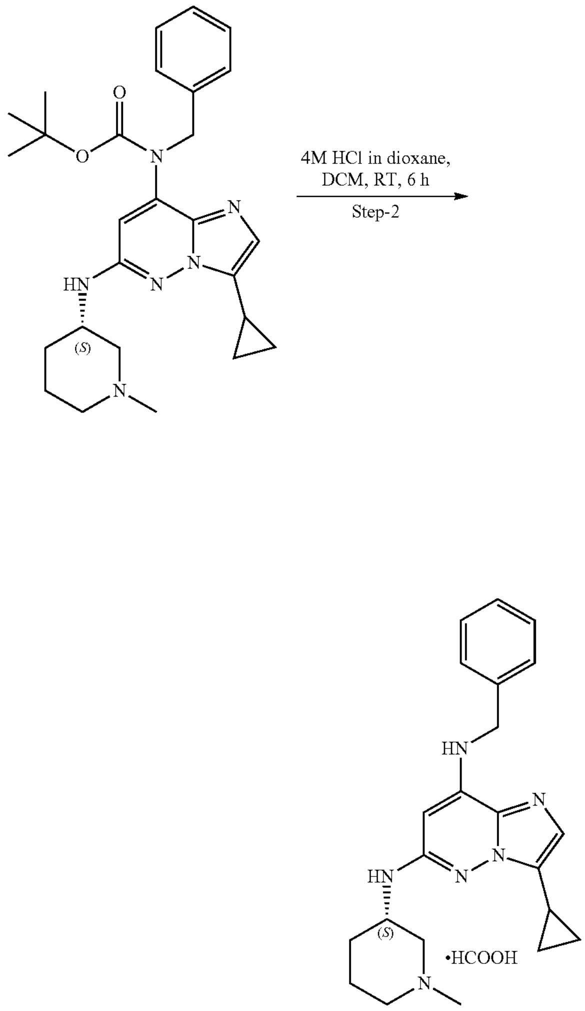

16

To a solution of tert-butyl (S)-benzyl(3-cyclopropyl-6-((1-methylpiperidin-3-yl)amino)imidazo[1,2-b]pyridazin-8-yl)carbamate (3) (0.1 g, 0.21 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford (S)—N8-benzyl-3-cyclopropyl-N6-(1-methylpiperidin-3-yl)imidazo[1,2-b]pyridazine-6,8-diamine (16) as an off white solid (28 mg, 35% yield). $R_f$=0.2 (9:1 DCM/MeOH). LCMS (m/z): 377.1 $(M+H)^+$. $^1$H NMR (400 MHz, DMSO-$d_6$): δ 8.15 (d, J=1.8 Hz, 1H), 7.32 (dd, J=6.3, 4.4 Hz, 4H), 7.22 (dt, J=6.6, 3.6 Hz, 1H), 6.89 (d, J=1.8 Hz, 1H), 6.00 (d, J=7.6 Hz, 1H), 5.37 (s, 1H), 4.38 (d, J=6.3 Hz, 2H), 3.74 (d, J=9.8 Hz, 1H), 2.86 (d, J=10.5 Hz, 1H), 2.44 (d, J=2.2 Hz, 1H), 2.15 (d, J=1.9 Hz, 3H), 1.98 (td, J=7.9, 4.1 Hz, 2H), 1.84 (s, 1H), 1.74 (d, J=10.5 Hz, 1H), 1.63 (s, 1H), 1.48 (d, J=11.7 Hz, 1H), 1.19 (d, J=12.0 Hz, 1H), 0.88 (dq, J=8.4, 2.9 Hz, 2H), 0.75 (hept, J=2.5 Hz, 2H).

Example 33

Synthetic Scheme for N6-((1-oxa-7-azaspiro[3.5]nonan-2-yl)methyl)-N8-benzyl-3-cyclopropylimidazo[1,2-b]pyridazine-6,8-diamine

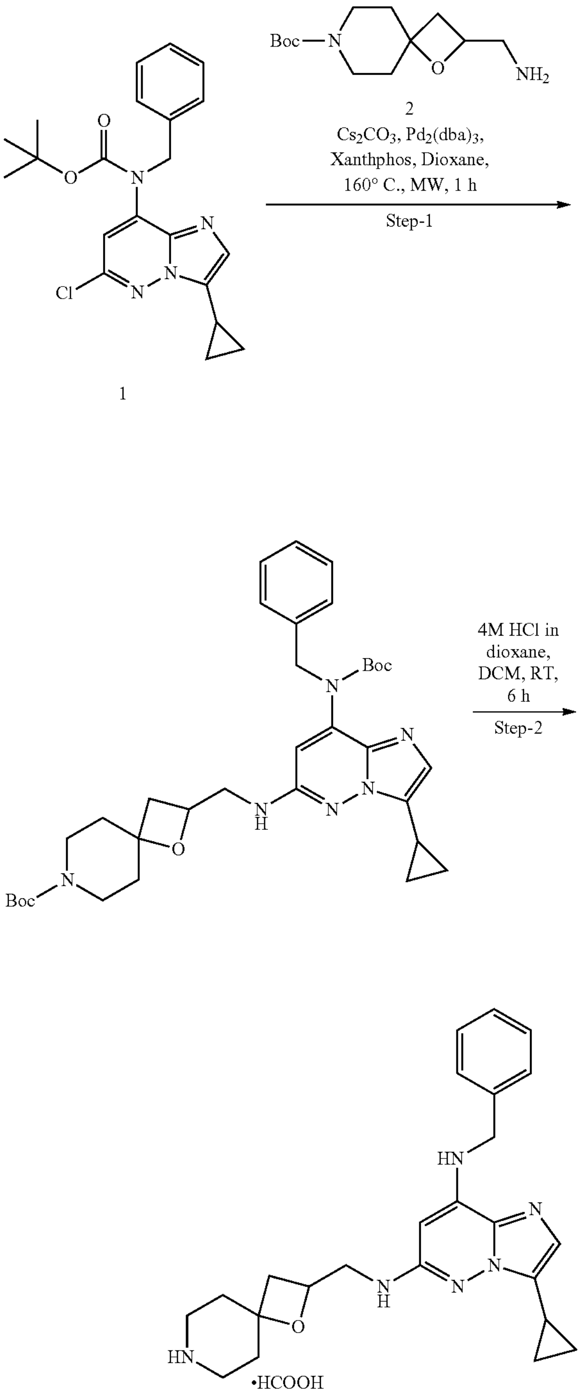

1

17

Synthesis of tert-butyl 2-(((8-(benzyl(tert-butoxycarbonyl)amino)-3-cyclopropylimidazo[1,2-b]pyridazin-6-yl)amino)methyl)-1-oxa-7-azaspiro[3.5]nonane-7-carboxylate

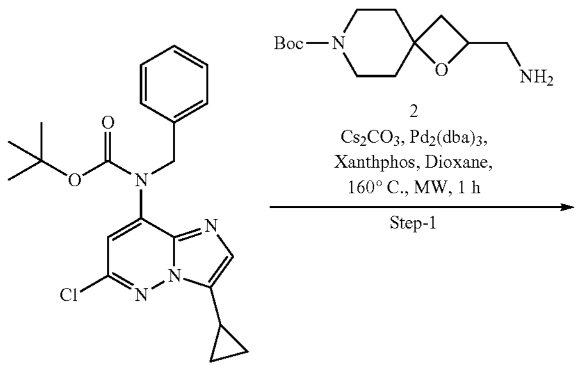

1

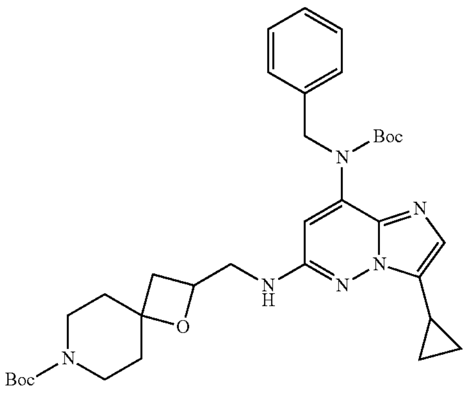

3

Under an atmosphere of argon 1,4,-dioxane (4 mL) was added to tert-butyl benzyl(6-chloro-3-cyclopropylimidazo[1,2-b]pyridazin-8-yl)carbamate (1) (0.2 g, 0.502 mmol, 1 eq.), $Cs_2CO_3$ (0.5 g, 1.507 mmol, 3 eq.), tert-butyl 2-(aminomethyl)-1-oxa-7-azaspiro[3.5]nonane-7-carboxylate (2) (0.172 g, 0.652 mmol, 1.3 eq.) and xantphos (0.030 g, 0.05 mmol, 0.1 eq.) at room temperature. The reaction mixture was degas with argon for 10 min and added Tris(dibenzylideneacetone)dipalladium (0.05 g, 0.05 mmol, 0.1 eq.) again degas with argon for 10 min and heated to 160 °C for 3 h in Microwave. The reaction mixture was diluted with ethyl acetate and filtered with celite. The organic phase was washed with water (3x20 mL), dried over sodium sulfate, filtered and concentrated under reduced pressure to provide crude product. Obtained crude compound was purified by silica phase column chromatography [with a gradient elution of 5-10% of MeOH/DCM] to afford tert-butyl 2-(((8-(benzyl(tert-butoxycarbonyl)amino)-3-cyclopropylimidazo[1,2-b]pyridazin-6-yl)amino)methyl)-1-oxa-7-azaspiro[3.5]nonane-7-carboxylate (3) as a yellow gum (0.12 g, quantitative) which was carried to next step without any further purification, $R_f$=0.3 (1:1 hexane/ethyl acetate). Note: Observed Cpd-1 de-boc as a major in TLC & LCMS. LCMS (m/z): 478.14 $(M+H)^+$.

Synthesis of N6-((1-oxa-7-azaspiro[3.5]nonan-2-yl)methyl)-N8-benzyl-3-cyclopropylimidazo[1,2-b]pyridazine-6,8-diamine

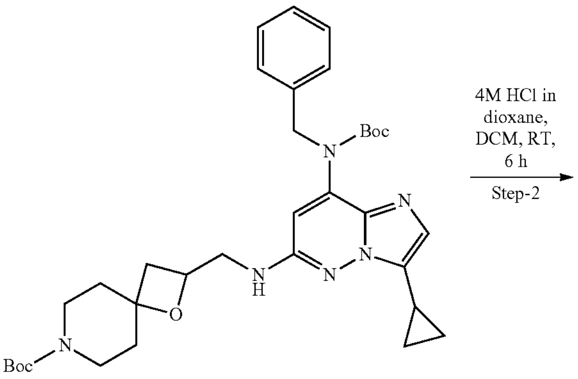

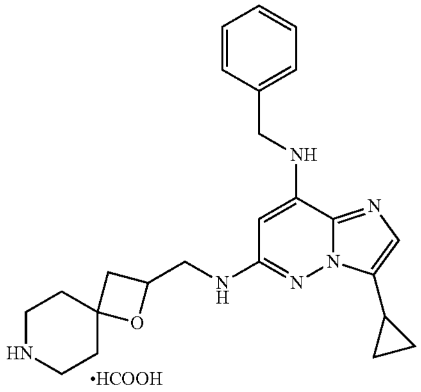

17

To a solution of tert-butyl 2-(((8-(benzyl(tert-butoxycarbonyl)amino)-3-cyclopropylimidazo[1,2-b]pyridazin-6-yl)amino)methyl)-1-oxa-7-azaspiro[3.5]nonane-7-carboxylate (3) (0.12 g, 0.194 mmol, 1 eq.) in DCM (5 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC to afford N6-((1-oxa-7-azaspiro[3.5]nonan-2-yl)methyl)-N8-benzyl-3-cyclopropylimidazo[1,2-b]pyridazine-6,8-diamine (17) as an off white solid (14 mg, 17% yield). $R_f$=0.1 (9:1 DCM/MeOH). LCMS (m/z): 419.37 $(M+H)^+$. $^1H$ NMR (400 MHz, DMSO-$d_6$): δ 7.38-7.27 (m, 5H), 7.22 (td, J=6.6, 2.4 Hz, 1H), 6.89 (d, J=1.7 Hz, 1H), 6.16 (t, J=5.7 Hz, 1H), 5.42 (d, J=1.8 Hz, 2H), 4.39 (d, J=6.3 Hz, 2H), 3.82 (s, 1H), 3.32-3.23 (m, 4H), 2.96 (dt, J=13.1, 5.8 Hz, 2H), 2.89 (t, J=6.1 Hz, 2H), 2.04 (td, J=12.9, 11.8, 6.1 Hz, 4H), 2.00-1.91 (m, 1H), 0.92-0.84 (m, 2H), 0.73 (d, J=5.3 Hz, 2H).

Example 34

Synthetic Scheme for N-benzyl-3-cyclopropyl-6-(piperidin-4-ylthio) imidazole [1, 2-b]pyridazin-8-aminehydrochloride (Note: Formate Salt Observed)

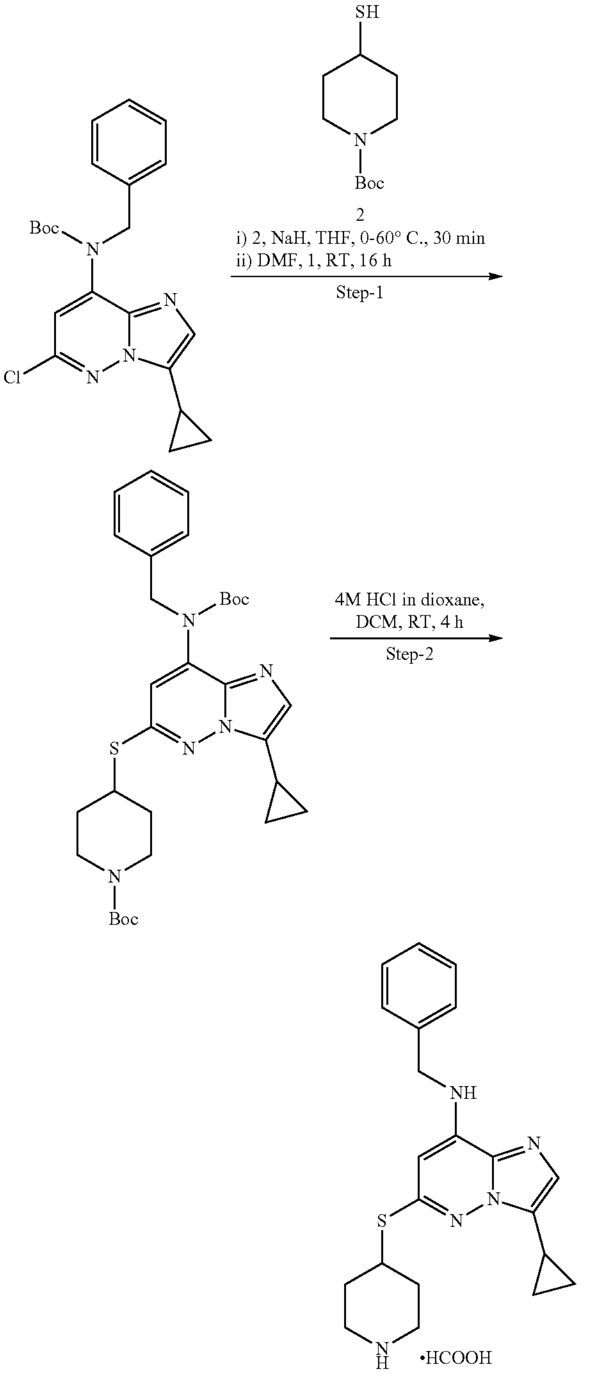

18

Step-1: Synthesis of tert-butyl 4-((8-(benzyl (tert-butoxycarbonyl) amino)-3-cyclopropylimidazo [1, 2-b]pyridazin-6-yl) thio) piperidine-1-carboxylate

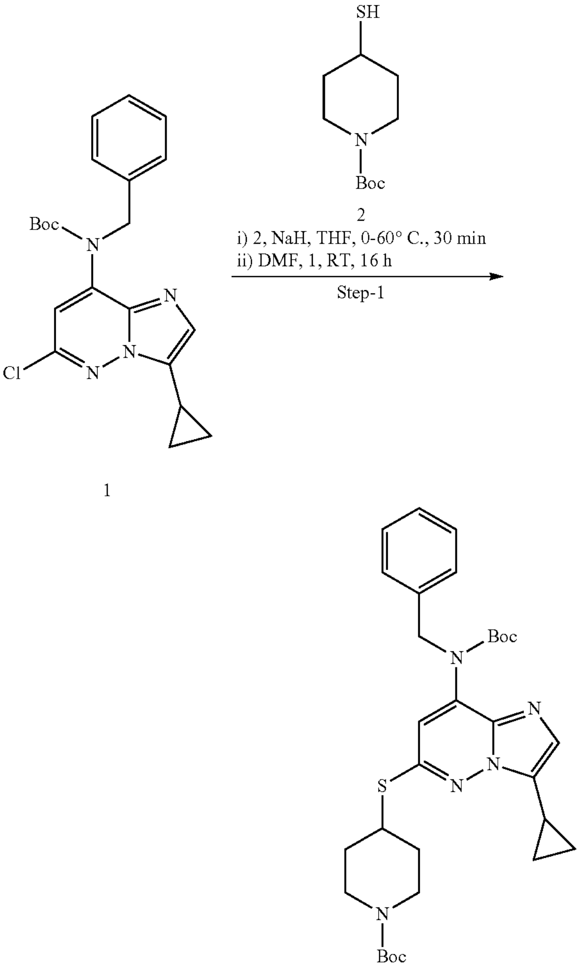

1

3

To a solution of tert-butyl 4-mercaptopiperidine-1-carboxylate (2) (327 mg, 1.507 mmol, 3 eq.) in DMF (3 mL) at 0 °C was added NaH (60% in mineral oil, (60 mg, 1.507 mmol, 3 eq.) and heated to 40 °C, stirred for 30 min. Reaction mixture was cooled at 0 °C and addition of tert-butyl benzyl(6-chloro-3-cyclopropylimidazo[1,2-b]pyridazin-8-yl)carbamate (1) (200 mg, 0.502 mmol, 1 eq.) in DMF (2 mL) was done. The resulting reaction mixture was stirred at room temperature for 16 h. After complete conversion by TLC, the reaction mixture was diluted with ice cold water (30 mL) and extracted with ethyl acetate (3×25 mL). The combined organic layer was washed with brine (25 mL), dried over sodium sulfate, filtered and evaporated under reduced pressure to get the crude compound. Obtained crude compound was purified by silica phase column chromatography (with a gradient elution of 15-20% of EtOAC: n-Hexane) to afford the title compound as tert-butyl 4-((8-(benzyl(tert-butoxycarbonyl)amino)-3-cyclopropylimidazo [1,2-b]pyridazin-6-yl)thio)piperidine-1-carboxylate (3) as brown oil. (Yield 200 mg, 70%). $R_f$=0.3(4:1 Hexane/EtOAc). (Note: LCMS analysis shows 68%). LCMS (m/z): 580.12 $(M+H)^+$.

Step-2: Synthesis of N-benzyl-3-cyclopropyl-6-(piperidin-4-ylthio) imidazo [1, 2-b]pyridazin-8-amine hydrochloride (Note: Formate Salt Observed.)

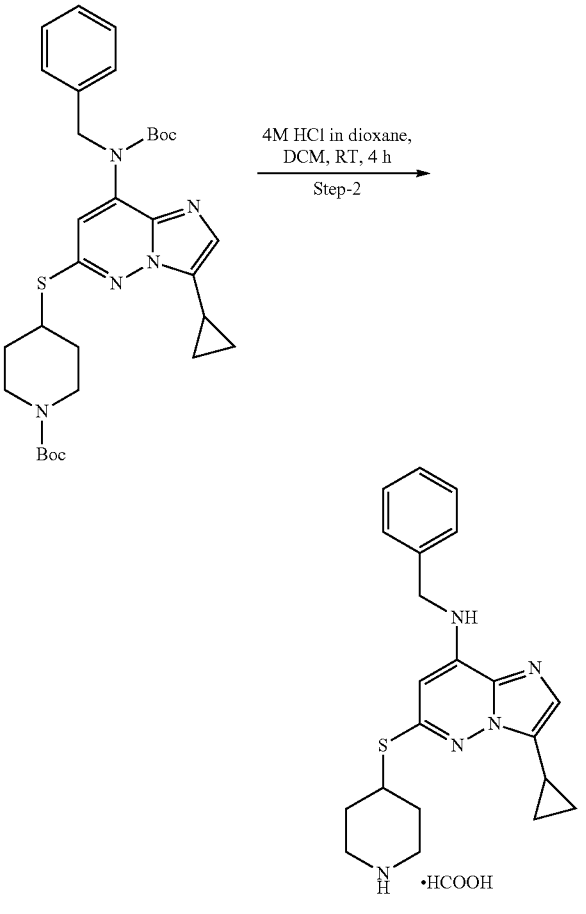

18

To a solution of tert-butyl 4-((8-(benzyl(tert-butoxycarbonyl)amino)-3-cyclopropylimidazo[1,2-b]pyridazin-6-yl)thio)piperidine-1-carboxylate (3) (200 mg 0.345 mmol, 1 eq.) in DCM (5 mL) at 0 °C was added 4M HCl in dioxane (0.8 mL) and stirred at room temperature for 4 h. After complete conversion by TLC, volatiles were evaporated under reduced pressure to get crude compound. Obtained crude compound was purified by Prep-HPLC by using formic acid buffer to afford the title compound N-benzyl-3-cyclopropyl-6-(piperidin-4-ylthio)imidazo[1,2-b]pyridazin-8-amine hydrochloride (18) as an off white solid. (Yield: 75 mg, 57.69%). $R_f$=0.1 (1:1Hexane/EtOAc). (Note: Formate salt observed.) LCMS (m/z): 380.20 $(M+H)^+$. $^1$HNMR (400 MHz, DMSO-$d_6$): δ 8.31 (s, 1H), 8.022 (t, J=6.4 Hz, 1H), 7.35-7.29 (m, 4H), 7.25-7.21 (m, 1H), 7.15 (s, 1H), 5.79 (s, 1H), 4.50 (d, J=6 Hz, 2H), 3.78-3.73 (m, 1H), 3.06-3.03 (m, 2H), 2.75-2.66 (m, 2H), 2.10-2.0 (m, 3H), 1.59-1.51 (m, 2H), 0.97-0.92 (m, 2H), 0.80-079 (m, 2H).

Example 35

Synthetic Scheme for N8-benzyl-3-cyclopropyl-N6-(2-(morpholin-2-yl)ethyl)imidazo[1,2-b]pyridazine-6,8-diamine formate

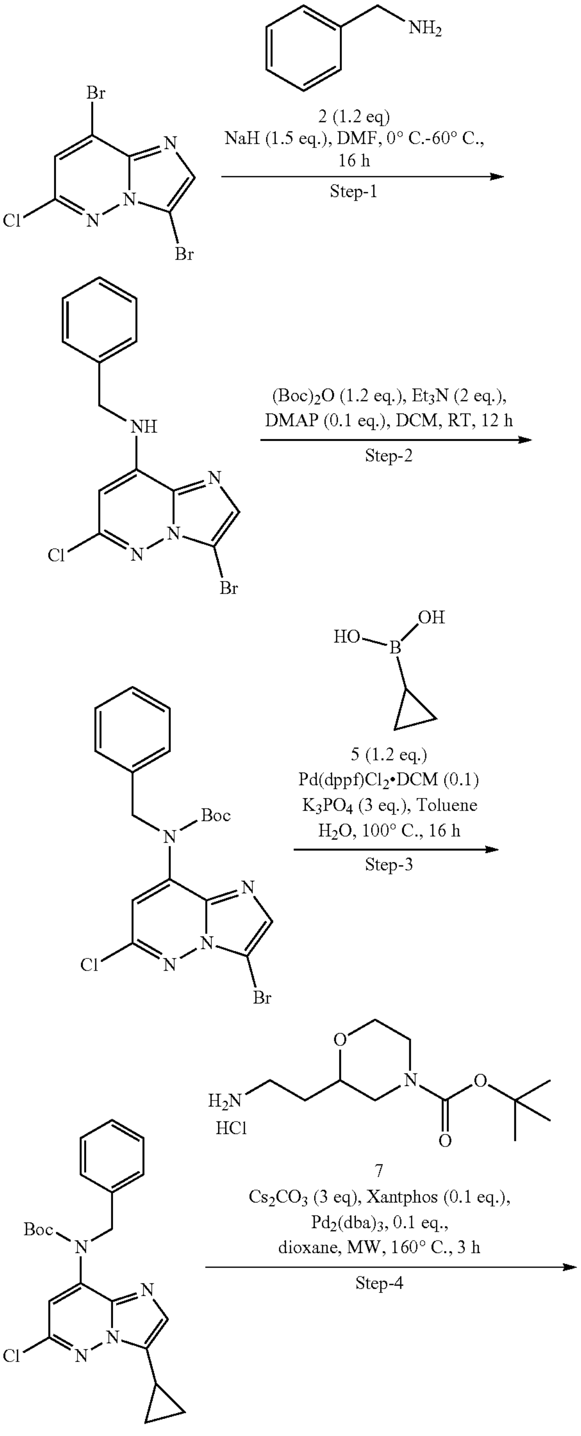

-continued

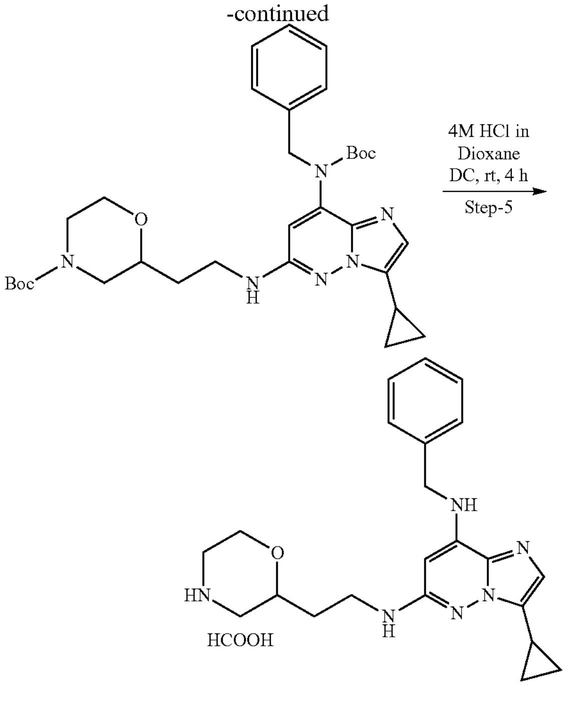

19

Synthesis of N-benzyl-3-bromo-6-chloroimidazo[1,2-b]pyridazin-8-amine

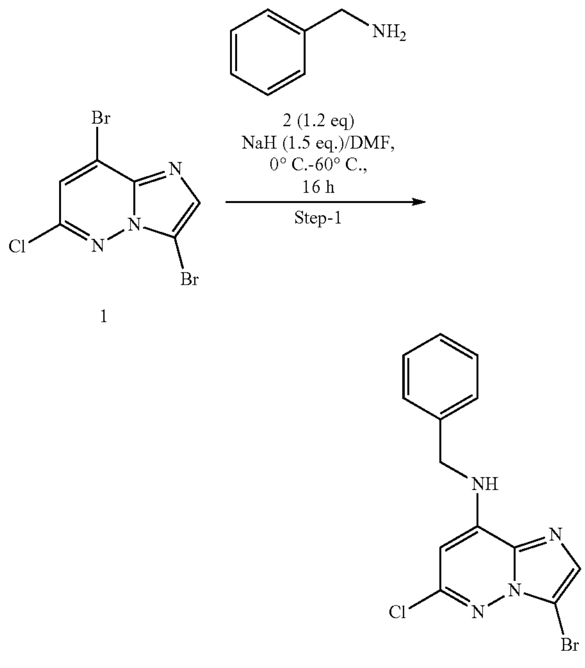

1

3

To the stirred solution of phenylmethanamine (2) (7.74 g, 72.26 mmol, 1.5 eq) in DMF (75 mL) at 0 °C was added 60% NaH (1.73 g, 72.26 mmol, 1.5 eq), stirred for 15 min later added 3,8-dibromo-6-chloroimidazo[1,2-b]pyridazine (1) (15 g, 48.17 mmol, 1 eq) and stirred at room temperature for 16 h. Progress of the reaction was monitored by TLC. Then the reaction mixture was diluted with ice cold water (100 mL) and extracted with ethyl acetate (3×100 mL). The combined organic layers were washed with brine solution (40 mL), dried over sodium sulfate and concentrated to provide crude. The crude material was purified by silica column chromatography with a gradient elution of 15-20% of EtOAc/Hexane to afford N-benzyl-3-bromo-6-chloroimidazo[1,2-b]pyridazin-8-amine (3) as off-white solid (8.5 g, 52%). TLC system: EtOAc/hexane (15:85), $R_f$value:−0.3; LCMS (m/z): 336 $(M+H)^+$; $^1$H NMR (400 MHz, DMSO-$d_6$) δ 8.68 (brs, 1H), 7.69 (s, 1H), 7.38-7.23 (m, 5H), 6.22 (s, 1H), 4.57 (s, 2H).

Synthesis of tert-butyl benzyl(3-bromo-6-chloroimidazo[1,2-b]pyridazin-8-yl)carbamate

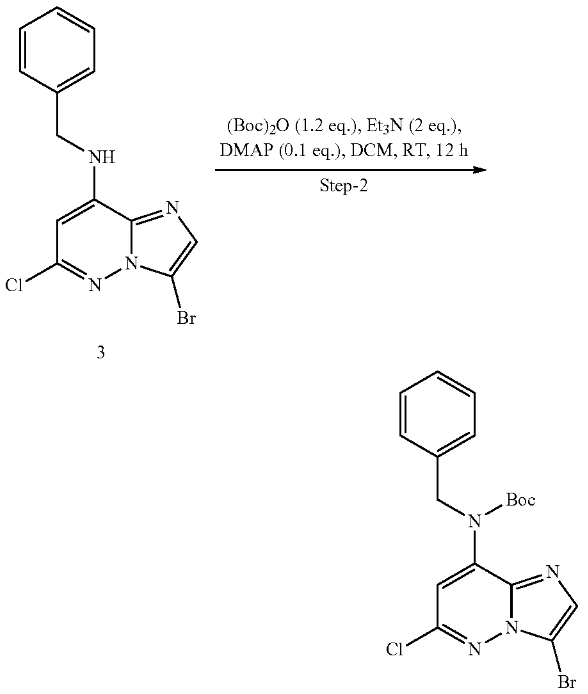

3

4

To a stirred solution of N-benzyl-3-bromo-6-chloroimidazo[1,2-b]pyridazin-8-amine (3) (5 g, 14.88 mmol, 1eq) in DCM (40 mL) at room temperature was added $Et_3N$ (4.17 mL, 29.76 mmol, 2 eq), Boc2O (5.12 mL, 22.32 mmol, 1.5 eq) and DMAP (0.181 g, 1.48 mmol, 0.1 eq). The reaction mixture was stirred at room temperature for 16 h. After completion of conversion by TLC, diluted with water and extracted with DCM (2×150 mL). The combined organic layers were washed with brine solution (100 mL), dried over sodium sulfate and concentrated to provide crude. The crude material was purified by silica column chromatography [with a gradient elution of 5-10% of EtOAc/Hexane] to afford tert-butyl benzyl(3-bromo-6-chloroimidazo[1,2-b]pyridazin-8-yl)carbamate (4) as an pale yellow (6 g, 92%). TLC system: EtOAc/hexane (10:90), $R_f$value:−0.6; LCMS (m/z): 436 $(M+H)^+$; $^1$HNMR (400 MHz, DMSO-$d_6$) δ 7.96 (d, J=4.0 Hz, 1H), 7.51 (s, 1H), 7.25-7.18 (m, 5H), 5.25 (s, 2H), 1.34 (m, 9H).

Synthesis of tert-butyl benzyl(6-chloro-3-cyclopropylimidazo[1,2-b]pyridazin-8-yl)carbamate

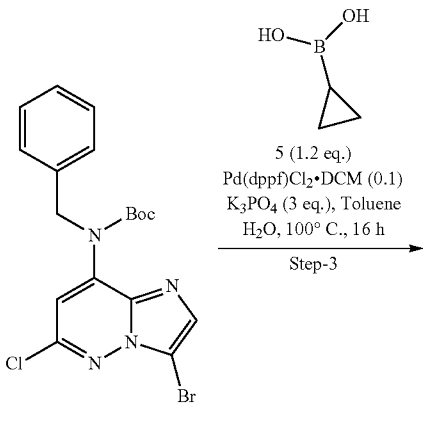

4

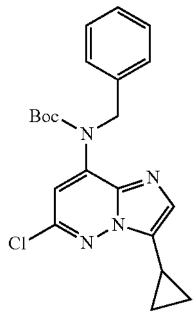

6

To the stirred solution of tert-butyl benzyl(3-bromo-6-chloroimidazo[1,2-b]pyridazin-8-yl)carbamate (4) (2 g, 4.58 mmol, 1eq) in toluene: water (3:1; 23 mL) was added cyclopropyl boronic acid (5) (0.47 g, 5.50 mmol, 1.2) and $K_3PO_4$ (2.91 g, 13.76 mmol, 3 eq) and degassed for 10 min later added $Pd(dppf)Cl_2$.DCM (0.37 g, 0.45 mmol, 0.1 eq) and stirred at 100 °C for 16 h. After completion of reaction by TLC, diluted with ice cold water (100 mL) and extracted with ethyl acetate (3×100 mL). The combined organic layers were washed with brine solution (60 mL), dried over sodium sulfate and concentrated to provide crude. The crude material was purified by silica phase column chromatography [with a gradient elution of 15-20% of EtOAc/Hexane] to afford tert-butyl benzyl(6-chloro-3-cyclopropylimidazo[1,2-b]pyridazin-8-yl)carbamate (6) as yellow (130 mg, 7%). TLC system: EtOAc/hexane (10:90), $R_f$value:−0.4; LCMS (m/z): 398.0 $(M+H)^+$; $^1$HNMR (400 MHz, DMSO-$d_6$) δ 7.55 (s, 1H), 7.34 (s, 1H), 7.28-7.17 (m, 5H), 5.30 (s, 2H), 2.15-2.08 (m, 1H), 1.35 (s, 9H), 1.05-1.00 (m, 2H), 0.82-0.78 (m, 2H).

Synthesis of tert-butyl 2-(2-((8-(benzyl(tert-butoxycarbonyl)amino)-3-cyclopropylimidazo[1,2-b]pyridazin-6-yl)amino)ethyl)morpholine-4-carboxylate

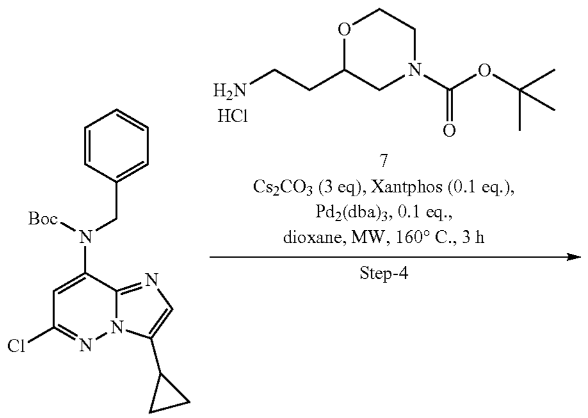

6

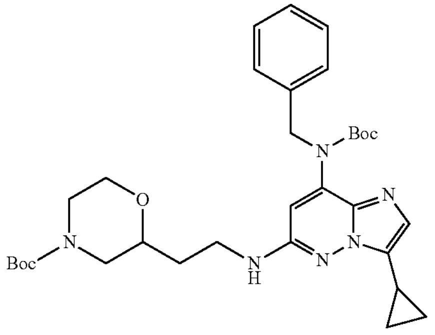

8

To a stirred solution of tert-butyl benzyl(6-chloro-3-cyclopropylimidazo[1,2-b]pyridazin-8-yl)carbamate (6) (150 mg, 0.37 mmol, 1eq) in dioxane was added tert-butyl 2-(2-aminoethyl)morpholine-4-carboxylate hydrogen chloride (7) (120.36 mg, 0.45 mmol, 1.2 eq), $Cs_2CO_3$ (427 mg, 1.31 mmol, 3.5 eq) and xanthphos (21.38 mg, 0.03 mmol, 0.1 eq) at room temperature, and degassed for 10 min later added $Pd_2(dba_3)$ (34.43 mg, 0.03 mmol, 0.1 eq) and heated at 160 °C for 3 h in MW. After completion of reaction by TLC, diluted with water (50 mL) and extracted with ethyl acetate (3×50 mL). The combined organic layers were washed with brine solution (30 mL), dried over sodium sulfate and concentrated to provide crude. The crude material was purified by silica phase column chromatography [with a gradient elution of 15-20% of EtOAc/Hexane] to afford tert-butyl 2-(2-((8-(benzyl(tert-butoxycarbonyl)amino)-3-cyclopropylimidazo[1,2-b]pyridazin-6-yl)amino)ethyl)morpholine-4-carboxylate (8) as yellow (130 mg, 7%). TLC system: EtOAc/hexane (10:90), $R_f$value:−0.4; LCMS (m/z): 592.0 $(M+H)^+$.

Synthesis of N8-benzyl-3-cyclopropyl-N6-(2-(morpholin-2-yl)ethyl)imidazo[1,2-b]pyridazine-6,8-diamine formate

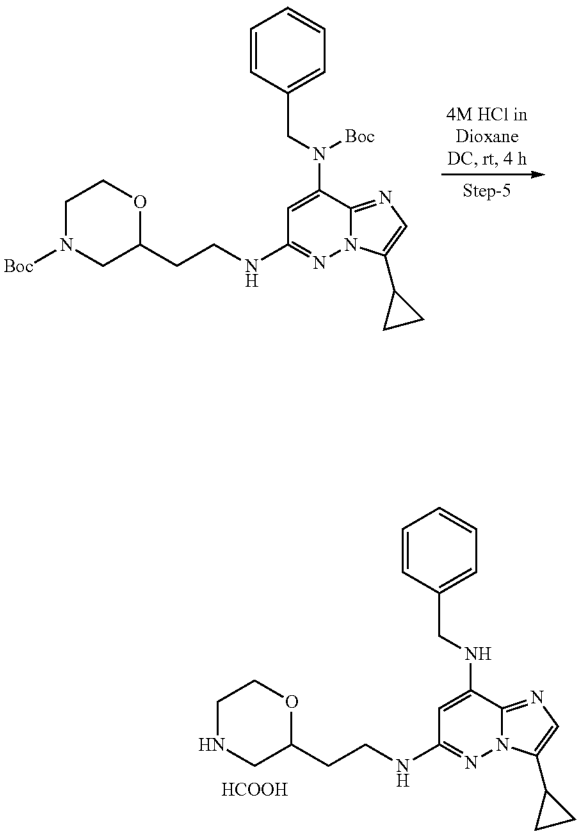

19

A solution of tert-butyl 2-(2-((8-(benzyl(tert-butoxycarbonyl)amino)-3-cyclopropylimidazo[1,2-b]pyridazin-6-yl) amino)ethyl)morpholine-4-carboxylate (8) (100 mg, 0.168 mmol, 1eq) in DCM (5 mL) at 0 °C was added 4M HCl in 1,4-dioxane (1 mL) drop-wise and stirred at room temperature for 4 h. After completion of reaction by TLC, the reaction mixture was subjected to rotary evaporator for removal of volatiles. The obtained residue purified by prep HPLC afforded N8-benzyl-3-cyclopropyl-N6-(2-(morpholin-2-yl)ethyl)imidazo[1,2-b]pyridazine-6,8-diamine formate (19) as an off white solid. Yield: 12 mg (18%). $R_f$=0.1 (4:1 $CHCl_3$/MeOH). LCMS (m/z): 392 $(M+H)^+$; $^1H$ NMR (500 MHz, DMSO-$d_6$): δ=8.24 (s, 1H), 7.35-7.22 (m, 5H), 7.21 (s, 1H), 6.89 (s, 1H), 6.15 (t, J=4 Hz, 1H), 5.31 (s, 1H), 4.40 (d, J=8 Hz, 2H), 3.72 (d, J=12 Hz 1H), 3.42 (t, J=12 Hz, 2H), 3.24-3.12 (m, 2H), 2.81 (d, J=12 Hz, 1H), 2.70 (t, J=12 Hz, 2H), 2.50-2.36 (m, 2H), 2.04-1.98 (m, 1H), 1.63-1.52 (m, 2H), 0.91-0.88 (m, 1H), 0.74 (t, J=4 Hz, 2H).

Example 36

Synthetic Scheme for 1-(4-((8-(benzyl amino)-3-cyclopropylimidazo [1, 2-b]pyridazin-6-yl) thio) piperidin-1-yl)-2, 2, 2-trifluoroethan-1-one

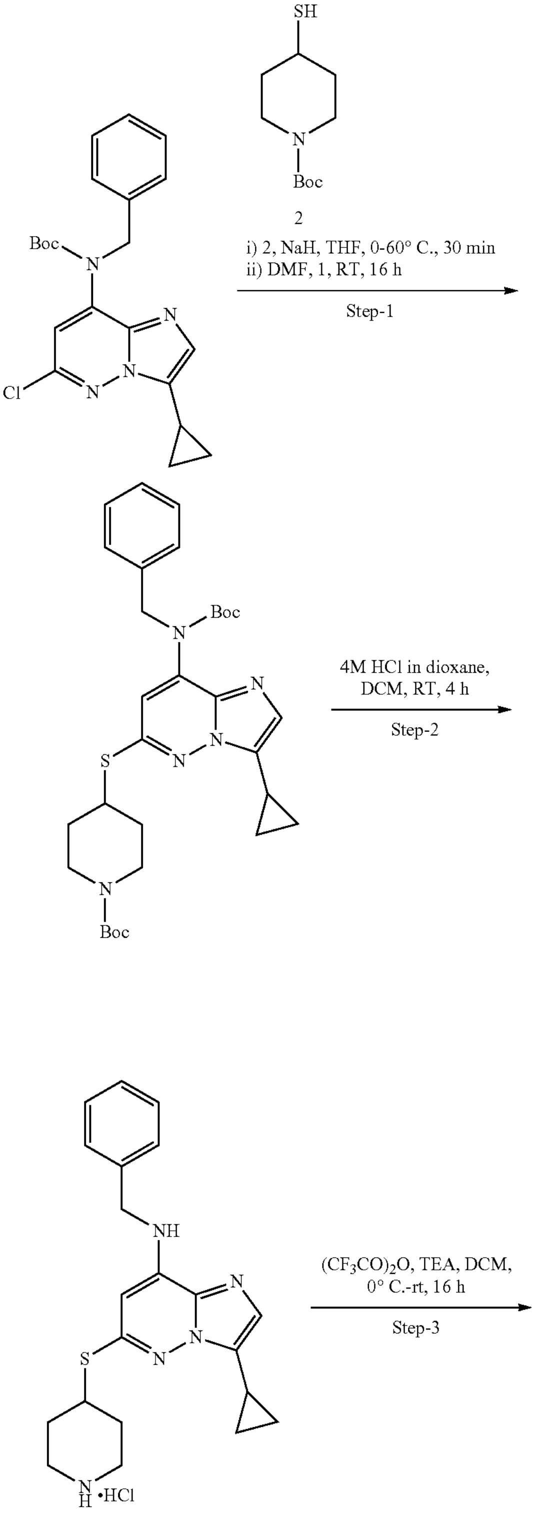

-continued

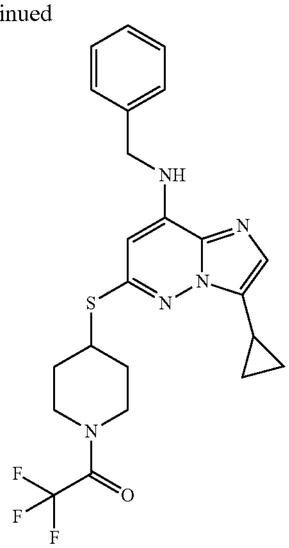

20

Step-1: Synthesis of tert-butyl 4-((8-(benzyl(tert-butoxycarbonyl)amino)-3-cyclopropylimidazo[1,2-b]pyridazin-6-yl)thio)piperidine-1-carboxylate To a solution of tert-butyl 4-mercaptopiperidine-1-carboxylate (2) (327 mg, 1.507 mmol, 3 eq.) in DMF (3 mL) at 0 °C was added NaH 60% in mineral oil (60 mg, 1.507 mmol, 3 eq.) and heated to 40 °C, stirred for 30 min. After this time, reaction mixture was cooled at 0 °C and added tert-butyl benzyl(6-chloro-3-cyclopropylimidazo[1,2-b]pyridazin-8-yl)carbamate (1) (200 mg, 0.502 mmol, 1 eq.) in DMF (2 mL). The resulting reaction mixture was stirred at room temperature for 16 h. Reaction was diluted with ice cold water (30 mL) and extracted with ethyl acetate (3×25 mL). The combined organic layer was washed with brine solution (25 mL), dried over sodium sulfate, evaporated under reduced pressure to get the crude compound. Obtained crude compound was purified by silica phase column chromatography [with a gradient elution of 15-20% of EtOAC: n-Hexane] to afford the title compound as tert-butyl 4-((8-(benzyl(tert-butoxycarbonyl)amino)-3-cyclopropylimidazo[1,2-b]pyridazin-6-yl)thio)piperidine-1-carboxylate (3) as brown oil. (Yield 200 mg, 70%). $R_f$=0.3(4:1 Hexane/EtOAc). (Note: LCMS analysis shows 68%). LCMS (m/z): 580.12 $(M+H)^+$.

Step-2: Synthesis of N-benzyl-3-cyclopropyl-6-(piperidin-4-ylthio) imidazo [1, 2-b]pyridazin-8-amine hydrochloride

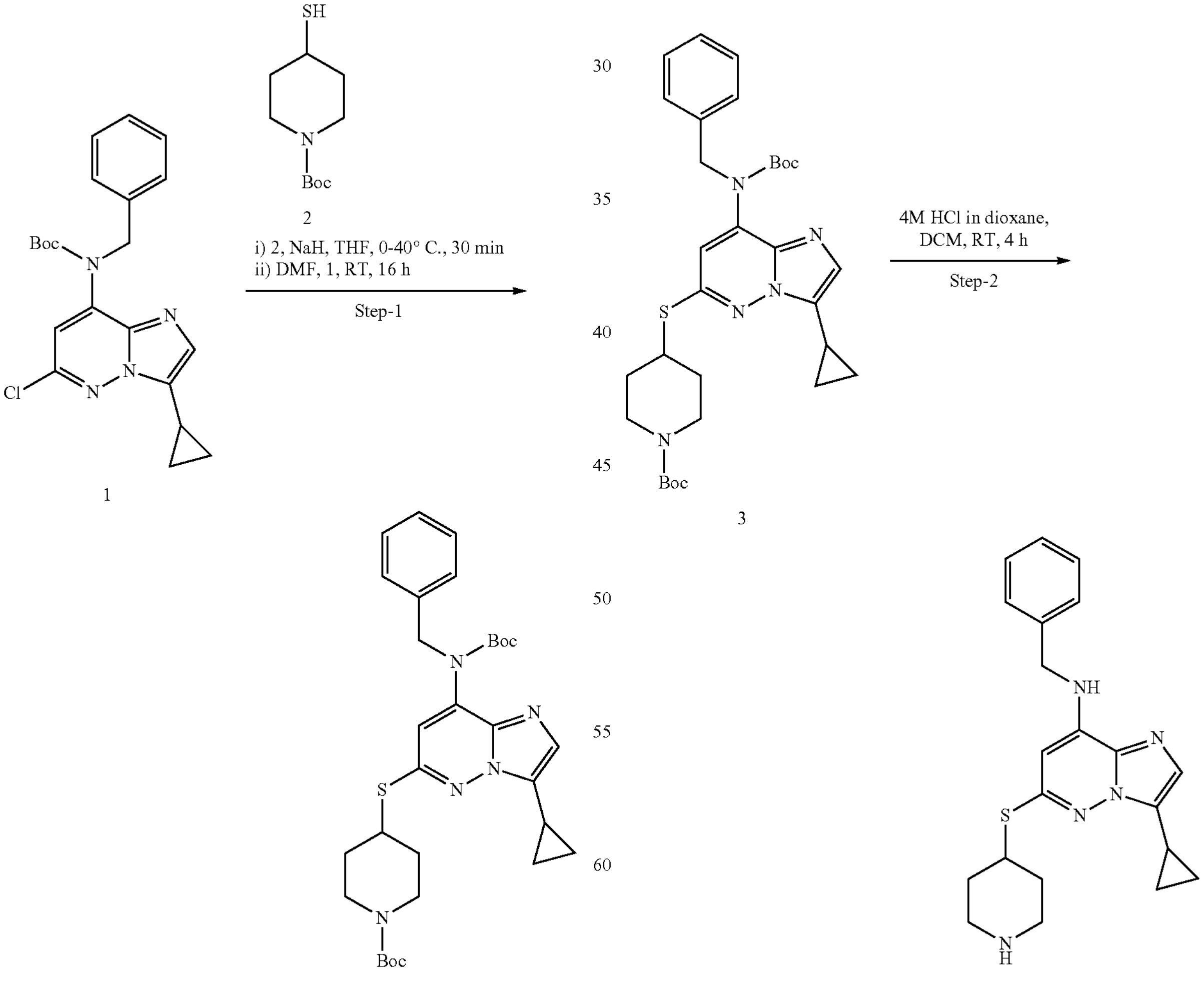

2
1
3
3
4

To a solution of tert-butyl 4-((8-(benzyl(tert-butoxycarbonyl)amino)-3-cyclopropylimidazo[1,2-b]pyridazin-6-yl)thio)piperidine-1-carboxylate (3) (200 mg, 0.345 mmol, 1 eq.) in DCM (5 mL) at 0 °C was added 4M HCl in dioxane (0.8 mL) and stirred at room temperature for 4 h. After complete conversion by TLC, volatiles were evaporated under reduced pressure to get crude compound. It was purified by Prep-HPLC by using formic acid buffer to afford the title compound N-benzyl-3-cyclopropyl-6-(piperidin-4-ylthio)imidazo[1,2-b]pyridazin-8-amine hydrochloride (4) as an off white solid. (Yield: 75 mg, 57.69%). $R_f$=0.1 (1:1 Hexane/EtOAc). LCMS (m/z): 380.20 $(M+H)^+$. $^1$HNMR (400 MHz, DMSO-$d_6$): δ 8.31 (s, 1H), 8.022 (t, J=6.4 Hz, 1H), 7.35-7.29 (m, 4H), 7.25-7.21 (m, 1H), 7.15 (s, 1H), 5.79 (s, 1H), 4.50 (d, J=6 Hz, 2H), 3.78-3.73 (m, 1H), 3.06-3.03 (m, 2H), 2.75-2.66 (m, 2H), 2.10-2.0 (m, 3H), 1.59-1.51 (m, 2H).

Step-3: Synthesis of 1-(4-((8-(benzylamino)-3-cyclopropylimidazo[1,2-b]pyridazin-6-yl)thio)piperidin-1-yl)-2,2,2-trifluoroethan-1-one

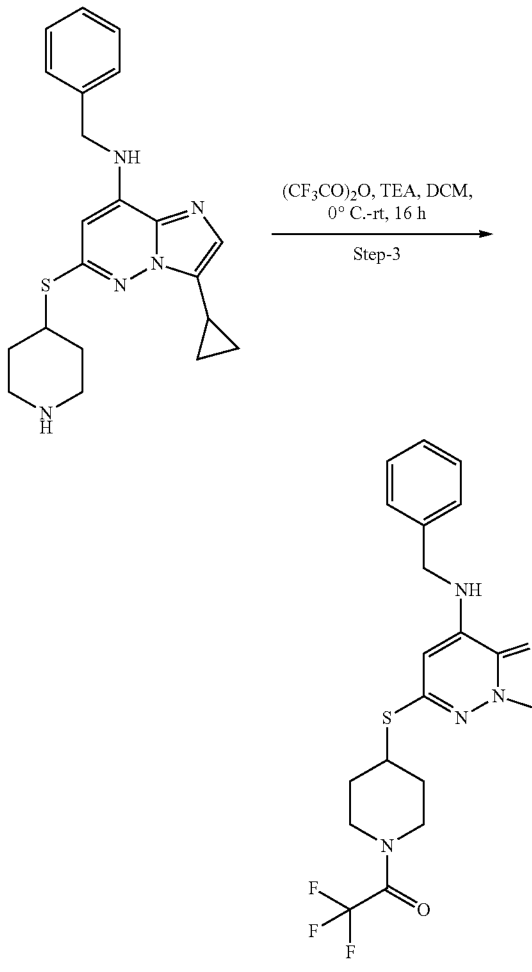

20

To a solution of N-benzyl-3-cyclopropyl-6-(piperidin-4-ylthio)imidazo[1,2-b]pyridazin-8-amine hydrochloride (4) (60 mg, 0.158 mmol, 1 eq.) in DCM (3 mL) at 0 °C was added triethylamine (0.033 mL, 0.237 mmol 1.5 eq.) followed by trifluoroacetic anhydride (0.022 mL, 0.158 mmol, 1 eq.) in DCM (0.5 mL). Reaction mixture was allowed to come to room temperature and stirred for 16 h. After complete conversion by TLC, reaction mixture was diluted with ice cold water (10 mL) and extracted with ethyl acetate (3×20 mL). The combined organic layer was washed with sodium bicarbonate solution (20 mL), brine (20 mL), dried over sodium sulfate, filtered and evaporated under reduced pressure to get crude compound as brown solid. Crude compound was purified by preparative HPLC by using formic acid buffer to afford the title compound as 1-(4-((8-(benzylamino)-3-cyclopropylimidazo[1,2-b]pyridazin-6-yl)thio)piperidin-1-yl)-2,2,2-trifluoroethan-1-one (20) as white solid. (Yield: 7 mg, 9.30%), $R_f$=0.6(1:1 Hexane/EtOAc). LCMS (m/z): 476.37 $(M+H)^+$. $^1$HNMR (400 MHz, DMSO-$d_6$) δ: 8.03 (t, J=5.2 Hz, 1H), 7.35-7.29 (m, 4H), 7.24-7.20 (m, 1H), 7.16 (s, 1H), 4.50 (d, J=4.8 Hz, 2H), 4.12-4.09 (m, 1H), 3.93-3.38 (m, 1H), 3.82-3.78 (m, 1H), 3.44-3.38 (m, 1H), 3.17 (t, J=11.6 Hz, 1H), 2.17-2.05 (m, 2H), 2.04-1.96 (m, 1H), 1.69-1.64 (m, 2H), 0.95-0.92 (m, 2H), 0.84-0.74 (m, 2H).

Example 37

Synthetic Scheme for N-benzyl-3-cyclopropyl-6-(piperidin-3-ylthio) imidazo[1,2-b]pyridazin-8-amine dihydrochloride

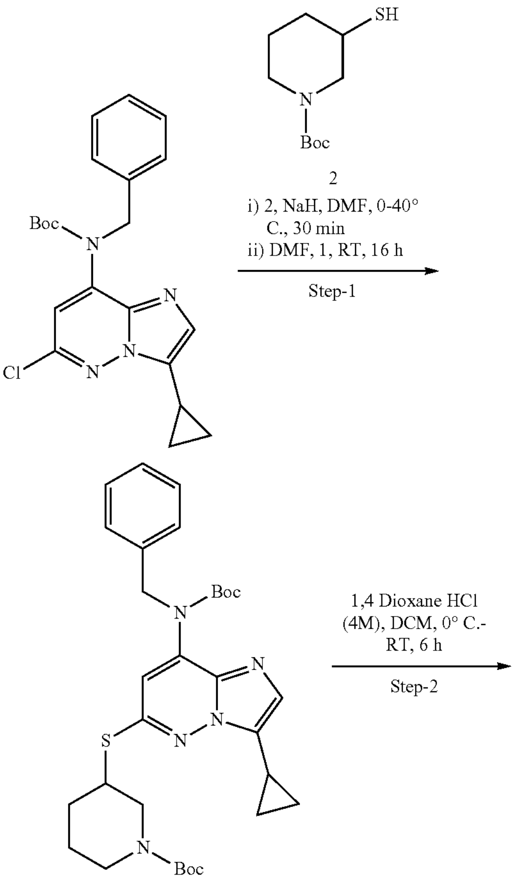

-continued

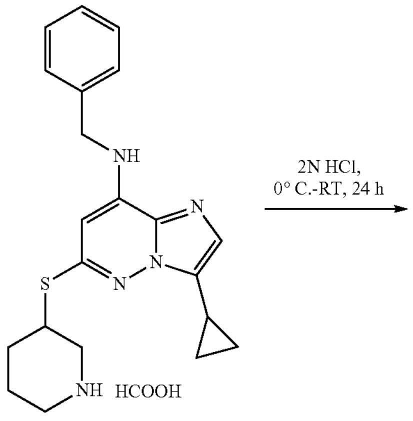

22

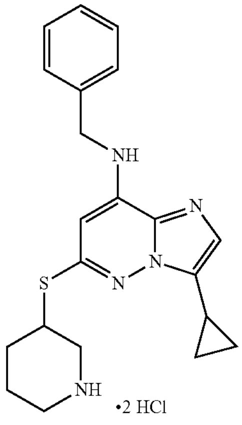

23

-continued

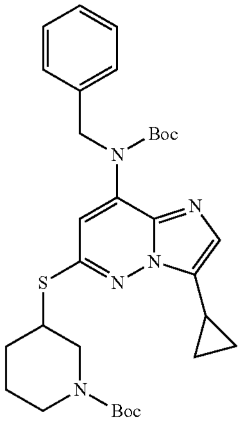

Step-1: Synthesis of tert-butyl 3-((8-(benzyl(tert-butoxycarbonyl)amino)-3-cyclopropylimidazo[1,2-b]pyridazin-6-yl)thio)piperidine-1-carboxylate

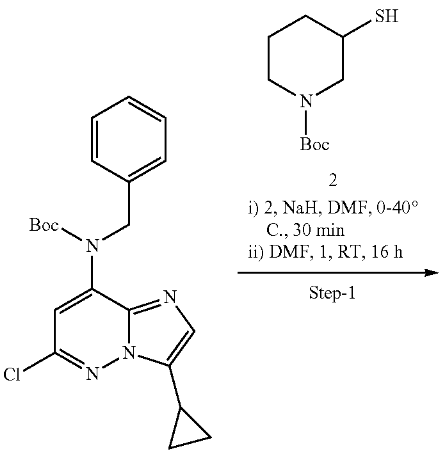

To a stirred solution of tert-butyl 3-mercaptopiperidine-1-carboxylate (2) (408 mg, 1.88 mmol, 3 eq.) in DMF was added NaH (60% dispersion in oil) (75 mg, 1.88 mmol, 3 eq.) at 0 °C. The reaction mixture was stirred at 40 °C for 30 minutes. Then tert-butyl benzyl (6-chloro-3-cyclopropylimidazo [1,2-b]pyridazin-8-yl)carbamate (1) (250 mg, 0.628 mmol, 1 eq.) in DMF was added at 0 °C. The reaction mixture was stirred at room temperature for 16 h. After complete conversion by TLC, the reaction mixture was quenched with ice cold water (10 mL) and extracted with ethyl acetate (3×25 mL). The combined organic layer was washed with brine (25 mL), dried over $Na_2SO_4$, filtered and evaporated under reduced pressure to get crude residue as brown oil. The residue was purified by column chromatography using silica (100-200) mesh, (with a gradient elution of 0-10% of EtOAC: n-Hexane) to afford the title compound as tert-butyl 3-((8-(benzyl(tert-butoxycarbonyl)amino)-3-cyclopropylimidazo[1,2-b]pyridazin-6-yl)thio)piperidine-1-carboxylate (3) as brown oil. Yield: (250 mg, 68.87%). $R_f$=0.4 (4:1 Hexane/EtOAc). LCMS (m/z): 580.1 $(M+H)^+$. $^1$H NMR (400 MHz, $CDCl_3$, TMS): δ=7.27-7.21 (m, 2H), 7.20-7.17 (m, 5H), 6.76 (s, 1H), 5.36 (s, 2H), 3.91 (s, 1H), 3.80-3.75 (m, 1H), 2.95 (s, 1H), 2.35-2.01 (m, 3H), 1.78-1.73 (m, 2H), 1.58-1.57 (m, 1H), 1.47-1.37 (m, 15H), 1.26-1.25 (m, 10H), 1.06-1.02 (m, 2H), 0.89-0.83 (m, 2H), 0.78 (s, 1H).

Step-2: Synthesis of N-benzyl-3-cyclopropyl-6-(piperidin-3-ylthio) imidazo [1,2-b]pyridazin-8-amine hydrochloride (Note: Formate salt observed)

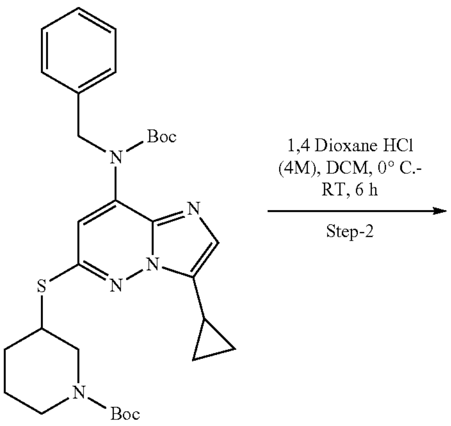

-continued

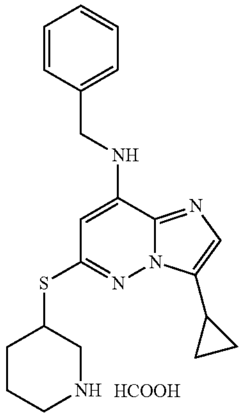

22

-continued

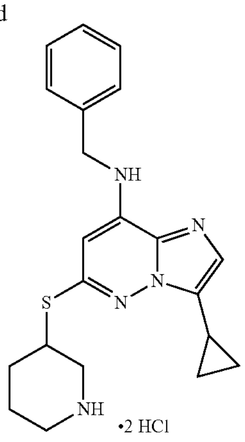

23

To a solution of tert-butyl 3-((8-(benzyl(tert-butoxycarbonyl)amino)-3-cyclopropylimidazo[1,2-b]pyridazin-6-yl)thio)piperidine-1-carboxylate (250 mg, 0.431 mmol, 1 eq.) in DCM (5 mL) was added 4M HCl in 1,4 dioxane (1.0 mL) at 0 °C. Reaction mixture was allowed to come to room temperature and stirred for 4 h. Volatiles were evaporated under reduced pressure to get crude compound as brown solid. The crude compound was purified by preparative HPLC using formic acid buffer to afford the title compound as N-benzyl-3-cyclopropyl-6-(piperidin-3-ylthio)imidazo[1,2-b]pyridazin-8-amine formate (22) as an off white solid. (Note: Obtained formate salt after preparative HPLC). Yield: (150 mg, 83.61%). $R_f$=0.1 (2:1 Hexane/EtOAc). LCMS (m/z): 380.15 (M+H)$^1$H NMR (400 MHz, DMSO, TMS): δ=8.23 (s, 1H) formic acid, 8.03 (s, 1H), 7.34-7.29 (m, 4H), 7.24-7.21 (s, 1H), 7.15-7.14 (m, 1H), 5.81 (d, J=3.6 Hz, 1H), 4.51 (m, 2H), 3.81-3.80 (m, 1H), 3.38 (d, J=12 Hz, 1H), 2.97 (d, J=12 Hz, 1H), 2.76 (t, J=10 Hz, 1H), 2.66 (t, J=8 Hz, 1H), 2.17-2.10 (m, 1H), 2.05-2.03 (m, 1H), 1.71-1.52 (m, 3H), 0.97 (d, J=8 Hz, 2H), 0.79-0.75 (m, 2H).

Step-3: Synthesis of N-benzyl-3-cyclopropyl-6-(piperidin-3-ylthio)imidazo[1,2-b]pyridazin-8-amine hydrochloride

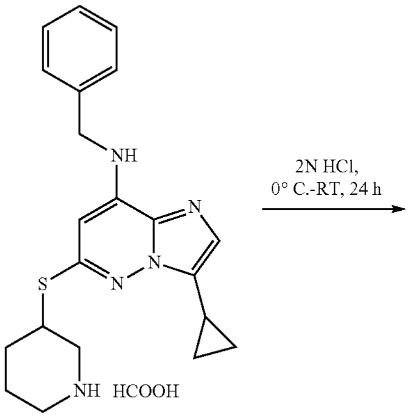

22

In a small RBF (10 mL), N-benzyl-3-cyclopropyl-6-(piperidin-3-ylthio)imidazo[1,2-b]pyridazin-8-amine formate (40 mg, 0.094 mmol, 1 eq.) in 2N HCl (2 mL) was lyophilized for 24 h, to afford the title compound as N-benzyl-3-cyclopropyl-6-(piperidin-3-ylthio)imidazo[1,2-b]pyridazin-8-amine dihydrochloride salt (23) as an off white solid. Yield: 45 mg (Quantitative conversion). $R_f$=0.1 (1:1 Hexane/EtOAc).

LCMS (m/z): 380.26 $(M+H)^+$. $^1$H NMR (400 MHz, DMSO, TMS): δ=9.55 (d, J=8.0 Hz, 1H), 9.08 (d, J=8.0 Hz, 1H), 8.81 (s, 1H), 7.72 (s, 1H), 7.42-7.36 (m, 2H), 7.35-7.33 (m, 2H), 7.29-7.25 (m, 1H), 6.41 (s, 1H), 4.60 (s, 2H), 4.12-4.07 (m, 1H), 3.66 (d, J=12 Hz, 1H), 3.22 (d, J=8.0 Hz, 1H), 3.08-3.00 (m, 1H), 2.88 (s, 1H), 2.38-2.35 (m, 1H), 2.08 (d, J=12 Hz, 1H), 1.87 (s, 2H), 1.75-1.66 (m, 1H), 1.09-1.07 (m, 2H), 0.85-0.78 (m, 2H).

Example 38

Synthetic Scheme for (S)-3-cyclopropyl-N-(1-phenylethyl)-6-(piperidin-4-ylthio)imidazo[1,2-b]pyridazin-8-amine hydrochloride

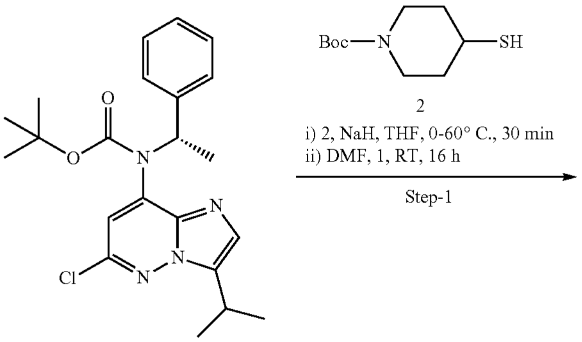

-continued

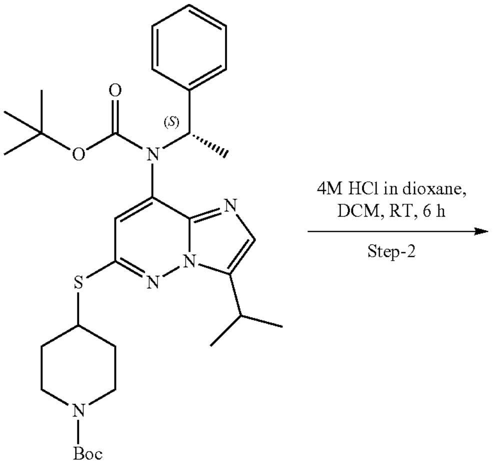

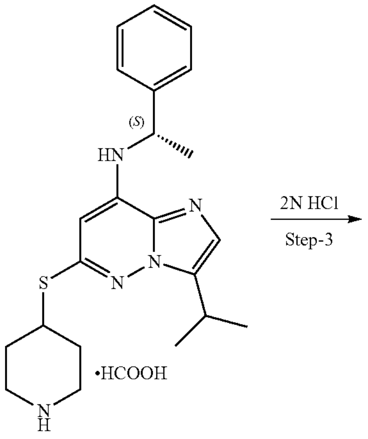

24

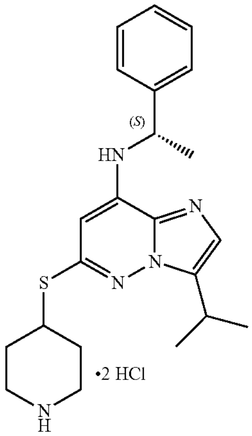

25

Synthesis of tert-butyl (S)-4-((8-((tert-butoxycarbonyl)(1-phenylethyl)amino)-3-isopropylimidazo[1,2-b]pyridazin-6-yl)thio)piperidine-1-carboxylate

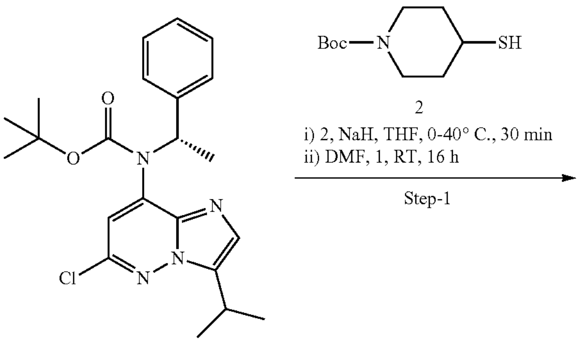

1

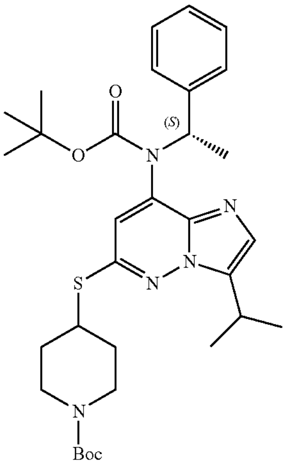

3

To a solution of tert-butyl 4-mercaptopiperidine-1-carboxylate (2) (0.31 g, 1.449 mmol, 3 eq.) in DMF (2 mL) at 0 °C was added NaH (60% in mineral oil, 0.057 g, 1.449 mmol, 3 eq.) and heated to 40 °C, stirred for 30 min. Then reaction mixture was cool to 0 °C and added a solution of tert-butyl (S)-(6-chloro-3-isopropylimidazo[1,2-b]pyridazin-8-yl)(1-phenylethyl)carbamate (1) (0.2 g, 0.483 mmol, 1 eq.) in DMF (2 mL). The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to afford tert-butyl (S)-4-((8-((tert-butoxycarbonyl)(1-phenylethyl)amino)-3-isopropylimidazo[1,2-b]pyridazin-6-yl)thio)piperidine-1-carboxylate (3) as a white gum (0.19 g, quantitative) which was carried to next step without any further purification, $R_f$=0.4 (7:3 Hexane/EtOAc).

Note: Observed Cpd-1 de-boc as a major in TLC & LCMS. LCMS (m/z): 596.21 $(M+H)^+$. $^1H$ NMR (400 MHz, DMSO-$d_6$): δ 7.48-7.41 (m, 3H), 7.34-7.24 (m, 3H), 6.54 (s, 1H), 5.49 (d, J=6.4 Hz, 1H), 3.84-3.80 (m, 4H), 3.01-32.89 (m, 5H), 2.06-2.02 (m, 2H), 1.92-1.89 (m, 2H) (m, 6H), 1.41 (s, 9H), 1.33 (s, 9H).

Synthesis of (S)-3-isopropyl-N-(1-phenylethyl)-6-(piperidin-4-ylthio)imidazo[1,2-b]pyridazin-8-amine

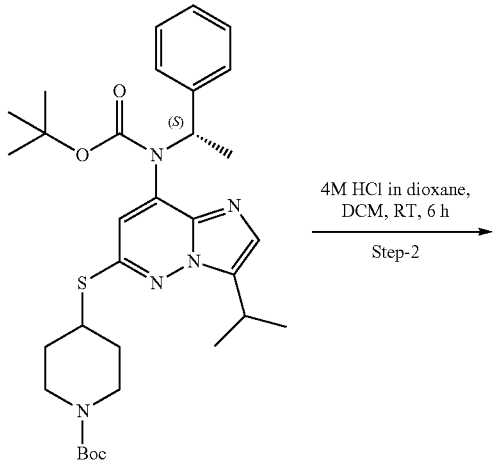

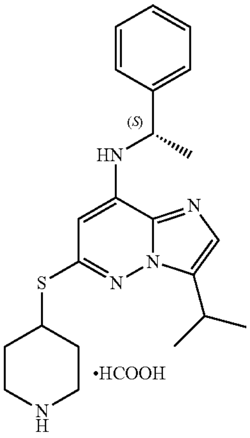

24

Synthesis of (S)-3-cyclopropyl-N-(1-phenylethyl)-6-(piperidin-4-ylthio)imidazo[1,2-b]pyridazin-8-amine hydrochloride

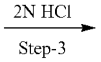

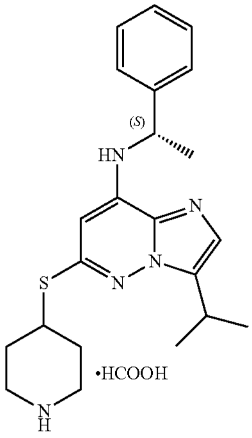

24

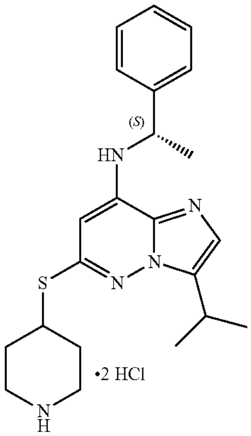

25

To a solution of tert-butyl (S)-4-((8-((tert-butoxycarbonyl)(1-phenylethyl)amino)-3-isopropylimidazo[1,2-b]pyridazin-6-yl)thio)piperidine-1-carboxylate (3) (0.19 g, 0.319 mmol, 1 eq.) in DCM (5 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (with formate buffer) to afford (S)-3-isopropyl-N-(1-phenylethyl)-6-(piperidin-4-ylthio)imidazo[1,2-b]pyridazin-8-amine (24) as an off white solid (38 mg, 30% yield). $R_f$=0.2 (9:1 DCM/MeOH). LCMS (m/z): 396.25 $(M+H)^+$. $^1$H NMR (400 MHz, DMSO-$d_6$): δ 8.33 (d, J=1.2 Hz, 1H), 7.76 (d, J=7.7 Hz, 1H), 7.48-7.41 (m, 2H), 7.36-7.28 (m, 2H), 7.23 (d, J=6.3 Hz, 2H), 5.73 (s, 1H), 4.82 (s, 1H), 3.76 (t, J=10.8 Hz, 1H), 3.25 (q, J=6.9 Hz, 1H), 3.06 (d, J=12.5 Hz, 2H), 2.74 (t, J=11.7 Hz, 2H), 2.06 (dd, J=22.3, 6.9 Hz, 2H), 1.55 (d, J=6.7 Hz, 2H), 1.54 (s, 3H), 1.32 (td, J=6.8, 1.3 Hz, 6H).

The obtained (S)-3-cyclopropyl-N-(1-phenylethyl)-6-(piperidin-4-ylthio)imidazo[1,2-b]pyridazin-8-amine (24) (0.012 g, 0.390 mmol, 1 eq.) in ACN/water (1:1 mL) was added 2N aq. HCl at 0 °C and lyophilized to afford (S)-3-cyclopropyl-N-(1-phenylethyl)-6-(piperidin-4-ylthio)imidazo[1,2-b]pyridazin-8-amine hydrochloride (25), (10 mg, 83% yield). $R_f$=0.1 (9:1 DCM/MeOH). LCMS (m/z): 396.21 $(M+H)^+$. $^1$H NMR (400 MHz, DMSO-$d_6$) δ 8.91-8.73 (s, 4H), 7.84 (s, 1H), 7.47 (d, J=7.6 Hz, 2H), 7.35 (t, J=7.5 Hz, 2H), 7.25 (t, J=7.2 Hz, 1H), 6.16 (s, 1H), 4.92 (s, 1H), 3.92 (d, J=10.1 Hz, 1H), 3.32 (s, 1H), 3.24 (s, 2H), 3.03 (d, J=11.2 Hz, 2H), 2.19 (d, J=13.9 Hz, 2H), 1.78 (dt, J=10.7, 4.3 Hz, 2H), 1.57 (s, 3H), 1.34-1.30 (m, 6H).

Example 39

Synthetic Scheme for (S)-3-methyl-N-(1-phenyl-ethyl)-6-(piperidin-4-yloxy)imidazo[1,2-b]pyridazin-8-amine hydrochloride

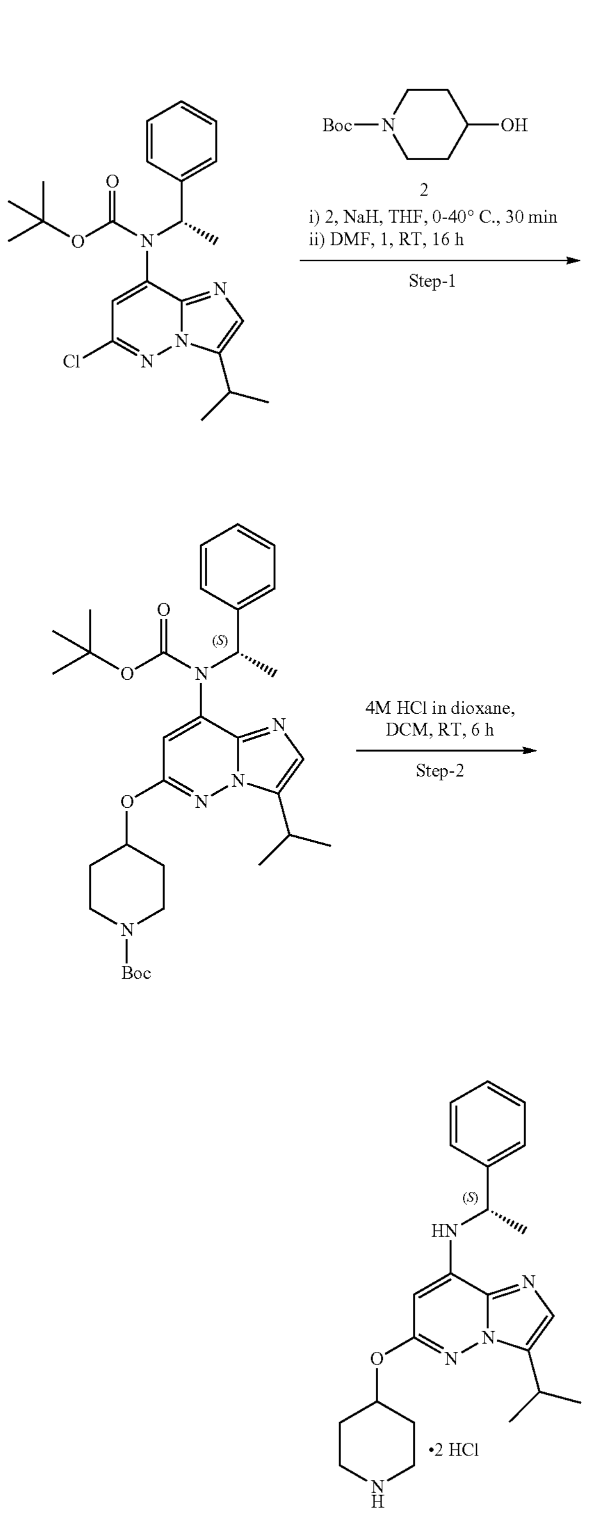

27

Synthesis of tert-butyl (S)-4-((8-((tert-butoxycarbonyl)(1-phenylethyl)amino)-3-isopropylimidazo[1,2-b]pyridazin-6-yl)oxy)piperidine-1-carboxylate

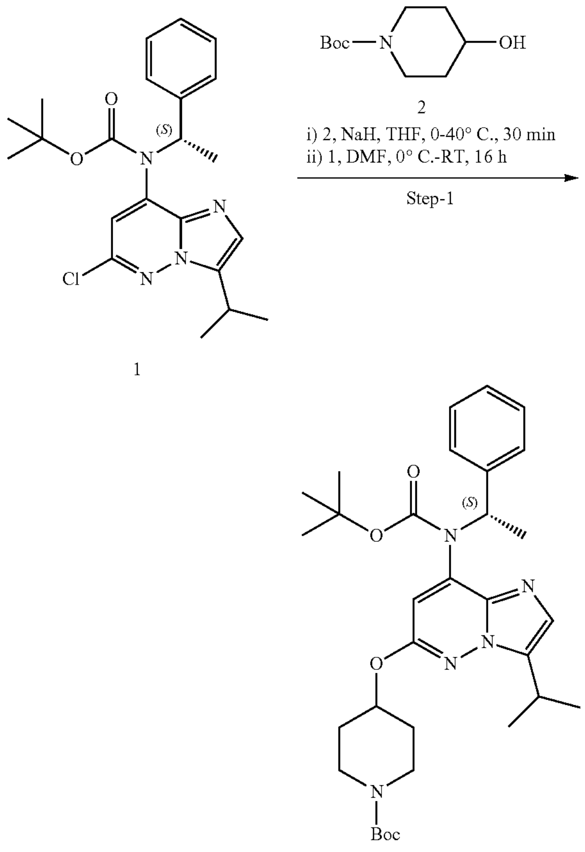

1

3

To a solution of tert-butyl 4-mercaptopiperidine-1-carboxylate (2) (0.31 g, 1.449 mmol, 3 eq.) in DMF (2 mL) at 0 °C was added NaH (60% in mineral oil, 0.057 g, 1.449 mmol, 3 eq.) and heated to 40 °C, stirred for 30 min. Then reaction mixture was cool to 0 °C and added a solution of tert-butyl (S)-(6-chloro-3-isopropylimidazo[1,2-b]pyridazin-8-yl)(1-phenylethyl)carbamate (1) (0.2 g, 0.483 mmol, 1 eq.) in DMF (2 mL). The resulting mixture was stirred at room temperature for 16 h. After this time, reaction mass was quenched with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to afford tert-butyl (S)-4-((8-((tert-butoxycarbonyl)(1-phenylethyl)amino)-3-isopropylimidazo[1,2-b]pyridazin-6-yl)oxy)piperidine-1-carboxylate (3) as a pale yellow solid (0.2 g, quantitative) which was carried to next step without any further purification, $R_f$=0.4 (7:3 Hexane/EtOAc).

$^1$H NMR (400 MHz, DMSO-$d_6$): δ 7.45 (d, J=7.6 Hz, 2H), 7.41 (s, 1H), 7.33 (t, J=7.6, Hz, 2H), 7.25 (t, J=7.2, Hz, 1H), 6.39 (s, 1H), 5.11-5.070 (m, 1H), 3.63 (t, J=7.6 Hz, 2H), 3.29-3.24 (m, 3H), 2.00-1.90 (m, 2H), 1.65-1.60 (m, 3H), 1.58 (s, 3H), 1.40 (s, 9H), 1.35-1.32 (m, 6H), 1.18 (s, 9H).

Synthesis of (S)-3-methyl-N-(1-phenylethyl)-6-(piperidin-4-yloxy)imidazo[1,2-b]pyridazin-8-amine hydrochloride

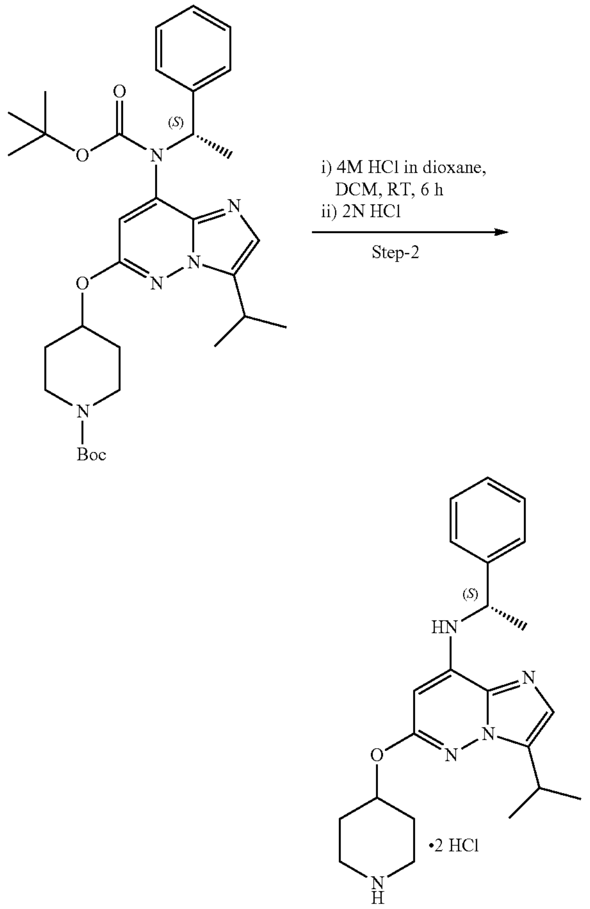

27

To a solution of tert-butyl (S)-4-((8-((tert-butoxycarbonyl)(1-phenylethyl)amino)-3-isopropylimidazo[1,2-b]pyridazin-6-yl)oxy)piperidine-1-carboxylate (3) (0.19 g, 0.319 mmol, 1 eq.) in DCM (5 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (formic acid buffer was used) to afford (S)-3-cyclopropyl-N-(1-phenylethyl)-6-(piperidin-4-ylthio)imidazo[1,2-b]pyridazin-8-amine. To get compound as a HCl salt, obtained formate salt was dissolved in ACN:water and treated with 2N aq. HCl at 0 °C and lyophilized to afford (S)-3-methyl-N-(1-phenylethyl)-6-(piperidin-4-yloxy)imidazo[1,2-b]pyridazin-8-amine hydrochloride (27) (102 mg, 82% yield). $R_f$=0.1 (9:1 DCM/MeOH). LCMS (m/z): 380.28 $(M+H)^+$. $^1H$ NMR (400 MHz, DMSO-$d_6$) δ 8.96 (s, 3H), 7.97 (s, 1H), 7.49 (dd, J=7.6, 2.7 Hz, 2H), 7.36 (td, J=7.7, 2.8 Hz, 2H), 7.27 (dd, J=7.4, 2.8 Hz, 1H), 5.97 (s, 1H), 5.12 (dt, J=8.1, 4.4 Hz, 1H), 4.95-4.87 (m, 1H), 3.32-3.25 (m, 1H), 3.18-3.09 (m, 5H), 2.16-2.15 (m, 2H), 1.97-1.90 (m, 2H), 1.56 (s, 3H), 1.32 (td, J=6.8, 2.9 Hz, 6H).

Example 40

Synthetic Scheme for 3-isopropyl-N—((S)-1-phenylethyl)-6-(piperidin-3-ylthio) imidazo [1, 2-b] pyridazin-8-amine hydrochloride salt

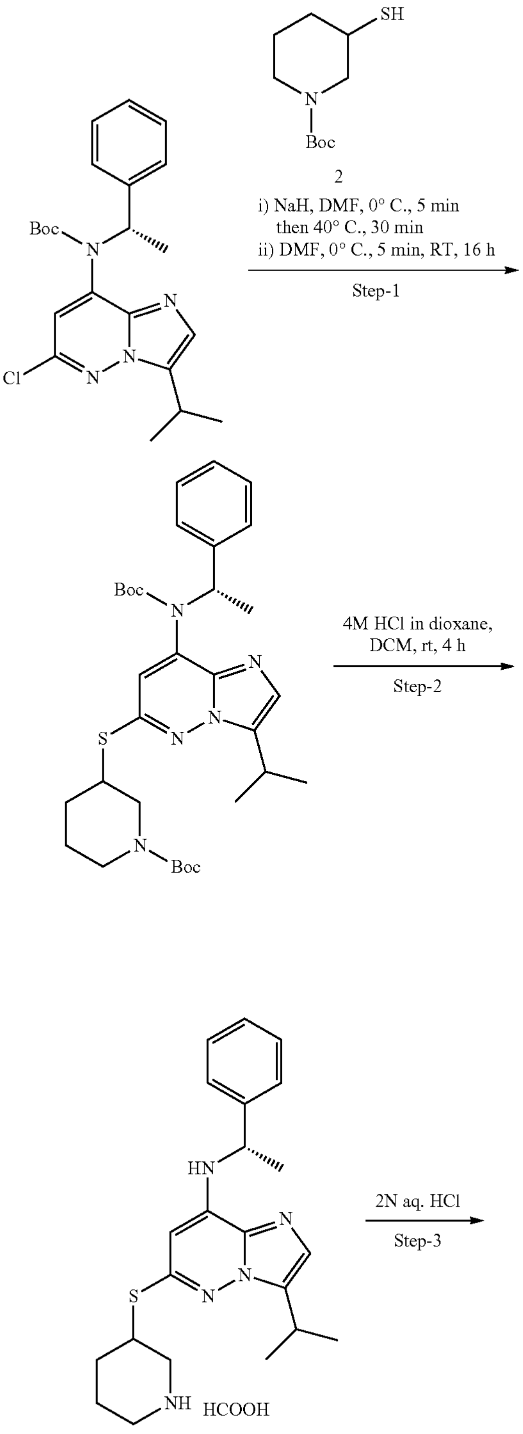

-continued

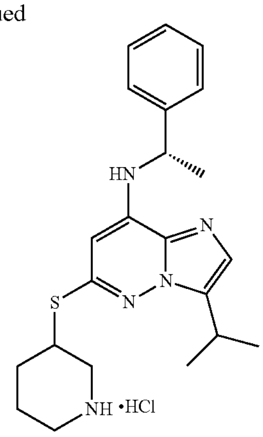

28

Step-1: Synthesis of tert-butyl 3-((8-((tert-butoxycarbonyl)((S)-1-phenylethyl)amino)-3-isopropylimidazo[1,2-b]pyridazin-6-yl)thio)piperidine-1-carboxylate

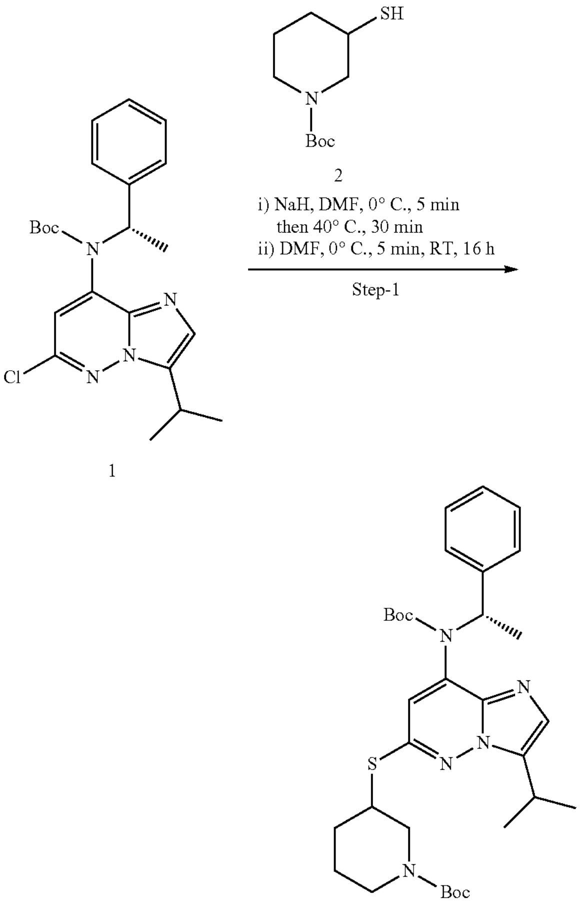

1 2 3

To a stirred solution of tert-butyl 3-mercaptopiperidine-1-carboxylate (314 mg, 1.449 mmol, 3 eq.) in DMF (3 mL) was added sodium hydride (60% dispersion in oil) (57.97 mg, 1.449 mmol, 3 eq.) at 0 °C. Reaction mixture was heated at 40 °C for 30 minutes. After this time, reaction mixture was cooled and tert-butyl (S)-(6-chloro-3-isopropylimidazo [1, 2-b]pyridazin-8-yl)(1-phenylethyl)carbamate (200 mg, 0.483 mmol, 1.0 eq.) in DMF (2 mL) was added at 0 °C. Reaction mixture was allowed to come to room temperature and stirred for 16 h. After complete conversion by TLC, the reaction mixture was cooled to room temperature; ice cold water (8.0 mL) was added to the reaction mixture and extracted with ethyl acetate (3×25 mL). Combined organic layer was washed with brine (25 mL), dried over sodium sulphate, filtered and evaporated under reduced pressure to afford the brown oil as crude compound. Crude compound was purified by silica gel column chromatography (with a gradient elution of 15-20% of EtOAc: n-Hexane) to afford the title compound as tert-butyl 3-((8-((tert-butoxycarbonyl)((S)-1-phenylethyl)amino)-3-isopropylimidazo[1,2-b]pyridazin-6-yl)thio)piperidine-1-carboxylate (3) as brown solid. (Yield 250 mg, 87%). $R_f$=0.3 (4:1 Hexane/EtOAc). LCMS (m/z): 596.28 $(M+H)^+$. $^1$H NMR (400 MHz, $CDCl_3$): δ 7.45-7.28 (m, 5H), 6.28 (s, 1H), 5.77-5.75 (m, 1H), 4.17-4.12 (m, 1H), 3.89-3.78 (m, 2H), 3.45 (s, 2H), 2.97 (s, 1H), 2.17-2.16 (m, 1H), 2.07 (s, 1H), 1.79 (m, 2H), 1.67-1.60 (m, 3H), 1.48-1.33 (m, 14H), 1.28 (s, 9H).

Step-2: Synthesis of 3-isopropyl-N—((S)-1-phenylethyl)-6-(piperidin-3-ylthio) imidazo [1, 2-b] pyridazin-8-amine

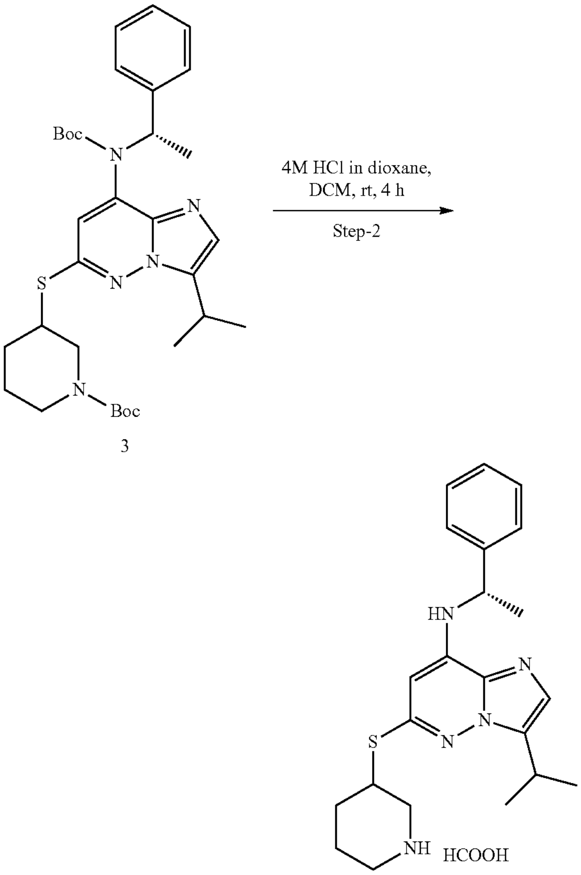

3 4

To a solution of tert-butyl 3-((8-((tert-butoxycarbonyl)((S)-1-phenylethyl)amino)-3-isopropylimidazo[1,2-b]pyridazin-6-yl)thio)piperidine-1-carboxylate (3) (250 mg, 0.420 mmol, 1 eq) in DCM (5 mL) at 0 °C was added 4M HCl in 1,4-dioxane (1 mL) drop-wise and stirred at room temperature for 4 h. After completion of reaction by TLC, the reaction mixture was subjected to rotary evaporator for removal of volatiles. The obtained residue was triturated with ether (2×5 mL), and evaporated under reduced pressure to get crude compound as brown solid. Crude compound was purified by preparative HPLC using formic acid buffer to afford the title compound as 3-isopropyl-N—((S)-1-phenylethyl)-6-(piperidin-3-ylthio)imidazo[1,2-b]pyridazin-8-amine formate salt (4) as white solid. Yield: 107 mg (64.47%). $R_f$=0.1 (1:1 Hexane/EtOAc). LCMS (m/z): 396.26 $(M+H)^+$. $^1H$ NMR (400 MHz, DMSO-$d_6$,): δ=9.29 (s, 1H), 9.08-8.96 (m, 2H), 7.90 (s, 1H), 7.48 (d, J=7.2 Hz, 2H), 7.36-7.33 (m, 2H), 7.26 (d, J=6.8 Hz, 1H), 6.23 (s, 1H), 4.94 (s, 1H), 4.02 (m, 1H), 3.56-3.37 (m, 6H), 3.21 (m, 2H), 3.05-3.01 (m, 1H), 2.87 (s, 2H), 2.07-1.98 (m, 1H), 1.83 (s, 2H), 1.57 (d, J=5.6 Hz, 4H), 1.34-1.23 (m, 6H).

Step-3: Synthesis of 3-isopropyl-N—((S)-1-phenylethyl)-6-(piperidin-3-ylthio) imidazo [1, 2-b] pyridazin-8-amine hydrochloride salt

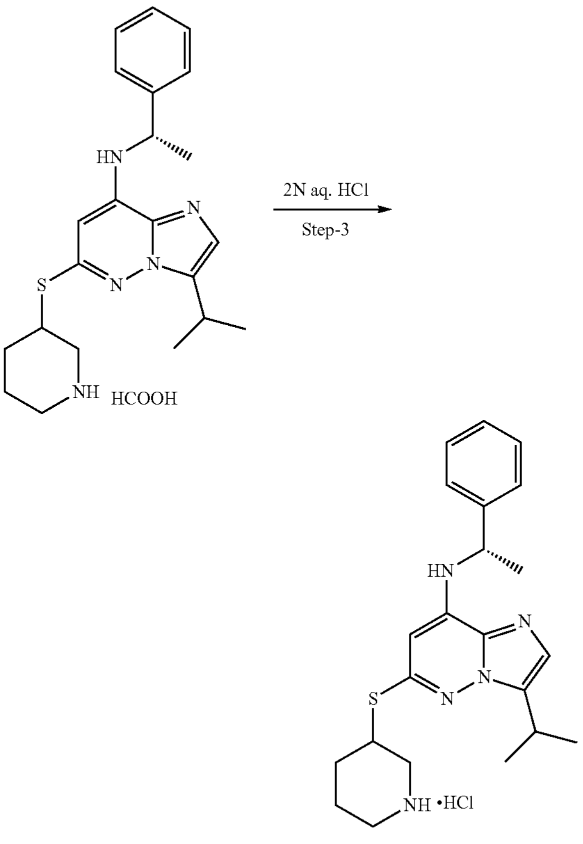

28

To a solution of N-benzyl-3-cyclopropyl-6-(piperidin-3-ylthio)imidazo [1,2-b]pyridazin-8-amine formate (40 mg, 0.094 mmol, 1 eq.) in 2N HCl (2 mL) was lyophilized for 24 h. to afford the title compound as 3-isopropyl-N—((S)-1-phenylethyl)-6-(piperidin-3-ylthio) imidazo [1, 2-b] pyridazin-8-amine hydrochloride (28) as white solid. (Yield: 45 mg, quantitative). $R_f$=0.1 (2:1 Hexane/EtOAc). LCMS (m/z): 380.26 $(M+H)^+$. $^1H$ NMR (400 MHz, DMSO): δ=9.38 (s, 1H), 9.15-9.02 (m, 2H), 7.93 (s, 1H), 7.48 (d, J=7.2 Hz, 2H), 7.34 (t, J=7.6 Hz, 2H), 7.25 (t, J=7.2 Hz, 1H), 6.25 (s, 1H), 4.95 (s, 1H), 4.05-4.02 (m, 1H), 3.56-3.42 (m, 2H), 3.21 (m, 1H), 3.07-2.98 (m, 1H), 2.87 (s, 1H), 2.07 (m, 1H), 1.84 (s, 2H), 1.70-1.60 (m, 1H), 1.57 (d, J=6.8 Hz, 3H), 1.34-1.28 (m, 6H).

Example 41

Synthetic Scheme for (S)-3-methyl-N-(1-phenylethyl)-6-(piperidin-4-yloxy)imidazo[1,2-b]pyridazin-8-amine hydrochloride

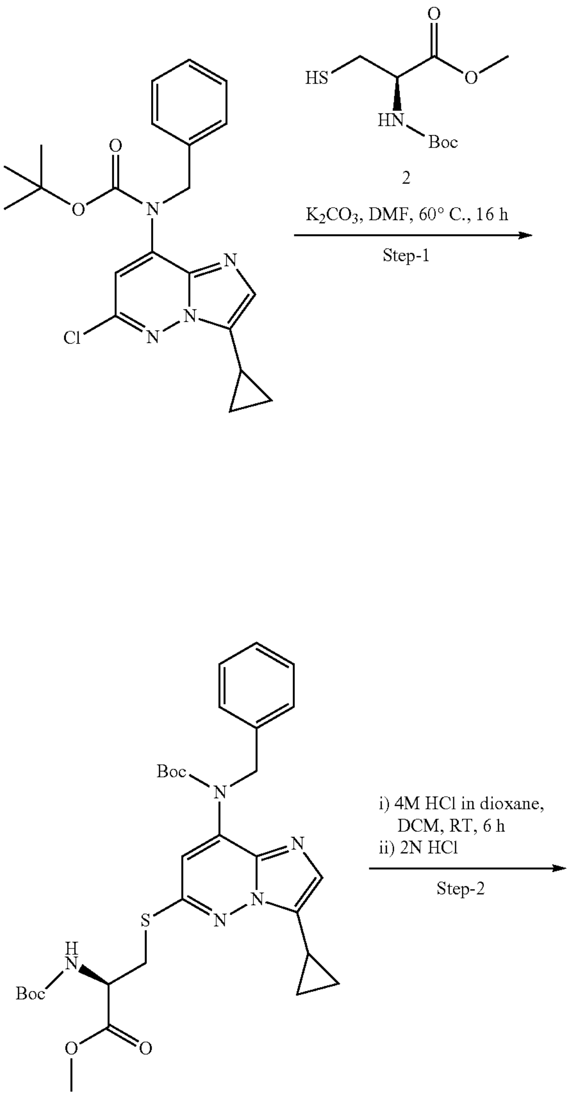

-continued

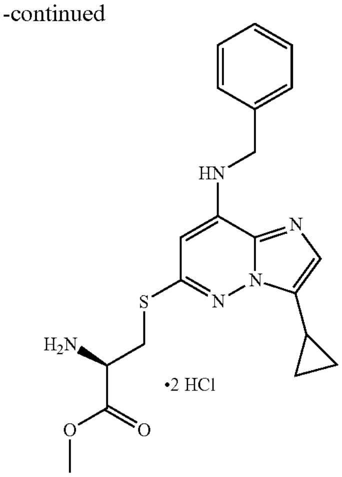

30

Synthesis of methyl S-(8-(benzyl(tert-butoxycarbonyl)amino)-3-cyclopropylimidazo[1,2-b]pyridazin-6-yl)-N-(tert-butoxycarbonyl)-L-cysteinate

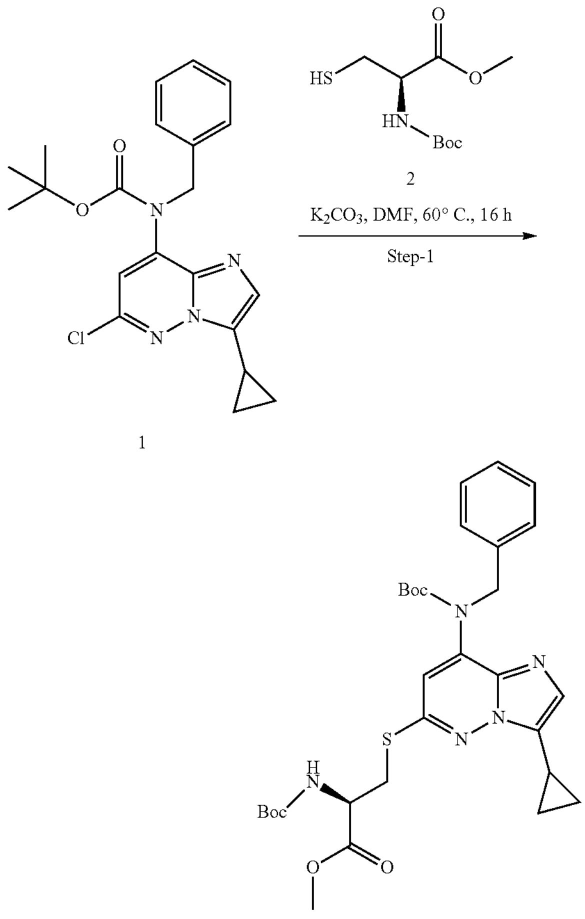

1

2

3

To a solution of methyl (tert-butoxycarbonyl)-L-cysteinate (2) (0.23 g, 1.005 mmol, 2 eq.) in DMF (5 mL) added $K_2CO_3$ (0.14 g, 1.005 mmol, 2 eq.) and tert-butyl benzyl(6-chloro-3-cyclopropylimidazo[1,2-b]pyridazin-8-yl)carbamate (1) (0.2 g, 0.502 mmol, 1 eq.) and heated at 60 °C for 16 h. After this time, reaction mass was diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to afford methyl S-(8-(benzyl(tert-butoxycarbonyl)amino)-3-cyclopropylimidazo[1,2-b]pyridazin-6-yl)-N-(tert-butoxycarbonyl)-L-cysteinate (3) as a pale yellow gum (0.2 g, quantitative) which was carried to next step without any further purification, $R_f$=0.3 (7:3 Hexane/EtOAc). Note: Observed Cpd-1 de-boc as a major in TLC & LCMS. LCMS (m/z): 598.19 $(M+H)^+$.

Synthesis of methyl S-(8-(benzylamino)-3-cyclopropylimidazo[1,2-b]pyridazin-6-yl)-L-cysteinate hydrochloride

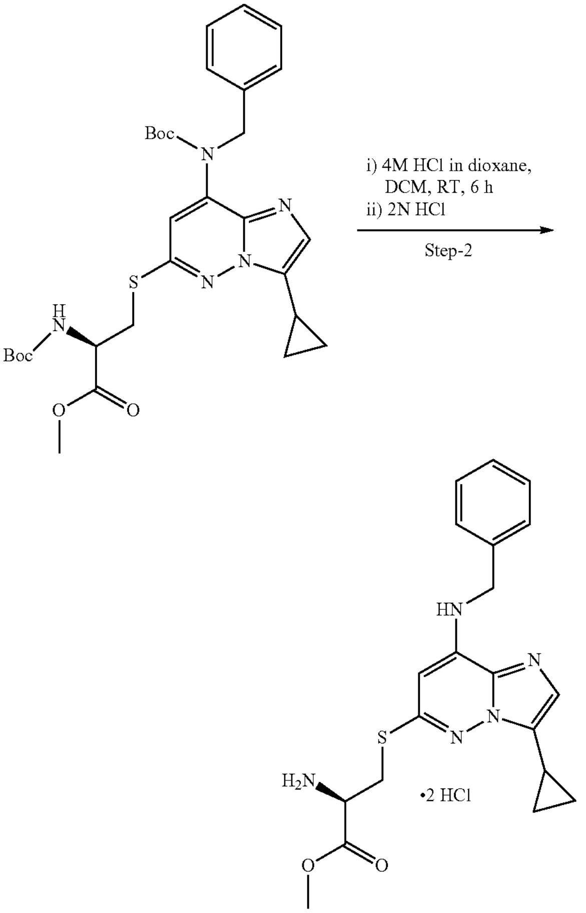

30

To a solution of methyl S-(8-(benzyl(tert-butoxycarbonyl)amino)-3-cyclopropylimidazo[1,2-b]pyridazin-6-yl)-N-(tert-butoxycarbonyl)-L-cysteinate (3) (0.13 g, 0.327 mmol, 1 eq.) in DCM (5 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (formic acid buffer was used) to afford (S)-3-cyclopropyl-N-(1-phenylethyl)-6-(piperidin-4-ylthio) imidazo[1,2-b]pyridazin-8-amine. To get compound as a HCl salt, obtained formate salt was dissolved in ACN:water and treated with 2N aq. HCl at 0 °C and lyophilized to afford methyl S-(8-(benzylamino)-3-cyclopropylimidazo[1,2-b] pyridazin-6-yl)-L-cysteinate hydrochloride (30), (12 mg, 9% yield). $R_f$=0.1 (9:1 DCM/MeOH). LCMS (m/z): 398.30 $(M+H)^+$. $^1H$ NMR (400 MHz, DMSO-$d_6$) δ 8.87-8.75 (m, 4H), 7.73 (s, 1H), 7.48-7.34 (m, 5H), 7.30 (q, J=6.8 Hz, 1H), 6.47 (s, 1H), 4.63 (t, J=6.3 Hz, 2H), 4.51 (s, 1H), 3.90-3.82 (m, 2H), 3.60 (q, J=7.0 Hz, 3H), 2.32 (dd, J=13.2, 6.9 Hz, 1H), 1.08 (dd, J=9.4, 5.3 Hz, 2H), 0.85 (dq, J=8.4, 4.6, 4.0 Hz, 2H).

Example 42

Synthetic Scheme for (S)-3-isopropyl-N8-(1-phenylethyl)-N6-(piperidin-4-yl)imidazo[1,2-b]pyridazine-6,8-diamine dihydrochloride

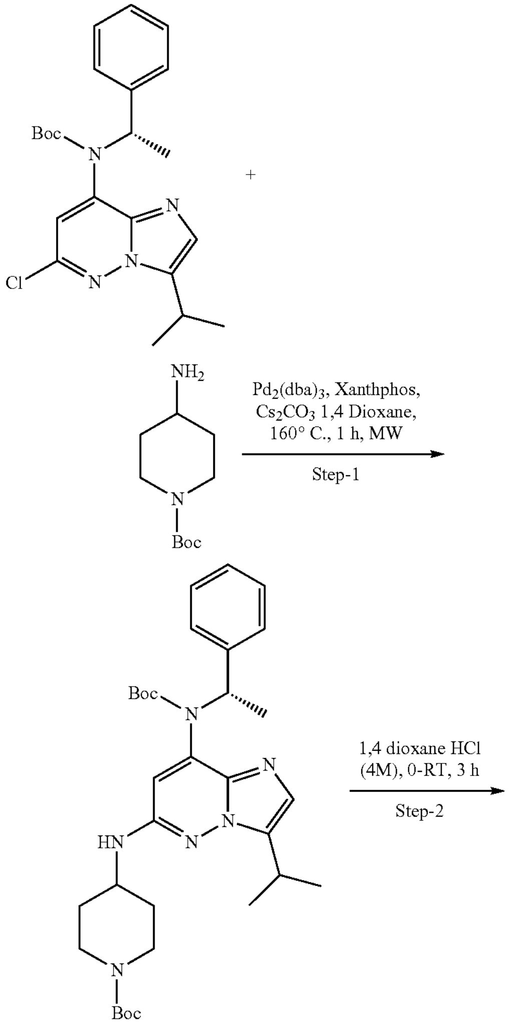

-continued

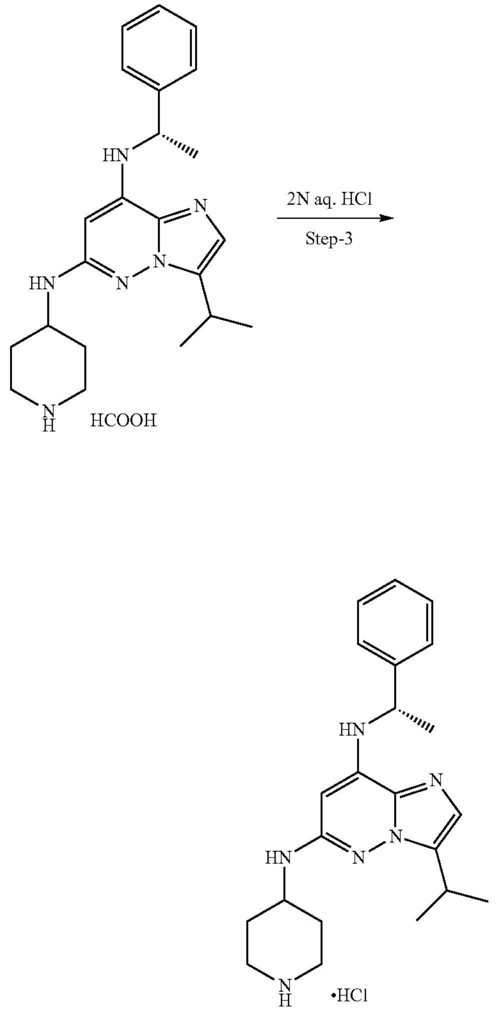

29

Step-1: Synthesis of tert-butyl (S)-4-((8-((tert-butoxycarbonyl)(1-phenylethyl)amino)-3 isopropylimidazo[1,2-b]pyridazin-6-yl)amino)piperidine-1-carboxylate

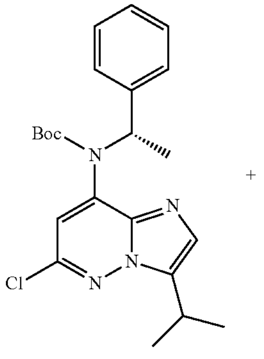

1

-continued

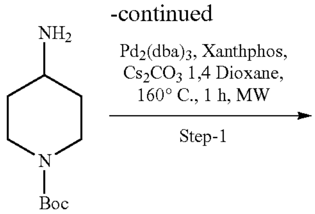

2

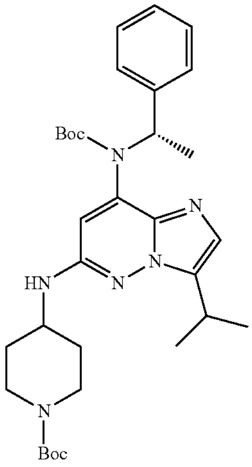

3

To a stirred solution of tert-butyl (S)-(6-chloro-3-isopropylimidazo[1,2-b]pyridazin-8-yl)(1-phenylethyl)carbamate (1) (250 mg, 0.603 mmol, 1eq.) in 1,4 Dioxane (5 mL) was added tert-butyl 4-aminopiperidine-1-carboxylate (2) (157 mg, 0.785 mmol, 1.3 eq.), cesium carbonate (588 mg, 1.811 mmol, 3 eq.) and xantphos (34.90 mg, 0.060 mmol, 0.1 eq.) at room temperature and degassed the reaction mixture under argon for 5 minutes. Then added $Pd_2(dba)_3$ (55.28 mg, 0.060 mmol, 0.1 eq.) and degassed under argon for 5 minutes. Reaction mixture was stirred at 160 °C for 1 h in microwave. After completion of reaction by TLC, reaction mixture was diluted with water (10 mL) and extracted with ethyl acetate (3×50 mL). The combined organic layer was washed with brine (10 mL), dried over sodium sulfate, filtered and evaporated under reduced pressure to get the crude compound. The crude compound was purified by silica phase column chromatography with a (gradient elution of 15-20% of EtOAc/Hexane) to afford the title compound (3) tert-butyl (S)-4-((8-((tert-butoxycarbonyl)(1-phenylethyl)amino)-3-isopropylimidazo[1,2-b]pyridazin-6-yl)amino)piperidine-1-carboxylate as brown solid. (Yield: 225 mg, 64.46%). $R_f$=0.2 (4:1Hexane/EtOAc). LCMS (m/z): 579.36 $(M+H)^+$. $^1$HNMR (400 MHz, DMSO-$d_6$) δ 7.55 (s, 1H), 7.33 (s, 1H), 7.26 (d, J=6.4 Hz, 1H), 7.19 (t, J=8.0 Hz, 1H), 6.90 (d, J=8.0 Hz, 1H), 6.85 (t, J=7.2 Hz, 1H), 5.22 (s, 2H), 3.58 (s, 3H), 2.15-2.10 (m, 1H), 1.36 (s, 9H), 1.06-1.01 (m, 2H), 0.83-0.80 (m, 2H).

Step-2: Synthesis of (S)-3-isopropyl-N8-(1-phenylethyl)-N6-(piperidin-4-yl)imidazo[1,2-b]pyridazine-6,8-diamine formate salt

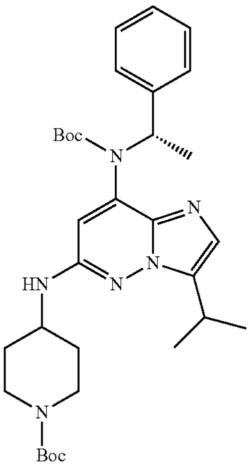

3

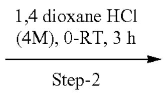

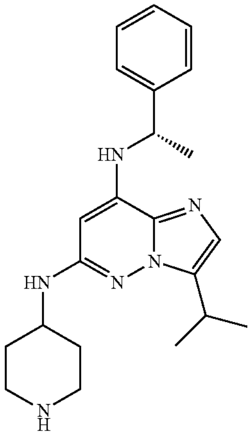

HCOOH

4

To a solution of tert-butyl (S)-4-((8-((tert-butoxycarbonyl)(1-phenylethyl)amino)-3-isopropylimidazo[1,2-b]pyridazin-6-yl)amino)piperidine-1-carboxylate (3) (225 mg, 0.389 mmol, 1eq.) in DCM (5 mL) at 0 °C was added 4M HCl in dioxane (2 mL) and stirred at room temperature for 3 h. After complete conversion by TLC, volatiles were evaporated under reduced pressure to get the crude compound as brown solid. The crude compound was purified by preparative HPLC by using formic acid buffer to afford the title compound (4) as (S)-3-isopropyl-N8-(1-phenylethyl)-N6-(piperidin-4-yl)imidazo[1,2-b]pyridazine-6,8-diamine as formate salt. For preparative HPLC used formic acid buffer, gives formate salt. (Yield: 115 mg, 69.69%). $R_f$=0.1 (1:1 Hexane/EtOAc). LCMS(m/z): 379.33 $(M+H)^+$. $^1$HNMR (400 MHz, DMSO-$d_6$/D2O/VT NMR) δ 7.39 (s, 1H), 7.33-7.30 (m, 2H), 7.06 (d, J=8.0 Hz, 1H), 6.95 (t, J=8.0 Hz, 1H), 5.32-5.19 (br, 2H), 4.51 (s, 2H), 3.87 (s, 3H), 3.53-3.51 (m, 2H), 3.24-3.22 (m, 2H), 2.71 (s, 3H), 2.44-2.42 (m, 1H), 2.26-2.23 (m, 1H), 2.14-2.10 (m, 2H), 1.96-1.93 (m, 1H), 1.06-1.02 (m, 2H), 0.87-0.83 (m, 2H).

Step-3: Synthesis of (S)-3-isopropyl-N8-(1-phenylethyl)-N6-(piperidin-4-yl)imidazo[1,2-b]pyridazine-6,8-diamine hydrochloride salt

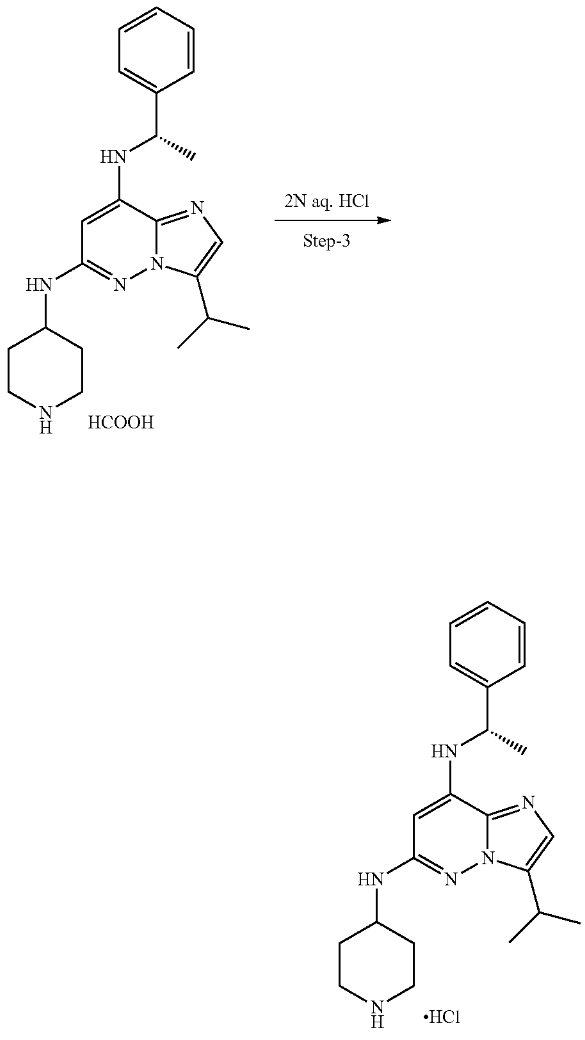

29

To a stirred solution of (S)-3-isopropyl-N8-(1-phenylethyl)-N6-(piperidin-4-yl)imidazo[1,2-b]pyridazine-6,8-diamine formate (4) (80 mg, 0.188 mmol, 1eq.) was added cold 2N HCl (1 mL) at 0 °C. Reaction mixture was lyophilized for 16 h to afford the title compound (S)-3-isopropyl-N8-(1-phenylethyl)-N6-(piperidin-4-yl)imidazo[1,2-b]pyridazine-6,8-diamine hydrochloride as white solid (29) (Yield: 65 mg, quantitative). $R_f$=0.1 (1:1Hexane/EtOAc). LCMS (m/z): 379.29 $(M+H)^+$. $^1$HNMR (400 MHz, DMSO) δ: 8.81 (s, 2H), 8.47 (s, 1H), 7.85 (s, 1H), 7.42 (m, 2H), 7.37-7.34 (m, 2H), 7.28-7.24 (m, 1H), 7.17 (m, 1H), 5.70 (s, 1H), 4.65-4.62 (m, 1H), 3.80 (s, 1H), 3.26-3.23 (m, 3H), 2.97 (s, 2H), 2.07-2.03 (m, 2H), 1.65-1.56 (m, 5H), 1.32-1.28 (m, 6H).

Example 43

Synthetic Scheme for N-(2-methoxybenzyl)-3-methyl-6-(piperidin-4-ylthio)imidazo[1,2-b]pyridazin-8-amine hydrochloride

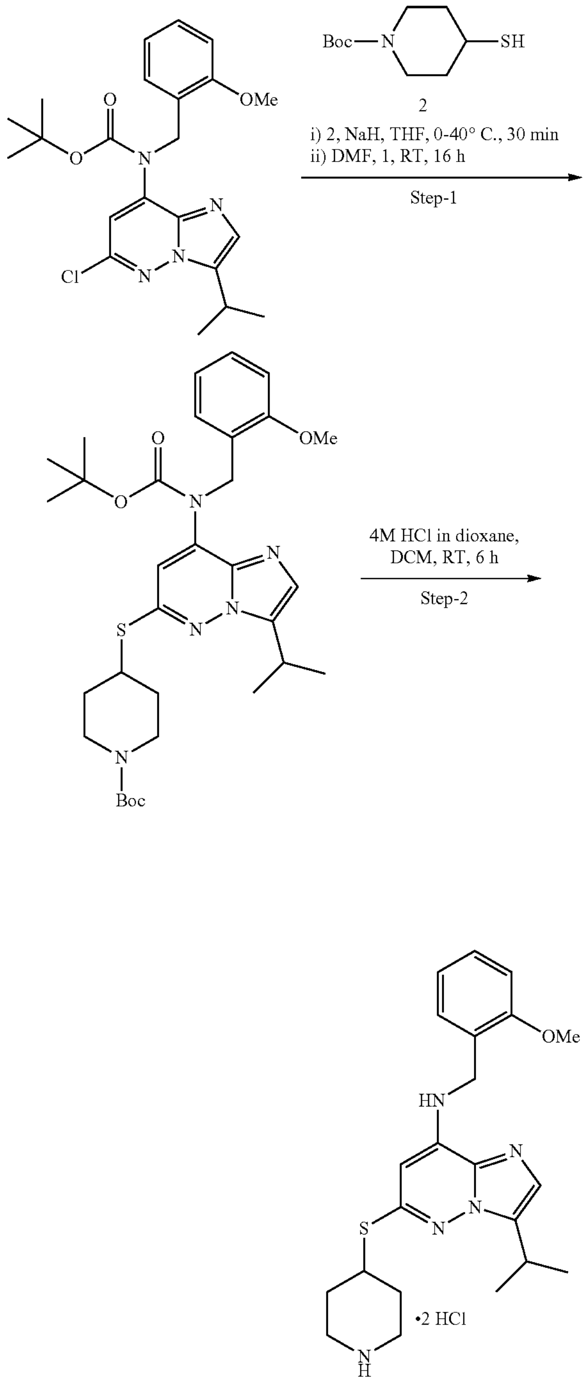

35

Synthesis of tert-butyl 4-((8-((tert-butoxycarbonyl)(2-methoxybenzyl)amino)-3-isopropylimidazo[1,2-b]pyridazin-6-yl)thio)piperidine-1-carboxylate

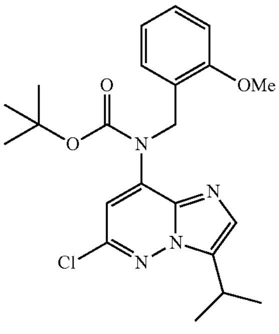

1

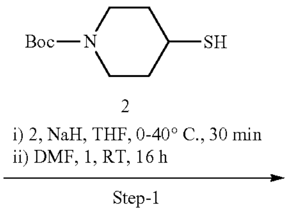

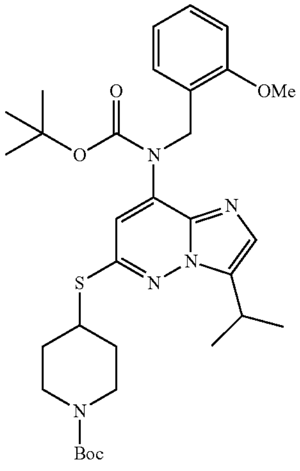

3

To a solution of tert-butyl 4-mercaptopiperidine-1-carboxylate (2) (0.32 g, 1.515 mmol, 2 eq.) in DMF (2 mL) at 0 °C was added NaH (60% in mineral oil, 0.090 g, 2.271 mmol, 3 eq.) and heated to 40 °C, stirred for 30 min. Then reaction mixture was cool to 0 °C and added a solution of tert-butyl (6-chloro-3-isopropylimidazo[1,2-b]pyridazin-8-yl)(2-methoxybenzyl)carbamate (1) (0.25 g, 0.757 mmol, 1 eq.) in DMF (2 mL). The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to afford tert-butyl (S)-4-((8-((tert-butoxycarbonyl)(1-phenylethyl)amino)-3-isopropylimidazo[1,2-b]pyridazin-6-yl)oxy)piperidine-1-carboxylate (3) as a pale yellow gum (0.18 g, quantitative) which was carried to next step without any further purification, $R_f$=0.5 (7:3 Hexane/EtOAc). Note: Observed Cpd-1 de-boc as a major in TLC & LCMS. LCMS (m/z): 612.1 $(M+H)^+$. $^1H$ NMR (400 MHz, DMSO-$d_6$): δ 7.46-7.30 (s, 1H), 7.19-7.10 (m, 2H), 6.93-6.77 (m, 2H), 6.51 (s, 1H), 5.16 (s, 2H), 4.04-3.92 (m, 2H), 3.90-3.77 (m, 2H), 3.59 (s, 3H), 3.04-3.03 (m, 2H), 2.07 (d, J=11.6 Hz, 2H), 1.59 (t, J=9.6 Hz, 2H), 1.40 (s, 9H), 1.39 (s, 9H), 1.36-1.34 (m, 6H).

Synthesis of N-(2-methoxybenzyl)-3-methyl-6-(piperidin-4-ylthio)imidazo[1,2-b]pyridazin-8-amine hydrochloride

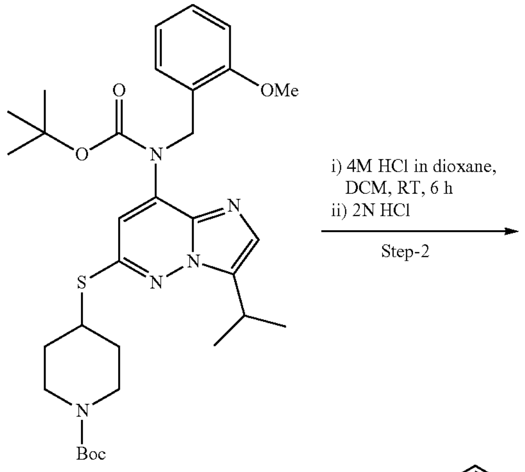

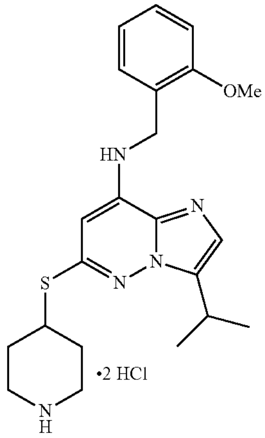

35

To a solution of tert-butyl 4-((8-((tert-butoxycarbonyl)(2-methoxybenzyl)amino)-3-isopropylimidazo[1,2-b]pyridazin-6-yl)thio)piperidine-1-carboxylate (3) (0.185 g, 0.361 mmol, 1 eq.) in DCM (6 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (formic acid buffer was used) afford N-(2-methoxybenzyl)-3-methyl-6-(piperidin-4-ylthio)imidazo[1,2-b]pyridazin-8-amine. To get compound as a HCl salt, obtained formate salt was dissolved in ACN:water and treated with 2N aq. HCl at 0 °C and lyophilized to afford N-(2-methoxybenzyl)-3-methyl-6-(piperidin-4-ylthio)imidazo[1,2-b]pyridazin-8-amine hydrochloride (35) as a white solid (55 mg, 49% yield). $R_f$=0.1 (9:1 DCM/MeOH). LCMS (m/z): 396.21 $(M+H)^+$. $^1H$ NMR (400 MHz, DMSO-$d_6$) δ 9.17 (s, 1H), 9.00 (s, 1H), 8.61 (s, 1H), 7.91 (s, 1H), 7.32 (q, J=8.9, 7.7 Hz, 2H), 7.11-7.03 (m, 1H), 6.94 (q, J=6.9 Hz, 1H), 6.45 (d, J=5.9 Hz, 1H), 4.54 (d, J=5.2 Hz, 2H), 4.10-3.95 (m, 2H), 3.87 (d, J=4.0 Hz, 3H), 3.45-3.35 (m, 1H), 3.34-3.25 (m, 2H), 3.12-3.00 (m, 2H), 2.30-2.20 (m, 2H), 1.95-80 (m, 2H), 1.35 (t, J=6.3 Hz, 6H).

Example 44

Synthetic Scheme for N-(2-methoxybenzyl)-3-methyl-6-(piperidin-4-ylthio)imidazo[1,2-b]pyridazin-8-amine hydrochloride

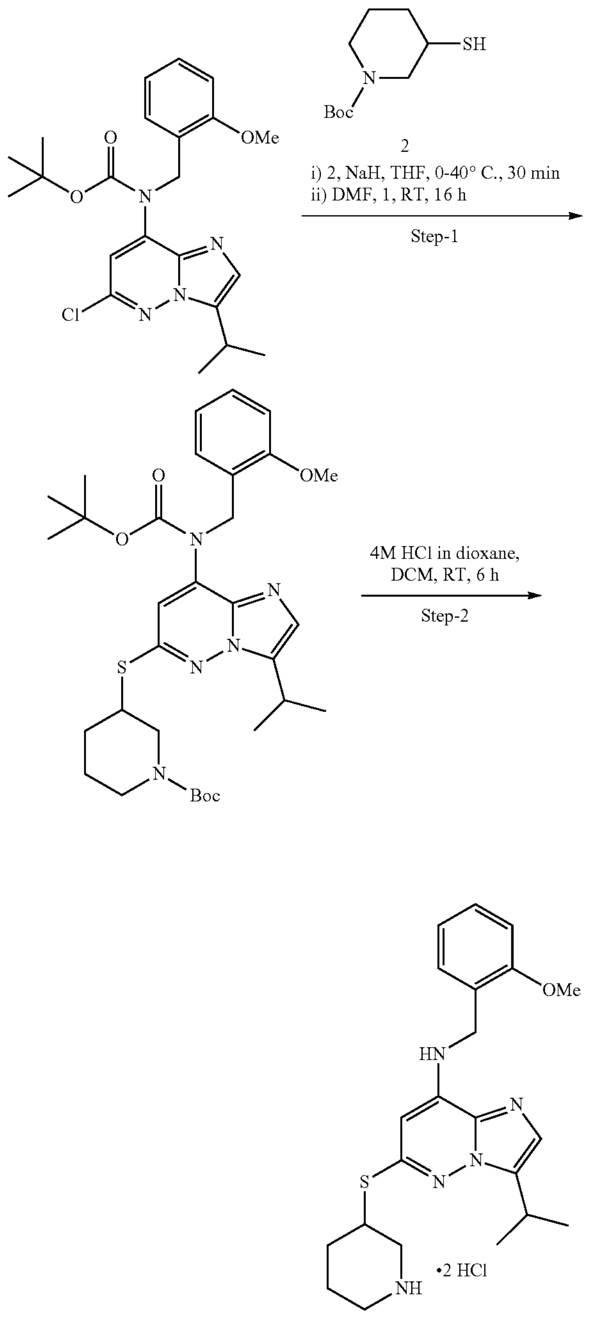

36

Synthesis of tert-butyl 3-((8-((tert-butoxycarbonyl)(2-methoxybenzyl)amino)-3-isopropylimidazo[1,2-b]pyridazin-6-yl)thio)piperidine-1-carboxylate

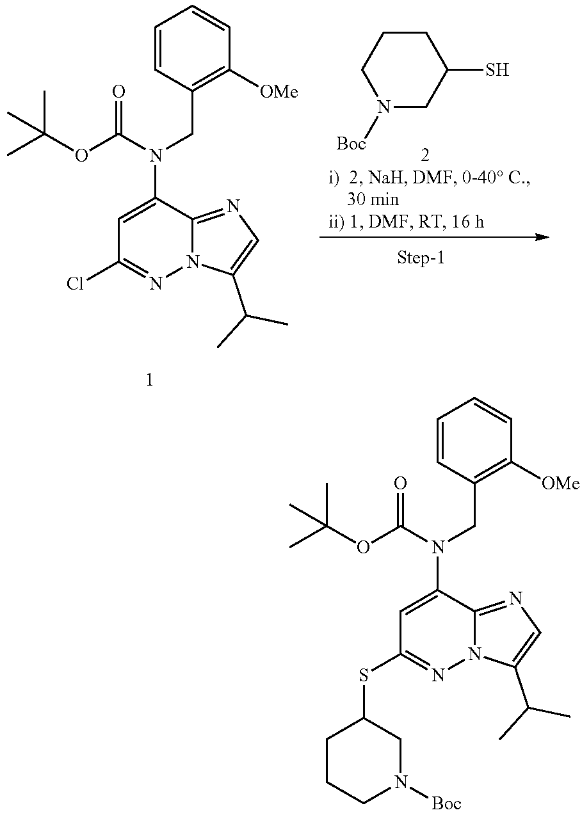

3

To a solution of tert-butyl 3-mercaptopiperidine-1-carboxylate (2) (0.32 g, 1.515 mmol, 2 eq.) in DMF (2 mL) at 0 °C was added NaH (60% in mineral oil, 0.090 g, 2.271 mmol, 3 eq.) and heated to 40 °C, stirred for 30 min. Then reaction mixture was cool to 0 °C and added a solution of tert-butyl (6-chloro-3-isopropylimidazo[1,2-b]pyridazin-8-yl)(2-methoxybenzyl)carbamate (1) (0.25 g, 0.757 mmol, 1 eq.) in DMF (2 mL). The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to afford tert-butyl 3-((8-((tert-butoxycarbonyl)(2-methoxybenzyl)amino)-3-isopropylimidazo[1,2-b]pyridazin-6-yl)thio)piperidine-1-carboxylate (3) as a yellow gum (0.185 g, quantitative) which was carried to next step without any further purification, $R_f$=0.5 (7:3 Hexane/EtOAc). Note: Observed Cpd-1 de-boc as a major in TLC & LCMS. LCMS (m/z): 612.2 $(M+H)^+$. $^1H$ NMR (400 MHz, DMSO-$d_6$): δ 7.50 (d, J=5.6 Hz, 1H), 7.30 (d, J=6.8 Hz, 1H), 7.19 (t, J=7.2 Hz, 1H), 7.06-7.05 (m, 1H), 6.91-6.83 (m, 2H), 5.16 (s, 2H), 3.91-3.90 (m, 3H), 3.63-3.62 (m, 2H), 3.61 (s, 3H), 3.19-3.18 (m, 1H), 2.11-1.09 (m, 2H), 1.40-1.37 (m, 2H), 1.35 (s, 9H), 1.34 (s, 9H), 1.24-1.04 (m, 6H).

Synthesis of N-(2-methoxybenzyl)-3-methyl-6-(piperidin-3-ylthio)imidazo[1,2-b]pyridazin-8-amine hydrochloride

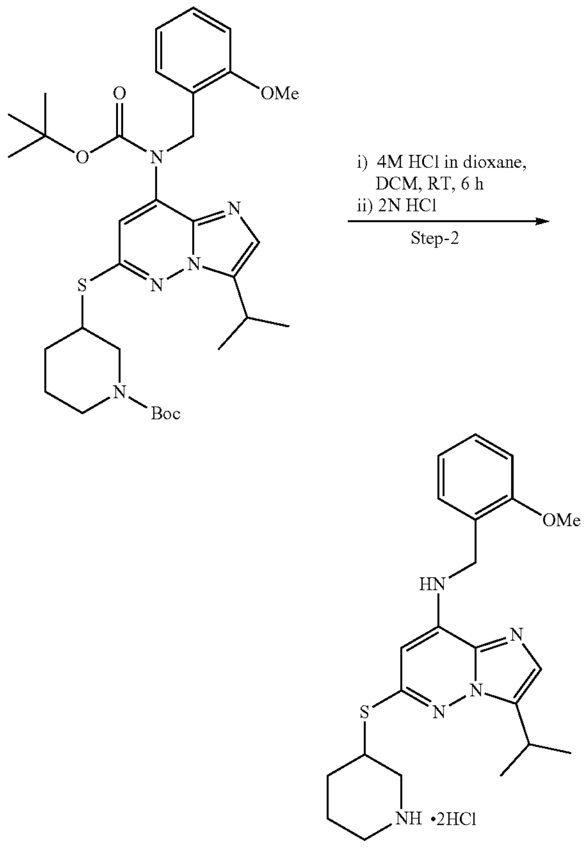

36

To a solution of tert-butyl 3-((8-((tert-butoxycarbonyl)(2-methoxybenzyl)amino)-3-isopropylimidazo[1,2-b]pyridazin-6-yl)thio)piperidine-1-carboxylate (3) (0.185 g, 0.361 mmol, 1 eq.) in DCM (6 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (formic acid buffer was used) to afford N-(2-methoxybenzyl)-3-methyl-6-(piperidin-3-ylthio)imidazo[1,2-b]pyridazin-8-amine. To get compound as a HCl salt, obtained formate salt was dissolved in ACN: water and treated with 2N aq. HCl at 0 °C and lyophilized to afford N-(2-methoxybenzyl)-3-methyl-6-(piperidin-3-ylthio)imidazo[1,2-b]pyridazin-8-amine hydrochloride (36) as a white solid (48 mg, 42% yield). $R_f$=0.1 (9:1 DCM/MeOH). LCMS (m/z): 396.23 $(M+H)^+$. $^1H$ NMR (400 MHz, DMSO-$d_6$) δ 9.52 (s, 1H), 9.21 (s, 1H), 8.66 (s, 1H), 7.93 (d, J=5.6 Hz, 1H), 7.33 (p, J=6.9, 6.4 Hz, 2H), 7.07 (dd, J=8.2, 5.3 Hz, 1H), 6.94 (q, J=6.8 Hz, 1H), 6.48 (d, J=5.4 Hz, 1H), 4.54 (t, J=5.7 Hz, 2H), 4.11 (dt, J=11.2, 6.0 Hz, 1H), 3.86 (s, 3H), 3.55 (ddd, J=19.9, 15.4, 9.1 Hz, 3H), 3.23 (d, J=12.0 Hz, 1H), 3.07 (d, J=12.2 Hz, 1H), 2.91 (s, 1H), 2.18-2.10 (m, 1H), 1.88 (td, J=8.6, 8.1, 4.4 Hz, 2H), 1.72 (dd, J=15.5, 8.8 Hz, 1H), 1.35 (q, J=6.6 Hz, 6H).

Example 45

Synthetic Scheme for (S)—N-(3-fluorophenyl)-3-isopropyl-6-(piperidin-3-yloxy)imidazo[1,2-b]pyridazin-8-amine hydrochloride

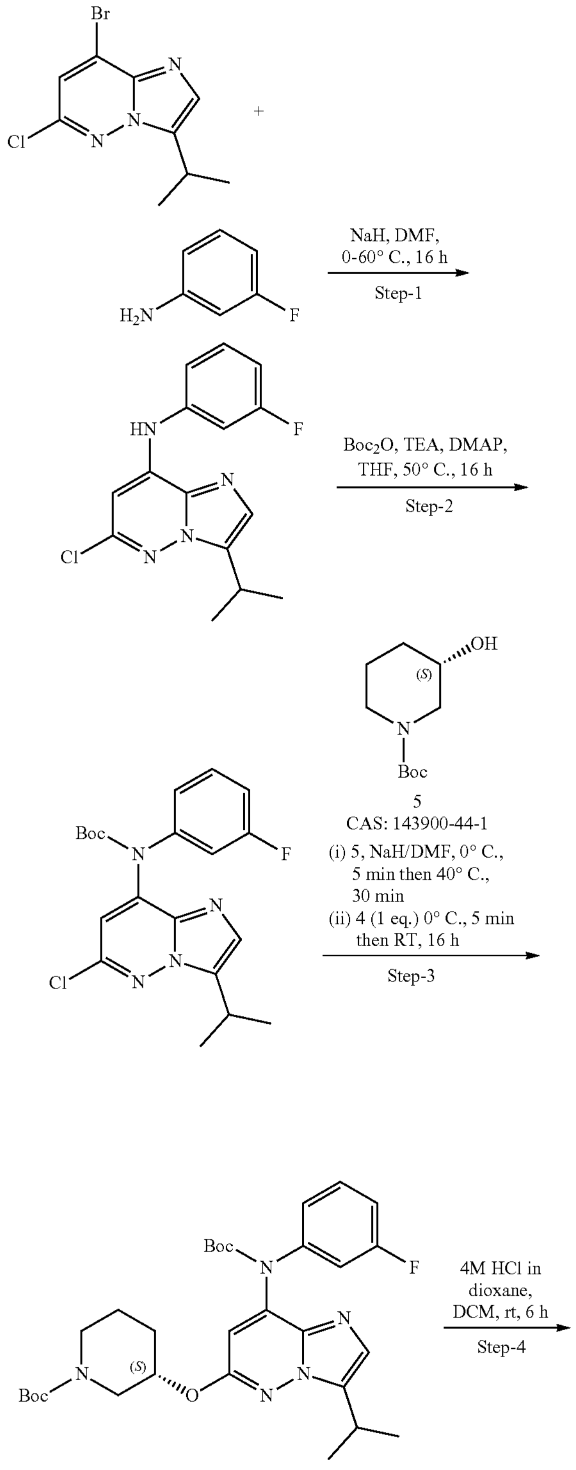

-continued

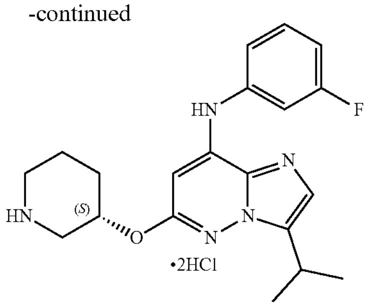

39

Synthesis of 6-chloro-N-(3-fluorophenyl)-3-isopropylimidazo[1,2-b]pyridazin-8-amine

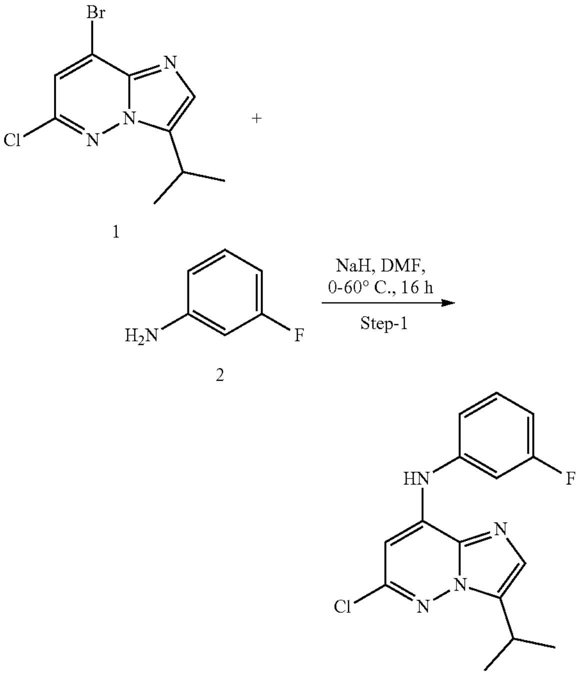

1

2

3

To a solution of 3-fluoroaniline (0.29 g, 1.360 mmol, 1.2 eq.), and in anhydrous DMF (5 mL) was added NaH (60% in mineral oil, 0.132 g, 3.295 mmol, 1.5 eq.) at 0 °C. The mixture was allowed to stir at RT for 15 min, then 8-bromo-6-chloro-3-isopropylimidazo[1,2-b]pyridazine (0.6 g, 2.197 mmol, 1 eq.) was added and heated to 60 °C for 16 h. After this time, reaction was quenched with ice cold water (6 mL) and product was extracted with EtOAc (2×30 mL). Combine organic layer was dried over $Na_2SO_4$, filtered and concentrated under reduced pressure. Obtained crude compound was purified by combiflash on silica column (EtOAc/hexane, gradient 0-50% EtOAc) to afford 6-chloro-N-(3-fluorophenyl)-3-isopropylimidazo[1,2-b]pyridazin-8-amine as a yellow gum (0.395 g, 58% yield). $R_f$=0.5 (7:3 Hexane/EtOAc). $^1$H NMR (400 MHz, DMSO): δ 9.98 (s, 1H), 7.48-7.44 (m, 2H), 7.34-7.28 (m, 2H), 7.04-7.01 (m, 1H), 6.54 (d, J=5.6 Hz, 1H), 3.37-3.29 (m, 1H), 1.36-1.29 (m, 6H).

Synthesis of tert-butyl (6-chloro-3-isopropylimidazo[1,2-b]pyridazin-8-yl)(3-fluorophenyl)carbamate

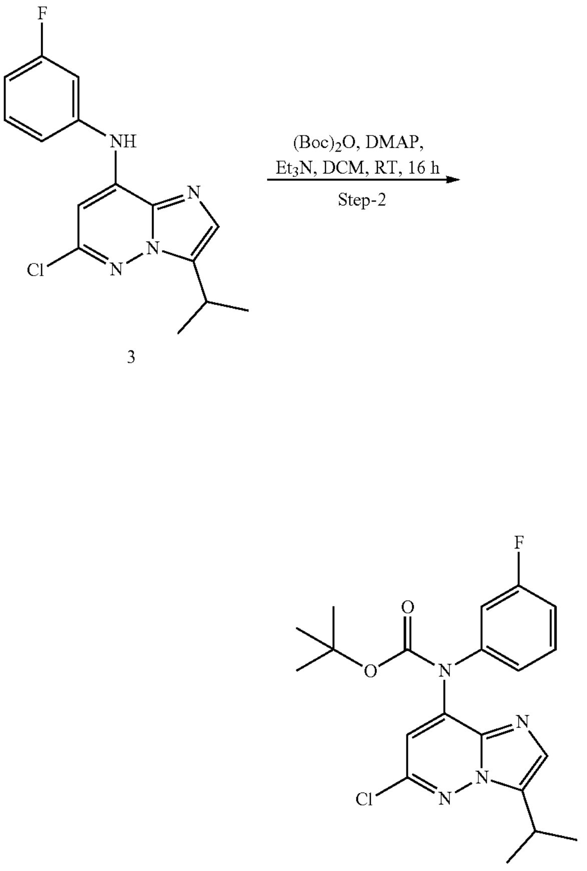

3

4

To a stirred solution of 6-chloro-N-(3-fluorophenyl)-3-isopropylimidazo[1,2-b]pyridazin-8-amine (0.35 g, 1.151 mmol, 1 eq.) in THE (5 mL) was added DIPEA (2.0 mL, 11.51 mmol, 10 eq.), $(Boc)_2O$ (2.6 mL, 11.51 mmol, 10 eq.) and DMAP (0.014 g, 0.115 mmol, 0.1 eq.) and stirred for 16 h at room temperature. The reaction mixture was concentered under reduced pressure. The obtained crude was diluted with water and extracted with EtOAc (2×10 mL). The combined organic layer was washed with brine solution (20 mL), dried over $Na_2SO_4$ concentrated under reduced pressure. The residue was purified by combiflash on silica column (EtOAc/hexane, gradient 0-40% EtOAc) to get tert-butyl (6-chloro-3-isopropylimidazo[1,2-b]pyridazin-8-yl)(3-fluorophenyl)carbamate as a yellow gum (0.35 g, 75% yield). $R_f$=0.8 (7:3 Hexane/EtOAc). $^1$H NMR (400 MHz): δ 7.22-7.61 (m, 1H), 7.44-7.34 (m, 1H), 7.31-7.25 (m, 1H), 7.19-6.98 (m, 3H), 3.64-3.58 (m, 1H), 1.35 (s, 9H).

Synthesis of tert-butyl (S)-3-((8-((tert-butoxycarbonyl)(3-fluorophenyl)amino)-3-isopropylimidazo[1,2-b]pyridazin-6-yl)oxy)piperidine-1-carboxylate

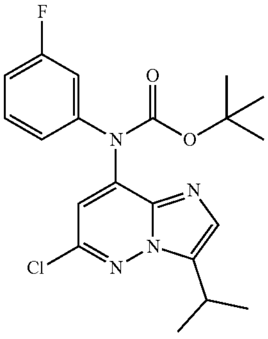

4

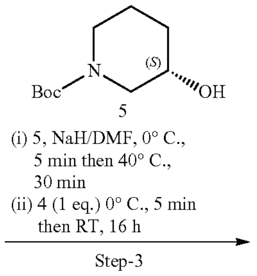

5

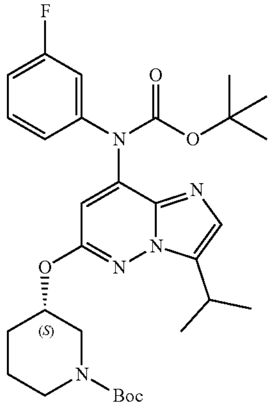

6

To a solution of tert-butyl (S)-3-hydroxypiperidine-1-carboxylate (5) (0.372 g, 1.492 mmol, 3 eq.) in DMF (2 mL) at 0 °C was added NaH (60% in mineral oil, 0.074 g, 1.856 mmol, 3 eq.) and heated to 40 °C, stirred for 30 min. Then reaction mixture was cool to 0 °C and added a solution of tert-butyl (6-chloro-3-isopropylimidazo[1,2-b]pyridazin-8-yl)(3-fluorophenyl)carbamate (4) (0.25 g, 0.618 mmol, 1 eq.) in DMF (2 mL). The resulting mixture was stirred at room temperature for 16 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. The obtained crude compound was purified by silica phase column chromatography [with a gradient elution of 5-10% of MeOH/DCM] to afford tert-butyl (S)-3-((8-((tert-butoxycarbonyl)(3-fluorophenyl)amino)-3-isopropylimidazo[1,2-b]pyridazin-6-yl)oxy)piperidine-1-carboxylate (6) as a yellow liquid (0.25 g, quantitative) which was carried to next step without any further purification, $R_f$=0.4 (2:8 Hexane/EtOAc). Note: Observed Cpd-1 de-boc as a major in TLC & LCMS. LCMS (m/z): 468.43 $(M+H)^+$ Synthesis of (S)—N-(3-fluorophenyl)-3-isopropyl-6-(piperidin-3-yloxy)imidazo[1,2-b]pyridazin-8-amine hydrochloride

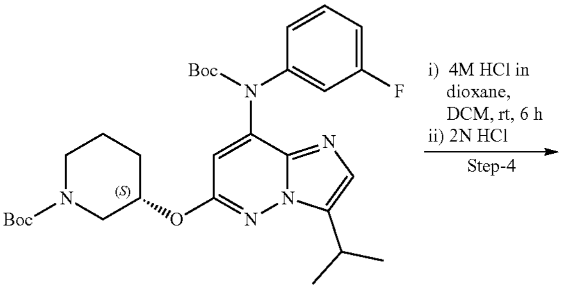

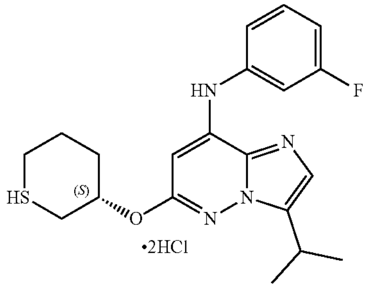

39

To a solution of tert-butyl (S)-3-((8-((tert-butoxycarbonyl)(3-fluorophenyl)amino)-3-isopropylimidazo[1,2-b]pyridazin-6-yl)oxy)piperidine-1-carboxylate (5) (0.25 g, 0.439 mmol, 1 eq.) in DCM (5 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (TFA buffer was used) to afford (S)—N-(3-fluorophenyl)-3-isopropyl-6-(piperidin-3-yloxy)imidazo[1,2-b]pyridazin-8-amine. To get compound as a HCl salt, obtained formate salt was dissolved in ACN:water and treated with 2N aq. HCl at 0 °C and lyophilized to afford (S)—N-(3-fluorophenyl)-3-isopropyl-6-(piperidin-3-yloxy)imidazo[1,2-b]pyridazin-8-amine hydrochloride as an off white solid (39), (38 mg, 32% yield). $R_f$=0.1 (9:1 DCM/MeOH). LCMS (m/z): 370.1 $(M+H)^+$. $^1H$ NMR (400 MHz, DMSO-$d_6$) δ 10.45 (s, 1H), 9.43 (d, J=11.5 Hz, 1H), 8.77 (s, 1H), 7.93 (s, 1H), 7.55 (dq, J=14.6, 7.4, 6.3 Hz, 1H), 7.33 (q, J=6.0 Hz, 2H), 7.11 (q, J=7.7 Hz, 1H), 6.55 (d, J=5.3 Hz, 1H), 5.35-5.28 (m, 1H), 3.32 (s, 3H), 3.13 (s, 1H), 3.09-2.96 (m, 1H), 2.07-1.87 (m, 3H), 1.80-1.64 (m, 1H), 1.38 (t, J=6.2 Hz, 6H).

Example 46

Synthetic Scheme for Synthesis of 3-isopropyl-N8-(2-methoxybenzyl)-N6-(piperidin-4-yl)imidazo[1,2-b]pyridazine-6,8-diamine hydrochloride

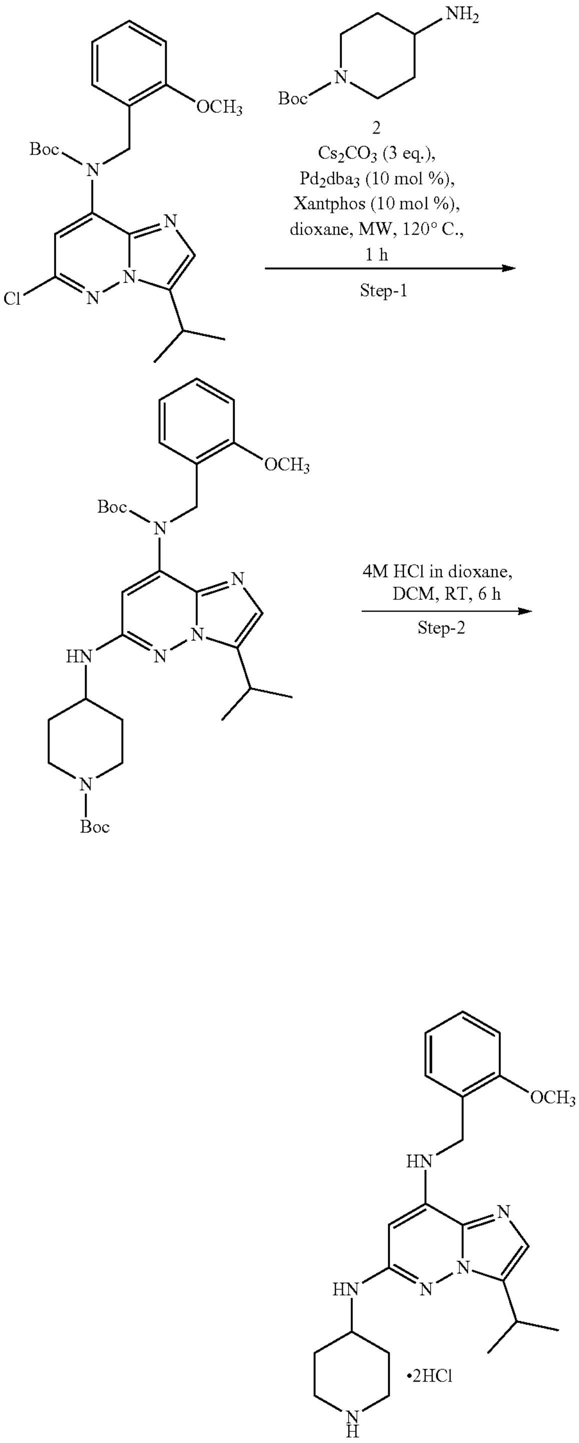

40

Synthesis of tert-butyl 4-((8-((tert-butoxycarbonyl)(2-methoxybenzyl)amino)-3-isopropylimidazo[1,2-b]pyridazin-6-yl)amino)piperidine-1-carboxylate

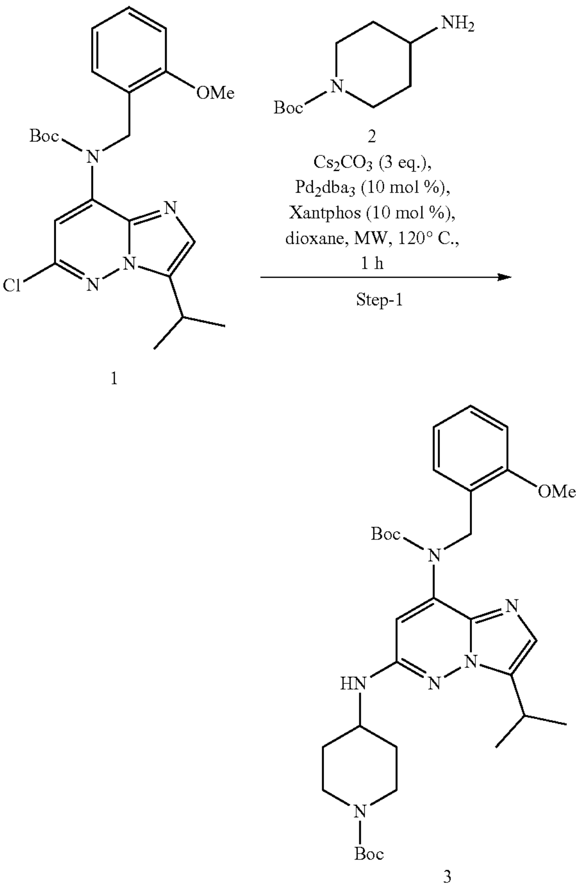

Under an atmosphere of argon 1,4,-dioxane (5 mL) was added to tert-butyl (6-chloro-3-isopropylimidazo[1,2-b]pyridazin-8-yl)(2-methoxybenzyl)carbamate (1) (0.25 g, 0.757 mmol, 1 eq.), $Cs_2CO_3$ (0.73 g, 2.271 mmol, 3 eq.), tert-butyl 4-aminopiperidine-1-carboxylate (2) (0.22 g, 1.136 mmol, 1.5 eq.) and xantphos (0.043 g, 0.0757 mmol, 0.1 eq.) at room temperature. The reaction mixture was degas with argon for 10 min and added Tris(dibenzylideneacetone)dipalladium (0.069 g, 0.0757 mmol, 0.1 eq.) again degas with argon for 10 min and heated to 120 °C for 1 h in Microvan. The reaction mixture was diluted with ethyl acetate and filtered with celite. The organic phase was washed with water (3x20 mL), dried over sodium sulfate, filtered and concentrated under reduced pressure to provide crude product. Obtained crude compound was purified by silica phase column chromatography [with a gradient elution of 50-60% of EtOAc/Hexane] to afford tert-butyl 4-((8-((tert-butoxycarbonyl)(2-methoxybenzyl)amino)-3-isopropylimidazo[1,2-b]pyridazin-6-yl)amino)piperidine-1-carboxylate (3) as a yellow gum (0.19 g, quantitative) which was carried to next step without any further purification, $R_f$=0.2 (2:8 hexane/ethyl acetate). Note: Observed Cpd-1 de-boc as a major in TLC & LCMS. LCMS (m/z): 595.1 $(M+H)^+$.

Synthesis of 3-isopropyl-N8-(2-methoxybenzyl)-N6-(piperidin-4-yl)imidazo[1,2-b]pyridazine-6,8-diamine hydrochloride

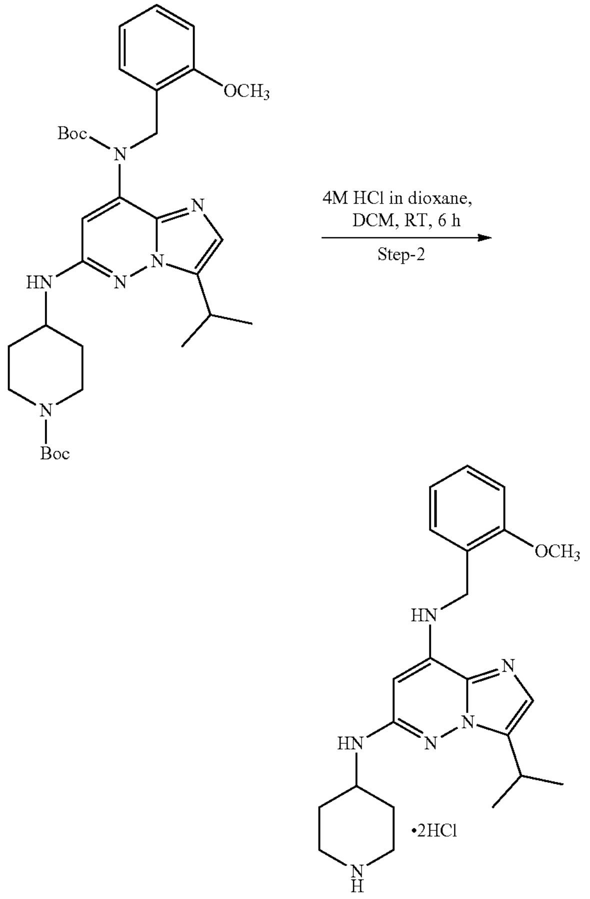

40

To a solution of tert-butyl 4-((8-((tert-butoxycarbonyl)(2-methoxybenzyl)amino)-3-isopropylimidazo[1,2-b]pyridazin-6-yl)amino)piperidine-1-carboxylate (3) (0.19 g, 0.319 mmol, 1 eq.) in DCM (5 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (formic acid buffer was used) to afford 3-isopropyl-N8-(2-methoxybenzyl)-N6-(piperidin-4-yl)imidazo[1,2-b]pyridazine-6,8-diamine. To get compound as a HCl salt, obtained formate salt was dissolved in ACN:water and treated with 2N aq. HCl at 0 °C and lyophilized to afford 3-isopropyl-N8-(2-methoxybenzyl)-N6-(piperidin-4-yl)imidazo[1,2-b]pyridazine-6,8-diamine hydrochloride (40) as an off white solid (38 mg, 24% yield). $R_f$=0.1 (9:1 DCM/MeOH). LCMS (m/z): 395.33 $(M+H)^+$. $^1$H NMR (400 MHz, DMSO-$d_6$) δ 8.80 (s, 1H), 8.03 (s, 1H), 7.82 (s, 1H), 7.33 (d, J=16.0 Hz, 2H), 7.19 (s, 1H), 7.08 (t, J=6.0 Hz, 1H), 6.95 (q, J=6.8 Hz, 1H), 5.87 (s, 1H), 4.43 (d, J=4.8 Hz, 2H), 3.88 (s, 3H), 3.32-3.27 (m, 4H), 3.02 (s, 2H), 2.11 (d, J=8.8 Hz, 2H), 1.68 (d, J=4.0 Hz, 2H), 1.35 (t, J=6.4 Hz, 6H).

Example 47

Synthetic Scheme for 3-isopropyl-6-(piperidin-4-ylthio)-N-(2-(trifluoromethoxy)benzyl)imidazo[1,2-b]pyridazin-8-AMIE hydrochloride

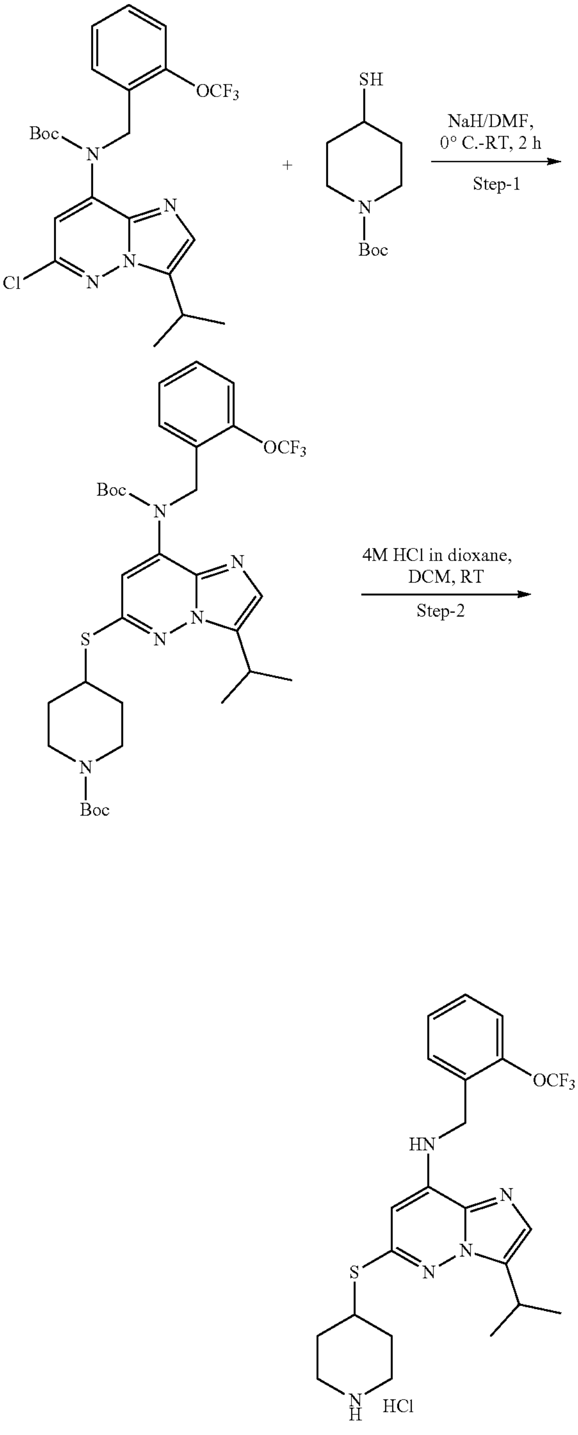

33a

Synthesis of tert-butyl 4-((8-((tert-butoxycarbonyl)(2-(trifluoromethoxy)benzyl)amino)-3-isopropylimidazo[1,2-b]pyridazin-6-yl)thio)piperidine-1-carboxylate Synthesis of 3-isopropyl-6-(piperidin-4-ylthio)-N-(2-(trifluoromethoxy)benzyl)imidazo[1,2-b]pyridazin-8-amie hydrochloride

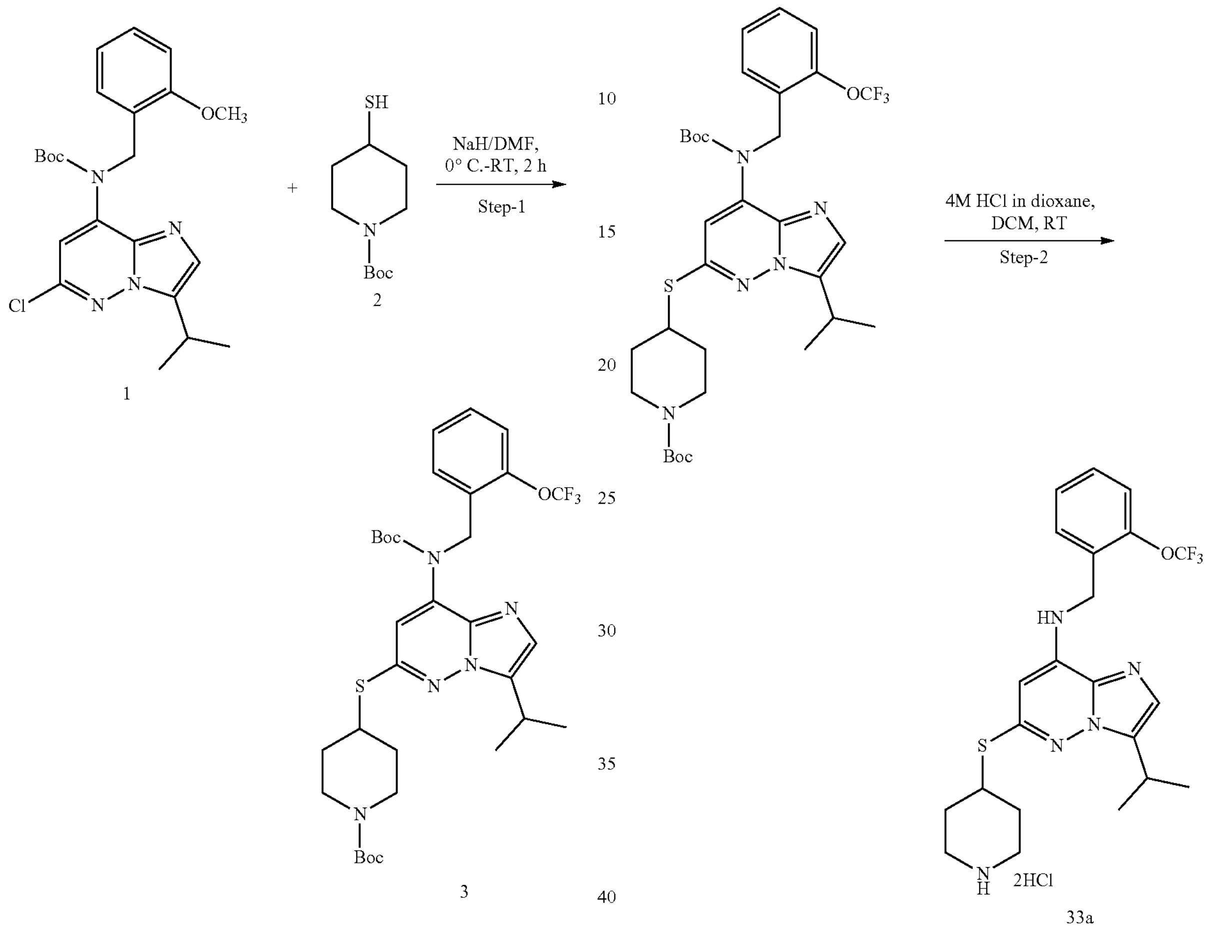

To a stirred solution of tert-butyl 4-mercaptopiperidine-1-carboxylate (2) (0.269 g, 1.23 mmol, 3eq.) in DMF (5 mL) was added sodium hydride (60% dispersion in mineral oil) (0.029 g, 1.23 mmol, 3 eq.) at 0 °C. Reaction mixture was stirred for 15 minutes and tert-butyl (6-chloro-3-isopropylimidazo[1,2-b]pyridazin-8-yl)(2-(trifluoromethoxy)benzyl) carbamate (1) (0.200 g, 0.41 mmol, 1 eq.) in DMF (3 mL) was added at 0 °C, then reaction mixture was allowed to attain room temperature and stirred for 2 h. Completion of reaction was monitored by TLC. After completion of reaction, it was diluted with water (50 mL), and extracted with ethyl acetate (3×50 ml). Combined organic layer was washed with brine (25 mL), dried over $Na_2SO_4$, and evaporated under reduced pressure to afford the crude compound. Crude compound was purified by column chromatography using ethyl acetate in hexane as eluting system to afford tert-butyl 4-((8-((tert-butoxycarbonyl)(2-(trifluoromethoxy)benzyl)amino)-3-isopropylimidazo[1,2-b]pyridazin-6-yl)thio)piperidine-1-carboxylate (120 mg, 43.70% yield). $R_f$=0.4 (2:8 Ethyl acetate: Hexane). LCMS (m/z): 666.26 $(M+H)^+$.

To a solution of tert-butyl 3-((8-((tert-butoxycarbonyl)(2-methoxybenzyl)amino)-3-isopropylimidazo[1,2-b]pyridazin-6-yl)thio)piperidine-1-carboxylate (3) (0.100 g, 0.150 mmol, 1 eq.) in DCM (5 mL) at 0 °C was added 4M HCl in dioxane (2 mL) and stirred at room temperature for 6 h. After completion of reaction by TLC, volatiles were evaporated under reduced pressure and obtained crude compound was purified by Prep-HPLC as an eluent afford N-(2-methoxybenzyl)-3-methyl-6-(piperidin-3-ylthio)imidazo[1,2-b]pyridazin-8-amine. The obtained free base was dissolved in ACN: water (1:1) and treated with 2N aq. HCl (0.5 ml) at 0 °C and lyophilized to afford 3-isopropyl-6-(piperidin-4-ylthio)-N-(2-(trifluoromethoxy)benzyl)imidazo[1,2-b]pyridazin-8-amie hydrochloride (33a) as a white solid (60 mg, quantitative yield). $R_f$=0.1 (9:1 DCM/MeOH). LCMS (m/z): 466.28 $(M+H)^+$. $^1$HNMR (400 MHz, DMSO-$d_6$) δ 9.01 (s, 1H), 8.82 (s, 1H), 8.58 (s, 1H), 7.77 (s, 1H), 7.52-7.35 (m, 4H), 6.26 (s, 1H), 4.69 (d, J=5.6 Hz, 2H), 3.98 (t, J=4 Hz, 2H), 3.40-3.26 (m, 3H), 3.05 (bs, 2H), 2.26-2.22 (m, 2H), 1.83-1.81 (m, 2H), 1.34 (d, J=6 Hz, 6H)

Example 48

Synthetic Scheme for 3-isopropyl-6-(piperidin-3-ylthio)-N-(2-(trifluoromethoxy)benzyl)imidazo[1,2-b]pyridazin-8-amine hydrochloride

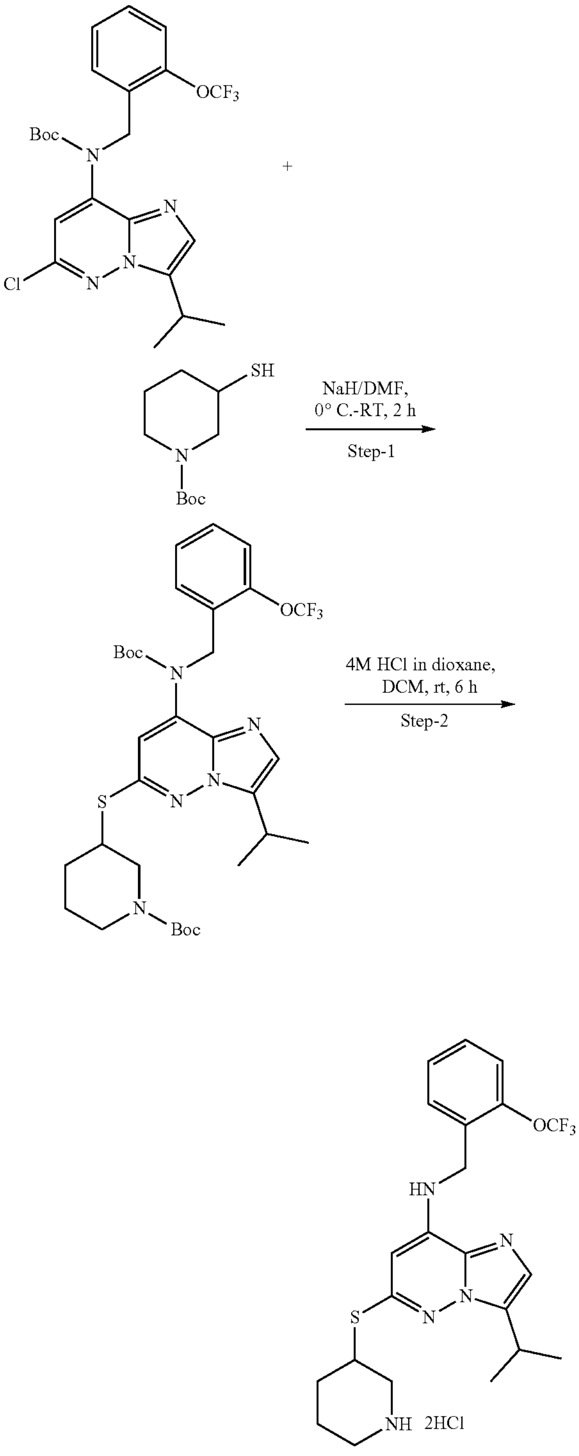

37

Synthesis of tert-butyl 3-((8-((tert-butoxycarbonyl)(2-(trifluoromethoxy)benzyl)amino)-3-isopropylimidazo[1,2-b]pyridazin-6-yl)thio)piperidine-1-carboxylate

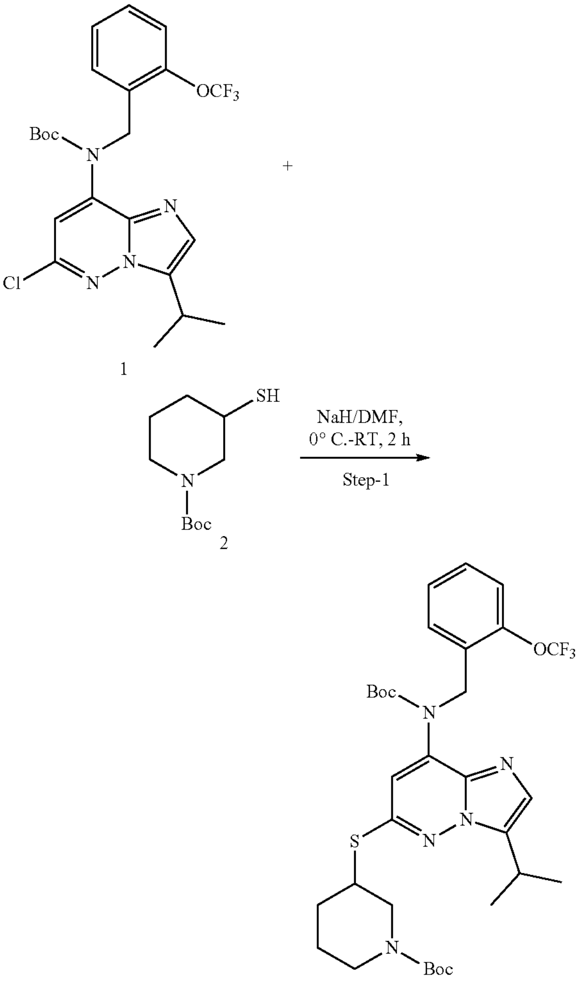

1 2 3

To a stirred solution of tert-butyl 3-mercaptopiperidine-1-carboxylate (2) (0.269 g, 1.23 mmol, 2 eq.) in DMF (3 mL) was added sodium hydride (60% dispersion in oil) (0.0297 mg, 1.23 mmol, 3 eq.) at 0 °C. Reaction mixture was stirred for 15 minutes and was added tert-butyl (6-chloro-3-isopropylimidazo[1,2-b]pyridazin-8-yl)(2-(trifluoromethoxy)benzyl)carbamate (1) (0.200 g, 0.41 mmol, 1 eq.) in DMF (3 mL), then reaction mixture was allowed to attain room temperature and stirred for 2 h. Completion of reaction was monitored on TLC. After completion of reaction, it was quenched with ice water (50 mL), and extracted with ethyl acetate (3×50 mL). Combined organic layer was washed with brine (25 mL), dried over $Na_2SO_4$, filtered and evaporated under reduced pressure to afford the crude compound. Crude compound was purified by column chromatography using EtOAc:hexane as eluting system to afford tert-butyl 3-((8-((tert-butoxycarbonyl)(2-(trifluoromethoxy)benzyl)amino)-3-isopropylimidazo[1,2-b]pyridazin-6-yl)thio)piperidine-1-carboxylate (3) as a yellow gum (0.140 g, 50.98% yield). LCMS (m/z): 666.25 $(M+H)^+$ Synthesis of 3-isopropyl-6-(piperidin-3-ylthio)-N-(2-(trifluoromethoxy)benzyl)imidazo[1,2-b]pyridazin-8-amine hydrochloride

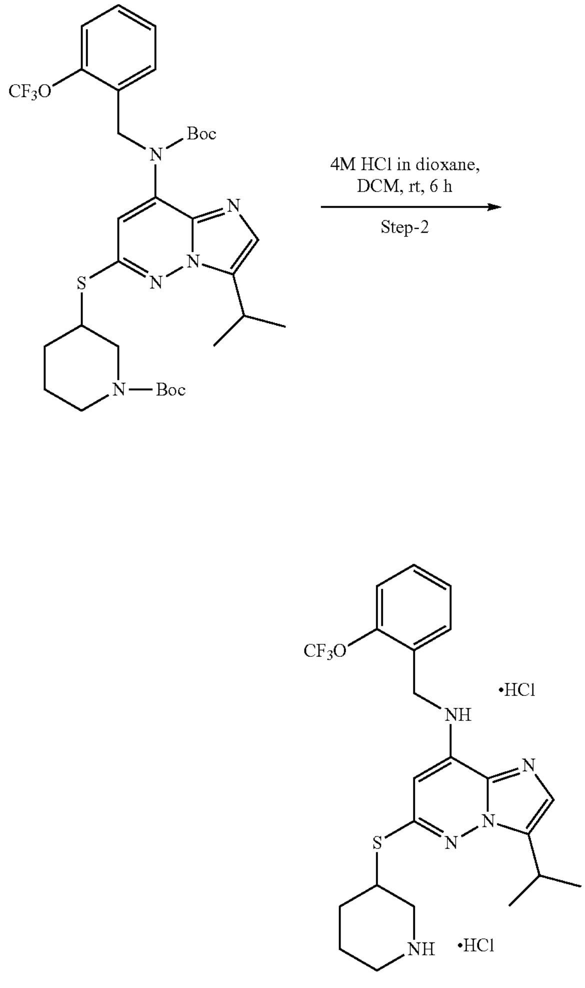

To a solution of tert-butyl 3-((8-((tert-butoxycarbonyl)(2-(trifluoromethoxy)benzyl)amino)-3-isopropylimidazo[1,2-b]pyridazin-6-yl)thio)piperidine-1-carboxylate (3) (0.100 g, 0.15 mmol, 1 eq.) in DCM (5 mL) at 0 °C was added 4M HCl in dioxane (1 mL) and stirred at room temperature for 6 h. After completion of reaction by TLC, volatiles were evaporated under reduced pressure and obtained crude compound was purified by Preparative-HPLC to afford 3-isopropyl-6-(piperidin-3-ylthio)-N-(2-(trifluoromethoxy)benzyl)imidazo[1,2-b]pyridazin-8-amine (37). The obtained free base was dissolved with ACN:water (1:1) and treated with 2N aq. HCl at 0 °C and lyophilized to afford of 3-isopropyl-6-(piperidin-3-ylthio)-N-(2-(trifluoromethoxy)benzyl)imidazo[1,2-b]pyridazin-8-amine hydrochloride as pale green solid (0.05 g, quantitative yield). $R_f$=0.3 (9:1 DCM/MeOH). LCMS (m/z): 466.24 $(M+H)^+$. $^1$HNMR (400 MHz, DMSO-$d_6$): δ 9.45 (s, 1H), 9.15 (s, 1H), 8.77 (s, 1H), 7.89 (d, J=5.6 Hz, 1H), 7.54-7.35 (m, 4H), 6.40 (d, J=5.6 Hz, 1H), 4.66 (d, J=10.4 Hz, 2H), 4.11-4.07 (m, 1H), 3.57-3.46 (m, 3H), 3.24-3.22 (d, J=8.4 Hz 1H), 3.11-3.01 (m, 1H), 2.89-2.86 (s, 1H), 2.13-2.108 (t, J=10.4 Hz, 1H), 1.86 (s, 2H), 1.74-1.65 (m, 1H), 1.36-1.33 (m, 6H).

Example 49

Synthetic Scheme for tert-butyl 4-((8-((tert-butoxycarbonyl) (2-(trifluoromethoxy)benzyl)amino)-3-isopropylimidazo[1,2-b]pyridazin-6-yl)amino)piperidine-1-carboxylate hydrochloride

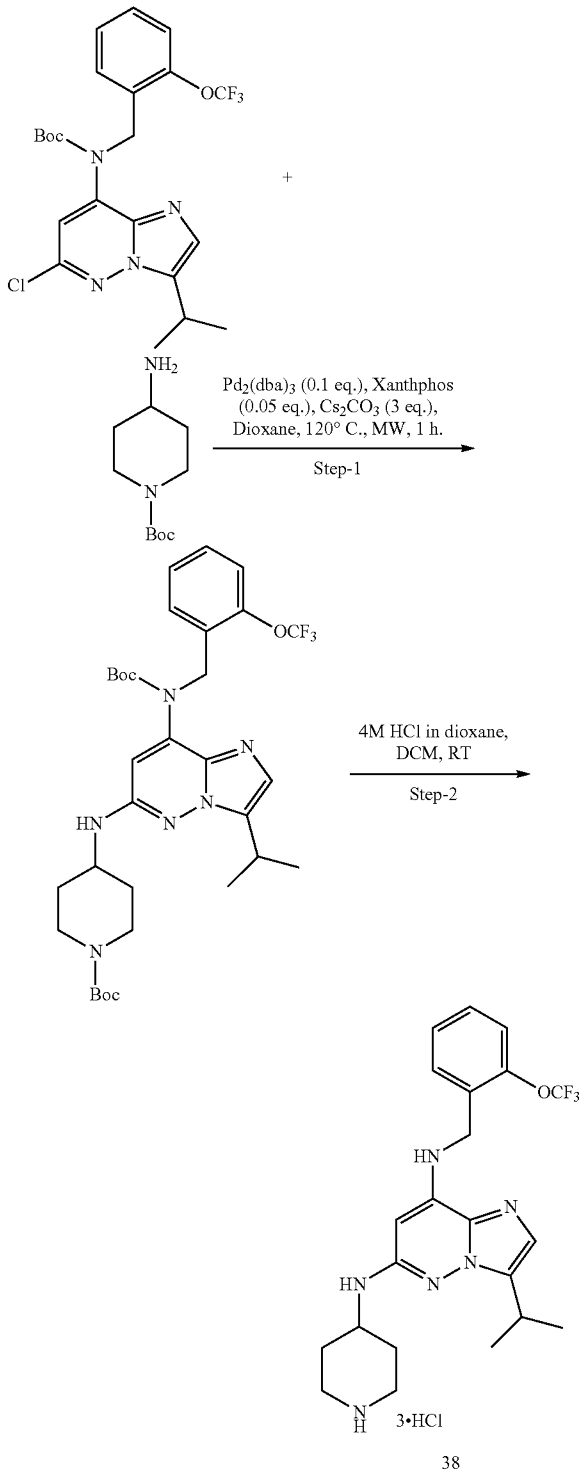

38

Synthesis of tert-butyl 4-((8-((tert-butoxycarbonyl)(2-(trifluoromethoxy)benzyl)amino)-3-isopropylimidazo[1,2-b]pyridazin-6-yl)amino)piperidine-1-carboxylate

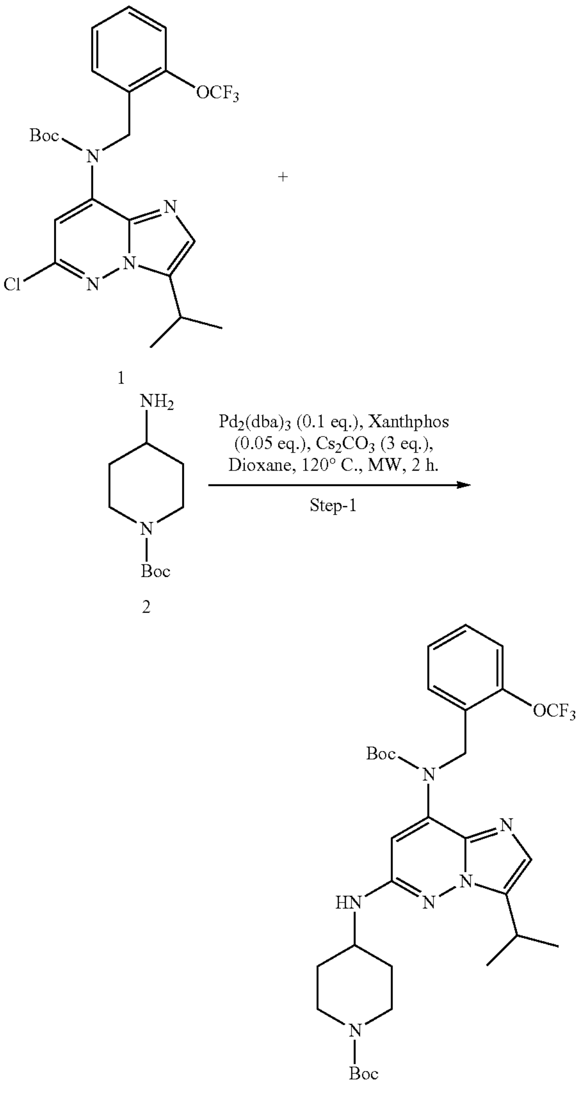

1

2

3

Under an atmosphere of argon, tert-butyl (6-chloro-3-isopropylimidazo[1,2-b]pyridazin-8-yl)(2-(trifluoromethoxy)benzyl)carbamate (1) (0.250 g, 0.51 mmol, 1 eq.), $Cs_2CO_3$ (0.503 g, 1.54 mmol, 3 eq.), tert-butyl 4-aminopiperidine-1-carboxylate (2) (0.206 g, 1.03 mmol, 2.0 eq.) and xantphos (0.029 g, 0.05 mmol, 0.1 eq.) in 1, 4-dioxane (4 mL) was degassed with argon for 10 min and added Tris (dibenzylideneacetone) dipalladium (0.047 g, 0.05 mmol, 0.1 eq.) again degassed with argon for 10 min and heated to 120 °C for 2 h in Microwave. Progress of reaction was monitor by TLC, after completion of reaction, the reaction mixture was diluted with ethyl acetate and filtered through celite bed. The organic phase was washed with water (3×50 mL), dried over sodium sulfate, filtered and concentrated under reduced pressure to provide crude product. Obtained crude compound was purified by silica phase column chromatography using ethyl acetate in hexane as a eluting system to afford tert-butyl 4-((8-((tert-butoxycarbonyl)(2-(trifluoromethoxy)benzyl)amino)-3-isopropylimidazo[1,2-b]pyridazin-6-yl)amino)piperidine-1-carboxylate (3) as a yellow gum (0.12 g, 35.88%) $R_f$=0.3 (1:1 hexane/ethyl acetate). LCMS (m/z): 649.1 $(M+H)^+$. $^1$HNMR (400 MHz, DMSO-$d_6$ NMR) δ 7.44-7.31 (m, 4H), 7.20-7.19 (d, J=5.2 Hz, 1H), 6.81 (m, 1H), 6.52 (d, J=5.2 Hz, 1H), 5.27 (d, J=5.2 Hz, 2H), 3.82-3.73 (m, 3H), 3.24-3.16 (m, 1H), 2.96 (bs, 2H), 1.96-1.94 (d, J=8 Hz, 2H), 1.41-1.29 (m, 26H).

Synthesis of tert-butyl 4-((8-((tert-butoxycarbonyl)(2-(trifluoromethoxy)benzyl)amino)-3-isopropylimidazo[1,2-b]pyridazin-6-yl)amino)piperidine-1-carboxylate hydrochloride

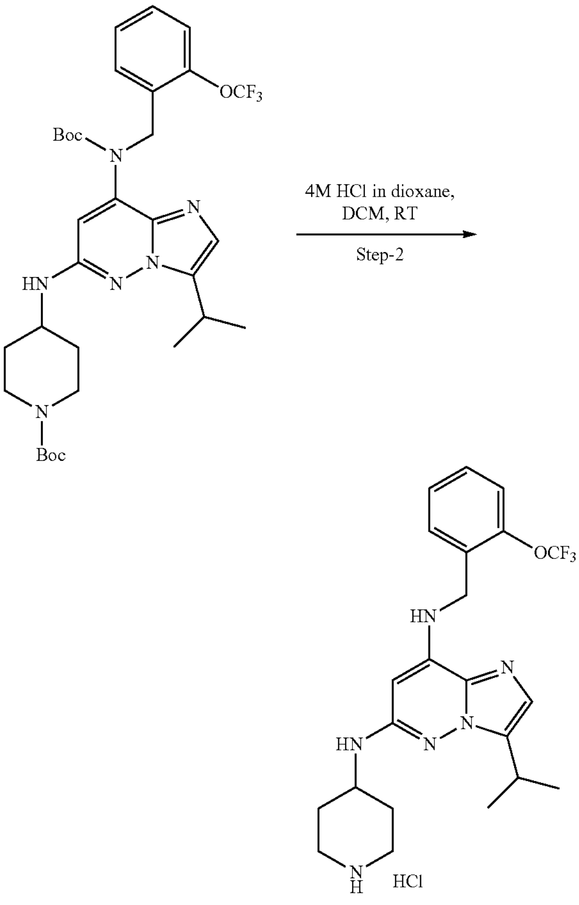

38

To a solution of tert-butyl tert-butyl 4-((8-((tert-butoxycarbonyl)(2-(trifluoromethoxy)benzyl)amino)-3-isopropylimidazo[1,2-b]pyridazin-6-yl)amino)piperidine-1-carboxylate (3) (0.100 g, 0.154 mmol, 1 eq.) in DCM (5 mL) at 0 °C was added 4M HCl in dioxane (1 mL) and stirred at room temperature for 6 h. After completion of reaction by TLC, volatiles were evaporated under reduced pressure to obtained crude compound. Crude was purified by Preparative-HPLC to afford N-(2-methoxybenzyl)-3-methyl-6-(piperidin-3-ylthio) imidazole [1, 2-b]pyridazin-8-amine. The obtained free base was dissolved in ACN: water (1:1) and treated with 2N aq. HCl at 0 °C and lyophilized to afford tert-butyl 4-((8-((tert-butoxycarbonyl)(2-(trifluoromethoxy)benzyl)amino)-3-isopropylimidazo[1,2-b]pyridazin-6-yl)amino)piperidine-1-carboxylate hydrochloride (38) as off white solid (60 mg, quantitative yield). $R_f$=0.1 (9:1 DCM/MeOH). LCMS (m/z): 449.1 (M+H). HNMR (400 MHz, DMSO-$d_6$ NMR) δ 8.77 (s, 2H), 8.20 (s, 1H), 7.81 (s, 1H), 7.54-7.38 (m, 4H), 7.17 (s, 1H), 5.79 (s, 1H), 4.54 (d, J=5.2 Hz, 2H), 3.85 (s, 1H), 3.27 (t, J=6.4 Hz, 3H), 3.01 (s, 2H), 2.09 (d, J=9.2 Hz, 2H), 1.64 (t, J=4.8 Hz 2H), 1.33 (d, J=6.8 Hz, 6H)

Example 50

Synthetic Scheme for N-benzyl-3-isopropyl-6-(piperidin-3-ylthio)imidazo[1,2-a]pyrazin-8-amine hydrochloride

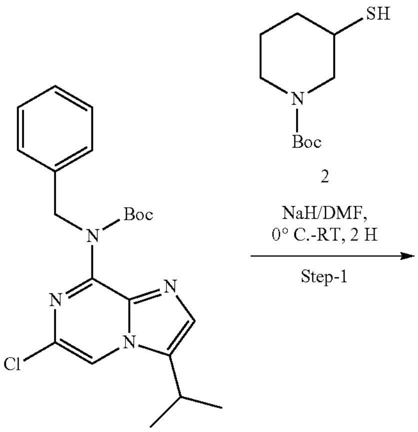

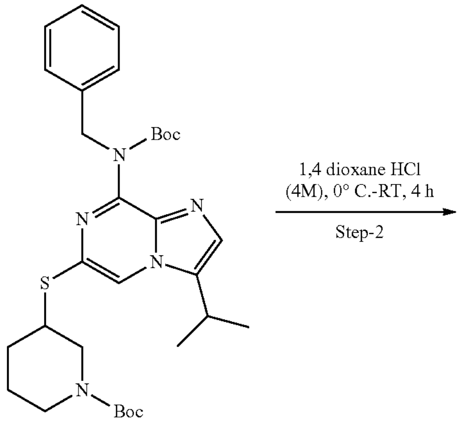

-continued

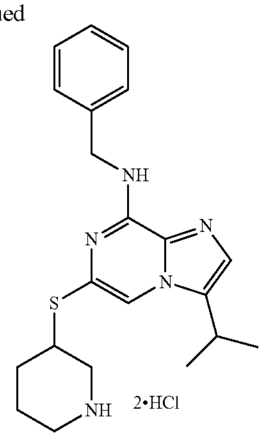

41

Step-1: Synthesis of tert-butyl 3-((8-(benzyl(tert-butoxycarbonyl)amino)-3-isopropylimidazo[1,2-a]pyrazin-6-yl)thio)piperidine-1-carboxylate

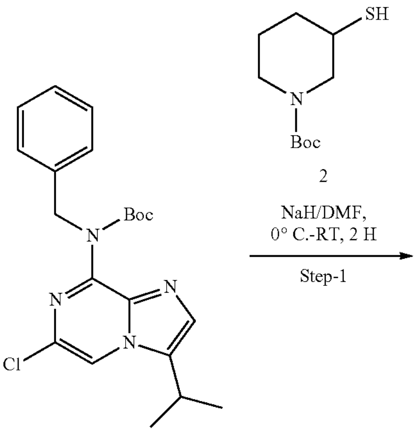

1

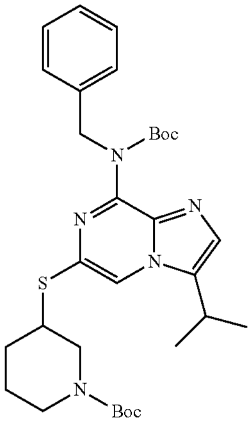

3 (Isomer-1)

To a stirred solution of tert-butyl 3-mercaptopiperidine-1-carboxylate (2) (1.21 g, 5.61 mmol, 2.5eq.) in DMF (15 mL) was added sodium hydride (60% dispersion in oil) (0.134 g, 5.61 mmol, 2.5eq.) at 0 °C. Reaction mixture was stirred for 15 minutes and tert-butyl benzyl(6-chloro-3-isopropylimidazo[1,2-a]pyrazin-8-yl)Carbamate (1) (0.9 g, 2.24 mmol, 1eq.) was added at 0 °C. Then reaction mixture was allowed to attain room temperature and stirred for 2 h. Completion of reaction was monitored by TLC. After completion of reaction, it was quenched with ice water (100 mL), and extracted with ethyl acetate (3x75 mL). Combined organic layer was washed with brine (100 mL), dried over $Na_2SO_4$, and evaporated under reduced pressure to afford the crude compound. Crude compound was purified chiral preparative HPLC to afford the title compound (3) Isomer-1 tert-butyl 3-((8-(benzyl(tert-butoxycarbonyl)amino)-3-isopropylimidazo[1,2-a]pyrazin-6-yl)thio)piperidine-1-carboxylate as off white solid. Yield: 620 mg, (46%). $R_f$=0.4 (8:2 Hexane/EtoAC). LCMS (m/z): 582.1 $(M+H)^+$. $^1H$ NMR (400 MHz, DMSO-$d_6$): δ=7.50 (d, J=6.8 Hz, 1H), 7.26-7.21 (m, 5H), 7.05 (s, 1H), 5.26 (d, J=6 Hz, 2H), 4.09-3.87 (m, 2H), 3.56 (s, 2H), 3.08-2.95(m, 1H), 2.09 (s, 1H), 1.96 (s, 1H), 1.64 (m, 2H), 1.51 (m, 1H), 1.41-1.04 (m, 24H).

Step-2: Synthesis of N-benzyl-3-isopropyl-6-(piperidin-3-ylthio)imidazo[1,2-a]pyrazin-8-amine hydrochloride

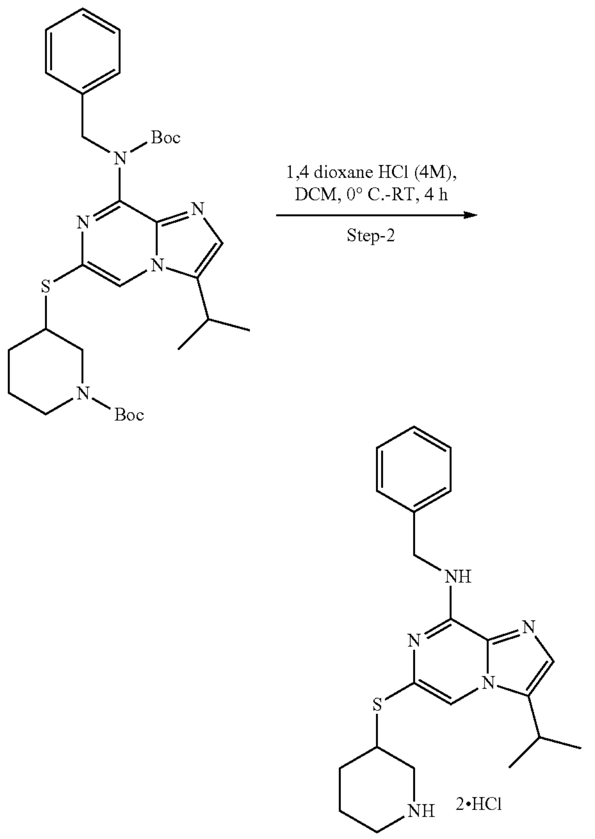

41

To a stirred solution of tert-butyl 3-((8-(benzyl(tert-butoxycarbonyl)amino)-3-isopropylimidazo[1,2-a]pyrazin-6-yl)thio)piperidine-1-carboxylate (3) Isomer-1 (0.3 g, 0.516 mmol, 1 eq.), in DCM (5 mL) was added 1,4 dioxane in HCl (4M) (5 mL) dropwise at 0 °C. The reaction mixture was stirred at room temperature for 4 h. After completion of reaction by TLC, volatiles were evaporated under reduced pressure to obtain crude compound. The crude compound was purified by titration using n-pentane & di-ethyl ether to afford the title compound (41)-N-benzyl-3-isopropyl-6-(piperidin-3-ylthio)imidazo[1,2-a]pyrazin-8-amine hydrochloride as off white solid. Yield: 290 mg (quantitative yield). $R_f$=0.1 (1:9, DCM in Methanol). LCMS (m/z): 382.1 $(M+H)^+$. $^1H$NMR (400 MHz, DMSO-$d_6$): δ 9.31 (s, 1H), 9.05 (s, 1H), 8.76 (s, 1H), 7.79 (s, 1H), 7.41-7.27 (m, 5H), 6.36 (s, 1H), 4.58 (s, 2H), 3.98-3.93 (m, 1H), 3.16-3.04 (m, 3H), 2.85 (d, J=9.2 Hz, 2H), 2.09-1.99 (m, 2H), 1.84 (s, 2H), 1.68-1.50 (m, 1H), 1.34-1.31 (m, 6H).

Example 51

Synthetic Scheme for N-benzyl-3-isopropyl-6-(piperidin-3-ylthio)imidazo[1,2-a]pyrazin-8-amine hydrochloride

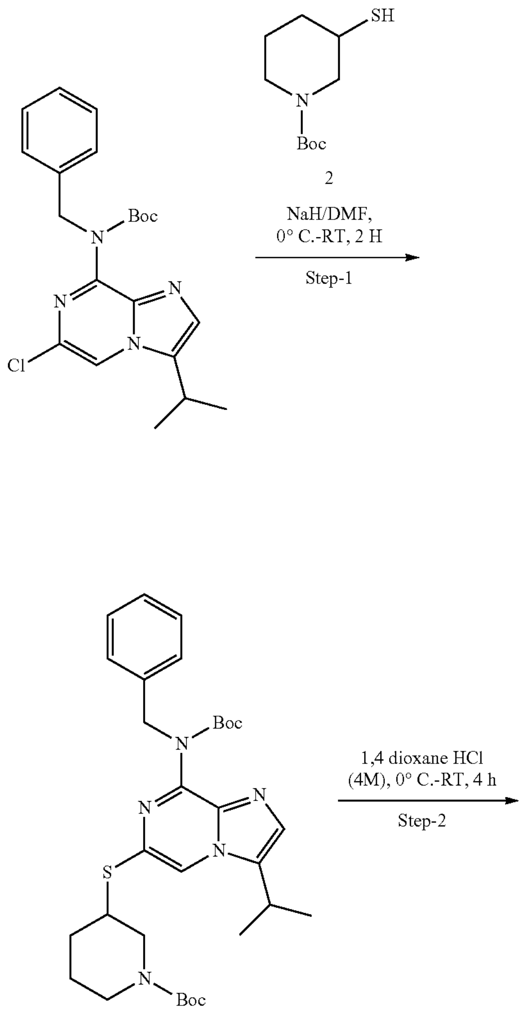

-continued

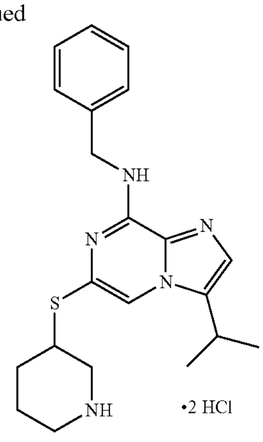

42

Step-1: Synthesis of tert-butyl 3-((8-(benzyl(tert-butoxycarbonyl)amino)-3-isopropylimidazo[1,2-a]pyrazin-6-yl)thio)piperidine-1-carboxylate

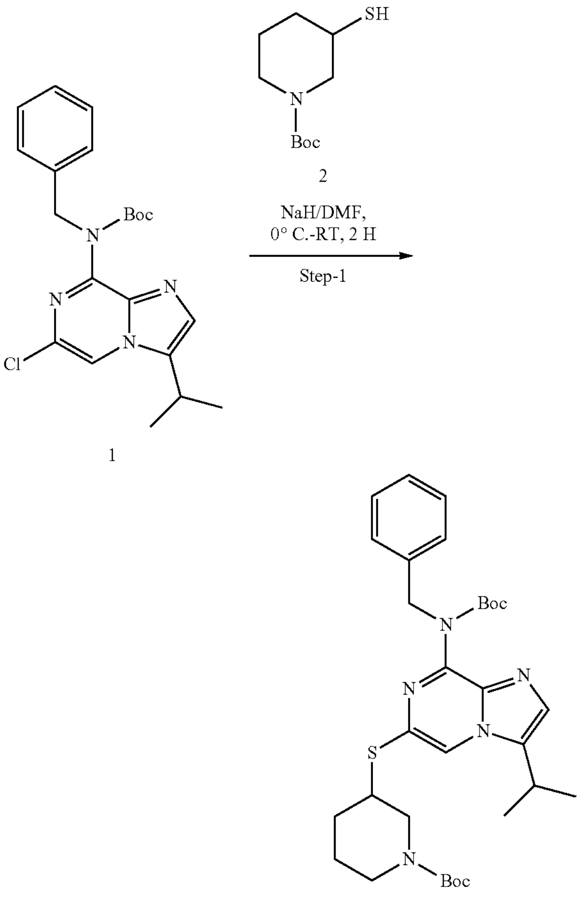

1

2

3(Isomer-2)

To a stirred solution of tert-butyl 3-mercaptopiperidine-1-carboxylate (2) (1.21 g, 5.61 mmol, 2.5eq.) in DMF (15 mL) was added sodium hydride (60% dispersion in oil) (0.134 g, 5.61 mmol, 2.5eq.) at 0 °C. Reaction mixture was stirred for 15 minutes and tert-butyl benzyl(6-chloro-3-isopropylimidazo[1,2-a]pyrazin-8-yl) Carbamate (1) (0.9 g, 2.24 mmol, 1eq.) was added at 0 °C. Then reaction mixture was allowed to attain room temperature and stirred for 2 h. Completion of reaction was monitored by TLC. After completion of reaction, it was quenched with ice water (100 mL), and extracted with ethyl acetate (3x75 mL). Combined organic layer was washed with brine (100 mL), dried over $Na_2SO_4$, filtered and evaporated under reduced pressure to afford the crude compound. Crude compound was purified chiral preparative HPLC to afford the title compound (3) Isomer-2 tert-butyl 3-((8-(benzyl(tert-butoxycarbonyl) amino)-3-isopropylimidazo[1,2-a]pyrazin-6-yl) thiol) piperidine-1-carboxylate as off white solid. (Yield: 620 mg, 46%). $R_f$=0.4 (8:2 Hexane/EtoAC). LCMS (m/z): 582.1 $(M+H)^+$. $^1H$ NMR (400 MHz, DMSO-$d_6$): δ=7.49 (s, 1H), 7.26-7.19 (m, 5H), 7.06 (s, 1H), 5.25 (s, 2H), 4.10-3.96 (m, 2H), 3.64-3.50 (m, 2H), 3.12-3.08 (m, 1H), 2.10-2.08 (m, 1H), 1.80-1.62 (m, 4H), 1.36-1.03 (m, 24H).

Step-2: Synthesis of N-benzyl-3-isopropyl-6-(piperidin-3-ylthio)imidazo[1,2-a]pyrazin-8-amine hydrochloride

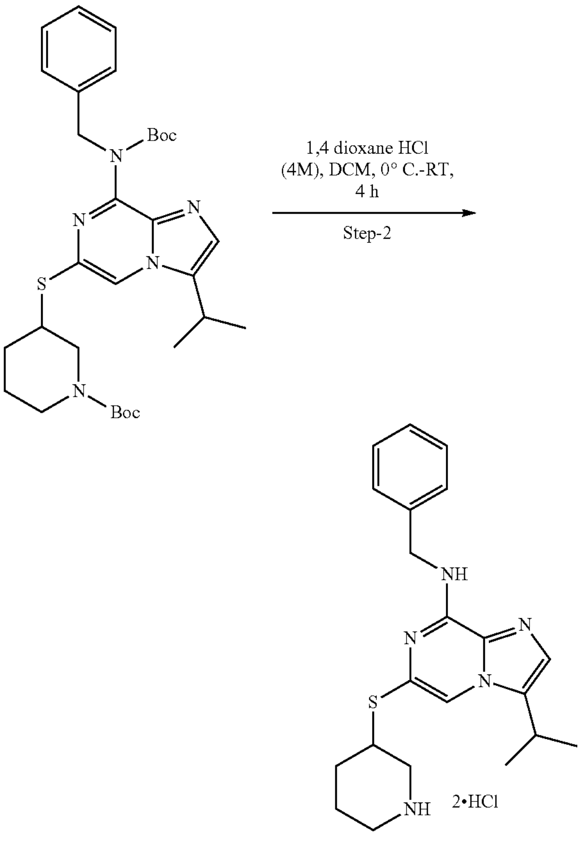

42

To a stirred solution of tert-butyl 3-((8-(benzyl(tert-butoxycarbonyl) amino)-3-isopropylimidazo[1,2-a]pyrazin-6-yl)thio)piperidine-1-carboxylate (3) (0.3 g, 0.516 mmol, 1 eq.) in DCM (5 mL) was added 1,4 dioxin in HCl (4M) (5 mL) dropwise at 0 °C. The reaction mixture was stirred at room temperature for 4 h. After completion of reaction by TLC, volatiles were evaporated under reduced pressure to obtain crude compound. The crude compound was purified by titration using n-pentane & di-ethyl ether to afford the title compound (42)-N-benzyl-3-isopropyl-6-(piperidin-3-ylthio)imidazo[1,2-a]pyrazin-8-amine hydrochloride as white solid. (220 mg, quantitative yield). $R_f$=0.1 (1:1 Hexane/EtoAC). LCMS (m/z): 382.1 (M+H)$^1$HNMR (400 MHz, DMSO-$d_6$): δ 9.41 (s, 1H), 9.10 (s, 1H), 8.86 (s, 1H), 7.86 (s, 1H), 7.43-7.28 (m, 5H), 6.42 (s, 1H), 4.61 (d, J=6 Hz, 2H), 4.08-4.05 (m, 1H), 3.74-3.44 (m, 3H), 3.24-3.21 (m, 1H), 3.06-3.04 (m, 1H), 3.30-2.89 (m, 1H), 2.12-2.10 (m, 1H), 1.86 (s, 2H), 1.69-1.67 (m, 1H), 1.35-1.31 (m, 6H).

Example 52

Synthetic Scheme for (R)-3-isopropyl-N6-(morpholin-2-ylmethyl)-N8-(2-(trifluoromethoxy)benzyl) imidazo[1,2-b]pyridazine-6,8-diamine hydrochloride

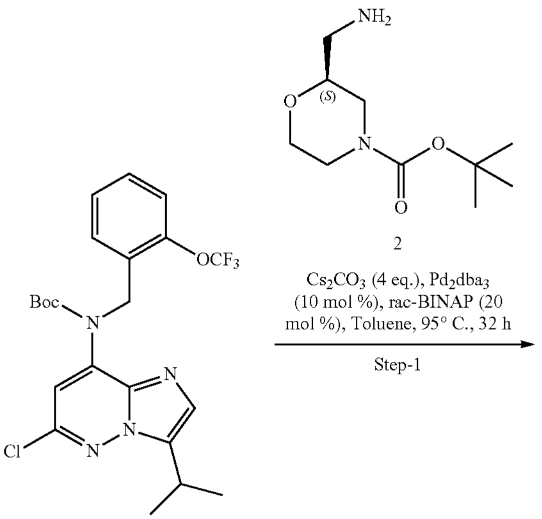

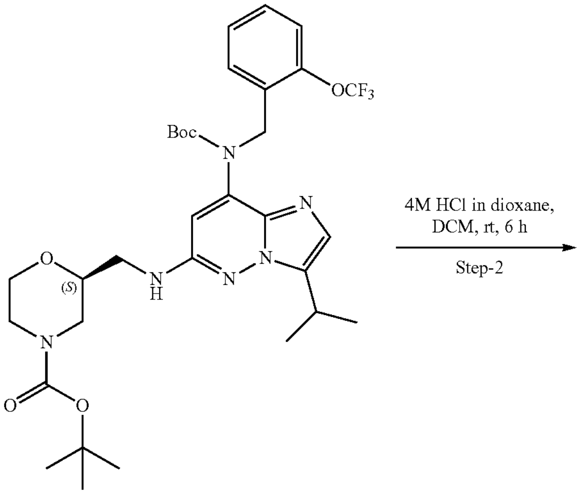

-continued

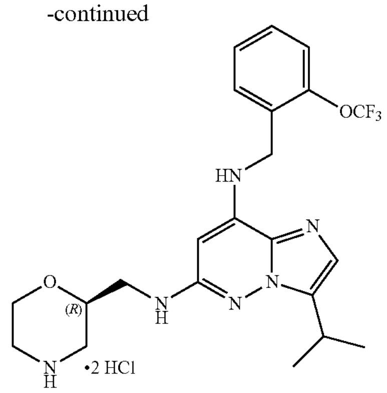

48

Synthesis of tert-butyl (S)-2-(((8-((tert-butoxycarbonyl)(2-(trifluoromethoxy)benzyl)amino)-3-isopropylimidazo[1,2-b]pyridazin-6-yl)amino)methyl)morpholine-4-carboxylate

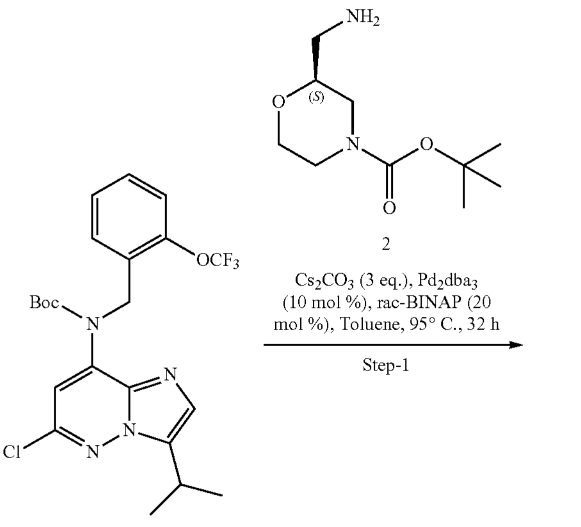

1

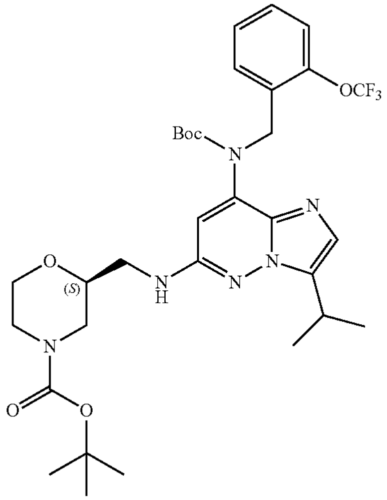

3

To a stirred solution of tert-butyl (6-chloro-3-isopropylimidazo[1,2-b]pyridazin-8-yl)(2-(trifluoromethoxy)benzyl)

carbamate (250 mg, 0.516 mmol, 1 eq.) in toluene (5 mL) was added tert-butyl (S)-2-(aminomethyl)morpholine-4-carboxylate (167 mg, 0.775 mmol, 1.5 eq.), $Cs_2CO_3$ (335 mg, 1.032 mmol, 2 eq.) and rac-BINAP (32 mg, 10 mol %) at room temperature. The reaction mixture was purged with argon for 5 min then added tris(dibenzylideneacetone)dipalladium (23 mg, 5 mol %) again degassed with argon for 5 min and finally, heated at 95 °C for 16 h. The reaction mixture cooled to RT and further added tert-butyl (S)-2-(aminomethyl)morpholine-4-carboxylate (167 mg, 0.775 mmol, 1.5 eq.), $Cs_2CO_3$ (335 mg, 1.032 mmol, 2 eq.) and rac-BINAP (32 mg, 10 mol %) were added at room temperature. The reaction mixture was degassed with argon for 5 min then added tris(dibenzylideneacetone)dipalladium (23 mg, 5 mol %) and again degassed with argon for 5 min and heated at 95 °C for 16 h. after this time, the reaction mixture was diluted with ethyl acetate and passed through celite bed. Filtrate was collected, washed with water (20 mL), brine, dried over $Na_2SO_4$ and concentrated in vacuum. The residue was purified by combiflash on silica column (EtOAc/hexane, gradient 0-30% EtOAc) to tert-butyl (S)-2-(((8-((tert-butoxycarbonyl)(2-(trifluoromethoxy)benzyl)amino)-3-isopropylimidazo[1,2-b]pyridazin-6-yl)amino)methyl)morpholine-4-carboxylate (3) as yellow solid (180 mg, 53% yield). $R_f$=0.2 (7:3, Hexane/EtOAc). $^1H$ NMR (400 MHz, DMSO): δ 7.47-7.26 (m, 4H), 7.21 (s, 1H), 7.03 (s, 1H), 6.58 (s, 1H), 5.27 (s, 2H), 4.08-3.97 (m, 1H), 3.93 (d, J=7.8 Hz, 1H), 3.83 (d, J=10.7 Hz, 2H), 3.69 (s, 1H), 3.57 (s, 1H), 3.25-3.17 (m, 1H), 2.84 (s, 2H), 1.98 (d, J=7.8 Hz, 1H), 1.45-1.03 (m, 24H).

Synthesis of (R)-3-isopropyl-N6-(morpholin-2-ylmethyl)-N8-(2-(trifluoromethoxy)benzyl)imidazo[1,2-b]pyridazine-6,8-diamine hydrochloride

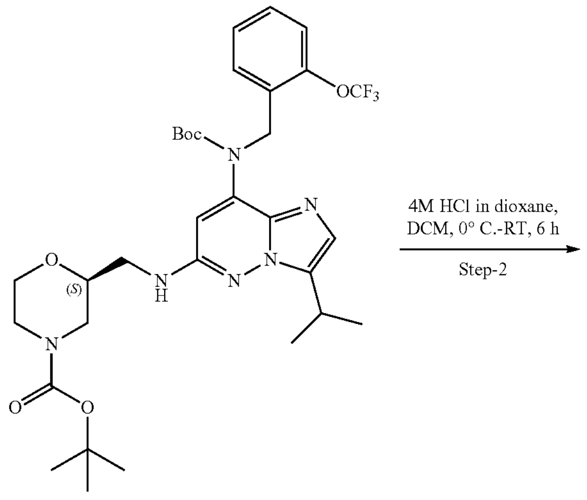

-continued

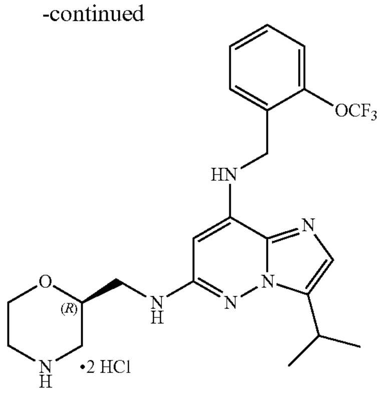

48

To a solution of tert-butyl (S)-2-(((8-((tert-butoxycarbonyl)(2-(trifluoromethoxy)benzyl)amino)-3-isopropylimidazo[1,2-b]pyridazin-6-yl)amino)methyl)morpholine-4-carboxylate (3) (0.18 g, 0.271 mmol, 1 eq.) in DCM (10 mL) at 0 °C was added 4M HCl in dioxane (2 mL) and stirred at RT for 6 h. After completion of conversion by TLC, the reaction mixture was subjected to rotary evaporator for removal of volatiles. The obtained residue was triturated with ether (3×30 mL), EtOAc (20 mL) and Hexane (20 mL) afforded (R)-3-isopropyl-N6-(morpholin-2-ylmethyl)-N8-(2-(trifluoromethoxy)benzyl)imidazo[1,2-b]pyridazine-6,8-diamine hydrochloride (48) as an off white solid (95 mg, 74% yield). $R_f$=0.1 (9:1 DCM/MeOH). LCMS (m/z): 465.1 $(M+H)^+$. $^1H$-NMR (400 MHz, DMSO) δ 14.74 (s, 1H), 9.41 (d, J=43.1 Hz, 3H), 8.39 (s, 1H), 7.86 (d, J=7.7 Hz, 1H), 7.63-7.30 (m, 4H), 7.25 (s, 1H), 5.88 (d, J=7.7 Hz, 1H), 4.55 (d, J=5.9 Hz, 2H), 3.94 (s, 3H), 3.85-3.61 (m, 2H), 3.18 (d, J=16.3 Hz, 2H), 2.95 (s, 1H), 2.80 (s, 1H), 1.34 (td, J=7.3, 2.8 Hz, 6H).

Example 53

Synthetic Scheme for (S)-3-isopropyl-N6-(morpholin-2-ylmethyl)-N8-(2-(trifluoromethoxy)benzyl)imidazo[1,2-b]pyridazine-6,8-diamine hydrochloride

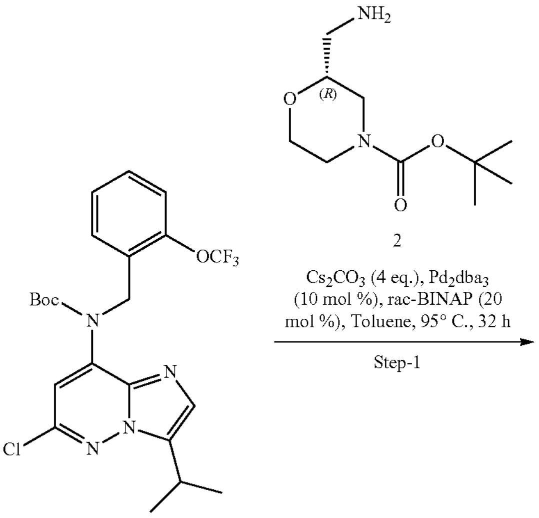

-continued

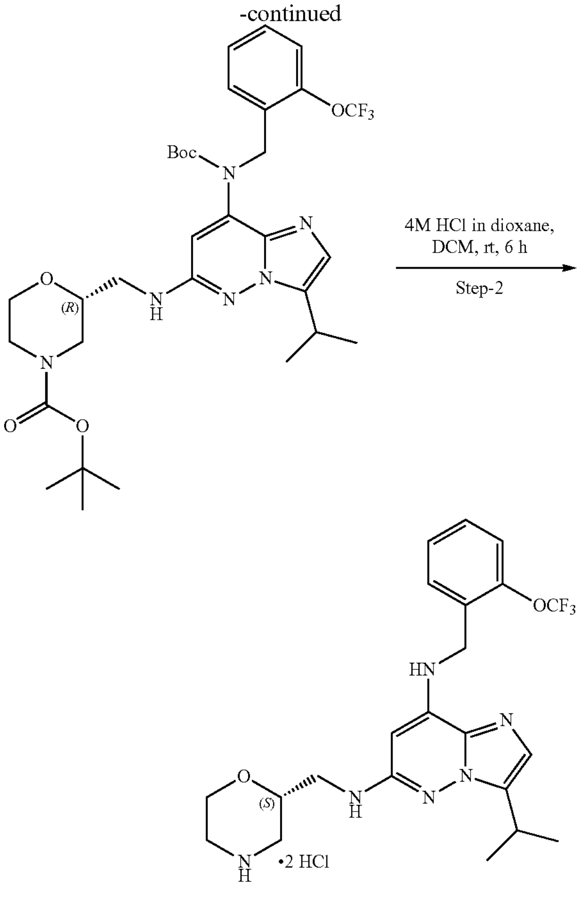

46

Synthesis of tert-butyl (R)-2-(((8-((tert-butoxycarbonyl)(2-(trifluoromethoxy)benzyl)amino)-3-isopropylimidazo[1,2-b]pyridazin-6-yl)amino)methyl)morpholine-4-carboxylate

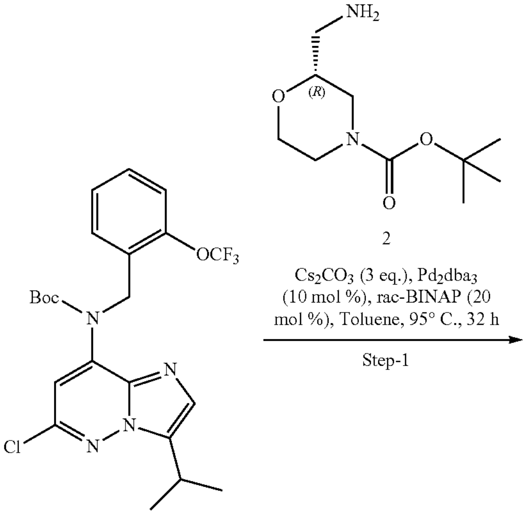

2

1

-continued

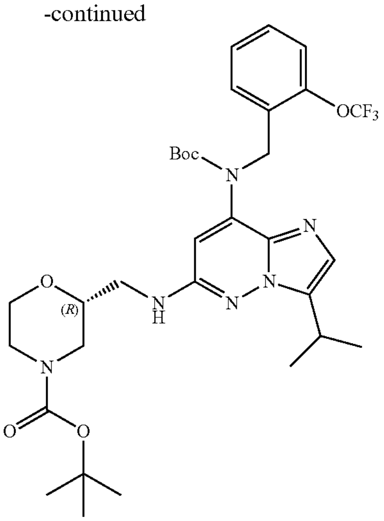

3

To a stirred solution of tert-butyl (6-chloro-3-isopropylimidazo[1,2-b]pyridazin-8-yl)(2-(trifluoromethoxy)benzyl) carbamate (0.250 g, 0.516 mmol, 1 eq.) in toluene (5 mL) was added tert-butyl (R)-2-(aminomethyl)morpholine-4-carboxylate (0.167 g, 0.775 mmol, 1.5 eq.), $Cs_2CO_3$ (0.335 g, 1.032 mmol, 2 eq.) and rac-BINAP (0.032 g, 10 mol %) at room temperature. The reaction mixture was purged with argon for 10 min then added tris(dibenzylideneacetone) dipalladium (0.023 g, 5 mol %) again purged with argon for 5 min and heated at 95 °C for 16 h. The reaction mixture cooled to room temperature and further added tert-butyl (S)-2-(aminomethyl)morpholine-4-carboxylate (0.167 g, 0.775 mmol, 1.5 eq.), $Cs_2CO_3$ (0.335 g, 1.032 mmol, 2 eq.) and rac-BINAP (0.032 g, 10 mol %) were added at room temperature. The reaction mixture was purged with argon for 5 min then added tris(dibenzylideneacetone)dipalladium (0.023 g, 5 mol %) again purged with argon for 5 min and heated at 95 °C for 16 h, progress of reaction was monitored by TLC. After completion of reaction, the reaction mixture was diluted with ethyl acetate and filtered through celite bed. The organic phase was washed with water (20 mL), brine, dried over $Na_2SO_4$, filtered and concentrated under reduced pressure to afford crude. Obtained crude compound was purified by column chromatography using ethyl acetate in hexane as a eluting system to afford tert-butyl (R)-2-(((8-((tert-butoxycarbonyl)(2-(trifluoromethoxy)benzyl)amino)-3-isopropylimidazo[1,2-b]pyridazin-6-yl)amino)methyl) morpholine-4-carboxylate (3) as yellow solid (0.110 g, 32.10% yield). $R_f$=0.2 (7:3, Hexane/EtOAc). LCMS (m/z): 665.1 $(M+H)^+$. $^1H$ NMR (400 MHz, $CDCl_3$): δ 7.41-7.40 (d, J=6.4 Hz, 1H), 7.21-7.17 (m, 4H), 6.42 (s, 1H), 5.42 (s, 2H), 4.53 (s, 1H), 3.90-3.88 (d, J=7.6 Hz, 3H), 3.64-3.50 (m, 3H), 3.33-3.29 (t, 2H), 2.94-2.90 (m, 1H), 2.75 (s, 1H), 1.45-1.35 (m, 24H).

Synthesis of (S)-3-isopropyl-N6-(morpholin-2-ylmethyl)-N8-(2-(trifluoromethoxy)benzyl)imidazo[1,2-b]pyridazine-6,8-diamine hydrochloride

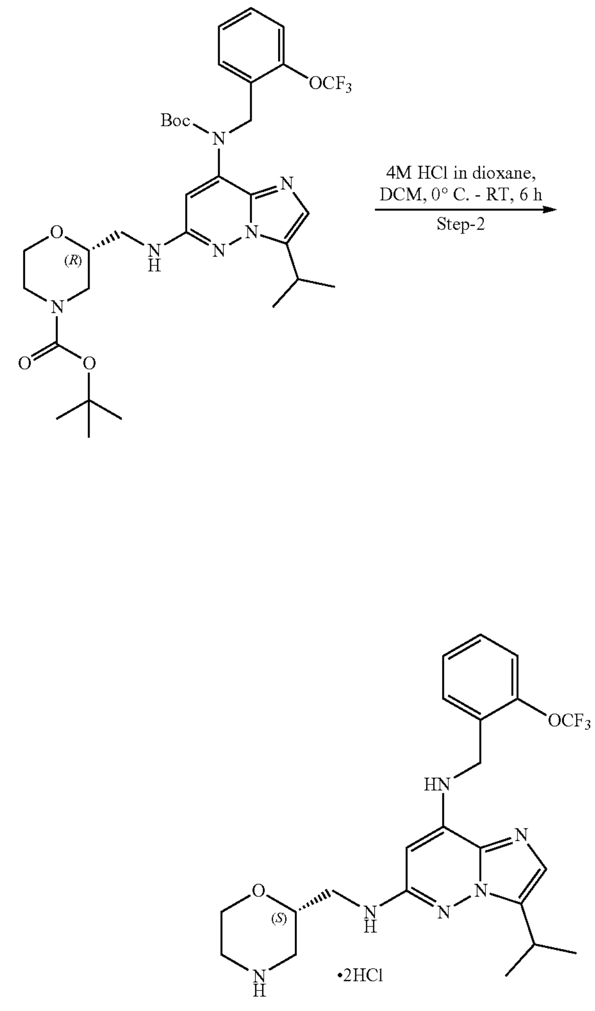

46

To a solution of tert-butyl (R)-2-(((8-((tert-butoxycarbonyl)(2-(trifluoromethoxy)benzyl)amino)-3-isopropylimidazo[1,2-b]pyridazin-6-yl)amino)methyl)morpholine-4-carboxylate (3) (0.11 g, 0.165 mmol, 1 eq.) in DCM (10 mL) at 0 °C was added 4M HCl in dioxane (2 mL) and stirred at room temperature for 6 h. After completion of reaction by TLC, volatiles were evaporated under reduced pressure to obtained crude compound. The obtained crude was triturated with ether (3×30 mL), EtOAc (20 mL) and Hexane (20 mL) afforded (S)-3-isopropyl-N6-(morpholin-2-ylmethyl)-N8-(2-(trifluoromethoxy)benzyl)imidazo[1,2-b]pyridazine-6,8-diamine hydrochloride (46) as an pale orange solid (0.090 g, quantitative). $R_f$=0.1 (9:1 DCM/MeOH). LCMS (m/z): 465.1 $(M+H)^+$. $^1$H-NMR (400 MHz, DMSO) δ 14.55 (bs, 1H), 9.29-9.23 (d, J=22.8 Hz, 2H), 8.22 (s, 1H), 7.82 (s, 1H), 7.54-7.39 (m, 4H), 7.21 (s, 1H), 5.85 (s, 1H), 4.55 (d, J=4.8 Hz, 2H), 3.98-3.94 (d, J=13.2 Hz, 2H), 3.71-3.68 (d, J=11.2 Hz, 1H), 3.24-3.15 (m, 5H), 2.95 (d, J=10.4 Hz 1H), 2.80 (d, J=10.4 Hz, 1H), 1.355-1.332 (m, 6H).

Example 54

Synthetic Scheme for (S)-3-isopropyl-6-(morpholin-2-ylmethoxy)-N-(2-(trifluoromethoxy)benzyl)imidazo [1,2-b]pyridazin-8-amine hydrochloride

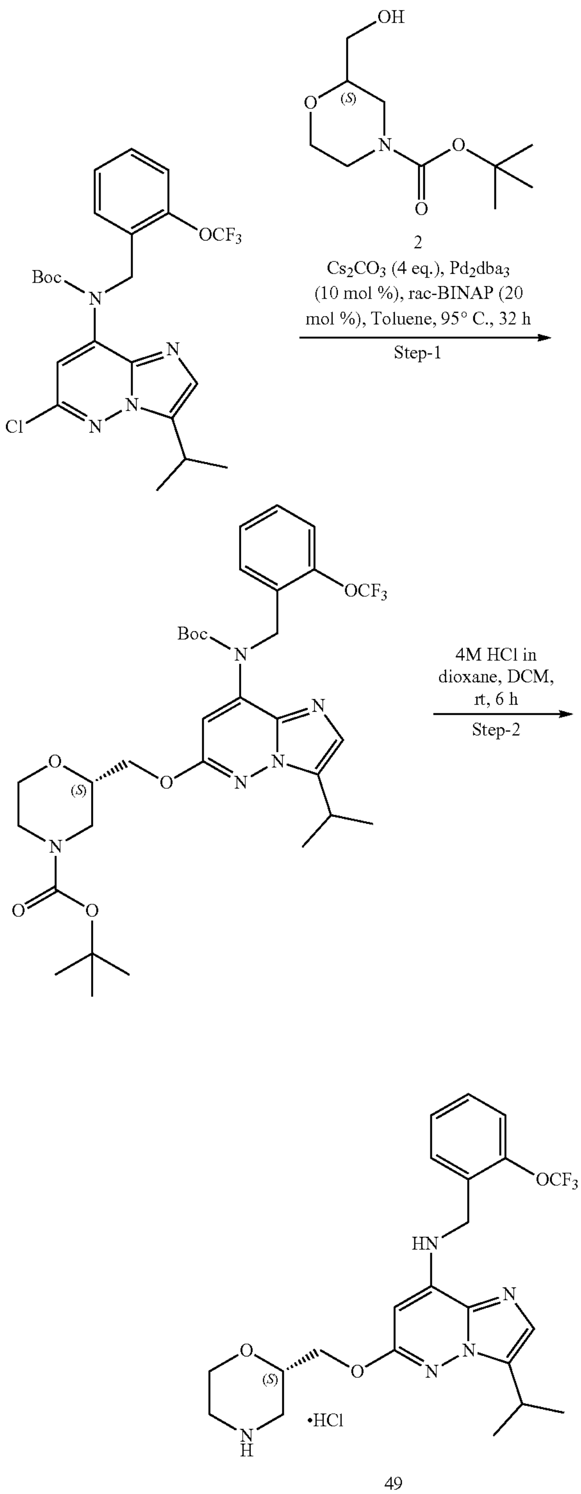

49

Synthesis of tert-butyl (S)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate

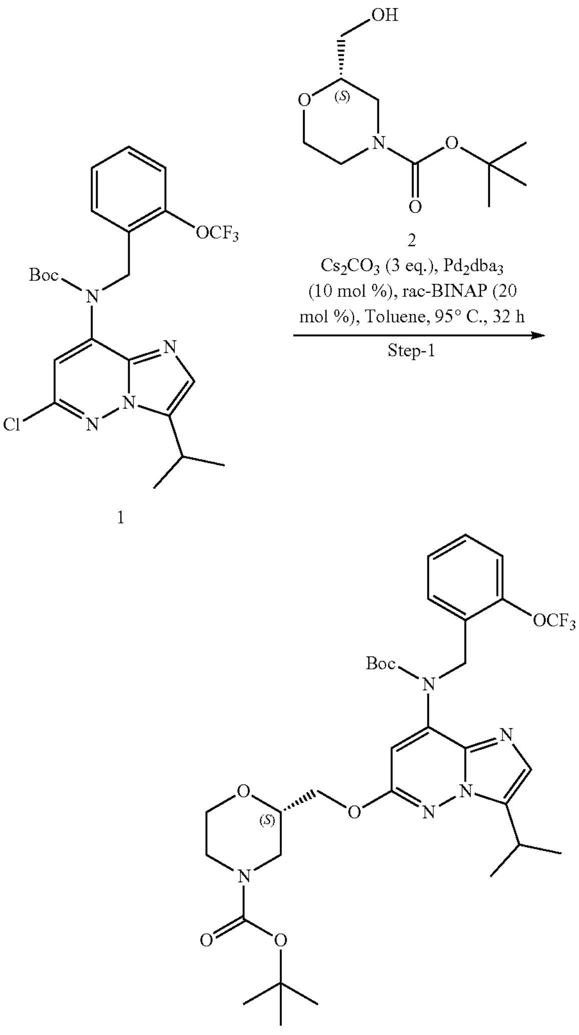

3

To a stirred solution of tert-butyl (6-chloro-3-isopropylimidazo[1,2-b]pyridazin-8-yl)(2-(trifluoromethoxy)benzyl) carbamate (1) (250 mg, 0.516 mmol, 1 eq.) in toluene (5 mL) was added tert-butyl (S)-2-(hydroxymethyl)morpholine-4-carboxylate (2) (168 mg, 0.775 mmol, 1.5 eq.), $Cs_2CO_3$ (335 mg, 1.032 mmol, 2 eq.) and rac-BINAP (32 mg, 10 mol %) at room temperature. The reaction mixture was degassed with argon for 5 min then added tris(dibenzylideneacetone) dipalladium (23 mg, 5 mol %) again degassed with argon for 5 min and heated at 95 °C for 16 h. The reaction mixture cooled to RT and further added tert-butyl (S)-2-(hydroxymethyl)morpholine-4-carboxylate (2) (168 mg, 0.775 mmol, 1.5 eq.), $Cs_2CO_3$ (335 mg, 1.032 mmol, 2 eq.) and rac-BINAP (32 mg, 10 mol %) were added at room temperature. The reaction mixture was degassed with argon for 5 min then added tris(dibenzylideneacetone)dipalladium (23 mg, 5 mol %) again degassed with argon for 5 min and heated at 95 °C for 16 h. The reaction mixture was diluted with ethyl acetate and passed through celite bed. The organic phase was washed with water (20 mL), brine, dried over $Na_2SO_4$ and concentrated under vacuum. The residue was purified by combiflash on silica column (EtOAc/hexane, gradient 0-30% EtOAc) to afford (S)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate (3) as yellow solid. (100 mg, 35% yield), $R_f$=0.3 (8:2: Hexane/EtOAc). $^1$H-NMR (400 MHz, DMSO): δ 7.56 (d, J=5.7 Hz, 1H), 7.45-7.19 (m, 4H), 6.91 (s, 1H), 5.33 (s, 2H), 4.33 (d, J=5.4 Hz, 2H), 3.78 (dd, J=49.4, 13.2 Hz, 3H), 3.48-3.35 (m, 2H), 2.86 (s, 2H), 2.72-2.55 (m, 1H), 1.50-1.14 (m, 24H).

Synthesis of (S)-3-isopropyl-6-(morpholin-2-ylmethoxy)-N-(2-(trifluoromethoxy)benzyl)imidazo[1,2-b]pyridazin-8-amine hydrochloride

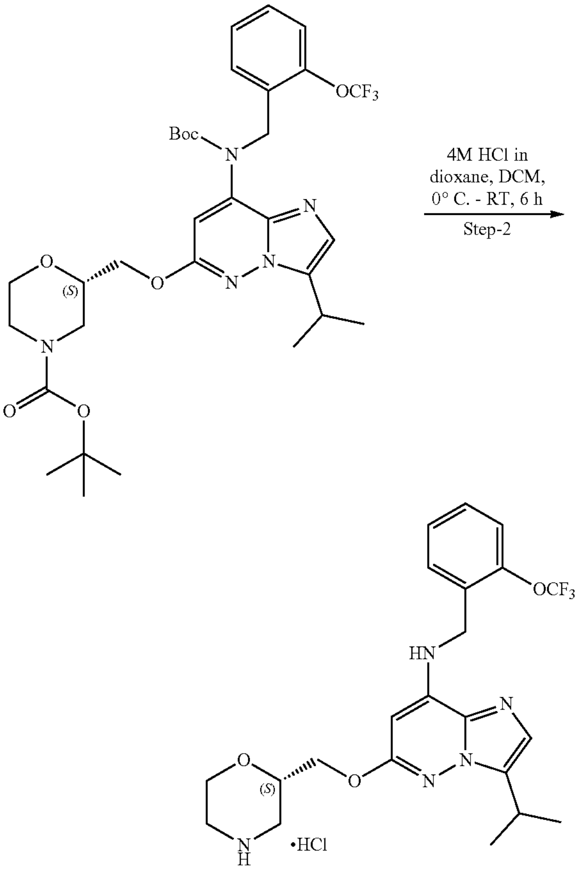

49

To a solution of tert-butyl (S)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate (3) (0.1 g, 0.150 mmol, 1 eq.) in DCM (10 mL) at 0 °C was added 4M HCl in dioxane (2 mL) and stirred at RT for 6 h. After completion of conversion by TLC, the reaction mixture was subjected to rotary evaporator for removal of volatiles. The obtained residue was triturated with ether (3x30 mL), EtOAc (20 mL) and Hexane (20 mL) afforded (S)-3-isopropyl-6-(morpholin-2-ylmethoxy)-N-(2-(trifluoromethoxy)benzyl)imidazo[1,2-b]pyridazin-8-amine hydrochloride (49) as an off white solid (42 mg, 59% yield). $R_f$=0.1 (9:1 DCM/MeOH). LCMS (m/z): 466.1 $(M+H)^+$. $^1$H-NMR (400 MHz, DMSO): δ 9.42 (d, J=36.0 Hz, 2H), 8.54 (s, 1H), 7.83 (s, 1H), 7.52-7.35 (m, 4H), 6.02 (s, 1H), 4.64 (d, J=5.0 Hz, 2H), 4.35 (dd, J=14.9, 8.3 Hz, 2H), 4.13 (s, 1H), 3.99 (d, J=13.3 Hz, 1H), 3.83-3.69 (m, 1H), 3.32 (d, J=13.4 Hz, 2H), 3.20 (d, J=13.0 Hz, 1H), 2.97 (s, 2H), 1.35 (d, J=6.9 Hz, 6H).

Example 55

Synthetic Scheme for (R)-3-isopropyl-6-(morpholin-2-ylmethoxy)-N-(2-(trifluoromethoxy)benzyl) imidazo [1,2-b]pyridazin-8-amine hydrochloride

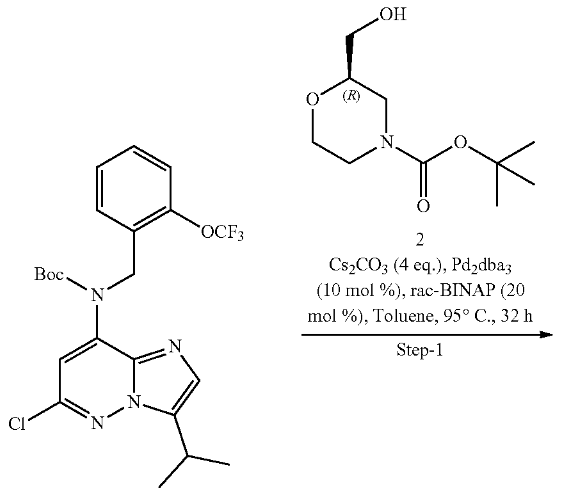

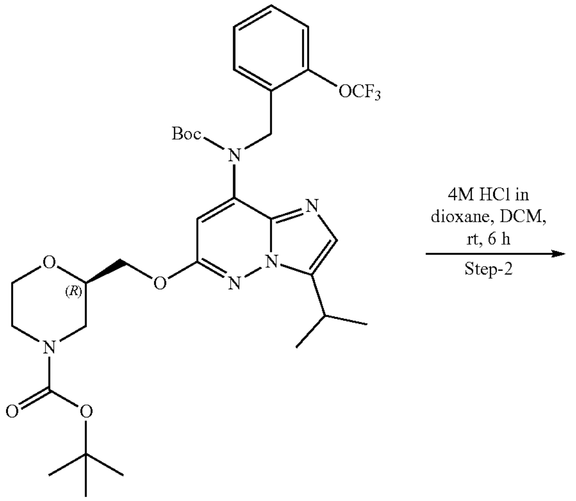

-continued

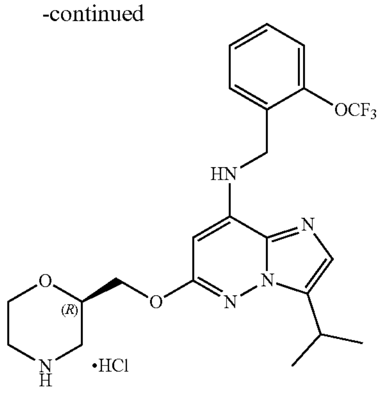

47

Synthesis of tert-butyl (R)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate

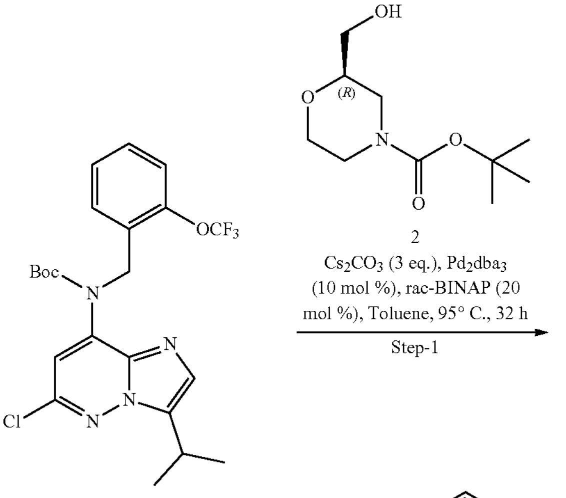

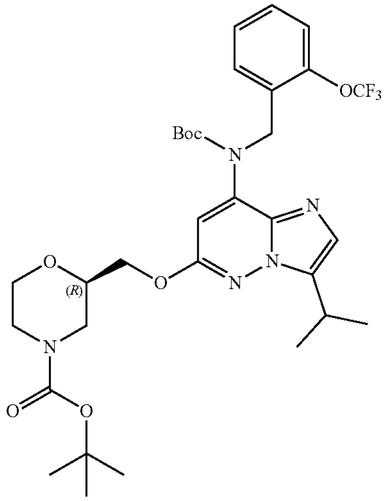

To a stirred solution of tert-butyl (6-chloro-3-isopropylimidazo[1,2-b]pyridazin-8-yl)(2-(trifluoromethoxy)benzyl) carbamate (1) (0.250 g, 0.516 mmol, 1 eq.) in toluene (5 mL)

was added tert-butyl (R)-2-(hydroxymethyl)morpholine-4-carboxylate (2) (0.168 g, 0.775 mmol, 1.5 eq.), $Cs_2CO_3$ (0.335 g, 1.032 mmol, 2 eq.) and rac-BINAP (0.032 g, 10 mol %) were added at room temperature. The reaction mixture was purged with argon for 5 min, then added tris(dibenzylideneacetone)dipalladium (0.023 g, 5 mol %) again purged with argon for 5 min and heated at 95 °C for 16 h. The reaction mixture cooled to room temperature and further added tert-butyl (S)-2-(hydroxymethyl)morpholine-4-carboxylate (2) (0.168 g, 0.775 mmol, 1.5 eq.), $Cs_2CO_3$ (0.335 g, 1.032 mmol, 2 eq.) and rac-BINAP (0.032 g, 10 mol %) were added at room temperature. The reaction mixture was purged with argon for 5 min then added tris(dibenzylideneacetone)dipalladium (0.023 g, 5 mol %) again purged with argon for 5 min and heated at 95 °C for 16 h. The reaction mixture was diluted with ethyl acetate and filtered through celite. The organic phase was washed with water (20 mL), brine, dried over $Na_2SO_4$ and concentrated under reduced pressure to provide crude product. Obtained crude compound was purified by column chromatography using ethyl acetate in hexane as a eluting system to afford (R)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate (3) as yellow solid. (0.065 g, 36% yield), $R_f$=0.3 (8:2: Hexane/EtOAc). LCMS (m/z): 666.1 $(M+H)^+$. $^1$H-NMR (400 MHz, $CDCl_3$). δ 7.44-7.38 (m, 2H), 7.30-7.19 (m, 3H), 6.73 (s, 1H), 5.47 (s, 2H), 4.39-4.34 (m, 2H), 3.97-3.84 (m, 3H), 3.62-3.60 (m, 2H,), 3.36-3.33 (m, 1H,), 3.10-2.80 (m, 2H), 1.59-1.43 (m, 24H).

Synthesis of (R)-3-isopropyl-6-(morpholin-2-ylmethoxy)-N-(2-(trifluoromethoxy)benzyl)imidazo[1,2-b]pyridazin-8-amine hydrochloride

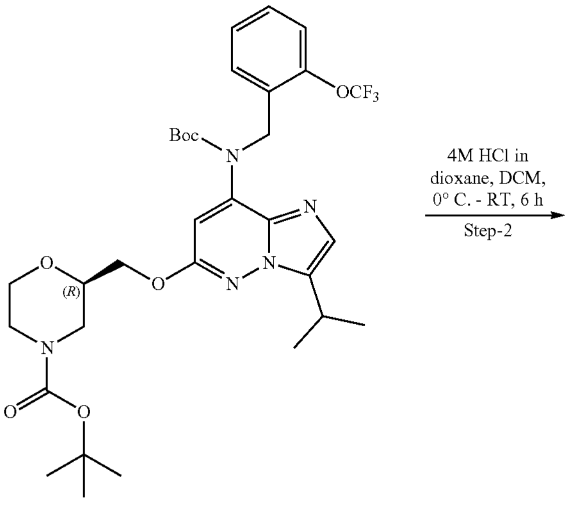

-continued

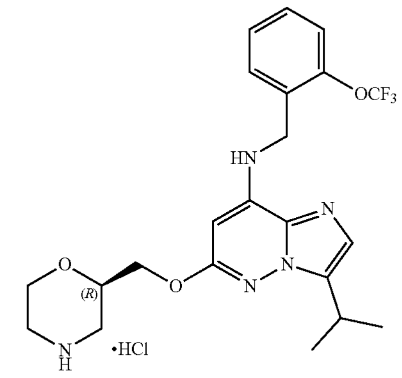

47

To a solution of tert-butyl (R)-2-(((8-((tert-butoxycarbonyl)(2-(trifluoromethoxy)benzyl)amino)-3-isopropylimidazo[1,2-b]pyridazin-6-yl)oxy)methyl)morpholine-4-carboxylate (3) (0.065 g, 0.097 mmol, 1 eq.) in DCM (10 mL) at 0 °C was added 4M HCl in Dioxane (2 mL) and stirred at room temperature for 6 h. After completion of reaction by TLC, volatiles were evaporated under reduced pressure to obtained crude compound. The obtained crude was triturated with ether (3×30 mL), EtOAc (20 mL) and Hexane (20 mL) afforded (R)-3-isopropyl-6-(morpholin-2-ylmethoxy)-N-(2-(trifluoromethoxy)benzyl)imidazo[1,2-b]pyridazin-8-amine hydrochloride (47) as an off white solid (0.032 g, quantitative). $R_f$=0.1 (9:1 DCM/MeOH). LCMS (m/z): 466.1 $(M+H)^+$. HPLC: 99.55%. $^1$H-NMR (400 MHz, DMSO): δ 9.42-9.34 (m, 2H), 8.52 (s, 1H), 7.80 (s, 1H), 7.51-7.36 (m, 4H), 6.01 (s, 1H), 4.64 (d, J=5.6 Hz, 2H), 4.37-4.28 (m, 2H), 4.11 (m, 1H), 3.99-3.96 (m, 1H), 3.79-3.73 (m, 1H), 3.32-3.29 (m, 2H), 3.20-3.17 (m, 1H), 3.01-2.88 (m, 2H), 1.35-133 (d, J=6.8 Hz, 6H).

Example 56

Synthetic Scheme for 3-isopropyl-6-(piperidin-4-yloxy)-N-(2-(trifluoromethoxy) benzyl)imidazo[1,2-b]pyridazin-8-amine hydrochloride

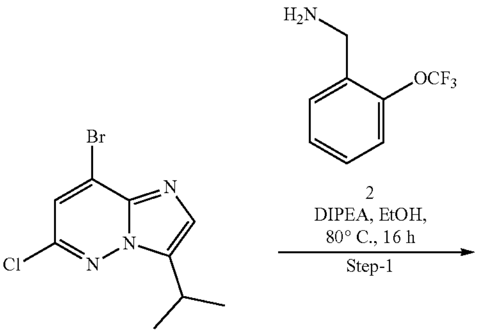

-continued

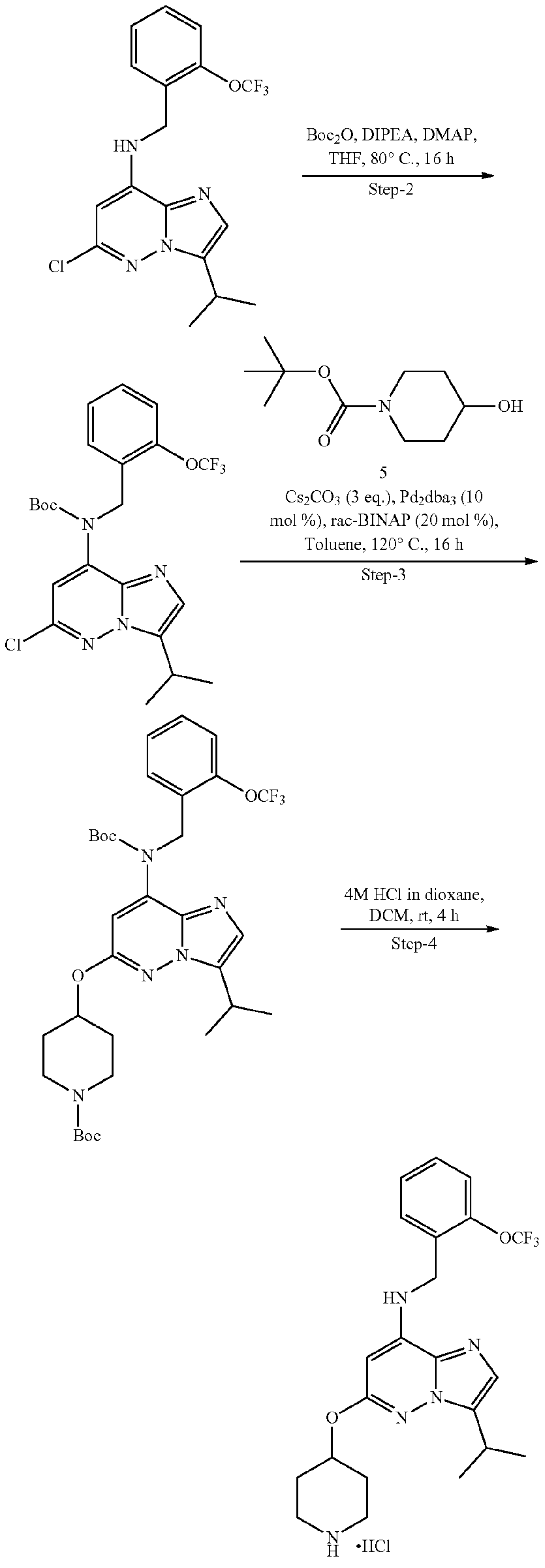

43

Step-1: Synthesis of 6-chloro-3-isopropyl-N-(2-(trifluoromethoxy)benzyl)imidazo[1,2-b]pyridazin-8-amine

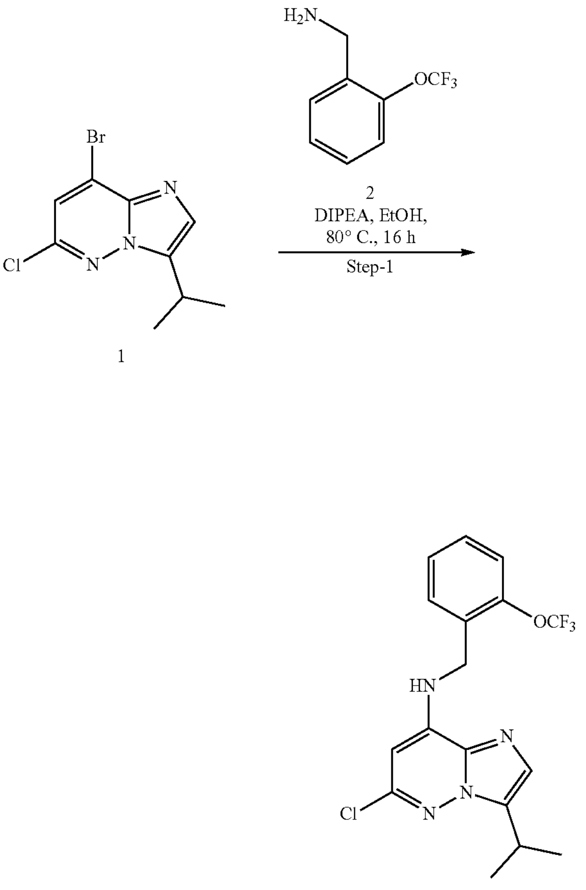

3

To a stirred solution of 8-bromo-6-chloro-3-isopropylimidazo[1,2-b]pyridazine (1) (2.5 g, 9.157, mmol, 1eq.) in ethanol (25 mL) was added (2-(trifluoromethoxy)phenyl) methanamine (2) (2.06 mL), 13.73 mmol, 1.5 eq.) and DIPEA (3.18 mL, 18.31 mmol, 2 eq.) at room temperature. The reaction mixture was heated at 80 °C for 16 h. After complete conversion by TLC, the reaction mixture was allowed to cool to room temperature; ethanol was evaporated under reduced pressure to get the crude residue. The crude residue was diluted with water (100 mL), extracted with ethyl acetate (3×75 mL). The combined organic layer was washed with brine (150 mL), dried over sodium sulphate, filtered and evaporated under reduced pressure to get the crude residue. The crude residue was purified by flash column chromatography (with gradient elution of 0-10% EtOAc/hexane) to afford the title compound as 6-chloro-3-isopropyl-N-(2-(trifluoromethoxy) benzyl) imidazo [1,2-b] pyridazin-8-amine (3) as yellow solid. (Yield: 2.5 g, 71%). $R_f$=0.4 (4:1 Hexane/EtOAc). LCMS (m/z): 385.0 $(M+H)^+$. $^1H$ NMR (400 MHz, DMSO-$d_6$): δ=8.39 (s, 1H), 7.42-7.33 (m, 5H), 5.99 (s, 1H), 4.62 (s, 2H), 3.28-3.20 (s, 1H), 1.31-1.29 (m, 6H).

Step-2: Synthesis of tert-butyl (6-chloro-3-isopropylimidazo [1, 2-b]pyridazin-8-yl)(2-(trifluoromethoxy)benzyl)carbamate

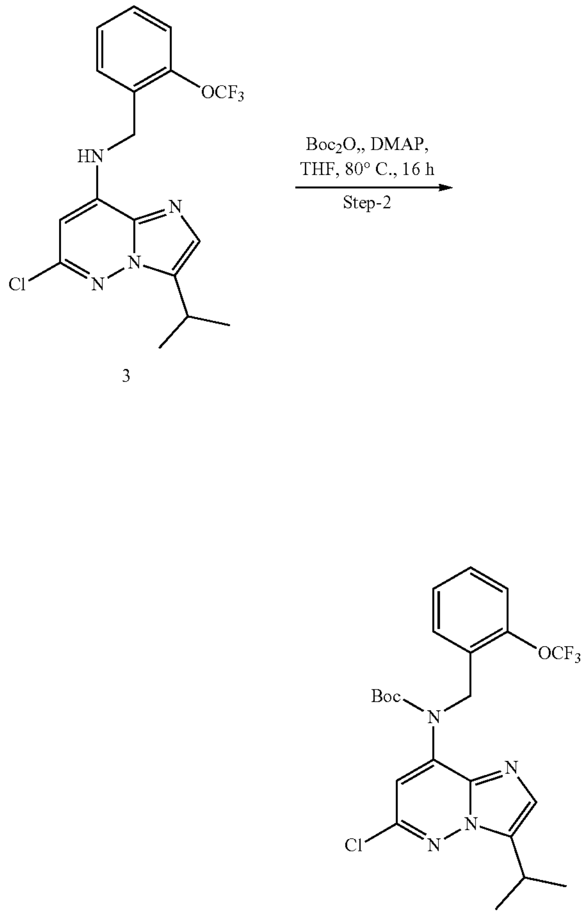

3

4

To a stirred solution of 6-chloro-3-isopropyl-N-(2-(trifluoromethoxy)benzyl)imidazo[1,2-b]pyridazin-8-amine (3) (2.5 g, 6.51 mmol, 1 eq.) in THF (25 mL) was added DIPEA (11.33 mL, 65.10 mmol, 10 eq.), Boc anhydride (14.19 mL, 65.10 mmol, 10 eq.) and DMAP (0.079 g, 0.651 mmol, 0.1 eq.) at room temperature. Reaction mixture was stirred at 80 °C for 16 h. After complete conversion by TLC, the reaction mixture was cooled, THF was evaporated under reduced pressure to get the crude residue. To the crude residue water (100 mL) was added, extracted with ethyl acetate (3×100 mL). The combined organic layer was washed with brine (100 mL), dried over sodium sulphate, filtered and evaporated under reduced pressure to get the crude residue. The crude residue was purified by flash column chromatography using silica gel (100-200) mesh (with a gradient elution of 0-10% of EtOAC: n-Hexane) to afford title compound as tert-butyl (6-chloro-3-isopropylimidazo [1,2-a]pyrazin-8-yl) (2-methoxybenzyl)carbamate (4) as yellow liquid. (Yield: 2.6 g, 82%). $R_f$=0.6 (4:1 Hexane/EtOAc). LCMS (m/z): 485.0 $(M+H)^+$. $^1H$ NMR (400 MHz, DMSO-$d_6$): δ=7.65-7.63 (m, 1H), 7.56-7.54 (m, 1H), 7.42-7.28 (m, 4H), 5.38 (m, 2H), 3.33-3.31 (m, 1H), 1.34-1.31 (m, 15H).

Step-3: Synthesis of tert-butyl 4-((8-((tert-butoxycarbonyl)(2-(trifluoromethoxy)benzyl)amino)-3-isopropylimidazo[1,2-b]pyridazin-6-yl)oxy)piperidine-1-carboxylate

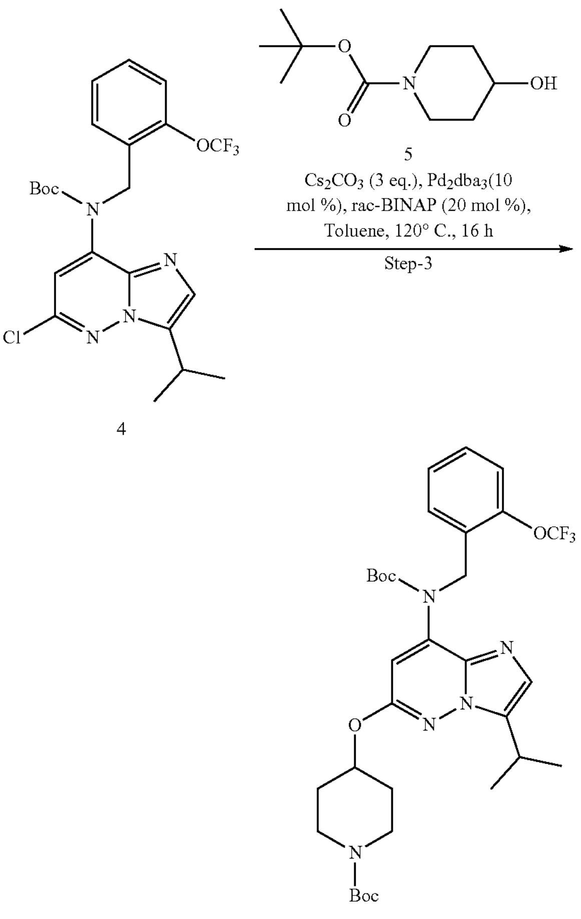

4

5

6

To a stirred solution of tert-butyl (6-chloro-3-isopropylimidazo[1,2-b]pyridazin-8-yl)(2-(trifluoromethoxy)benzyl) carbamate (4) (0.250 g, 0.516 mmol, 1 eq.) in toluene (5 mL) was added $Cs_2CO_3$ (0.335 g, 1.033 mmol, 2 eq.) and rac-BINAP (0.032 g, 0.051 mmol, 0.1 eq.) and tert-butyl 4-hydroxypiperidine-1-carboxylate (5) (0.155 g, 0.774 mmol, 1.5 eq.) at room temperature. Degassed the reaction mixture under argon for 10 minutes. Then addition of Tris (dibenzylideneacetone) dipalladium (0.023 g, 0.025 mmol, 0.05 eq.) was done. Reaction mixture was heated at 120 °C for 16 h. After this time, added $Cs_2CO_3$ (0.335 g, 1.033 mmol, 2 eq.) and rac-BINAP (0.032 g, 0.051 mmol, 0.1 eq.) and tert-butyl 4-hydroxypiperidine-1-carboxylate (5) (0.155 g, 0.774 mmol, 1.5 eq.) at room temperature to the reaction mas. Degassed the reaction mixture under argon for 10 minutes. Then addition of Tris (dibenzylideneacetone) dipalladium (0.023 g, 0.025 mmol, 0.05 eq.) was done. Reaction mixture was again heated at 120 °C for another 16 h. After complete conversion by TLC, reaction mixture was cooled, water (25 mL) was added, extracted with ethyl acetate (3×50 mL), washed with brine (50 mL), dried over sodium sulphate, filtered and evaporated under reduced pressure to get crude residue. The residue was purified by column chromatography using silica gel (100-200) mesh (with a gradient elution of 0-10% EtOAc/hexane) to afford the title compound as tert-butyl 4-((8-((tert-butoxycarbonyl)(2-(trifluoromethoxy)benzyl)amino)-3-isopropylimidazo[1,2-b]pyridazin-6-yl)oxy)piperidine-1-carboxylate (6) as a brown solid. Yield: (0.2 g, 59%). $R_f$=0.3 (2:1 Hexane/EtOAc). LCMS (m/z): 650.1 $(M+H)^+$; $^1H$ NMR (400 MHz, DMSO-$d_6$): δ=7.60-7.55 (m, 1H), 7.46-7.28 (m, 4H), 6.88-6.85 (m, 1H), 5.34 (d, J=13.2 Hz, 2H), 5.12-5.09 (m, 1H), 3.64-3.61 (m, 2H), 3.41-3.24 (m, 3H), 2.02-2.01 (m, 2H), 1.69-1.65 (m, 2H), 1.47-1.23 (m, 24H).

Step-4: Synthesis of 3-isopropyl-6-(piperidin-4-yloxy)-N-(2-(trifluoromethoxy) benzyl) imidazo [1, 2-b]pyridazin-8-amine hydrochloride

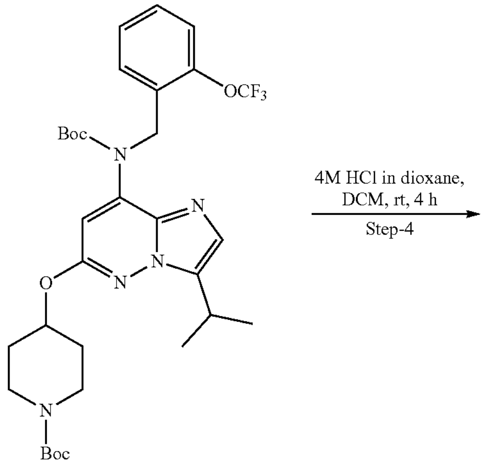

6

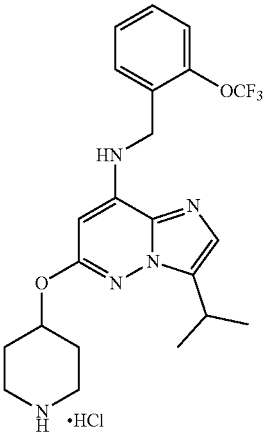

43

To a stirred solution of tert-butyl 4-((8-((tert-butoxycarbonyl)(2-(trifluoromethoxy)benzyl)amino)-3-isopropylimidazo[1,2-b]pyridazin-6-yl)oxy)piperidine-1-carboxylate (6) (0.200 g, 0.308 mmol, 1eq.) in DCM (4 mL) at 0 °C was added 4M HCl in 1,4-dioxane (1 mL) drop-wise. Reaction mixture was stirred at room temperature for 4 h. After complete conversion by TLC, the reaction mixture was subjected to rotary evaporator for removal of volatiles. The obtained residue was triturated with diethyl ether (3×10 mL), EtOAc (2×10 mL) and lyophilized for 24 h. to get the title compound as 3-isopropyl-6-(piperidin-4-yloxy)-N-(2-(trifluoromethoxy)benzyl)imidazo[1,2-b]pyridazin-8-amine hydrochloride as pale orange solid (43). (Yield: 0.200 g, quantitative). $R_f$=0.1 (4:1 Hexane/EtOAc). LCMS (m/z): 450.1 $(M+H)^+$ $^1H$ NMR (400 MHz, DMSO-$d_6$): δ=8.96 (s, 2H), 8.62 (s, 1H), 7.84 (s, 1H), 7.53-7.36 (m, 4H), 6.0 (s, 1H), 5.16 (s, 1H), 4.63 (d, J=4 Hz, 2H), 3.34-3.10 (m, 5H), 2.17-2.16 (m, 2H), 1.96-1.94 (m, 2H), 1.34-1.33 (m, 6H).

Example 57

Synthetic Scheme for N-(3-fluorophenyl)-3-isopropyl-6-(piperidin-4-ylthio)imidazo[1,2-b]pyridazin-8-amine hydrochloride

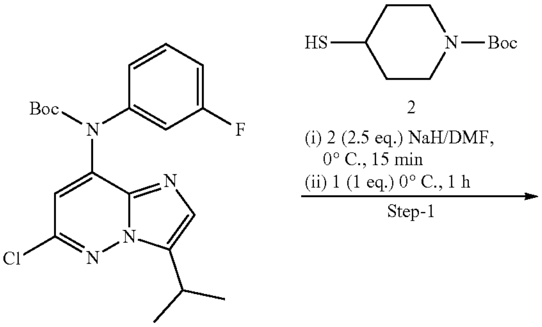

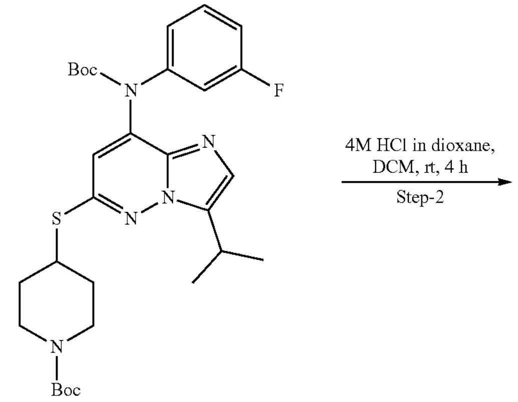

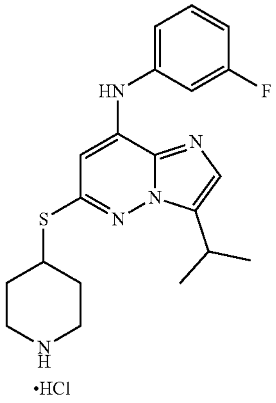

44

Step-1: Synthesis of tert-butyl 4-((8-((tert-butoxy-carbonyl)(3-fluorophenyl)amino)-3-isopropylimidazo[1,2-b]pyridazin-6-yl)thio)piperidine-1-carboxylate

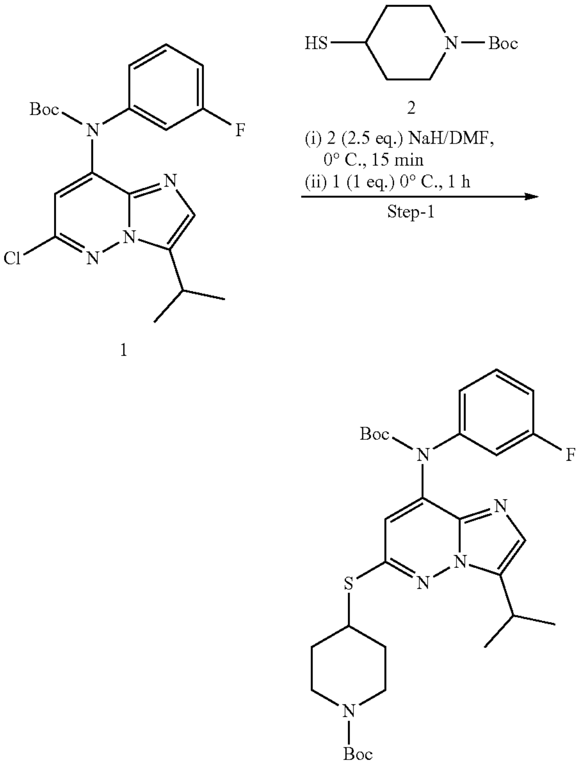

1

2

3

To a stirred solution of tert-butyl 4-mercaptopiperidine-1-carboxylate (2) (0.2 g, 0.495 mmol, 2.5 eq.) in DMF (3 mL) at 0 °C was added NaH (60% in mineral oil, (0.049 g, 1.23 mmol, 2.5 eq.). Reaction mixture was stirred at 0 °C for 10 minutes. Then addition of tert-butyl (6-chloro-3-isopropylimidazo[1,2-b]pyridazin-8-yl)(3-fluorophenyl)carbamate (1) (0.200 g, 0.495 mmol, 2.5 eq.) in DMF (2 mL) was done at 0 °C. Reaction mixture was stirred at 0 °C for 1 h. After complete conversion by TLC, water (10 mL) was added, extracted with ethyl acetate (3×50 mL). The combined organic layer was washed with brine solution (10 mL), dried over sodium sulfate, filtered and evaporated under reduced pressure to get the crude residue as brown oil. Purification was done by flash column chromatography (with a gradient elution of 10-15% of EtOAC: n-Hexane) to afford the title compound as tert-butyl 4-((8-((tert-butoxy-carbonyl)(3-fluorophenyl)amino)-3-isopropylimidazo[1,2-b]pyridazin-6-yl)thio)piperidine-1-carboxylate (3) as white solid (Yield: 0.2 g, 69%).

$R_f$=0.3(4:1 Hexane/EtOAc). Note: LCMS analysis shows 89% of product along with mono de-boc of product 6%. LCMS (m/z): 586.1 $(M+H)^+$. $^1$H-NMR (400 MHz, DMSO-$d_6$): δ=7.46 (m, 1H), 7.36 (m, 1H), 7.24 (m, 1H), 7.17-7.10 (m, 3H), 3.96-3.94 (m, 1H), 3.84 (m, 2H), 3.04 (m, 2H), 2.12-2.09 (m, 2H), 1.62-1.57 (m, 3H), 1.40-1.35 (m, 24H).

Step-2: Synthesis of N-(3-fluorophenyl)-3-isopropyl-6-(piperidin-4-ylthio)imidazo[1,2-b]pyridazin-8-amine hydrochloride

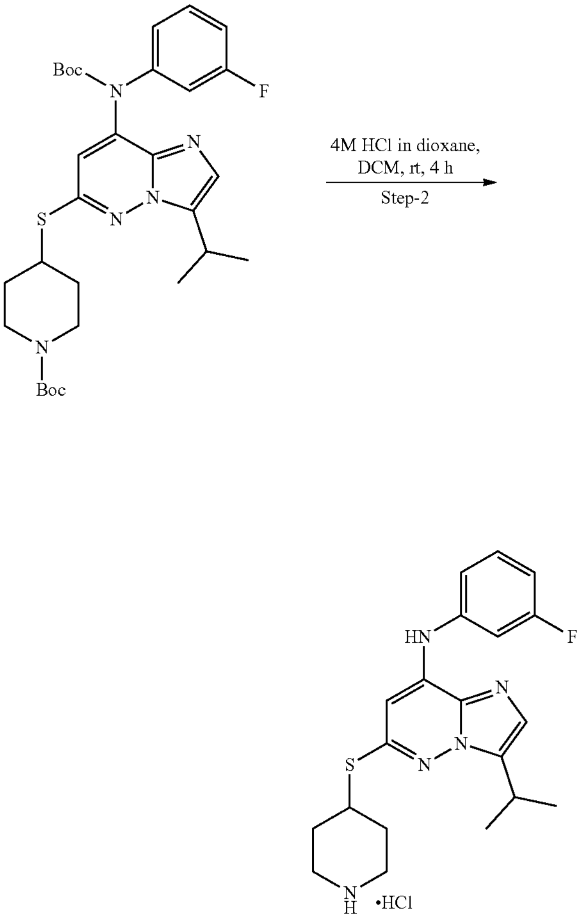

44

To a stirred solution of tert-butyl 4-((8-((tert-butoxycarbonyl)(3-fluorophenyl)amino)-3-isopropylimidazo[1,2-b]pyridazin-6-yl)thio)piperidine-1-carboxylate (3) (0.200 g, 0.341 mmol, 1eq.) in DCM (4 mL) at 0 °C was added 4M HCl in dioxane (2 mL). Reaction mixture was allowed to come to room temperature and stirred for 4 h. After completion of conversion by TLC, volatiles were evaporated under reduced pressure and obtained crude compound. Crude compound was triturated with n-pentane (10 mL), diethyl ether (2×10 mL) and lyophilized for 24 h. to afford the title compound N-(3-fluorophenyl)-3-isopropyl-6-(piperidin-4-ylthio)imidazo[1,2-b]pyridazin-8-amine hydrochloride as a white solid (44) (Yield: 0.175 g, quantitative). $R_f$=0.1 (1:1Hexane/EtOAc). LCMS (m/z): 386.0 $(M+H)^+$. $^1$H-NMR (400 MHz, DMSO-$d_6$): δ=10.40 (s, 1H), 9.16 (br. s, 1H), 8.95 (br. s, 1H), 7.89 (s, 1H), 7.52-7.46 (q, J=7.6 Hz, 1H), 7.28 (d, J=8.4 Hz, 2H), 7.07 (t, J=8.0 Hz, 1H), 6.80 (s, 1H), 4.06-4.01 (m, 1H), 3.45-3.38 (m, 1H), 3.27 (m, 2H), 3.08-3.05 (m, 2H), 2.29-2.26 (m, 2H), 1.91-1.83 (m, 2H), 1.36 (d, J=7.2 Hz, 6H).

Example 58

Synthetic Scheme for N-(3-fluorophenyl)-3-isopropyl-6-(piperidin-4-yloxy)imidazo[1,2-b]pyridazin-8-amine hydrochloride

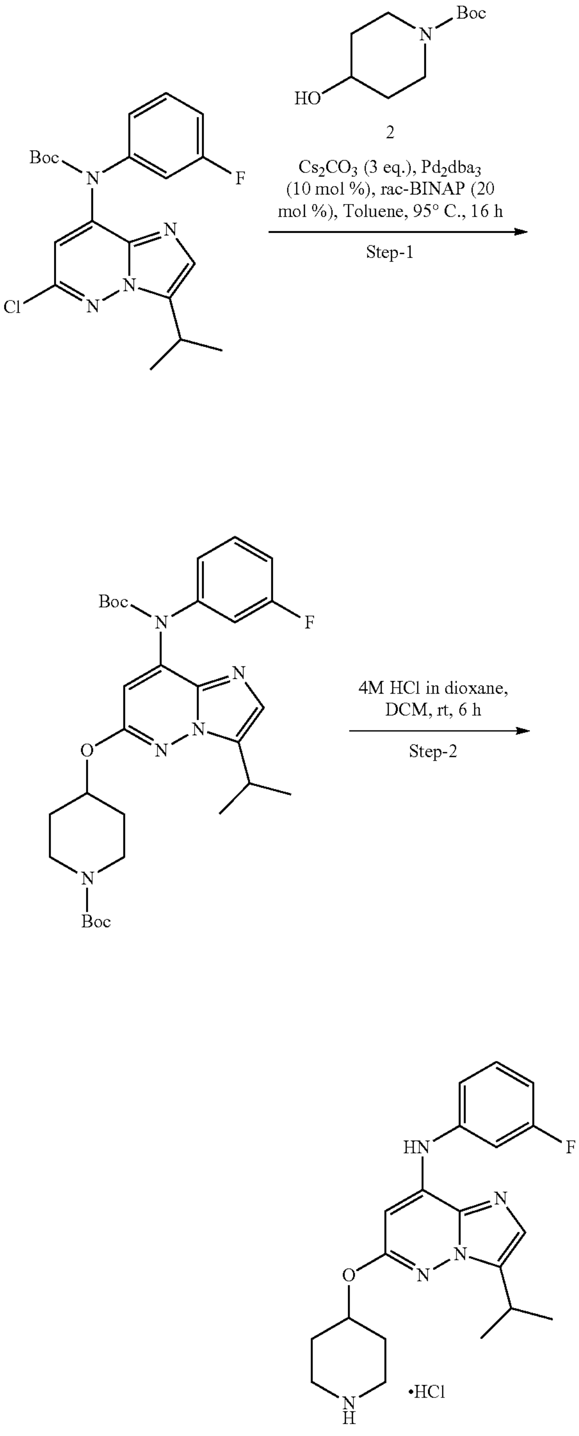

50

Synthesis of tert-butyl 4-((8-((tert-butoxycarbonyl)(3-fluorophenyl)amino)-3-isopropylimidazo[1,2-b]pyridazin-6-yl)oxy)piperidine-1-carboxylate

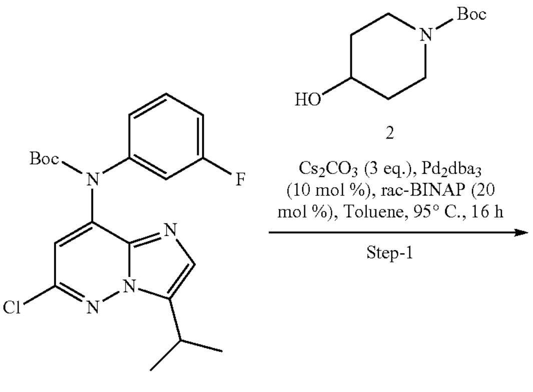

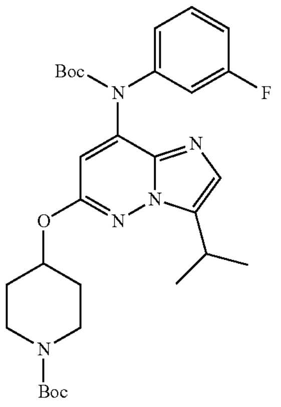

3

To a stirred solution of tert-butyl (6-chloro-3-isopropylimidazo[1,2-b]pyridazin-8-yl)(3-fluorophenyl)carbamate (1) (0.25 g, 0.618 mmol, 1 eq.) in toluene (5 mL) was added $Cs_2CO_3$ (0.803 g, 2.472 mmol, 4 eq.), tert-butyl 4-hydroxypiperidine-1-carboxylate (2) (0.372 g, 1.854 mmol, 3 eq.) and rac-BINAP (0.077 g, 20 mol %) at room temperature. The reaction mixture was degassed with argon for 10 min and added tris(dibenzylideneacetone)dipalladium (0.056 g, 10 mol %) again degassed with argon for 10 min and heated to 100 °C for 16 h. The reaction mixture was diluted with ethyl acetate and passed through celite bed. The organic phase was washed with water (3×20 mL), dried over sodium sulfate, filtered and concentrated under reduced pressure to provide crude product. Obtained crude compound was purified by flash chromatography with a gradient elution of 10-20% of EtOAc/Hexane] to afford tert-butyl 4-((8-((tert-butoxycarbonyl)(3-fluorophenyl)amino)-3-isopropylimidazo[1,2-b]pyridazin-6-yl)oxy)piperidine-1-carboxylate (3) as a yellow gum (0.13 mg, 32% yield), $R_f$=0.3 (2:8 hexane/ethyl acetate). $^1H$ NMR (400 MHz, DMSO) δ 7.44-7.32 (m, 2H), 7.28 (d, J=10.2 Hz, 1H), 7.21-7.06 (m, 2H), 6.90 (d, J=6.8 Hz, 1H), 5.14 (s, 1H), 3.63 (s, 2H), 3.28 (d, J=7.1 Hz, 3H), 2.02 (s, 2H), 1.69 (d, J=8.6 Hz, 2H), 1.51-1.08 (m, 24H).

Synthesis of N-(3-fluorophenyl)-3-isopropyl-6-(piperidin-4-yloxy)imidazo[1,2-b]pyridazin-8-amine hydrochloride

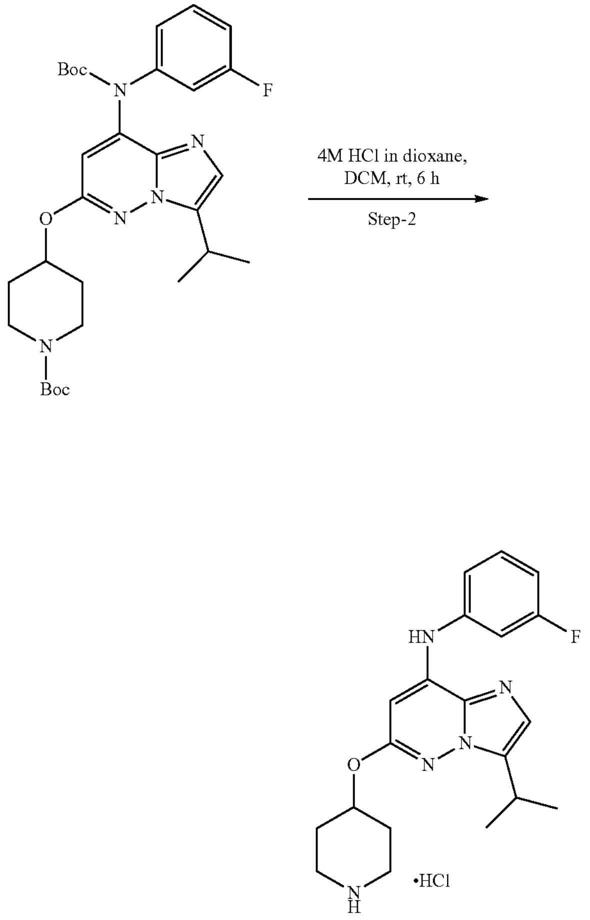

50

To a solution of tert-butyl 4-((8-((tert-butoxycarbonyl)(3-fluorophenyl)amino)-3-isopropylimidazo[1,2-b]pyridazin-6-yl)oxy)piperidine-1-carboxylate (3) (0.13 g, 0.22 mmol, 1 eq.) in DCM (10 mL) at 0 °C was added 4M HCl in dioxane (2 mL) and stirred at RT for 6 h. After completion of reaction by TLC, the reaction mixture was subjected to rotary evaporator for removal of volatiles. The obtained residue was triturated with ether (3×30 mL), EtOAc (20 mL) and Hexane (20 mL) afford N-(3-fluorophenyl)-3-isopropyl-6-(piperidin-4-yloxy)imidazo[1,2-b]pyridazin-8-amine hydrochloride (50) as an off white solid (76 mg, 66% yield). $R_f$=0.1 (9:1 DCM/MeOH). LCMS (m/z): 380.0 $(M+H)^+$. 1H-NMR (400 MHz, DMSO) δ 10.38 (s, 1H), 8.95 (s, 2H), 7.91 (s, 1H), 7.51 (dd, J=15.0, 8.2 Hz, 1H), 7.34-7.14 (m, 2H), 7.06 (t, J=7.7 Hz, 1H), 6.56 (s, 1H), 5.22 (s, 1H), 3.37-3.30 (m, 1H), 3.23 (s, 2H), 3.13 (s, 2H), 2.18 (s, 2H), 2.01 (s, 2H), 1.36 (d, J=6.9 Hz, 6H).

Example 59

Synthetic Scheme for N8-(3-fluorophenyl)-3-isopropyl-N6-(piperidin-4-yl)imidazo[1,2-b]pyridazine-6,8-diamine hydrochloride

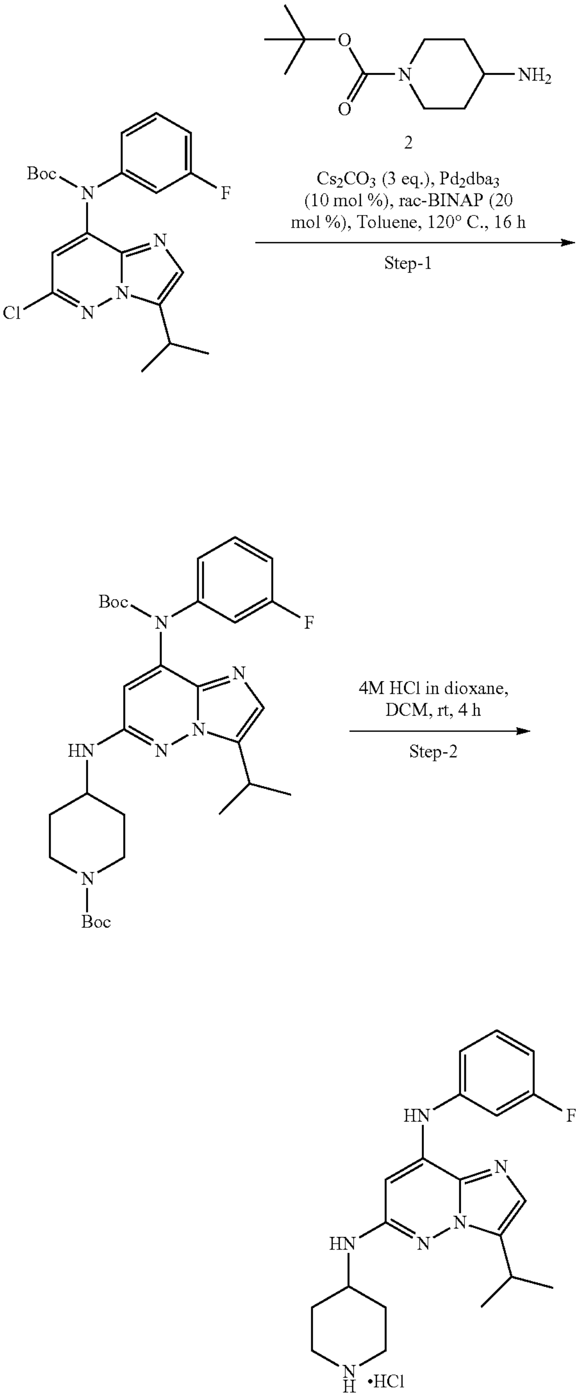

45

Step-1: Synthesis of tert-butyl 4-((8-((tert-butoxycarbonyl)(3-fluorophenyl)amino)-3-isopropylimidazo[1,2-b]pyridazin-6-yl)amino)piperidine-1-carboxylate

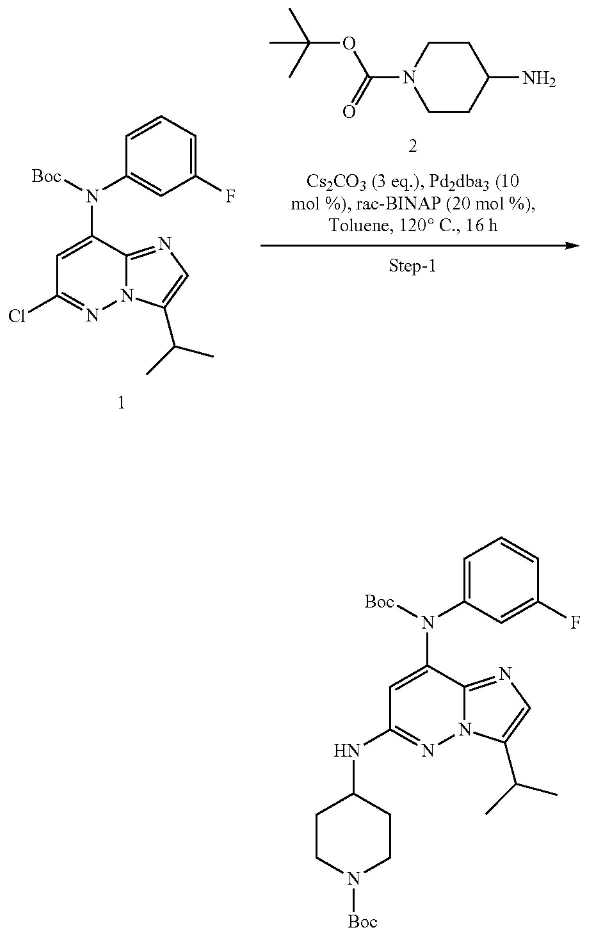

1

2

3

To a stirred solution of tert-butyl (6-chloro-3-isopropylimidazo[1,2-b]pyridazin-8-yl)(3-fluorophenyl)carbamate (1) (0.200 g, 0.495 mmol, 1eq.) in Toluene (5 mL) was added tert-butyl 4-aminopiperidine-1-carboxylate (2) (0.297 g, 1.485 mmol, 3 eq.), cesium carbonate (0.643 g, 1.98 mmol, 4 eq.) and rac BINAP (0.061 g, 0.099 mmol, 0.2eq.) at room temperature and degassed the reaction mixture under argon for 5 minutes. Then added $Pd_2(dba)_3$ (0.045 g, 0.0495 mmol, 0.1 eq.) and degassed the reaction mixture under argon for 5 minutes. Reaction mixture was stirred at 120 °C for 16 h. After complete conversion by TLC, reaction mixture was diluted with water (50 mL) and extracted with ethyl acetate (3x50 mL). The combined organic layer was washed with brine (50 mL), dried over sodium sulphate and evaporated under reduced pressure to get the crude residue. The crude residue was purified by silica phase column chromatography with a (gradient elution of 15-20% of EtOAc/Hexane) to afford the title compound (3) as tert-butyl 4-((8-((tert-butoxycarbonyl)(3-fluorophenyl)amino)-3-isopropylimidazo[1,2-b]pyridazin-6-yl)amino)piperidine-1-carboxylate as yellow oil. (Yield: 0.090 g, 32%). $R_f$=0.3 (4:1Hexane/EtOAc). LCMS(m/z): 569.1 $(M+H)^+$.

Step-2: Synthesis of N8-(3-fluorophenyl)-3-isopropyl-N6-(piperidin-4-yl)imidazo[1,2-b]pyridazine-6,8-diamine hydrochloride

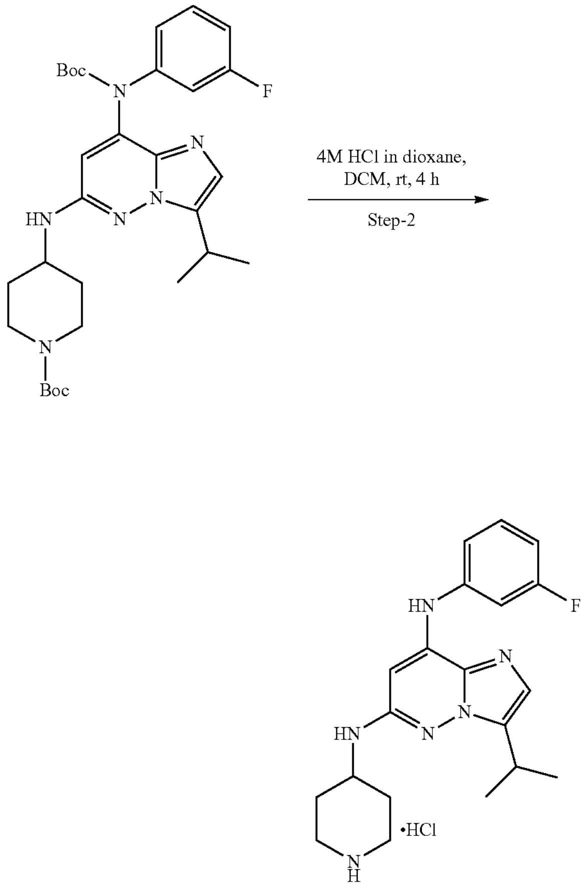

45

To a stirred solution of tert-butyl 4-((8-((tert-butoxycarbonyl)(3-fluorophenyl)amino)-3-isopropylimidazo[1,2-b]pyridazin-6-yl)amino)piperidine-1-carboxylate (3) (0.090 g, 0.158 mmol, 1eq.) in DCM (4 mL) at 0 °C was added 4M HCl in 1,4-dioxane (1 mL) drop-wise. Reaction mixture was allowed to come to room temperature and stirred at room temperature for 4 h. After completion conversion by TLC, the reaction mixture was subjected to rotary evaporator for removal of volatiles. The obtained residue was triturated with n-Pentane (10 mL), diethyl ether (3x10 mL), and lyophilized for 24 h to get the title compound N8-(3-fluorophenyl)-3-isopropyl-N6-(piperidin-4-yl)imidazo[1,2-b]pyridazine-6,8-diamine hydrochloride (45) as an off white solid. (Yield: 0.065 g, quantitative). $R_f$=0.1 (1:1Hexane/EtOAc). LCMS (m/z): 369.1 $(M+H)^+$ $^1H$ NMR (400 MHz, DMSO-$d_6$,): δ=10.16 (s, 1H), 8.91 (s, 2H), 7.89 (s, 1H), 7.52-7.47 (q, J=8 Hz, 1H), 7.35 (m, 1H), 7.24 (d, J=8.4 Hz, 2H), 7.03 (t, J=6.8 Hz, 1H), 6.69 (s, 1H), 3.90 (s, 1H), 3.38-3.27 (m, 3H), 3.03 (s, 2H), 2.14-2.11 (m, 2H), 1.73-1.70 (m, 2H), 1.34 (d, J=6.8 Hz, 6H).

Example 60
Synthetic Scheme for 3-isopropyl-6-(piperidin-3-ylthio)-N-(3-(trifluoromethoxy)phenyl)imidazo[1,2-b]pyridazin-8-amine hydrochloride
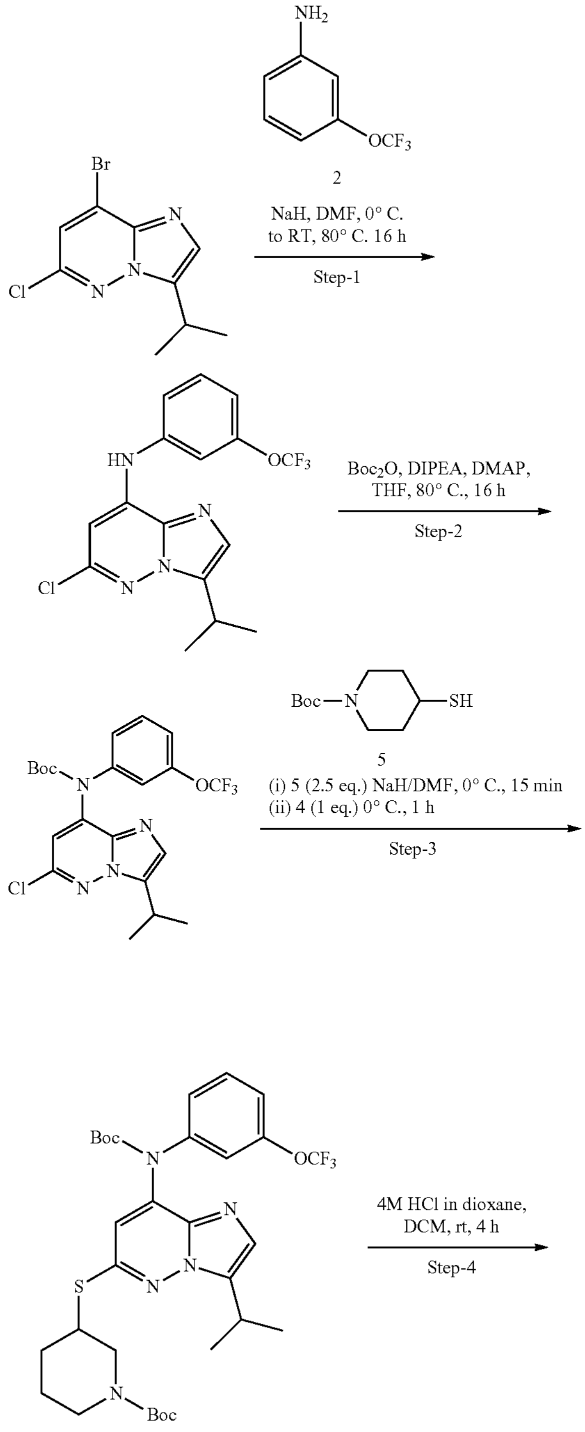
-continued
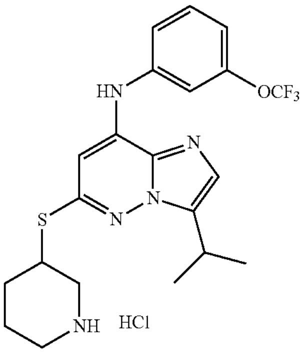
58
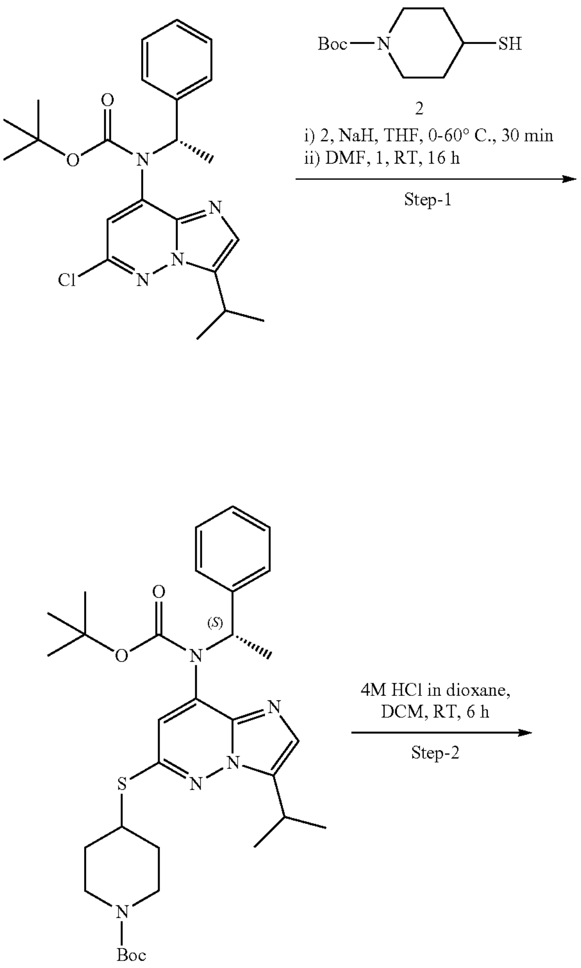

Step-1: Synthesis of 6-chloro-3-isopropyl-N-(3-(trifluoromethoxy)phenyl)imidazo[1,2-b]pyridazin-8-amine

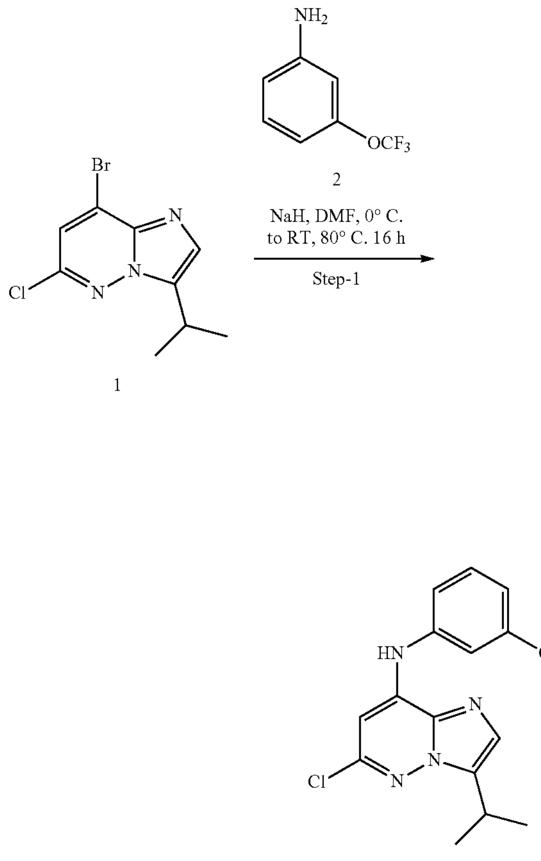

1 2 3

To a stirred solution of 3-(trifluoromethoxy)aniline (2) (0.97 mL), 7.29 mmol, 2 eq.), in DMF (5 mL) was added sodium hydride (60% dispersion in oil) (0.437 g, 10.94 mmol, 3eq.) at 0 °C. Reaction mixture was stirred at room temperature for 30 minutes. Then addition of 8-bromo-6-chloro-3-isopropylimidazo[1,2-b]pyridazine (1) (1 g, 3.64 mmol, 1eq.) in DMF (5 mL) was done at 0 °C. Reaction mixture was allowed to come to room temperature and stirred at 80 °C for 16 h. After complete conversion by TLC, reaction mixture was cooled, quenched with ice cold water (50 mL), extracted with ethyl acetate (2×50 mL). The combined organic layer washed with brine (25 mL), dried over sodium sulphate, filtered and evaporated under reduced pressure to get crude residue. The residue was purified by flash column chromatography using silica gel (100-200) mesh (EtOAc/hexane, gradient 5-10% EtOAc) to afford the title compound as 6-chloro-3-isopropyl-N-(3-(trifluoromethoxy)phenyl)imidazo[1,2-b]pyridazin-8-amine (3) as a yellow solid. Yield: (1.1 g, 81%). $R_f$=0.5 (4:1 Hexane/EtOAc). LCMS (m/z): 371.0 $(M+H)^+$. $^1H$ NMR (400 MHz, DMSO-$d_6$): δ=10.04 (s, 1H), 7.57-7.46 (m, 4H), 7.18-7.16 (m, 1H), 6.53-6.52 (m, 1H), 3.32-3.26 (m, 1H), 1.34 (d, J=6.8 Hz, 6H).

Step-2: Synthesis of tert-butyl (6-chloro-3-isopropylimidazo[1,2-b]pyridazin-8-yl)(3-(trifluoromethoxy)phenyl)carbamate

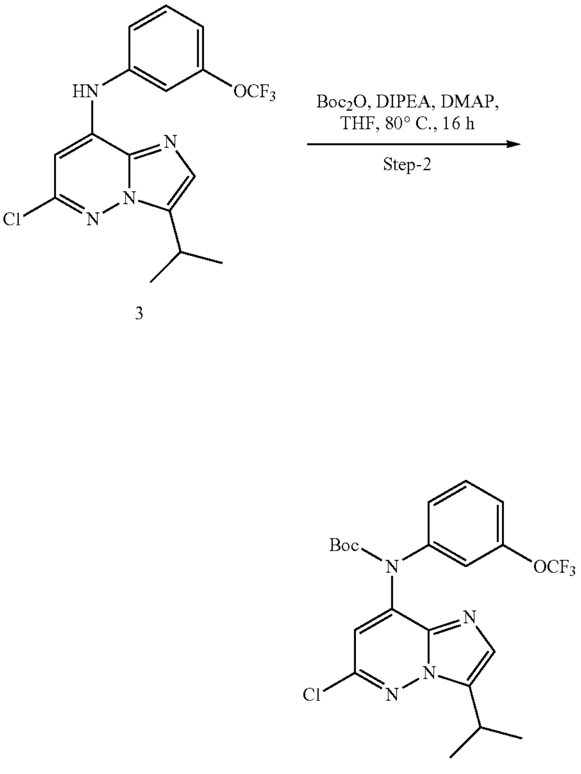

3 4

To a stirred solution of 6-chloro-3-isopropyl-N-(3-(trifluoromethoxy)phenyl)imidazo[1,2-b]pyridazin-8-amine (3) (1.1 g, 2.97 mmol, 1 eq.) in THF (15 mL) was added DIPEA (5.17 mL, 29.72 mmol, 10 eq.), $(Boc)_2O$ (6.82 mL, 29.72 mmol, 10 eq.) and DMAP (0.036 g, 0.297 mmol, 0.1 eq.) at room temperature. Reaction mixture was stirred at 80 °C for 16 h. The reaction mixture was allowed to cool to room temperature, volatile portion was removed under reduced pressure, obtained crude compound was diluted with water (15 mL) and product was extracted with ethyl acetate (3×50 mL). The combined organic layer washed with brine (25 mL), dried over sodium sulphate, filtered and evaporated under reduced pressure to get crude residue as brown oil. The residue was purified by column chromatography using silica gel (100-200) mesh (EtOAc/hexane, gradient 5-10% EtOAc) to afford the title compound as tert-butyl (6-chloro-3-isopropylimidazo[1,2-b]pyridazin-8-yl)(3-(trifluoromethoxy)phenyl)carbamate (4) as a yellow oil. Yield: (1.1 g, 79%). $R_f$=0.8 (4:1 Hexane/EtOAc). $^1H$-NMR (400 MHz, DMSO-$d_6$): δ=7.60 (s, 1H), 7.49-7.48 (m, 1H), 7.46-7.44 (m, 2H), 7.33-7.31 (m, 1H), 7.28-7.26 (m, 1H), 3.34 (m, 1H), 1.37 (s, 9H), 1.33 (d, J=6.8 Hz, 6H).

Step-3: Synthesis of tert-butyl 3-((8-((tert-butoxycarbonyl)(3-(trifluoromethoxy)phenyl)amino)-3-isopropylimidazo[1,2-b]pyridazin-6-yl)thio)piperidine-1-carboxylate

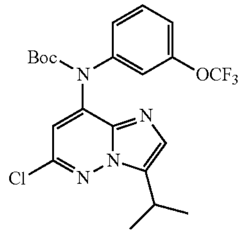

4

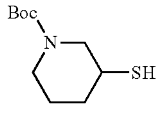

5

(i) 5 (2.5 eq.) NaH/DMF, 0° C., 15 min
(ii) 4 (1 eq.) 0° C., 1 h

Step-3

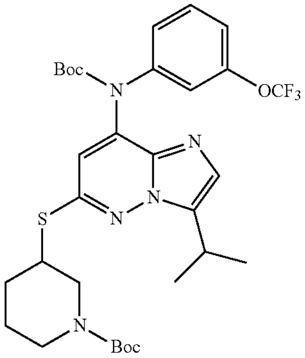

6

To a stirred solution of tert-butyl 3-mercaptopiperidine-1-carboxylate (5) (0.288 g, 1.32 mmol, 2.5 eq.) in DMF (3 mL) at 0 °C was added NaH (60% in mineral oil, (0.053 g, 1.32 mmol, 2.5 eq.) at 0 °C. Reaction mixture was stirred at 0 °C for 10 minutes. Then added tert-butyl (6-chloro-3-isopropylimidazo[1,2-b]pyridazin-8-yl)(3-(trifluoromethoxy)phenyl)carbamate (4) (0.250 g, 0.531 mmol, 1 eq.) in DMF (3 mL) at 0 °C. Reaction mixture was stirred at 0 °C for 1 h. After complete conversion by TLC, reaction mixture was cooled, quenched with ice cold water (25 mL) and extracted with ethyl acetate (3x25 mL). The combined organic layer was washed with brine solution (25 mL), dried over sodium sulphate, filtered and evaporated under reduced pressure to get crude residue as brown oil. Crude residue was purified by silica phase column chromatography (EtOAc/hexane, with gradient 0-10% EtOAc), to afford the title compound as (6) as tert-butyl 3-((8-((tert-butoxycarbonyl)(3-(trifluoromethoxy)phenyl)amino)-3-isopropylimidazo[1,2-b]pyridazin-6-yl)thio)piperidine-1-carboxylate as a yellow oil. (Yield=0.230 g, 66%), $R_f$=0.4 (4:1 Hexane/EtOAc). LCMS (m/z): 652.1 $(M+H)^+$.

Step-4: Synthesis of 3-isopropyl-6-(piperidin-3-ylthio)-N-(3-(trifluoromethoxy)phenyl)imidazo[1,2-b]pyridazin-8-amine hydrochloride

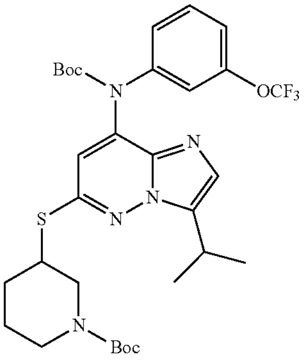

4M HCl in dioxane,
DCM, rt, 4 h

Step-4

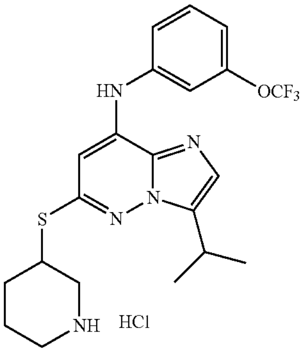

58

To a stirred solution of tert-butyl 3-((8-((tert-butoxycarbonyl)(3-(trifluoromethoxy)phenyl)amino)-3-isopropylimidazo[1,2-b]pyridazin-6-yl)thio)piperidine-1-carboxylate (6) (0.230 g, 0.353 mmol, 1eq) in DCM (5 mL) at 0 °C was added 4M HCl in 1,4-dioxane (3 mL) drop-wise and stirred at room temperature. After completion of reaction by TLC, the reaction mixture was subjected to rotary evaporator for removal of volatiles. The obtained residue was submitted for preparative HPLC (by using TFA buffer) to afford TFA salt of as 3-isopropyl-6-(piperidin-3-ylthio)-N-(3-(trifluoromethoxy)phenyl)imidazo[1,2-b]pyridazin-8-amine (TFA salt). To get compound as a HCl salt, obtained TFA salt was dissolved in ACN:water and treated with 2N aq. HCl at 0 °C and lyophilized to afford the title compound as 3-isopropyl-6-(piperidin-3-ylthio)-N-(3-(trifluoromethoxy)phenyl)imidazo[1,2-b]pyridazin-8-amine hydrochloride (58) as an off white solid (0.070 g, 40% yield). $R_f$=0.1 (9:1 DCM/MeOH). LCMS (m/z): 452.19 $(M+H)^+$. $^1$H-NMR (400 MHz, DMSO-$d_6$): δ=10.55 (s, 1H), 9.53-9.51(br. s, 1H), 9.23-9.20 (br. s, 1H), 7.94 (s, 1H), 7.60 (t, J=8 Hz, 1H), 7.50 (d, J=8.4 Hz, 1H), 7.43 (s, 1H), 7.22 (d, J=7.6 Hz, 1H), 6.83 (s, 1H), 4.15-4.10 (m, 1H), 3.62-3.52 (m, 2H), 3.26-3.23 (m, 1H), 3.12-3.04 (q, J=10.8 Hz, 1H), 2.91 (m, 1H), 2.16-2.14 (m, 1H), 1.89 (s, 2H), 1.73-1.72 (m, 1H), 1.38 (d, J=6.8 Hz, 6H).

Example 61

Synthetic Scheme for 3-isopropyl-6-(piperidin-3-ylthio)-N-(2-(trifluoromethyl)phenyl)imidazo[1,2-b]pyridazin-8-amine hydrochloride

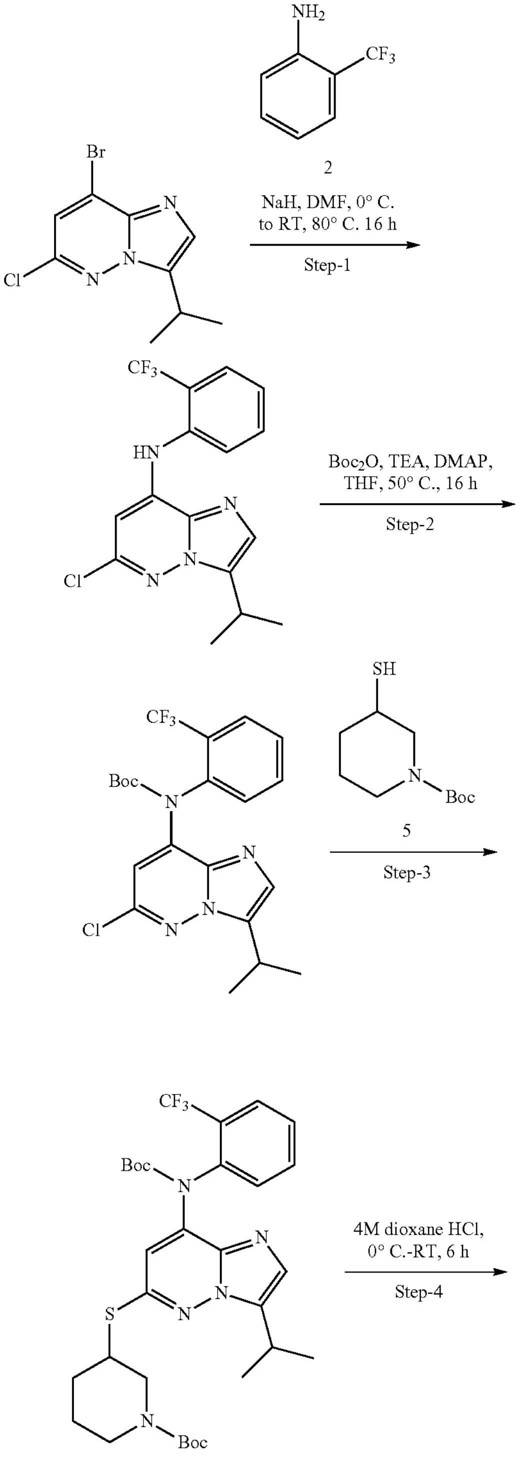

-continued

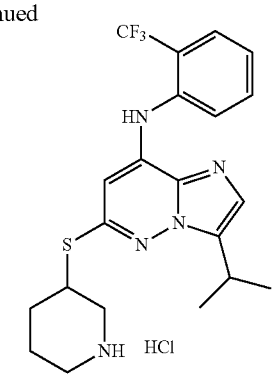

61

Step-1: Synthesis of 6-chloro-3-isopropyl-N-(2-(trifluoromethyl)phenyl)imidazo[1,2-b]pyridazin-8-amine

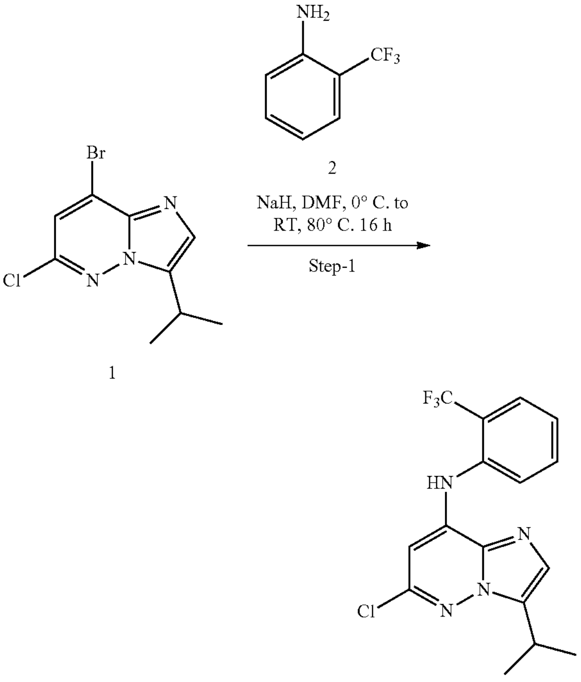

To a stirred solution of 2-(trifluoromethyl)aniline (2) (0.91 mL, 7.29 mmol, 2 eq.) in DMF (5 mL) was added sodium hydride (60% dispersion in oil) (0.43 g, 10.94 mmol, 3 eq.) at 0 °C. Reaction mixture was stirred at 0 °C for 30 minutes. Then addition of 8-bromo-6-chloro-3-isopropylimidazo[1,2-b]pyridazine (1) (1 g, 3.64 mmol, 1eq.) in DMF (5 mL) was done at 0 °C. Reaction mixture stirred at 80 °C for 16 h. After complete conversion by TLC, reaction mixture was cooled, quenched with ice cold water (50 mL), extracted with ethyl acetate (3×50 mL). The combined organic layer washed with brine (50 mL), dried over sodium sulphate, evaporated under reduced pressure to get crude residue. The residue was purified by column chromatography using silica gel (100-200) mesh (EtOAc/hexane, gradient 10% EtOAc) to afford the title compound as 6-chloro-3-isopropyl-N-(2-(trifluoromethyl)phenyl)imidazo[1,2-b]pyridazin-8-amine (3) as a brown oil. (Yield: 1 g, 77.5%). $R_f$=0.35 (20% EtOAc in Hexane). LCMS (m/z): 355.0 $(M+H)^+$. $^1H$ NMR (400 MHz, DMSO-$d_6$): δ=9.57 (s, 1H), 7.89-7.88 (m, 1H), 7.83-7.80 (m, 1H), 7.64-7.61 (m, 2H), 7.45 (s, 1H), 5.64 (s, 1H), 3.33-3.26 (m, 1H), 1.33 (d, J=6.8 Hz, 6H).

Step-2: Synthesis of tert-butyl (6-chloro-3-isopropylimidazo[1,2-b]pyridazin-8-yl)(2-(trifluoromethyl)phenyl)carbamate

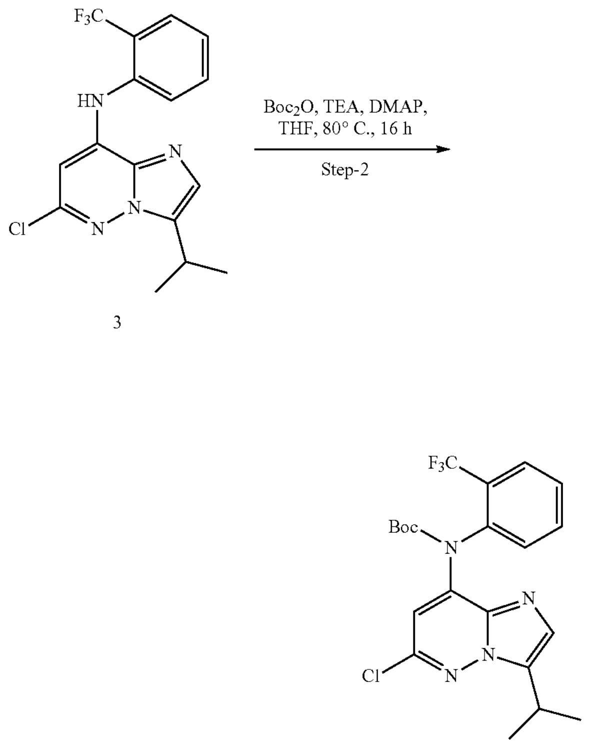

3

4

To a stirred solution of 6-chloro-3-isopropyl-N-(2-(trifluoromethyl)phenyl)imidazo[1,2-b]pyridazin-8-amine (3) (1 g, 2.82 mmol, 1 eq.) in THF (15 mL) was added DIPEA (4.9 mL, 28.2 mmol, 10 eq.), $(Boc)_2O$ (6.48 mL, 28.2 mmol, 10 eq.) and DMAP (0.034 g, 0.28 mmol, 0.1 eq.) at room temperature. Reaction mixture was stirred at 80 °C for 16 h. The reaction mixture was allowed to cool to room temperature. THF was evaporated, added water (50 mL), extracted with ethyl acetate (3x50 mL). The combined organic layer was washed with brine (2x25 mL), dried over sodium sulphate, and evaporated under reduced pressure to get crude residue as brown oil. The residue was purified by column chromatography using silica gel (100-200) mesh (EtOAc/hexane, gradient 12-15% EtOAc) to afford the title compound as tert-butyl (6-chloro-3-isopropylimidazo[1,2-b]pyridazin-8-yl)(2-(trifluoromethyl)phenyl)carbamate (4) as pale yellow viscous liquid. Yield: (1 g, 78%). $R_f$=0.44 (20% EtOAc in Hexane). LCMS (m/z): 455.0 $(M+H)^+$. $^1H$ NMR (400 MHz, DMSO-$d_6$): δ 7.82-7.80 (m, 1H), 7.66-7.60 (m, 2H), 7.53-7.50 (m, 2H), 7.27 (s, 1H), 3.33 (s, 1H), 1.35 (s, 9H), 1.30 (d, 6H).

Step-3: Synthesis of tert-butyl 3-((8-((tert-butoxycarbonyl)(2-(trifluoromethyl)phenyl)amino)-3-isopropylimidazo[1,2-b]pyridazin-6-yl)thio)piperidine-1-carboxylate

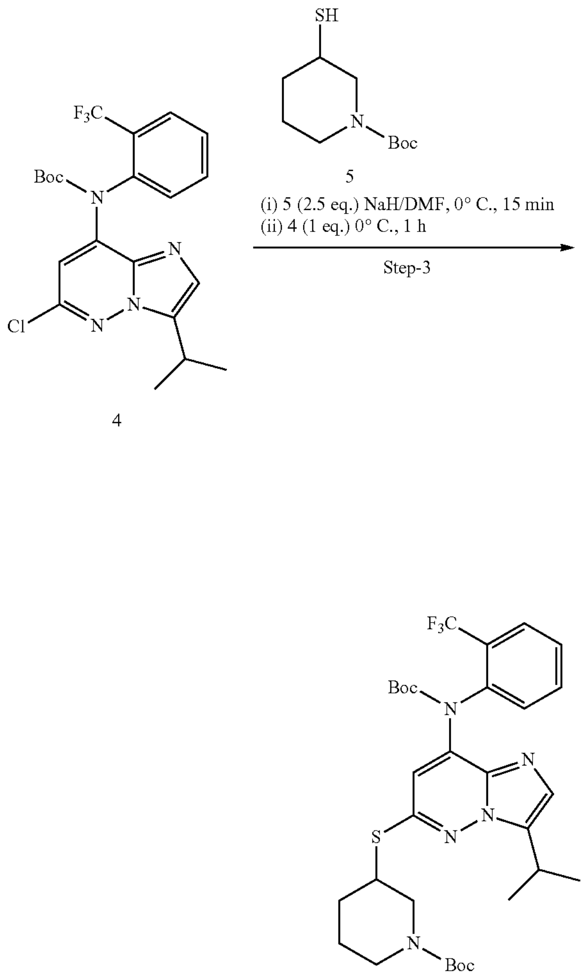

4

5

6

To a stirred solution of tert-butyl 3-mercaptopiperidine-1-carboxylate (5) (0.298 g, 1.37 mmol, 2.5 eq.) in DMF (3 mL) at 0 °C was added NaH (80% in mineral oil, (0.055 g, 1.37 mmol, 2.5 eq.) at 0 °C. Reaction mixture was stirred at 0 °C for 15 minutes. Then addition of tert-butyl (6-chloro-3-isopropylimidazo[1,2-b]pyridazin-8-yl)(2-(trifluoromethyl)phenyl)carbamate (4) (0.250 g, 0.550 mmol, 1 eq.) in DMF (3 mL) was done at 0 °C. Reaction mixture was stirred at 0 °C for 1 h. After complete conversion by TLC, reaction mixture was cooled, quenched with ice cold water (50 mL) and extracted with ethyl acetate (3x25 mL). The combined organic layer was washed with brine solution (25 mL), dried over sodium sulphate, evaporated under reduced pressure to get crude residue as brown oil. Crude residue was purified by silica phase column chromatography (EtOAc/hexane, with gradient 12% EtOAc), to afford the title compound as tert-butyl 3-((8-((tert-butoxycarbonyl)(2-(trifluoromethyl)phenyl)amino)-3-isopropylimidazo[1,2-b]pyridazin-6-yl)thio)piperidine-1-carboxylate (6) as viscous colourless oil. (Yield=0.230 g, 65.8%), $R_f$=0.19 (20% EtOAc in Hexane). LCMS (m/z): 636.1 $(M+H)^+$ Step-4: Synthesis of 3-isopropyl-6-(piperidin-3-ylthio)-N-(2-(trifluoromethyl)phenyl) imidazo[1,2-b] pyridazin-8-amine hydrochloride

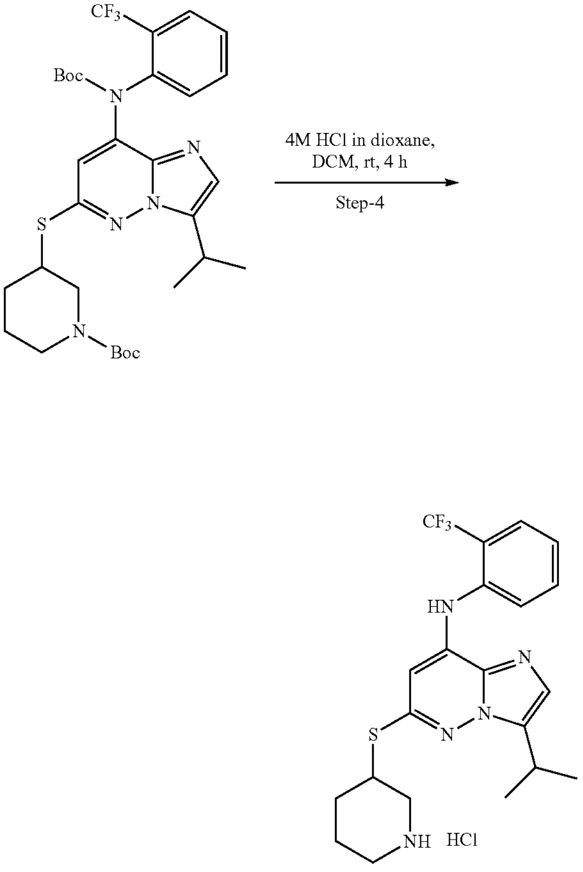

61

To a stirred solution of tert-butyl 3-((8-((tert-butoxycarbonyl)(2-(trifluoromethyl)phenyl)amino)-3-isopropylimidazo[1,2-b]pyridazin-6-yl)thio)piperidine-1-carboxylate (6a) (0.200 g, 0.37 mmol, 1eq.) in DCM (5 mL) at 0 °C was added 4M HCl in 1,4-dioxane (3 mL) drop-wise and stirred at room temperature for 4 h. After completion of reaction by TLC, the reaction mixture was subjected to rotary evaporator for removal of volatiles. The obtained residue was submitted for preparative HPLC by using TFA buffer to get TFA salt of 3-isopropyl-6-(piperidin-3-ylthio)-N-(2-(trifluoromethyl)phenyl) imidazo[1,2-b]pyridazin-8-amine. To get compound as a HCl salt, obtained TFA salt was dissolved in ACN: water and treated with 2N aq. HCl at 0 °C and lyophilized to afford the title compound as 3-isopropyl-6-(piperidin-3-ylthio)-N-(2-(trifluoromethyl)phenyl) imidazo [1,2-b]pyridazin-8-amine hydrochloride as a white solid (61) (0.202 g, 89.05% yield), $R_f$=0.1 (10% MeOH in DCM). LCMS (m/z): 436.2 $(M+H)^+$. $^1H$ NMR (400 MHz, DMSO-$d_6$): δ 9.63 (s, 1H), 9.24-9.05 (m, 2H), 7.92-7.90 (m, 1H), 7.85-7.81 (m, 1H), 7.75 (s, 1H), 7.65-7.61 (m, 2H), 5.84 (s, 1H), 4.07-4.01 (m, 1H), 3.60-3.48 (m, 2H), 3.24-3.17 (m, 1H), 3.11-3.03 (m, 1H), 2.89 (m, 1H), 2.33 (m, 1H), 2.13-2.10 (m, 2H), 1.85-1.67 (m, 1H), 1.39-1.35 (m, 6H).

Example 62

Synthetic Scheme for 3-isopropyl-6-(piperidin-3-ylthio)-N-(2-(trifluoromethoxy)phenyl)imidazo[1,2-b]pyridazin-8-amine hydrochloride

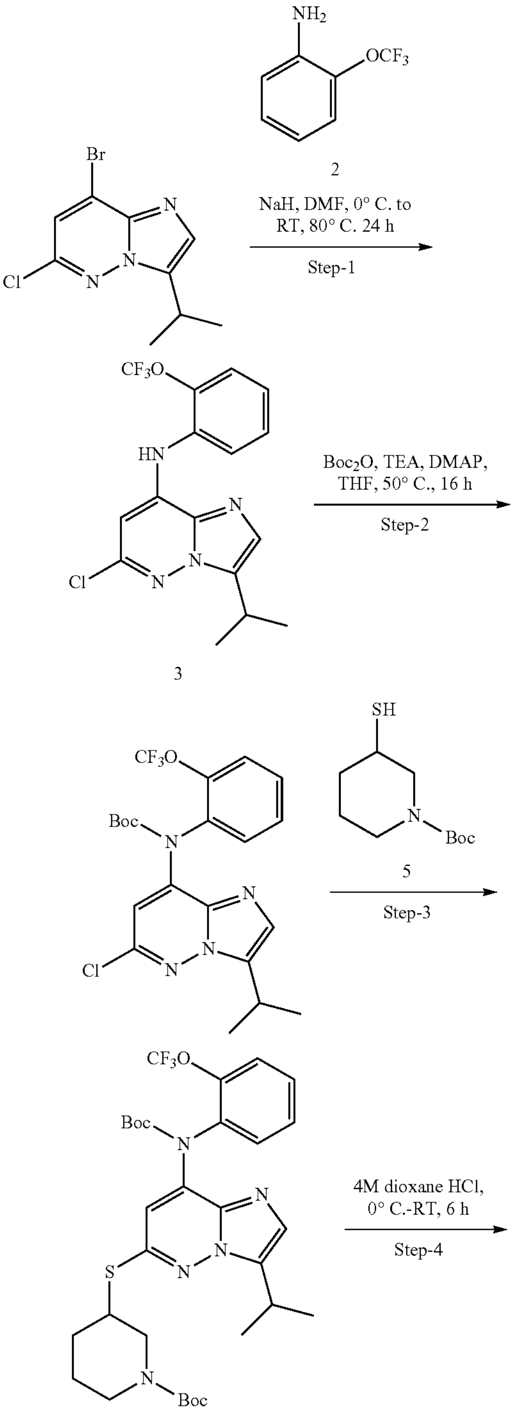

-continued

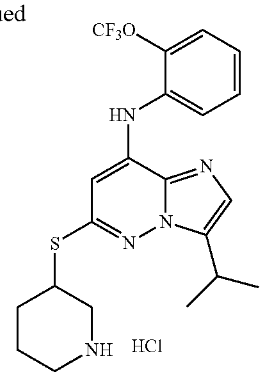

60

Step-1: Synthesis of 6-chloro-3-isopropyl-N-(2-(trifluoromethoxy)phenyl)imidazo[1,2-b]pyridazin-8-amine

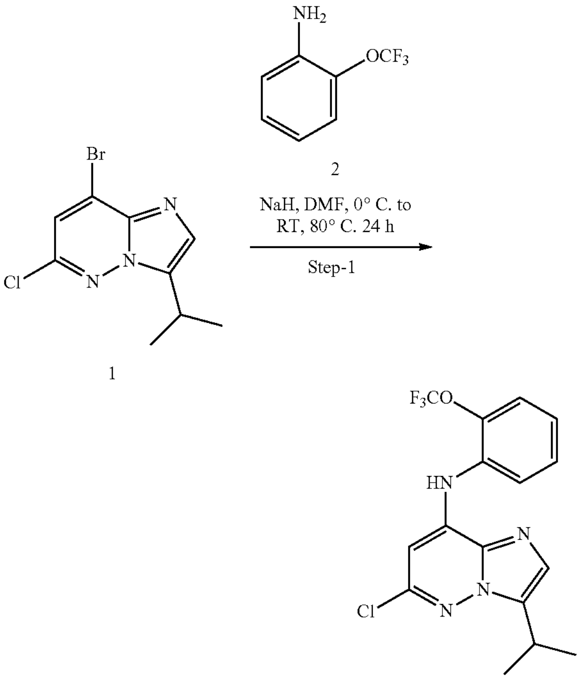

To a stirred solution of 2-(trifluoromethoxy)aniline (2) (1.49 mL), 10.94 mmol, 3 eq.) in DMF (5 mL) was added sodium hydride (80% dispersion in oil) (0.43 g, 10.94 mmol, 3 eq.) at 0 °C. Reaction mixture was stirred at 0 °C for 30 minutes. Then addition of 8-bromo-6-chloro-3-isopropylimidazo[1,2-b]pyridazine (1) (1 g, 3.64 mmol, 1eq.) in DMF (5 mL) was done at 0 °C. Reaction mixture stirred at 80 °C for 24 h. After complete conversion by TLC, reaction mixture was cooled, quenched with ice cold water (50 mL), extracted with ethyl acetate (3×50 mL). The combined organic layer washed with brine (50 mL), dried over sodium sulphate, evaporated under reduced pressure to get crude residue. The residue was purified by column chromatography using silica gel (100-200) mesh (EtOAc/hexane, gradient 10-12% EtOAc) to afford the title compound as 6-chloro-3-isopropyl-N-(2-(trifluoromethoxy)phenyl)imidazo[1,2-b]pyridazin-8-amine (3) as a brown oil. (Yield: 1 g, 74.07%). $R_f$=0.53 (20% EtOAc in Hexane). LCMS (m/z): 371.0 (M+H). H NMR (400 MHz, DMSO-$d_6$): δ=9.74 (s, 1H), 7.62-7.47 (m, 5H), 5.88 (s, 1H), 3.33 (m, 1H), 1.35 (d, J=6.8 Hz, 6H).

Step-2: Synthesis of tert-butyl (6-chloro-3-isopropylimidazo[1,2-b]pyridazin-8-yl)(2-(trifluoromethoxy)phenyl)carbamate

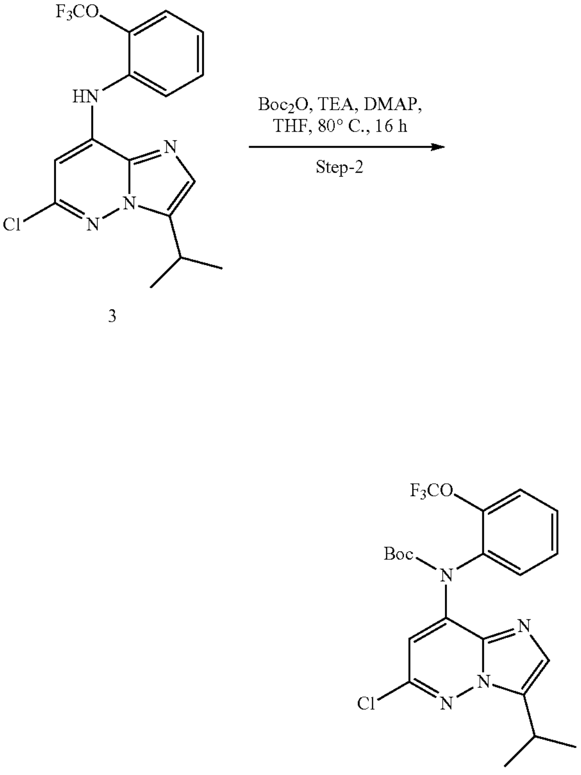

To a stirred solution of 6-chloro-3-isopropyl-N-(2-(trifluoromethoxy)phenyl)imidazo[1,2-b]pyridazin-8-amine (3) (1 g, 2.69 mmol, 1 eq.) in THF (15 mL) was added DIPEA (4.6 mL, 26.9 mmol, 10 eq.), $(Boc)_2O$ (6.1 mL, 26.9 mmol, 10 eq.) and DMAP (0.032 g, 0.26 mmol, 0.1 eq.) at room temperature. Reaction mixture was stirred at 80 °C for 16 h. The reaction mixture was allowed to cool to room temperature. THF was evaporated, added water (50 mL), extracted with ethyl acetate (3×50 mL). The combined organic layer was washed with brine (2×25 mL), dried over sodium sulphate, and evaporated under reduced pressure to get crude residue as brown oil. The residue was purified by column chromatography using silica gel (100-200) mesh (EtOAc/hexane, gradient 18% EtOAc) to afford the title compound as tert-butyl (6-chloro-3-isopropylimidazo[1,2-b]pyridazin-8-yl)(2-(trifluoromethoxy)phenyl)carbamate (4) as pale yellow viscous liquid. Yield: (1 g, 83%). $R_f$=0.38 (20% EtOAc in Hexane). LCMS (m/z): 471.0 $(M+H)^+$. $^1H$ NMR (400 MHz, DMSO-$d_6$): δ 7.53 (s, 1H), 7.49-7.42 (m, 3H), 7.36-7.32 (m, 1H), 7.14 (s, 1H), 3.32-3.29 (s, 1H), 1.38 (s, 9H), 1.30 (d, J=6.8 Hz, 6H).

Step-3: Synthesis of tert-butyl 3-((8-((tert-butoxycarbonyl)(2-(trifluoromethoxy)phenyl)amino)-3-isopropylimidazo[1,2-b]pyridazin-6-yl)thio)piperidine-1-carboxylate

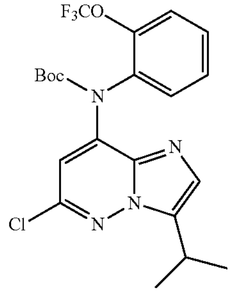

4

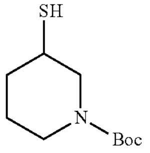

5

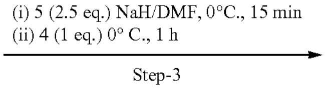

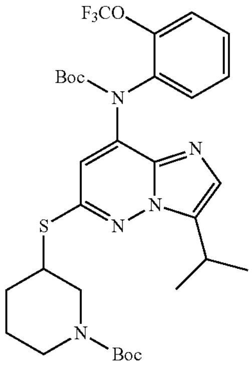

6

To a stirred solution of tert-butyl 3-mercaptopiperidine-1-carboxylate (5) (0.287 g, 1.33 mmol, 2.5 eq.) in DMF (3 mL) at 0 °C was added NaH (80% in mineral oil, (0.053 g, 1.33 mmol, 2.5 eq.) at 0 °C. Reaction mixture was stirred at 0 °C for 10 minutes. Then addition of tert-butyl (6-chloro-3-isopropylimidazo[1,2-b]pyridazin-8-yl)(2-(trifluoromethoxy)phenyl)carbamate (4) (0.250 g, 0.53 mmol, 1 eq.) in DMF (3 mL) was done at 0 °C. Reaction mixture was stirred at 0 °C for 1 h. After complete conversion by TLC, reaction mixture was cooled, quenched with ice cold water (50 mL) and extracted with ethyl acetate (3×25 mL). The combined organic layer was washed with brine solution (25 mL), dried over sodium sulphate, evaporated under reduced pressure to get crude residue as brown oil. Crude residue was purified by silica phase column chromatography (EtOAc/hexane, with gradient 16% EtOAc), to afford the title compound as tert-butyl 3-((8-((tert-butoxycarbonyl)(2-(trifluoromethoxy)phenyl)amino)-3-isopropylimidazo[1,2-b]pyridazin-6-yl)thio)piperidine-1-carboxylate (6) as viscous colourless oil. (Yield=0.240 g, 69.5%) $R_f$=0.15 (20% EtOAc in Hexane). LCMS (m/z): 652.1 (M+H).

Synthesis of 3-isopropyl-6-(piperidin-3-ylthio)-N-(2-(trifluoromethoxy)phenyl)imidazo[1,2-b]pyridazin-8-amine hydrochloride

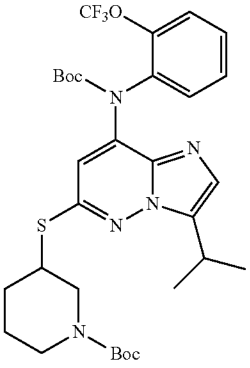

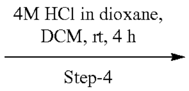

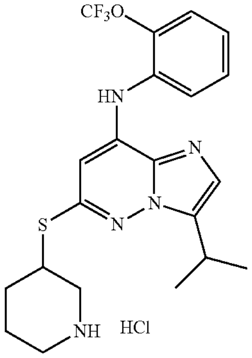

60

To a stirred solution of tert-butyl 3-((8-((tert-butoxycarbonyl)(2-(trifluoromethoxy)phenyl)amino)-3-isopropylimidazo[1,2-b]pyridazin-6-yl)thio)piperidine-1-carboxylate (6) (0.180 g, 0.32 mmol, 1eq.) in DCM (5 mL) at 0 °C was added 4M HCl in 1,4-dioxane (3 mL) drop-wise and stirred at room temperature for 4 h. After completion of reaction by TLC, the reaction mixture was subjected to rotary evaporator for removal of volatiles. The obtained residue was submitted for preparative HPLC by using TFA buffer to get TFA salt of 3-isopropyl-6-(piperidin-3-ylthio)-N-(2-(trifluoromethoxy)phenyl)imidazo[1,2-b]pyridazin-8-amine. To get compound as a HCl salt, obtained TFA salt was dissolved in ACN: water and treated with 2N HCl at 0 °C and lyophilized to afford the title compound as 3-isopropyl-6-(piperidin-3-ylthio)-N-(2-(trifluoromethoxy)phenyl)imidazo[1,2-b]pyridazin-8-amine hydrochloride as a white solid (60) (0.145 g, 90.5% yield), $R_f$=0.1 (10% MeOH in DCM). LCMS (m/z): 452.1 $(M+H)^+$. $^1H$ NMR (400 MHz, DMSO-$d_6$): δ 10.05 (s, 1H), 9.94-9.42 (m, 1H), 9.19-9.16 (m, 1H), 7.90 (s, 1H), 7.61-7.48 (m, 4H), 6.20 (s, 1H), 4.12-4.06 (m, 1H), 3.60-3.50 (m, 2H), 3.24-3.21 (m, 1H), 3.10-3.02 (m, 1H), 2.89 (m, 1H), 2.13-2.11 (m, 1H), 1.85 (m, 2H), 1.73-1.65 (m, 1H), 1.38-1.35 (m, 6H).

Example 63

Synthetic Scheme for 3-isopropyl-6-(piperidin-3-ylthio)-N-(3-(trifluoromethyl)phenyl)imidazo[1,2-b]pyridazin-8-amine hydrochloride

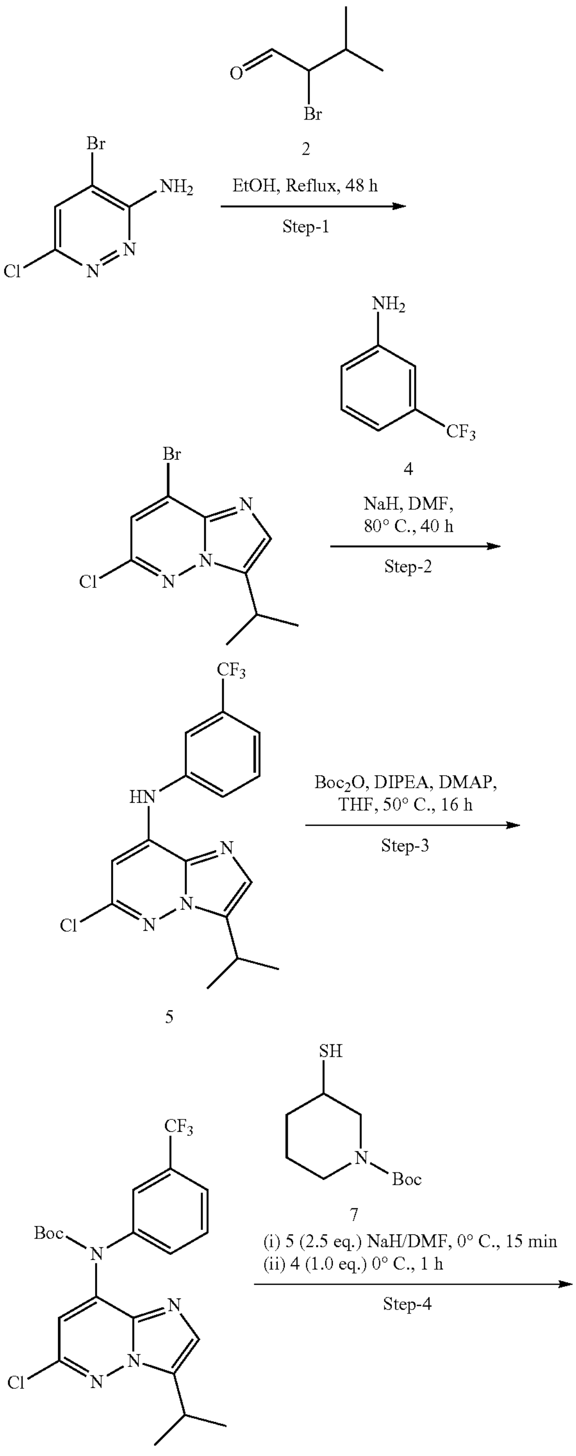

-continued

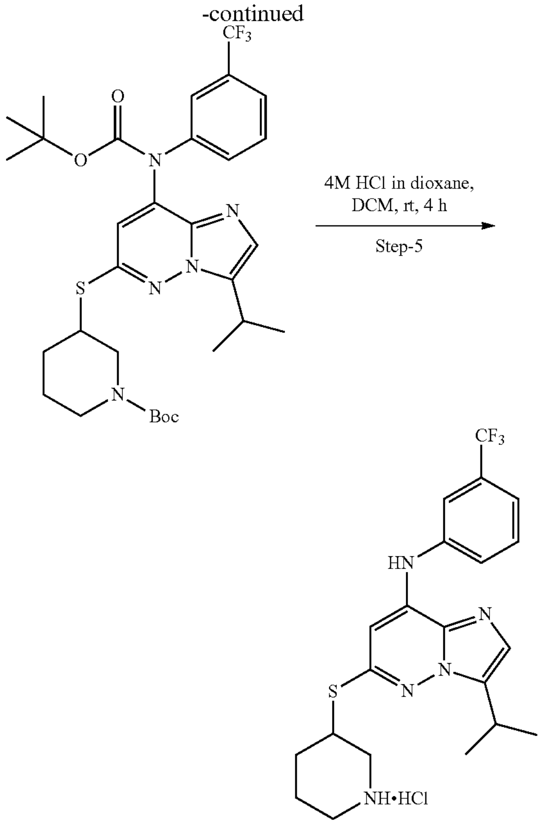

57

Step-1: Synthesis of 8-bromo-6-chloro-3-isopropylimidazo[1,2-b]pyridazine

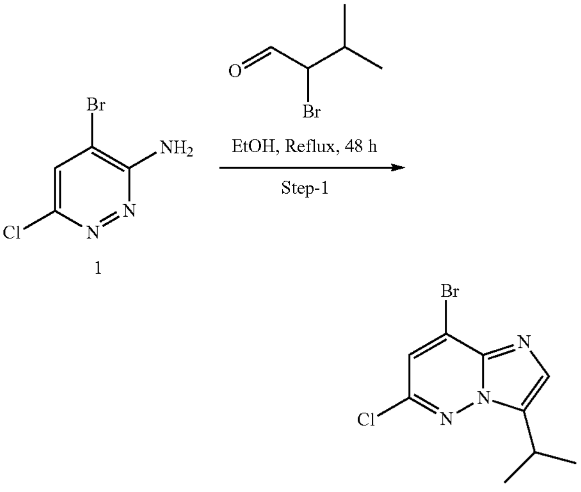

2

To a stirred solution of 4-bromo-6-chloropyridazin-3-amine (10.0 g, 48.3 mmol, 1.0 eq.) in ethanol (100 mL) was added 2-bromo-3-methylbutanal (55.75 g, 338.2 mmol, 7.0 eq.) at room temperature. Reaction mixture was heated at 100 °C for 48 h. Progress of the reaction was monitored by TLC. After this time, reaction mixture was cooled to room temperature. Volatile portion was evaporated under reduced pressure to get crude residue. To the crude residue, water (50 mL) was added, extracted with ethyl acetate (3×500 mL). Combined organic layer was washed with brine (100 mL), saturated aqueous sodium bicarbonate solution (100 mL), dried over anhydrous sodium sulphate, filtered and evaporated under reduced pressure. The obtained crude compound was purified by column chromatography using silica gel (100-200) mesh system (with gradient elution of 5-10% EtOAc) to afford the title compound as 8-bromo-6-chloro-3-isopropylimidazo[1,2-b]pyridazine (3) as brown oil. (Yield: 9.4 g, 71.64%). $R_f$=0.5 (4:1 Hexane/EtOAc). $^1$H NMR (400 MHz, $CDCl_3$): δ=7.86 (s, 1H), 7.71 (s, 1H), 3.44 (hept, J=6.8 Hz, 1H), 1.41 (d, J=6.8 Hz, 6H). LCMS (m/z): 274 $(M+H)^+$ Step-2: Synthesis of 6-chloro-3-isopropyl-N-(3-(trifluoromethyl)phenyl)imidazo[1,2-b]pyridazin-8-amine

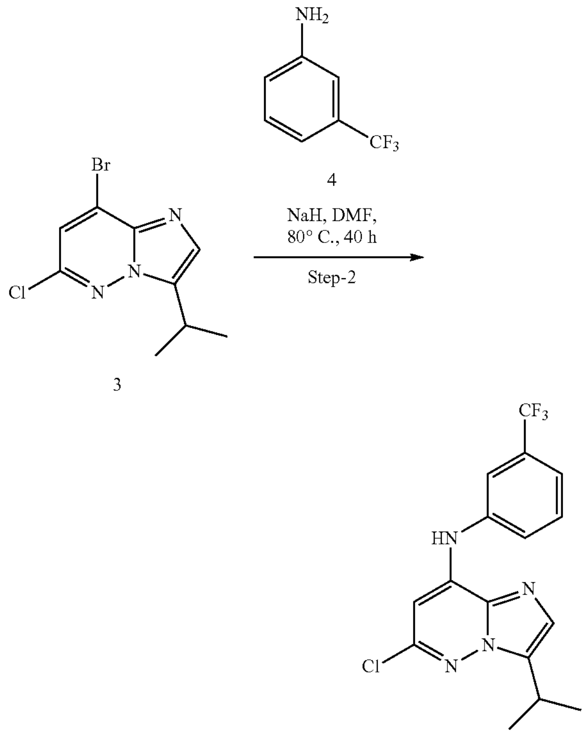

4

3

5

To a stirred solution of 3-trifluoromethyl aniline (1.176 g, 7.29 mmol, 2.0 eq.) in DMF was added NaH (60% dispersion in mineral oil, 0.292 g, 7.29 mmol, 2.0 eq.) at 0 °C. This mixture was stirred at 0 °C for 30 min. Then added compound 3 (1.0 g, 3.64 mmol, 1.0 eq.) in DMF and the resulting mixture was stirred at 80 °C for 40 h. After completion of the conversion by TLC, reaction mixture was cooled to 0 °C, quenched with ice cold water (30 mL), then extracted with ethyl acetate (2×50 mL). The combined organic extracts were washed with brine (50 mL), dried over $Na_2SO_4$, filtered, and evaporated. The residue was purified by combi-flash on silica column (EtOAc/hexane, 1:5) to afford 6-chloro-3-isopropyl-N-(3-(trifluoromethyl)phenyl)imidazo[1,2-b]pyridazin-8-amine as a white solid. Yield: 0.690 g (53.4%). $R_f$=0.5 (4:1 Hexane/EtOAc). $^1$H NMR (400 MHz, DMSO-$d_6$): δ=10.06 (s, 1H), 7.79 (d, J=8.4 Hz, 1H), 7.77 (s, 1H), 7.66 (t, J=8.0 Hz, 1H), 7.54 (d, J=8.0 Hz, 1H), 7.48 (s, 1H), 6.50 (s, 1H), 3.31 (s, 1H), 1.34 (d, J=7.2 Hz, 6H). LCMS (m/z): 355.0 $(M+H)^+$ Step-3: Synthesis of tert-butyl (6-chloro-3-isopropylimidazo[1,2-b]pyridazin-8-yl)(3-(trifluoromethyl)phenyl)carbamate

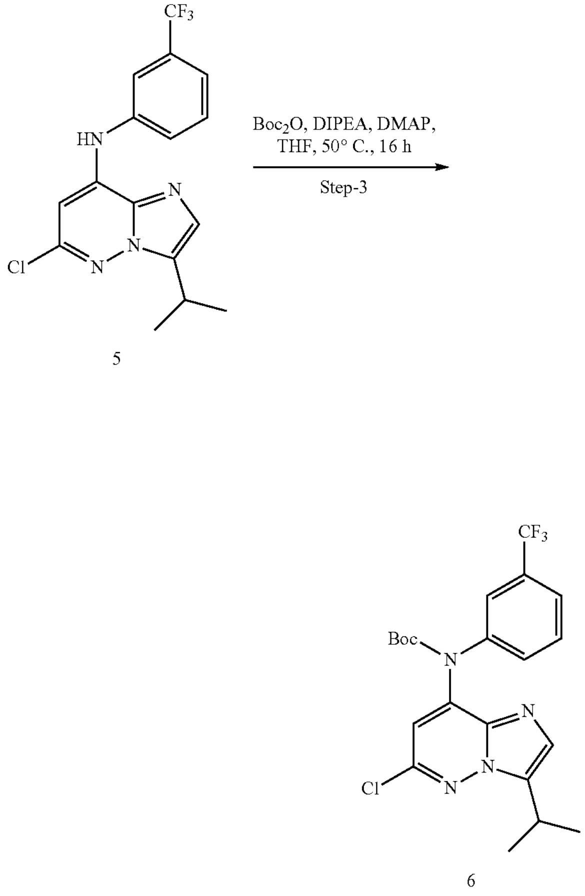 [SMILES: CC(C)c1cnc2c(Nc3cccc(C(F)(F)F)c3)cc(Cl)nn12 ; CC(C)c1cnc2c(N(C(=O)OC(C)(C)C)c3cccc(C(F)(F)F)c3)cc(Cl)nn12]

5

6

To a stirred solution of 6-chloro-3-isopropyl-N-(3-(trifluoromethyl)phenyl)imidazo[1,2-b]pyridazin-8-amine (0.650 g, 1.83 mmol, 1.0 eq), $(Boc)_2O$ (4.2 mL, 18.36 mmol, 10.0 eq.), DIPEA (3.2 mL, 18.36 mmol, 10.0 eq.) and DMAP (22 mg, 0.18 mmol, 0.1 eq.) in THF (18 mL) were stirred at 50 °C for 16 h. The reaction mixture was allowed to cool to room temperature and THF was evaporated under reduced pressure. The obtained residue was diluted with water (30 mL) and extracted with ethyl acetate (2×50 mL). The combined organic layer was washed with brine (30 mL), dried over anhydrous $Na_2SO_4$, filtered and evaporated under reduced pressure. The residue was purified by combi-flash column (EtOAc/hexane, gradient 0-10% EtOAc) to afford the title compound as tert-butyl (6-chloro-3-isopropylimidazo[1,2-b]pyridazin-8-yl)(3-(trifluoromethyl)phenyl)carbamate as a yellow oil. Yield: 0.8 g (96.03%). $R_f$=0.8 (4:1 Hexane/EtOAc). $^1$H NMR (400 MHz, DMSO-$d_6$): δ 7.78 (s, 1H), 7.67-7.54 (m, 4H), 7.53 (s, 1H), 3.33 (m, 1H), 1.37 (s, 9H), 1.33 (d, J=7.2 Hz, 6H). LCMS (m/z): 454.98 $(M+H)^+$ Step-4: Synthesis of tert-butyl 3-((8-((tert-butoxycarbonyl)(3-(trifluoromethyl)phenyl)amino)-3-isopropylimidazo[1,2-b]pyridazin-6-yl)thio)piperidine-1-carboxylate

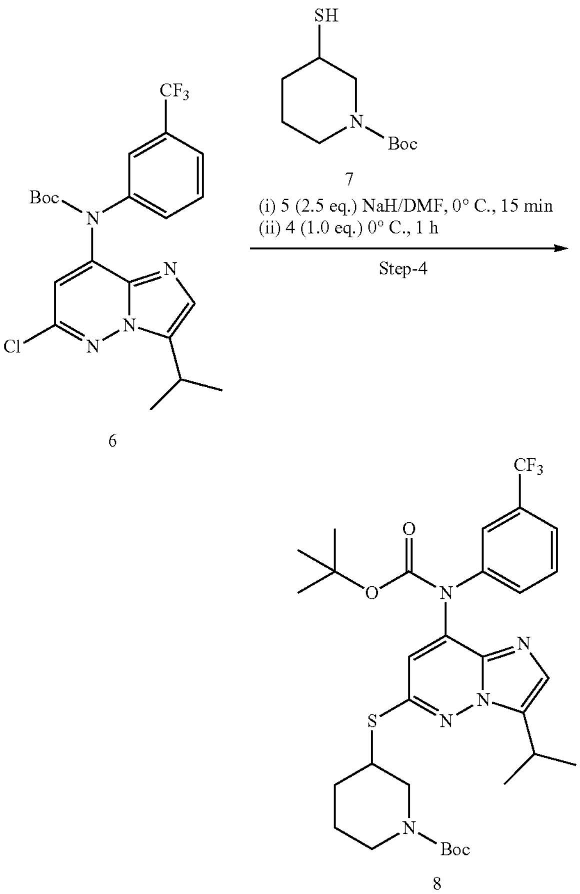

To a stirred solution of tert-butyl 3-mercaptopiperidine-1-carboxylate (7) (0.300 g, 1.37 mmol, 2.5 eq.) in DMF (3 mL) was added NaH (60% in mineral oil, 0.055 g, 1.37 mmol, 2.5 eq.) at 0 °C. This mixture was stirred at 0 °C for 10 min. Then addition of tert-butyl (6-chloro-3-isopropylimidazo[1,2-b]pyridazin-8-yl)(3-(trifluoromethyl)phenyl) carbamate (6) (0.250 g, 0.550 mmol, 1.0 eq.) in DMF (3 mL) was done at 0 °C. The resulting mixture was stirred at 0 °C for 1 h. After completion of conversion by TLC, reaction mixture was quenched with ice cold water (30 mL) and extracted with ethyl acetate (2×50 mL). The combined organic layer was washed with brine solution (30 mL), dried over anhydrous $Na_2SO_4$, filtered and evaporated under reduced pressure. The obtained crude compound was purified by combi-flash column (EtOAc/hexane, gradient 0-10%), to afford the title compound 8 as tert-butyl 3-((8-((tert-butoxycarbonyl)(3-(trifluoromethyl)phenyl)amino)-3-isopropylimidazo[1,2-b]pyridazin-6-yl)thio)piperidine-1-carboxylate as a colorless syrup. (Yield=0.200 g, 57.3%). $R_f$=0.5 (4:1 Hexane/EtOAc). $^1$H NMR (400 MHz, DMSO-$d_6$): δ 7.75 (s, 1H), 7.66-7.52 (m, 3H), 7.46 (s, 1H), 7.30 (s, 1H), 4.20-3.80 (m, 3H), 3.70-3.40 (m, 2H), 3.20-2.92 (m, 1H), 2.18-2.05 (m, 1H), 1.92-1.74 (m, 1H), 1.73-1.46 (m, 2H), 1.45-1.17 (m, 18H), 1.10-0.96 (m, 4H), 0.90-0.80 (m, 2H). LCMS (m/z): 636.2 $(M+H)^+$ Step-5: Synthesis of 3-isopropyl-6-(piperidin-3-ylthio)-N-(3-(trifluoromethyl)phenyl)imidazo[1,2-b]pyridazin-8-amine hydrochloride

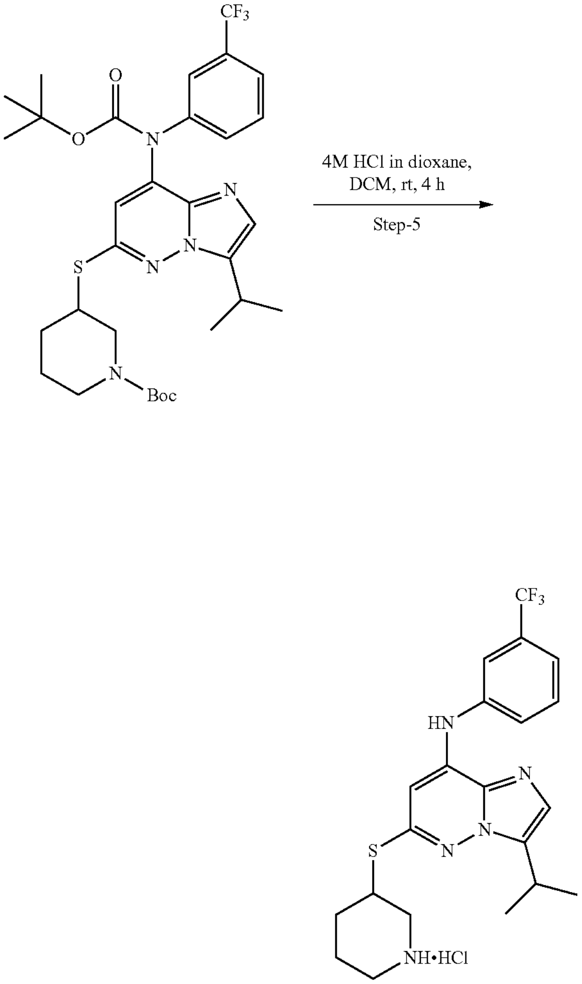

57

To a stirred solution of 8 (0.200 g, 0.31 mmol, 1.0 eq) in $CH_2C_{12}$ (2 mL) at 0 °C was added 4M HCl in 1,4-dioxane (2 mL) drop-wise and stirred at room temperature for 4 h. After completion of the reaction by TLC, the reaction mixture was evaporated under reduced pressure for removal of volatiles. The obtained residue was purified by preparative HPLC by using TFA buffer, to get TFA salt of 57. This compound was treated with aq. 2M HCl (2 mL) and lyophilized for 24 h to get the title compound as 3-isopropyl-6-(piperidin-3-ylthio)-N-(3-(trifluoromethyl)phenyl)imidazo[1,2-b]pyridazin-8-amine hydrochloride as a white solid (57). Yield: 92 mg (62.1%); $R_f$=0.31 (4:1 $CH_2Cl_2$/MeOH). $^1$H NMR (400 MHz, DMSO-$d_6$,): δ=10.36 (s, 1H), 9.32 (d, J=8.0 Hz, 1H), 9.08 (d, J=8.8 Hz, 1H), 7.84-7.60 (m, 4H), 7.59-7.50 (d, J=7.6 Hz, 1H), 6.71 (s, 1H), 4.15-4.01 (m, 1H), 3.60 (d, J=11.2 Hz, 1H), 3.51 (quintet, J=6.8 Hz, 1H), 3.24 (d, J=11.6 Hz, 1H), 3.09 (q, J=10.4 Hz, 1H), 2.97-2.82 (m, 1H), 2.18-2.11 (m, 1H), 1.93-1.82 (m, 2H), 1.77-1.62 (m, 1H), 1.37 (d, J=7.2 Hz, 3H), 1.36 (d, J=6.8 Hz, 3H). LCMS (m/z): 436.0 $(M+H)^+$ Example 64
Synthetic Scheme for N-(2, 6-difluorobenzyl)-3-isopropyl-6-(piperidin-4-ylthio) imidazo[1,2-b] pyridazin-8-amine hydrochloride
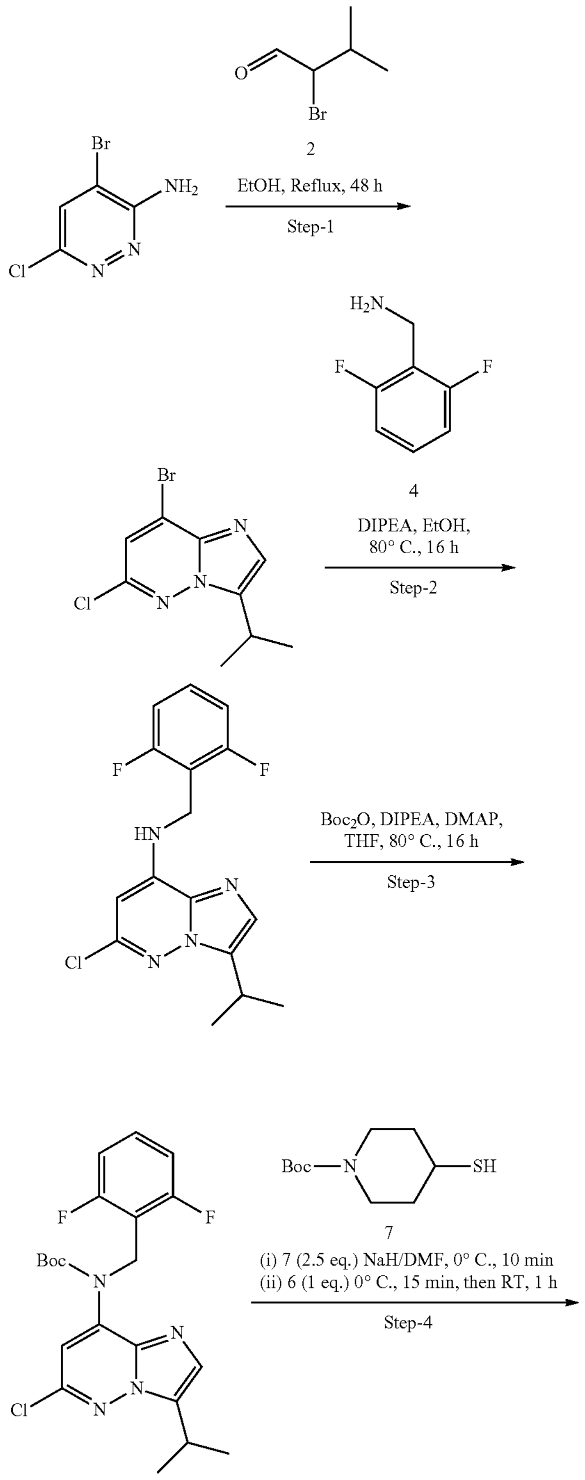
-continued
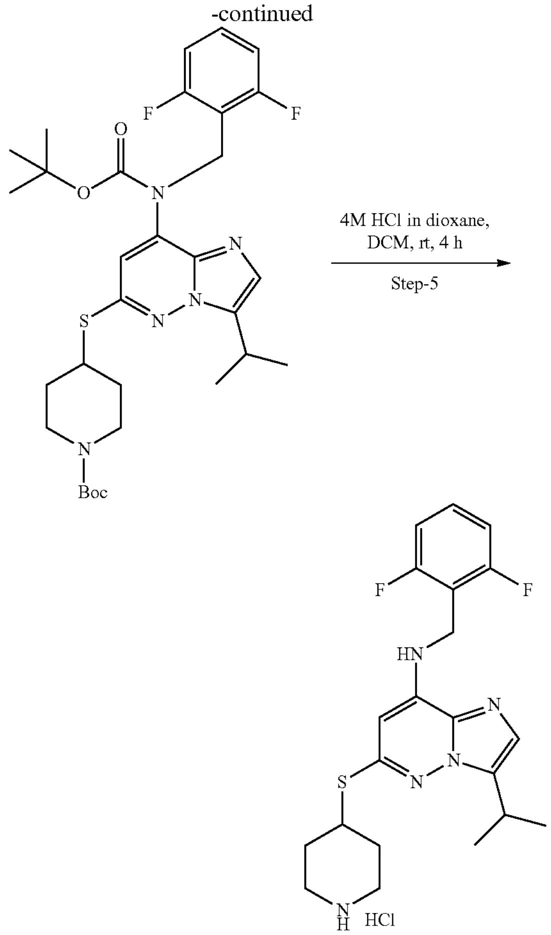
52
Step-1: Synthesis of 8-bromo-6-chloro-3-isopropylimidazo[1,2-b]pyridazine
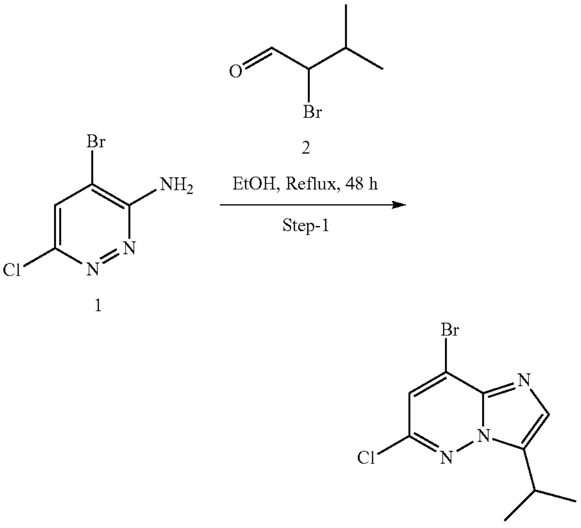
3

To a stirred solution of 4-bromo-6-chloropyridazin-3-amine (1) (10 g, 47.98 mmol, 1 eq.) in ethanol (100 mL) was added 2-bromo-3-methylbutanal (2) (55.75 g, 33.58 mmol, 7 eq.) at room temperature. Reaction mixture was heated to reflux at 100 °C 48 h. After complete conversion by TLC, the reaction mixture was cooled to room temperature. Ethanol was evaporated under reduced pressure to get crude residue, water (500 mL) was added, extracted with ethyl acetate (3×500 mL), washed with brine (100 mL), saturated sodium bicarbonate (100 mL), dried over sodium sulphate and evaporated under reduced pressure to get crude. Crude residue was purified by column chromatography using silica gel (100-200) mesh system (with gradient elution of 5-10% EtOAc) to afford the title compound as 8-bromo-6-chloro-3-isopropylimidazo[1,2-b]pyridazine (3) as brown solid. (Yield: 9.4 g, 71.64%). $R_f$=0.5 (4:1 Hexane/EtOAc). LCMS (m/z): 273.9 $(M+H)^+$ $^1H$ NMR (400 MHz, DMSO-$d_6$): δ 7.86 (s, 1H), 7.71 (s, 1H), 3.37-3.27 (m, 1H), 1.33 (d, J=6.8 Hz, 6H).

Step-2: Synthesis of 6-chloro-N-(2,6-difluorobenzyl)-3-isopropylimidazo[1,2-b]pyridazin-8-amine

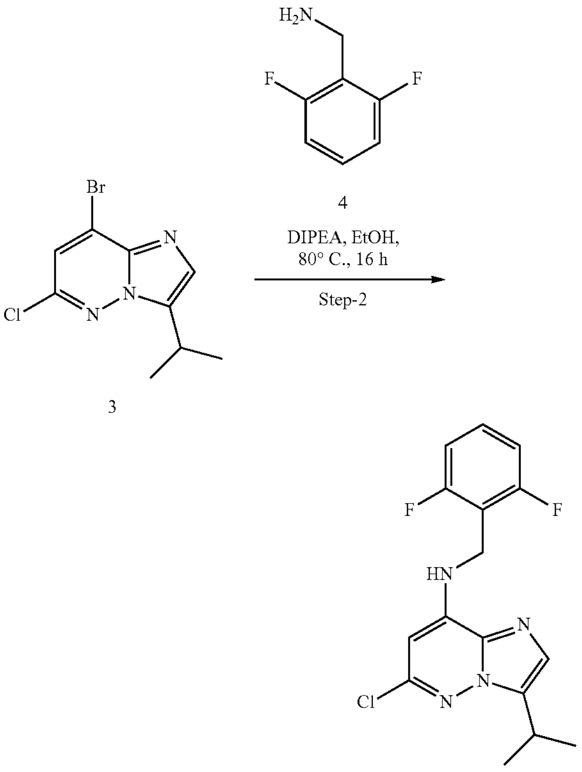

4

3

5

To a stirred solution of 8-bromo-6-chloro-3-isopropylimidazo[1,2-b]pyridazine (3) (1 g, 3.64, mmol, 1 eq.), in ethanol (10 mL) was added (2,6-difluorophenyl)methanamine (4) (0.654 mL, 5.47 mmol, 1.5 eq.), and DIPEA (1.27 mL, 7.29 mmol, 2 eq.)) at room temperature. The reaction mixture was heated to reflux at 80 °C for 16 h. After conversion by TLC, reaction mixture was cooled, concentrated under reduced pressure to get the crude residue. To the crude residue water (50 mL) was added, extracted with ethyl acetate (3×50 mL), washed with brine (25 mL), dried over sodium sulphate, filtered and evaporated to get crude residue. The residue was purified by column chromatography using silica column (100-200) mesh (with gradient elution of 0-10% Hexane/EtOAc) to afford the title compound 6-chloro-N-(2,6-difluorobenzyl)-3-isopropylimidazo[1,2-b]pyridazin-8-amine (5) as an off white solid. (Yield: 1.10 g, 90%). $R_f$=0.3 (4:1 Hexane/EtOAc). LCMS (m/z): 337.0 $(M+H)^+$. $^1H$ NMR (400 MHz, DMSO-$d_6$): δ=8.25 (m, 1H), 7.44-7.39 (m, 1H), 7.31 (s, 1H), 7.15-7.05 (m, 2H), 6.21 (s, 1H), 4.60 (s, 2H), 3.34 (m, 1H), 1.29 (d, J=6.8 Hz, 6H).

Step-3: Synthesis of tert-butyl (6-chloro-3-isopropylimidazo[1,2-b]pyridazin-8-yl)(2,6-difluorobenzyl) carbamate

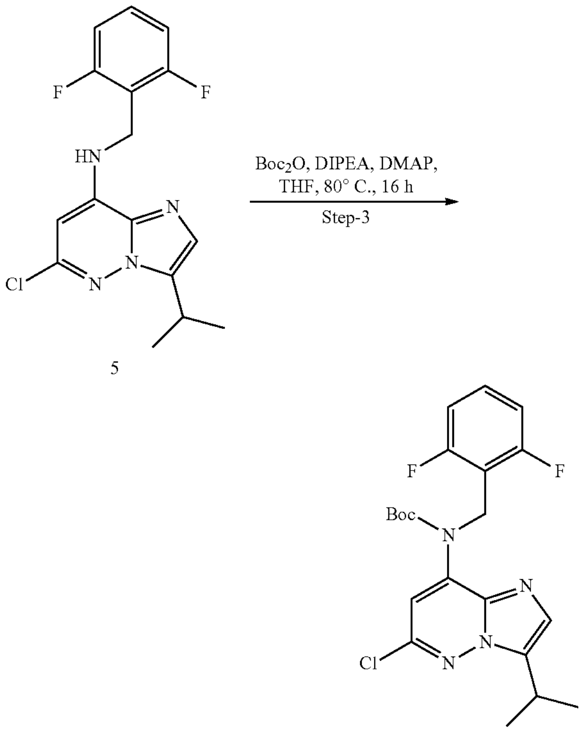

5

6

To a stirred solution of 6-chloro-N-(2,6-difluorobenzyl)-3-isopropylimidazo[1,2-b]pyridazin-8-amine (5) (1.1 g, 3.27 mmol, 1 eq.) in THF (10 mL) was added DIPEA (5.70 mL, 32.73 mmol, 10 eq.), Boc anhydride (7.51 mL, 32.73 mmol, 10 eq.) and DMAP (0.039 g, 0.327 mmol, 0.1 eq.) at room temperature. Reaction mixture was stirred at 80 °C for 16 h. The reaction mixture was allowed to cool to room temperature, THF was evaporated under reduced pressure to get the crude residue. To the crude residue water (50 mL) was added, extracted with ethyl acetate (3×50 mL), washed with brine (50 mL), dried over sodium sulphate, filtered and evaporated under reduced pressure to get the crude residue. The residue was purified by combiflash on silica column (with gradient elution of 5-10% EtOAc/Hexane) to afford the title compound as tert-butyl (6-chloro-3-isopropylimidazo[1,2-b]pyridazin-8-yl)(2,6-difluorobenzyl)carbamate (6) as light yellow solid. (Yield: 1.1 g, 77%). $R_f$=0.8 (4:1 Hexane/EtOAc). LCMS (m/z): 437.08 $(M+H)^+$. $^1H$ NMR (400 MHz, DMSO-$d_6$): δ=7.64 (s, 1H), 7.37-7.33 (m, 1H), 7.27 (s, 1H), 7.04-7.00 (m, 2H), 5.37 (s, 2H), 3.35-3.32 (m, 1H), 1.34 (m, 15H).

Step-4: Synthesis of tert-butyl 4-((8-((tert-butoxycarbonyl)(2,6-difluorobenzyl)amino)-3-isopropylimidazo[1,2-b]pyridazin-6-yl)thio)piperidine-1-carboxylate

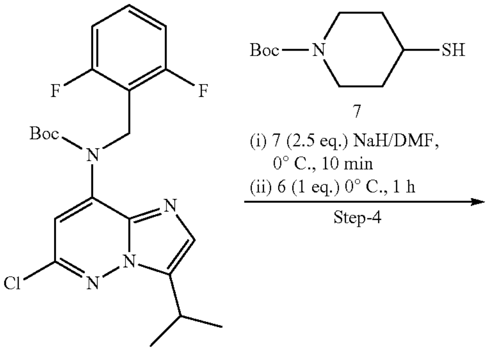

6

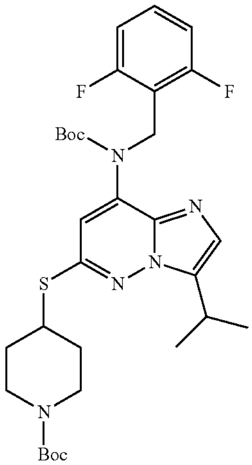

8

To a stirred solution of tert-butyl 4-mercaptopiperidine-1-carboxylate (7) (0.311 g, 1.433 mmol, 2.5 eq.) in DMF (3 mL) at 0 °C was added NaH (60% in mineral oil, (0.057 g, 1.43 mmol, 2.5 eq.). Reaction mixture was stirred at 0 °C for 10 minutes. Then tert-butyl (6-chloro-3-isopropylimidazo[1,2-b]pyridazin-8-yl)(2,6-difluorobenzyl)carbamate (6) (0.250 g, 0.573 mmol, 1 eq.) in DMF (3 mL) was added to the above reaction mass at 0 °C. Reaction mixture was stirred at 0 °C for 1 h. After complete conversion by TLC, water (15 mL) was added to the reaction mass, extracted with ethyl acetate (3×50 mL), washed with brine (25 mL), dried over sodium sulphate, and evaporated under reduced pressure to get the crude residue. Purification was done by silica phase column chromatography (with a gradient elution of 15-20% of EtOAC:n-Hexane) to afford the title compound as tert-butyl 4-((8-((tert-butoxycarbonyl)(2,6-difluorobenzyl)amino)-3-isopropylimidazo[1,2-b]pyridazin-6-yl)thio)piperidine-1-carboxylate (8) as yellow oil.(Yield: 0.2 g, 56%). $R_f$=0.3(4:1 Hexane/EtOAc). LCMS (m/z): 618.24 $(M+H)^+$.

Step-5: Synthesis of N-(2,6-difluorobenzyl)-3-isopropyl-6-(piperidin-4-ylthio)imidazo[1,2-b]pyridazin-8-amine hydrochloride

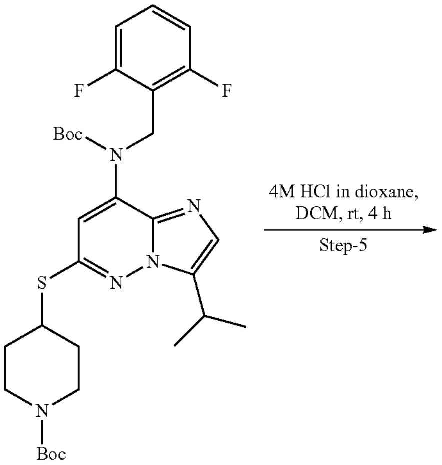

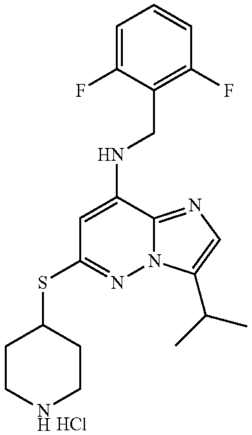

52

To a stirred solution of tert-butyl 4-((8-((tert-butoxycarbonyl)(2,6-difluorobenzyl)amino)-3-isopropylimidazo[1,2-b]pyridazin-6-yl)thio)piperidine-1-carboxylate (8) (0.200 g, 0.324 mmol, 1eq.) in DCM (5 mL) at 0 °C was added 4M HCl in 1,4-dioxane (2 mL) and stirred for 4 h. After complete conversion of reaction by TLC, the reaction mixture was subjected to rotary evaporator for removal of volatiles to get the crude residue as white solid. The obtained residue was triturated with diethyl ether (2×10 mL), ethyl acetate (2×10 mL), and dried by lyophilization for 24 h. to afford the title compound as N-(2,6-difluorobenzyl)-3-isopropyl-6-(piperidin-4-ylthio)imidazo[1,2-b]pyridazin-8-amine hydrochloride (52) as white solid. (Yield: 0.070 g, 47%). $R_f$=0.1 (9:1 $CHCl_3$/MeOH). LCMS (m/z): 418.1 $(M+H)^+$. $^1H$ NMR (400 MHz, DMSO-$d_6$): δ=9.11 (m, 1H), 8.95 (m, 1H), 8.55 (s, 1H), 7.82 (s, 1H), 7.51-7.44 (m, 1H), 7.17 (t, J=8 Hz, 2H), 6.52 (s, 1H)), 4.61 (d, J=4.8 Hz, 2H), 4.06-4.03 (m, 1H), 3.41-3.28 (m, 3H), 3.08-3.06 (m, 2H), 2.33-2.26 (m, 2H), 1.92-1.84 (m, 2H), 1.33 (d, J=6.8 Hz, 6H).

Example 65

Synthetic Scheme for 3-isopropyl-6-(piperidin-4-ylthio)-N-(2-(trifluoromethyl)benzyl)imidazo[1,2-b]pyridazin-8-amine hydrochloride

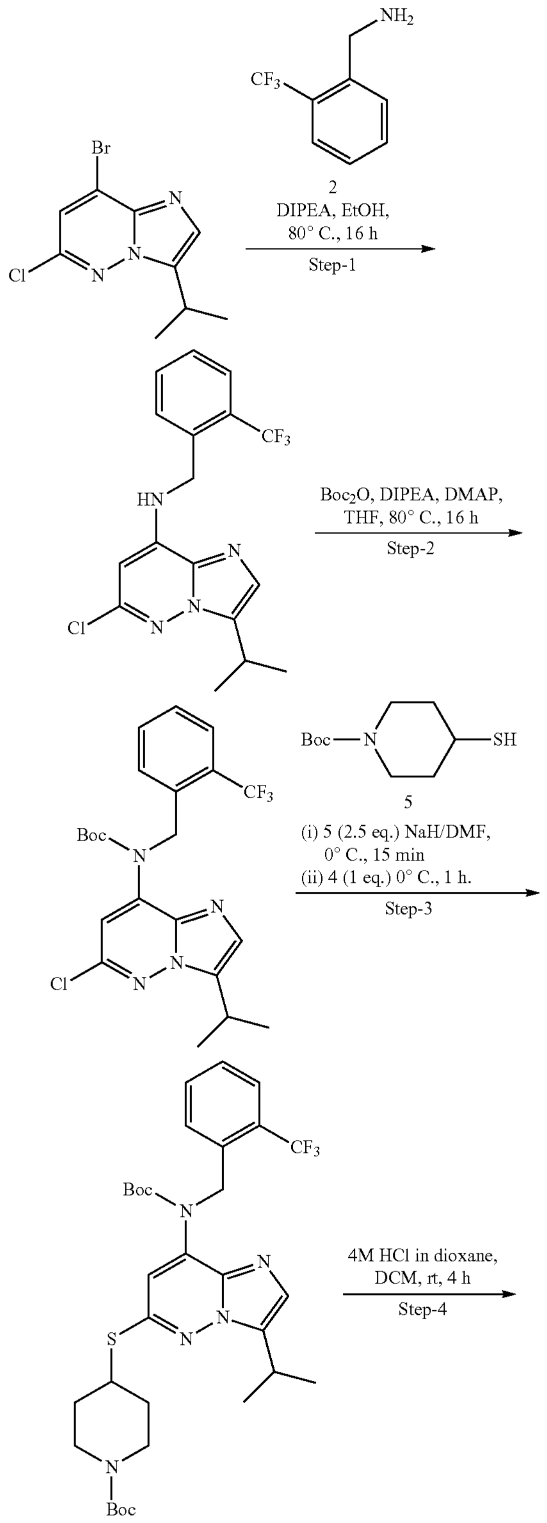

-continued

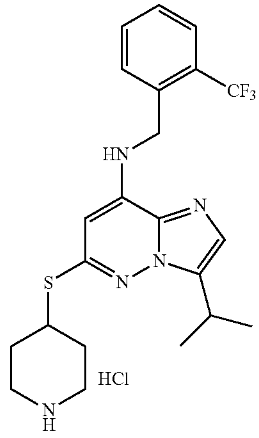

53

Step-1: Synthesis of 6-chloro-3-isopropyl-N-(2-(trifluoromethyl)benzyl)imidazo[1,2-b]pyridazin-8-amine

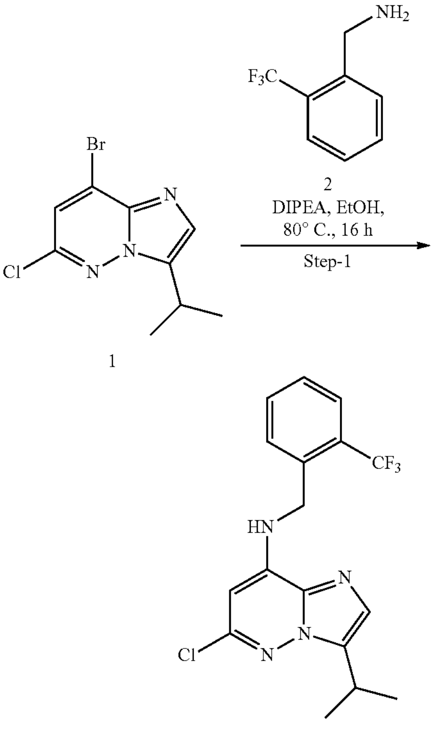

To a stirred solution of 8-bromo-6-chloro-3-isopropylimidazo[1,2-b]pyridazine (1) (1 g, 3.64 mmol, 1 eq.) in ethanol (10 mL) was added (2-(trifluoromethyl)phenyl)methanamine (2) (0.767 mL), 5.47 mmol, 1.5 eq.), and DIPEA (1.27 mL, 7.29 mmol, 2 eq.) at room temperature. The reaction mixture was heated at 80 °C for 16 h. After complete conversion by TLC, reaction mixture was cooled, ethanol was evaporated under reduced pressure, water (50 mL) was added, extracted with ethyl acetate (3×50 mL). The combined organic layer washed with brine (50 mL), dried over sodium sulphate, filtered and concentrated under reduced pressure to get crude residue. Obtained crude compound was purified by column chromatography on silica column (with gradient elution of 10-15% EtOAc/hexane) to afford the title compound as 6-chloro-3-isopropyl-N-(2-(trifluoromethyl)benzyl)imidazo[1,2-b]pyridazin-8-amine (3) as yellow oil.(Yield: 1.1 g, 82%). $R_f$=0.4 (4:1 Hexane/EtOAc). LCMS (m/z): 369.0 $(M+H)^+$ Step-2: Synthesis of tert-butyl (6-chloro-3-isopropylimidazo[1,2-b]pyridazin-8-yl)(2-(trifluoromethyl)benzyl)carbamate

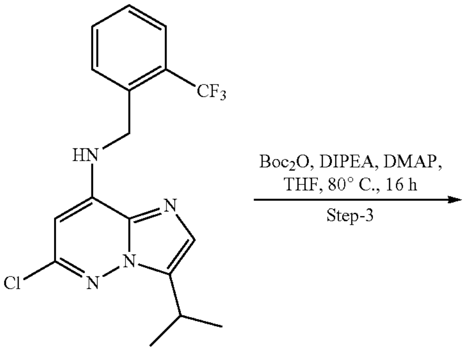

3

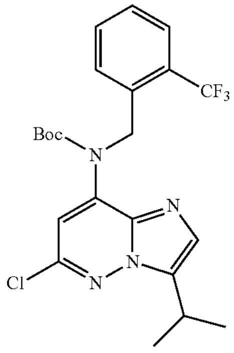

4

To a stirred solution of 6-chloro-3-isopropyl-N-(2-(trifluoromethyl)benzyl)imidazo[1,2-b]pyridazin-8-amine (3) (1.1 g, 2.98 mmol, 1 eq.) in THF (15 mL) was added DIPEA (5.20 mL, 29.89 mmol, 10 eq.), Boc anhydride (6.85 mL, 29.89 mmol, 10 eq.) and DMAP (0.036 g, 0.298 mmol, 0.1 eq.) at room temperature. Reaction mixture was stirred at 80 °C for 16 h. After complete conversion by TLC, the reaction mixture was allowed to cool to RT. Volatile portion was removed under reduced pressure from reaction mass, obtained crude was diluted with water (50 mL) extracted with ethyl acetate (3×50 mL), washed with brine (50 mL), dried over sodium sulphate, evaporated under reduced pressure to get crude residue. The residue was purified by column chromatography on silica gel column (100-200) mesh (with gradient elution of 5-10% EtOAc/hexane) to afford the title compound as tert-butyl (6-chloro-3-isopropylimidazo[1,2-b]pyridazin-8-yl)(2-(trifluoromethyl)benzyl)carbamate (5) as yellow oil. (Yield: 1.1 g, 79%). $R_f$=0.8 (4:1 Hexane/EtOAc). LCMS (m/z): 469.04 (84%)$(M+H)^+$.

Step-3: Synthesis of tert-butyl 4-((8-((tert-butoxycarbonyl)(2-(trifluoromethyl)benzyl)amino)-3-isopropylimidazo[1,2-b]pyridazin-6-yl)thio)piperidine-1-carboxylate

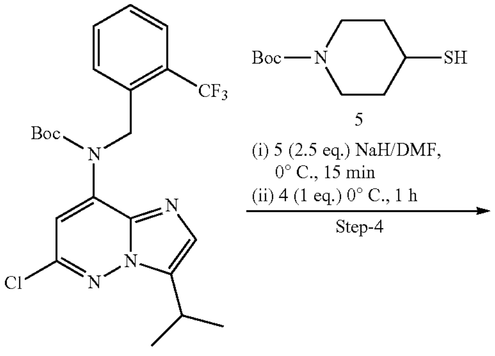

4

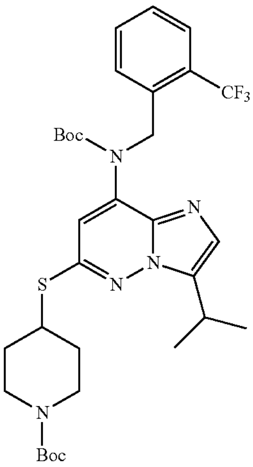

6

To a stirred solution of tert-butyl 4-mercaptopiperidine-1-carboxylate (5) (0.280 g, 1.33 mmol, 2.5 eq.) in DMF (3 mL) at 0 °C was added NaH (60% in mineral oil, (0.053 g, 1.33 mmol, 2.5eq.). Reaction mixture was stirred at 0 °C for 10 minutes. Then addition of tert-butyl (6-chloro-3-isopropylimidazo[1,2-b]pyridazin-8-yl)(2-(trifluoromethyl)benzyl)carbamate (4) (0.250 g, 0.534 mmol, 1 eq.) in DMF (3 mL) was done at 0 °C. Reaction mixture was stirred at 0 °C for 1 h. After complete conversion by TLC, water (50 mL) was added and product was extracted with ethyl acetate (3×50 mL). Combined organic layer was washed with brine (25 mL), dried over sodium sulphate, filtered and concentrated under reduced pressure to get the crude residue as brown oil. Obtained crude compound was purified by silica gel column chromatography (with a gradient elution of 10-15% of EtOAc: n-Hexane) to afford the title compound as tert-butyl 4-((8-((tert-butoxycarbonyl)(2-(trifluoromethyl)benzyl)amino)-3-isopropylimidazo[1,2-b]pyridazin-6-yl)thio)piperidine-1-carboxylate (6) as an off white solid. (Yield: 0.210 g, 60%). $R_f$=0.3(4:1 Hexane/EtOAc). LCMS (m/z): 650.1 $(M+H)^+$. $^1$H-NMR (400 MHz, DMSO-$d_6$): δ=7.74-7.60 (m, 3H), 7.48 (s, 1H), 7.45-7.41 (m, 1H), 7.27 (s, 1H), 5.42 (s, 2H), 3.96-3.82 (m, 3H), 3.02 (br. s, 2H), 2.09-2.06 (m, 2H), 1.63-1.53 (m, 2H), 1.39-1.30 (m, 25H).

Step-4: Synthesis of 3-isopropyl-6-(piperidin-4-ylthio)-N-(2-(trifluoromethyl)benzyl)imidazo[1,2-b]pyridazin-8-amine hydrochloride

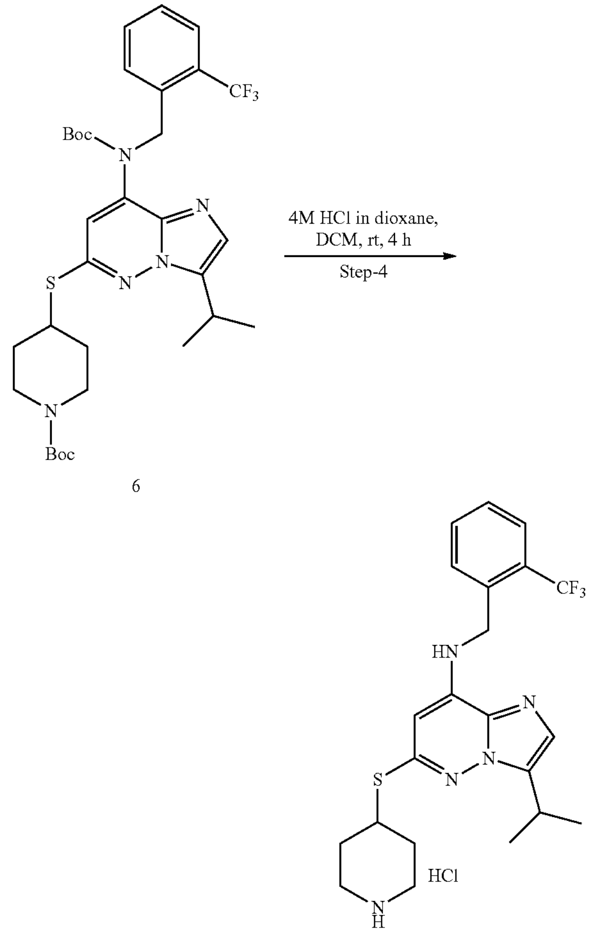

6

53

To a stirred solution of tert-butyl 4-((8-((tert-butoxycarbonyl)(2-(trifluoromethyl)benzyl)amino)-3-isopropylimidazo[1,2-b]pyridazin-6-yl)thio)piperidine-1-carboxylate (6) (0.210 g, 0.323 mmol, 1eq.) in DCM (5 mL) at 0 °C was added 4M HCl in 1,4-dioxane (2 mL) and stirred at room temperature for 4 h. After complete conversion by TLC, the reaction mixture was subjected to rotary evaporator for removal of volatiles. Obtained residue was purified by preparative HPLC using TFA as buffer to afford 3-isopropyl-6-(piperidin-4-ylthio)-N-(2-(trifluoromethyl)benzyl)imidazo[1,2-b]pyridazin-8-amine (TFA salt). To get compound as HCl salt, obtained TFA salt was dissolved in ACN:water and treated with 2N aq. HCl at 0 °C and lyophilized to afford the title compound as 3-isopropyl-6-(piperidin-4-ylthio)-N-(2-(trifluoromethyl)benzyl)imidazo[1,2-b]pyridazin-8-amine hydrochloride as a white solid (53). Yield=(170 g, quantitative). $R_f$=0.1 (9:1 DCM/MeOH). LCMS (m/z): 366.9 $(M+H)^+$. $^1$H-NMR (400 MHz, DMSO-$d_6$): δ=9.12 (br. s, 1H), 8.91 (br. s, 1H), 8.73 (s, 1H), 7.80 (d, J=8 Hz, 2H), 7.68-7.52 (m, 3H), 6.21 (s, 1H), 4.73 (m, 2H), 4.01-3.96 (m, 1H), 3.42-3.35 (m, 1H), 3.27 (d, J=12 Hz, 2H), 3.04 (d, J=10.4 Hz, 2H), 2.26-2.23 (m, 2H), 1.87-1.80 (m, 2H), 1.35 (d, J=6.8 Hz, 6H).

Example 66

Synthetic Scheme for 3-isopropyl-6-(piperidin-4-ylthio)-N-(3-(trifluoromethoxy)benzyl)imidazo[1,2-b]pyridazin-8-amine hydrochloride

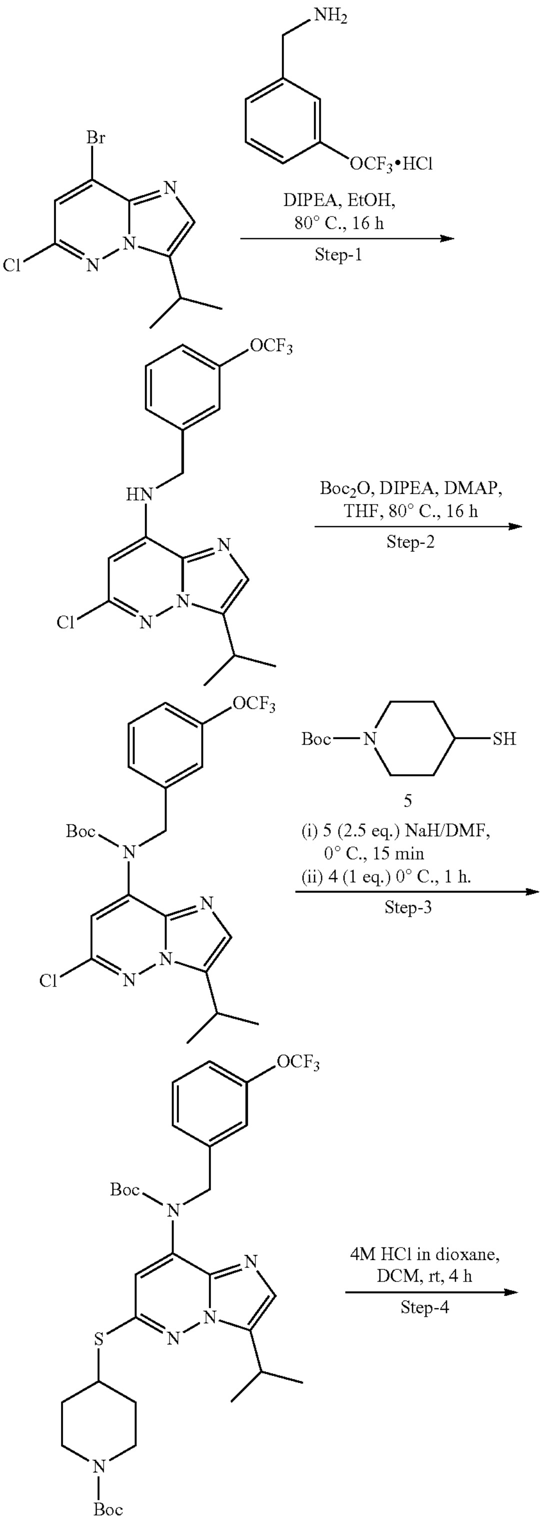

-continued

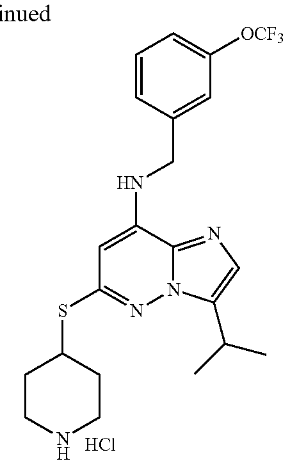

54

Step-1: Synthesis of 6-chloro-3-isopropyl-N-(3-(trifluoromethoxy)benzyl)imidazo[1,2-b]pyridazin-8-amine

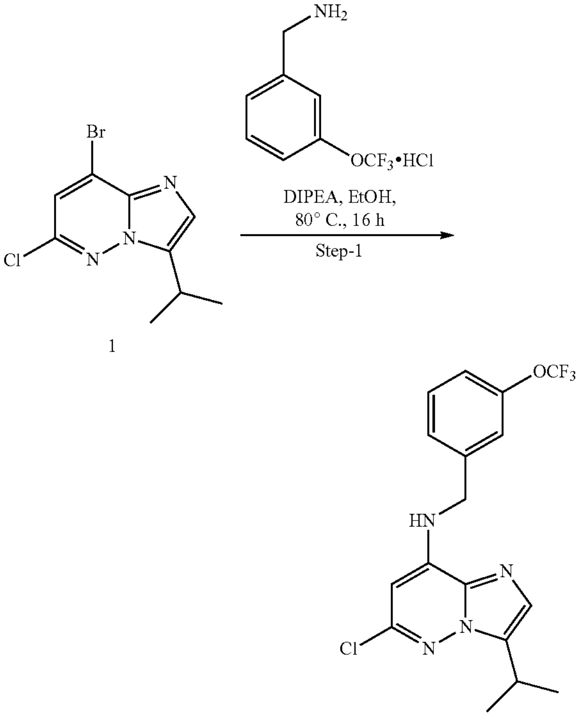

1

3

To a stirred solution of 8-bromo-6-chloro-3-isopropylimidazo[1,2-b]pyridazine (1) (1 g, 3.64 mmol, 1eq.) in ethanol (10 mL) was added DIPEA (1.90 mL, 10.94 mmol, 3 eq.) and (3-(trifluoromethoxy)phenyl)methanamine hydrochloride (1.66 g, 7.29 mmol, 2 eq.) at room temperature. The reaction mixture was heated at 80 °C for 16 h. After conversion by TLC, reaction mixture was cooled, ethanol was evaporated under reduced pressure to get the crude residue. To the crude water (100 mL) was added, extracted with EtOAc (3×50 mL). The combined organic layer washed with brine (50 mL), dried over sodium sulphate, and evaporated under reduced pressure to get crude residue. The residue was purified by combiflash on silica column (EtOAc/hexane, gradient 5-10% EtOAc) to afford the title compound as 6-chloro-3-isopropyl-N-(3-(trifluoromethoxy)benzyl)imidazo[1,2-b]pyridazin-8-amine (3) as white solid. Yield: 0.9 g, 64%). $R_f$=0.4 (4:1 Hexane/EtOAc). LCMS (m/z): 385.0 $(M+H)^+$. $^1$H-NMR (400 MHz, DMSO-$d_6$): δ 8.53-8.50 (m, 1H), 7.49-7.41 (m, 3H), 7.34 (s, 1H), 7.25 (d, J=7.6 Hz, 1H), 6.15 (s, 1H), 4.61 (s, 2H), 3.34-3.20 (m, 1H), 1.30 (d, J=6.8 Hz, 6H).

Step-2: Synthesis of tert-butyl (6-chloro-3-isopropylimidazo[1,2-b]pyridazin-8-yl)(3-(trifluoromethoxy)benzyl)carbamate

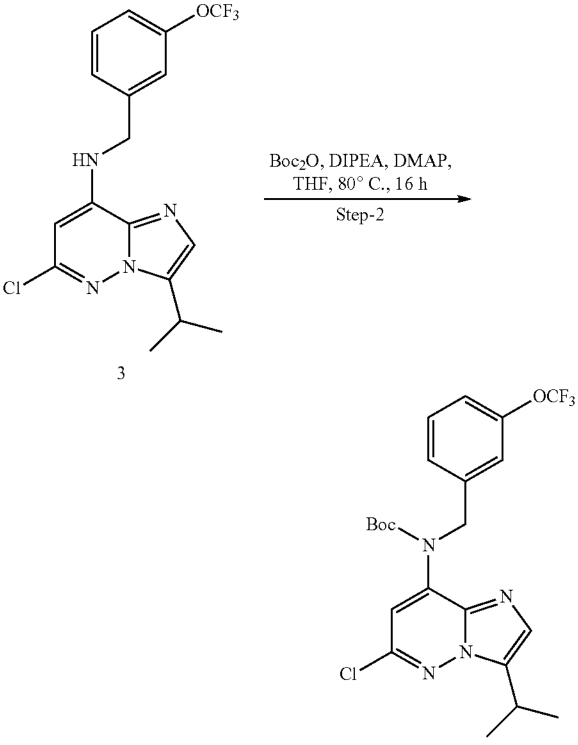

3

4

To a stirred solution of 6-chloro-3-isopropyl-N-(3-(trifluoromethoxy)benzyl)imidazo[1,2-b]pyridazin-8-amine (3) (0.9 g, 2.34 mmol, 1 eq.) in THF (10 mL) was added DIPEA (4.08 mL, 23.43 mmol, 10 eq.) $(Boc)_2O$ (5.37 mL, 23.43 mmol, 10 eq.) and DMAP (0.028 g, 0.23 mmol, 0.1 eq.) in THF (15 mL) were stirred for 16 h at 80 °C. The reaction mixture was allowed to cool to room temperature, THF was evaporated under reduced pressure, water (50 mL) was added, extracted with ethyl acetate (3×50 mL), washed with brine (50 mL), dried over sodium sulphate, filtered and evaporated under reduced pressure. The residue was purified by combiflash on silica column (EtOAc/hexane, gradient 0-5% EtOAc) to afford the title compound as tert-butyl (6-chloro-3-isopropylimidazo[1,2-b]pyridazin-8-yl)(3-(trifluoromethoxy)benzyl)carbamate (4) as a yellow oil. Yield: 0.9 g, 79%). $R_f$=0.8 (4:1 Hexane/EtOAc). LCMS (m/z): 484.92 $(M+H)^+$. $^1$H NMR (400 MHflz, DMSO-$d_6$): δ=7.65 (s, 1H), 7.44-7.40 (m, 2H), 7.33-7.29 (m, 2H), 7.22-7.20 (m, 1H), 5.31 (s, 2H), 3.34 (m, 1H), 1.33-1.31 (m, 15H).

Step-3: Synthesis of tert-butyl 4-((8-((tert-butoxy-carbonyl)(3-(trifluoromethoxy)benzyl)amino)-3-isopropylimidazo[1,2-b]pyridazin-6-yl)thio)piperidine-1-carboxylate

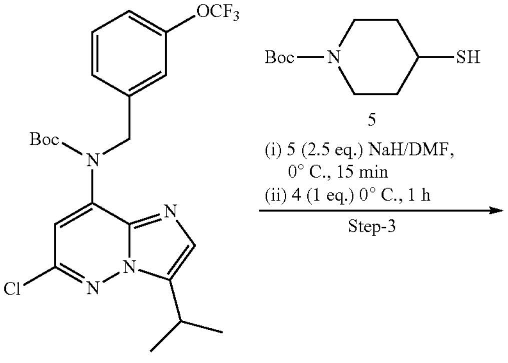

4

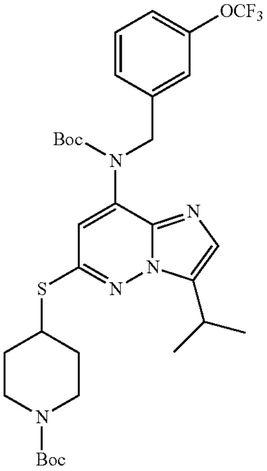

6

To a stirred solution of tert-butyl 4-mercaptopiperidine-1-carboxylate (5) (0.280 g, 1.29 mmol, 2.5 eq.) in DMF (3 mL) at 0 °C was added NaH (60% in mineral oil, (0.051 g, 1.29 mmol, 2.5 eq.) and stirred for 15 min. Then added a solution of tert-butyl (6-chloro-3-isopropylimidazo[1,2-b]pyridazin-8-yl)(3-(trifluoromethoxy)benzyl)carbamate (4) (0.25 g, 0.516 mmol, 1 eq.) in DMF (3 mL) at 0 °C and stirred for 1 h. After complete conversion by TLC, reaction mixture was diluted with ice cold water (30 mL), and extracted with ethyl acetate (3×50 mL), washed with brine (25 mL), dried over sodium sulphate and evaporated under reduced pressure to get crude residue. Crude residue was purified by silica phase column chromatography (EtOAc/hexane, gradient 10-15% EtOAc) to afford the tert-butyl 4-((8-((tert-butoxycarbonyl)(3-(trifluoromethoxy)benzyl)amino)-3-isopropylimidazo[1,2-b]pyridazin-6-yl)thio)piperidine-1-carboxylate (6) as a yellow oil. (0.2 g, 58% yield). $R_f$=0.3 (4:1 Hexane/EtOAc). LCMS (m/z): 666.1 $(M+H)^+$.

Step-4: Synthesis of 3-isopropyl-6-(piperidin-4-ylthio)-N-(3-(trifluoromethoxy)benzyl)imidazo[1,2-b]pyridazin-8-amine hydrochloride

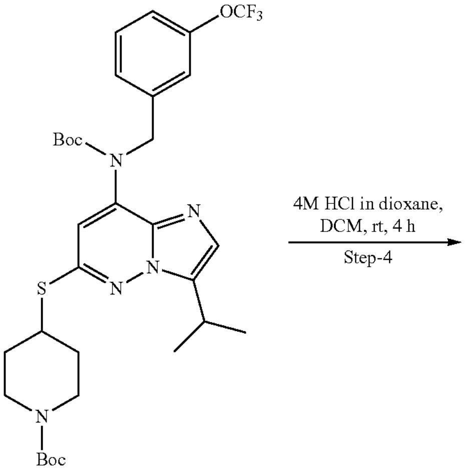

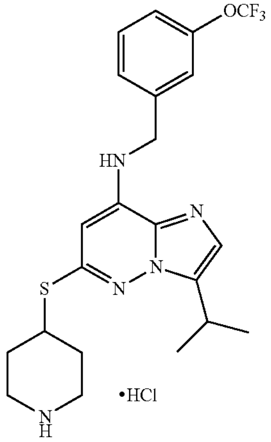

54

To a stirred solution of tert-butyl 4-((8-((tert-butoxycarbonyl)(3-(trifluoromethoxy)benzyl)amino)-3-isopropylimidazo[1,2-b]pyridazin-6-yl)thio)piperidine-1-carboxylate (6) (0.2 g, 0.300 mmol, 1 eq.) in DCM (5 mL) at 0 °C was added 4M HCl in dioxane (2 mL) and stirred at RT for 4 h. After complete conversion by TLC, volatiles were evaporated under reduced pressure and obtained crude compound was purified by Prep-HPLC (TFA buffer was used) to afford 3-isopropyl-6-(piperidin-4-ylthio)-N-(3-(trifluoromethoxy)benzyl)imidazo[1,2-b]pyridazin-8-amine as TFA salt. To get compound as a HCl salt, obtained TFA salt was dissolved in ACN: water and treated with 2N aq. HCl at 0 °C and lyophilized to afford the title compound as 3-isopropyl-6-(piperidin-4-ylthio)-N-(3-(trifluoromethoxy)benzyl)imidazo[1,2-b]pyridazin-8-amine hydrochloride (54) as an off white solid. (Yield: 0.120 g, 79%). $R_f$=0.1 (9:1 DCM/MeOH). LCMS (m/z): 466.0 $(M+H)^+$ $^1$H-NMR (400 MHz, DMSO-$d_6$): δ=9.10-8.90 (m, 3H), 7.91 (s, 1H), 7.52-7.45 (m, 3H), 7.29 (d, J=7.6 Hz, 1H), 6.47 (s, 1H), 4.68 (d, J=6 Hz, 2H), 4.03-3.98 (m, 1H), 3.41-3.35 (m, 1H), 3.29-3.26 (m, 2H), 3.09-3.04 (m, 2H), 2.25-2.22 (m, 2H), 1.88-1.80 (m, 2H). 1.34 (d, J=6.8 Hz, 6H).

Example 67

Synthetic Scheme 3-isopropyl-6-(piperidin-4-ylthio)-N-(3-(trifluoromethyl)benzyl)imidazo[1,2-b]pyridazin-8-amine hydrochloride

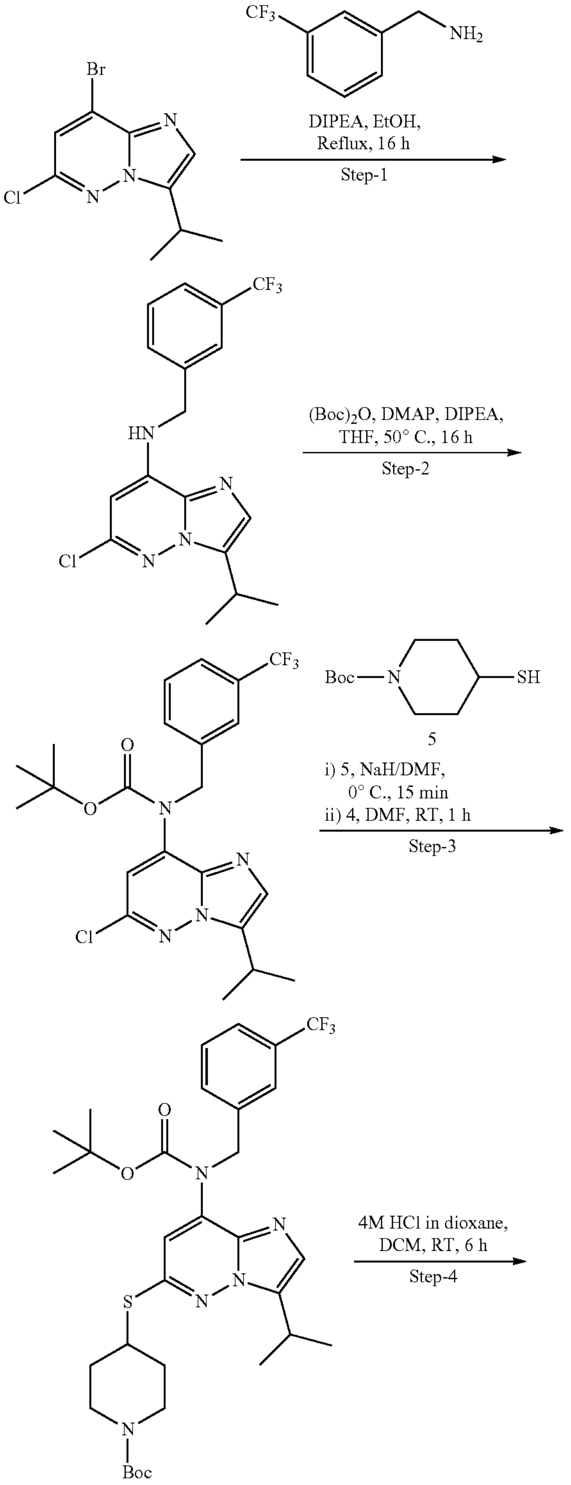

-continued

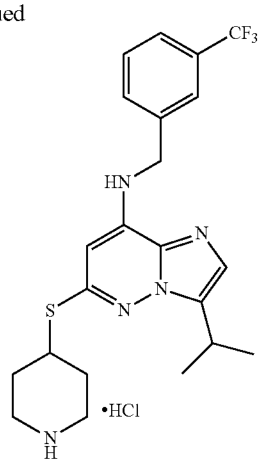

55

Synthesis of 6-chloro-3-isopropyl-N-(3-(trifluoromethyl)benzyl)imidazo[1,2-b]pyridazin-8-amine

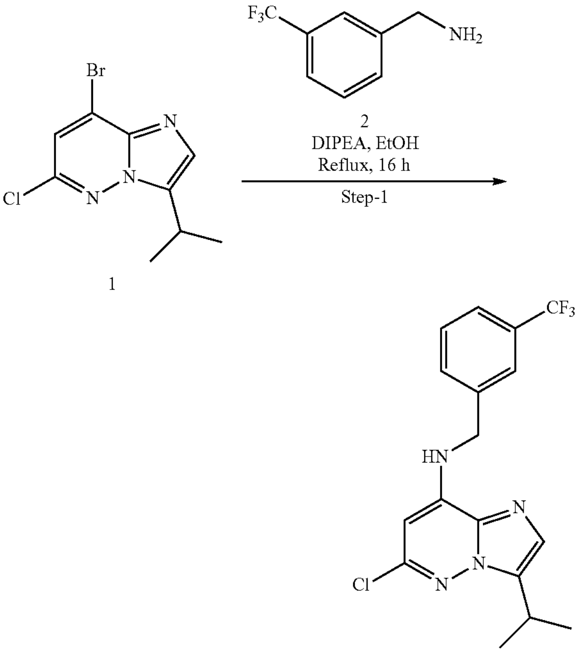

1

3

A mixture of 8-bromo-6-chloro-3-isopropylimidazo[1,2-b]pyridazine (1.0 g, 3.65 mmol, 1 eq.), (3-(trifluoromethyl)phenyl)methanamine (1.27 g, 7.299 mmol, 2 eq.), and DIPEA (1.9 mL, 10.947 mmol) in EtOH (10 mL) was heated to reflux for 16 h. The reaction mixture was allowed to cool to room temperature and then concentered under reduce pressure the obtained crude material was diluted with water and EtOAc. The aqueous layer was separated and extracted with EtOAc (2×50 mL). The combined extracts were washed with water, brine, dried over $Na_2SO_4$, filtered, and evaporated. The residue was purified by combiflash on silica column (EtOAc/hexane, gradient 0-30% EtOAc) to 6-chloro-3-isopropyl-N-(3-(trifluoromethyl)benzyl)imidazo

[1,2-b]pyridazin-8-amine (3) as a yellow gum (1 g, 75% yield). $R_f$=0.3 (2:8 Hexane/EtOAc). $^1$H NMR (400 MHz, DMSO-$d_6$): δ 8.21 (s, 2H), 7.90 (s, 1H), 7.78 (t, J=8.0 Hz, 2H), 7.67 (t, J=7.6 Hz, 1H), 4.16 (s, 2H), 3.65-3.59 (m, 1H), 1.31-1.24 (m, 6H).

Synthesis of tert-butyl (6-chloro-3-isopropylimidazo[1,2-b]pyridazin-8-yl)(3-(trifluoromethyl)benzyl)carbamate

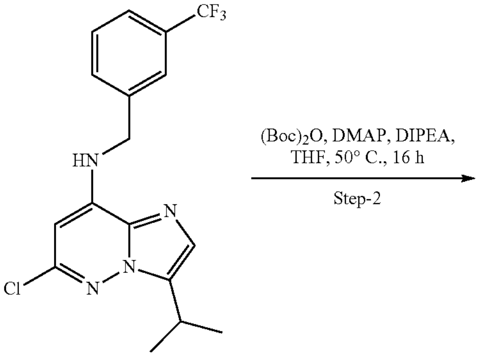

3

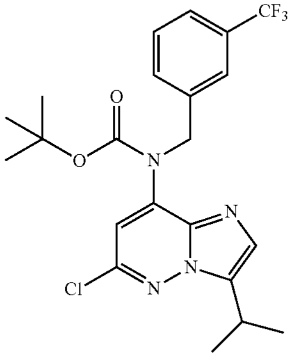

4

A stirred solution of 6-chloro-3-isopropyl-N-(3-(trifluoromethyl)benzyl)imidazo[1,2-b]pyridazin-8-amine (3) (1 g, 2.717 mmol, 1 eq.), $(Boc)_2O$ (6.2 mL, 27.17 mmol, 10 eq.), DMAP (26 mg, 0.271 mmol, 0.1 eq.) and DIPEA (4.7 mL, 27.17 mmol, 10 eq.) in THF (10 mL) were stirred for 16 h at 50 °C. The reaction mixture was allowed to cool to room temperature. EtOAc (150 mL) was added, and the organic layer was washed with water (2×100 mL) and saturated aqueous $NaHCO_3$(100 mL) and dried over $Na_2SO_4$, filtered, and evaporated. The residue was purified by combiflash on silica column (EtOAc/hexane, gradient 0-20% EtOAc) to afford tert-butyl (6-chloro-3-isopropylimidazo[1,2-b]pyridazin-8-yl)(3-(trifluoromethyl)benzyl)carbamate (4) as a yellow gum (1.0 g, 79% yield). $R_f$=0.5 (2:8 Hexane/EtOAc). $^1$H-NMR (400 MHz, DMSO-$d_6$): δ 7.68-7.42 (m, 6H), 4.21 (d, J=6.0 Hz, 2H), 3.39-3.34 (m, 1H), 1.39-1.32 (m, 15H).

Synthesis of tert-butyl 4-((8-((tert-butoxycarbonyl)(3-(trifluoromethyl)benzyl)amino)-3-isopropylimidazo[1,2-b]pyridazin-6-yl)thio)piperidine-1-carboxylate (6)

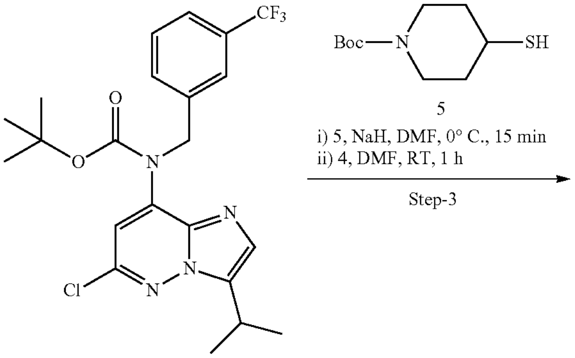

4

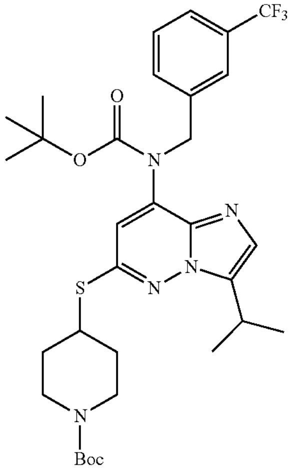

6

To a solution of tert-butyl 4-mercaptopiperidine-1-carboxylate (5) (0.289 g, 1.335 mmol, 1 eq.) in DMF (2 mL) at 0 °C was added NaH (60% in mineral oil, 0.053 g, 1.335 mmol, 2.5 eq.) and stirred for 15 min. Then added a solution of tert-butyl (6-chloro-3-isopropylimidazo[1,2-b]pyridazin-8-yl)(3-(trifluoromethyl)benzyl)carbamate (4) (0.25 g, 0.534 mmol, 1 eq.) in DMF (2 mL). The resulting mixture was stirred at room temperature for 1 h. Reaction diluted with ice cold water (10 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 10-20% of Hexane/EtOAc] to tert-butyl 4-((8-((tert-butoxycarbonyl)(3-(trifluoromethyl)benzyl)amino)-3-isopropylimidazo[1,2-b]pyridazin-6-yl)thio)piperidine-1-carboxylate (6) as a yellow gum (0.2 g, 58% yield). $R_f$=0.3 (8:2 Hexane/EtOAc). $^1$H-NMR (400 MHz, DMSO-$d_6$): δ 7.65 (s, 1H), 7.61-7.52 (m, 3H), 7.48 (s, 1H), 7.08 (s, 1H), 5.25 (s, 2H), 3.94-3.91 (m, 2H), 3.06-3.02 (m, 2H), 2.08-2.05 (m, 2H), 1.93-1.87 (m, 2H), 1.62-1.52 (m, 2H), 1.39-1.32 (m, 24H).

Synthesis of 3-isopropyl-6-(piperidin-4-ylthio)-N-(3-(trifluoromethyl)benzyl)imidazo[1,2-b]pyridazin-8-amine hydrochloride

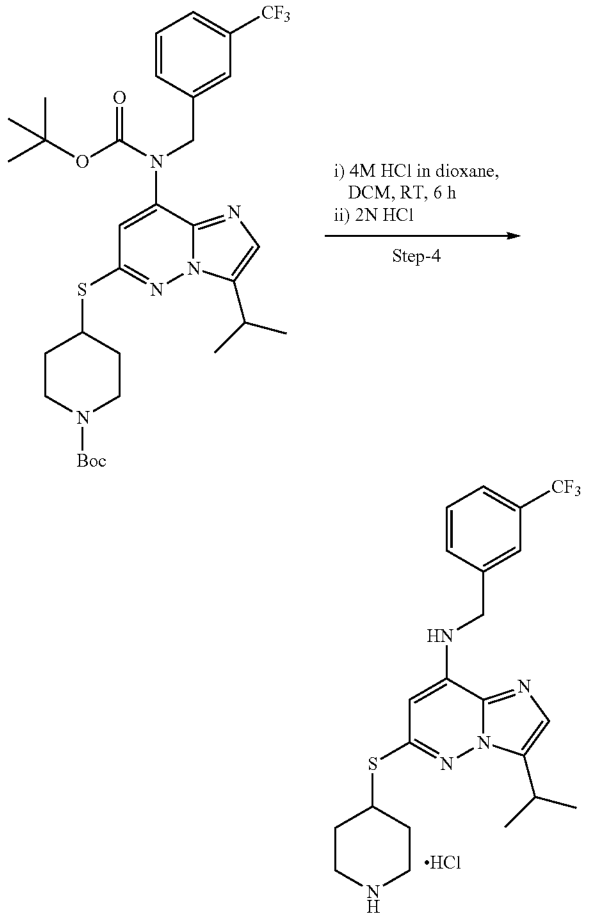

55

To a solution of tert-butyl 4-((8-((tert-butoxycarbonyl)(3-(trifluoromethyl)benzyl)amino)-3-isopropylimidazo[1,2-b]pyridazin-6-yl)thio)piperidine-1-carboxylate (6) (0.2 g, 0.308 mmol, 1 eq.) in DCM (10 mL) at 0 °C was added 4M HCl in dioxane (1 mL) and stirred at RT for 6 h. After completion of conversion by TLC, volatiles were evaporated under reduced pressure and obtained crude compound was purified by Prep-HPLC (TFA buffer was used) to afford 3-isopropyl-6-(piperidin-4-ylthio)-N-(3-(trifluoromethyl)benzyl)imidazo[1,2-b]pyridazin-8-amine. To get compound as a HCl salt, obtained formate salt was dissolved in ACN:water and treated with 2N aq. HCl at 0 °C and lyophilized to afford 3-isopropyl-6-(piperidin-4-ylthio)-N-(3-(trifluoromethyl)benzyl)imidazo[1,2-b]pyridazin-8-amine hydrochloride (55) as an off white solid (136 mg, 91% yield). $R_f$=0.1 (9:1 DCM/MeOH). LCMS (m/z): 450.1 $(M+H)^+$. $^1H$ NMR (400 MHz, DMSO-$d_6$) δ 9.15-8.98 (m, 3H), 7.93 (s, 1H), 7.82 (s, 1H), 7.75 (d, J=7.6 Hz, 1H), 7.67-7.58 (m, 2H), 6.53 (s, 1H), 4.73 (d, J=5.6 Hz, 2H), 4.01 (d, J=10.4 Hz, 1H), 3.42-3.35 (m, 1H), 3.27 (d, J=12.4 Hz, 2H), 3.06 (t, J=9.2 Hz, 2H), 2.25 (d, J=11.6 Hz, 2H), 1.85 (dd, J=8.8 Hz, 2H), 1.35 (d, J=8.0 Hz, 6H).

Example 68

Synthetic Scheme for N-(2,4-difluorobenzyl)-3-isopropyl-6-(piperidin-4-ylthio)imidazo[1,2-b]pyridazin-8-amine hydrochloride

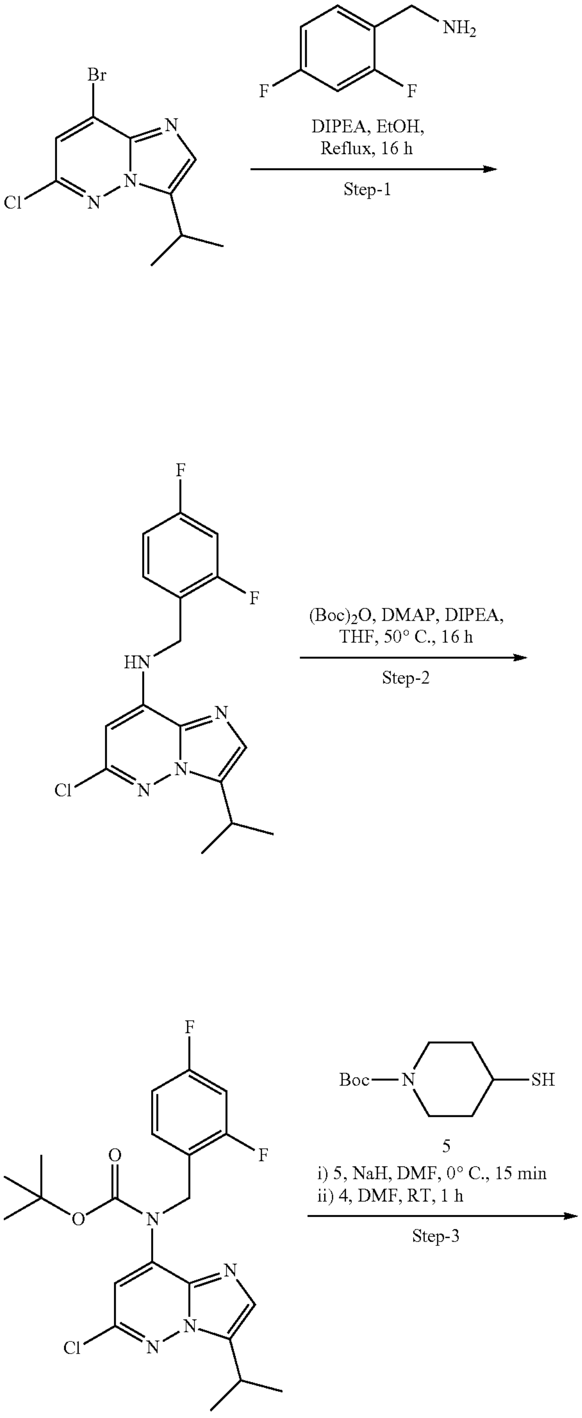

-continued

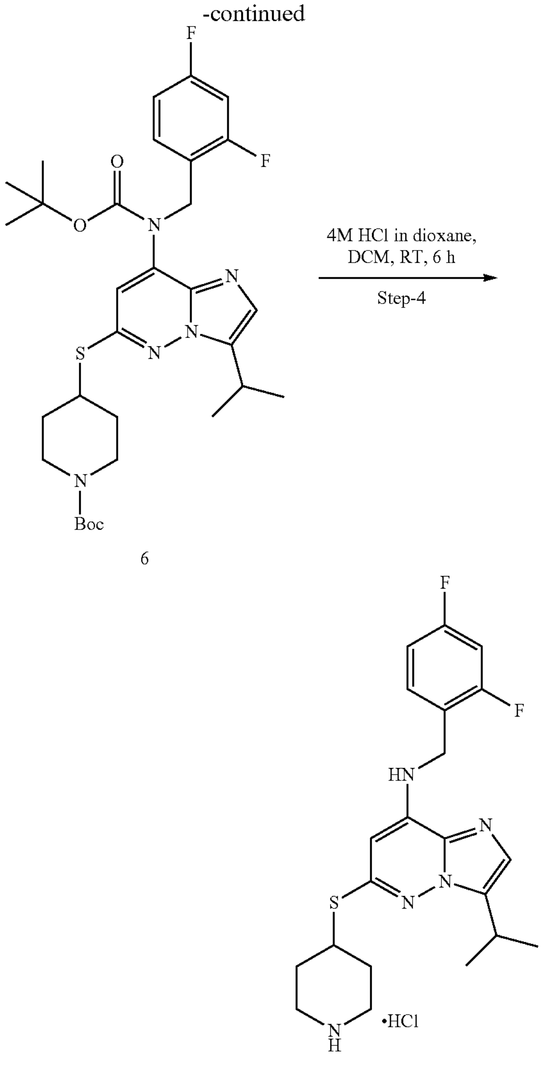

6

56

Synthesis of 6-chloro-N-(2,4-difluorobenzyl)-3-isopropylimidazo[1,2-b]pyridazin-8-amine A mixture of 8-bromo-6-chloro-3-isopropylimidazo[1,2-b]pyridazine (1.0 g, 3.64 mmol, 1 eq.), (2,4-difluorophenyl) methanamine (1.04 g, 7.299 mmol, 2 eq.), and DIPEA (1.9 mL, 10.92 mmol) in EtOH (10 mL) was heated to reflux for 16 h. The reaction mixture was allowed to cool to room temperature and then concentered under reduce pressure the obtained crude material was diluted with water and EtOAc. The aqueous layer was separated and extracted with EtOAc (2×50 mL). The combined extracts were washed with water, brine, dried over $Na_2SO_4$, filtered, and evaporated. The residue was purified by combiflash on silica column (EtOAc/hexane, gradient 0-30% EtOAc) to 6-chloro-N-(2, 4-difluorobenzyl)-3-isopropylimidazo[1,2-b]pyridazin-8-amine (3) as a yellow gum (1 g, 83% yield). $R_f$=0.4 (2:8 Hexane/EtOAc). $^1$H NMR (400 MHz, DMSO-$d_6$): δ 8.21 (s, 1H), 7.26 (t, J=6.8 Hz, 1H), 7.19 (d, J=6.4 Hz, 1H), 7.33 (d, J=3.6 Hz, 1H), 7.64-7.58 (m, 1H), 7.42-7.37 (m, 2H), 7.25-7.18 (m, 2H), 7.08-7.03 (m, 1H), 4.57 (s, 2H), 3.29-3.24 (m, 1H), 1.30 (d, J=5.2 Hz, 6H).

Synthesis of tert-butyl (6-chloro-3-isopropylimidazo[1,2-b]pyridazin-8-yl)(2,4-difluorobenzyl)carbamate

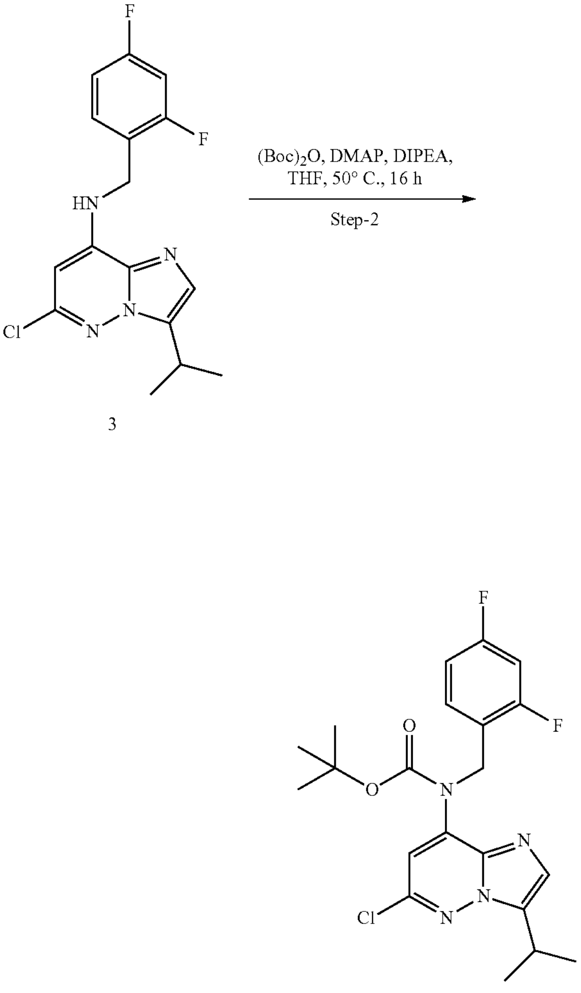

3

4

To a stirred solution of 6-chloro-N-(2,4-difluorobenzyl)-3-isopropylimidazo[1,2-b]pyridazin-8-amine (1 g, 2.97 mmol, 1 eq.), $(Boc)_2O$ (6.8 mL, 29.76 mmol, 10 eq.), DMAP (36 mg, 0.297 mmol, 0.1 eq.) and DIPEA (5.3 mL, 29.76 mmol, 10 eq.) in THF (10 mL) were stirred for 16 h at 50 °C. The reaction mixture was allowed to cool to room temperature. EtOAc (150 mL) was added, and the organic layer was washed with water (2×100 mL) and saturated aqueous $NaHCO_3$(100 mL) and dried over $Na_2SO_4$, filtered, and evaporated. The residue was purified by combiflash on silica column (EtOAc/hexane, gradient 0-20% EtOAc) to afford tert-butyl (6-chloro-3-isopropylimidazo[1,2-b] pyridazin-8-yl)(2,4-difluorobenzyl)carbamate (4) as a yellow gum (0.7 g, 54% yield). $R_f$=0.5 (2:8 Hexane/EtOAc). $^1$H NMR (400 MHz, DMSO-$d_6$): δ 7.65 (s, 1H) 7.50-7.42 (m, 2H), 7.20-7.15 (m, 1H), 7.05-7.00 (m, 1H), 5.30 (s, 2H), 3.39-3.34 (m, 1H), 1.35-1.32 (m, 15H).

Synthesis of tert-butyl 4-((8-((tert-butoxycarbonyl)(2,4-difluorobenzyl)amino)-3-isopropylimidazo[1,2-b]pyridazin-6-yl)thio)piperidine-1-carboxylate

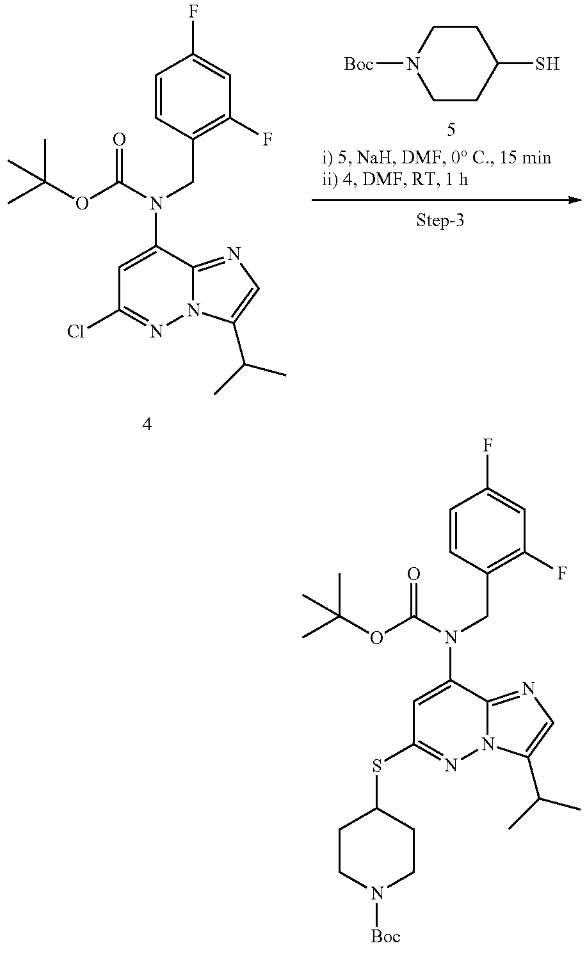

To a solution of tert-butyl 4-mercaptopiperidine-1-carboxylate (5) (0.311 g, 1.433 mmol, 1 eq.) in DMF (2 mL) at 0 °C was added NaH (60% in mineral oil, 0.057 g, 1.433 mmol, 2.5 eq.) and stirred for 15 min. Then added a solution of tert-butyl (6-chloro-3-isopropylimidazo[1,2-b]pyridazin-8-yl)(2,4-difluorobenzyl)carbamate (4) (0.25 g, 0.573 mmol, 1 eq.) in DMF (2 mL). The resulting mixture was stirred at room temperature for 1 h. Reaction diluted with ice cold water (30 mL) and extracted with ethyl acetate (3×20 mL). The combined organic layer was washed with brine solution (30 mL), dried over sodium sulfate, filtered and concentrated under reduced pressure to provide crude product. Obtained crude compound was purified by silica phase column chromatography [with a gradient elution of 20% of Hexane/EtOAc] to tert-butyl 4-((8-((tert-butoxycarbonyl)(2,4-difluorobenzyl)amino)-3-isopropylimidazo[1,2-b]pyridazin-6-yl)thio)piperidine-1-carboxylate (6) as a yellow gum (0.22 g, 62% yield). $R_f$=0.2 (8:2 Hexane/EtOAc). $^1$H-NMR (400 MHz, DMSO-$d_6$): δ 7.48-7.43 (m, 2H), 7.19-7.13 (m, 1H), 7.07 (s, 1H), 7.03-6.99 (m, 1H), 5.22 (s, 2H), 3.93-3.83 (m, 3H), 3.02-3.01 (m, 3H), 2.08-2.06 (m, 2H), 1.62-1.53 (m, 2H), 1.39-1.33 (m, 24H).

Synthesis of N-(2,4-difluorobenzyl)-3-isopropyl-6-(piperidin-4-ylthio)imidazo[1,2-b]pyridazin-8-amine hydrochloride

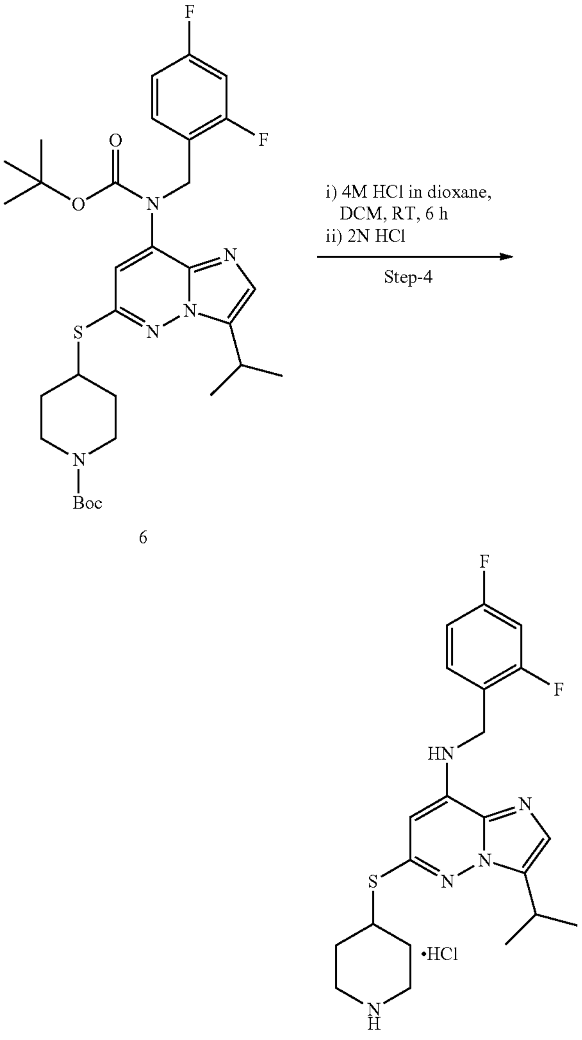

To a solution of tert-butyl 4-((8-((tert-butoxycarbonyl)(2,4-difluorobenzyl)amino)-3-isopropylimidazo[1,2-b]pyridazin-6-yl)thio)piperidine-1-carboxylate (6) (0.22 g, 0.324 mmol, 1 eq.) in DCM (10 mL) at 0 °C was added 4M HCl in dioxane (2 mL) and stirred at RT for 6 h. After completion of conversion by TLC, volatiles were evaporated under reduced pressure and obtained crude compound was purified by Prep-HPLC (formic acid buffer was used) to afford N-(2,4-difluorobenzyl)-3-isopropyl-6-(piperidin-4-ylthio)imidazo[1,2-b]pyridazin-8-amine. To get compound as a HCl salt, obtained formate salt was dissolved in ACN:water and treated with 2N aq. HCl at 0 °C and lyophilized to afford N-(2,4-difluorobenzyl)-3-isopropyl-6-(piperidin-4-ylthio)imidazo[1,2-b]pyridazin-8-amine hydrochloride as a white solid (56, 48 mg, 33% yield). $R_f$=0.1 (9:1 DCM/MeOH). LCMS (m/z): 418.1 $(M+H)^+$. $^1$H-NMR (400 MHz, DMSO-$d_6$): δ 9.14-8.96 (m, 2H), 8.73 (s, 1H), 7.87 (s, 1H), 7.52 (q, J=7.2 Hz, 1H), 6.29 (q, J=9.2 Hz, 1H), 7.09 (t, J=6.0 Hz, 1H), 6.49 (s, 1H), 4.62 (d, J=5.6 Hz, 2H), 4.01 (t, J=10.4 Hz, 1H), 3.41-3.35 (m, 1H), 3.28 (d, J=12.4 Hz, 2H), 3.06 (d, J=10.4 Hz, 2H), 2.27 (t, J=11.6 Hz, 2H), 1.90-1.82 (m, 2H), 1.34 (d, J=4.0 Hz, 6H).

Example 69

Synthetic Scheme for N-(2,6-difluorophenyl)-3-isopropyl-6-(piperidin-3-ylthio)imidazo[1,2-b]pyridazin-8-amine hydrochloride

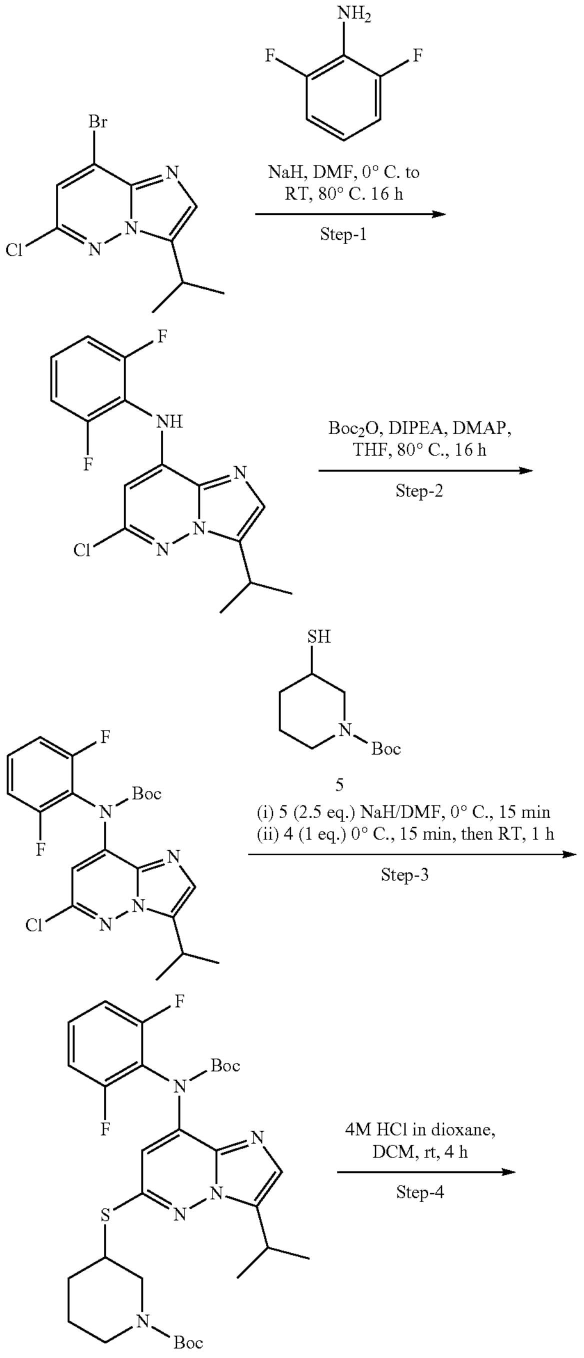

-continued

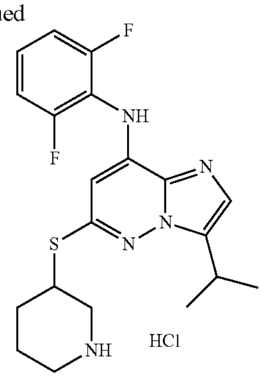

59

Step-1: Synthesis of 6-chloro-N-(2,6-difluorophenyl)-3-isopropylimidazo[1,2-b]pyridazin-8-amine

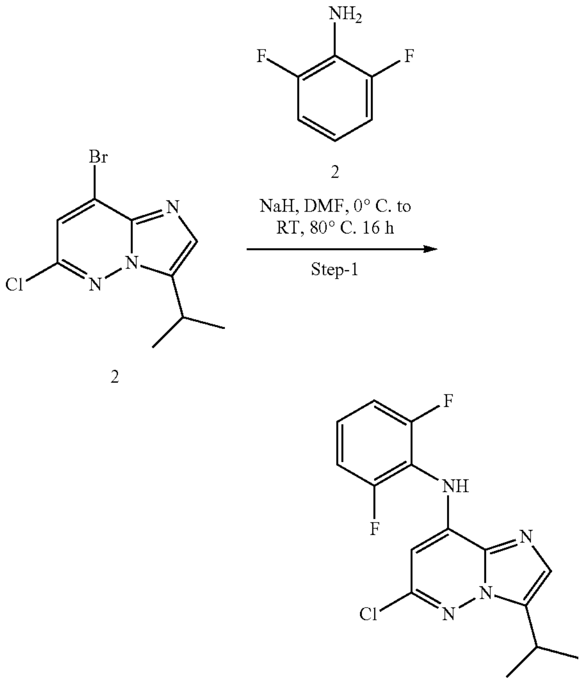

3

To a stirred solution of 2,6-difluoroaniline (2) (1.17 mL), 10.94 mmol, 3 eq.) in DMF (5 mL) was added sodium hydride (60% dispersion in oil) (0.437 g, 10.94 mmol, 3 eq.) at 0 °C. Reaction mixture was stirred at 0 °C for 30 minutes. Then addition of 8-bromo-6-chloro-3-isopropylimidazo[1,2-b]pyridazine (1) (1 g, 3.64 mmol, 1eq.) in DMF (5 mL) was done at 0 °C. Reaction mixture stirred at 0 °C for 1 hr. After complete conversion by TLC, reaction mixture was cooled, quenched with ice cold water (50 mL), extracted with ethyl acetate (3×50 mL). The combined organic layer washed with brine (50 mL), dried over sodium sulphate, filtered and evaporated under reduced pressure to get crude residue. The residue was purified by flash column chromatography using silica gel (100-200 mesh) (EtOAc/hexane, gradient 0-10% EtOAc) to afford the title compound as 6-chloro-N-(2,6-difluorophenyl)-3-isopropylimidazo[1,2-b]pyridazin-8-amine (3) as a brown oil. (Yield: 1 g, 85%). $R_f$=0.4 (4:1 Hexane/EtOAc). LCMS (m/z): 323.0 $(M+H)^+$. $^1H$ NMR (400 MHz, DMSO-$d_6$): δ=9.66 (s, 1H), 7.53-7.46 (m, 2H), 7.30 (t, J=8.4 Hz, 2H), 5.81 (s, 1H), 3.34-3.27 (m, 1H), 1.34 (d, J=6.8 Hz, 6H).

Step-3: Synthesis of tert-butyl (6-chloro-3-isopropylimidazo[1,2-b]pyridazin-8-yl)(2,6-difluorophenyl) carbamate

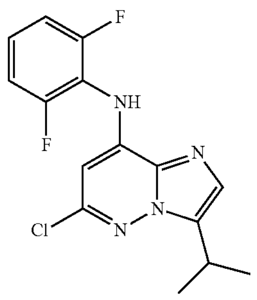

3

$Boc_2O$, DIPEA, DMAP, THF, 80° C., 16 h

Step-2

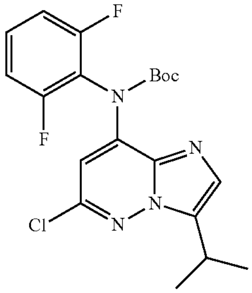

4

To a stirred solution of 6-chloro-N-(2,6-difluorophenyl)-3-isopropylimidazo[1,2-b]pyridazin-8-amine (3) (1 g, 3.10 mmol, 1 eq.) in THF (15 mL) was added, DIPEA (5.17 mL, 29.72 mmol, 10 eq.), $(Boc)_2O$ (6.82 mL, 29.72 mmol, 10 eq.) and DMAP (0.036 g, 0.297 mmol, 0.1 eq.) at room temperature. Reaction mixture was stirred at 80 °C for 16 h. The reaction mixture was allowed to cool to room temperature. THF was evaporated, added water (50 mL), extracted with ethyl acetate (3×50 mL). The combined organic layer was washed with brine (2×25 mL), dried over sodium sulphate, filtered and evaporated under reduced pressure to get crude residue as brown oil. The residue was purified by column chromatography using silica gel (100-200) mesh (EtOAc/hexane, gradient 5-10% EtOAc) to afford the title compound as tert-butyl (6-chloro-3-isopropylimidazo[1,2-b]pyridazin-8-yl)(2,6-difluorophenyl)carbamate (4) as a yellow oil. Yield: (1 g, 76%). $R_f$=0.8 (4:1 Hexane/EtOAc). LCMS (m/z): 422.86 $(M+H)^+$. $^1H$ NMR (400 MHz, DMSO-$d_6$): δ 7.49-7.44 (m, 3H), 7.19 (t, J=8.8 Hz, 2H), 3.33-3.26 (m, 1H), 1.42 (s, 9H), 1.30 (d, J=6.8 Hz, 6H).

Step-4: Synthesis of tert-butyl 3-((8-((tert-butoxycarbonyl)(2,6-difluorophenyl)amino)-3-isopropylimidazo[1,2-b]pyridazin-6-yl)thio)piperidine-1-carboxylate

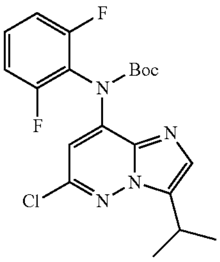

4

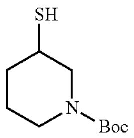

5

(i) 5 (2.5 eq.) NaH/DMF, 0° C., 15 min
(ii) 4 (1 eq.) 0° C., 1 h

Step-3

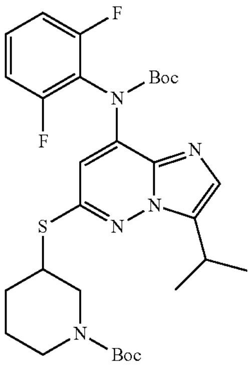

6

To a stirred solution of tert-butyl 3-mercaptopiperidine-1-carboxylate (5) (0.321 g, 1.48 mmol, 2.5 eq.) in DMF (3 mL) at 0 °C was added NaH (60% in mineral oil, (0.059 g, 1.48 mmol, 2.5 eq.). Reaction mixture was stirred at 0 °C for 10 minutes. Then addition of tert-butyl (6-chloro-3-isopropylimidazo[1,2-b]pyridazin-8-yl)(2,6-difluorophenyl)carbamate (4) (0.250 g, 0.592 mmol, 1 eq.) in DMF (3 mL) was done at 0 °C. Reaction mixture was stirred at 0 °C for 1 h. After complete conversion by TLC, reaction mixture was cooled, quenched with ice cold water (10 mL) and extracted with ethyl acetate (3×25 mL). The combined organic layer was washed with brine solution (25 mL), dried over sodium sulphate, filtered and evaporated under reduced pressure to get crude residue as brown oil. Crude residue was purified by silica phase column chromatography (EtOAc/hexane, with gradient 10-15% EtOAc), to afford the title compound as tert-butyl 3-((8-((tert-butoxycarbonyl)(2,6-difluorophenyl)amino)-3-isopropylimidazo[1,2-b]pyridazin-6-yl)thio)piperidine-1-carboxylate (6) as a yellow oil. (Yield=0.220 g, 61%),$R_f$=0.3 (4:1 Hexane/EtOAc). Note: Observed Cpd-6 88% along with de-boc of Cpd-6 5% by LCMS. LCMS (m/z): 604.1 $(M+H)^+$.

Step-5: Synthesis of N-(2,6-difluorophenyl)-3-isopropyl-6-(piperidin-3-ylthio)imidazo[1,2-b]pyridazin-8-amine hydrochloride

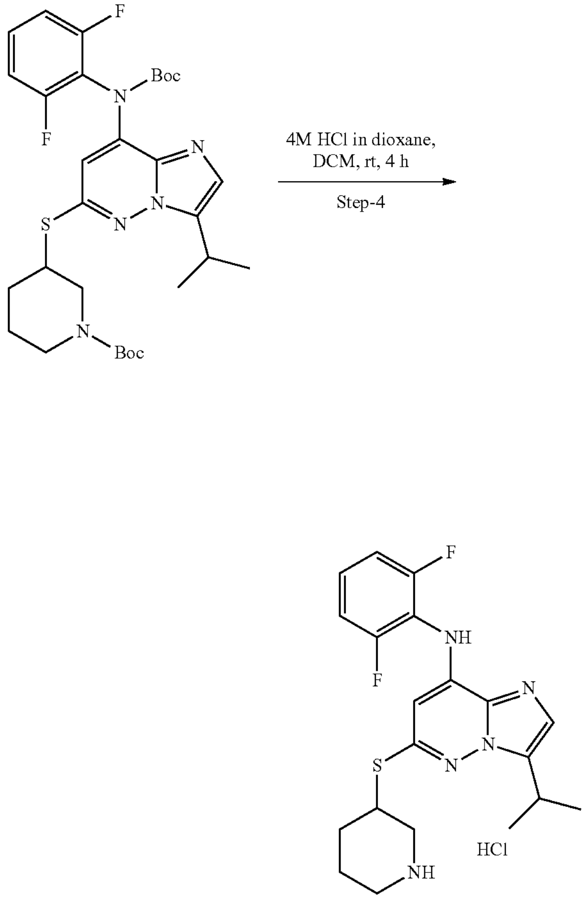

59

To a stirred solution of tert-butyl 3-((8-((tert-butoxycarbonyl)(2,6-difluorophenyl)amino)-3-isopropylimidazo[1,2-b]pyridazin-6-yl)thio)piperidine-1-carboxylate (0.220 g, 0.353 mmol, 1eq.) in DCM (5 mL) at 0 °C was added 4M HCl in 1,4-dioxane (3 mL) drop-wise and stirred at room temperature for 4 h. After completion of reaction by TLC, the reaction mixture was subjected to rotary evaporator for removal of volatiles. The obtained residue was submitted for preparative HPLC by using TFA buffer to get TFA salt of N-(2,6-difluorophenyl)-3-isopropyl-6-(piperidin-3-ylthio)imidazo[1,2-b]pyridazin-8-amine. To get compound as a HCl salt, obtained TFA salt was dissolved in ACN: water and treated with 2N aq. HCl at 0 °C and lyophilized to afford the title compound as N-(2,6-difluorophenyl)-3-isopropyl-6-(piperidin-3-ylthio)imidazo[1,2-b]pyridazin-8-amine hydrochloride as a white solid (59). (0.130 g, 81% yield). $R_f$=0.1 (9:1 DCM/MeOH). LCMS (m/z): 404.17 $(M+H)^+$. $^1$H-NMR (400 MHz, DMSO-$d_6$): δ 9.95 (s, 1H), 9.41-9.39 (m, 1H), 9.16-9.14 (m, 1H), 7.83 (s, 1H), 7.53-7.47 (m, 1H), 7.32 (t, J=8.4 Hz, 2H), 6.03 (s, 1H), 4.11-4.06 (m, 1H), 3.61-3.48 (m, 2H), 3.24-3.17 (m, 1H), 3.11-3.03 (q, J=10.4 Hz, 1H), 2.90 (m, 1H), 2.14-2.11 (m, 1H), 2.20 (m, 2H), 1.70-1.68 (m, 1H), 1.37 (d, J=6.8 Hz, 6H).

Example 70

Synthetic Scheme for N-(2-(1H-pyrazol-1-yl)benzyl)-3-isopropyl-6-(piperidin-4-ylthio)imidazo[1,2-b]pyridazin-8-amine hydrochloride

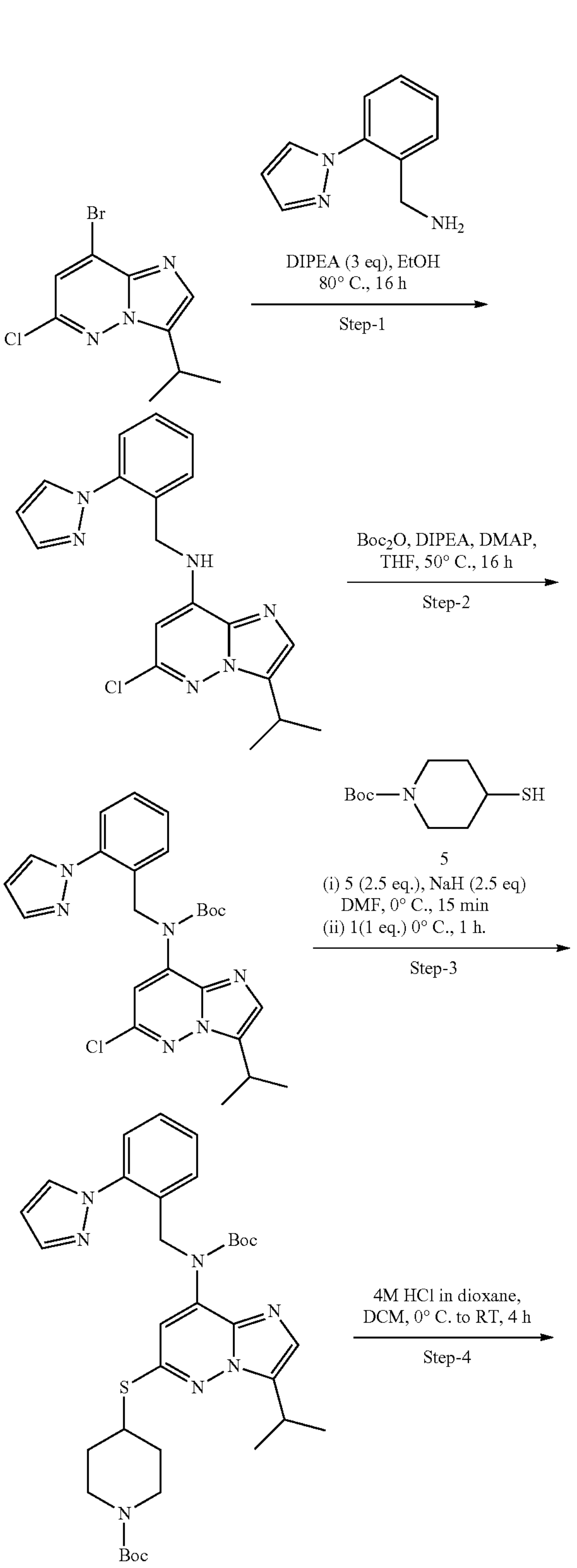

-continued

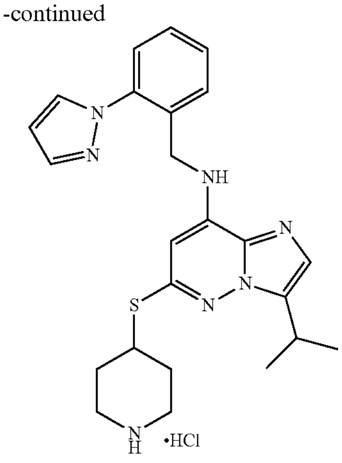

62

Step-1: Synthesis of N-(2-(1H-pyrazol-1-yl)benzyl)-6-chloro-3-isopropylimidazo[1,2-b]pyridazin-8-amine

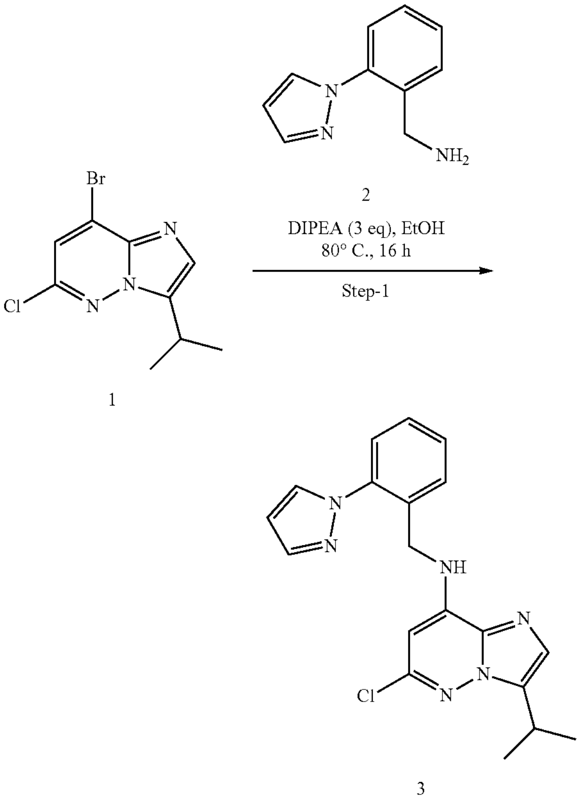

To a stirred solution of 8-bromo-6-chloro-3-isopropylimidazo[1,2-b]pyridazine (1) (0.5 g, 1.82 mmol, 1.0 eq.) in EtOH (10 mL) was added DIPEA (1.14 mL, 5.57 mmol, 3.0 eq.) and (2-(1H-pyrazol-1-yl)phenyl)methanamine (2) (0.628 mL, 4.927 mmol, 1.5 eq) at room temperature. The mixture was heated at 80 °C for 16 h. The progress of the reaction was monitored by TLC. After this time, the reaction mixture was cooled to room temperature and volatile portion was concentrated under reduced pressure. The obtained mass was diluted with water (100 mL), and extracted with ethyl acetate (3x50 mL). The combined organic layer was washed with brine solution (100 mL), dried over anhydrous sodium sulphate, filtered and concentrated under reduced pressure. The obtained crude was purified by combi-flash column (25-30% of EtOAc in Hexane) to afford the title compound N-(2-(1H-pyrazol-1-yl)benzyl)-6-chloro-3-isopropylimidazo[1,2-b]pyridazin-8-amine (3) (0.6 g, 89.81%) as a brown oil. $R_f$=0.4 (5:5 Hexane/EtOAc). LCMS (m/z): 367.0 $(M+H)^+$. $^1$H NMR (400 MHz, DMSO-$d_6$): δ 8.30-8.29 (m, 1H), 8.21 (d, J=2.4 Hz, 1H), 7.84 (s, 1H), 7.50-7.40 (m, 4H), 7.34 (s, 1H), 6.59-6.48 (s, 1H), 5.92 (s, 1H), 4.52 (s, 2H), 3.29-3.39 (m, 1H), 1.31-1.26 (d, J=11.2 Hz, 6H).

Step-2: Synthesis of tert-butyl (2-(1H-pyrazol-1-yl)benzyl)(6-chloro-3-isopropylimidazo[1,2-b]pyridazin-8-yl)carbamate

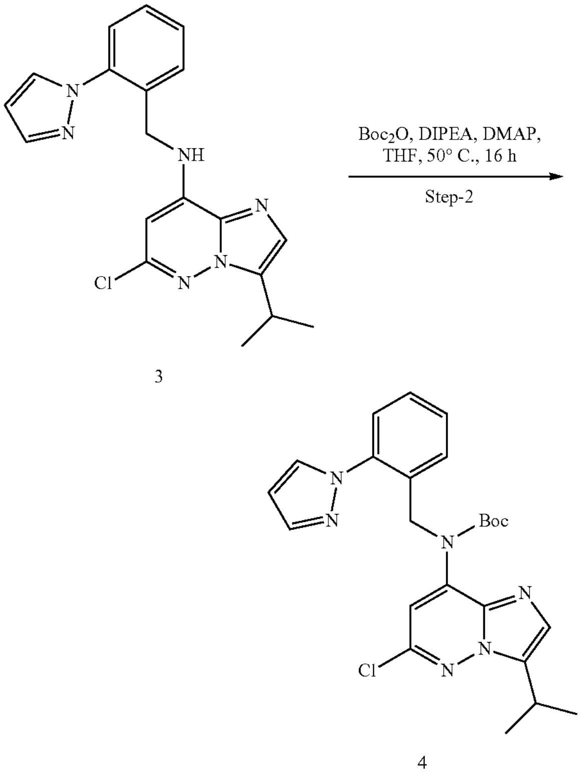

To a stirred solution of N-(2-(1H-pyrazol-1-yl)benzyl)-6-chloro-3-isopropylimidazo[1,2-b]pyridazin-8-amine (3) (0.6 g, 1.69 mmol, 1.0 eq.) in THF (6 mL) was added DIPEA (3 mL, 16.39 mmol, 10.0 eq.), Boc anhydride (3.57 mL, 16.39 mmol, 10.0 eq.) and DMAP (0.019 g, 0.169 mmol, 0.1 eq.) at room temperature. The resulting mixture was heated at 50 °C for 16 h. Progress of the reaction was monitored by TLC. After this time, the reaction mixture was cooled to room temperature. The volatile portion was concentrated under reduced pressure. The obtained mass was diluted with $H_2O$ (100 mL), and extracted with ethyl acetate (3x50 mL). The combined organic layer was washed with brine (50 mL), dried over anhydrous sodium sulphate, filtered and concentrated under reduced pressure. The obtained crude was purified by combi-flash column (12-15% of EtOAc in Hexane) to afford the title compound tert-butyl (2-(1H-pyrazol-1-yl)benzyl)(6-chloro-3-isopropylimidazo[1,2-b]pyridazin-8-yl)carbamate (4) (0.5 g, 65.47%) as yellow oil. $R_f$=0.6 (3:7, Hexane/EtOAc). LCMS (m/z): 415.1 $(M+H)^+$. $^1H$ NMR (400 MHz, DMSO-$d_6$): δ 7.85 (d, J=4.0 Hz, 1H), 7.64 (d, J=4.0 Hz, 2H), 7.58 (s, 1H), 7.46-7.28 (m, 4H), 7.16 (s, 1H), 6.31-6.30 (m, 1H), 5.30 (s, 1H), 3.33-3.28 (m, 1H), 1.30-1.25 (m, 15H).

Step-3: Synthesis of tert-butyl 4-((8-((2-(1H-pyrazol-1-yl)benzyl)(tert-butoxycarbonyl)amino)-3-isopropylimidazo[1,2-b]pyridazin-6-yl)thio)piperidine-1-carboxylate

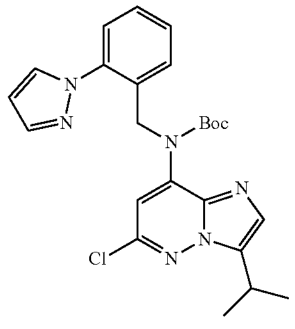

4

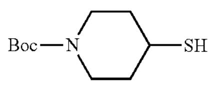

5

(i) 5 (2.5 eq.) NaH (2.5 eq.) DMF, 0° C., 15 min
(ii) 1 (1.0 eq.) 0° C., 1 h
Step-3

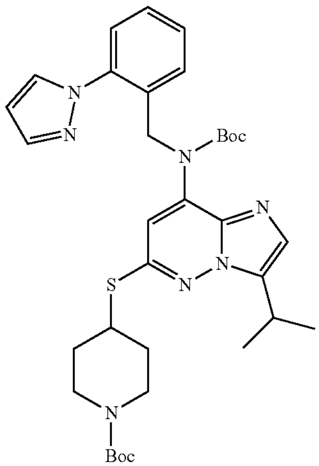

6

To a solution of tert-butyl 4-mercaptopiperidine-1-carboxylate (5) (0.295 g, 1.36 mmol, 2.5 eq.) in DMF (3 mL) was added NaH (60% in mineral oil, 0.065 g, 1.36 mmol, 2.5 eq.) at 0 °C. The mixture was stirred at 0 °C for 30 min. Then addition of tert-butyl (2-(1H-pyrazol-1-yl)benzyl)(6-chloro-3-isopropylimidazo[1,2-b]pyridazin-8-yl)carbamate (4) (0.250 g, 0.544 mmol, 1.0 eq.) in DMF (6 mL) was done at 0 °C. The stirring was continued at the same temperature for 30 min. After 30 min, reaction mixture was quenched with ice-cold water (50 mL) and extracted with ethyl acetate (3×50 mL). The combined organic layer was washed with brine (30 mL), dried over anhydrous sodium sulphate, filtered and concentrated under reduced pressure. The obtained crude was purified by column chromatography on silica gel (12-15% of EtOAc in Hexane), to afford the title compound tert-butyl 4-((8-((2-(1H-pyrazol-1-yl)benzyl)(tert-butoxycarbonyl)amino)-3-isopropylimidazo[1,2-b]pyridazin-6-yl)thio)piperidine-1-carboxylate (6) (0.300 g, 86.50%) as a yellow oil. $R_f$=0.3 (8:2 Hexane/EtOAc). LCMS (m/z): 648.1 $(M+H)^+$.

Step-4: Synthesis N-(2-(1H-pyrazol-1-yl)benzyl)-3-isopropyl-6-(piperidin-4-ylthio)imidazo[1,2-b]pyridazin-8-amine hydrochloride

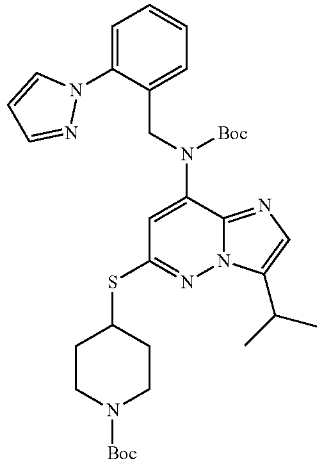

6

4M HCl in dioxane, DCM, 0° C. to RT, 4 h
Step-4

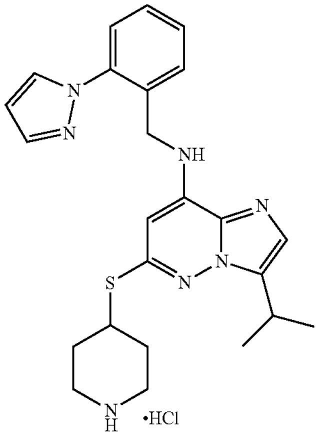

62

To a solution of tert-butyl 4-((8-((2-(1H-pyrazol-1-yl)benzyl)(tert-butoxycarbonyl)amino)-3-isopropylimidazo[1,2-b]pyridazin-6-yl)thio)piperidine-1-carboxylate (6) (0.200 g, 0.463 mmol, 1.0 eq.) in $CH_2Cl_2$ (15 mL) was added 4M HCl in dioxane (6 mL) at 0 °C and stirred at room temperature for 4 h. Progress of the reaction was monitored by TLC. After this time, volatile portion was concentrated under reduced pressure. The obtained crude was triturated with diethyl ether (2×5 mL) fallowed by pentane (2×3 mL) and lyophilized for 24 h to afford the title compound as N-(2-(1H-pyrazol-1-yl)benzyl)-3-isopropyl-6-(piperidin-4-ylthio)imidazo[1,2-b]pyridazin-8-amine hydrochloride (62, 0.180 g, 80.35%) as an off white solid. $R_f$=0.1 (1:1 Hexane/EtOAc). LCMS (m/z): 448.1 $(M+H)^+$. HPLC: 97.81%. $^1H$ NMR (400 MHz, DMSO-$d_6$): δ 9.01 (s, 1H), 8.85 (s, 1H), 8.57 (s, 1H), 8.19 (d, J=2 Hz, 1H), 7.81 (d, J=1.2 Hz, 1H), 7.75 (s, 1H), 7.55-7.54 (m, 1H), 7.49-7.42 (m, 3H), 6.57-

6.51 (m, 1H), 4.54-4.52 (m, 2H), 3.99-3.94 (m, 1H), 3.64 (m, 1H), 3.37-3.26 (m, 3H), 3.05-3.02 (m, 2H), 2.24-2.21 (m, 2H), 1.86-1.77 (m, 2H), 1.33 (d, J=6.8 Hz, 6H).

Example 71

Synthetic Scheme for 3-isopropyl-N—((S)-1-phenylethyl)-6-(piperidin-3-ylthio) imidazo [1, 2-a] pyrazin-8-amine di hydrochloride

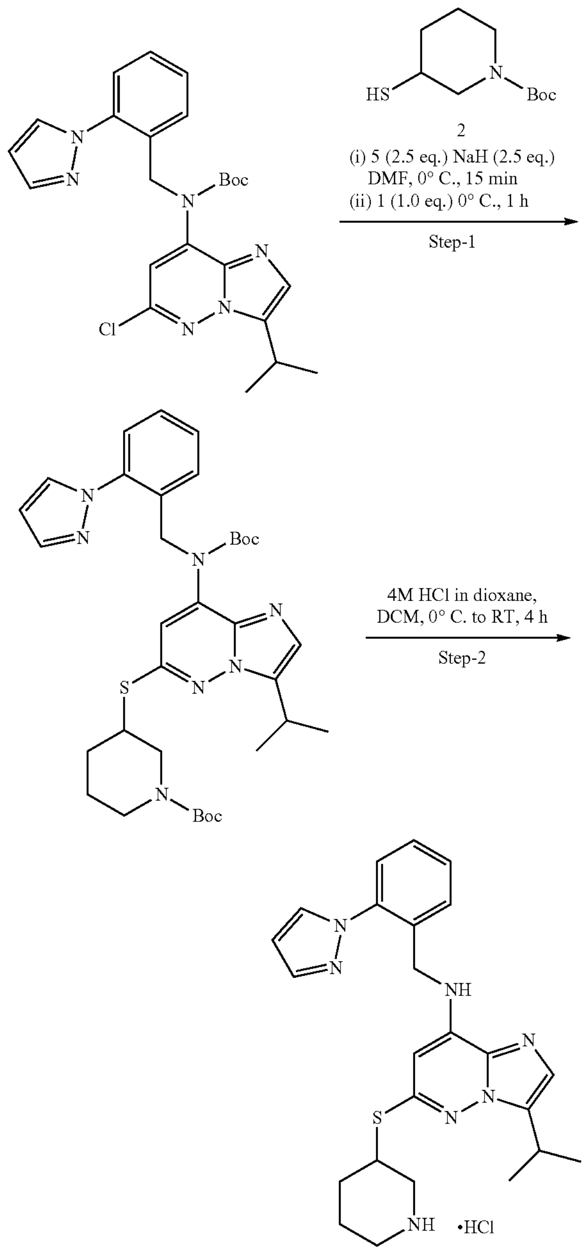

63

Step-1: Synthesis of tert-butyl 3-((8-((2-(1H-pyrazol-1-yl)benzyl)(tert-butoxycarbonyl)amino)-3-isopropylimidazo[1,2-b]pyridazin-6-yl)thio)piperidine-1-carboxylate

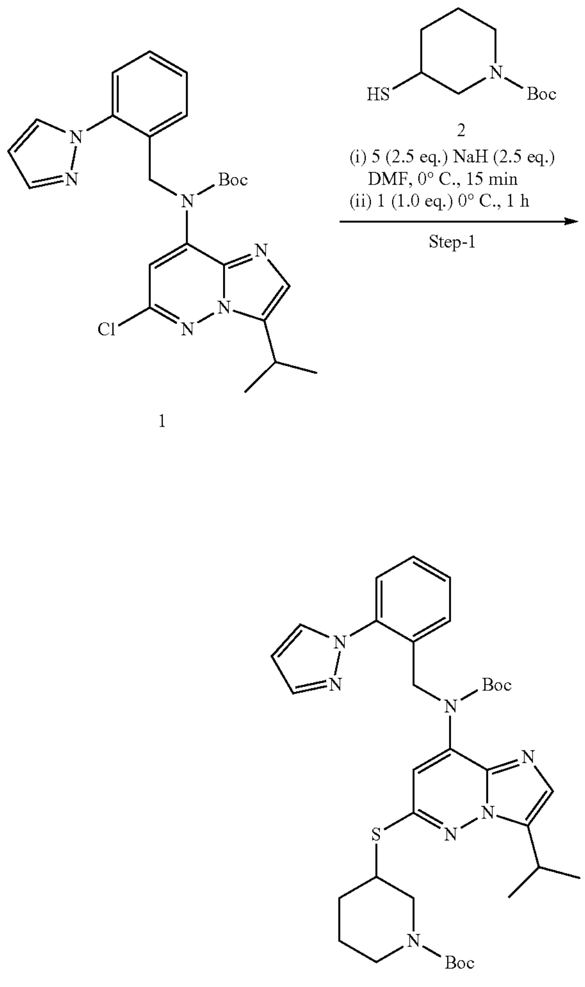

3

To a solution of tert-butyl 3-mercaptopiperidine-1-carboxylate (2) (0.295 g, 1.36 mmol, 5.0 eq.) in DMF (6 mL) was added NaH (60% in mineral oil, 0.065 g, 1.36 mmol, 2.5 eq.) at 0 °C and stirred at the same temperature for 30 min. Then addition of tert-butyl (2-(1H-pyrazol-1-yl) benzyl) (6-chloro-3-isopropylimidazo [1, 2-b]pyridazin-8-yl) carbamate (1) (0.250 g, 0.544 mmol, 1.0 eq.) in DMF (2 mL) was done at 0 °C. The resulting mixture was stirred at 0 °C for 30 min. After this time reaction mixture was quenched with ice-cold water (50 mL) and extracted with ethyl acetate (3×50 mL). The combined organic layer was washed with brine (30 mL), dried over anhydrous sodium sulphate, filtered and concentrated under reduced pressure. The obtained crude was purified by column chromatography on silica gel (15-20% of EtOAc in Hexane) to afford the title compound tert-butyl 3-((8-((tert-butoxycarbonyl)((S)-1-phenylethyl)amino)-3-isopropylimidazo[1,2-a]pyrazin-6-yl)thio)piperidine-1-carboxylate (3) (0.180 g, 51.90%) as a yellow oil. $R_f$=0.3 (4:1, Hexane/EtOAc); LCMS (m/z): 648.1 $(M+H)^+$.

Step-2: Synthesis N-(2-(1H-pyrazol-1-yl)benzyl)-3-isopropyl-6-(piperidin-3-ylthio)imidazo[1,2-b]pyridazin-8-amine hydrochloride

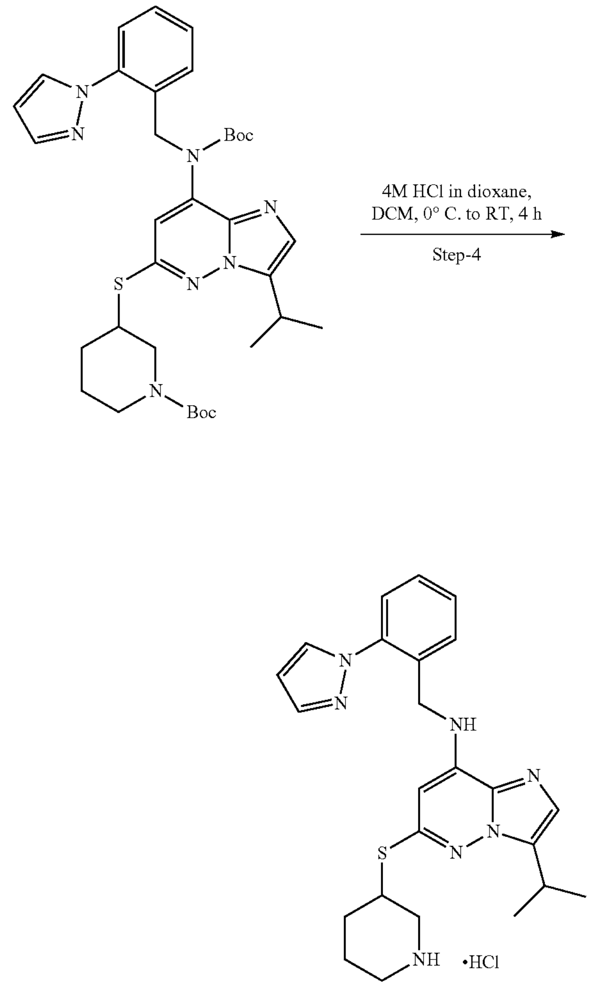

63

To a solution of tert-butyl 3-((8-((2-(1H-pyrazol-1-yl)benzyl)(tert-butoxycarbonyl)amino)-3-isopropylimidazo[1,2-b]pyridazin-6-yl)thio)piperidine-1-carboxylate (3) (0.180 g, 0.277 mmol, 1.0 eq.) in $CH_2Cl_2$ (9 mL) was added 4M HCl in dioxane (3.6 mL) at 0 °C and stirred at RT for 4 h. Progress of the reaction was monitored by TLC. After this time, volatile portion was concentrated under reduced pressure to get crude. The obtained crude was triturated with diethyl ether (2×5 mL) fallowed by pentane (2×3 mL) and lyophilized for 24 h to afford the title compound N-(2-(1H-pyrazol-1-yl)benzyl)-3-isopropyl-6-(piperidin-3-ylthio)imidazo[1,2-b]pyridazin-8-amine hydrochloride (63, 0.170 g, quantitative) as an off white solid. $R_f$=0.1 (1:1, Hexane/EtOAc). LCMS (m/z): 448.1 $(M+H)^+$. HPLC: 97.28%. $^1H$ NMR (400 MHz, DMSO-$d_6$): δ 9.31 (s, 1H), 9.06 (s, 1H), 8.59 (s, 1H), 8.19 (d, J=2 Hz, 1H), 7.81 (d, J=1.6 Hz, 1H), 7.76 (s, 1H), 7.55-7.42 (m, 4H), 6.57-6.56 (m, 1H), 6.14 (s, 1H), 4.54-4.53 (d, J=5.6 Hz, 2H), 4.07-4.02 (m, 1H), 3.58-3.55 (m, 2H), 3.49-3.42 (m, 1H), 3.05-3.02 (m, 1H), 2.90-2.89 (m, 1H), 2.13-2.10 (m, 1H), 1.86-1.83 (m, 2H), 1.73-1.68 (m, 1H), 1.35-1.31 (m, 6H).

Example 72

Synthetic Scheme for N-(2-ethoxybenzyl)-3-isopropyl-6-(piperidin-4-ylthio)imidazo[1,2-b]pyridazin-8-amine hydrochloride

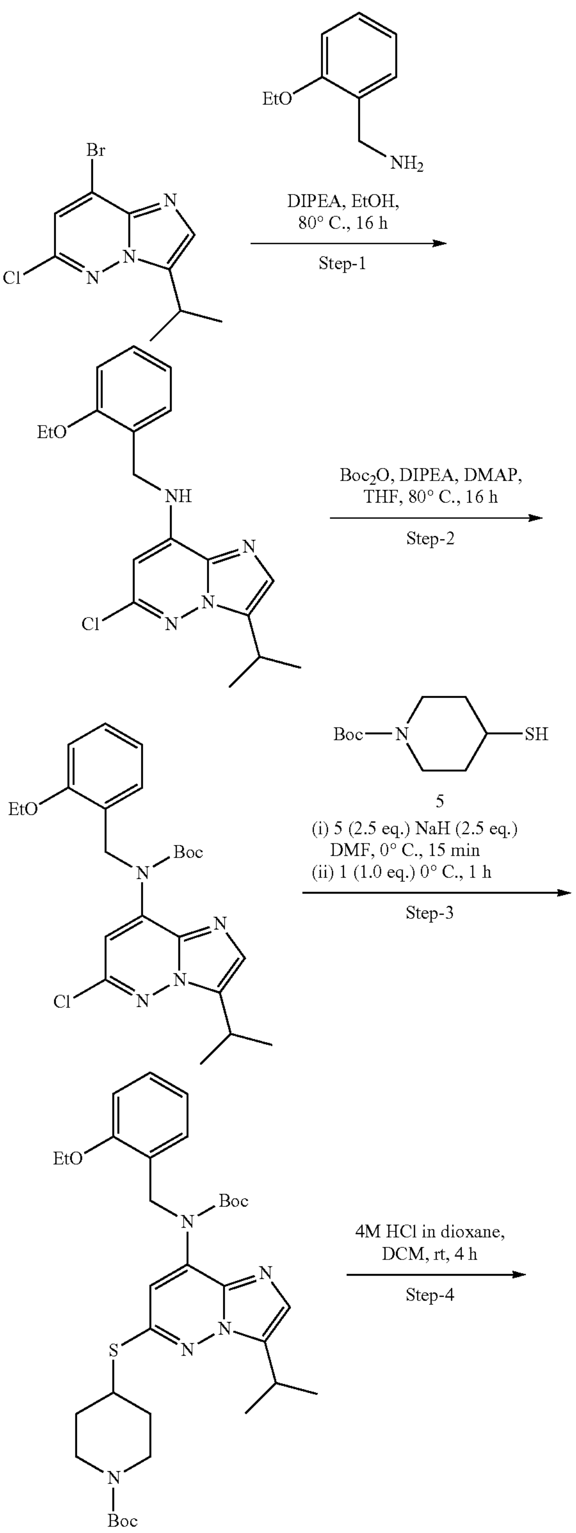

-continued

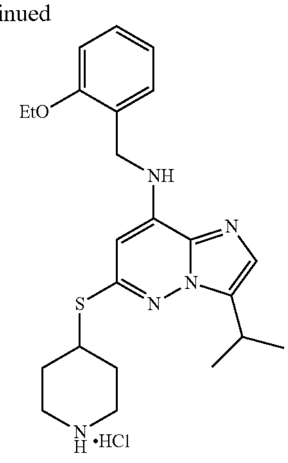

65

Step-1: Synthesis of 6-chloro-N-(2-ethoxybenzyl)-3-isopropylimidazo[1,2-b]pyridazin-8-amine

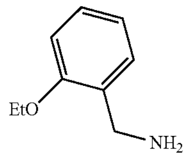

2

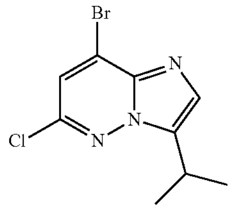

1

DIPEA, EtOH,
80° C., 16 h
Step-1

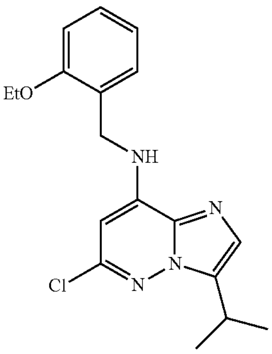

3

To a stirred solution of 8-bromo-6-chloro-3-isopropylimidazo[1,2-b]pyridazine (1) (0.2 g, 0.729 mmol, 1.0 eq.) in ethanol (5 mL) was added DIPEA (0.381 mL, 2.18 mmol, 3.0 eq.) and (2-ethoxyphenyl)methanamine (2) (0.22 mL), 1.46 mmol, 2.0 eq.) at ambient temperature. The reaction mixture was heated at 80 °C for 12 h. After complete conversion by TLC, the reaction mixture was allowed to cool to room temperature, ethanol was evaporated under reduced pressure to get the crude residue. The crude residue was diluted with water (25 mL), extracted with ethyl acetate (3×25 mL). The combined organic layer was washed with brine (25 mL), dried over sodium sulphate, filtered, and evaporated under reduced pressure to get the crude residue. The crude residue was purified by column chromatography using silica gel (100-200) mesh (with gradient elution of 12-15% EtOAc/hexane) to afford the title compound as 6-chloro-N-(2-ethoxybenzyl)-3-isopropylimidazo[1,2-b]pyridazin-8-amine (3) as yellow oil. (Yield: 0.2 g, 79%). $R_f$=0.4 (4:1 Hexane/EtOAc). LCMS (m/z): 345.0 $(M+H)^+$. $^1H$ NMR (400 MHz, DMSO-$d_6$): δ=8.20, (s, 1H), 7.32 (s, 1H), 7.28-7.19 (m, 2H), 7.01 (d, J=8.8 Hz 1H), 6.88 (t, J=7.2 Hz, 1H), 6.07 (s, 1H), 4.48 (s, 2H), 4.18-3.96 (m, 2H) 3.30-3.18 (s, 1H), 1.48-1.35 (t, J=6.8 Hz, 3H), 1.30 (d, J=6.8 Hz, 6H).

Step-2: Synthesis of tert-butyl (6-chloro-3-isopropylimidazo[1,2-b]pyridazin-8-yl)(2-ethoxybenzyl)carbamate

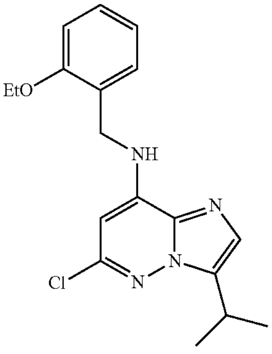

3

$Boc_2O$, DIPEA, DMAP,
THF, 80° C., 16 h
Step-2

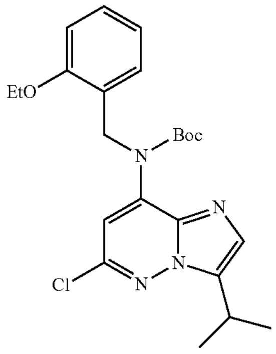

4

To a stirred solution of 6-chloro-N-(2-ethoxybenzyl)-3-isopropylimidazo[1,2-b]pyridazin-8-amine (3) (0.200 g, 0.581 mmol, 1.0 eq.) in THF (5 mL) was added DIPEA (1.0 mL, 5.81 mmol, 10.0 eq.), Boc anhydride (1.33 mL, 5.81 mmol, 10.0 eq.) and DMAP (0.007 g, 0.058 mmol, 0.1 eq.) at room temperature. Reaction mixture was stirred at 80 °C for 16 h. After complete conversion by TLC, the reaction mixture was cooled to room temperature, THE was evaporated under reduced pressure to get the crude residue. To the crude residue water (20 mL) was added, extracted with ethyl acetate (3×25 mL). The combined organic layer was washed with brine (10 mL), dried over sodium sulphate, filtered and evaporated under reduced pressure to get the crude residue. The crude residue was purified by column chromatography using silica gel (100-200) mesh (with a gradient elution of 7-10% of EtOAc: n-Hexane) to afford title compound as tert-butyl (6-chloro-3-isopropylimidazo[1,2-b]pyridazin-8-yl)(2-ethoxybenzyl)carbamate (4) as brown oil. (Yield: 0.210 g, 81%). $R_f$=0.6 (4:1 Hexane/EtOAc). LCMS (m/z): 445.1 $(M+H)^+$. $^1H$ NMR (400 MHz, DMSO-$d_6$): δ=7.643 (s, 1H), 7.30 (d, J=7.2 Hz 1H), 7.27 (s, 1H), 7.19 (t, J=7.2 Hz, 1H), 6.89-6.80 (m, 2H), 5.262 (s, 2H), 4.09-3.98 (m, 1H), 3.80-3.68 (m, 2H), 1.41-1.26 (m, 15H), 0.88-0.72 (t, J=6.8 Hz, 3H).

Step-3: Synthesis of tert-butyl 4-((8-((tert-butoxycarbonyl)(2-ethoxybenzyl)amino)-3-isopropylimidazo[1,2-b]pyridazin-6-yl)thio)piperidine-1-carboxylate

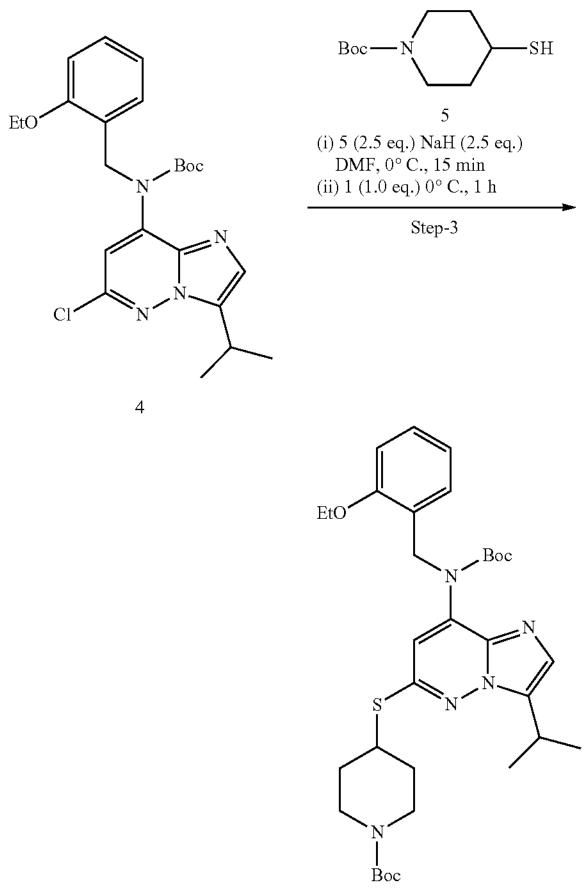

4 5 6

To a stirred solution of tert-butyl 4-mercaptopiperidine-1-carboxylate (5) (0.256 g, 1.182 mmol, 2.5 eq.) in DMF (2 mL) at 0 °C was added NaH (60% in mineral oil, 0.047 g, 1.182 mmol, 2.5 eq.) and stirred for 10 minutes. Then added a solution of tert-butyl(6-chloro-3-isopropylimidazo[1,2-b]pyridazin-8-yl)(2-ethoxybenzyl)carbamate (4) (0.210 g, 0.473 mmol, 1.0 eq.) in DMF (2 mL). The resulting mixture was stirred at room temperature for 1 h. Reaction mixture was diluted with ice cold water (25 mL) and extracted with ethyl acetate (3×25 mL). The combined organic layer washed with brine (25 mL), dried over sodium sulfate, evaporated under reduced pressure to provide crude compound. Obtained crude compound was purified by silica phase column chromatography using silica gel (100-200) mesh [with a gradient elution of 15-20% of Hexane/EtOAc] to afford the title compound as tert-butyl 4-((8-((tert-butoxycarbonyl)(2-ethoxybenzyl)amino)-3-isopropylimidazo[1,2-b]pyridazin-6-yl)thio)piperidine-1-carboxylate (6) as a yellow oil. (0.150 g, 50% yield). $R_f$=0.3 (4:1 Hexane/EtOAc). LCMS (m/z): 626.23 $(M+H)^+$.

Step-4: Synthesis of N-(2-ethoxybenzyl)-3-isopropyl-6-(piperidin-4-ylthio)imidazo[1,2-b]pyridazin-8-amine hydrochloride

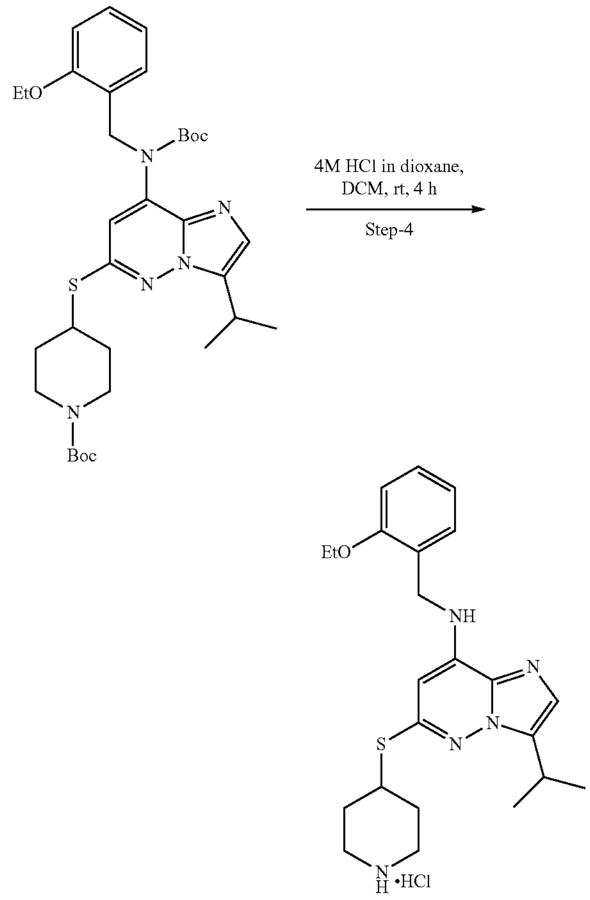

65

To a stirred solution of tert-butyl 4-((8-((tert-butoxycarbonyl)(2-ethoxybenzyl)amino)-3-isopropylimidazo[1,2-b]pyridazin-6-yl)thio)piperidine-1-carboxylate (6) (0.150 g, 0.240 mmol, 1eq.) in DCM (4 mL) at 0 °C was added 4M HCl in 1,4-dioxane (2 mL) drop-wise. Reaction mixture was stirred at room temperature for 4 h. After complete conversion by TLC, the reaction mixture was subjected to rotary evaporator for removal of volatiles. The obtained residue was triturated with diethyl ether (3×10 mL), EtOAc (2×10 mL) and lyophilized for 24 h. to get the title compound as N-(2-ethoxybenzyl)-3-isopropyl-6-(piperidin-4-ylthio)imidazo[1,2-b]pyridazin-8-amine hydrochloride as white solid (65). (Yield: 0.080 g, 72%). $R_f$=$R_f$=0.1 (9:1 DCM/MeOH). LCMS (m/z): 426.1 $(M+H)^+$. $^1H$ NMR (400 MHz, DMSO-$d_6$): δ=9.19-8.77 (m, 2H), 8.44 (s, 1H), 7.79 (s, 1H), 7.39-7.20 (m, 2H), 7.03 (d, J=8.0 Hz, 1H), 6.91 (t, J=7.2 Hz, 1H), 6.36 (s, 1H), 4.51 (d, J=5.6 Hz, 2H), 4.11 (q, J=6.8, 7.2 Hz, 2H), 4.06-3.93 (m, 1H) 3.35-3.23 (m, 3H), 3.12-2.97 (m, 2H), 2.32-2.18 (m, 2H), 1.93-1.75 (m, 2H), 1.45-1.28 (m, 9H).
Example 73
Synthetic Scheme for N-(2-isopropoxybenzyl)-3-isopropyl-6-(piperidin-4-ylthio)imidazo[1,2-b]pyridazin-8-amine hydrochloride
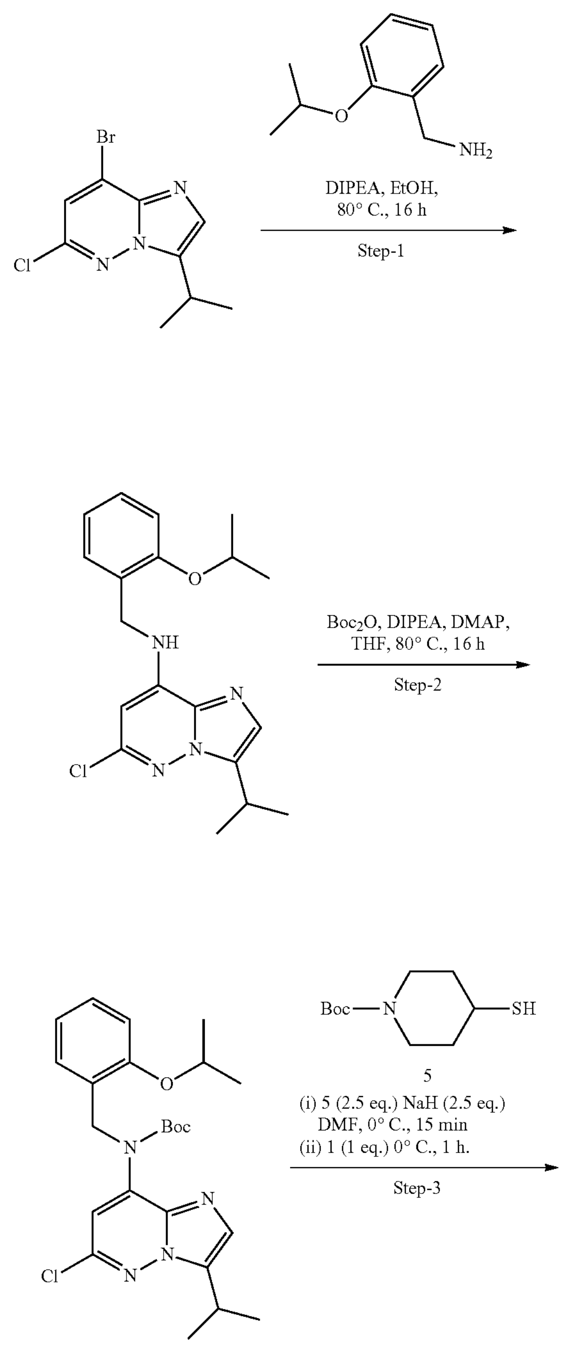
-continued
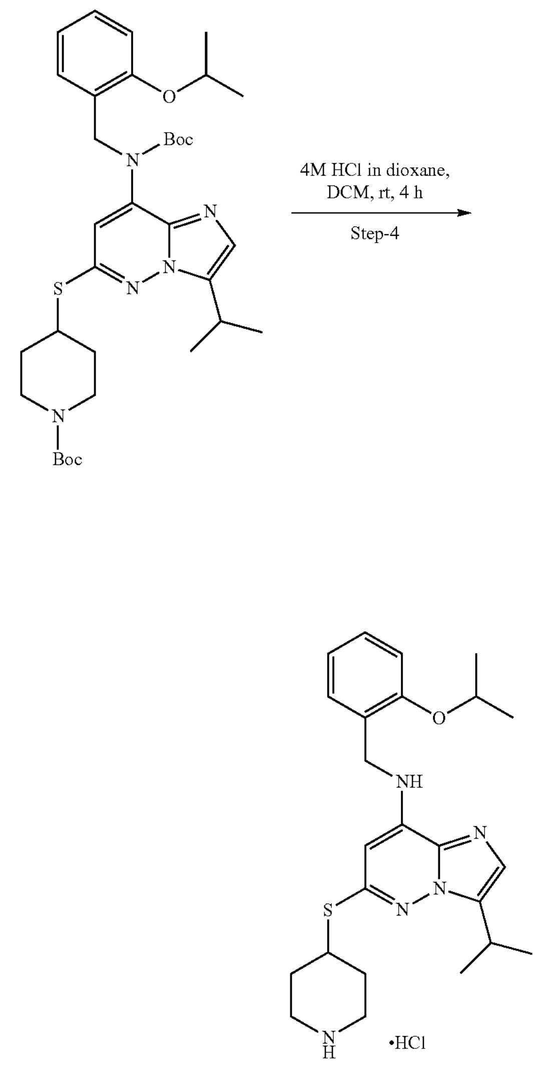
67
Step-1: Synthesis of 6-chloro-N-(2-isopropoxybenzyl)-3-isopropylimidazo[1,2-b]pyridazin-8-amine
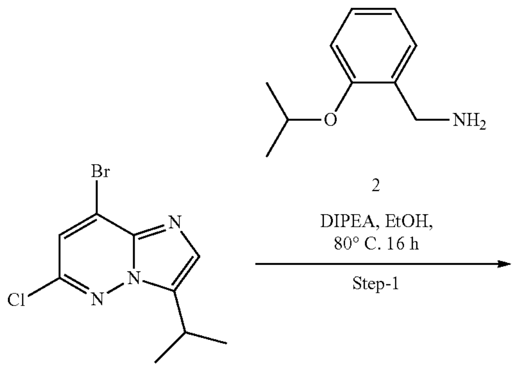
1

-continued

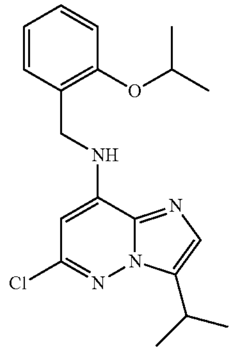

3

-continued

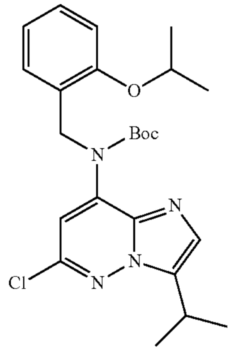

4

To a stirred solution of 8-bromo-6-chloro-3-isopropylimidazo[1,2-b]pyridazine (1) (0.2 g, 0.729 mmol, 1.0 eq.) in ethanol (5 mL) was added DIPEA (0.381 mL, 2.18 mmol, 3.0 eq.) and (2-isopropoxyphenyl)methanamine (2) (0.241 g, 1.45 mmol, 2eq.) at ambient temperature, Then reaction mixture was heated at 80 °C for 12 h. After complete conversion by TLC, reaction mixture was cooled, reaction mixture was heated at 80 °C for 16 h. After complete conversion by TLC, the reaction mixture was allowed to cool to room temperature, ethanol was evaporated under reduced pressure to get the crude residue. The crude residue was diluted with water (25 mL), extracted with ethyl acetate (3×25 mL). The combined organic layer was washed with brine (25 mL), dried over sodium sulphate, filtered and concentrated under reduced pressure to get the crude residue. The crude residue was purified by column chromatography using silica gel (100-200) mesh (with gradient elution of 15-20% EtOAc/hexane) to afford the title compound as 6-chloro-N-(2-isopropoxybenzyl)-3-isopropylimidazo[1,2-b]pyridazin-8-amine (3) as a brown oil (0.210 gm, 80%). $R_f$=0.5 (7:3 Hexane/EtOAc). LCMS (m/z): 359.37 $(M+H)^+$. $^1$H NMR (400 MHz, DMSO-$d_6$): δ=8.19 (s, 1H), 7.33 (s, 1H) 7.29-7.18 (m, 2H), 7.03 (d, J=8.4 Hz, 1H) 6.86 (t, J=7.6, 7.2 Hz, 1H), 6.07 (s, 1H), 4.78-4.64 (m, 1H), 4.46 (s, 2H), 3.32-3.19 (m, 1H) 1.42-1.21 (m, 12H)

Step-2: Synthesis of tert-butyl (6-chloro-3-isopropylimidazo[1,2-b]pyridazin-8-yl)(2-isopropoxybenzyl) carbamate To a stirred solution of 6-chloro-N-(2-isopropoxybenzyl)-3-isopropylimidazo[1,2-b]pyridazin-8-amine (3) (0.21 g, 0.586 mmol, 1.0 eq.) in THF (6 mL) was added DIPEA (1.02 mL, 5.86 mmol, 10.0 eq.), Boc anhydride (1.34 mL, 5.86 mmol, 10.0 eq.) and DMAP (0.007 g, 0.058 mmol, 0.1 eq.) at ambient temperature. Reaction mixture was stirred at 80 °C for 16 h. After complete conversion by TLC, the reaction mixture was cooled, THF was evaporated under reduced pressure to get the crude residue. To the crude residue, water (20 mL) was added and extracted with ethyl acetate (3×25 mL). The combined organic layer was washed with brine (25 mL), dried over sodium sulphate, evaporated under reduced pressure to get the crude residue. The crude residue was purified by column chromatography using silica gel (100-200) mesh (with a gradient elution of 6-10% of EtOAc: n-Hexane) to afford title compound as tert-butyl (6-chloro-3-isopropylimidazo[1,2-b]pyridazin-8-yl)(2-isopropoxybenzyl)carbamate (4) as brown oil. (Yield: 0.230 g, 85%). $R_f$=0.6 (4:1 Hexane/EtOAc). LCMS (m/z): 459.1 $(M+H)^+$. $^1$H NMR (400 MHz, DMSO-$d_6$): δ=7.64 (s, 1H), 7.36 (d, J=7.6 Hz, 1H), 7.22 (s, 1H), 7.17 (t, J=8.4, 7.2 Hz, 1H), 6.89-6.80 (m, 2H), 5.22 (s, 2H), 4.44-4.32 (m, 1H), 3.41-3.32 (m, 1H), 1.37 (s, 9H), 1.34 (d, J=6.8 Hz, 6H), 0.78 (d, J=5.6 Hz, 6H).

Step-3: Synthesis of tert-butyl 4-((8-((tert-butoxycarbonyl)(2-isopropoxybenzyl)amino)-3-isopropylimidazo[1,2-b]pyridazin-6-yl)thio)piperidine-1-carboxylate

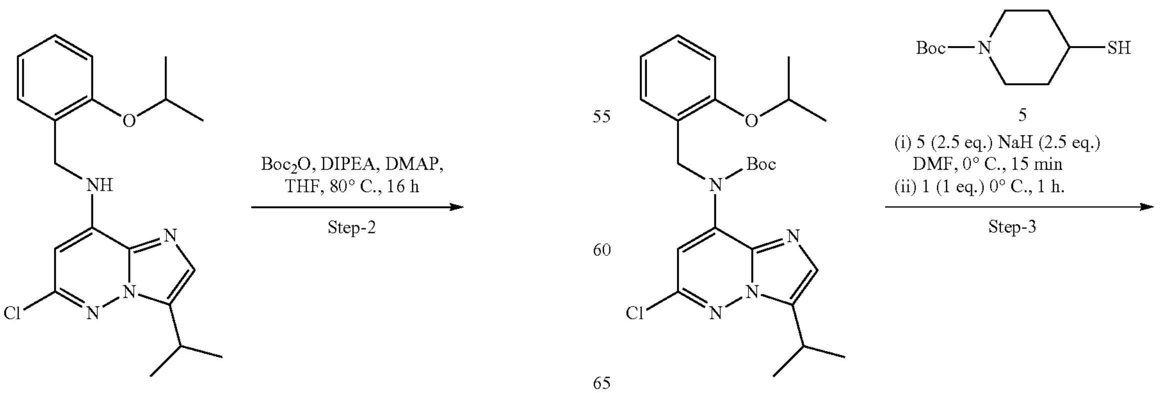

3 4

-continued

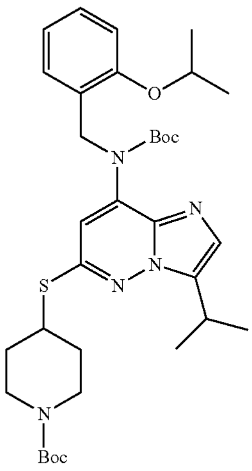

6

To a stirred solution of tert-butyl 4-mercaptopiperidine-1-carboxylate (5) (0.272 g, 1.25 mmol, 2.5 eq.) in DMF (3 mL) at 0 °C was added NaH (60% in mineral oil, 0.050 g, 1.25 mmol, 2.5 eq.) and stirred for 10 minutes. Then added a solution of (4) (0.230 g, 0.502 mmol, 1.0 eq.) in DMF (2 mL). The resulting reaction mixture was stirred at room temperature for 1 h. Reaction mixture was diluted with ice cold water (25 mL) and extracted with EtOAc (3×25 mL). The combined organic layer washed with brine (25 mL), dried over $Na_2SO_4$, filtered and concentrated under reduced pressure to provide crude residue. Crude residue was purified by silica phase column chromatography using silica gel (100-200) mesh (EtOAc/hexane, gradient 0-30% EtOAc) to afford the title compound as tert-butyl 4-((8-((tert-butoxycarbonyl)(2-isopropoxybenzyl)amino)-3-isopropylimidazo[1,2-b]pyridazin-6-yl)thio)piperidine-1-carboxylate (6) as a yellow oil. (0.250 g, 78% yield). $R_f$=0.4 (7:3 Hexane/EtOAc). LCMS (m/z): 640.34M+H)$^+$;

Step-4: Synthesis of N-(2-isopropoxybenzyl)-3-isopropyl-6-(piperidin-4-ylthio)imidazo[1,2-b]pyridazin-8-amine hydrochloride

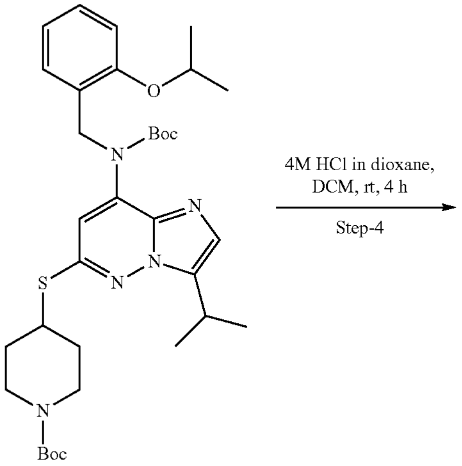

-continued

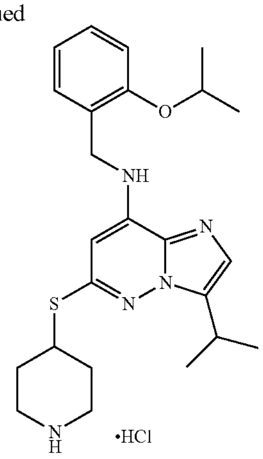

67

To a stirred solution of tert-butyl 4-((8-((tert-butoxycarbonyl)(2-isopropoxybenzyl)amino)-3-isopropylimidazo[1,2-b]pyridazin-6-yl)thio)piperidine-1-carboxylate (6) (0.250 g, 0.391 mmol, 1.0 eq.) in DCM (4 mL) at 0 °C was added 4M HCl in 1,4-dioxane (2 mL). Reaction mixture was stirred at room temperature for 4 h. After complete conversion by TLC, the reaction mixture was subjected to rotary evaporator for removal of volatiles. The obtained residue was purified by Prep-HPLC (TFA buffer was used). To get compound as a HCl salt, obtained TFA salt was dissolved in ACN: water and treated with 2N aq. HCl at 0 °C and lyophilized to afford title compound as N-(2-isopropoxybenzyl)-3-isopropyl-6-(piperidin-4-ylthio)imidazo[1,2-b]pyridazin-8-amine hydrochloride (67) as an off white solid. (0.035 g, 19% yield). $R_f$=0.1 (9:1 DCM/MeOH). LCMS (m/z): 440.45M+H)$^+$; $^1$H NMR (400 MHz, DMSO-$d_6$): δ=9.13 (s, 1H), 8.97 (s, 1H), 8.66 (s, 1H), 7.89 (s, 1H), 7.32 (dd, J=7.6, 1.2 Hz 1H), 7.25 (t, J=8.4, 7.2 Hz 1H), 7.05 (d, J=8.0 Hz, 1H), 6.88 (t, J=7.6, 7.2 Hz, 1H), 6.41 (s, 1H), 4.26-4.13 (m, 1H), 4.49 (d, J=5.6 Hz, 2H), 4.07-3.94 (m, 1H), 3.42-3.33 (m, 1H), 3.32-3.20 (m, 2H), 3.12-2.96 (m, 2H), 2.31-2.19 (m, 2H), 1.94-1.75 (m, 2H), 1.42-1.28 (m, 12H).

Example 74

Synthetic Scheme for N-(2-(difluoromethoxy)benzyl)-3-isopropyl-6-(piperidin-4-ylthio)imidazo[1,2-b]pyridazin-8-amine hydrochloride

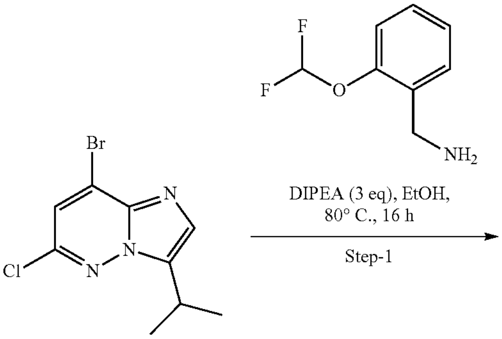

-continued

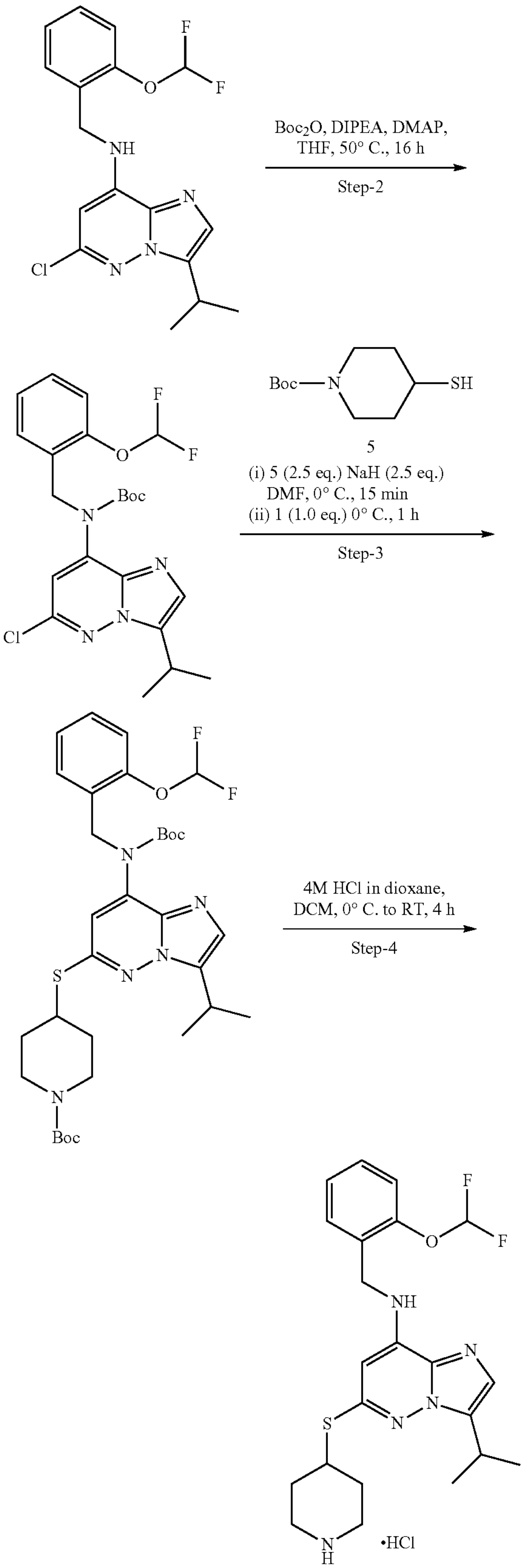

66

Step-1: Synthesis of 6-chloro-N-(2-(difluoromethoxy)benzyl)-3-isopropylimidazo[1,2-b]pyridazin-8-amine

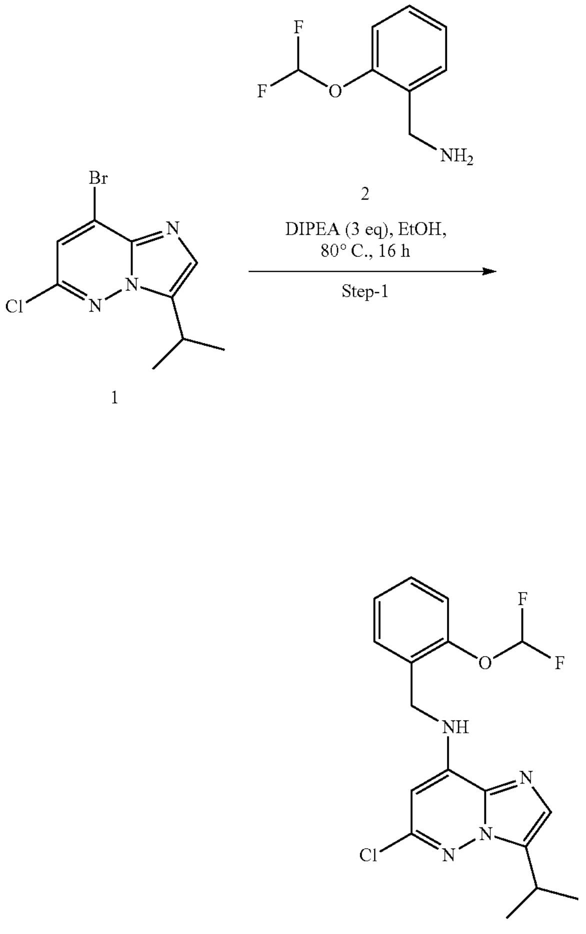

3

To a stirred solution of 8-bromo-6-chloro-3-isopropylimidazo[1,2-a]pyrazine (1) (0.2 g, 0.729 mmol, 1.0 eq.) in EtOH (4 mL) was added DIPEA (0.4 mL, 4.35 mmol, 3.0 eq.) and (2-(difluoromethoxy)phenyl)methanamine (2) (0.2 g, 1.45 mmol, 2.0 eq.) at room temperature. The reaction mixture was heated at 80 °C for 16 h. Progress of the reaction was monitored by TLC. After this time, the reaction mixture was cooled to room temperature and volatile portion was concentrated under reduced pressure. The obtained mass was diluted with $H_2O$ (100 mL), and extracted with ethyl acetate (3x50 mL). The combined organic layer was washed with brine (100 mL), dried over anhydrous sodium sulphate, filtered and concentrated under reduced pressure. The obtained crude was purified by combi-flash column (EtOAc/hexane, 1:6) to afford the title compound (S)-6-chloro-3-isopropyl-N-(1-phenylethyl) imidazo [1, 2-a] pyrazin-8-amine (3) (0.200 g, 74.85%) as a brown oil. $R_f$=0.4 (1:1, Hexane/EtOAc). LCMS (m/z): 367.0 $(M+H)^+$. $^1H$ NMR (400 MHz, DMSO-$d_6$): δ 8.32 (s, 1H), 7.48-7.11 (m, 6H), 6.02 (s, 1H), 4.57 (s, 2H), 3.25-3.22 (m, 1H), 1.31 (d, J=8 Hz), 6H).

Step-2: Synthesis of tert-butyl (6-chloro-3-isopropylimidazo[1,2-b]pyridazin-8-yl)(2-(difluoromethoxy)benzyl)carbamate

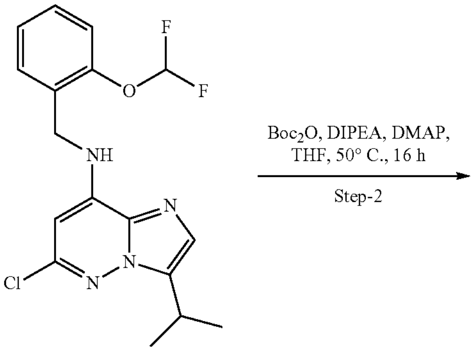

3

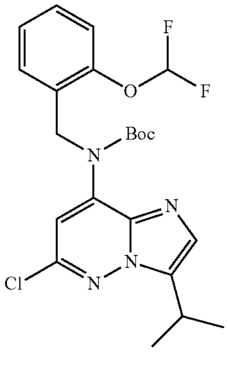

4

To a stirred solution of 6-chloro-N-(2-(difluoromethoxy)benzyl)-isopropylimidazo[1,2-b]pyridazin-8-amine (3) (0.200 g, 0.545 mmol, 1.0 eq.) in THF (10 mL) was added DIPEA (2 mL, 5.45 mmol, 10.0 eq.), Boc anhydride (2 mL, 5.45 mmol, 10.0 eq.) and DMAP (6.65 mg, 0.054 mmol, 0.1 eq.) at room temperature. The mixture was heated at 50 °C for 16 h. Progress of the reaction was monitored by TLC. After this time, the reaction mixture was cooled to room temperature. Volatile portion was concentrated under reduced pressure. The obtained mass was diluted with water (100 mL), and extracted with ethyl acetate (3×50 mL). The combined organic layer was washed with brine (50 mL), dried over anhydrous sodium sulphate, filtered and concentrated under reduced pressure. The obtained crude was purified by combi-flash column (EtOAc/hexane, 1:6) to afford the title compound tert-butyl (S)-(6-chloro-3-isopropylimidazo [1, 2-a]pyrazin-8-yl)(1-phenylethyl)carbamate (4) (0.250 g, 98.20%) as yellow oil. $R_f$=0.7 (8:2 Hexane/EtOAc). LCMS (m/z): 467.07 $(M+H)^+$. $^1$H NMR (400 MHz, DMSO-$d_6$): δ 7.65 (s, 1H), 7.47 (d, J=7.6 Hz, 2H), 7.38 (s, 1H), 7.32-7.28 (m, 1H), 7.19-6.93 (m, 3H), 5.33 (s, 2H), 1.35-1.32 (m, 15H). $^{19}$F NMR: (s, −80.062).

Step-3: Synthesis of tert-butyl 4-((8-((tert-butoxycarbonyl)(2-(difluoromethoxy)benzyl)amino)-3-isopropylimidazo[1,2-b]pyridazin-6-yl)thio)piperidine-1-carboxylate

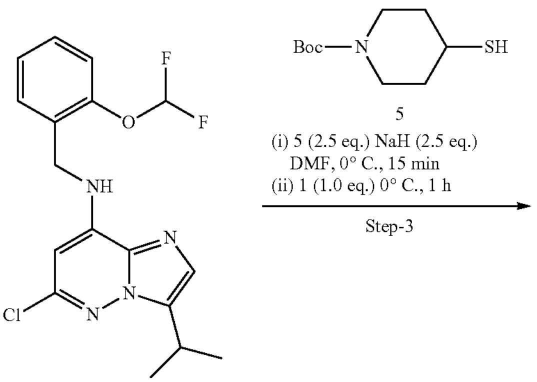

4

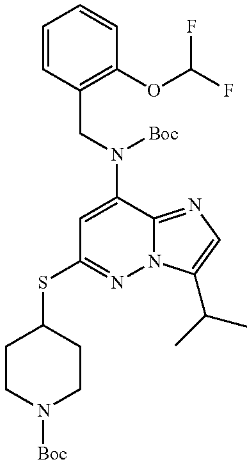

6

To a solution of tert-butyl 4-mercaptopiperidine-1-carboxylate (5) (0.290 g, 1.33 mmol, 2.5 eq.) in DMF (3 mL) was added NaH (60% in mineral oil, 0.064 g, 1.33 mmol, 2.5 eq.) at 0 °C. The mixture was stirred at the same temperature for 30 min. Then addition of tert-butyl (6-chloro-3-isopropylimidazo[1,2-b]pyridazin-8-yl)(2-(difluoromethoxy)benzyl)carbamate (4) (0.250 g, 0.535 mmol, 1.0 eq.) in DMF (2 mL) was done at 0 °C. The resulting mixture was stirred at 0 °C for 30 min. Progress of the reaction was monitored by TLC. After this time, reaction mixture was quenched with ice-cold water (50 mL) and extracted with ethyl acetate (3×50 mL). The combined organic layer was washed with brine (30 mL), dried over anhydrous sodium sulphate, filtered and concentrated under reduced pressure. The obtained crude was purified by column chromatography on silica gel (12-15% of EtOAc in Hexane) to afford the title compound tert-butyl 4-((8-((tert-butoxycarbonyl)(2-(difluoromethoxy)benzyl)amino)-3-isopropylimidazo[1,2-b]pyridazin-6-yl)thio)piperidine-1-carboxylate (6) (0.300 g, 86.49%) as a yellow oil. $R_f$=0.3 (8:2 Hexane/EtOAc). LCMS (m/z): 648.3 $(M+H)^+$.

Step-4: Synthesis N-(2-(difluoromethoxy)benzyl)-3-isopropyl-6-(piperidin-4-ylthio)imidazo[1,2-b]pyridazin-8-amine hydrochloride

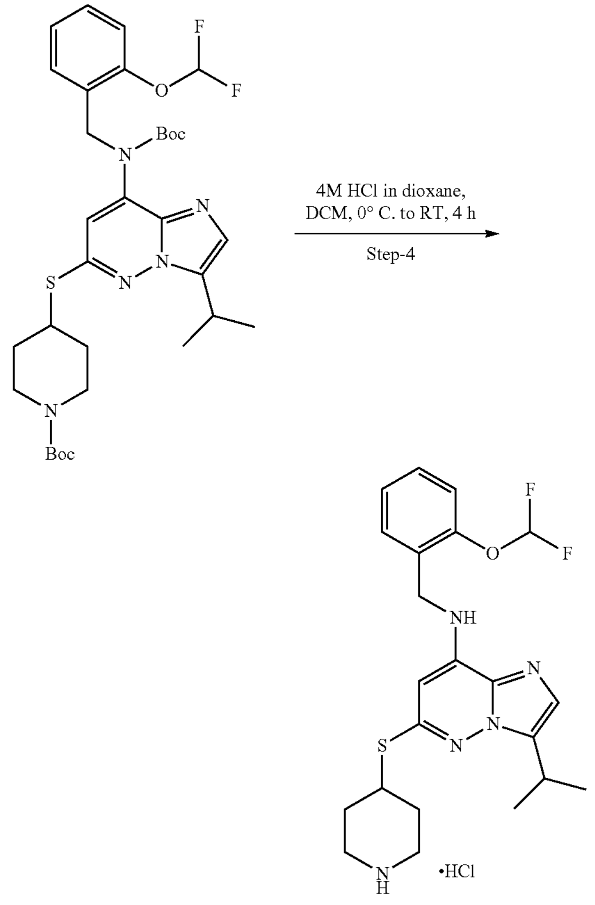

66

To a solution of tert-butyl 4-((8-((tert-butoxycarbonyl)(2-(difluoromethoxy)benzyl)amino)-3-isopropylimidazo[1,2-b]pyridazin-6-yl)thio)piperidine-1-carboxylate (6) (0.300 g, 0.151 mmol, 1.0 eq.) in DCM (4 mL) was added 4M HCl in dioxane (2 mL) at. 0 °C and stirred at RT for 4 h. Progress of the reaction was monitored by TLC. After this time, volatile portion was concentrated under reduced pressure to get crude compound. The obtained crude was purified by Prep-HPLC using formic acid buffer to afford the title compound as an off-white solid (Note: Formate salt observed.) This compound was added acetonitrile (1 mL) and cooled to 0 °C and added 2N HCl (2 mL) at 0 °C and lyophilized for 24 h to afford the title compound N-(2-(difluoromethoxy)benzyl)-3-isopropyl-6-(piperidin-4-ylthio)imidazo[1,2-b]pyridazin-8-amine hydrochloride (66, 0.126 g, quantitative) as an off white solid. $R_f$=0.1 (1:1Hexane/EtOAc). LCMS (m/z): 448.1 $(M+H)^+$. HPLC: 99.91%. $^1$HNMR (400 MHz, DMSO-$d_6$): δ 9.12 (s, 1H), 8.95 (s, 1H), 8.69 (s, 1H), 7.88 (s, 1H), 7.49-7.12 (m, 5H), 6.38 (s, 1H), 4.59 (d, J=5.6 Hz, 2H), 4.40-3.97 (m, 1H), 3.42-3.35 (s, 1H), 3.29-3.26 (m, 2H), 3.09-3.01 (m, 2H), 2.27-2.23 (m, 2H), 1.89-1.80 (m, 2H), 1.34 (d, J=6.8 Hz, 6H).

Example 75

Synthetic Scheme for N-(2-(dimethylamino)benzyl)-3-isopropyl-6-(piperidin-4-ylthio)imidazo[1,2-b]pyridazin-8-amine hydrochloride

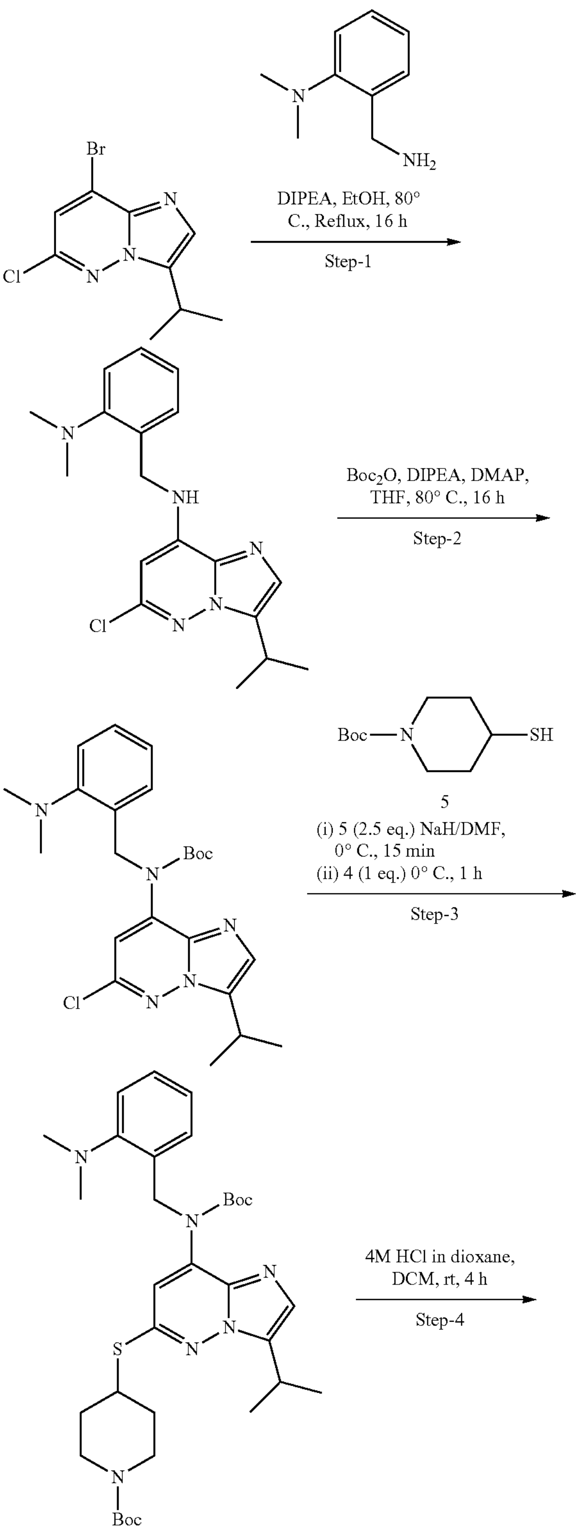

-continued

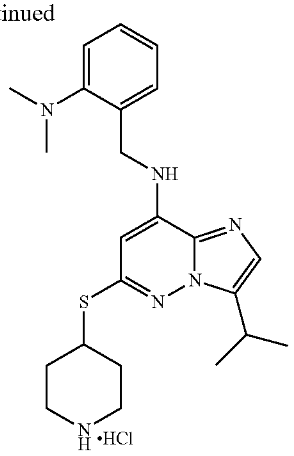

64

Step-1: Synthesis of 6-chloro-N-(2-(dimethylamino) benzyl)-3-isopropylimidazo[1,2-b]pyridazin-8-amine

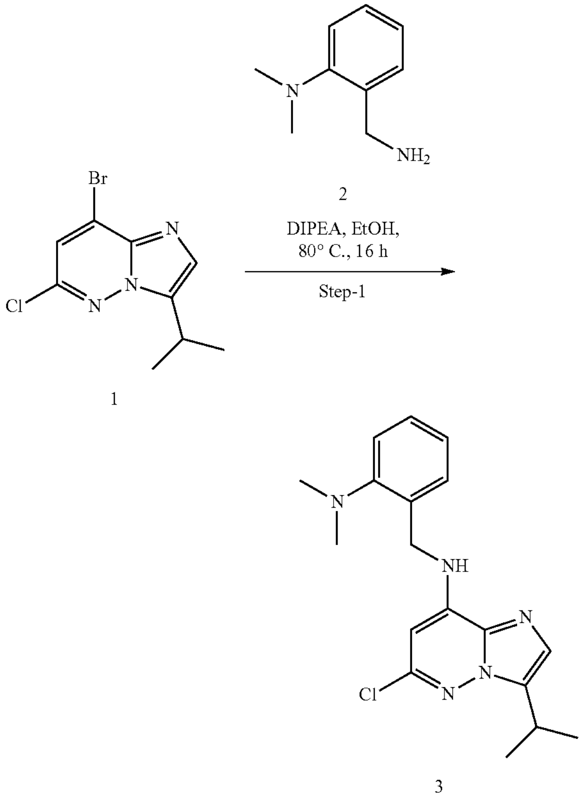

To a stirred solution of 8-bromo-6-chloro-3-isopropylimidazo[1,2-b]pyridazine (1) (0.25 g, 0.912 mmol, 1eq.) in ethanol (10 mL) was added DIPEA (0.317 mL, 1.82 mmol, 2 eq.) and 2-(aminomethyl)-N,N-dimethylaniline(2) (0.205 g, 1.36 mmol, 1.5 eq.) at room temperature. The reaction mixture was heated at 80 °C for 16 h. After complete conversion by TLC, the reaction mixture was allowed to cool to room temperature, ethanol was evaporated under reduced pressure, obtained crude was diluted with water (25 mL) and product was extracted with ethyl (2×25 mL). The combined organic layer washed with, brine (25 mL), dried over sodium sulphate, and evaporated to get the crude residue. The crude residue was purified by silica gel column chromatography using silica gel (100-200) mesh (EtOAc/hexane, gradient 0-10% EtOAc) to afford the title compound 6-chloro-N-(2-(dimethylamino)benzyl)-3-isopropylimidazo[1,2-b]pyridazin-8-amine (3) as a yellow oil. (Yield: 0.250 g, 80%). $R_f$=0.4 (4:1 Hexane/EtOAc). LCMS (m/z): 344.17 $(M+H)^+$. $^1H$ NMR (400 MHz, DMSO-$d_6$): δ 8.53 (m, 1H), 7.32-7.30 (m, 2H), 7.24-7.15 (m, 2H), 6.99 (t, J=8 Hz, 1H), 6.04 (s, 1H), 4.51 (d, J=4.0 Hz, 2H), 4.52-4.51 (m, 2H), 3.27-3.16 (m, 1H), 2.71 (m, 6H), 1.28 (d, J=4.0 Hz, 6H).

Step-2: Synthesis of tert-butyl (6-chloro-3-isopropylimidazo[1,2-b]pyridazin-8-yl)(2-(dimethylamino) benzyl)carbamate

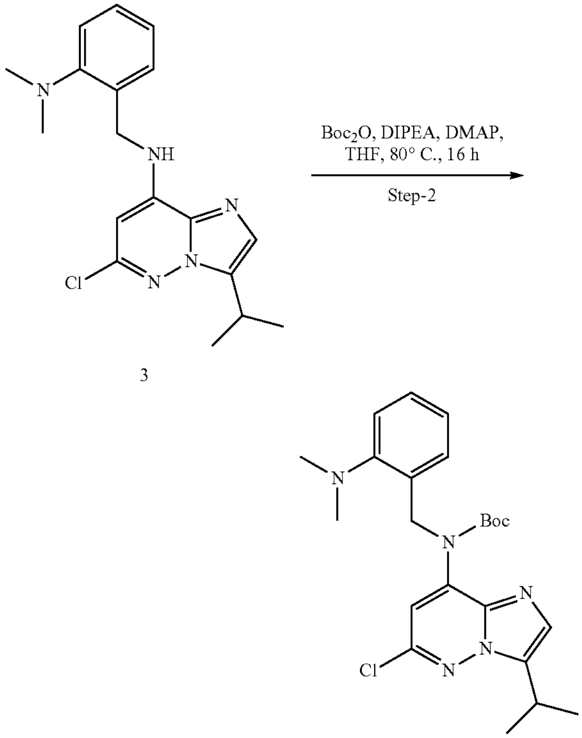

4

To a stirred solution of 6-chloro-N-(2-(dimethylamino) benzyl)-3-isopropylimidazo[1,2-b]pyridazin-8-amine (3) (0.250 g, 7.28 mmol, 1 eq.) in THF (10 mL) was added DIPEA (1.26 mL, 7.28 mmol, 10 eq.), Boc anhydride (1.67 mL, 7.28 mmol, 10 eq.) and DMAP (0.008 g, 0.072 mmol, 0.1 eq.) at room temperature. Reaction mixture was stirred at 80 °C for 16 h. The reaction mixture was allowed to cool to room temperature, THF was evaporated, water (25 mL)was added and product was extracted with EtOAc (3×25 mL). The combined organic layer washed with brine (25 mL) and dried over sodium sulphate, filtered and evaporated under reduced pressure to get the crude residue. The residue was purified by column chromatography using silica gel (100-200) mesh (EtOAc/hexane, gradient 0-10% EtOAc) to afford the title compound as tert-butyl (6-chloro-3-isopropylimidazo[1,2-b]pyridazin-8-yl)(2-(dimethylamino)benzyl)carbamate (4) as a yellow oil. (Yield: 0.250 g, 80%). $R_f$=0.7 (4:1 Hexane/EtOAc). LCMS (m/z): 444.1 $(M+H)^+$. $^1$H NMR (400 MHz, DMSO-$d_6$): δ=7.63 (s, 1H), 7.34-7.31 (m, 2H), 7.17 (t, J=7.2 Hz, 1H), 7.09-7.07 (m, 1H), 6.98 (t, J=7.2 Hz, 1H), 5.33 (s, 2H), 3.35-3.28 (m, 1H), 2.45 (s, 6H), 1.33-1.31 (m, 15H).

Step-3: Synthesis of tert-butyl 4-((8-((tert-butoxycarbonyl)(2-(dimethylamino)benzyl)amino)-3-isopropylimidazo[1,2-b]pyridazin-6-yl)thio)piperidine-1-carboxylate

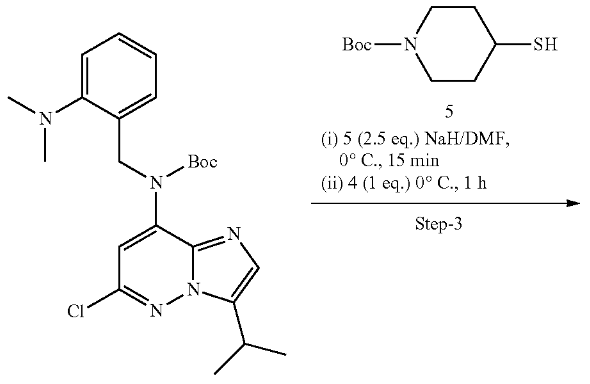

4

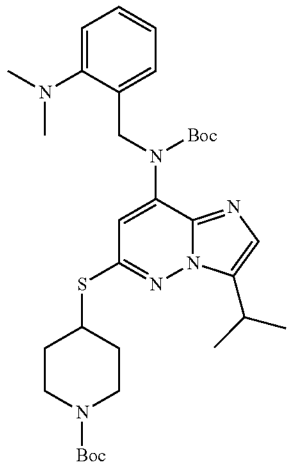

6

To a stirred solution tert-butyl 4-mercaptopiperidine-1-carboxylate (5) (0.306 g, 1.41 mmol, 2.5eq.) in DMF (3 mL) at 0 °C was added NaH (60% in mineral oil, (0.056 g, 1.41 mmol, 2.5 eq.). Reaction mixture was stirred at 0 °C for 10 minutes. After this time added, tert-butyl (6-chloro-3-isopropylimidazo[1,2-b]pyridazin-8-yl)(2-(dimethylamino)benzyl)carbamate (4) (0.250 g, 0.56 mmol, 1 eq.) in DMF (2 mL) to the above reaction mass. The resulting reaction mixture was stirred at 0 °C for 1 h. After complete conversion by TLC, the reaction mixture was diluted with ice cold water (30 mL) to get an off white solid. Off white solid filtered through Buchner funnel and dried under reduced pressure to get crude compound as white solid. Obtained white solid was purified by column chromatography (EtOAc/hexane, gradient 10-15% EtOAc) to afford the title compound as (6) tert-butyl 4-((8-((tert-butoxycarbonyl)(2-(dimethylamino)benzyl)amino)-3-isopropylimidazo[1,2-b]pyridazin-6-yl)thio)piperidine-1-carboxylate as an off white solid. (Yield: 0.275 g, 78%). $R_f$=0.3(4:1 Hexane/EtOAc). LCMS (m/z): 625.2 $(M+H)^+$.

Step-4: Synthesis of N-(2-(dimethylamino)benzyl)-3-isopropyl-6-(piperidin-4-ylthio)imidazo[1,2-b]pyridazin-8-amine hydrochloride

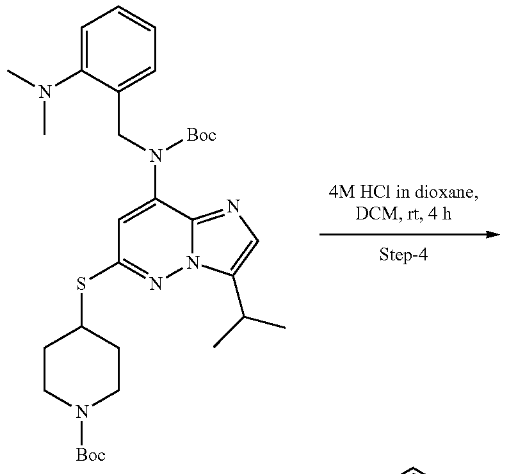

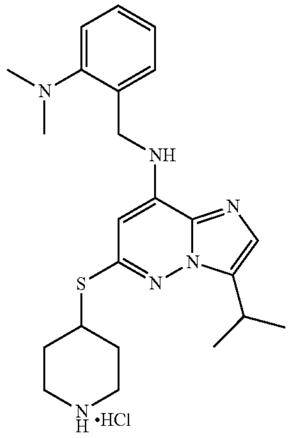

64

To a stirred solution of tert-butyl 4-((8-((tert-butoxycarbonyl)(2-(dimethylamino)benzyl)amino)-3-isopropylimidazo[1,2-b]pyridazin-6-yl)thio)piperidine-1-carboxylate (6) (0.275 g, 0.440 mmol, 1eq.) in DCM (5 mL) at 0 °C was added 4M HCl in 1,4-dioxane (5 mL) drop-wise and stirred at 0 °C. Reaction mixture was allowed to come to room temperature and stirred for 4 h. After completion of reaction by TLC, the reaction mixture was subjected to rotary evaporator for removal of volatiles to get crude white solid. The obtained residue was triturated with diethyl ether (3×10 mL), EtOAc (3×10 mL) and lyophilized for 24 h. to afford the title compound N-(2-(dimethylamino)benzyl)-3-isopropyl-6-(piperidin-4-ylthio)imidazo[1,2-b]pyridazin-8-amine hydrochloride (64) as a white solid. (Yield: 0.210 g, quantitative). $R_f$=0.1 (4:1 $CHCl_3$/MeOH). LCMS (m/z): 425.2 $(M+H)^+$. $^1$H NMR (400 MHz, DMSO-$d_6$,): δ=9.23 (br. s, 1H), 9.07 (br. s, 2H), 8.01 (s, 1H), 7.44-7.26 (m, 4H), 6.59 (s, 1H), 4.82 (s, 2H), 4.06-4.00 (m, 1H), 3.44-3.34 (m, 1H), 3.28-3.24 (m, 2H), 3.08-2.97 (m, 8H), 2.26-2.23 (m, 2H), 1.91-1.82 (m, 2H), 1.33 (d, J=6.8 Hz, 6H).

Example 76
Synthetic Scheme for N-(2-ethoxybenzyl)-3-isopropyl-6-(piperidin-4-ylthio)imidazo[1,2-b]pyridazin-8-amine hydrochloride
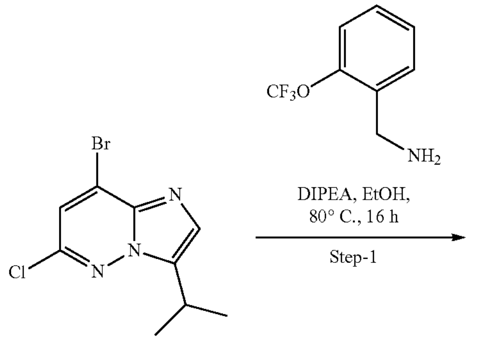
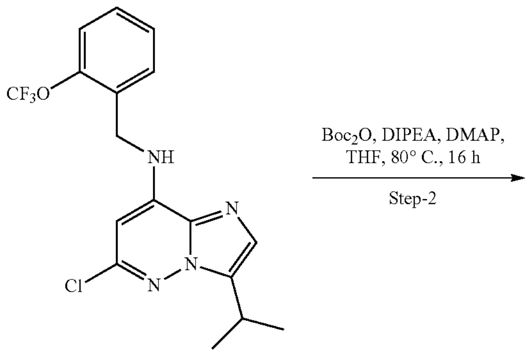
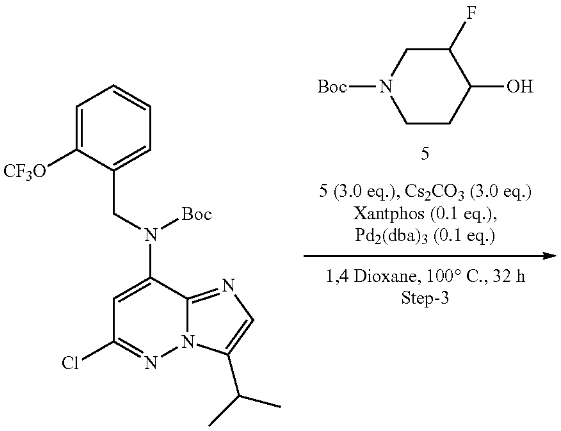
-continued
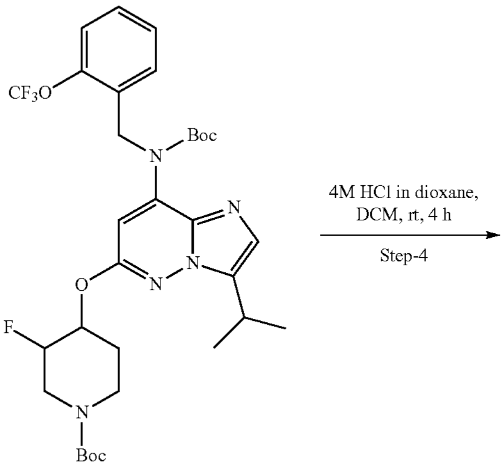
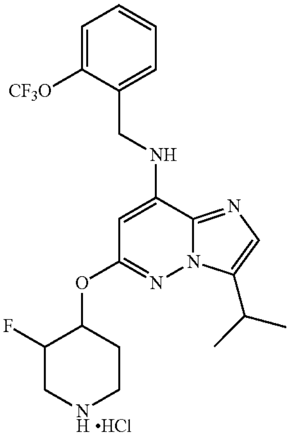
70
Step-1: Synthesis of 6-chloro-3-isopropyl-N-(2-(trifluoromethoxy)benzyl)imidazo[1,2-b]pyridazin-8-amine
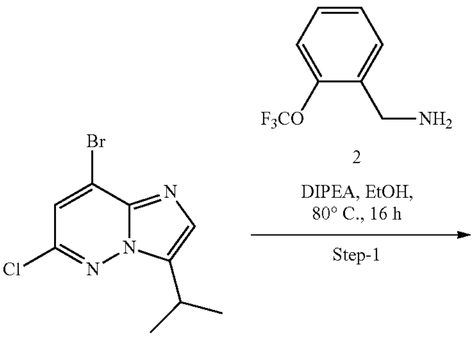
1

-continued

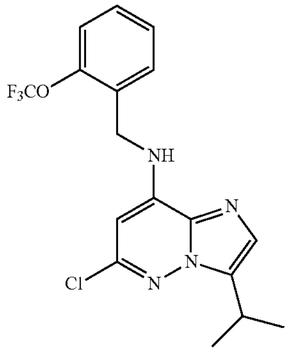

3

To a stirred solution of 8-bromo-6-chloro-3-isopropylimidazo[1,2-b]pyridazine (1) (0.800 g, 2.92 mmol, 1.0 eq.) in ethanol (10 mL) was added DIPEA (1.016 mL, 5.839 mmol, 2.0 eq.) and (2-(trifluoromethoxy)phenyl)methanamine (2) (0.837 g, 4.379 mmol, 1.5 eq.), at room temperature. The reaction mixture was heated at 80 °C for 16 h. After complete conversion by TLC, the reaction mixture was allowed to reach to room temperature and ethanol was evaporated under reduced pressure to get the crude residue. The crude residue was diluted with water (30 mL) and extracted with ethyl acetate (3×50 mL). The combined organic layer was washed with brine (25 mL), dried over sodium sulphate, filtered and evaporated under reduced pressure to get the crude residue. The crude residue was purified by column chromatography using silica gel (100-200) mesh (with gradient elution of 10-15% EtOAc/hexane) to afford the title compound as 6-chloro-3-isopropyl-N-(2-(trifluoromethoxy)benzyl)imidazo[1,2-b]pyridazin-8-amine (3) as brown solid. (Yield: 0.740 g, 66%). $R_f$=0.3 (4:1 Hexane/EtOAc). LCMS (m/z): 385.0M+H)$^+$; $^1$H NMR (400 MHz, DMSO-$d_6$): δ=8.39 (s, 1H), 7.48-7.31 (m, 5H), 5.99 (s, 1H), 4.62 (s, 2H), 3.29-3.20 (m, 1H), 1.31-1.29 (d, J=6.8 Hz, 6H).

Step-2: Synthesis of tert-butyl (6-chloro-3-isopropylimidazo[1,2-b]pyridazin-8-yl)(2-(trifluoromethoxy)benzyl)carbamate -continued

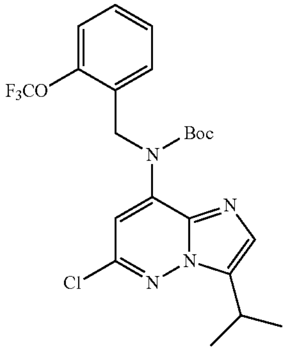

4

To a stirred solution of 6-chloro-3-isopropyl-N-(2-(trifluoromethoxy)benzyl)imidazo[1,2-b]pyridazin-8-amine (3) (0.740 g, 1.927 mmol, 1.0 eq.) in THF (10 mL) was added DIPEA (3.36 mL, 19.270 mmol, 10.0 eq.), Boc anhydride (4.422 mL, 19.270 mmol, 10.0 eq.) and DMAP (0.023 g, 0.193 mmol, 0.1 eq.) at room temperature. Reaction mixture was stirred at 80 °C for 16 h. After complete conversion by TLC, the reaction mixture was cooled, THF was evaporated under reduced pressure to get the crude residue. Obtained crude was diluted with water (30 mL) and product was extracted with ethyl acetate (3×40 mL). The combined organic layer was washed with brine (20 mL), dried over sodium sulphate, filtered and concentrated under reduced pressure to get the crude residue. The crude residue was purified by column chromatography using silica gel (100-200) mesh (with a gradient elution of 5-10% of EtOAc: n-Hexane) to afford title compound as tert-butyl (6-chloro-3-isopropylimidazo[1,2-b]pyridazin-8-yl)(2-(trifluoromethoxy)benzyl)carbamate (4) as colour less oil. (Yield: 0.850 g, 91%). $R_f$=0.5 (4:1 Hexane/EtOAc). LCMS (m/z): 485.02M+H)$^+$; $^1$H NMR (400 MHz, DMSO-$d_6$): δ=7.66 (s, 1H), 7.56 (dd, J=7.6, 1.6 Hz, 1H), 7.42 (s, 1H), 7.41-7.33 (m, 2H), 7.33-7.27, (m, 1H), 5.39 (s, 2H), 3.37-3.32 (m, 1H), 1.37-1.30 (m, 15H).

Step-3: Synthesis of tert-butyl 4-((8-((tert-butoxycarbonyl)(2-(trifluoromethoxy)benzyl)amino)-3-isopropylimidazo[1,2-b]pyridazin-6-yl)oxy)-3-fluoropiperidine-1-carboxylate

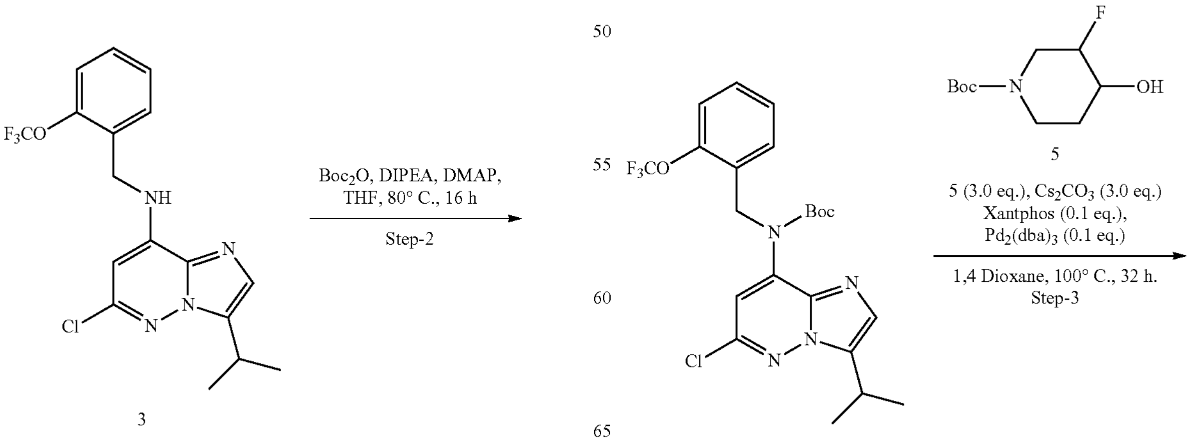

3

4

-continued

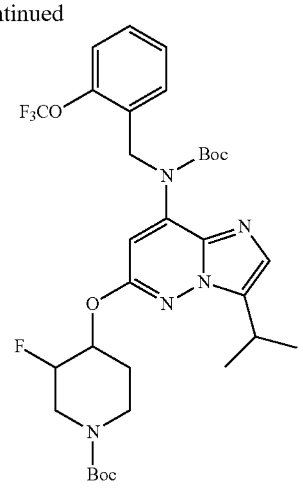

6

To a stirred solution of tert-butyl (6-chloro-3-isopropylimidazo[1,2-b]pyridazin-8-yl)(2-(trifluoromethoxy)benzyl) carbamate (4) (250 mg, 0.516 mmol, 1.0 eq.) in 1,4 dioxane (5 mL) was added tert-butyl 3-fluoro-4-hydroxypiperidine-1-carboxylate (5) (169 mg, 0.775 mmol, 1.5 eq.), $Cs_2CO_3$ (252 mg, 0.775 mmol, 1.5 eq.) and Xantphos (15 mg, 5 mol %) at ambient temperature. The reaction mixture was purged with argon for 10 min then added tris(dibenzylideneacetone) dipalladium (24 mg, 5 mol %) again degassed with argon for 10 min and heated at 100 °C for 16 h. After this time, the reaction mixture cooled to RT and further added tert-butyl 3-fluoro-4-hydroxypiperidine-1-carboxylate (5) (169 mg, 0.775 mmol, 1.5 eq.), $Cs_2CO_3$ (252 mg, 0.775 mmol, 1.5 eq.) and Xantphos (15 mg, 5 mol %) were added at room temperature. The reaction mixture was degassed with argon for 10 min then added tris(dibenzylideneacetone)dipalladium (24 mg, 5 mol %) again degassed with argon for 10 min and heated at 100 °C for 16 h. The reaction mixture was diluted with ethyl acetate and passed through celite bed. The organic phase was washed with water (20 mL), brine, dried over $Na_2SO_4$ filtered and concentrated under vacuum. The residue was purified by flash column chromatography on silica column (EtOAc/hexane, gradient 17-20% EtOAc) to afford tert-butyl 4-((8-((tert-butoxycarbonyl)(2-(trifluoromethoxy)benzyl)amino)-3-isopropylimidazo[1,2-b] pyridazin-6-yl)oxy)-3-fluoropiperidine-1-carboxylate (6) as brown oil. (Diastereomer-I-50 mg, Diastereomer-II –90 mg 40% yield), $R_f$=0.4 (4:1 Hexane/EtOAc). LCMS (m/z): 668.19 $(M+H)^+$.

Step-4: Synthesis of 6-((3-fluoropiperidin-4-yl) oxy)-3-isopropyl-N-(2-(trifluoromethoxy)benzyl) imidazo[1,2-b]pyridazin-8-amine hydrochloride

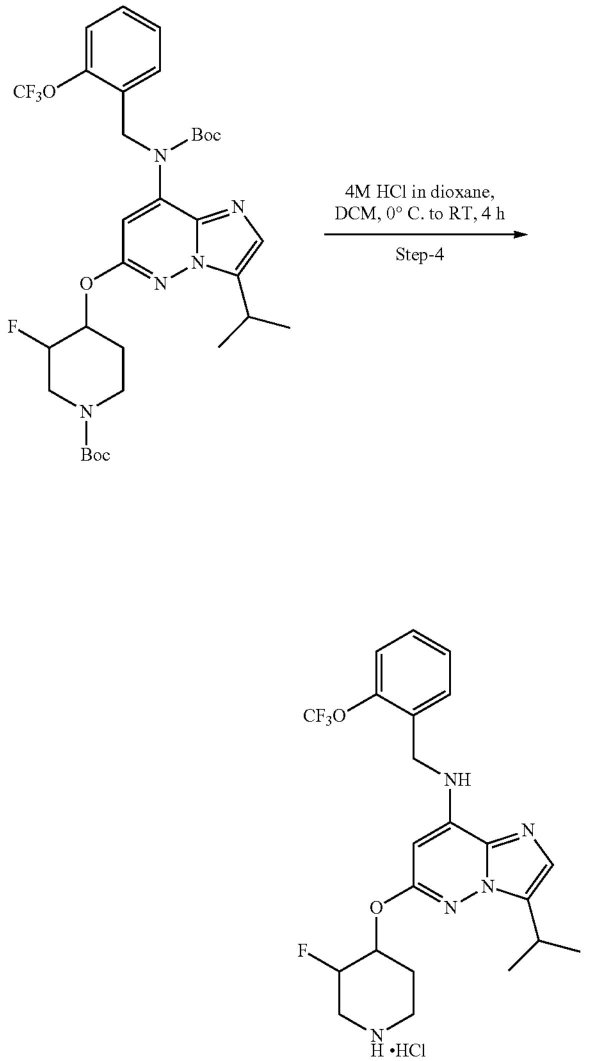

70

To a stirred solution of tert-butyl 4-((8-((tert-butoxycarbonyl)(2-(trifluoromethoxy)benzyl)amino)-3-isopropylimidazo[1,2-b]pyridazin-6-yl)oxy)-3-fluoropiperidine-1-carboxylate (6) (0.050 g, 0.075 mmol, 1.0 eq.) in DCM (1.0 mL) at 0 °C was added 4M HCl in 1,4-dioxane (1.0 mL). Reaction mixture was stirred at room temperature for 4 h. After complete conversion by TLC, the reaction mixture was subjected to rotary evaporator for removal of volatiles. The obtained residue was triturated with diethyl ether (3×2 mL), EtOAc (2×2 mL) and lyophilized for 24 h to get the title compound as 6-((3-fluoropiperidin-4-yl)oxy)-3-isopropyl-N-(2-(trifluoromethoxy)benzyl)imidazo[1,2-b]pyridazin-8-amine (70) as an white solid. (0.002 g, 5% yield). $R_f$=0.1 (9:1 DCM/MeOH). LCMS (m/z): 468.41M+H$)^+$; $^1H$ NMR (400 MHz, $CD_3OD$): δ=7.83 (s, 1H), 7.61 (d, J=7.6 Hz 1H), 7.52-7.47 (m, 1H), 7.42-7.38 (m, 2H), 6.35 (s, 1H), 5.47 (s, 1H), 5.18 (d, $J_{H-F}$=44.4 Hz, 1H), 4.70 (s, 2H), 3.66-3.51 (m, 2H), 3.52-3.42 (m, 1H), 3.39-3.30 (m, 2H), 2.46-2.25 (m, 2H), 1.34 (d, J=6.8 Hz, 6H).

Step-4: Synthesis of 6-((3-fluoropiperidin-4-yl)oxy)-3-isopropyl-N-(2-(trifluoromethoxy)benzyl)imidazo[1,2-b]pyridazin-8-amine hydrochloride

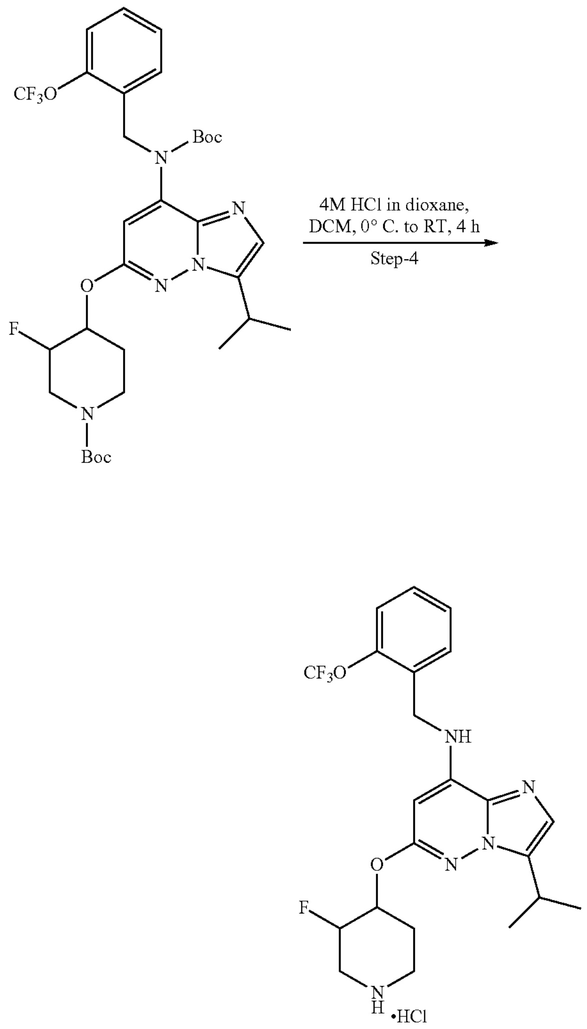

69

To a stirred solution of tert-butyl 4-((8-((tert-butoxycarbonyl)(2-(trifluoromethoxy)benzyl)amino)-3-isopropylimidazo[1,2-b]pyridazin-6-yl)oxy)-3-fluoropiperidine-1-carboxylate (6) (0.090 g, 0.075 mmol, 1.0 eq.) in DCM (1.0 mL) at 0 °C was added 4M HCl in 1,4-dioxane (2.0 mL). Reaction mixture was stirred at room temperature for 4 h. After complete conversion by TLC, the reaction mixture was subjected to rotary evaporator for removal of volatiles. The obtained residue was triturated with diethyl ether (3×2 mL), EtOAc (2×2 mL) and lyophilized for 24 h. to get the title compound as 6-((3-fluoropiperidin-4-yl)oxy)-3-isopropyl-N-(2-(trifluoromethoxy)benzyl)imidazo[1,2-b]pyridazin-8-amine (69) as an white solid. (0.020 g, 28% yield). $R_f$=0.1 (9:1 DCM/MeOH). LCMS (m/z): 468.34 $(M+H)^+$. $^1H$ NMR (400 MHz, DMSO-$d_6$): δ=9.71 (d, J=10.0 Hz, 1H), 8.87 (d, J=10.0 Hz, 2H), 8.71 (s, 1H), 7.88 (s, 1H), 7.54-7.21 (m, 3H), 6.11 (s, 1H), 5.36-5.24 (m, 2H), 4.66 (d, J=6 Hz, 2H), 3.60-3.50 (m, 1H), 3.43-3.40 (m, 1H), 3.38-3.31 (m, 1H), 3.29-3.25 (m, 1H), 3.20-3.15 (m, 1H), 2.22-2.18 (m, 1H), 2.11-2.03 (m, 1H), 1.34 (dd, J=6.8, 1.6 Hz, 6H).

Example 77

Synthetic Scheme for 6-((3,3-difluoropiperidin-4-yl)oxy)-3-isopropyl-N-(2-(trifluoromethoxy)benzyl)imidazo[1,2-b]pyridazin-8-amine hydrochloride

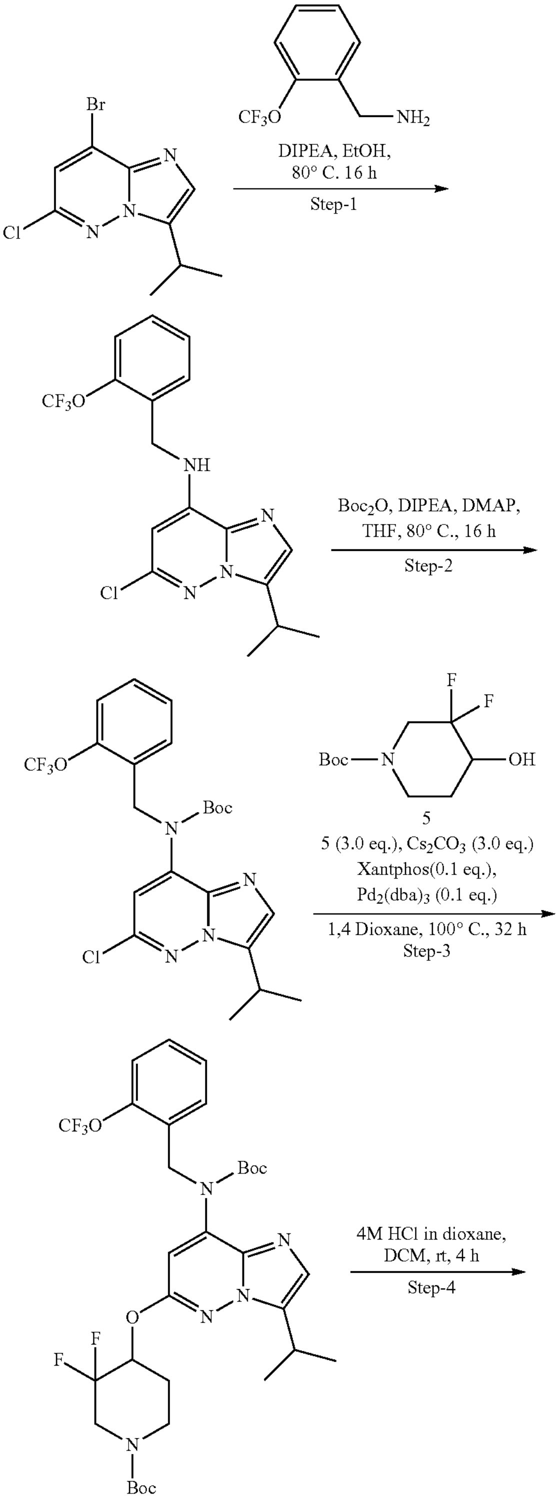

-continued

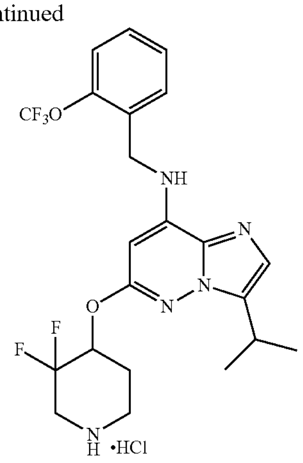

71

Step-1: Synthesis of 6-chloro-3-isopropyl-N-(2-(trifluoromethoxy)benzyl)imidazo[1,2-b]pyridazin-8-amine

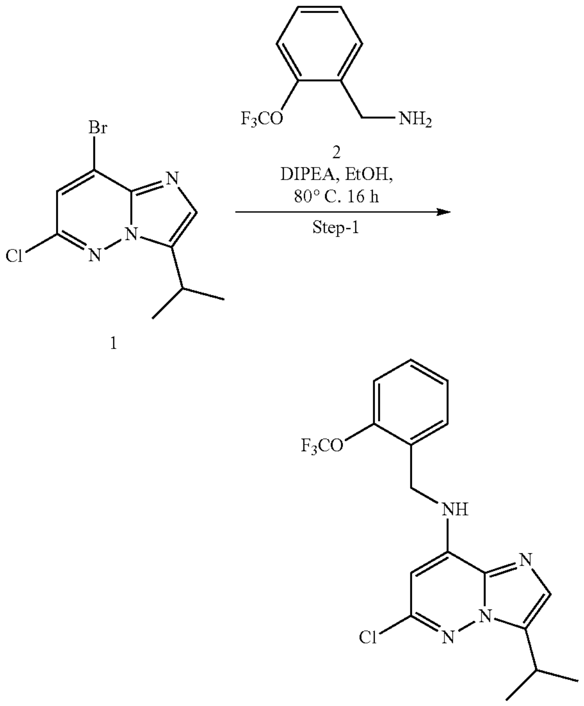

3

To a stirred solution of 8-bromo-6-chloro-3-isopropylimidazo[1,2-b]pyridazine (1) (0.800 g, 2.92 mmol, 1.0 eq.) in ethanol (10 mL) was added DIPEA (1.016 mL, 5.839 mmol, 2.0 eq.) and (2-(trifluoromethoxy)phenyl)methanamine (2) (0.837 g, 4.379 mmol, 1.5 eq.), at room temperature. The reaction mixture was heated at 80 °C for 16 h. After complete conversion by TLC, the reaction mixture was allowed to cooled, ethanol was evaporated under reduced pressure to get the crude residue. The crude residue was diluted with water (30 mL), extracted with ethyl acetate (3×50 mL). The combined organic layer was washed with brine (25 mL), dried over sodium sulphate, evaporated under reduced pressure to get the crude residue. The crude residue was purified by column chromatography using silica gel (100-200) mesh (with gradient elution of 10-15% EtOAc/hexane) to afford the title compound as 6-chloro-3-isopropyl-N-(2-(trifluoromethoxy)benzyl)imidazo[1,2-b]pyridazin-8-amine (3) as brown solid. (Yield: 0.740 g, 66%). $R_f$=0.3 (4:1 Hexane/EtOAc). LCMS (m/z): 385.0M+H)$^+$; $^1$H NMR (400 MHz, DMSO-$d_6$): δ=8.39 (s, 1H), 7.48-7.31 (m, 5H), 5.99 (s, 1H), 4.62 (s, 2H), 3.29-3.20 (m, 1H), 1.31-1.29 (d, J=6.8 Hz, 6H).

Step-2: Synthesis of tert-butyl (6-chloro-3-isopropylimidazo[1,2-b]pyridazin-8-yl)(2-(trifluoromethoxy)benzyl)carbamate

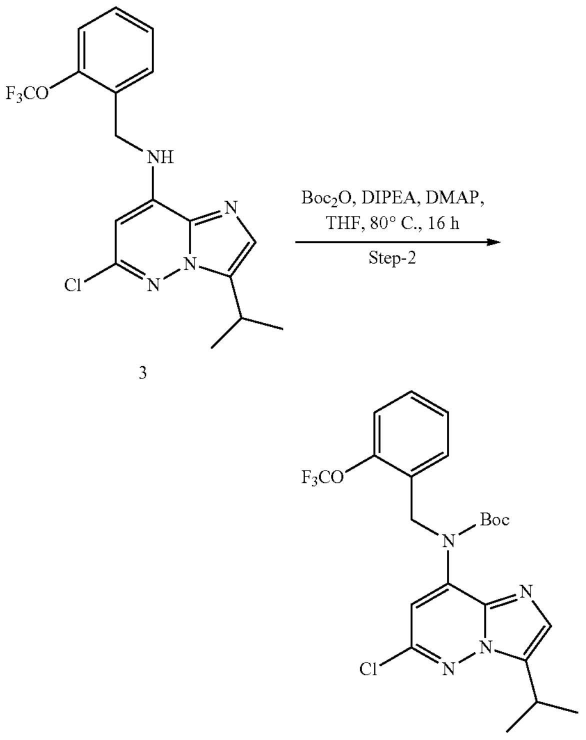

4

To a stirred solution of 6-chloro-3-isopropyl-N-(2-(trifluoromethoxy)benzyl)imidazo[1,2-b]pyridazin-8-amine (3) (0.740 g, 1.927 mmol, 1.0 eq.) in THF (10 mL) was added DIPEA (3.36 mL, 19.270 mmol, 10.0 eq.), Boc anhydride (4.422 mL, 19.270 mmol, 10.0 eq.) and DMAP (0.023 g, 0.193 mmol, 0.1 eq.) at room temperature. Reaction mixture was stirred at 80 °C for 16 h. After complete conversion by TLC, the reaction mixture was cooled, THF was evaporated under reduced pressure to get the crude residue. To the crude residue water (30 mL) was added, extracted with ethyl acetate (3×40 mL). The combined organic layer was washed with brine (20 mL), dried over sodium sulphate and evaporated under reduced pressure to get the crude residue. The crude residue was purified by column chromatography using silica gel (100-200) mesh (with a gradient elution of 5-10% of EtOAc: n-Hexane) to afford title compound as tert-butyl (6-chloro-3-isopropylimidazo[1,2-b]pyridazin-8-yl)(2-(trifluoromethoxy)benzyl)carbamate (4) as colour less oil.

(Yield: 0.850 g, 91%). $R_f$=0.5 (4:1 Hexane/EtOAc). LCMS (m/z): 485.02M+H)$^+$; $^1$H NMR (400 MHz, DMSO-$d_6$): δ=7.66 (s, 1H), 7.56 (dd, J=7.6, 1.6 Hz, 1H), 7.42 (s, 1H), 7.41-7.33 (m, 2H), 7.33-7.27, (m, 1H), 5.39 (s, 2H), 3.37-3.32 (m, 1H), 1.37-1.30 (m, 15H).

Step-3: Synthesis of tert-butyl 4-((8-((tert-butoxycarbonyl)(2-(trifluoromethoxy)benzyl)amino)-3-isopropylimidazo[1,2-b]pyridazin-6-yl)oxy)-3,3-difluoropiperidine-1-carboxylate

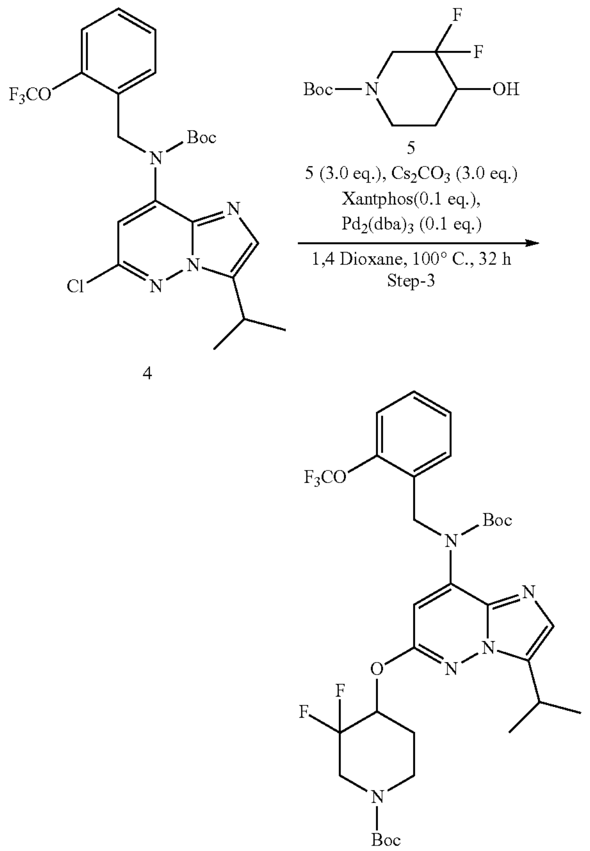

4

5

6

To a stirred solution of tert-butyl (6-chloro-3-isopropylimidazo[1,2-b]pyridazin-8-yl)(2-(trifluoromethoxy)benzyl) carbamate (4) (250 mg, 0.516 mmol, 1.0 eq.) in 1,4 dioxane (5 mL) was added tert-butyl 3,3-difluoro-4-hydroxypiperidine-1-carboxylate (5) (184 mg, 0.775 mmol, 1.5 eq.), $Cs_2CO_3$ (252 mg, 0.775 mmol, 1.5 eq.) and Xantphos (15 mg, 5 mol %) at ambient temperature. The reaction mixture was purged with argon for 10 min then added tris(dibenzylideneacetone)dipalladium (24 mg, 5 mol %) again degassed with argon for 10 min and heated at 100 °C for 16 h. The reaction mixture cooled to RT and further added tert-butyl 3,3-difluoro-4-hydroxypiperidine-1-carboxylate (5) (184 mg, 0.775 mmol, 1.5 eq.), $Cs_2CO_3$ (252 mg, 0.775 mmol, 1.5 eq.) and (15 mg, 5 mol %) were added at room temperature. The reaction mixture was degassed with argon for 10 min then added tris(dibenzylideneacetone)dipalladium (24 mg, 5 mol %) again degassed with argon for 10 min and heated at 100 °C for 16 h. The reaction mixture was diluted with ethyl acetate and passed through celite bed. The organic phase was washed with water (20 mL), brine, dried over $Na_2SO_4$ and concentrated under vacuum. The residue was purified by combiflash on silica column (EtOAc/hexane, gradient 0-30% EtOAc) to afford tert-butyl 4-((8-((tert-butoxycarbonyl)(2-(trifluoromethoxy)benzyl)amino)-3-isopropylimidazo[1,2-b]pyridazin-6-yl)oxy)-3,3-difluoropiperidine-1-carboxylate (6) as yellow oil. (50 mg, 14% yield), $R_f$=0.3 (8:2 Hexane/EtOAc). (0.050 g, 50% yield). $R_f$=0.3 (4:1 Hexane/EtOAc). LCMS (m/z): 686.45 (M+H)$^+$.

Step-4: Synthesis of 6-((3,3-difluoropiperidin-4-yl)oxy)-3-isopropyl-N-(2-(trifluoromethoxy)benzyl)imidazo[1,2-b]pyridazin-8-amine hydrochloride

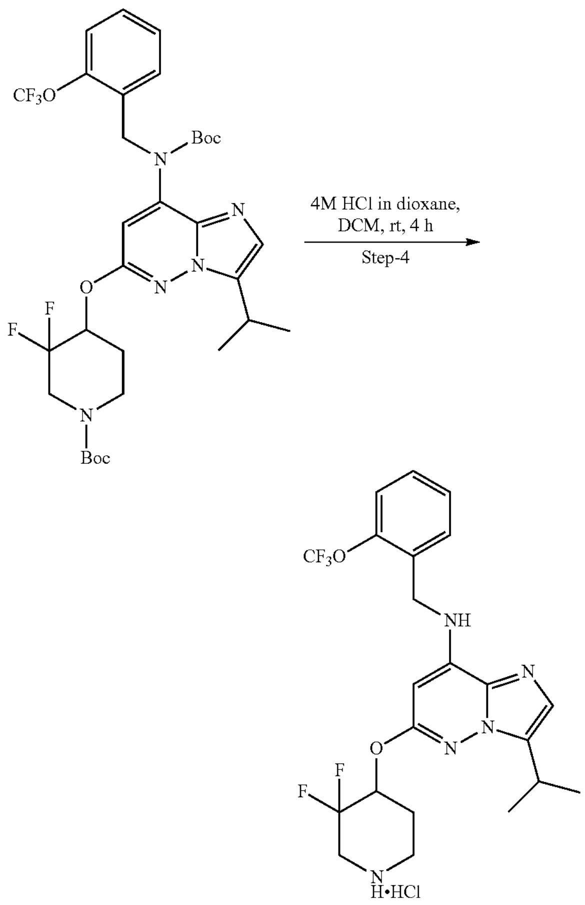

71

To a stirred solution of tert-butyl 4-((8-((tert-butoxycarbonyl)(2-(trifluoromethoxy)benzyl)amino)-3-isopropylimidazo[1,2-b]pyridazin-6-yl)oxy)-3, 3-difluoropiperidine-1-carboxylate (6) (0.050 g, 0.073 mmol, 1.0 eq.) in DCM (1 mL) at 0 °C was added 4M HCl in 1,4-dioxane (1 mL) drop-wise. Reaction mixture was stirred at room temperature for 4 h. After complete conversion by TLC, the reaction mixture was subjected to rotary evaporator for removal of volatiles. The obtained residue was triturated with diethyl ether (3×2 mL), EtOAc (2×2 mL) and lyophilized for 24 h. to get the title compound as 6-((3,3-difluoropiperidin-4-yl)oxy)-3-isopropyl-N-(2-(trifluoromethoxy)benzyl)imidazo[1,2-b]pyridazin-8-amine hydrochloride as white solid (71)

(Yield: 0.020 g, 38%). $R_f$=0.1 (9:1 DCM/MeOH). LCMS (m/z): 426.1 $(M+H)^+$; $^1$H NMR (400 MHz, DMSO-$d_6$): δ=10.05 (s, 1H), 9.64 (s, 1H), 8.50 (s, 1H), 7.69 (s, 1H), 7.56-7.32 (m, 4H), 5.99 (s, 1H), 5.67-5.51 (m, 1H), 4.64 (d, J=5.6 Hz, 2H), 3.81-3.69 (m, 2H), 3.39-3.28 (m, 1H), 3.28-3.16 (m, 2H), 2.43-2.34 (m, 1H), 2.15-2.01 (m, 1H), 1.34 (dd, J=6.8, 3.2 Hz, 6H).
Example 78
Synthetic Scheme for N-(4-fluoro-2-methoxybenzyl)-3-isopropyl-6-(piperidin-4-ylthio)imidazo[1,2-b]pyridazin-8-amine hydrochloride
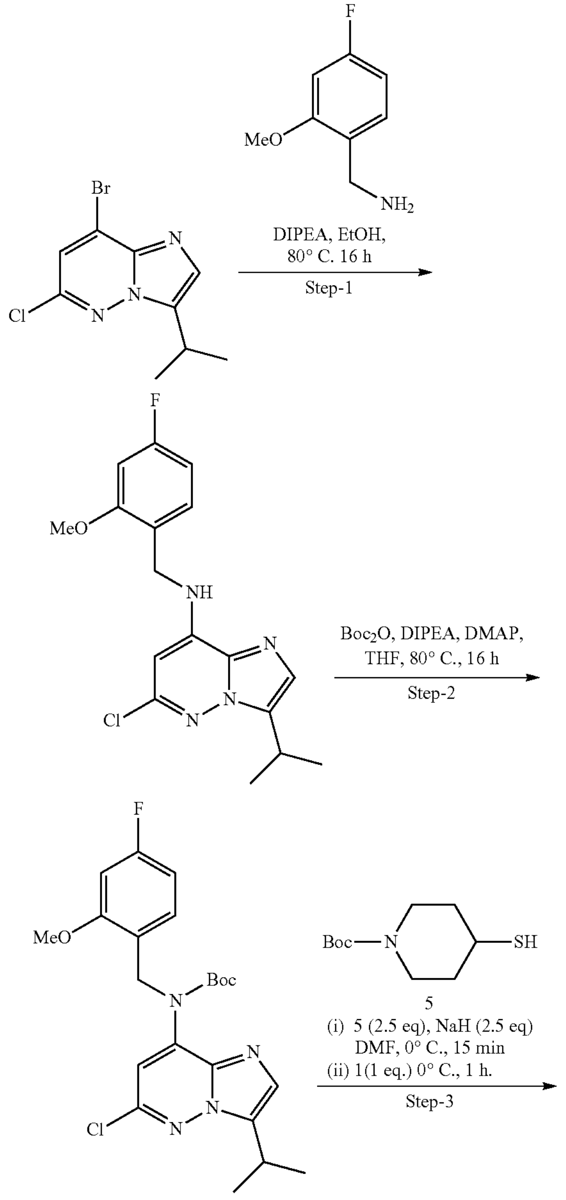
-continued
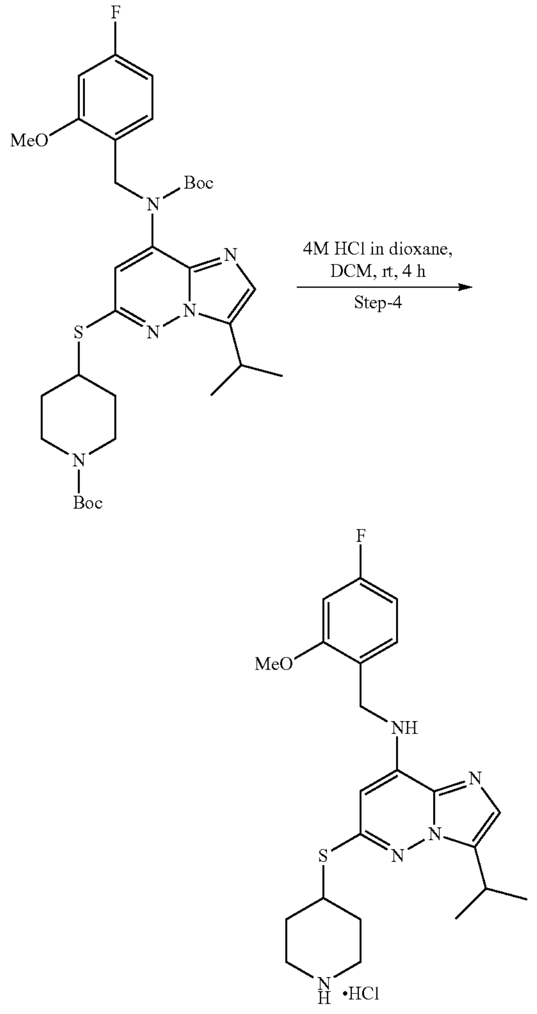
72
Step-1: Synthesis of 6-chloro-N-(4-fluoro-2-methoxybenzyl)-3-isopropylimidazo[1,2-b]pyridazin-8-amine
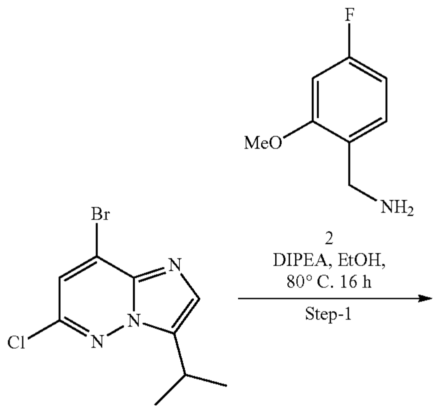
1

-continued

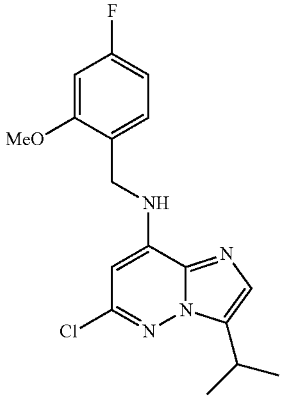

3

-continued

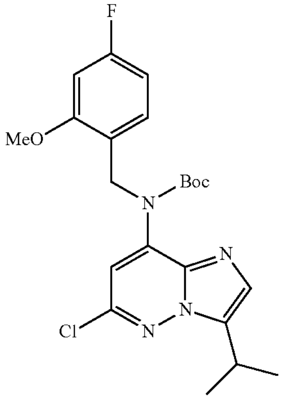

4

To a stirred solution of 8-bromo-6-chloro-3-isopropylimidazo[1,2-b]pyridazine (1) (0.5 g, 1.831 mmol, 1.0 eq.) in ethanol (5 mL) was added DIPEA (0.95 mL, 5.5 mmol, 3.0 eq.) and (4-fluoro-2-methoxyphenyl)methanamine (2) (0.454 g, 2.93 mmol, 1.6 eq.) at room temperature. The reaction mixture was heated at 80 °C for 16 h. After complete conversion by TLC, reaction mixture was cooled to room temperature, ethanol was evaporated under reduced pressure to get the crude residue. The crude residue was diluted with water (25 mL), extracted with ethyl acetate (3×30 mL). The combined organic layer was washed with brine (25 mL), dried over sodium sulphate, filtered and evaporated under reduced pressure to get the crude residue. The crude residue was purified by column chromatography using silica gel (100-200) mesh (with gradient elution of 12-15% EtOAc/hexane) to afford the title compound as 6-chloro-N-(4-fluoro-2-methoxybenzyl)-3-isopropylimidazo[1,2-b]pyridazin-8-amine (3) as white solid. (Yield: 0.5 g, 78%). $R_f$=0.3 (4:1 Hexane/EtOAc). LCMS (m/z): 349.0 $(M+H)^+$; $^1$H NMR (400 MHz, DMSO-$d_6$): δ=8.17 (t, J=6.8, 6.0 Hz 1H), 7.33 (s, 1H), 7.20 (t, J=8.0, 7.2 Hz, 1H), 6.94 (dd, J=11.2, 2.4 Hz, 1H), 6.72 (td, J=8.8, 8.4, 2.4 Hz, 1H), 6.03 (s, 1H), 4.44 (s, 2H), 3.87 (s, 3H) 3.31-3.18 (m, 1H), 1.3 (d, J=6.8 Hz, 6H).

Step-2: Synthesis of tert-butyl (6-chloro-3-isopropylimidazo[1,2-b]pyridazin-8-yl)(4-fluoro-2-methoxybenzyl)carbamate To a stirred solution of 6-chloro-N-(4-fluoro-2-methoxybenzyl)-3-isopropylimidazo[1,2-b]pyridazin-8-amine (3) (0.5 g, 1.444 mmol, 1.0 eq.) in THF (5 mL) was added DIPEA (2.16 mL, 14.44 mmol, 10.0 eq.), Boc anhydride (2.8 mL, 14.44 mmol, 10.0 eq.) and DMAP (0.015 g, 0.144 mmol, 0.1 eq.) at room temperature. Reaction mixture was stirred at 80 °C for 16 h. After complete conversion by TLC, the reaction mixture was cooled to room temperature and volatile portion was removed under reduced pressure to get the crude residue. To the crude residue water (25 mL) was added and extracted with ethyl acetate (3×30 mL). The combined organic layer was washed with brine (25 mL), dried over sodium sulphate, filtered and concentrated under reduced pressure to get the crude residue. The crude residue was purified by column chromatography using silica gel (100-200) mesh (with a gradient elution of 5-10% of EtOAC: n-Hexane) to afford title compound as tert-butyl (6-chloro-3-isopropylimidazo[1,2-b]pyridazin-8-yl)(4-fluoro-2-methoxybenzyl)carbamate (4) as colour less oil. (Yield: 0.550 g, 85%). $R_f$=0.6 (4:1 Hexane/EtOAc). LCMS (m/z): 449.1M+H)$^+$; $^1$H NMR (400 MHz, DMSO-$d_6$): δ=7.64 (s, 1H), 7.33 (s, 1H), 7.29 (t, J=8.4, 7.2 Hz, 1H), 6.81 (dd, J=11.2, 2.4 Hz, 1H), 6.67 (td, J=8.4, 2.4 Hz, 1H), 5.17 (s, 2H), 3.55 (s, 3H), 3.37-3.28 (m, 1H), 1.38-1.29 (m, 15H).

Step-3: Synthesis of tert-butyl 4-((8-((tert-butoxycarbonyl)(4-fluoro-2-methoxybenzyl)amino)-3-isopropylimidazo[1,2-b]pyridazin-6-yl)thio)piperidine-1-carboxylate

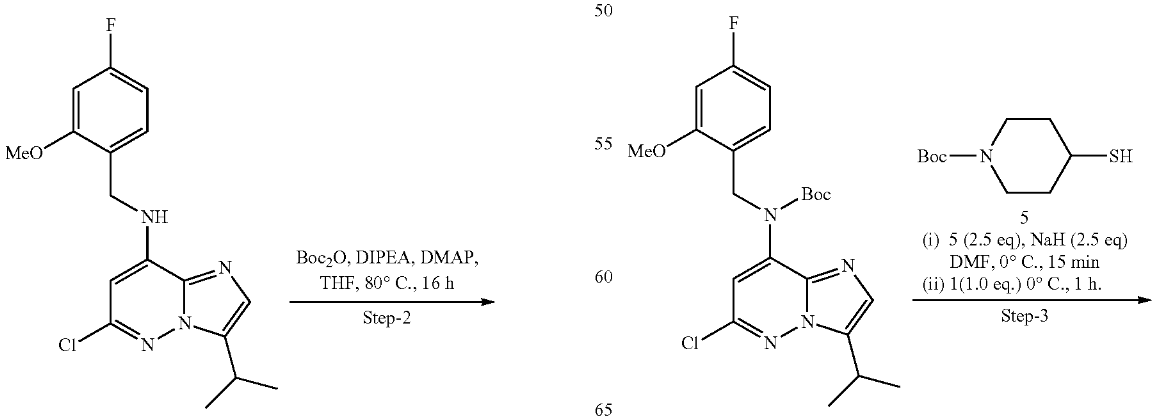

3 4

-continued

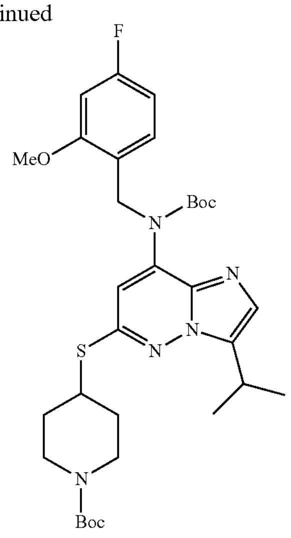

6

To a solution of tert-butyl 4-mercaptopiperidine-1-carboxylate (5) (0.222 g, 1.026 mmol, 2.2 eq.) in DMF (2 mL) at 0 °C was added NaH (60% in mineral oil, 0.044 g, 1.116 mmol, 2.5 eq.) and stirred for 15 minutes. Then added a solution of tert-butyl (6-chloro-3-isopropylimidazo[1,2-b]pyridazin-8-yl)(4-fluoro-2-methoxybenzyl)carbamate (4) (0.200 g, 0.46 mmol, 1.0 eq.) in DMF (2 mL). The resulting mixture was stirred at room temperature for 1 h. After this time, reaction mixture was diluted with ice cold water (25 mL) and extracted with ethyl acetate (3×25 mL). The combined organic layer washed with brine (25 mL), dried over sodium sulfate, evaporated under reduced pressure to provide crude compound. Obtained crude compound was purified by silica phase column chromatography using silica gel (100-200) mesh [with a gradient elution of 08-11% of Hexane/EtOAc] to afford the title compound as tert-butyl 4-((8-((tert-butoxycarbonyl)(4-fluoro-2-methoxybenzyl)amino)-3-isopropylimidazo[1,2-b]pyridazin-6-yl)thio)piperidine-1-carboxylate (6) as a colour less solid. (0.248 g, 85% yield). $R_f$=0.3 (4:1 Hexane/EtOAc). LCMS (m/z): 630.38 $(M+H)^+$.

Step-4: Synthesis of N-(4-fluoro-2-methoxybenzyl)-3-isopropyl-6-(piperidin-4-ylthio)imidazo[1,2-b]pyridazin-8-amine hydrochloride

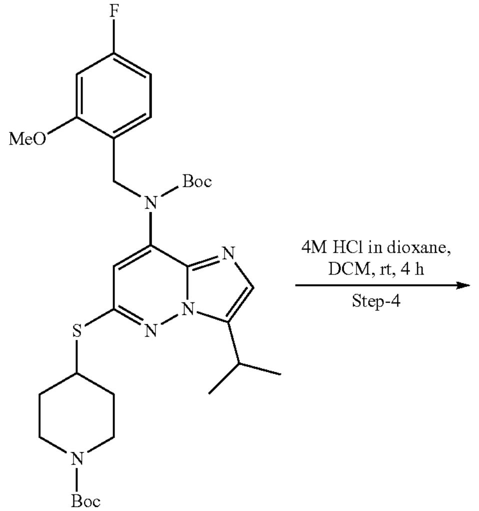

-continued

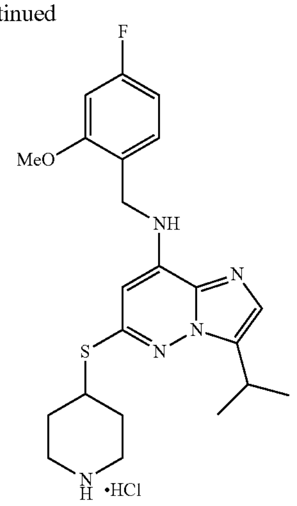

72

To a stirred solution of tert-butyl 4-((8-((tert-butoxycarbonyl)(4-fluoro-2-methoxybenzyl)amino)-3-isopropylimidazo[1,2-b]pyridazin-6-yl)thio)piperidine-1-carboxylate (6) (0.235 g, 0.37 mmol, 1.0 eq.) in DCM (3 mL) at 0 °C was added 4M HCl in 1,4-dioxane (2 mL) drop-wise. Reaction mixture was stirred at room temperature for 5 h. After complete conversion by TLC, the reaction mixture was subjected to rotary evaporator for removal of volatiles. The obtained residue was purified by Prep-HPLC (TFA buffer was used) to afford. To get compound as a HCl salt, obtained TFA salt was dissolved in ACN: water and treated with 2N aq. HCl at 0 °C and lyophilized to afford title compound as N-(4-fluoro-2-methoxybenzyl)-3-isopropyl-6-(piperidin-4-ylthio)imidazo[1,2-b]pyridazin-8-amine hydrochloride (72) as an white solid. (0.115 g, 71% yield). $R_f$=0.1 (9:1 DCM/MeOH). LCMS (m/z): 430.32M+H)$^+$; $^1$H NMR (400 MHz, DMSO-$d_6$): δ=9.14 (s, 1H), 8.98 (s, 1H), 8.58 (s, 1H), 7.88 (s, 1H), 7.34 (t, J=8.0, 7.2 Hz, 1H), 6.96 (dd, J=11.2, 2.4 Hz, 1H), 6.74 (td, J=8.4, 2.4 Hz, 1H), 6.43 (s, 1H), 4.47 (d, J=5.6 Hz, 2H), 4.08-3.96 (m, 1H), 3.85 (s, 3H), 3.43-3.32 (m, 1H), 3.31-3.22 (m, 2H), 3.11-2.93 (m, 2H), 2.26 (d, J=11.2 Hz, 2H), 1.92-1.76 (m, 2H), 1.33 (d, J=6.8 Hz, 6H).

Example 79

Synthetic Scheme for N-(4-fluoro-2-methoxybenzyl)-3-isopropyl-6-(piperidin-3-ylthio)imidazo[1,2-b]pyridazin-8-amine hydrochloride

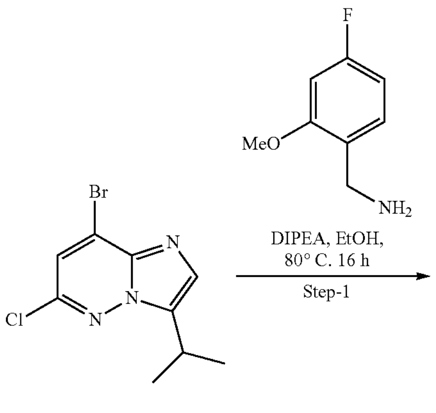

-continued
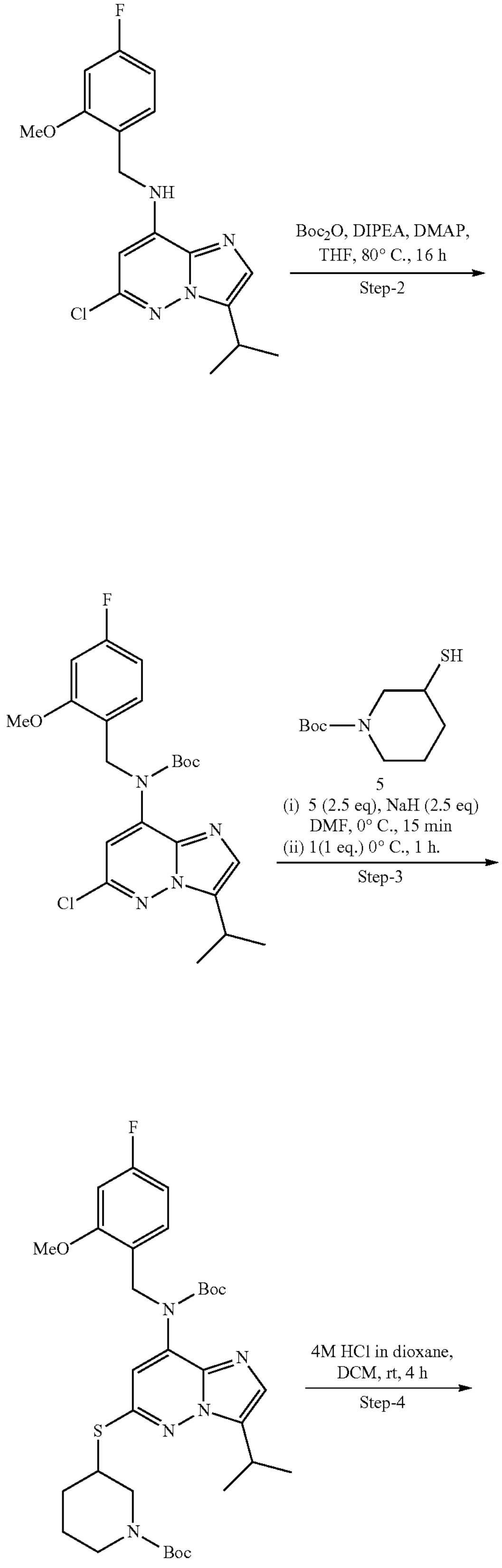
-continued
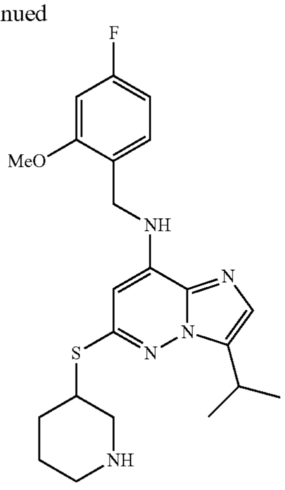
79
Step-1: Synthesis of 6-chloro-N-(4-fluoro-2-methoxybenzyl)-3-isopropylimidazo[1,2-b]pyridazin-8-amine
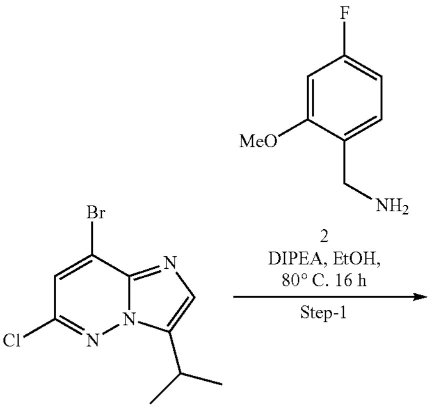
1
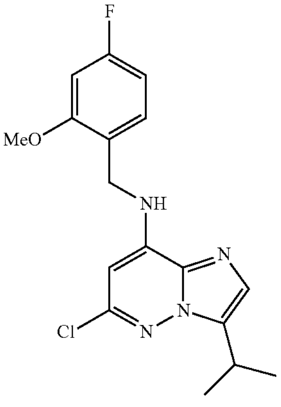
3
To a stirred solution of 8-bromo-6-chloro-3-isopropylimidazo[1,2-b]pyridazine (1) (0.5 g, 1.831 mmol, 1.0 eq.) in ethanol (5 mL) was added DIPEA (0.95 mL, 5.5 mmol, 3.0 eq.) and (4-fluoro-2-methoxyphenyl)methanamine (2) (0.454 g, 2.93 mmol, 1.6 eq.) at room temperature. The reaction mixture was heated at 80 °C for 16 h. After complete conversion by TLC, reaction mixture was cooled, the reaction mixture was allowed to cool to room temperature, and ethanol was evaporated under reduced pressure to get the crude residue. The crude residue was diluted with water (25 mL), extracted with ethyl acetate (3x30 mL). The combined organic layer was washed with brine (25 mL), dried over sodium sulphate, filtered and evaporated under reduced pressure to get the crude residue. The crude residue was purified by column chromatography using silica gel (100-200) mesh (with gradient elution of 12-15% EtOAc/hexane) to afford the title compound as 6-chloro-N-(4-fluoro-2-methoxybenzyl)-3-isopropylimidazo[1,2-b]pyridazin-8-amine (3) as white solid. (Yield: 0.500 g, 78%). $R_f$=0.3 (4:1 Hexane/EtOAc). LCMS (m/z): 349.0M+H)$^+$; $^1$H NMR (400 MHz, DMSO-$d_6$): δ=8.17 (t, J=6.8, 6.0 Hz 1H), 7.33 (s, 1H), 7.20 (t, J=8.0, 7.2 Hz, 1H), 6.94 (dd, J=11.2, 2.4 Hz, 1H), 6.72 (td, J=8.8, 8.4, 2.4 Hz, 1H), 6.03 (s, 1H), 4.44 (s, 2H), 3.87 (s, 3H) 3.31-3.18 (m, 1H), 1.3 (d, J=6.8 Hz, 6H).

Step-2: Synthesis of tert-butyl (6-chloro-3-isopropylimidazo[1,2-b]pyridazin-8-yl)(4-fluoro-2-methoxybenzyl)carbamate

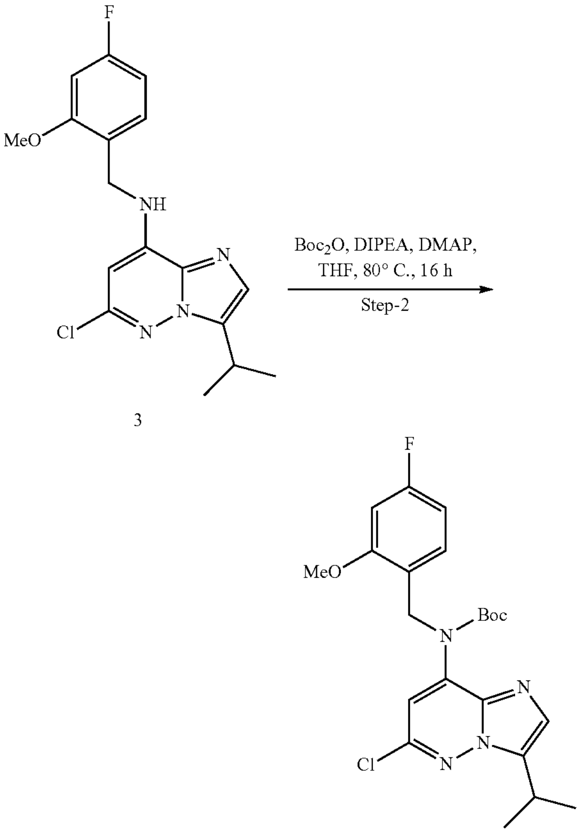

3

4

To a stirred solution of 6-chloro-N-(4-fluoro-2-methoxybenzyl)-3-isopropylimidazo[1,2-b]pyridazin-8-amine (3) (0.5 g, 1.444 mmol, 1.0 eq.) in THF (5 mL) was added DIPEA (2.16 mL, 14.44 mmol, 10.0 eq.), Boc anhydride (2.8 mL, 14.44 mmol, 10.0 eq.) and DMAP (0.015 g, 0.144 mmol, 0.1 eq.) at room temperature. Reaction mixture was stirred at 80 °C for 16 h. After complete conversion by TLC, the reaction mixture was cooled, THF was evaporated under reduced pressure to get the crude residue. Obtained crude compound was diluted with water (25 mL) and product was extracted with ethyl acetate (3x30 mL). The combined organic layer was washed with brine (25 mL), dried over sodium sulphate, filtered and evaporated under reduced pressure to get the crude residue. The crude residue was purified by column chromatography using silica gel (100-200) mesh (with a gradient elution of 5-10% of EtOAC: n-Hexane) to afford title compound as tert-butyl (6-chloro-3-isopropylimidazo[1,2-b]pyridazin-8-yl)(4-fluoro-2-methoxybenzyl)carbamate (4) as colour less oil. (Yield: 0.550 g, 85%). $R_f$=0.6 (4:1 Hexane/EtOAc). LCMS (m/z): 449.1M+H)$^+$; $^1$H NMR (400 MHz, DMSO-$d_6$): δ=7.64 (s, 1H), 7.33 (s, 1H), 7.29 (t, J=8.4, 7.2 Hz, 1H), 6.81 (dd, J=11.2, 2.4 Hz, 1H), 6.67 (td, J=8.4, 2.4 Hz, 1H), 5.17 (s, 2H), 3.55 (s, 3H), 3.37-3.28 (m, 1H), 1.38-1.29 (m, 15H).

Step-3: Synthesis of tert-butyl 3-((8-((tert-butoxycarbonyl)(4-fluoro-2-methoxybenzyl)amino)-3-isopropylimidazo[1,2-b]pyridazin-6-yl)thio)piperidine-1-carboxylate

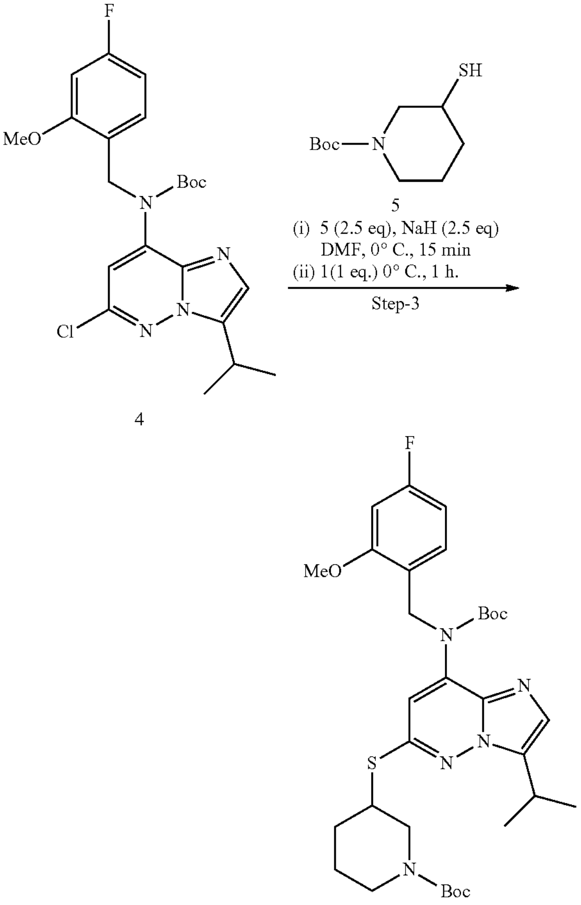

4

5

6

To a solution of tert-butyl 3-mercaptopiperidine-1-carboxylate (5) (0.222 g, 1.026 mmol, 2.2 eq.) in DMF (2 mL) at 0 °C was added NaH (60% in mineral oil, 0.044 g, 1.116 mmol, 2.5 eq.) and stirred for 15 minutes. Then added a solution of tert-butyl (6-chloro-3-isopropylimidazo[1,2-b]pyridazin-8-yl)(4-fluoro-2-methoxybenzyl)carbamate (4) (0.200 g, 0.46 mmol, 1.0 eq.) in DMF (2 mL). The resulting mixture was stirred at room temperature for 1 h. Reaction mixture was diluted with ice cold water (25 mL) and extracted with ethyl acetate (3×25 mL). The combined organic layer washed with brine (25 mL), dried over sodium sulfate, filtered and concentrated under reduced pressure to provide crude compound. Obtained crude compound was purified by silica phase column chromatography using silica gel (100-200) mesh [with a gradient elution of 08-12% of Hexane/EtOAc] to afford the title compound as tert-butyl 3-((8-((tert-butoxycarbonyl)(4-fluoro-2-methoxybenzyl)amino)-3-isopropylimidazo[1,2-b]pyridazin-6-yl)thio)piperidine-1-carboxylate (6) as a colour less liquid. (0.240 g, 83% yield). $R_f$=0.2 (4:1 Hexane/EtOAc). LCMS (m/z): 630.1 $(M+H)^+$.

Step-4: Synthesis of N-(4-fluoro-2-methoxybenzyl)-3-isopropyl-6-(piperidin-3-ylthio)imidazo[1,2-b]pyridazin-8-amine formate

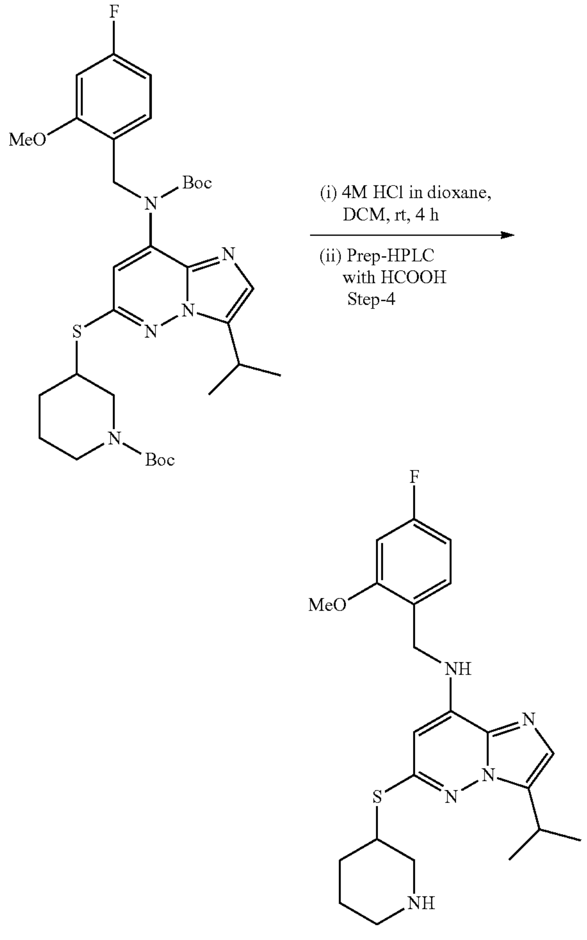

79

To a stirred solution of tert-butyl 4-((8-((tert-butoxycarbonyl)(4-fluoro-2-methoxybenzyl)amino)-3-isopropylimidazo[1,2-b]pyridazin-6-yl)thio)piperidine-1-carboxylate (6) (0.230 g, 0.365 mmol, 1.0 eq.) in DCM (3 mL) at 0 °C was added 4M HCl in 1,4-dioxane (5 mL) drop-wise. Reaction mixture was stirred at room temperature for 5 h. After complete conversion by TLC, the reaction mixture was subjected to rotary evaporator for removal of volatiles. The obtained residue was purified by Prep-HPLC (HCOOH buffer was used) to afford compound as partial HCOOH salt, was dissolved in ACN:water and lyophilized for 24 hours to afford title compound as N-(4-fluoro-2-methoxybenzyl)-3-isopropyl-6-(piperidin-3-ylthio)imidazo[1,2-b]pyridazin-8-amine formate (79) as an white solid. (0.075 g, 43% yield). $R_f$=0.1 (9:1 DCM/MeOH). LCMS (m/z): 430.37M+H)$^+$; $^1$H NMR (400 MHz, DMSO-$d_6$): δ=8.18 (br s, 2H), 7.83 (t, J=6.4 Hz, 1H), 7.25 (s, 1H), 7.19 (t, J=8.0, 7.2 Hz, 1H), 6.94 (dd, J=11.2, 2.4 Hz, 1H), 6.72 (td, J=8.4, 2.4 Hz, 1H), 5.81 (s, 1H), 4.41 (d, J=4.0 Hz, 2H), 3.98-3.90 (m, 1H), 3.87 (s, 3H), 3.52 (dd, J=12.4, 3.6 Hz, 1H), 3.41-3.36 (m, 1H), 3.15 (d, J=12.4 Hz, 1H), 2.99 (t, J=11.6, 10.8 Hz, 1H), 2.84 (t, J=12.4, 10.8 Hz, 1H), 2.17-2.04 (m, 1H), 1.88-1.71 (m, 1H), 1.67-1.55 (m, 1H), 1.38-1.28 (m, 6H).

Example 80

Synthetic Scheme for N-(4-fluoro-2-(trifluoromethyl)benzyl)-3-isopropyl-6-(piperidin-4-ylthio)imidazo[1,2-b]pyridazin-8-amine hydrochloride

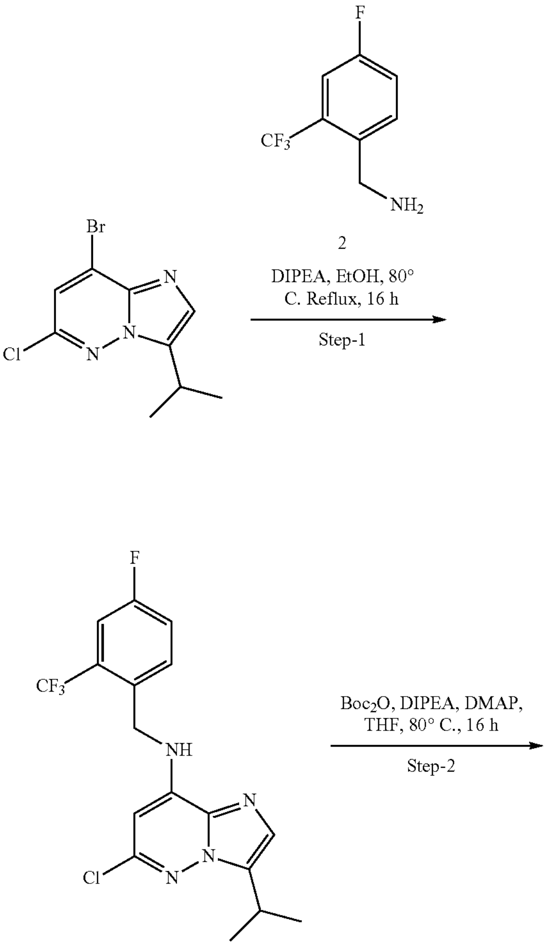

-continued

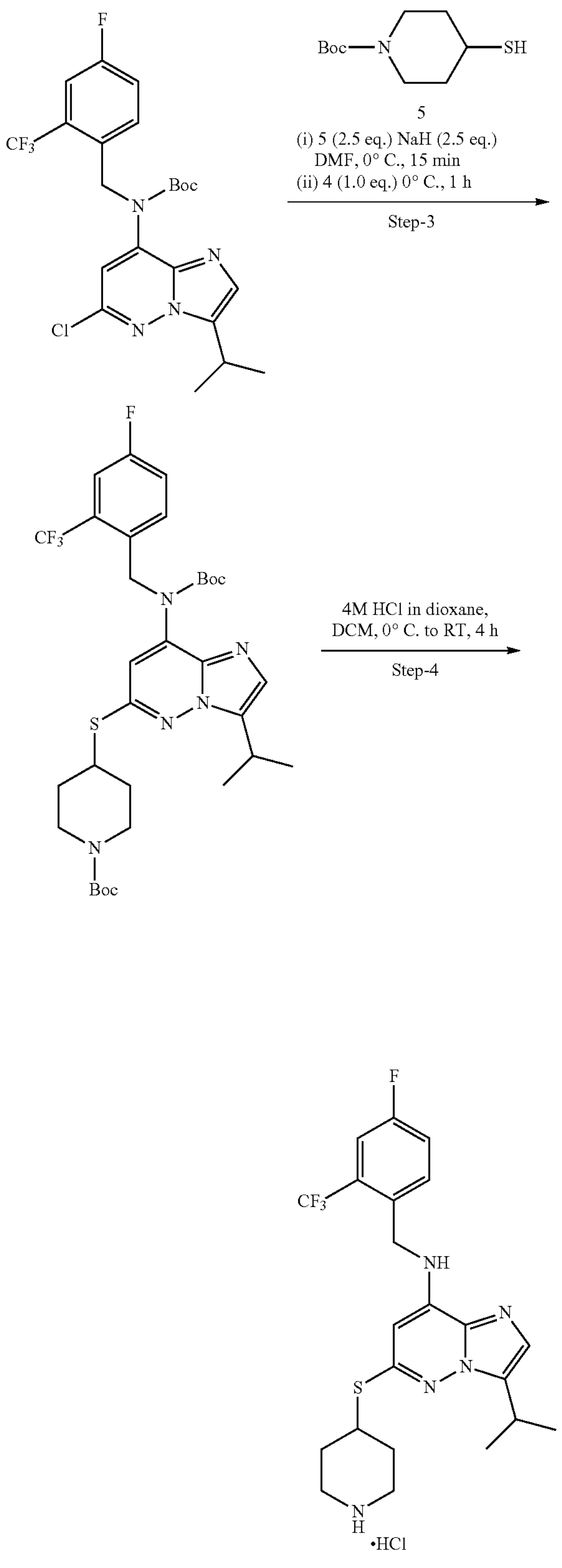

80

Step-1: Synthesis of 6-chloro-N-(4-fluoro-2-(trifluoromethyl)benzyl)-3-isopropylimidazo[1,2-b]pyridazin-8-amine

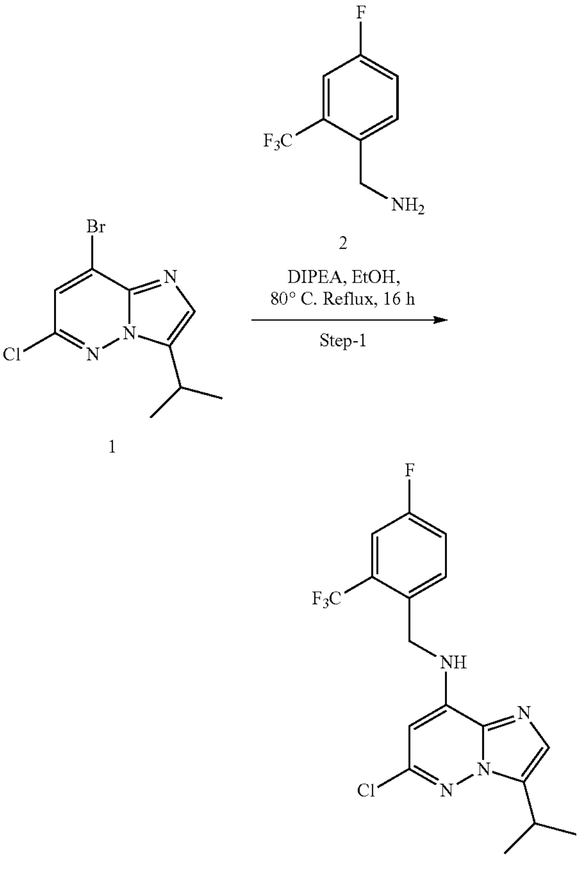

3

To a stirred solution of 8-bromo-6-chloro-3-isopropylimidazo [1,2-b]pyridazine (1) (1.0 g, 3.649 mmol, 1 eq.) in ethanol (10 mL) was added DIPEA (1.27 mL, 7.299 mmol, 2.0 eq.) and (4-fluoro-2-(trifluoromethyl)phenyl)methanamine (2) (0.805 mL, 5.474 mmol, 1.5 eq.) at room temperature. The reaction mixture was heated at 80 °C for 16 h. Progress of reaction was monitored by TLC, the reaction mixture was cool to room temperature. Ethanol was concentrated under reduced pressure, water (50 mL) was added, extracted with EtOAc (2×50 mL). The combined organic layer washed with brine (50 mL), dried over $Na_2SO_4$, concentrated under reduced pressure to afford the brown oil as crude residue. The crude residue was purified by silica gel column chromatography (EtOAc/hexane, gradient 0-10% EtOAc) to afford the title compound as 6-chloro-N-(4-fluoro-2-(trifluoromethyl)benzyl)-3-isopropylimidazo[1,2-b]pyridazin-8-amine (3) as a yellow oil. (Yield: 0.650 g, 46%). $R_f$=0.5 (4:1 Hexane/EtOAc). LCMS (m/z): 387.38 $(M+H)^+$. $^1H$ NMR (400 MHz, DMSO-$d_6$): δ 8.46 (br. s, 1H), 7.67 (d, J=8.8 Hz, 1H), 7.50 (d, J=5.6 Hz, 2H), 7.37 (s, 1H), 5.93 (s, 1H), 4.69 (s, 2H), 3.29-3.22 (m, 1H), 1.31 (d, J=6.8 Hz, 6H).

Step-2: Synthesis of tert-butyl (6-chloro-3-isopropylimidazo[1,2-b]pyridazin-8-yl)(4-fluoro-2-(trifluoromethyl)benzyl)carbamate

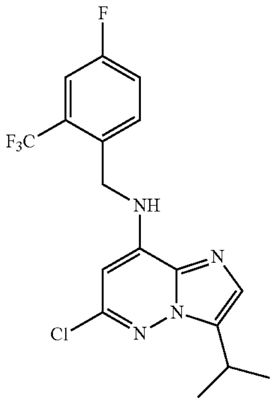

3

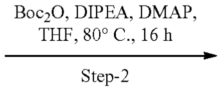

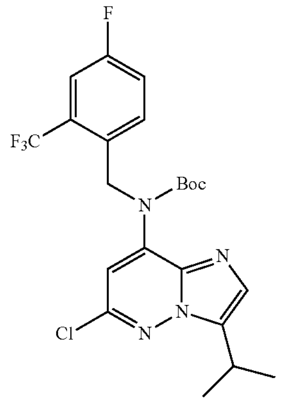

4

To a stirred solution of 6-chloro-N-(4-fluoro-2-(trifluoromethyl)benzyl)-3-isopropylimidazo[1,2-b]pyridazin-8-amine (3) (0.650 g, 1.68 mmol, 1.0 eq.) in THF (10 mL) was added DIPEA (2.93 mL, 16.83 mmol, 10 eq.), $(Boc)_2O$ (3.86 mL, 16.83 mmol, 10 eq.) and DMAP (0.021 g, 0.168 mmol, 0.1 eq.) at room temperature. Reaction mixture was stirred at 80 °C for 16 h. The reaction mixture was allowed to cool to room temperature, THF was concentrated, water (50 mL) was added, extracted with EtOAc (3×50 mL). The combined organic layer washed with brine (25 mL), dried over $Na_2SO_4$, concentrated under reduced pressure to get the brown oil as crude residue. The residue was purified by silica gel column chromatography (EtOAc/hexane, gradient 5-10% EtOAc) to afford the title compound as tert-butyl (6-chloro-3-isopropylimidazo[1,2-b]pyridazin-8-yl)(4-fluoro-2-(trifluoromethyl)benzyl)carbamate (4) as a yellow oil. (Yield: 0.70 g, 85%). $R_f$=0.8 (4:1 Hexane/EtOAc). LCMS (m/z): 487.04 $(M+H)^+$. $^1H$ NMR (400 MHz, DMSO-$d_6$): δ 7.78-7.75 (m, 1H), 7.64 (s, 1H), 7.62-7.59 (m, 2H), 7.53-7.48 (m, 1H), 5.44 (s, 2H), 3.35-3.28 (m, 1H), 1.33-1.31 (m, 15H).

Step-3: Synthesis of tert-butyl 4-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate

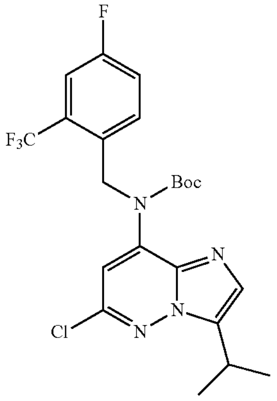

4

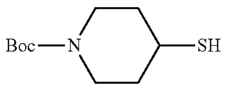

5

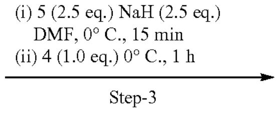

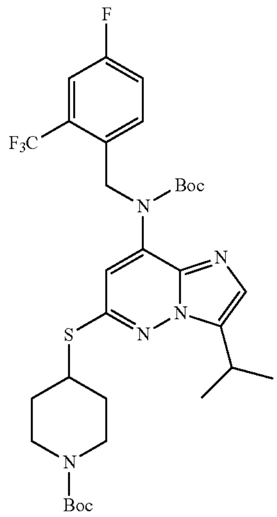

6

To a stirred solution tert-butyl 4-mercaptopiperidine-1-carboxylate (5) (0.279 g, 1.28 mmol, 2.5 eq.) in DMF (3 mL) at 0 °C was added NaH (60% in mineral oil, (0.051 g, 1.28 mmol, 2.5 eq.). Reaction mixture was stirred at 0 °C for 10 minutes. Then addition of tert-butyl (6-chloro-3-isopropylimidazo[1,2-b]pyridazin-8-yl)(4-fluoro-2-(trifluoromethyl)benzyl)carbamate (4) (0.250 g, 0.514 mmol, 1.0 eq.) in DMF (2 mL) was done. The reaction mixture was stirred at 0 °C for 1 h. Progress of reaction was monitored by TLC, the reaction mixture was diluted with ice cold water (50 mL) to get an off white solid. Off white solid filtered through Buchner and dried under reduced pressure and purified by silica gel column chromatography (EtOAc/hexane, gradient 5-10% EtOAc) to afford the title compound as (6) tert-butyl 4-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate as white solid. (Yield: 0.275 g, 80%). $R_f$=0.5 (4:1 Hexane/EtOAc). LCMS (m/z): 668.27 $(M+H)^+$.

Step-4: Synthesis of N-(4-fluoro-2-(trifluoromethyl) benzyl)-3-isopropyl-6-(piperidin-4-ylthio)imidazo[1,2-b]pyridazin-8-amine hydrochloride

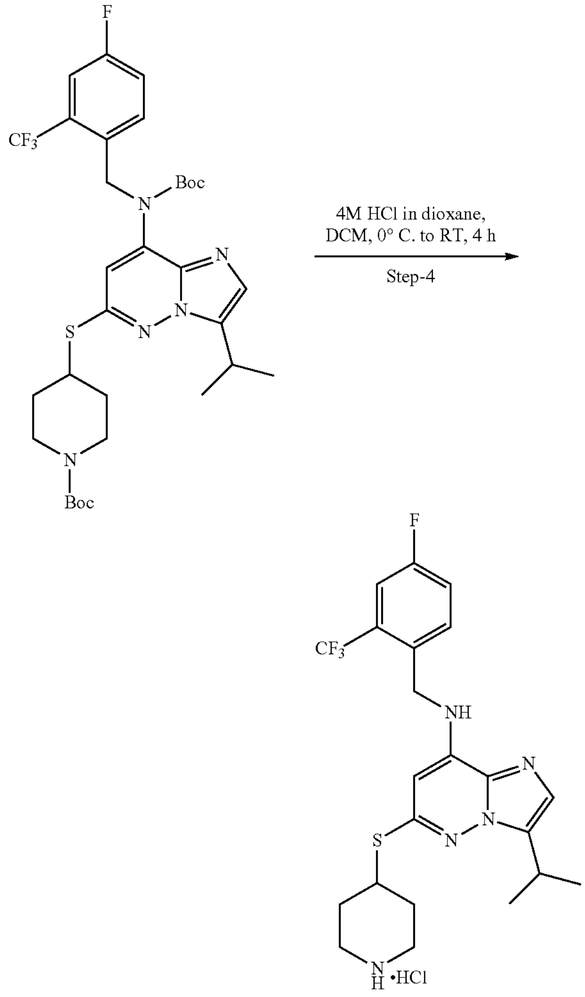

80

To a stirred solution of tert-butyl 4-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate (6) (0.275 g, 0.412 mmol, 1.0 eq.) in DCM (5 mL) at 0 °C was added 4M HCl in 1,4-dioxane (3 mL) drop-wise. Reaction mixture was allowed to come to room temperature and stirred for 4 h. Progress of reaction was monitored by TLC, the reaction mixture was subjected to rotary evaporator for removal of volatiles to get the brown solid as crude residue. The residue was purified by preparative HPLC using TFA buffer to afford the N-(4-fluoro-2-(trifluoromethyl)benzyl)-3-isopropyl-6-(piperidin-4-ylthio)imidazo[1,2-b]pyridazin-8-amine as TFA salt as an off white solid. Obtained TFA salt was basified with $NaHCO_3$solution (5 mL),water (5 mL) was added and extracted with DCM (3×25 mL), dried over $Na_2SO_4$ and concentrated under reduced pressure, to afford the N-(4-fluoro-2-(trifluoromethyl)benzyl)-3-isopropyl-6-(piperidin-4-ylthio)imidazo[1,2-b]pyridazin-8-amine as an off white solid. To get compound as a HCl salt, obtained amine was dissolved in ACN: water and treated with 2N aq. HCl (3 mL) at 0 °C and lyophilized for 24 h. to afford the title compound as N-(4-fluoro-2-(trifluoromethyl)benzyl)-3-isopropyl-6-(piperidin-4-ylthio)imidazo[1,2-b]pyridazin-8-amine hydrochloride (80) as an off white solid. (Yield: 0.135 g, quantitative). $R_f$=0.1 (4:1 $CHCl_3$/MeOH). LCMS (m/z): 468.31 $(M+H)^+$. $^1H$ NMR (400 MHz, DMSO-$d_6$,): δ=9.16 (m, 1H), 8.99-8.96 (m, 1H), 8.83 (s, 1H), 7.88 (s, 1H), 7.72-7.64 (m, 2H), 7.57-7.52 (m, 1H), 6.33 (s, 1H), 4.70 (d, J=4.8 Hz, 2H), 4.03-3.98 (m, 1H), 3.43-3.36 (m, 1H), 3.29-3.26 (m, 2H), 3.09-3.01 (m, 2H), 2.33-2.24 (m, 2H), 1.90-1.80 (m, 2H), 1.35 (d, J=6.8 Hz, 6H).

Example 81

Synthetic Scheme for Synthesis of N-(4-fluoro-2-(trifluoromethyl)benzyl)-3-isopropyl-6-(piperidin-3-ylthio)imidazo[1,2-b]pyridazin-8-amine hydrochloride

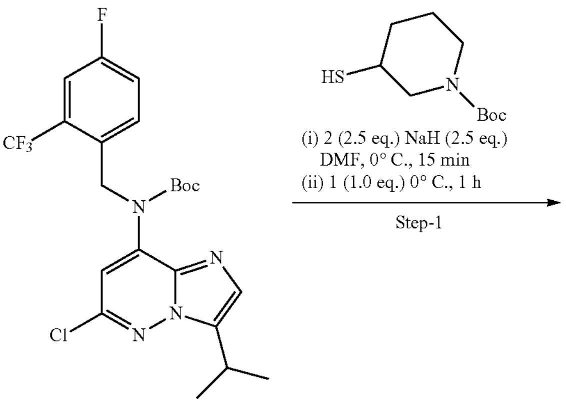

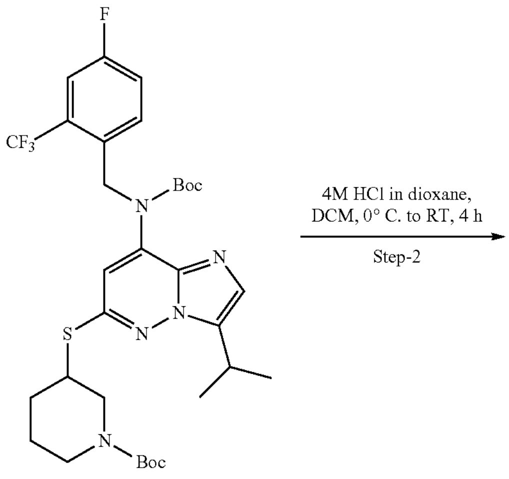

-continued

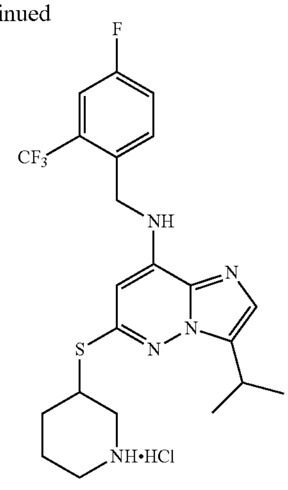

81

Step-1: Synthesis of tert-butyl 3-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate

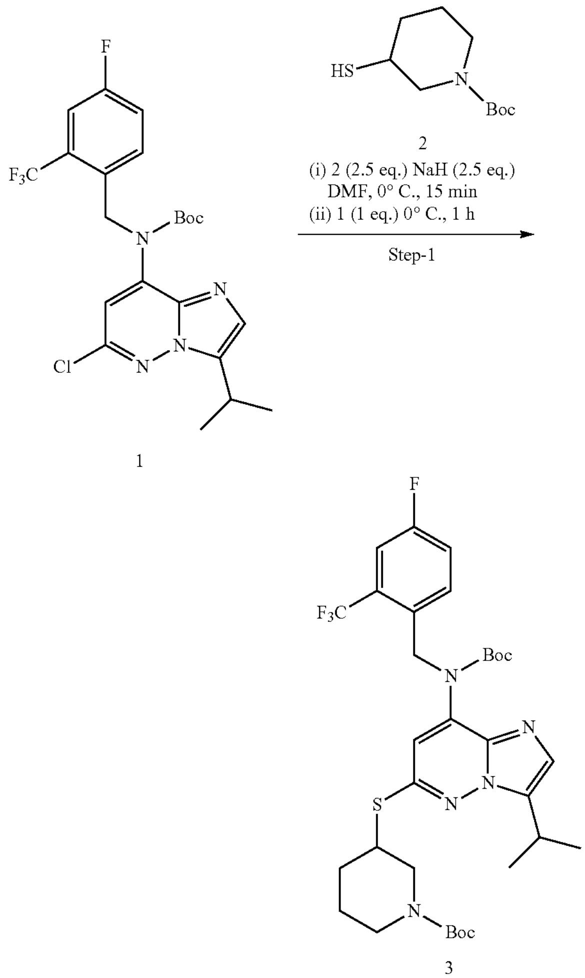

To a stirred solution tert-butyl 3-mercaptopiperidine-1-carboxylate (2) (0.279 g, 1.28 mmol, 2 0.5 eq.) in DMF (3 mL) at 0 °C was added NaH (60% in mineral oil), (0.051 g, 1.28 mmol, 2.5 eq.). Reaction mixture was stirred at 0 °C for 10 minutes. Then addition of tert-butyl (6-chloro-3-isopropylimidazo[1,2-b]pyridazin-8-yl)(4-fluoro-2-(trifluoromethyl)benzyl)carbamate (1) (0.250 g, 0.514 mmol, 1.0 eq.) in DMF (2 mL) was done. The resulting reaction mixture was stirred at 0 °C for 1 h. Progress of reaction was monitored by TLC, the reaction mixture was diluted with ice-cold water (30 mL), extracted with EtOAc (3×50 mL), washed with brine (25 mL), dried over $Na_2SO_4$, concentrated under reduced pressure to afford the brown oil as crude residue. Crude residue was purified by silica gel column chromatography (EtOAc/hexane, gradient 10-15% EtOAc) to afford the title compound as (3) as tert-butyl 3-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate as a yellow oil. (Yield: 0.270 g, 78%). $R_f$=0.5 (4:1 Hexane/EtOAc). LCMS (m/z): 668.14 $(M+H)^+$.

Step-2: Synthesis of N-(4-fluoro-2-(trifluoromethyl)benzyl)-3-isopropyl-6-(piperidin-3-ylthio)imidazo[1,2-b]pyridazin-8-amine hydrochloride

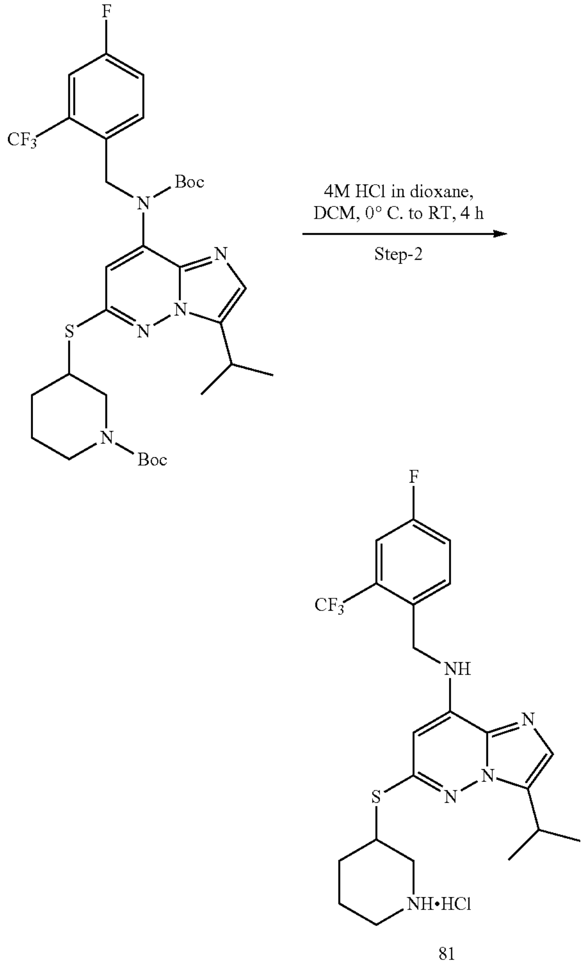

To a stirred solution of tert-butyl 3-((8-((tert-butoxycarbonyl)(4-fluoro-2-(trifluoromethyl)benzyl)amino)-3-isopropylimidazo[1,2-b]pyridazin-6-yl)thio)piperidine-1-carboxylate (3) (0.270 g, 0.404 mmol, 1.0 eq.) in DCM (5 mL) at 0 °C was added 4M HCl in 1,4-dioxane (3 mL) drop-wise. Reaction mixture was stirred at room temperature for 4 h. Progress of reaction was monitored by TLC. The reaction mixture was subjected to rotary evaporator for removal of volatiles to get crude residue. Crude residue was purified by Prep-HPLC using TFA buffer to afford the title compound as N-(4-fluoro-2-(trifluoromethyl)benzyl)-3-isopropyl-6-(piperidin-3-ylthio)imidazo[1,2-b]pyridazin-8-amine as TFA salt. TFA salt was dissolved in water (25 mL), extracted with DCM (3x25 mL), dried over $Na_2SO_4$ and concentrated under reduced pressure to get an off white solid. To get compound as a HCl salt, obtained amine was dissolved in ACN: water and treated with 2N aq. HCl (2 mL) at 0 °C and lyophilized for 24 h. to afford the title compound as N-(4-fluoro-2-(trifluoromethyl)benzyl)-3-isopropyl-6-(piperidin-3-ylthio)imidazo[1,2-b]pyridazin-8-amine hydrochloride (81) as Pale blue solid. (Yield: 0.139 g, quantitative). $R_f$=0.1 (9:1 $CH_2Cl_2$/MeOH). LCMS (m/z): 468.29 $(M+H)^+$. $^1H$ NMR (400 MHz, DMSO-$d_6$,): δ 9.47-9.45 (m, 1H), 9.16-9.14 (m, 1H), 8.81 (s, 1H), 7.87 (s, 1H), 7.72-7.52 (m, 3H), 6.34 (s, 1H), 4.70 (d, J=4.8 Hz, 2H), 4.12-4.06 (m, 1H), 3.59-3.48 (m, 2H), 3.24-3.21 (m, 1H), 3.07-3.05 (m, 1H), 2.90 (m, 1H), 2.13-2.08 (m, 1H), 1.87 (m, 2H), 1.73-1.63 (m, 1H), 1.34 (d, J=6.8 Hz, 6H).

Example 82

Synthetic Scheme for 3-isopropyl-6-(piperidin-4-ylthio)-N-(2-(trifluoromethoxy)benzyl)imidazo[1,2-b]pyridazin-8-amine

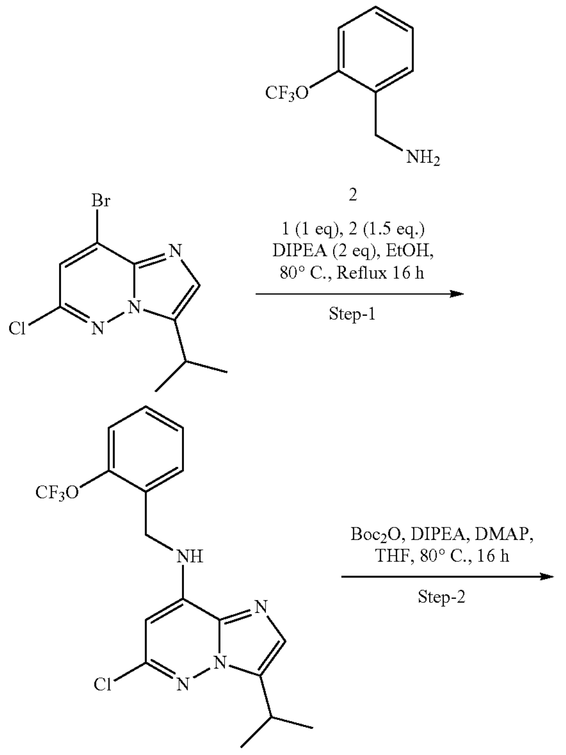

-continued

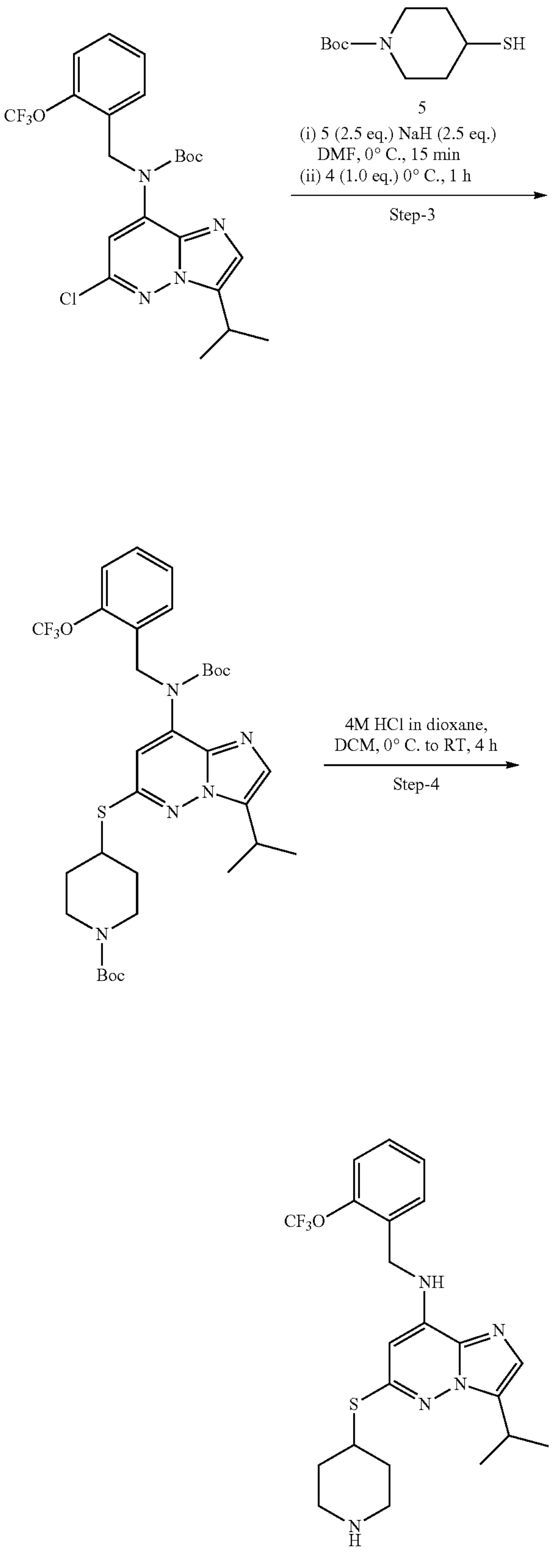

33

Step-1: Synthesis of 6-chloro-3-isopropyl-N-(2-(trifluoromethoxy)benzyl)imidazo[1,2-b]pyridazin-8-amine

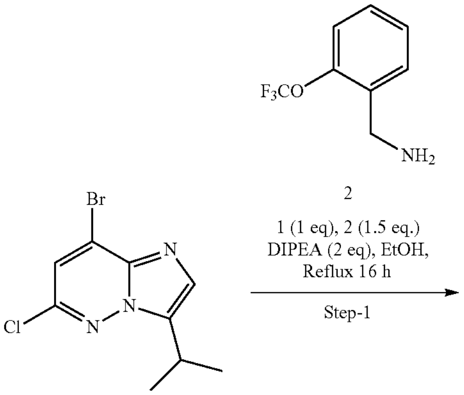

2

1

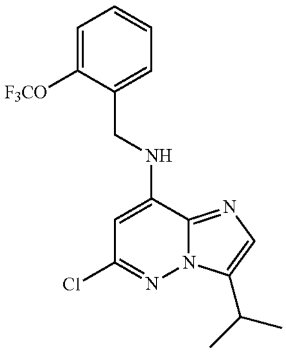

3

To a stirred solution of 8-bromo-6-chloro-3-isopropylimidazo[1,2-b]pyridazine (1) (4.0 g, 14.59 mmol, 1 eq.) and (2-(trifluoromethoxy)phenyl)methanamine (2) (3.29 g, 21.89 mmol, 1.5 eq.) in EtOH (40 mL) was added DIPEA (5.08 mL, 29.19 mmol, 2 eq.) and stirred for 16 h at 80 °C. Progress of reaction was monitored by TLC, after completion of reaction, volatiles were evaporated reduced pressure to get crude compound. The obtained crude compound was diluted with water (200 mL), extracted with EtOAc (2×200 mL). The combined extracts were washed with brine (100 mL), dried over $Na_2SO_4$, and concentrated under reduced pressure to provide crude compound. Crude compound was purified by silica gel column chromatography (EtOAc/hexane, gradient 0-10% EtOAc) as an eluting system to afford the title compound as 6-chloro-3-isopropyl-N-(2-(trifluoromethoxy)benzyl)imidazo[1,2-b]pyridazin-8-amine. (3) as white solid. (Yield: 4 g, 71%). $R_f$=0.4 (4:1 Hexane/EtOAc). LCMS (m/z): 385.1 $(M+H)^+$. $^1H$ NMR (400 MHz, DMSO-$d_6$): δ 8.39 (s, 1H), 7.43-7.34 (m, 5H), 5.99 (s, 1H), 4.63 (br s, 2H), 3.33-3.22 (m, 1H), 1.31 (d, J=6.8 Hz, 6H).

Step-2: Synthesis of tert-butyl (6-chloro-3-isopropylimidazo[1,2-b]pyridazin-8-yl)(2-(trifluoromethoxy)benzyl)carbamate

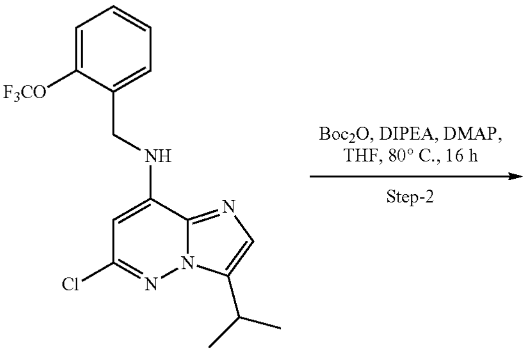

3

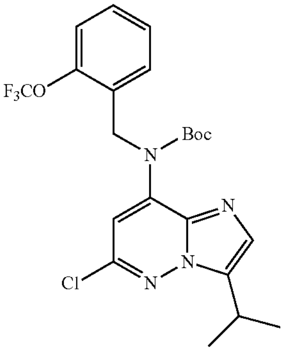

4

To a stirred solution of 6-chloro-3-isopropyl-N-(2-(trifluoromethoxy)benzyl)imidazo[1,2-b]pyridazin-8-amine (3) (4 g, 10.41 mmol, 1 eq.) in THF (40 mL) was added DIPEA (18.12 mL, 104.16 mmol, 10 eq.), $(Boc)_2O$ (23.90 mL, 104.16 mmol, 10 eq.) and DMAP (0.127 g, 1.041 mmol, 0.1 eq.) and stirred at 80 °C for 16 h. Progress of reaction was monitored by TLC. After completion of reaction, the reaction mixture was concentered under reduced pressure to get crude residue. The obtained crude was diluted with water (100 mL), extracted with EtOAc (2×100 mL). The combined organic layer washed with brine (100 mL), dried over $Na_2SO_4$, concentrated under reduced pressure to afford the brown oil as crude compound. Crude compound was purified by silica gel column chromatography (EtOAc/hexane, gradient 0-10% EtOAc) as an eluting system to afford the title compound as tert-butyl (6-chloro-3-isopropylimidazo[1,2-b]pyridazin-8-yl)(2-(trifluoromethoxy)benzyl)carbamate. (4) as a yellow oil. (Yield: 4.5 g, 89%). $R_f$=0.4 (4:1 Hexane/EtOAc). LCMS (m/z): 485.1 $(M+H)^+$. $^1H$ NMR (400 MHz, DMSO-$d_6$): δ7.65 (s, 1H), 7.57-7.54 (m, 1H), 7.41 (s, 1H), 7.39-7.27 (m, 3H), 5.39 (s, 2H), 3.37-3.32 (m, 1H). 1.34-1.31 (m, 15H).

Step-3: Synthesis of tert-butyl 4-((8-((tert-butoxycarbonyl)(2-(trifluoromethoxy)benzyl)amino)-3-isopropylimidazo[1,2-b]pyridazin-6-yl)thio)piperidine-1-carboxylate

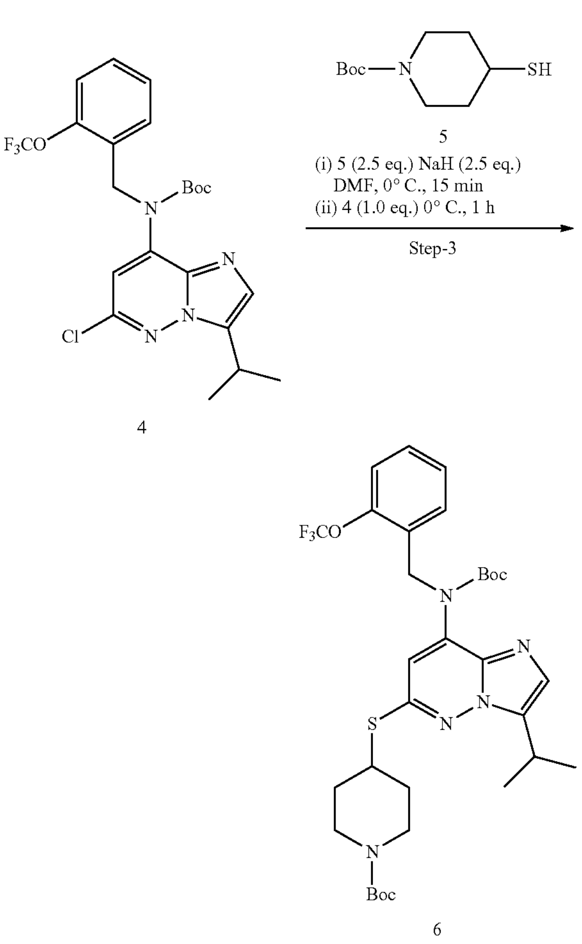

To a stirred solution of tert-butyl 4-mercaptopiperidine-1-carboxylate (5) (2.24 g, 10.33 mmol, 2.5 eq.) in DMF (10 mL) was added sodium hydride (60% dispersion in oil) (0.413 g, 10.33 mmol, 2.5 eq.) at 0 °C. Reaction mixture was stirred at 0 °C for 10 minutes. Then addition of tert-butyl (6-chloro-3-isopropylimidazo[1,2-b]pyridazin-8-yl)(2-(trifluoromethoxy)benzyl)carbamate. (4) (2 g, 4.132 mmol, 1 eq.) in DMF (10 mL) was added at 0 °C. Reaction mixture was stirred at 0 °C for 1 h. Progress of reaction was monitored by TLC. After complete conversion by TLC, the reaction mixture was diluted with ice cold water to get an off white solid, filtered through Buchner funnel and dried under reduced pressure to get crude compound as an off white solid. Crude compound was purified by column chromatography using silica gel (EtOAc/hexane, gradient 0-12% EtOAc) to afford the title compound as tert-butyl 4-((8-((tert-butoxycarbonyl)(2-(trifluoromethoxy)benzyl)amino)-3-isopropylimidazo[1,2-b]pyridazin-6-yl)thio)piperidine-1-carboxylate as yellow oil. (Yield: 2.4 g, 87%). $R_f$=0.4 (4:1 Hexane/EtOAc). LCMS (m/z): 666.36 $(M+H)^+$. $^1H$ NMR (400 MHz, DMSO-$d_6$) δ: 7.56-7.54 (m, 1H), 7.49 (s, 1H), 7.37-7.27 (s, 2H), 7.07 (s, 1H), 5.75 (s, 1H), 5.31 (s, 2H), 3.94-3.82 (m, 3H), 3.02-2.95 (m, 2H), 2.08-2.05 (m, 3H), 1.62-1.52 (m, 2H), 1.39-1.33 (m, 24H).

Step-4: Synthesis of 3-isopropyl-6-(piperidin-4-ylthio)-N-(2-(trifluoromethoxy)benzyl)imidazo[1,2-b]pyridazin-8-amine

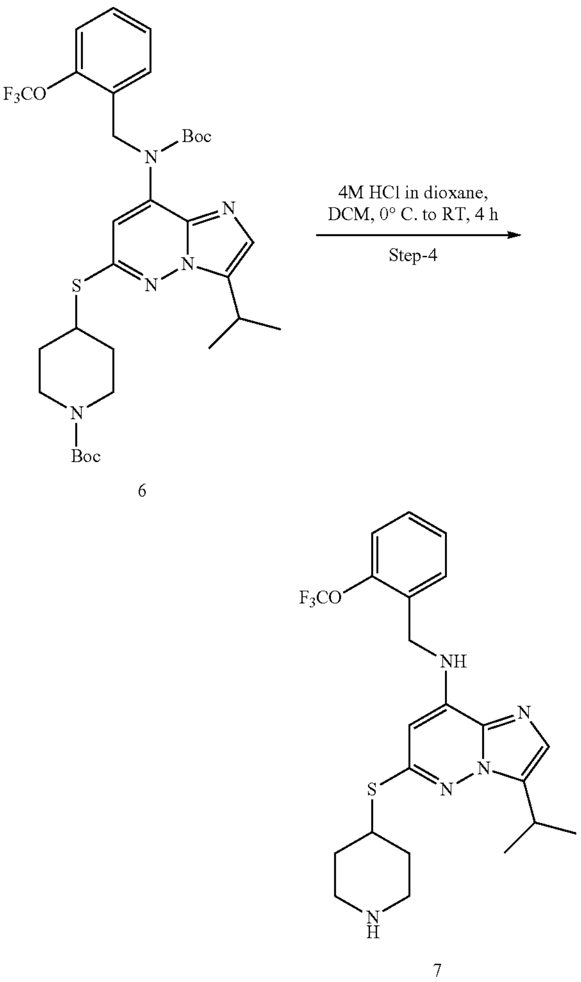

To a solution of tert-butyl 4-((8-((tert-butoxycarbonyl)(2-(trifluoromethoxy)benzyl)amino)-3-isopropylimidazo[1,2-b]pyridazin-6-yl)thio)piperidine-1-carboxylate. (6) (2.4 g, 3.60 mmol, 1 eq.) in DCM (5 mL) at 0 °C was added 4M HCl in 1,4 dioxane (10 mL) and stirred at room temperature for 4 h. Progress of reaction was monitored on TLC, volatiles were evaporated under reduced pressure to afford brown oil as crude residue. To the crude residue water (50 mL) was added, extracted with EtOAc (2×50 mL). Aqueous layer basified with $NaHCO_3$(10 mL) and extracted with EtOAc (3×50 mL), washed with brine (50 mL), dried over $Na_2SO_4$, concentrated under reduced pressure to afford the title compound as 3-isopropyl-6-(piperidin-4-ylthio)-N-(2-(trifluoromethoxy)benzyl)imidazo[1,2-b]pyridazin-8-amine (7) as yellow solid. (Yield: 1 g, 59%). $R_f$=0.1 (9:1 DCM/MeOH). LCMS (m/z): 466.36 $(M+H)^+$. $^1H$ NMR (400 MHz, DMSO-$d_6$) δ: 7.98 (t, J=6.4 Hz, 1H), 7.41-7.32 (m, 4H), 7.23 (s, 1H), 5.66 (s, 1H), 4.56 (d, J=6 Hz, 2H), 3.73-3.67 (m, 1H), 3.27-3.22 (m, 1H), 2.94-2.90 (m, 2H), 2.57-2.49 (m, 2H), 1.95-1.89 (m, 2H), 1.49-1.40 (m, 2H), 1.32 (d, J=6.8 Hz, 6H).

Synthesis of 3-isopropyl-6-(piperidin-4-ylthio)-N-(2-(trifluoromethoxy)benzyl)imidazo[1,2-b]pyridazin-8-amine, phosphoric acid salt

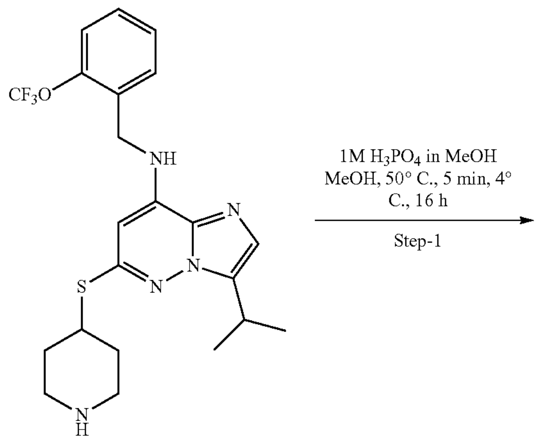

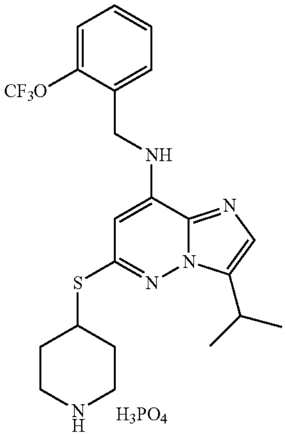

33b

To a solution of 3-isopropyl-6-(piperidin-4-ylthio)-N-(2-(trifluoromethoxy)benzyl)imidazo[1,2-b]pyridazin-8-amine (7) (100 mg, 0.215 mmol, 1 eq.) in MeOH (1 mL) at 50 °C was added 1M $H_3PO_4$ in MeOH (0.215 mL, 0.215 mmol, 1 eq) and stirred at 50 °C for 5 min. The reaction mixture was cooled to room temperature and was kept at 4 °C for 16 h. The precipitate was collected by filtration, then triturated with n-pentane and dried to afford the title compound as 3-isopropyl-6-(piperidin-4-ylthio)-N-(2-(trifluoromethoxy)benzyl)imidazo[1,2-b]pyridazin-8-amine, phosphoric acid salt as white solid (33b). (Yield: 45 mg. quantitative). $R_f$=0.1 (9:1 DCM/MeOH). LCMS (m/z): 466.32 $(M+H)^+$. $^1H$ NMR (400 MHz, DMSO-$d_6$) δ: 8.02 (t, J=5.6 Hz, 1H), 7.39-7.34 (m, 4H), 7.25 (s, 1H), 5.69 (s, 1H), 4.56 (d, J=4.4 Hz, 2H), 3.80-3.76 (m, 1H), 3.29-3.26 (m, 3H), 3.09-3.05 (m, 2H), 2.07-2.04 (m, 2H), 1.62-1.54 (m, 2H), 1.32 (d, J=6.8 Hz, 6H).

Synthesis of 3-isopropyl-6-(piperidin-4-ylthio)-N-(2-(trifluoromethoxy)benzyl)imidazo[1,2-b]pyridazin-8-amine methanesulfonate

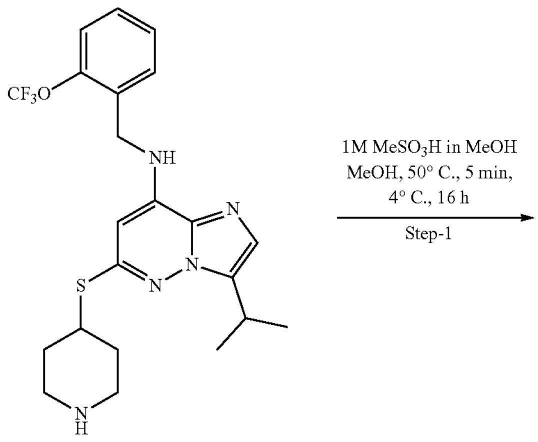

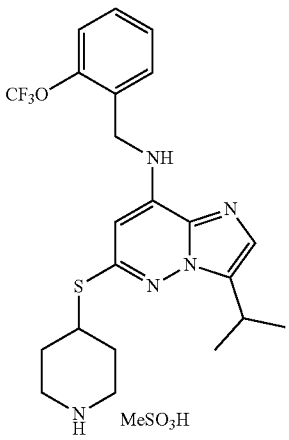

33c

To a solution of 3-isopropyl-6-(piperidin-4-ylthio)-N-(2-(trifluoromethoxy)benzyl)imidazo[1,2-b]pyridazin-8-amine (100 mg, 0.215 mmol, 1 eq.) in MeOH (1 mL) at 50 °C was added 1M $MeSO_3H$ in MeOH (0.215 mL, mmol, 1 eq.) and stirred at 50 °C for 5 min. The reaction mixture was cooled to room temperature and kept at 0 °C for 16 h. The reaction mixture was concentrated and triturated with n-pentane to afford the title compound as 3-isopropyl-6-(piperidin-4-ylthio)-N-(2-(trifluoromethoxy)benzyl)imidazo[1,2-b]pyridazin-8-amine methanesulfonate as a pale yellow gummy solid. (Yield: 105 mg. quantitative). $R_f$=0.1 (9:1 DCM/MeOH). LCMS (m/z): 466.37 $(M+H)^+$. $^1H$ NMR (400 MHz, DMSO-$d_6$) δ: 8.71 (m, 1H), 8.52-8.50 (m, 1H), 8.22 (m, 1H), 7.75 (s, 1H), 7.52-7.37 (m, 4H), 6.29 (s, 1H), 4.63 (d, J=4.8 Hz, 2H), 4.01-3.96 (m, 1H), 3.40-3.28 (m, 3H), 3.10-3.03 (m, 2H), 2.33 (m, 3H), 2.25-2.22 (m, 2H), 1.84-1.75 (m, 2H), 1.34 (d, J=6.8 Hz, 6H).

Synthesis of (3-isopropyl-6-(piperidin-4-ylthio)-N-(2-(trifluoromethoxy)benzyl)imidazo[1,2-b]pyridazin-8-amine citrate salt

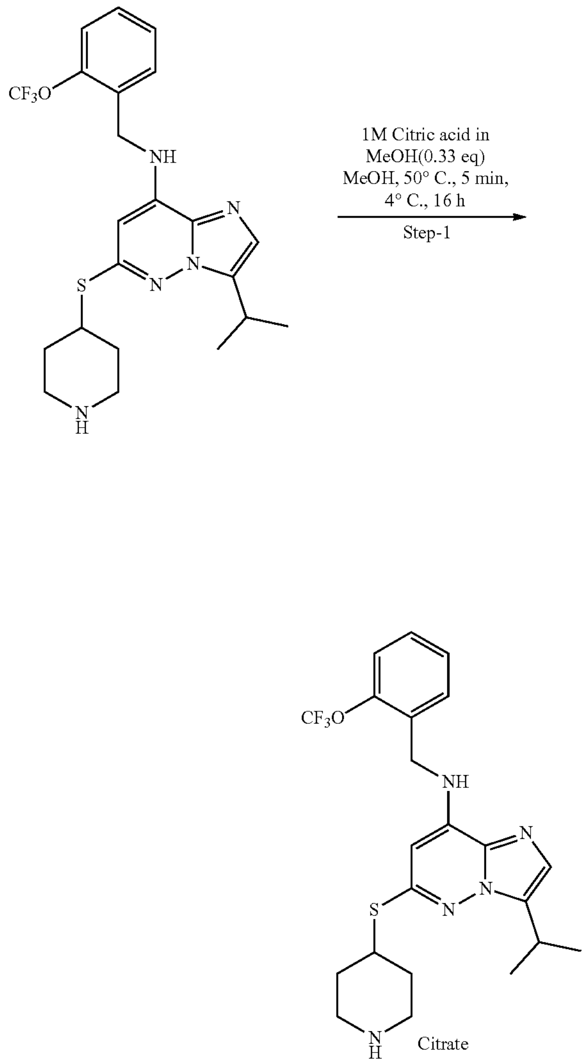

33e

To a solution of 3-isopropyl-6-(piperidin-4-ylthio)-N-(2-(trifluoromethoxy)benzyl)imidazo[1,2-b]pyridazin-8-amine (50 mg, 0.107 mmol, 0.33 eq.) in MeOH (1 mL) at 50 °C was added 1M citric acid in MeOH (0.035 mL, 0.035 mmol, 0.33 eq.) and stirred at 50 °C for 5 min. The reaction mixture was cooled to room temperature and kept at 0 °C for 16 h. The reaction mixture was concentrated and triturated with n-pentane to afford (3-isopropyl-6-(piperidin-4-ylthio)-N-(2-(trifluoromethoxy)benzyl)imidazo[1,2-b]pyridazin-8-amine citrate salt as an off white solid compound (33e). (Yield: 33 mg. quantitative). $R_f$=0.1 (9:1 DCM/MeOH). LCMS (m/z): 466.30 $(M+H)^+$. $^1$H NMR (400 MHz, DMSO-$d_6$) δ: 8.02 (m, 1H), 7.40-7.35 (m, 4H), 7.25 (s, 1H), 5.69 (s, 1H), 4.57 (d, J=4 Hz, 2H), 3.78 (m, 1H), 3.27-3.26 (m, 1H), 3.06 (d, J=12 Hz, 2H), 2.75-2.72 (m, 2H), 2.50-2.46 (m, 4H), 2.04 (d, J=10.8 Hz, 2H), 1.57-1.55 (m, 2H), 1.33 (d, J=6.8 Hz, 6H).

Synthesis of 3-isopropyl-6-(piperidin-4-ylthio)-N-(2-(trifluoromethoxy)benzyl)imidazo[1,2-b]pyridazin-8-amine sulfate

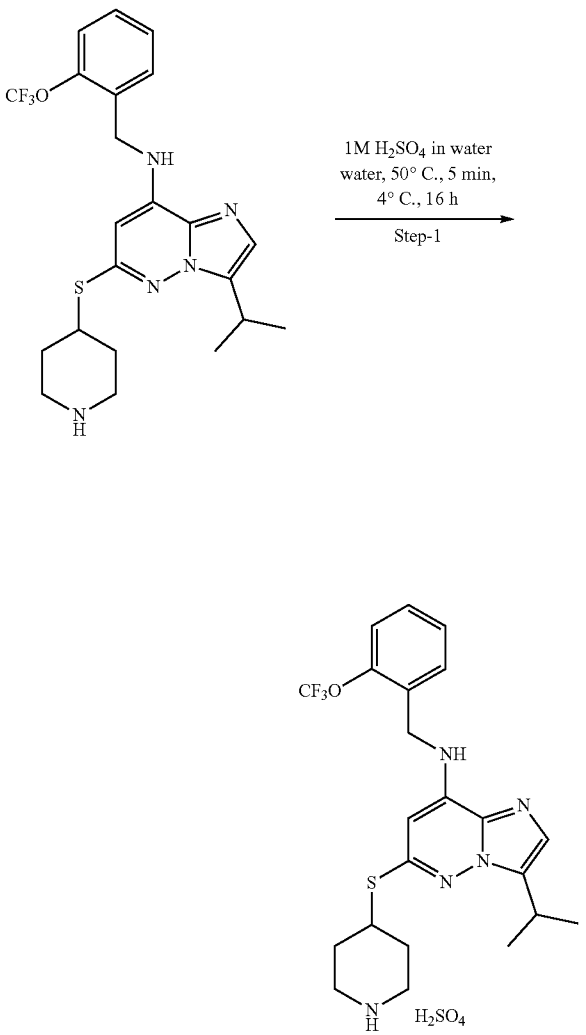

33d

Step-1: Synthesis of 3-isopropyl-6-(piperidin-4-ylthio)-N-(2-(trifluoromethoxy)benzyl)imidazo[1,2-b]pyridazin-8-amine sulfate To a solution of 3-isopropyl-6-(piperidin-4-ylthio)-N-(2-(trifluoromethoxy)benzyl)imidazo[1,2-b]pyridazin-8-amine (50 mg, 0.107 mmol, 1 eq.) in water (1 mL) at 50 °C was added 1M $H_2SO_4$ in water (0.107 mL, 0.107 mmol, 1 eq.) and stirred at 50 °C for 5 min. The reaction mixture was cooled to room temperature, and dried under lyophilization to afford the title compound as 3-isopropyl-6-(piperidin-4-ylthio)-N-(2-(trifluoromethoxy)benzyl)imidazo[1,2-b]pyridazin-8-amine sulfate as an off-white solid. (Yield: 58 mg. quantitative). $R_f$=0.1 (9:1 DCM/MeOH). LCMS (m/z): 466.30 $(M+H)^+$. $^1$H NMR (400 MHz, DMSO-$d_6$) δ: 8.53 (m, 1H), 8.36 (m, 1H), 8.05 (t, J=6.0 Hz, 1H), 7.46-7.35 (m, 5H), 5.88 (s, 1H), 4.60 (d, J=4.8 Hz, 2H), 3.95-3.90 (m, 1H), 3.36-3.28 (m, 3H), 3.06-3.03 (m, 2H), 2.24-2.21 (m, 2H), 1.80-1.73 (m, 2H), 1.33 (d, J=6.8 Hz, 6H).

Example 83

Synthesis of 6-((3-fluoropiperidin-4-yl)thio)-3-isopropyl-N-(2-(trifluoromethoxy)benzyl)imidazo[1,2-b]pyridazin-8-amine hydrochloride

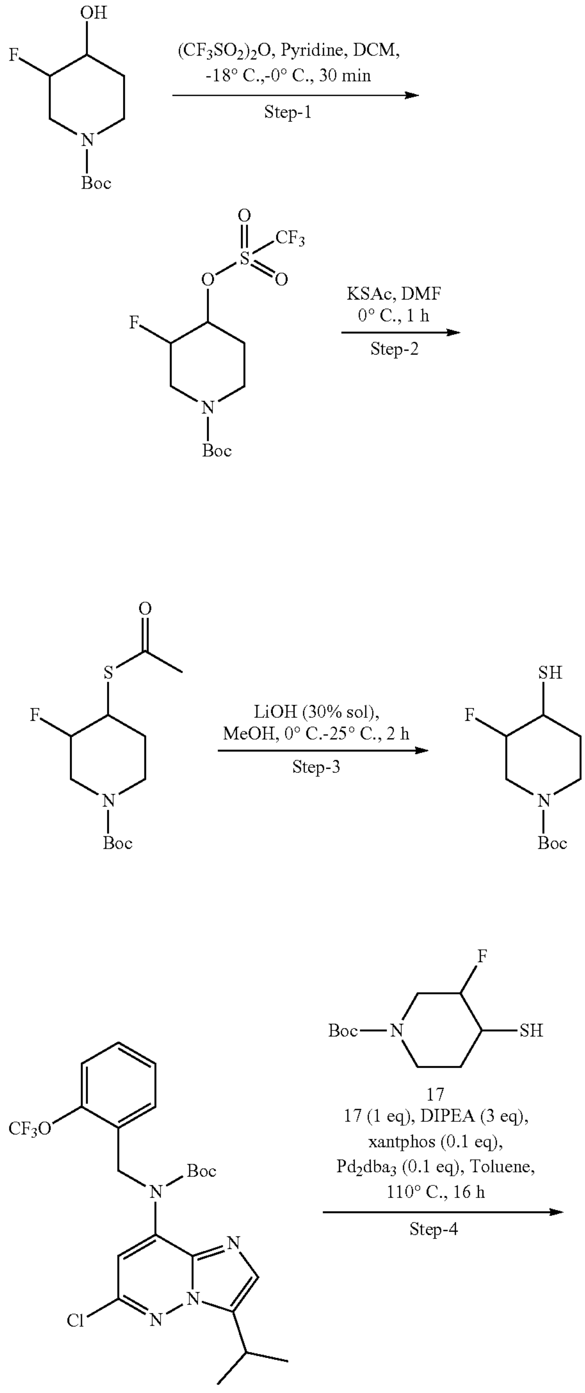

-continued

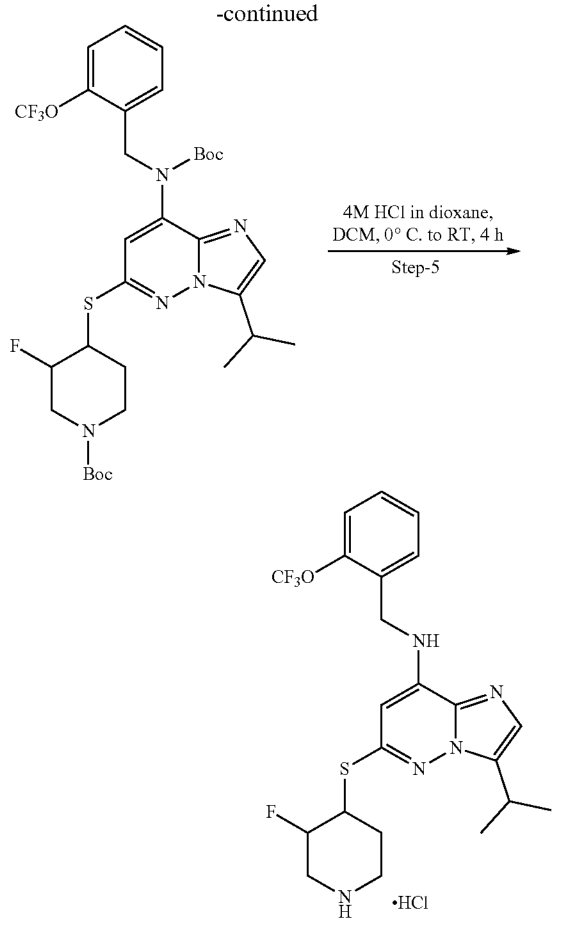

74

Step-1. Synthesis of tert-butyl 3-fluoro-4-(((trifluoromethyl)sulfonyl)oxy)piperidine-1-carboxylate

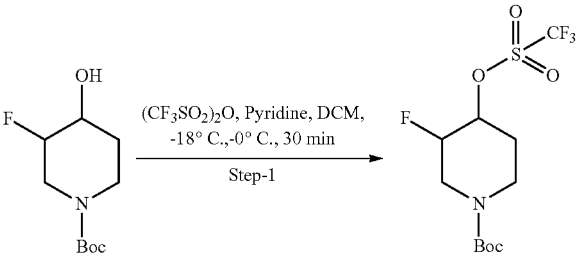

14 15

To a stirred solution of tert-butyl 3-fluoro-4-hydroxypiperidine-1-carboxylate 14 (3 g, 13.68 mmol, 1 equiv) in DCM (40 mL) was added pyridine (2.76 mL, 34.21 mmol, 2.5 equiv) at 0 °C. Then addition of trifluoromethanesulfonyl chloride (3.45 mL, 20.52 mmol, 1.5 equiv) at −18 °C. The reaction mixture was allowed to stir for 30 min. Progress of the reaction was monitored by TLC. After completion, reaction mixture was diluted with ice-cold water and extracted with DCM (3×35 mL). The combined organic layer was washed with brine solution (30 mL), dried over $Na_2SO_4$ and evaporated under reduced pressure to get the crude residue. The crude residue was triturated with diethyl ether (20 mL) and solid obtained was filtered off and washed with diethyl ether (2×10 mL). The combined filtrate was concentrated in vacuo to afford desired product tert-butyl 3-fluoro-4-(((trifluoromethyl)sulfonyl)oxy)piperidine-1-carboxylate (15) as reddish-brown oil which was carried to next step without any further purification. Yield: (3.6 g, 74.84%). $R_f$=~0.75 (40% EtOAc/Hexane).

Step-2. Synthesis of tert-butyl 4-(acetylthio)-3-fluoropiperidine-1-carboxylate

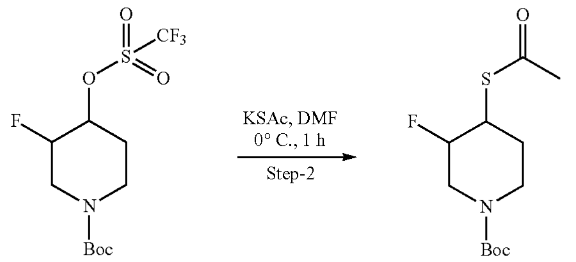

15 16

To a stirred solution of tert-butyl 3-fluoro-4-(((trifluoromethyl)sulfonyl)oxy)piperidine-1-carboxylate 15 (3.6 g, 10.25 mmol, 1 equiv) in DMF (12 mL) was added potassium thioacetate (1.76 g, 15.37 mmol, 1.5 equiv) at 0 °C. Reaction mixture was stirred at 0 °C for 1 h. Progress of the reaction was monitored by TLC. After completion of reaction, it was cooled and poured into crushed ice water, extracted with diethyl ether (3×40 mL). The combined organic layer was washed with brine solution (35 mL), dried over $Na_2SO_4$ and evaporated under reduced pressure to get the crude compound. The crude compound was purified by silica gel (100-200 mesh) column chromatography using 4% EtOAc/Hexane as eluent to afford Diastereomer-I (450 mg, 15.85%) and 6% EtOAc/Hexane as eluent to afford Diastereomer-II (720 mg, 25.40%) of title compound 16 tert-butyl 4-(acetylthio)-3-fluoropiperidine-1-carboxylate, both as brown oil. Due to reactivity issue of Diastereomer-I, only Diastereomer-II was used for further synthesis. Yield: Diastereomer-I (450 mg, 15.85%). Diastereomer-II (720 mg, 25.40%). Diastereomer-I: $R_f$=~0.55 (20% EtOAc/Hexane). Diastereomer-II: $R_f$=0.50 (20% EtOAc/Hexane). GCMS m/z calcd for $C_{12}H_{20}$ $FNO_3S$, 277.11; found 277.1.

Step-3. Synthesis of tert-butyl 3-fluoro-4-mercaptopiperidine-1-carboxylate

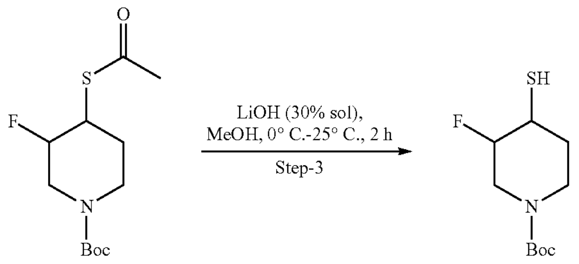

16 17

To a stirred solution of tert-butyl 4-(acetylthio)-3-fluoropiperidine-1-carboxylate 16 (720 mg, 2.59 mmol, 1 equiv) in methanol (5 mL) was added 30% aq. LiOH·$H_2O$ (327 mg, 7.79 mmol, 3 equiv) dropwise at 0 °C. Reaction mixture was allowed to warm to room temperature and stirred for 2 h. After complete conversion by TLC, reaction mixture was evaporated in vacuo. The residue was dissolved in water and pH was adjusted to 6 using saturated aqueous citric acid solution. The product was extracted with dichloromethane (3×25 mL), the organic phase was combined, dried over $Na_2SO_4$ and evaporated under reduced pressure to get the crude compound. The crude compound was purified by silica phase (100-200 mesh) column chromatography using 6% EtOAc/Hexane as eluent to afford the title compound tert-butyl 3-fluoro-4-mercaptopiperidine-1-carboxylate (17) as brown oil. Yield: (480 mg, 78.56%). $R_f$=~0.5 (20% EtOAc/Hexane). GCMS m/z calcd for $C_{10}H_{18}FNO_2S$, 235.10; found 235.1. $^1$HNMR (400 MHz, DMSO-$d_6$): δ 4.62 (d, J=47.2 Hz, 1H), 4.22-4.07 (m, 2H), 3.90-2.81 (m, 1H), 3.15-2.71 (m, 3H), 2.67 (d, 1H), 1.78-1.74 (m, 1H), 1.66-1.55 (m, 1H), 1.36 (s, 9H) ppm. $^{19}$F NMR (400 MHz, DMSO-$d_6$) δ:−74.77 (s), −197.55 to −198.66 (m) ppm.

Step-4. Synthesis of tert-butyl 4-((8-((tert-butoxycarbonyl)(2-(trifluoromethoxy)benzyl)amino)-3-isopropylimidazo[1,2-b]pyridazin-6-yl)thio)-3-fluoropiperidine-1-carboxylate

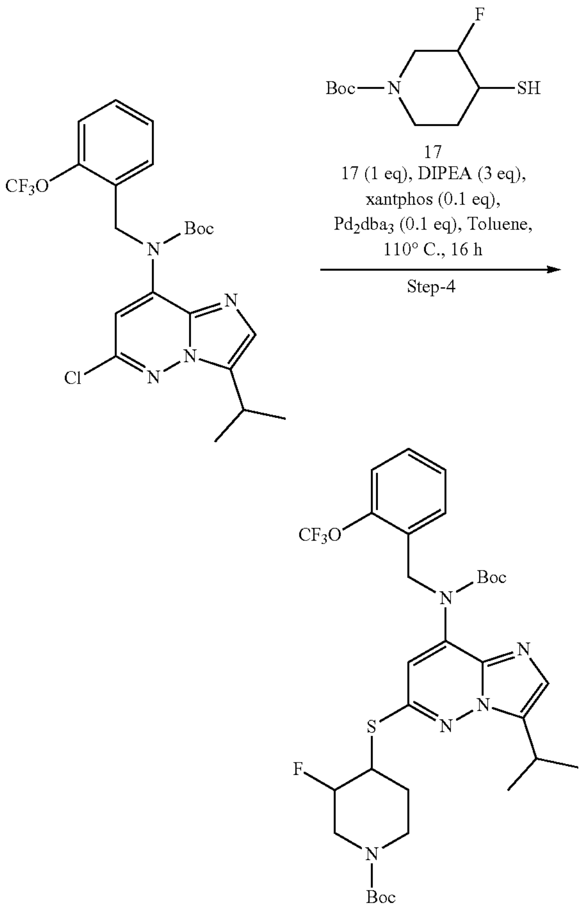

To a stirred solution of tert-butyl (6-chloro-3-isopropylimidazo[1,2-b]pyridazin-8-yl)(2-(trifluoromethoxy)benzyl)

carbamate (7'c) (72 mg, 0.15 mmol, 1 equiv) in toluene (5 mL), tert-butyl 3-fluoro-4-mercaptopiperidine-1-carboxylate (17) (35 mg, 0.15 mmol, 1 equiv), DIPEA (0.08 mL, 0.45 mmol, 3 equiv) and xantphos (8.1 mg, 10 mol %) were added at room temperature. The reaction mixture was purged with argon for 10 min then added tris(dibenzylideneacetone)dipalladium (12.8 mg, 10 mol %) again purged with argon for 5 min and heated at 110 °C for 16 h. Progress of the reaction was monitored by TLC. After completion of reaction, the reaction mixture was diluted with ethyl acetate and filtered through celite bed. The organic phase was washed with water (20 mL), brine, dried over $Na_2SO_4$ and concentrated under reduced pressure to afford crude. Obtained crude compound was purified by silica gel (100-200 mesh) column chromatography using 10% EtOAc/hexane as a eluent to afford tert-butyl 4-((8-((tert-butoxycarbonyl)(2-(trifluoromethoxy)benzyl)amino)-3-isopropylimidazo[1,2-b]pyridazin-6-yl)thio)-3-fluoropiperidine-1-carboxylate as off white solid. Yield: (100 mg, 98.1% yield). $R_f$=-0.35 (15% EtOAc/Hexane). LCMS m/z calcd for $C_{22}H_{25}F_4N_5OS$ 483.17; found 484.0 $(M+H)^+$.

Step-5. Final compound (74') synthesized as per general procedure discussed earlier (General Procedure-3)

| No. | Structure | IUPAC Name | Yield | LCMS | $^1$H NMR, $D_2O$ exchange & $^{19}$F NMR |
|---|---|---|---|---|---|
| 73 | 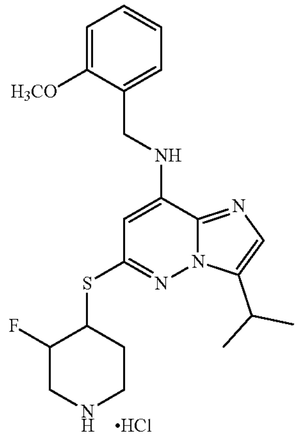 [SMILES: COc1ccccc1CNc1cc(SC2CCNCC2F)nn2c(C(C)C)cnc12 ; Cl] | 6-((3-fluoropiperidin-4-yl)thio)-3-isopropyl-N-(2-methoxybenzyl) imidazo[1,2-b]pyridazin-8-amine hydrochloride | 42.4 mg (88.3%) | 430.1 [M + H]+ | $^1$H NMR (400 MHz, DMSO-d6): δ 9.38 (brs, 1H), 8.78 (brs, 1H), 8.15 (brs, 1H), 7.61 (s, 1H), 7.30 - 7.24 (m, 2H), 7.04 (d, J = 8 Hz, 1H), 6.90 (t, J = 7.2 Hz, 1H), 6.21 (s, 1H), 4.70 (d, J = 72.2 Hz, 1H), 4.48 (d, J = 4.48 Hz, 2H), 4.31 - 4.20 (m, 1H), 3.85 (s, 3H), 3.68 - 3.62 (m, 1H), 3.51 - 3.50 (m, 1H), 3.33 - 3.28 (m, 2H), 3.16 - 3.08 (m, 1H), 2.19 - 2.16 (m, 1H), 2.06 - 1.97 (m, 1H), 1.33 - 1.30 (m, 6H); 19F NMR (400 MHz, DMSO-d6): δ -193.73 ppm. |
| 74 | 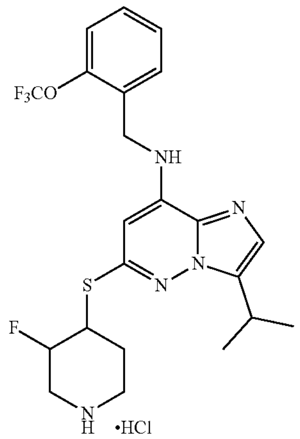 [SMILES: CC(C)c1cnc2c(NCc3ccccc3OC(F)(F)F)cc(SC3CCNCC3F)nn12 ; Cl] | 6-((3-fluoropiperidin-4-yl)thio)-3-isopropyl-N-(2-(trifluoromethoxy) benzyl)imidazo [1,2-b] pyridazin-8-amine hydrochloride | 36.86 mg (70.96%) | LCMS m/z calcd for $C_{22}H_{25}F_4N_5OS$ 483.17; found 484.0 (M + H)+ | $^1$H NMR (400 MHz, $DMSO-d_6$): δ 9.57 (brs, 1H), 8.82 (brs, 1H), 8.51 (s, 1H), 7.69 (s, 1H), 7.49 - 7.35 (m, 4H), 6.23 (s, 1H), 5.25 (d, J = 46.8 Hz, 1H), 4.63 (d, J = 5.2 Hz, 2H), 4.33 - 4.20 (m, 2H), 3.32 - 3.29 (m, 2H), 3.16 - 3.08 (m, 1H), 2.19 - 2.16 (m, 1H), 2.07 - 1.96 (m, 1H), 1.34 - 1.31 (m, 6H); $^{19}$F NMR (400 MHz, $DMSO-d_6$): δ -56.00, -193.66 ppm. |

-continued

| No. | Structure | IUPAC Name | Yield | LCMS | $^1$H NMR, $D_2O$ exchange & $^{19}$F NMR |
|---|---|---|---|---|---|
| 77 | 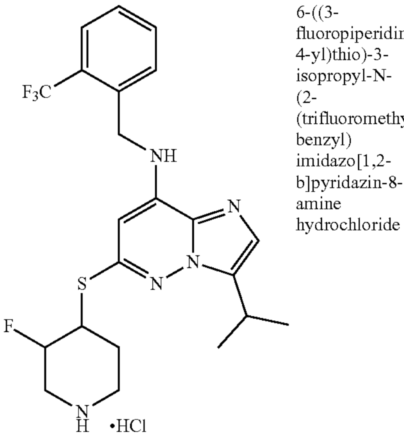 | 6-((3-fluoropiperidin-4-yl)thio)-3-isopropyl-N-(2-(trifluoromethyl)benzyl)imidazo[1,2-b]pyridazin-8-amine hydrochloride | 44 mg (42.69%) | 468.37 $[M + H]^+$ | $^1$H NMR (400 MHz, DMSO-$d_6$): δ 9.57 (brs, 1H), 8.82 (brs, 1H), 8.51 (s, 1H), 7.69 (s, 1H), 7.49 - 7.35 (m, 4H), 6.23 (s, 1H), 5.25 (d, J = 46.8 Hz, 1H), 4.63 (d, J = 5.2 Hz, 2H), 4.33 - 4.20 (m, 1H), 3.67 - 3.64 (m, 2H), 3.32 - 3.29 (m, 2H), 3.16 - 3.08 (m, 1H), 2.19 - 2.16 (m, 1H), 2.07 - 1.96 (m, 1H), 1.34 - 1.31 (m, 6H); $^{19}$F NMR (400 MHz, DMSO-$d_6$): δ -56.00, -193.66 ppm. |

Example 85

Synthesis of 6-((3,3-difluoropiperidin-4-yl)thio)-3-isopropyl-N-(2-(trifluoromethoxy)benzyl)imidazo[1,2-b]pyridazin-8-amine hydrochloride Scheme-4

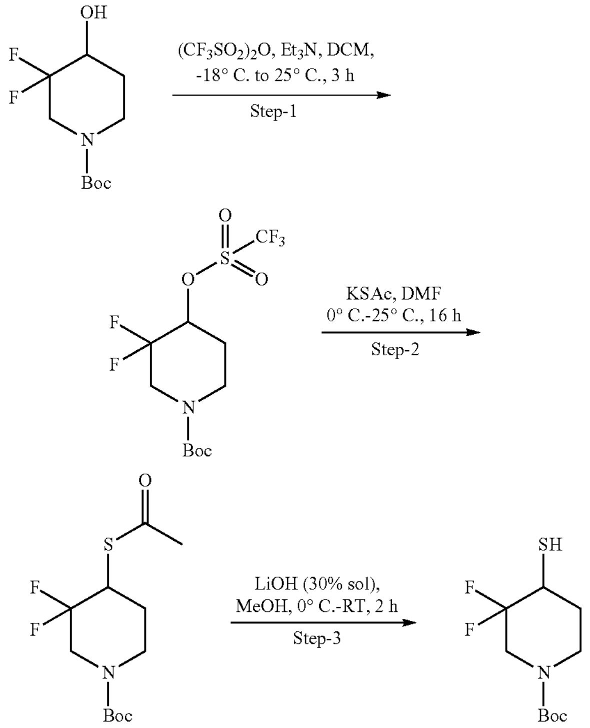

-continued

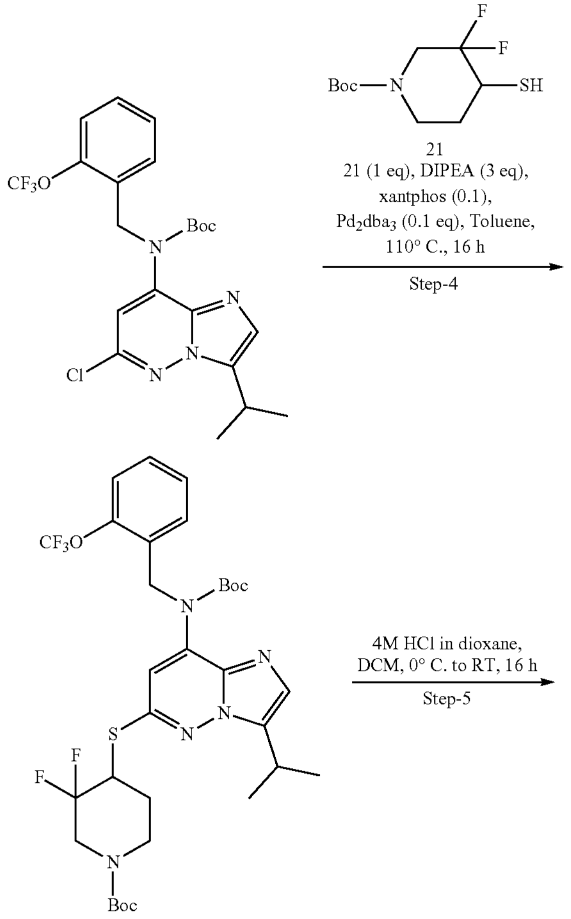

-continued

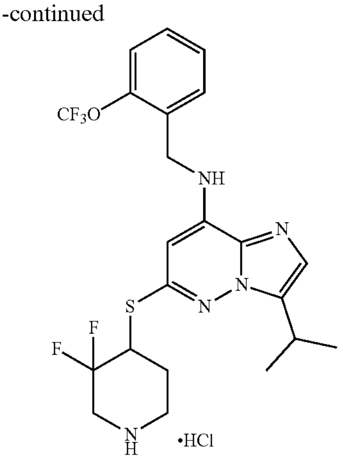

76

Step-1. Synthesis of tert-butyl 3,3-difluoro-4-(((trifluoromethyl)sulfonyl)oxy)piperidine-1-carboxylate

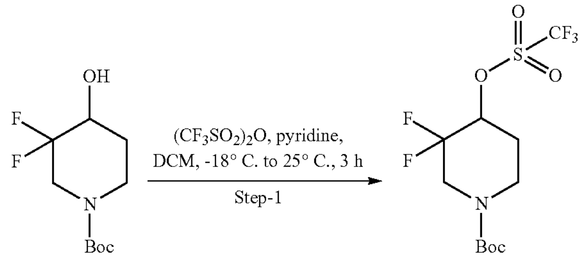

18 19

To a stirred solution of tert-butyl 3,3-difluoro-4-hydroxypiperidine-1-carboxylate 18 (2 g, 8.43 mmol, 1 equiv) in DCM (40 mL) was added pyridine (1.70 mL, 21.07 mmol, 2.5 equiv) at 0 °C. Then addition of trifluoromethanesulfonyl chloride (1.69 mL, 10.12 mmol, 1.2 equiv) was done at −18 °C. The reaction mixture was allowed to warm to room temperature and continued stirring for 2 h. Progress of the reaction was monitored by TLC. After completion, reaction mixture was diluted with ice-cold water and extracted with DCM (3x15 mL). The combined organic layer was washed with brine solution (20 mL), dried over $Na_2SO_4$ and evaporated under reduced pressure to get crude tert-butyl 3,3-difluoro-4-(((trifluoromethyl)sulfonyl)oxy)piperidine-1-carboxylate (19) as brown oil which was carried to next step without any further purification. Yield: (2.2 g, 70.74%). $R_f$=~0.75 (40% EtOAc/Hexane). GCMS m/z calcd for $C_{11}H_{16}F_5NO_5S$, 369.07; found 369.0.

Step-2. Synthesis of tert-butyl 4-(acetylthio)-3,3-difluoropiperidine-1-carboxylate

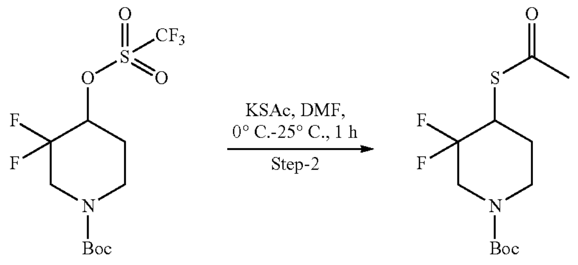

19 20

To a stirred solution of tert-butyl 3,3-difluoro-4-(((trifluoromethyl)sulfonyl)oxy)piperidine-1-carboxylate 19 (2.2 g, 5.96 mmol, 1 equiv) in DMF (8 mL) was added potassium thioacetate (1.02 g, 8.94 mmol, 1.5 equiv) at 0 °C. Reaction mixture was stirred at 0 °C for 1 h. Progress of the reaction was monitored by TLC. After completion, reaction mixture was cooled and poured into crushed ice water, extracted with diethyl ether (3x30 mL). The combined organic layer was washed with brine solution (25 mL), dried over $Na_2SO_4$ and evaporated under reduced pressure to get the crude compound. The crude compound was purified by silica gel (100-200 mesh) column chromatography using EtOAc/Hexane (6%) as eluent to afford the title compound tert-butyl 4-(acetylthio)-3,3-difluoropiperidine-1-carboxylate 20 as brown oil. Yield: (920 mg, 52.30%). $R_f$=~0.50 (20% EtOAc/Hexane). GCMS m/z calcd for $C_{12}H_{19}F_2NO_3S$, 295.11; found 295.1.

Step-3. Synthesis of tert-butyl 3,3-difluoro-4-mercaptopiperidine-1-carboxylate

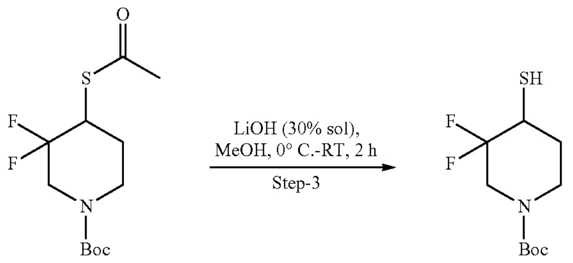

20 21

To a stirred solution of tert-butyl 4-(acetylthio)-3,3-difluoropiperidine-1-carboxylate 20 (800 mg, 2.71 mmol, 1 equiv) in methanol (5 mL) was added 30% aqueous $LiOH{\cdot}H_2O$ (341 mg, 8.13 mmol, 3 equiv) dropwise at 0 °C. Reaction mixture was allowed warm to room temperature and stirred for 2 h. After complete conversion by TLC, reaction mixture was evaporated in vacuo. The residue was dissolved in water and pH was adjusted to 6 using saturated aqueous citric acid solution. The product was extracted with dichloromethane (2x20 mL), the organic phase was combined, dried over $Na_2SO_4$ and evaporated under reduced pressure to get the crude compound. The crude compound was purified by silica gel (100-200 mesh) column chromatography using EtOAc/Hexane (6%) as eluent to afford the title compound tert-butyl 3,3-difluoro-4-mercaptopiperidine-1-carboxylate (21) as brown oil. Yield: (550 mg, 80.17%). $R_f$=~0.50 (20% EtOAc/Hexane). GCMS m/z calcd for $C_{10}H_{17}F_2NO_2S$, 253.09; found 253.0.

Step-4. Synthesis of tert-butyl 4-((8-((tert-butoxycarbonyl)(2-(trifluoromethoxy)benzyl)amino)-3-isopropylimidazo[1,2-b]pyridazin-6-yl)thio)-3,3-difluoropiperidine-1-carboxylate

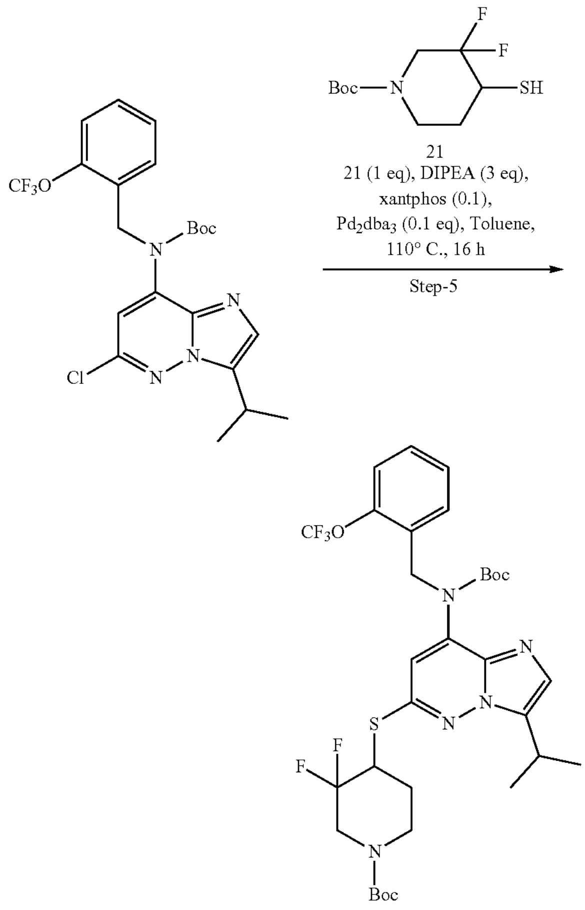

To a stirred solution of tert-butyl (6-chloro-3-isopropylimidazo[1,2-b]pyridazin-8-yl)(2-(trifluoromethoxy)benzyl) carbamate (21) (100 mg, 0.39 mmol, 1 equiv) in toluene (5 mL), tert-butyl 3,3-difluoro-4-mercaptopiperidine-1-carboxylate (21) (191 mg, 0.39 mmol, 1 equiv.), DIPEA (0.21 mL, 1.18 mmol, 3 equiv) and xantphos (22 mg, 10 mol %) were added at room temperature. The reaction mixture was purged with argon for 10 min then added tris(dibenzylideneacetone)dipalladium (36 mg, 10 mol %) again purged with argon for 5 min and heated at 110 °C for 16 h. The progress of reaction was monitored by TLC. After completion of reaction, the reaction mixture was diluted with ethyl acetate and filtered through celite bed. The organic phase was washed with water (20 mL), brine, dried over $Na_2SO_4$ and concentrated under reduced pressure to afford crude. The crude compound was purified by silica gel (100-200 mesh) column chromatography using 9% EtOAc/Hexane as eluent to afford tert-butyl 4-((8-((tert-butoxycarbonyl)(2-(trifluoromethoxy)benzyl)amino)-3-isopropylimidazo[1,2-b] pyridazin-6-yl)thio)-3,3-difluoropiperidine-1-carboxylate (23) as white solid. Yield: (125 mg, 45.29%). $R_f$=-0.3 (15% EtOAc/Hexane). LCMS m/z calcd for $C_{32}H_{40}F_5N_5O_5S$ 701.27; found 702.36 $(M+H)^+$.

Step-5. Final compound 76 synthesized as per general procedure discussed earlier (General Procedure-3)

Example 86

| No. | Structure | IUPAC Name | Yield | LCMS | $^1H$ NMR, $D_2O$ exchange & $^{19}F$ NMR |
|---|---|---|---|---|---|
| 75 | 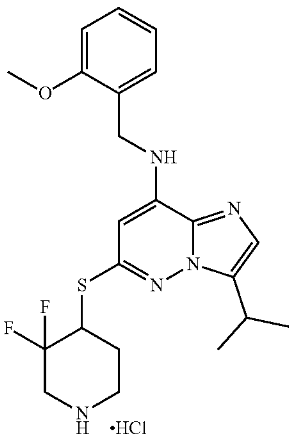 [SMILES: COc1ccccc1CNc1cc(SC2CCNCC2(F)F)nn2c(C(C)C)cnc12 ; Cl] | 6-((3,3-difluoropiperidin-4-yl)thio)-3-isopropyl-N-(2-methoxybenzyl) imidazo[1,2-b]pyridazin-8-amine hydrochloride | 101 mg (82.11%) | 448.1 [M + H]+ | $^1H$ NMR (400 MHz, DMSO-$d_6$): δ 10.55 (brs, 1H), 9.54 (brs, 1H), 8.60 (s, 1H), 7.84 (s, 1H), 7.31 - 7.27 (m, 2H), 7.04 (d, J = 8 Hz, 1H), 6.91 (t, J = 7.6 Hz, 1H), 6.48 (s, 1H), 4.70 - 4.60 (dd, 1H), 4.52 (d, J = 7.2 Hz, 2H), 3.90 - 3.66 (m, 5H), 3.49 - 3.43 (m, 1H), 3.33 - 3.30 (m, 1H), 3.24 - 3.18 (m, 1H), 2.44 (s, 1H), 2.06 - 1.97 (m, 1H), 1.32 (t, J = 7.2 Hz, 6H); $^{19}F$ NMR (400 MHz, DMSO-$d_6$): δ -101.76, -106.33 ppm. |

-continued

| No. | Structure | IUPAC Name | Yield | LCMS | $^1$H NMR, $D_2O$ exchange & $^{19}$F NMR |
|---|---|---|---|---|---|
| 76 | 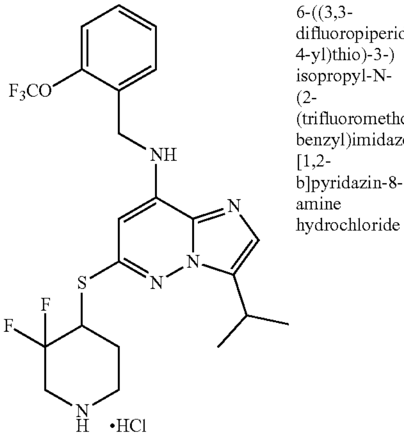 | 6-((3,3-difluoropiperidin-4-yl)thio)-3-)isopropyl-N-(2-(trifluoromethoxy)benzyl)imidazo[1,2-b]pyridazin-8-amine hydrochloride | 46 mg (47.92%) | 502.39 $[M + H]^+$ | $^1$H NMR (400 MHz, (brs, 1H), 9.51 (brs, 1H), 8.72 (s, 1H), 7.79 (s, 1H), 7.51 – 7.35 (m, 4H), 6.39 (s, 1H), 4.69 – 4.59 (m, 3H), 3.90 – 3.89 (m, 1H), 3.87 – 3.84 (m, 1H), 3.51 – 3.41 (m, 1H), 3.32 – 3.30 (m, 1H), 3.23 – 3.16 (m, 1H), 2.44 (s, 1H), 2.07 – 1.95 (m, 1H), 1.33 (t, J = 6.8 Hz, 6H); 19F NMR (400 MHz, DMSO-d6): δ −55.98, −101.78, −106.36 ppm. |

Example 87

Synthetic Scheme for (S)—N-(3-fluorophenyl)-6-(piperidin-3-yloxy)-3-(trifluoromethyl)imidazo[1,2-b]pyridazin-8-amine hydrochloride

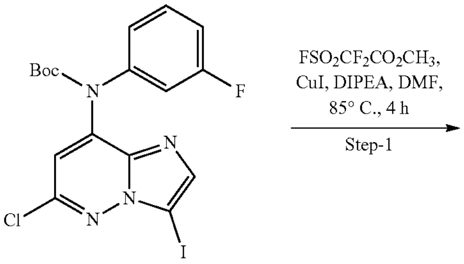

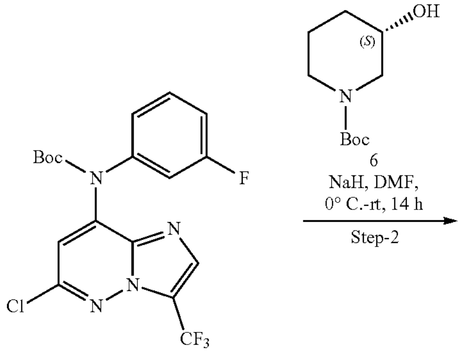

-continued

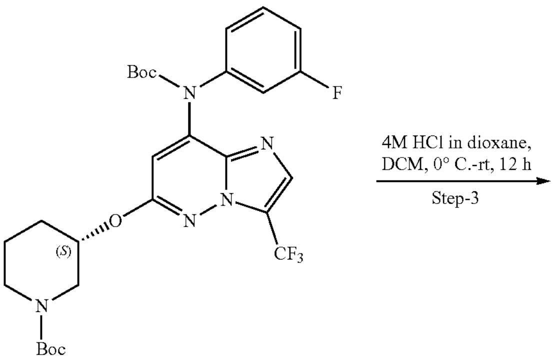

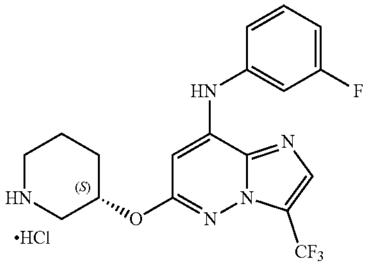

82

Step-1: Synthesis of tert-butyl (6-chloro-3-(trifluoromethyl)imidazo[1,2-b]pyridazin-8-yl)(3-fluorophenyl)carbamate

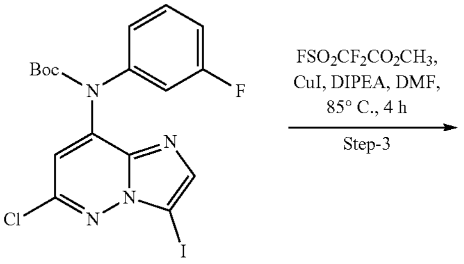

4

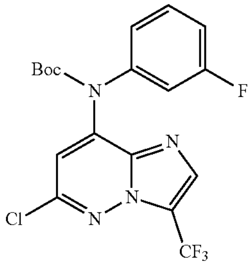

5

To a stirred solution of tert-butyl (6-chloro-3-iodoimidazo[1,2-b]pyridazin-8-yl)(3-fluorophenyl)carbamate (4) (500 mg, 1.02 mmol, 1 equiv) in DMF (10 mL) was added CuI (487 mg, 2.55 mmol, 2.5 equiv), DIPEA (1.78 mL, 10.23 mmol, 10 equiv) at room temperature. The reaction mixture was stirred for 10 minutes and then added Methyl 2,2-difluoro-2-(fluorosulfonyl)acetate (1.97 g, 10.23 mmol, 10 equiv) at room temperature. The reaction mixture was then heated to 85 °C for 4 h. After completion of the reaction, reaction mixture was cooled down to room temperature and then filtered through celite bed, washed with EtOAc (2×20 mL). The organic layer was combined and washed with brine (20 mL), dried over $Na_2SO_4$ and concentrated in vacuo. The crude residue obtained was purified by combi flash column chromatography using 10% EtOAc/Hexane as eluent to afford tert-butyl (6-chloro-3-(trifluoromethyl)imidazo[1,2-b]pyridazin-8-yl)(3-fluorophenyl)carbamate (5). Yield: (295 mg, 67%). $R_f$=–0.5 (10% EtOAc/Hexane). LCMS m/z calcd for $C_{18}H_{15}ClF_4N_4O_2$ 430.08; found 431.1 $(M+H)^+$.

Step-2. Synthesis of tert-butyl (S)-3-((8-((tert-butoxycarbonyl)(3-fluorophenyl)amino)-3-(trifluoromethyl)imidazo[1,2-b]pyridazin-6-yl)oxy)piperidine-1-carboxylate

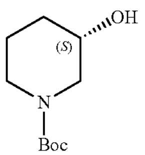

6

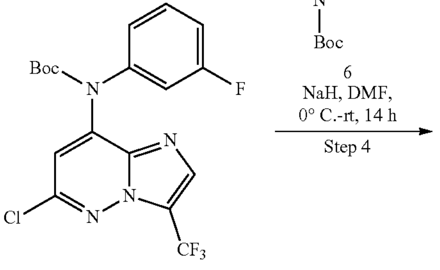

5

-continued

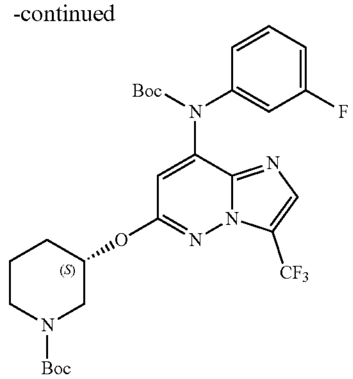

7

To a stirred solution of tert-butyl (S)-3-hydroxypiperidine-1-carboxylate (6) (160.19 mg, 0.84 mmol, 1.5 equiv) in DMF (4 mL) was added sodium hydride (60% dispersion in mineral oil) (45 mg, 1.114 mmol, 2.0 equiv) at 0 °C. Reaction mixture was stirred for 15 minutes and tert-butyl (6-chloro-3-(trifluoromethyl)imidazo[1,2-b]pyridazin-8-yl)(3-fluorophenyl)carbamate (5) (240 mg, 0.56 mmol, 1 equiv) was added at 0 °C. Then reaction mixture was allowed to attain room temperature and stirred for 14 h. Completion of the reaction was monitored by TLC. After completion, the reaction mixture was quenched with ice water, and extracted with ethyl acetate (3×15 ml). Combined organic layer was washed with brine (15 mL), dried over $Na_2SO_4$, and evaporated under reduced pressure to afford the crude compound. Crude compound was purified by combiflash column chromatography using 14% EtOAc/Hexane as eluent to afford the title compound tert-butyl (S)-3-((8-((tert-butoxycarbonyl)(3-fluorophenyl)amino)-3-(trifluoromethyl)imidazo[1,2-b]pyridazin-6-yl)oxy)piperidine-1-carboxylate (7) as colourless liquid. Yield: (260 mg, 78.54%). $R_f$=–0.4 (20% EtOAc/Hexane). LCMS m/z calcd for $C_{28}H_{33}F_4N_5O_5$ 595.24; found 596.22 $(M+H)^+$.

Step-3. Synthesis of (S)—N-(3-fluorophenyl)-6-(piperidin-3-yloxy)-3-(trifluoromethyl)imidazo[1,2-b]pyridazin-8-amine hydrochloride

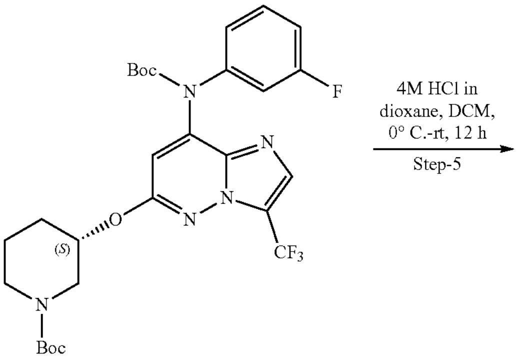

-continued

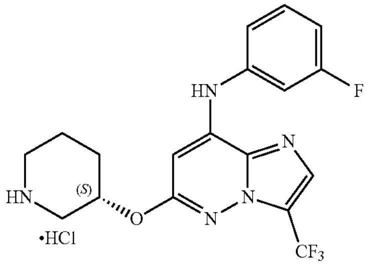

82

To a stirred solution of tert-butyl (S)-3-((8-((tert-butoxycarbonyl)(3-fluorophenyl)amino)-3-(trifluoromethyl)imidazo[1,2-b]pyridazin-6-yl)oxy)piperidine-1-carboxylate (7) (250 mg, 0.42 mmol, 1equiv.) in DCM (5 mL) at 0 °C was dropwise added 4M HCl in 1,4-dioxane (4 mL). Reaction mixture was allowed to warm to room temperature and stirred for 12 h. After completion of reaction as indicated by TLC, the reaction mixture was subjected to rotary evaporator for removal of volatiles to get crude white solid. The obtained residue was triturated with n-pentane (3×10 mL), diethyl ether (2×10 mL) to afford the title compound (S)—N-(3-fluorophenyl)-6-(piperidin-3-yloxy)-3-(trifluoromethyl)imidazo[1,2-b]pyridazin-8-amine hydrochloride (82) as a white solid. Yield: (150 mg, 91%). $R_f$=~0.1 (10% MeOH/DCM). LCMS m/z calcd for $C_{18}H_{17}F_4N_5O$ 395.14; found 396.1 $(M+H)^+$. $^1H$ NMR (400 MHz, DMSO-$d_6$): δ=9.93 (s, 1H), 9.19 (brs, 1H), 8.62 (brs, 1H), 8.11 (s, 1H), 7.52-7.46 (m, 1H), 7.31-7.27 (m, 2H), 7.07-7.02 (m, 1H), 6.33 (s, 1H), 5.17 (s, 1H), 3.38-3.28 (m, 2H), 3.10 (m, 2H), 1.97-1.95 (m, 3H), 1.68-1.66 (m, 1H) ppm; $^{19}F$ NMR (400 MHz, DMSO-$d_6$): δ −60.54, −111.45 ppm.

Example 88

Synthetic Scheme for N-benzyl-6-(piperidin-4-ylthio)-3-(trifluoromethyl)imidazo[1,2-b]pyridazin-8-amine hydrochloride

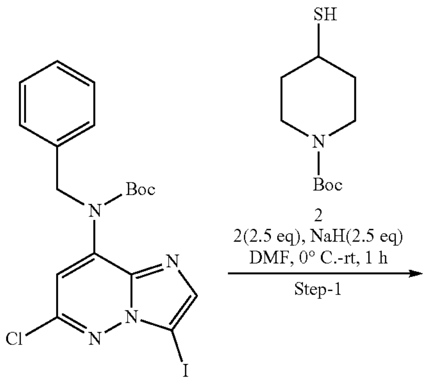

-continued

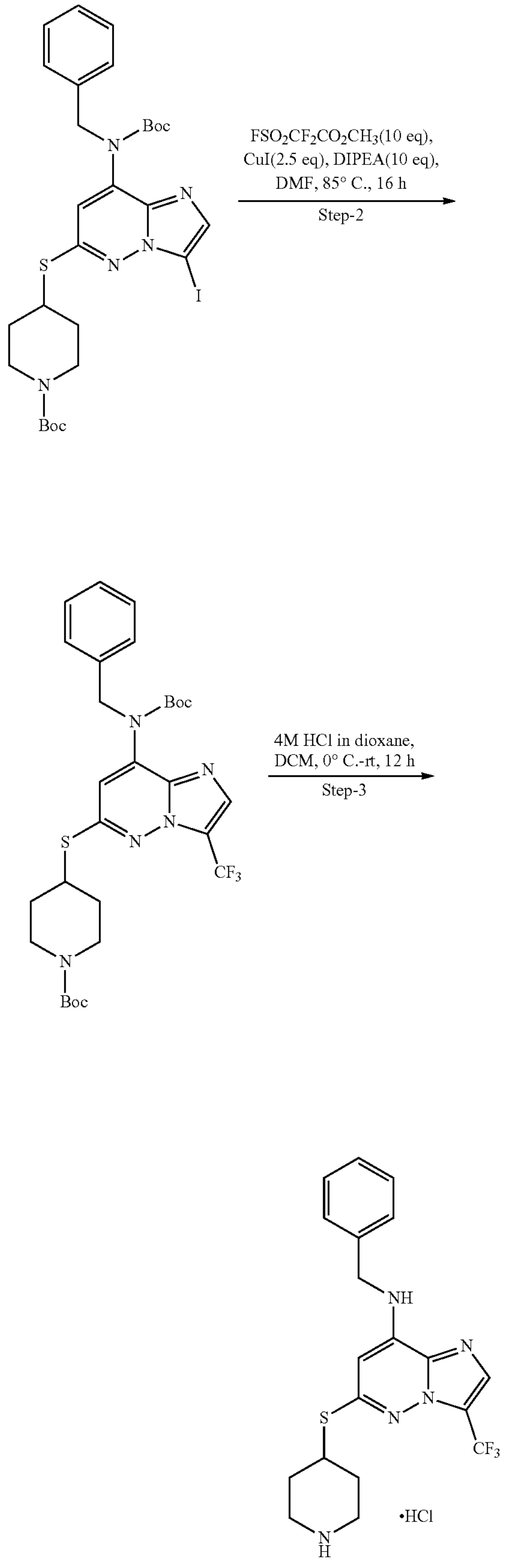

78

Step-1: Synthesis of tert-butyl 4-((8-(benzyl(tert-butoxycarbonyl)amino)-3-iodoimidazo[1,2-b]pyridazin-6-yl)thio)piperidine-1-carboxylate

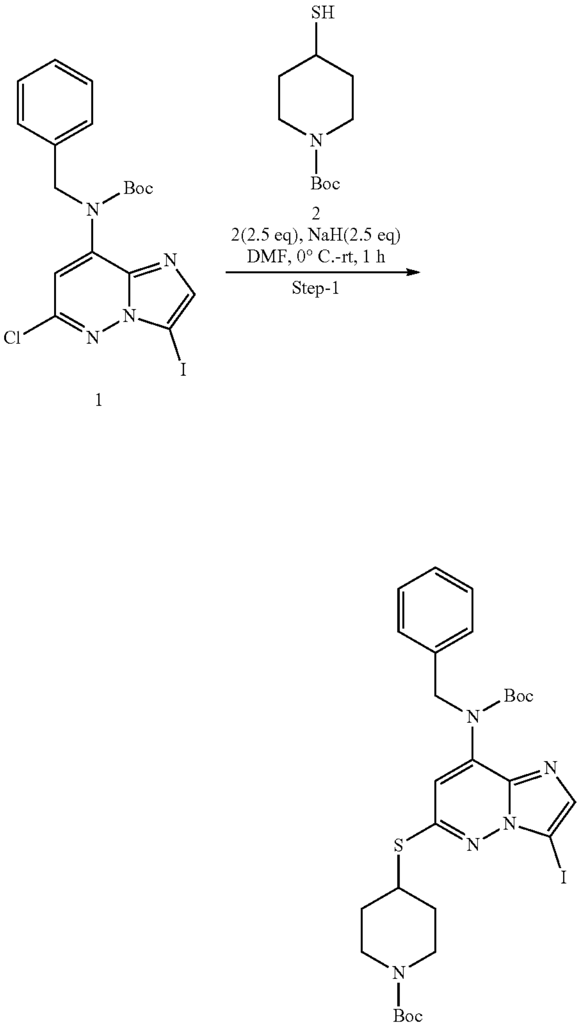

1

2

3

To a stirred solution of tert-butyl 4-mercaptopiperidine-1-carboxylate (2) (99 mg, 0.64 mmol, 2.5 equiv) in DMF (2 mL) was added sodium hydride (60% dispersion in mineral oil) (26 mg, 0.64 mmol, 2.5 equiv) at 0 °C. Reaction mixture was stirred for 15 minutes and tert-butyl benzyl(6-chloro-3-iodoimidazo[1,2-b]pyridazin-8-yl)carbamate (1) (125 mg, 0.26 mmol, 1 equiv) was added at 0 °C. Then reaction mixture was allowed to attain room temperature and stirred for 1 h. After completion, the reaction mixture was quenched with ice water, and extracted with EtOAc (3×15 ml). Combined organic layer was washed with brine (15 mL), dried over $Na_2SO_4$, and evaporated under reduced pressure to afford the crude compound. Crude compound was purified by combiflash column chromatography using 16% EtOAc/Hexane as eluent to afford the title compound tert-butyl 4-((8-(benzyl(tert-butoxycarbonyl)amino)-3-iodoimidazo[1,2-b]pyridazin-6-yl)thio)piperidine-1-carboxylate (3) as colourless liquid. Yield: (170 mg, 98.8%). $R_f$=–0.35 (20% EtOAc/Hexane). LCMS m/z calcd for $C_{28}H_{36}IN_5O_4S$ 665.15; found 666.22 $(M+H)^+$.

Step-2: Synthesis of tert-butyl 4-((8-(benzyl(tert-butoxycarbonyl)amino)-3-(trifluoromethyl)imidazo[1,2-b]pyridazin-6-yl)thio)piperidine-1-carboxylate

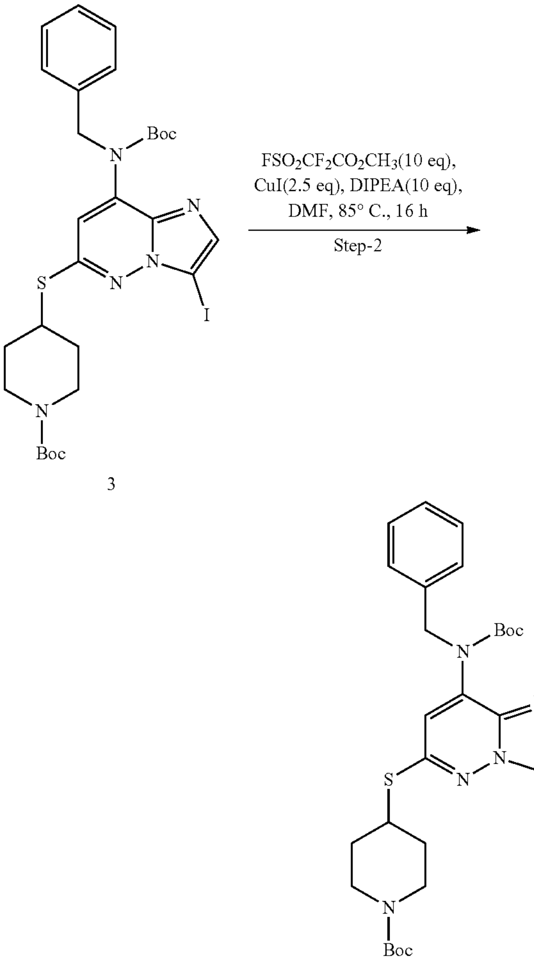

3

4

To a stirred solution of tert-butyl 4-((8-(benzyl(tert-butoxycarbonyl)amino)-3-iodoimidazo[1,2-b]pyridazin-6-yl)thio)piperidine-1-carboxylate (3) (170 mg, 0.26 mmol, 1 equiv) in DMF (10 mL) was added CuI (121 mg, 0.64 mmol, 2.5 equiv), DIPEA (0.45 mL, 2.55 mmol, 10 equiv) at room temperature. The reaction mixture was stirred for 10 minutes and then added Methyl 2,2-difluoro-2-(fluorosulfonyl)acetate (490 mg, 2.55 mmol, 10 equiv) at room temperature. The reaction mixture was then heated to 85 °C for 16 h. After completion of the reaction, reaction mixture was cooled down to room temperature and then filtered through celite bed, washed with EtOAc (2×20 mL). The organic layer was combined and washed with brine (20 mL), dried over $Na_2SO_4$ and concentrated in vacuo. The crude residue obtained was purified by combi flash column chromatography using 15% EtOAc/Hexane as eluent to afford tert-butyl 4-((8-(benzyl(tert-butoxycarbonyl)amino)-3-(trifluoromethyl)imidazo[1,2-b]pyridazin-6-yl)thio)piperidine-1-carboxylate (4). Yield: (80 mg, 51.61%). $R_f$=~0.35 (10% EtOAc/Hexane). LCMS m/z calcd for $C_{29}H_{36}F_3N_5O_4S$ 607.24; found 608.29 $(M+H)^+$.

Step-3: Synthesis of N-benzyl-6-(piperidin-4-yl-thio)-3-(trifluoromethyl)imidazo[1,2-b]pyridazin-8-amine hydrochloride

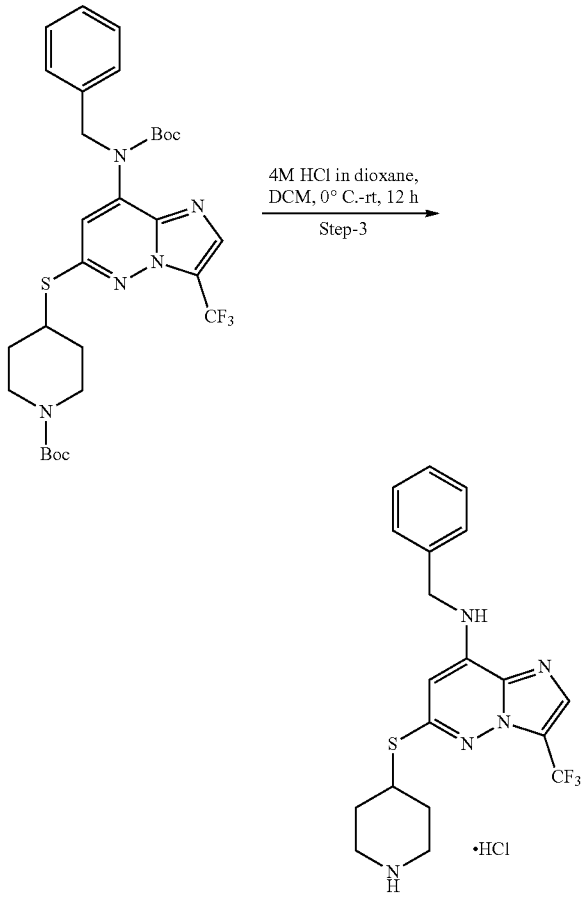

78

To a stirred solution of tert-butyl 4-((8-(benzyl(tert-butoxycarbonyl)amino)-3-(trifluoromethyl)imidazo[1,2-b]pyridazin-6-yl)thio)piperidine-1-carboxylate (4) (80 mg, 0.13 mmol, 1equiv.) in DCM (3 mL) at 0 °C was dropwise added 4M HCl in 1,4-dioxane (1.5 mL). Reaction mixture was allowed to warm to room temperature and stirred for 12 h. After completion of reaction as indicated by TLC, the reaction mixture was subjected to rotary evaporator for removal of volatiles to get crude white solid. The obtained residue was triturated with n-pentane (3×10 mL), diethyl ether (2×10 mL) to afford the crude compound which was then further purified using preparative HPLC to afford title compound N-benzyl-6-(piperidin-4-ylthio)-3-(trifluoromethyl)imidazo[1,2-b]pyridazin-8-amine hydrochloride (78) as a white solid. Yield: (42 mg, 72.41%). $R_f$=~0.1 (10% MeOH/DCM). LCMS m/z calcd for $C_{19}H_{20}F_3N_5S$ 407.14; found 408.29 $(M+H)^+$. $^1H$ NMR (400 MHz, DMSO-$d_6$): δ=8.90 (brs, 1H), 8.81 (brs, 1H), 8.55 (t, J 6.4 Hz, 1H), 8.03 (s, 1H), 7.38-7.31 (m, 4H), 7.26-7.23 (m, 1H), 6.09 (s, 1H), 4.56 (d, J=4.4 Hz, 2H), 3.85-3.79 (m, 1H), 3.27-3.24 (m, 2H), 3.02-2.94 (m, 2H), 2.21-2.18 (m, 2H), 1.81-1.71 (m, 2H) ppm; 19F NMR (400 MHz, DMSO-$d_6$): δ −60.42 ppm.

Example 89

Synthetic Scheme for tert-butyl benzyl (6-bromo-3-cyclopropylimidazo [1, 2-a]pyrazin-8-yl) carbamate (Scaffold-1)

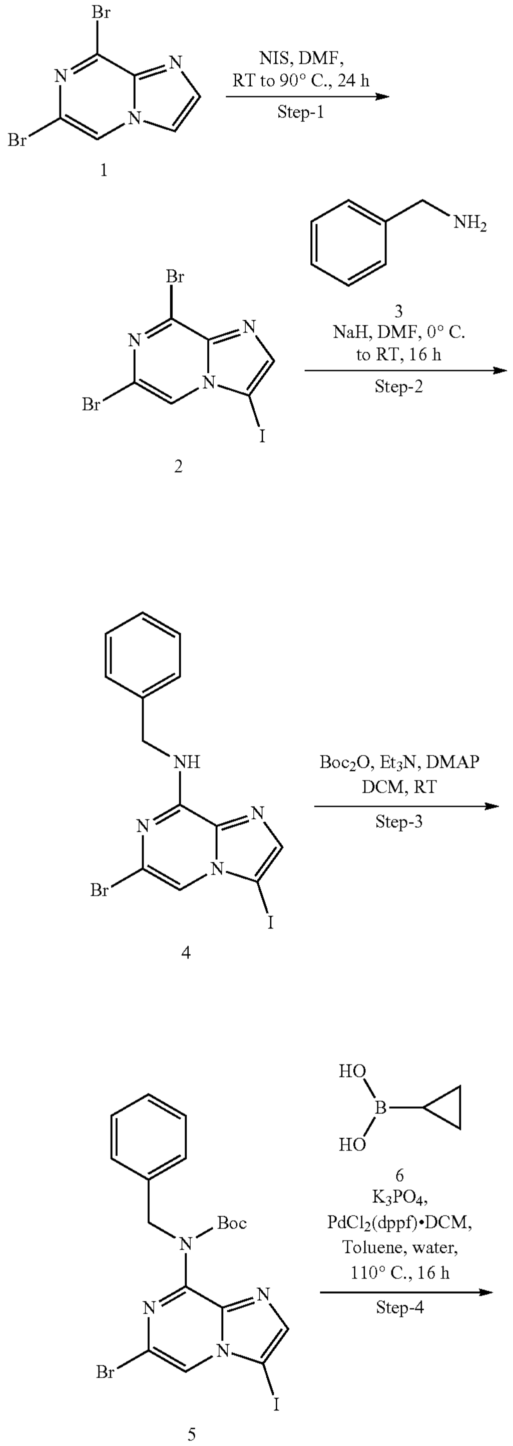

-continued

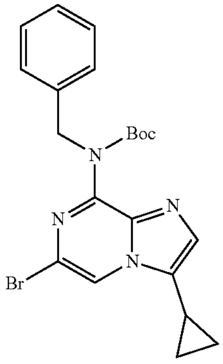

7

Step-1: Synthesis of 6, 8-dibromo-3-iodoimidazo [1, 2-a]pyrazine

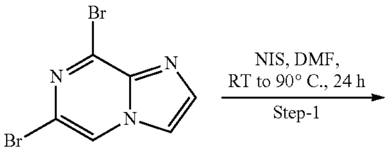

1

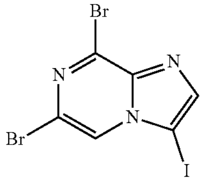

2

To a stirred solution of 6,8-dibromoimidazo [1,2-a]pyrazine (1) (10 g, 36.23 mmol, 1 eq.) in DMF (100 mL) was added N-Iodosuccinamide (12.11 g, 54.34 mmol, 1.5 eq.) at room temperature. Reaction mixture was heated at 90 °C for 24 h. Completion of reaction was monitored on TLC and LCMS analysis. Reaction mixture was cooled and poured into crushed ice water (2 lit) to get brown solid. This brown solid was filtered through Buchner funnel, washed with n-pentane (100 mL) and dried under reduced pressure to afford the title compound (2) as 6,8-dibromo-3-iodoimidazo [1,2-a]pyrazine as brown solid. Yield: (12 g, 82.41%). $R_f$=0.7 (4:1 Hexane/EtOAc). LCMS (m/z): 401.6 $(M+H)^+$. H NMR (400 MHz, $CDCl_3$, TMS): δ=8.24 (s, 1H), 7.93 (s, 1H).

Step-2: Synthesis of N-benzyl-6-bromo-3-iodoimidazo [1, 2-a]pyrazin-8-amine

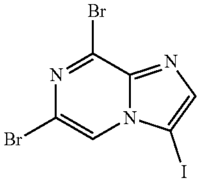

2

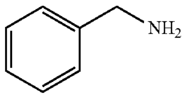

3

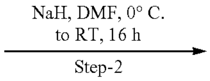

-continued

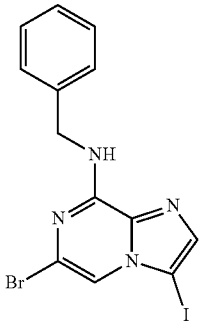

4

To a stirred solution of phenylmethanamine (3) (3.80 mL, 34.82 mmol, 2 eq.) in DMF (40 mL) was added sodium hydride (60% dispersion in oil) (1.39 g, 34.82 mmol, 2 eq.) at 0 °C. Reaction mixture was stirred at room temperature for 30 minutes. Then addition of 6,8-dibromo-3-iodoimidazo[1,2-a]pyrazine (7 g, 17.41 mmol, 1eq.) in DMF (30 mL) was done at 0 °C. Reaction mixture was allowed to come to room temperature and stirred for 16 h. Completion of reaction was monitored on TLC and LCMS analysis. The reaction mixture was poured on crushed ice water (approx. 2 lit), to get off white solid. It was filtered through Buchner funnel, washed with n-pentane (100 mL) and dried under reduced pressure to afford the title compound (4)N-benzyl-6-bromo-3-iodoimidazo [1,2-a]pyrazin-8-amine as an off white solid compound. (Yield: 5 g, 67.29%), $R_f$=0.6 (4:1 Hexane/EtOAc). LCMS (m/z): 429.0 $(M+H)^+$. $^1$H NMR (400 MHz, $CDCl_3$, TMS): δ=7.58 (s, 1H), 7.50 (s, 1H), 7.43-7.28 (m, 5H), 6.35 (s, 1H), 4.78 (d, J=5.6 Hz, 2H).

Step-3: tert-butyl benzyl(6-bromo-3-iodoimidazo[1, 2-a]pyrazin-8-yl)carbamate

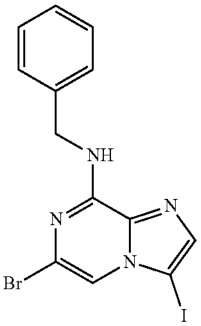

4

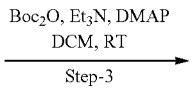

-continued

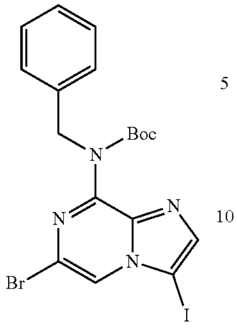

5

To a stirred solution of N-benzyl-6-bromo-3-iodoimidazo [1,2-a]pyrazin-8-amine (4) (5 g, 11.70 mmol, 1 eq.) in DCM (50 mL) was added triethylamine (3.26 mL 23.41 mmol, 2 eq.), Boc anhydride (5.38 mL, 23.41 mmol, 2 eq.) and DMAP (4-dimethylamino pyridine) (0.286 g, 2.34 mmol, 0.2 eq.) at room temperature. Reaction mixture was stirred at room temperature for 16 h. Completion of reaction was monitored on TLC. Reaction mixture was diluted with water (200 mL), extracted with ethyl acetate (3×200 mL), washed with brine (200 mL), and dried over $Na_2SO_4$, evaporated under reduced pressure to get crude compound as yellow oil. Obtained crude compound was purified by flash column chromatography using silica phase (100-200) mesh, (with a gradient elution of 15-20% of EtOAc: n-Hexane) to afford the title compound (5) as a tert-butyl benzyl (6-bromo-3-iodoimidazo [1, 2-a]pyrazin-8-yl) carbamate as yellow solid. (Yield: 5.5 g, 89.14%).

$R_f$=0.6 (4:1 Hexane/EtOAc). LCMS (m/z): 528.52 $(M+H)^+$. $^1H$ NMR (400 MHz, $CDCl_3$, TMS): δ=8.04 (s, 1H), 7.79 (s, 1H), 7.43-7.41 (m, 2H), 7.23 (s, 2H), 7.19-7.16 (m, 1H), 5.20 (s, 2H), 1.37 (s, 9H).

Step-4: Synthesis of tert-butyl benzyl (6-bromo-3-cyclopropylimidazo [1, 2-a]pyrazin-8-l) carbamate

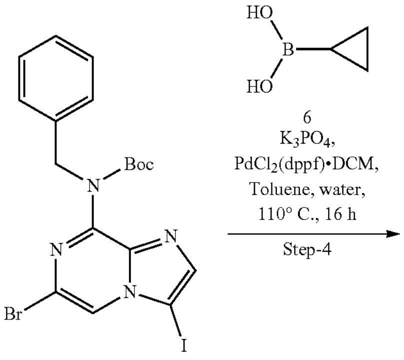

5

-continued

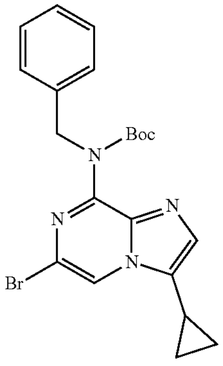

7

To a stirred solution of tert-butyl benzyl(6-bromo-3-iodoimidazo[1,2-a]pyrazin-8-yl)carbamate (5) (1 g, 1.89 mmol, 1eq.) in toluene (16 mL) and water (4 mL) was added cyclopropylboronic acid (6) (0.195 g, 2.27 mmol, 1.2 eq.), potassium phosphate (1.20 g, 5.69 mmol, 3 eq.) at room temperature. Degassed the reaction mixture under argon for 10 minutes. Then addition of $PdCl_2$(dppf).DCM (0.154 g, 0.189 mmol, 0.1 eq.) was done at room temperature, degassed the reaction mixture under argon for 10 minutes. Reaction mixture was stirred at 110 °C for 16 h. Completion of reaction was monitored on TLC. The reaction mixture was diluted with water (50 mL), extracted with ethyl acetate (3×50 mL), washed with brine (50 mL), dried over $Na_2SO_4$ and evaporated under reduced pressure to get the crude compound as brown oil. The crude compound was purified by flash column chromatography on silica column (with a gradient elution of 15-20% EtOAc/Hexane) to afford the title compound (7) as tert-butyl benzyl (6-bromo-3-cyclopropylimidazo [1, 2-a]pyrazin-8-yl) carbamate as brown oil. (Yield: 0.300 g, 35.79%). $R_f$=0.4 (4:1 Hexane/EtOAc). LCMS (m/z): 442.86 $(M+H)^+$. $^1H$ NMR (400 MHz, $CDCl_3$, TMS): δ=8.10 (s, 1H), 7.46 (d, J=0.8 Hz, 2H), 7.44 (s, 1H), 7.27 (s, 2H), 7.19-7.17 (m, 1H), 5.19 (s, 2H), 1.79 (m, 1H), 1.36 (s, 9H), 1.11-1.06 (m, 2H), 0.77-0.73 (m, 2H).

Example 90

Synthetic Scheme for N-benzyl-3-cyclopropyl-6-(piperidin-4-ylthio) imidazo [1, 2-a]pyrazin-8-amine formate salt

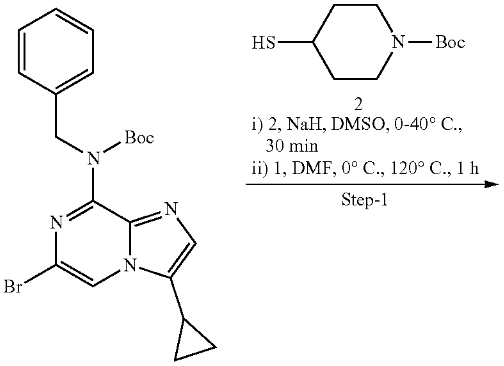

-continued

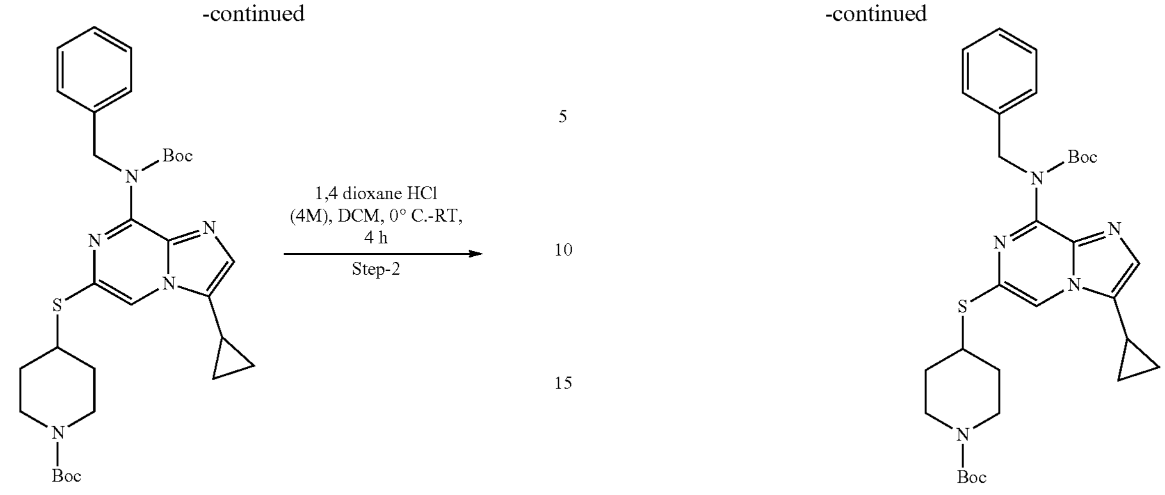

3

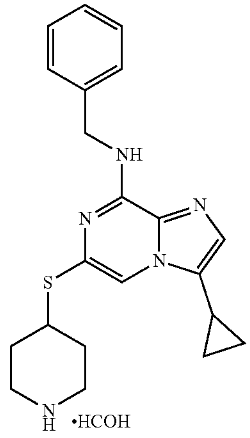

21

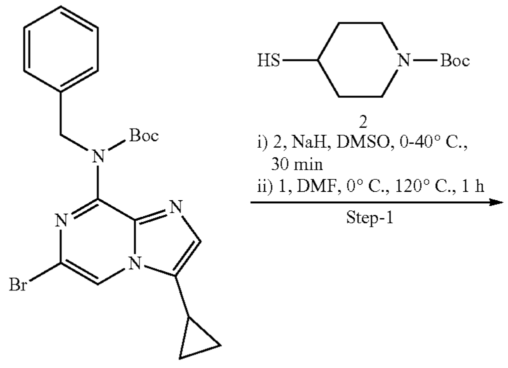

1

Step-1: Synthesis of tert-butyl 4-((8-(benzyl (tert-butoxycarbonyl) amino)-3-cyclopropylimidazo[1,2-a]pyrazin-6-yl) thio) piperidine-1-carboxylate To a solution tert-butyl 4-mercaptopiperidine-1-carboxylate (2) (368 mg, 1.696 mmol, 3 eq.) in DMSO (3 mL) at 0 °C was added NaH (60% in mineral oil), (40.72 mg, 1.696 mmol, 3 eq.) and reaction mixture was heated at 40 °C for 30 minutes. Reaction mixture was cooled and added tert-butyl benzyl(6-bromo-3-cyclopropylimidazo[1,2-a]pyrazin-8-yl)carbamate (1) (250 mg, 0.565 mmol, 1 eq.) in DMSO (2 mL) at 0 °C. The resulting reaction mixture was stirred under microwave irradiation at 120° for 1 h. After complete conversion of reaction by TLC, the reaction mixture was diluted with ice cold water (30 mL) and extracted with ethyl acetate (3×25 mL). The combined organic layer was washed with brine (30 mL), dried over sodium sulphate, filtered and evaporated under reduced pressure to get the crude compound. Crude compound was purified by silica phase column chromatography (with a gradient elution of 20-25% of EtOAC/Hexane) to afford the title compound as tert-butyl 4-((8-(benzyl (tert-butoxycarbonyl) amino)-3-cyclopropylimidazo [1,2-a]pyrazin-6-yl)thio)piperidine-1-carboxylate (3) as brown oil. (Yield: 200 mg, 61.16%), $R_f$=0.4 (4:1 Hexane/EtOAc). LCMS (m/z): 580.09 $(M+H)^+$ −100. (LCMS shows mass of cpd-3 along with mono deboc of cpd-3).

Step-2: Synthesis of N-benzyl-3-cyclopropyl-6-(piperidin-4-ylthio)imidazo[1,2-a]pyrazin-8-amine hydrochloride

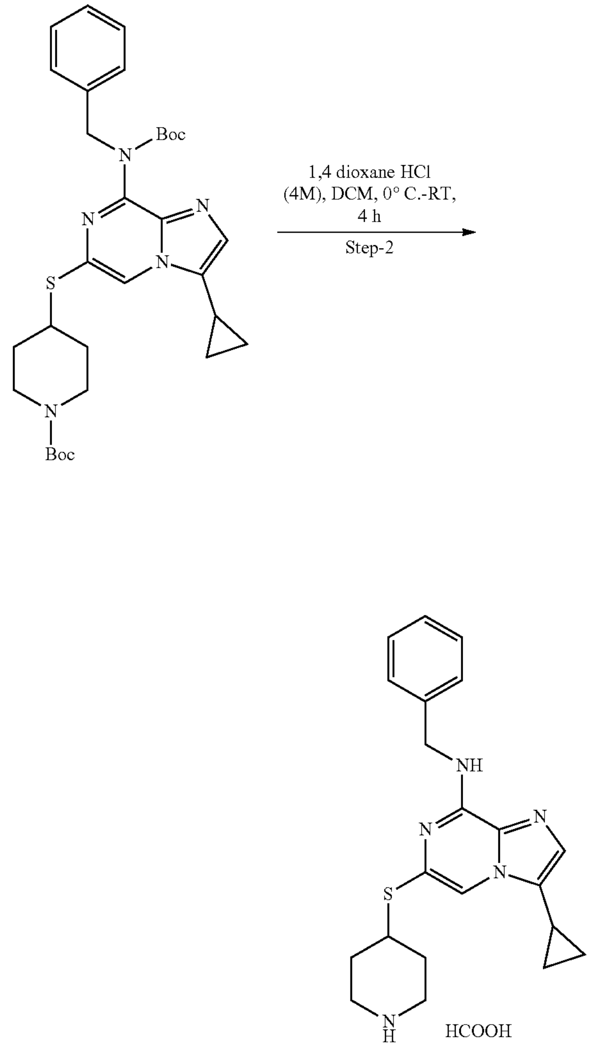

21

To a stirred solution of tert-butyl 4-((8-(benzyl(tert-butoxycarbonyl)amino)-3-cyclopropylimidazo[1,2-a]pyrazin-6-yl)thio)piperidine-1-carboxylate (3) (170 mg, 0.293 mmol, 1eq.) in DCM (5 mL) was added 4M HCl in dioxane (0.8 mL) at 0 °C. Reaction mixture was stirred at room temperature for 4 h. After complete conversion by TLC, volatiles were evaporated under reduced pressure to get the crude compound as brown oil. It was purified by Prep-HPLC by using formic acid buffer to get title compound as N-benzyl-3-cyclopropyl-6-(piperidin-4-ylthio)imidazo[1,2-a]pyrazin-8-amine formate salt (21) as an off white solid (Yield: 65 mg, 58.55%). $R_f$=0.1 (1:1Hexane/EtOAc). LCMS (m/z): 380.38 $(M+H)^+$ $^-$100. $^1$HNMR (400 MHz, DMSO-$d_6$) δ: 8.29-8.26 (m, 2H), 7.70-7.69 (m, 1H), 7.33-7.31 (m, 2H), 7.27 (t, J=7.2 Hz, 2H), 7.21-7.19 (m, 2H), 4.62 (d, J=6.0 Hz, 2H), 3.42-3.35 31 (m, 2H), 2.94 (d, J=12.8 Hz, 2H), 1.98-1.95 (m, 1H), 1.80 (d, J=13.2 Hz, 2H), 1.47-1.39 (m, 2H), 1.22-0.81 (m, 2H), 0.67-0.65 (m, 2H).

Example 91

Synthetic Scheme for N-benzyl-3-isopropyl-6-(piperidin-3-ylthio) imidazo [1, 2-a]pyrazin-8-amine formate salt

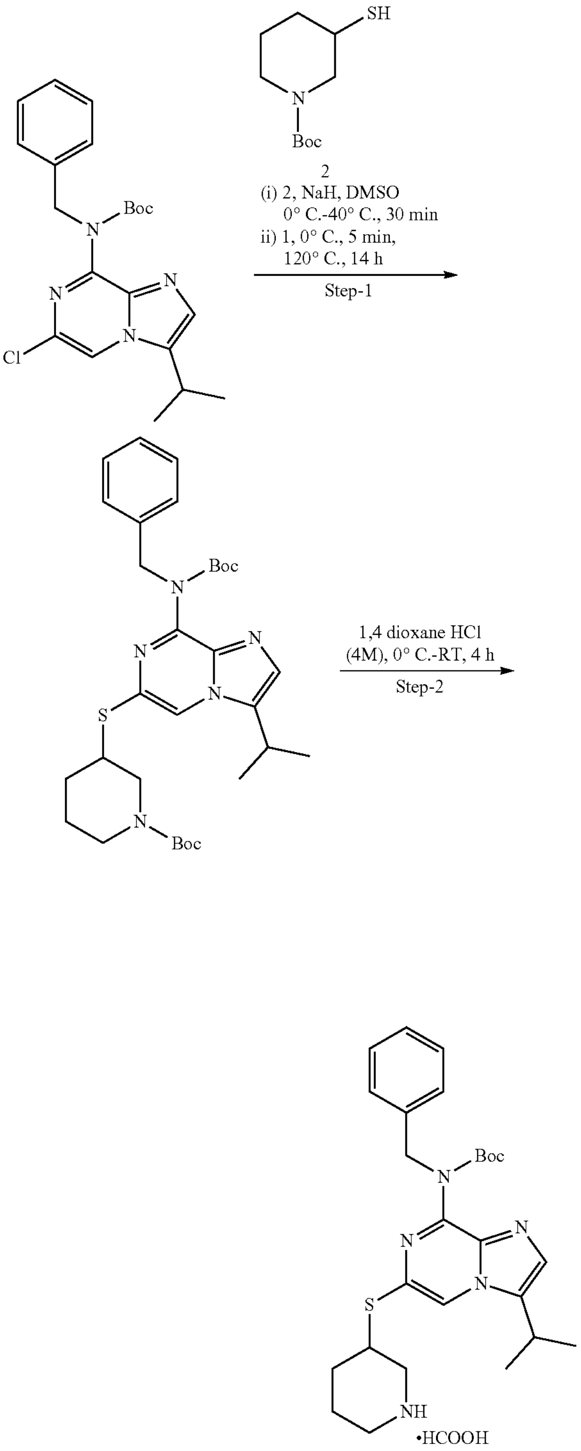

26

Step-1: Synthesis of tert-butyl 3-((8-(benzyl(tert-butoxycarbonyl)amino)-3-isopropylimidazo[1,2-a]pyrazin-6-yl)thio)piperidine-1-carboxylate

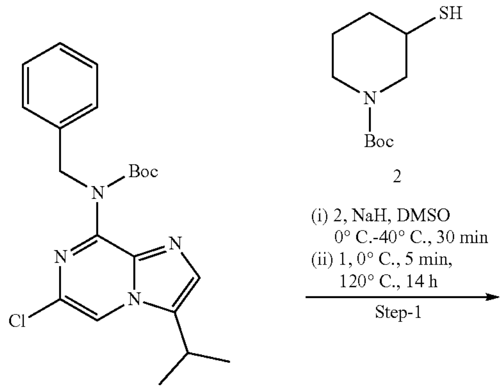

2

1

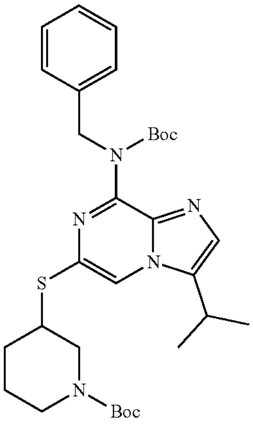

3

In a sealed tube, to a stirred solution of tert-butyl 3-mercaptopiperidine-1-carboxylate (2) (217 mg, 1.00 mmol, 2 eq.) in DMSO (3 mL) was added sodium hydride (60% dispersion in oil) (60 mg, 1.5 mmol, 3 eq.) at 0 °C. Reaction mixture was heated at 40 °C for 30 minutes. After this time, reaction mixture was cooled to 0 °C and tert-butyl benzyl (6-chloro-3-isopropylimidazo [1, 2-a]pyrazin-8-yl) carbamate (200 mg, 0.50 mmol, 1eq.) (1) in DMSO (2 mL) was added. Reaction mixture was heated at 120 °C for 14 h. After complete conversion by TLC, the reaction mixture was cooled to room temperature, diluted with water (15 mL), and extracted with ethyl acetate (3×50 mL). Combined organic layer was washed with brine (25 mL), dried over $Na_2SO_4$, filtered and evaporated under reduced pressure to get the crude compound as brown oil. Crude compound was purified by CombiFlash on silica column (4 g),(gradient elution with 0-20% EtOAc/hexane) to afford the title compound (3) tert-butyl 3-((8-(benzyl(tert-butoxycarbonyl)amino)-3-isopropylimidazo[1,2-a]pyrazin-6-yl)thio)piperidine-1-carboxylate as brown oil. (Yield: 75 mg, 25.81%). $R_f$=0.4 (4:1 Hexane/EtOAc). (Note: LCMS analysis shows 14% of cpd-3 and 73% of monodeboc of cpd-3.) LCMS (m/z): 582.33 $(M+H)^+$ Step-2: Synthesis of N-benzyl-3-isopropyl-6-(piperidin-3-ylthio) imidazo [1, 2-a]pyrazin-8-amine hydrochloride. (Note: Formate Salt Observed.)

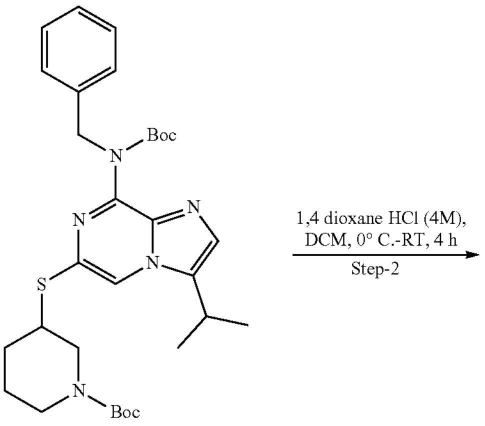

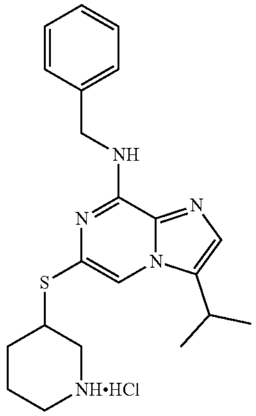

26

To a stirred solution of tert-butyl 3-((8-(benzyl(tert-butoxycarbonyl)amino)-3-isopropylimidazo[1,2-a]pyrazin-6-yl)thio)piperidine-1-carboxylate (3) (75 mg, 0.129 mmol, 1 eq.), in DCM (4 mL) was added (4M) 1,4 dioxane in HCl (1 mL) dropwise at 0 °C. The reaction mixture was stirred at room temperature for 4 h. After complete conversion by TLC, the reaction mixture was subjected to rotary evaporator for removal of volatiles to get the crude compound as brown solid. The crude compound was purified by preparative HPLC using formic acid buffer to afford the title compound N-benzyl-3-isopropyl-6-(piperidin-3-ylthio)imidazo[1,2-a]pyrazin-8-amine formate salt. (26) as pale brown solid. (Yield: 20 mg, (37.11%). $R_f$=0.1 (1:1 Hexane/EtOAc). (Note: Formate salt observed.) LCMS (m/z): 382.29 $(M+H)^+$ $^1H$ NMR (400 MHz, DMSO-$d_6$): δ =8.29-8.26 ((m, 2H), 7.61 (d, J=3.6 Hz, 1H), 7.37-7.36 (m, 2H), 7.32-7.27 (m, 3H), 7.22-7.18 (m, 1H), 4.69-4.58 (m, 2H), 3.41-3.40 (m, 1H), 3.25-3.19 (m, 1H), 3.10-3.07 (m, 1H), 2.84-2.81 (m, 1H), 2.59-2.43 (m, 2H), 1.92 (s, 1H), 1.61-1.60 (m, 1H), 1.46-1.36 (m, 2H), 1.27-1.25 (m, 6H).

Example 92

Synthetic Scheme for N8-benzyl-3-cyclopropyl-N6-(piperidin-4-yl)imidazo[1,2-a]pyrazine-6,8-diamine hydrochloride

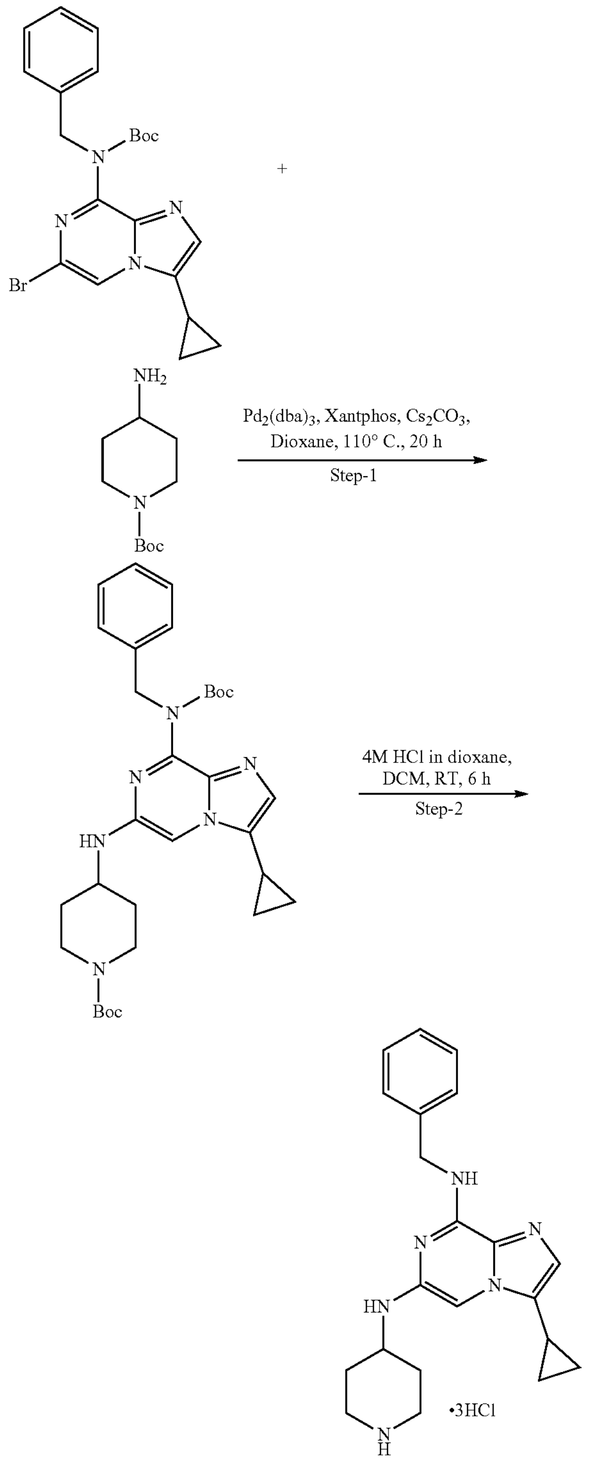

31

Synthesis of tert-butyl 4-((8-(benzyl(tert-butoxycarbonyl)amino)-3-cyclopropylimidazo[1,2-a]pyrazin-6-yl)amino)piperidine-1-carboxylate

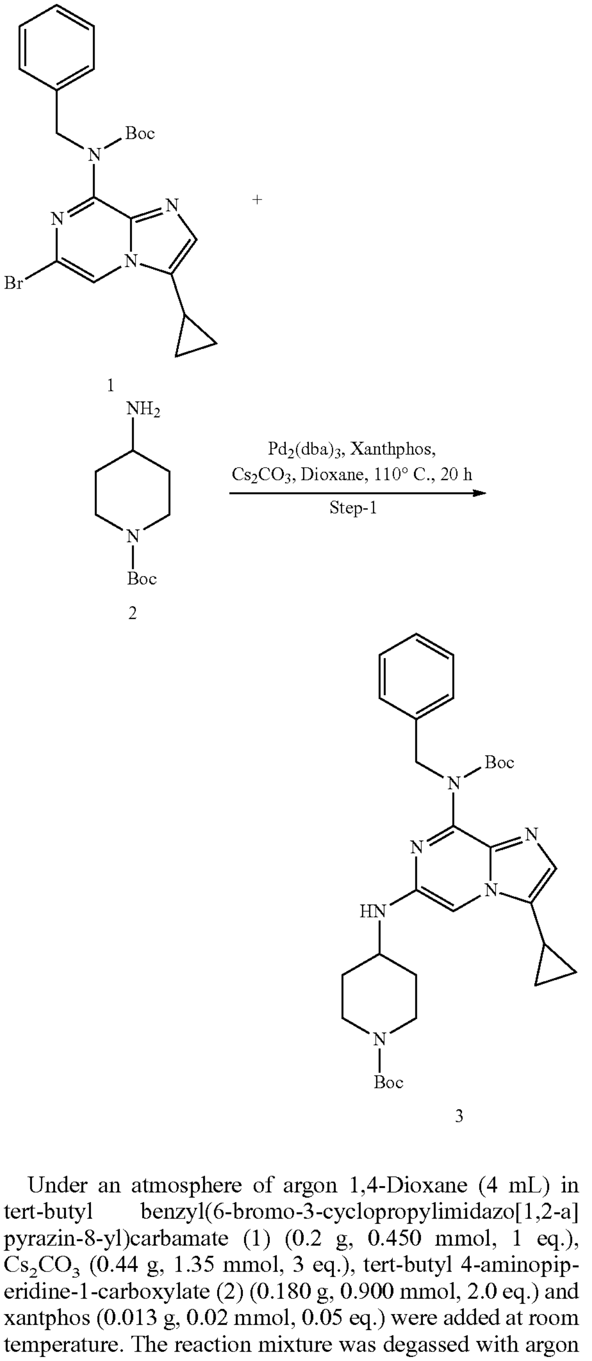

1

2

3

Under an atmosphere of argon 1,4-Dioxane (4 mL) in tert-butyl benzyl(6-bromo-3-cyclopropylimidazo[1,2-a]pyrazin-8-yl)carbamate (1) (0.2 g, 0.450 mmol, 1 eq.), $Cs_2CO_3$ (0.44 g, 1.35 mmol, 3 eq.), tert-butyl 4-aminopiperidine-1-carboxylate (2) (0.180 g, 0.900 mmol, 2.0 eq.) and xantphos (0.013 g, 0.02 mmol, 0.05 eq.) were added at room temperature. The reaction mixture was degassed with argon for 10 min and added tris(dibenzylideneacetone)dipalladium (0.04 g, 0.04 mmol, 0.1 eq.) again degassed with argon for 10 min and heated to 110 °C for 20 h. Progress of reaction was monitored by TLC. After completion of reaction, reaction mixture diluted with ethyl acetate and passed through celite. The organic phase washed with water (3×100 mL), dried over sodium sulfate, filtered and concentrated under reduced pressure to get crude product. Obtained crude compound was purified by silica phase column chromatography with a gradient elution of 5-20% of ethyl acetate/ hexane to afford tert-butyl 4-((8-(benzyl(tert-butoxycarbonyl)amino)-3-cyclopropylimidazo[1,2-a]pyrazin-6-yl)amino)piperidine-1-carboxylate (3) as a yellow gum (0.05 g, 20% yield). $R_f$=0.2 (2:8 ethyl acetate/hexane). LCMS (m/z): 563.28 $(M+H)^+$.

Synthesis of N8-benzyl-3-cyclopropyl-N6-(piperidin-4-yl)imidazo[1,2-a]pyrazine-6,8-diamine hydrochloride

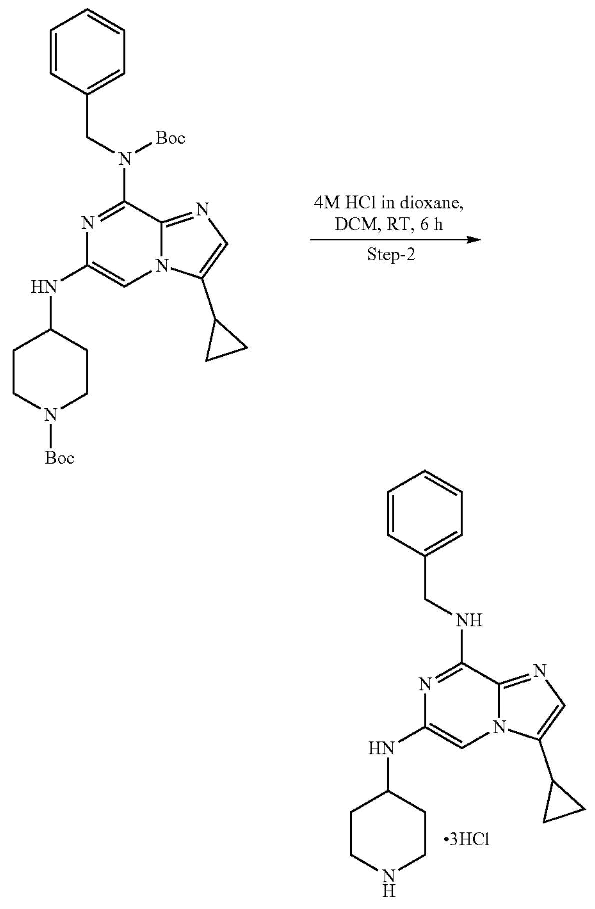

31

To a solution of tert-butyl 4-((8-(benzyl(tert-butoxycarbonyl)amino)-3-cyclopropylimidazo[1,2-a]pyrazin-6-yl)amino)piperidine-1-carboxylate (3) (0.05 g, 0.08 mmol, 1 eq.) in DCM (5 mL) at 0 °C was added 4M HCl in dioxane (1 mL) and stirred at room temperature for 6 h. After completion of reaction by TLC, volatiles were evaporated under reduced pressure and obtained crude compound was purified by Preparative HPLC to afford 3-cyclopropyl-N-(3-fluorophenyl)-6-((1-methylpiperidin-4-yl)oxy)imidazo[1,2-b]pyridazin-8-amine. The obtained free base was diluting with ACN: water and treated with 2N aq. HCl at 0 °C and lyophilized to afford N8-benzyl-3-cyclopropyl-N6-(piperidin-4-yl)imidazo[1,2-a]pyrazine-6,8-diamine hydrochloride as an off white solid (31, 0.02 g, quantitative). $R_f$=0.3 (9:1 DCM/MeOH). LCMS (m/z): 363.32 $(M+H)^+$. $^1$HNMR (400 MHz, DMSO-$d_6$): δ 11.23 (s, 1H), 10.70 (d, J=6.4 Hz, 1H), 9.05 (s, 2H), 7.43-7.30 (m, 5H), 7.19 (d, J=6.0 Hz, 1H), 5.28 (d, J=4.8 Hz, 2H), 4.83 (d, J=5.2 Hz, 2H), 4.45 (s, 1H), 3.31-3.32 (m, 2H), 3.08-3.06 (m, 2H), 1.94 (s, 2H), 1.81-1.76 (t, J=6.0 Hz, 2H), 1.00-0.97 (m, 2H), 0.76-0.74 (m, 2H).

Example 93

Synthetic Scheme for (S)-3-isopropyl-N-(1-phenylethyl)-6-(piperidin-4-ylthio) imidazo [1,2-a]pyrazin-8-amine dihydrochloride

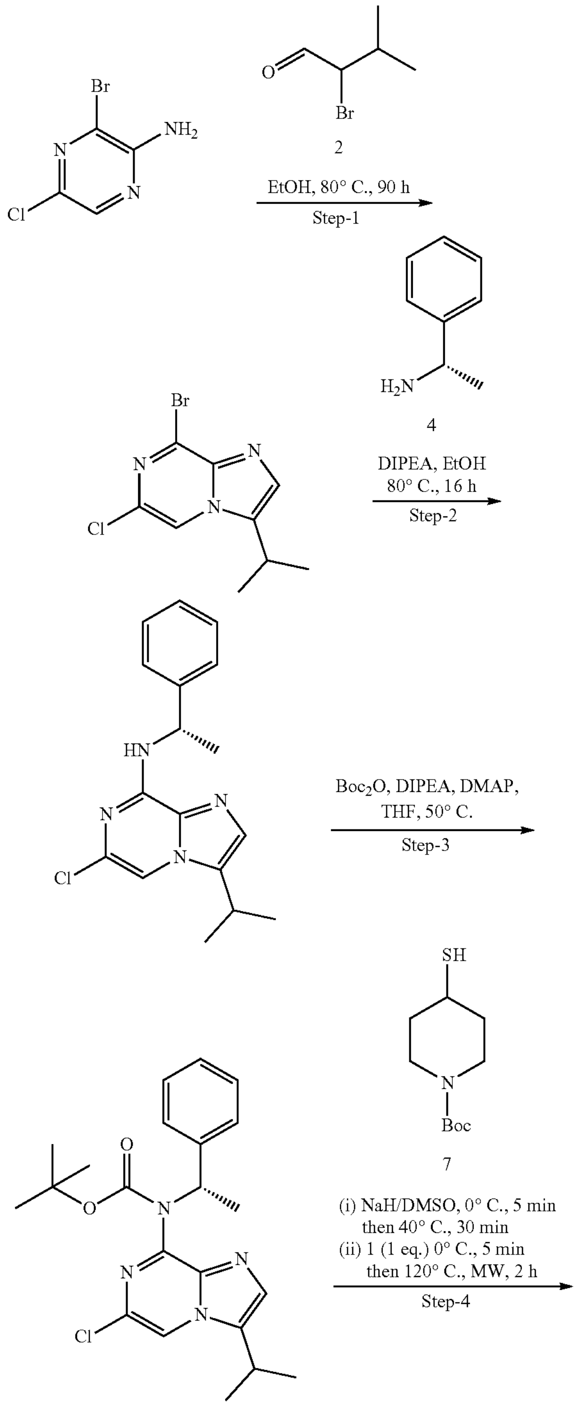

-continued

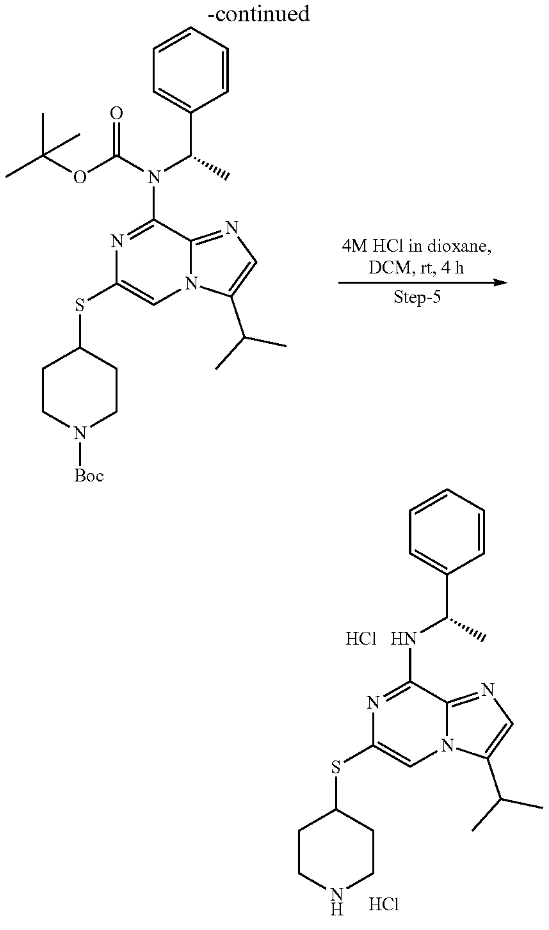

32

Step-1: Synthesis of 8-bromo-6-chloro-3-isopropylimidazo[1, 2-a]pyrazine

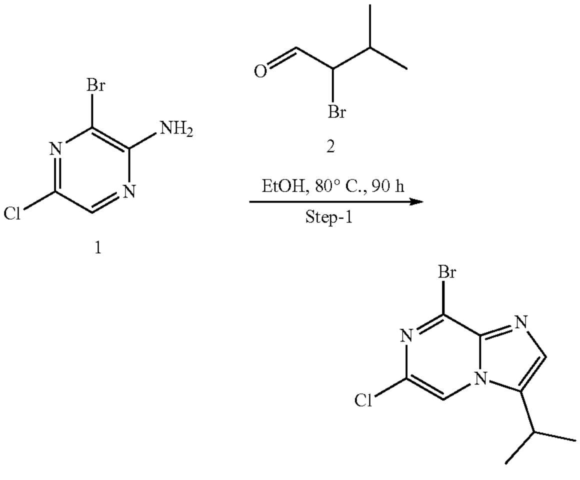

1

2

3

A mixture of 3-bromo-5-chloropyrazin-2-amine (1) (5 g, 24.154 mmol, 1 eq.) in IPA (isopropanol) (50 mL) was added 2-bromo-3-methylbutanal (2) (40.09 g, 241.54 mmol, 10 eq.) at room temperature. The reaction mixture was heated at 80 °C for 90 h. Progress of the reaction was monitored by TLC. The reaction mixture was cooled to room temperature. IPA was evaporated under reduced pressure to get the crude residue. Crude residue was diluted with water (300 mL), extracted with ethyl acetate (3x250 mL). Combined organic layer was washed with saturated sodium bicarbonate solution (50 mL), brine (50 mL), dried over sodium sulphate, filtered and evaporated under reduced pressure to get the crude compound. Crude compound was purified by flash column chromatography on silica gel (with gradient elution of 0-30% EtOAc: Hexane) to afford the title compound as 8-bromo-6-chloro-3-isopropylimidazo [1, 2-a]pyrazine (3) as yellow solid.

Yield: (1.5 g, 22%). $R_f$=0.4 (4:1 Hexane/EtOAc). LCMS (m/z): 273.9 $(M+H)^+$. $^1H$ NMR (400 MHz, $CDCl_3$, TMS): δ=7.98-7.96 (m, 1H), 7.72-7.71 (m, 1H), 3.24-3.18 (m, 1H), 1.47-1.44 (m, 1H).

Step-2: Synthesis of (S)-6-chloro-3-isopropyl-N-(1-phenylethyl) imidazo [1, 2-a]pyrazin-8-amine

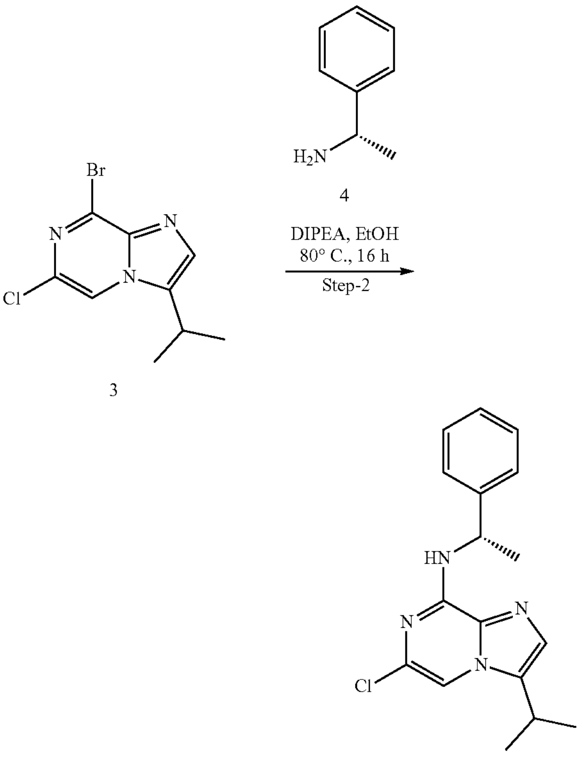

4

3

5

To a stirred solution of (3) 8-bromo-6-chloro-3-isopropylimidazo[1,2-a]pyrazine (3) (0.9 g, 3.284 mmol, 1 eq.) in EtOH (10 mL) was added DIPEA (1.14 mL, 6.569 mmol, 2 eq.) and (S)-1-phenylethan-1-amine (4) (0.628 mL, 4.927 mmol, 1.5 eq.) at room temperature. Reaction mixture was heated at 80 °C for 16 h. Completion of reaction was monitored on TLC. The reaction mixture was allowed to cool to room temperature; ethanol was evaporated under reduced pressure to get the crude residue as brown oil. The crude residue was diluted with water (100 mL), extracted with ethyl acetate (3×50 mL). The combined organic layer was washed with brine (100 mL), dried over sodium sulphate, filtered and evaporated under reduced pressure to get crude compound. The crude compound was purified by flash column chromatography on silica gel on silica column (with gradient elution of EtOAc/hexane 0-20%) to afford the title compound as (S)-6-chloro-3-isopropyl-N-(1-phenylethyl) imidazo [1, 2-a]pyrazin-8-amine (5) as a brown oil. Yield: (0.9 g, 87.29%). $R_f$=0.4 (4:1 Hexane/EtOAc). LCMS (m/z): 315.1 $(M+H)^+$. $^1H$ NMR (400 MHz, $CDCl_3$, TMS): δ=7.49 (d, J=7.6 Hz, 2H), 7.37-7.27 (m, 5H), 5.52-5.47 (m, 1H), 3.13-3.06 (m, 1H), 1.69 (d, J=6.8 Hz, 3H), 1.40-1.36 (m, 6H).

Step-3: Synthesis of tert-butyl (S)-(6-chloro-3-isopropylimidazo [1, 2-a]pyrazin-8-yl)(1-phenylethyl) carbamate

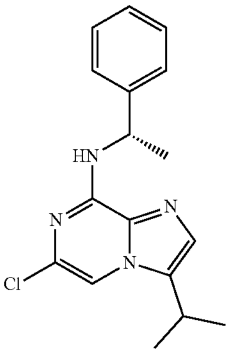

5

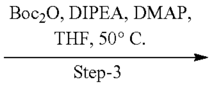

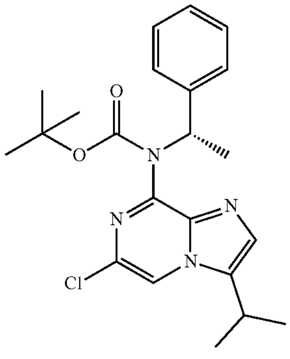

6

To a stirred solution of (S)-6-chloro-3-isopropyl-N-(1-phenylethyl)imidazo[1,2-a]pyrazin-8-amine (5) (0.9 g, 2.858 mmol, 1 eq.) in THF (10 mL) was added DIPEA (4.97 mL, 28.58 mmol, 10 eq.), Boc anhydride (6.56 mL, 28.58 mmol, 10 eq.), and DMAP (0.034 g, 0.28 mmol, 0.1 eq.) at room temperature. Reaction mixture was heated at 50 °C for 16 h. Progress of the reaction was monitored on TLC. After this time, reaction mixture was cooled; THF was evaporated under reduced pressure to get the crude residue. To the crude residue water (15 mL) was added, extracted with ethyl acetate (3×50 mL). The combined organic layer was washed with brine (50 mL), dried over sodium sulphate, filtered and evaporated under reduced pressure to get the crude compound as brown oil. The crude compound was purified by flash column chromatography on silica gel (with gradient elution of EtOAc/hexane 0-20%) to afford the title compound tert-butyl (S)-(6-chloro-3-isopropylimidazo [1,2-a] pyrazin-8-yl)(1-phenylethyl)Carbamate (6) as yellow oil. Yield: (0.9 g, 75.88%). $R_f$=0.5 (4:1 Hexane/EtOAc). LCMS (m/z): 415.1 $(M+H)^+$. $^1H$ NMR (400 MHz, DMSO, TMS): δ=8.71 (d, J=1.2 Hz, 1H), 7.72 (s, 1H), 7.55 (d, J=7.6 Hz, 2H), 7.30 (t, J=7.6 Hz, 2H), 7.20 (t, J=7.2 Hz, 1H), 5.75 (d, J=1.2 Hz, 1H), 5.45-5.40 (m, 1H), 3.42-3.32 (m, 1H), 1.57 (d, J=7.2 Hz, 3H), 1.32-1.29 (m, 6H), 1.15 (s, 9H).

Step-4: Synthesis of tert-butyl (S)-4-((8-((tert-butoxycarbonyl)(1-phenylethyl)amino)-3-isopropylimidazo[1,2-a]pyrazin-6-yl)thio)piperidine-1-carboxylate

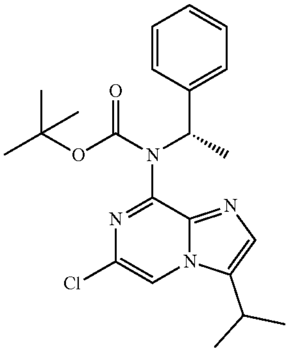

6

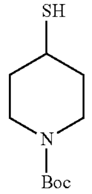

7

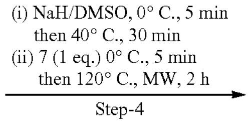

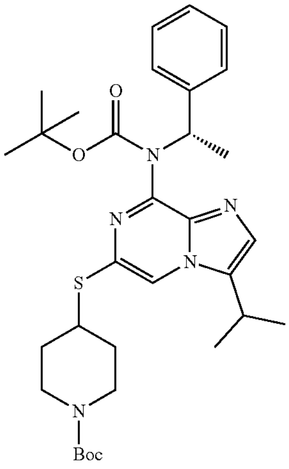

8

To a stirred solution of tert-butyl 4-mercaptopiperidine-1-carboxylate (7) (0.393 gm, 1.81 mmol, 3 eq.) in DMSO (3 mL) at 0 °C was added NaH (60% in mineral oil,) (0.072 gm, 1.81 mmol, 3 eq.). Reaction mixture was heated at 40 °C for 30 min. Reaction mixture was cool to 0 °C. Then addition of tert-butyl (S)-(6-chloro-3-isopropylimidazo [1, 2-a]pyrazin-8-yl) (1-phenylethyl) carbamate (6) (0.250 gm, 0.603 mmol, 1eq.) in DMSO (2 mL) was done at 0 °C. Reaction mixture was heated at 120 °C for 2 h under microwave irradiation. Progress of the reaction was monitored on TLC. Reaction mixture was cooled, quenched with ice cold water (15 mL) and extracted with ethyl acetate (3×50 mL). The combined organic layer was washed with brine solution (30 mL), dried over sodium sulphate, evaporated under reduced pressure to get crude compound as yellow oil. Crude compound was purified by silica phase column chromatography (with a gradient elution of 15-20% of EtOAc/Hexane), to afford the title compound as tert-butyl (S)-4-((8-((tert-butoxycarbonyl)(1-phenylethyl)amino)-3-isopropylimidazo[1,2-a]pyrazin-6-yl)thio)piperidine-1-carboxylate (8) as a yellow oil. Yield: (0.100 g, 27.85%). $R_f$=0.4 (4:1 Hexane/EtOAc). Note: Observed Cpd-8 70.64% as a major and Cpd-8 di de-boc 21.52% on TLC & LCMS. LCMS (m/z): 596.2 $(M+H)^+$ Step-5: Synthesis of (S)-3-isopropyl-N-(1-phenylethyl)-6-(piperidin-4-ylthio) imidazo [1, 2-a] pyrazin-8-amine hydrochloride salt

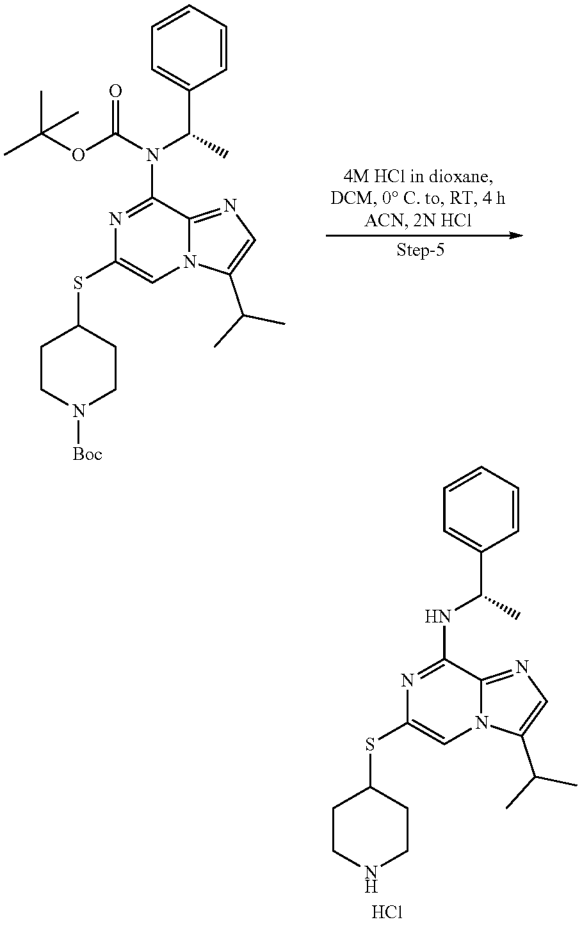

32

To a stirred solution of tert-butyl (S)-4-((8-((tert-butoxycarbonyl)(1-phenylethyl)amino)-3-isopropylimidazo[1,2-a]pyrazin-6-yl)thio)piperidine-1-carboxylate (8) (0.1 g, 0.168 mmol, 1 eq.) in DCM (4 mL) at 0 °C was added 4M HCl in dioxane (2 mL). Reaction mixture was allowed to come to room temperature and stirred for 4 h. After completion of conversion by TLC, volatiles (DCM and HCl in 1, 4 Dioxane) were evaporated under reduced pressure to get crude compound as brown solid. Obtained crude was purified by Prep-HPLC using formic acid buffer to afford the title compound as (S)-3-isopropyl-N-(1-phenylethyl)-6-(piperidin-4-ylthio) imidazo [1, 2-a]pyrazin-8-amine formate salt as an off white solid. This compound was added acetonitrile (1 mL) and cooled to 0 °C and added 2N HCl (1 mL) at 0 °C and lyophilized for 24 h. to afford the title compound as (S)-3-isopropyl-N-(1-phenylethyl)-6-(piperidin-4-ylthio) imidazo[1,2-a]pyrazin-8-amine dihydrochloride. (32) as an off white solid. (Yield: 0.018 g, quantitative). $R_f$=0.1 (1:1Hexane/EtOAc). LCMS (m/z): 396.21 $(M+H)^+$. HPLC purity 97.01%. $^1$HNMR (400 MHz, DMSO) δ: 8.80-8.67 (m, 3H), 7.86 (d, J=6.0 Hz, 1H), 7.73 (s, 1H), 7.48-7.45 (m, 2H), 7.36-7.31 (m, 2H), 7.26-7.21 (m, 1H), 5.34 (d, J=6.4 Hz, 1H), 3.78-3.56 (m, 1H), 3.32-3.25 (m, 2H), 3.10 (s, 1H), 2.94 (s, 1H), 2.69 (s, 1H), 2.08 (d, J=8.4 Hz, 1H), 1.75 (m, 2H), 1.61-1.57 (m, 4H), 1.31-1.26 (m, 6H).

Example 94

Synthetic Scheme for 3-isopropyl-N—((S)-1-phenylethyl)-6-(piperidin-3-ylthio) imidazo [1, 2-a] pyrazin-8-amine hydrochloride

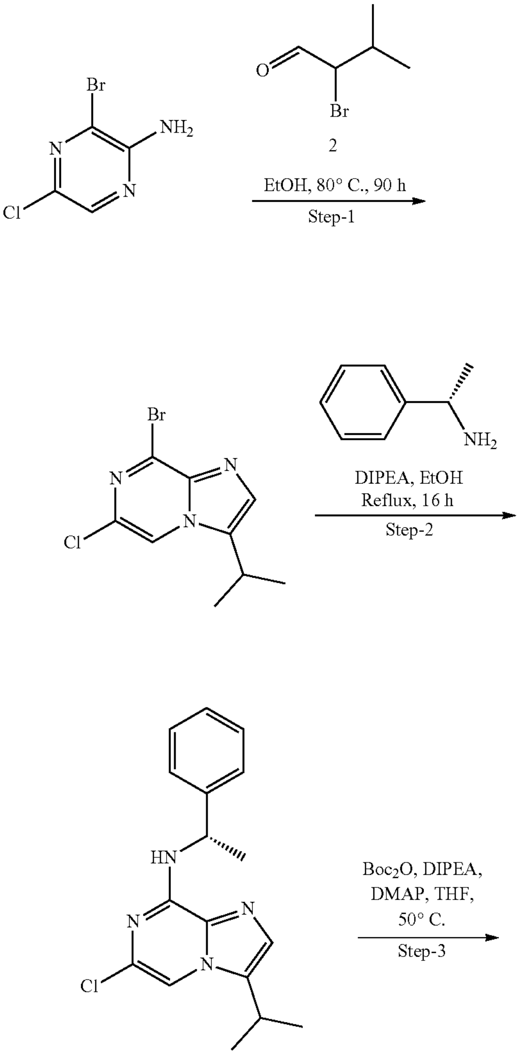

-continued

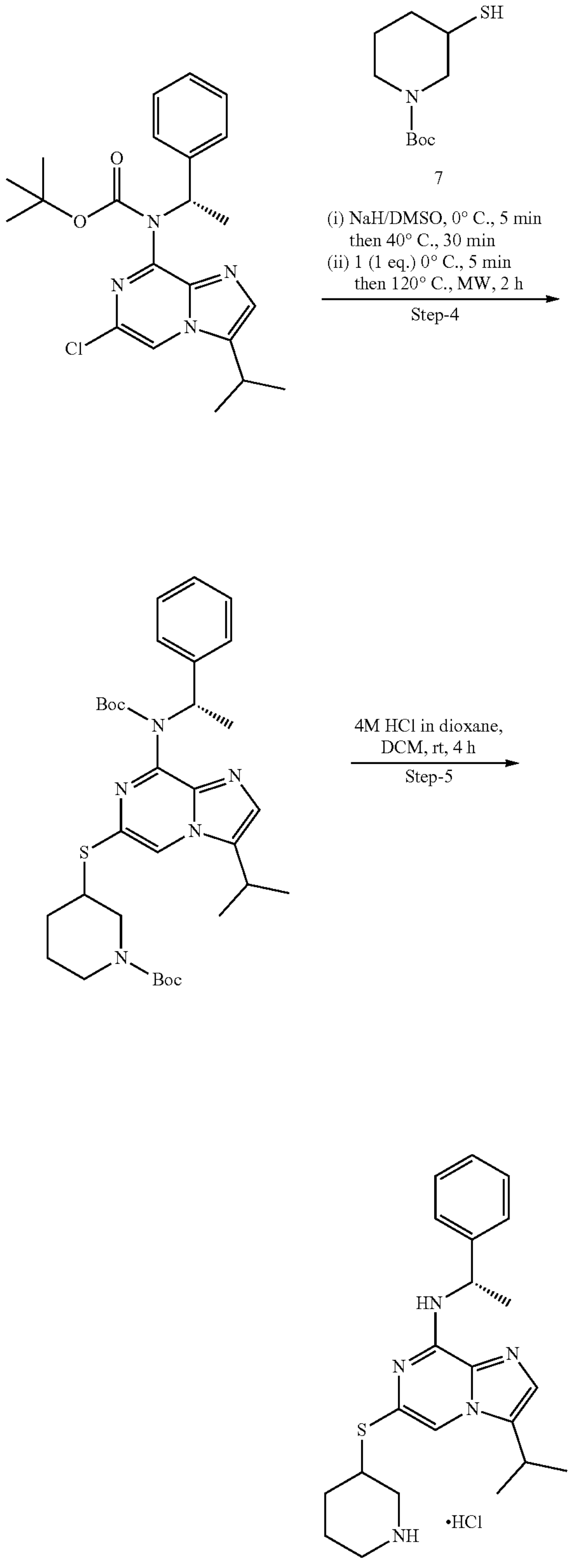

34

Step-1: Synthesis of 8-bromo-6-chloro-3-isopropylimidazo[1, 2-a]pyrazine

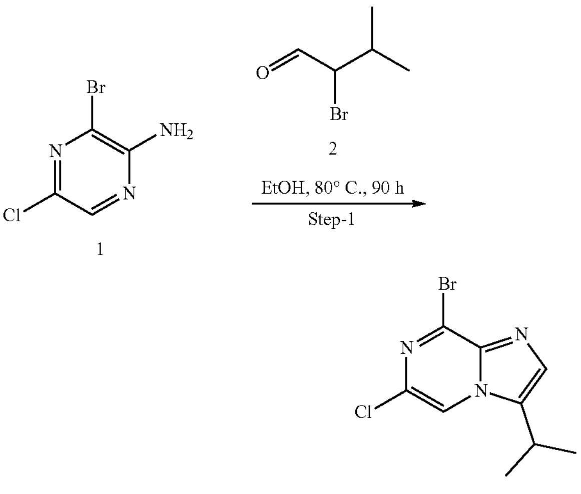

3

A mixture of 3-bromo-5-chloropyrazin-2-amine (1) (5 g, 24.154 mmol, 1 eq.) in IPA (isopropanol) (50 mL) was added 2-bromo-3-methylbutanal (2) (40.09 g, 241.54 mmol, 10 eq.) at room temperature. The reaction mixture was heated at 80 °C for 90 h. Progress of the reaction was monitored by TLC. After this time, volatile portion was evaporated under reduced pressure to get the crude residue. Crude residue was diluted with water (50 mL), extracted with ethyl acetate (3×50 mL). Combined organic layer was washed with saturated sodium bicarbonate solution (50 mL), brine (50 mL), dried over sodium sulphate, filtered and evaporated under reduced pressure to get the crude compound. Crude compound was purified by flash column chromatography (with gradient elution of 0-30% EtOAc: Hexane) to afford the title compound as 8-bromo-6-chloro-3-isopropylimidazo [1, 2-a]pyrazine (3) as yellow solid. Yield: (1.5 g, 22%). $R_f$=0.4 (4:1 Hexane/EtOAc). LCMS (m/z): 273.9 $(M+H)^+$ 1H NMR (400 MHz, $CDCl_3$, TMS): δ=7.98-7.96 (m, 1H), 7.72-7.71 (m, 1H), 3.24-3.18 (m, 1H), 1.47-1.44 (m, 1H).

Step-2: Synthesis of (S)-6-chloro-3-isopropyl-N-(1-phenylethyl) imidazo [1, 2-a]pyrazin-8-amine

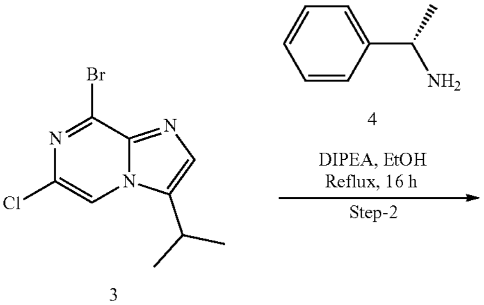

3

-continued

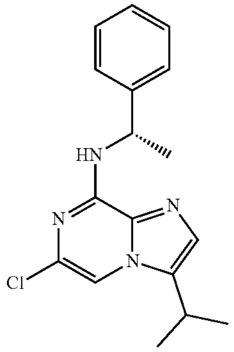

5

-continued

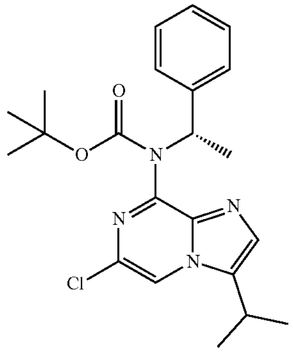

6

To a stirred solution of 8-bromo-6-chloro-3-isopropylimidazo[1,2-a]pyrazine (3) (0.9 g, 3.284 mmol, 1 eq.) in EtOH (10 mL) was added DIPEA (1.14 mL, 6.569 mmol, 2 eq.) and (S)-1-phenylethan-1-amine (4) (0.628 mL, 4.927 mmol, 1.5 eq.) at room temperature. Reaction mixture was heated at 80 °C for 16 h. progress of the reaction was monitored by TLC. The reaction mixture was allowed to cool to room temperature; ethanol was evaporated under reduced pressure to get the crude residue as brown oil. The crude residue was diluted with water (25 mL), extracted with ethyl acetate (3×50 mL). The combined organic layer was washed with brine (10 mL), dried over sodium sulphate, filtered and evaporated under reduced pressure to get crude compound. The crude compound was purified by flash column chromatography (with gradient elution of EtOAc/hexane 0-20%) to afford the title compound as (S)-6-chloro-3-isopropyl-N-(1-phenylethyl) imidazo [1, 2-a]pyrazin-8-amine (5) as a brown oil. Yield: (0.9 g, 87.29%). $R_f$=0.4 (4:1 Hexane/EtOAc). LCMS (m/z): 315.1 $(M+H)^+$. $^1$H NMR (400 MHz, $CDCl_3$, TMS): δ=7.49 (d, J=7.6 Hz, 2H), 7.37-7.27 (m, 5H), 5.52-5.47 (m, 1H), 3.13-3.06 (m, 1H), 1.69 (d, J=6.8 Hz, 3H), 1.40-1.36 (m, 6H).

Step-3: Synthesis of tert-butyl (S)-(6-chloro-3-isopropylimidazo [1, 2-a]pyrazin-8-yl)(1-phenylethyl) carbamate

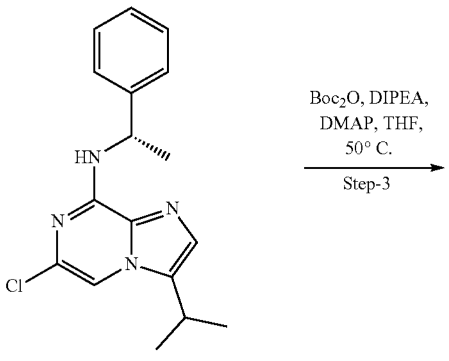

5

To a stirred solution of (S)-6-chloro-3-isopropyl-N-(1-phenylethyl)imidazo[1,2-a]pyrazin-8-amine (5) (0.9 g, 2.858 mmol, 1 eq.) in THF (10 mL) was added DIPEA (4.97 mL, 28.58 mmol, 10 eq.), Boc anhydride (6.56 mL, 28.58 mmol, 10 eq.), and DMAP (0.034 g, 0.28 mmol, 0.1 eq.) at room temperature. Reaction mixture was heated at 50 °C. 16 h. progress of the reaction was monitored on TLC. The reaction mixture was cooled; THF was evaporated under reduced pressure to get the crude residue. To the crude residue water (10 mL) was added, extracted with ethyl acetate (3×50 mL). The combined organic layer was washed with brine (10 mL), dried over sodium sulphate, filtered and evaporated under reduced pressure to get the crude compound as brown oil. The crude compound was purified by flash column chromatography on silica column (with gradient elution of EtOAc/hexane 0-20%) to afford the title compound tert-butyl (S)-(6-chloro-3-isopropylimidazo [1, 2-a]pyrazin-8-yl)(1-phenylethyl)Carbamate (6) as yellow oil. Yield: (0.9 g, 75.88%). $R_f$=0.5 (4:1 Hexane/EtOAc). LCMS (m/z): 415.1 (M+H)+. $^1$H NMR (400 MHz, DMSO, TMS): δ=8.71 (d, J=1.2 Hz, 1H), 7.72 (s, 1H), 7.55 (d, J=7.6 Hz, 2H), 7.30 (t, J=7.6 Hz, 2H), 7.20 (t, J=7.2 Hz, 1H), 5.75 (d, J=1.2 Hz, 1H), 5.45-5.40 (m, 1H), 3.42-3.32 (m, 1H), 1.57 (d, J=7.2 Hz, 3H), 1.32-1.29 (m, 6H), 1.15 (s, 9H).

Step-4: Synthesis of tert-butyl 3-((8-((tert-butoxycarbonyl) ((S)-1-phenylethyl) amino)-3-isopropylimidazo [1, 2-a]pyrazin-6-yl) thio) piperidine-1-carboxylate

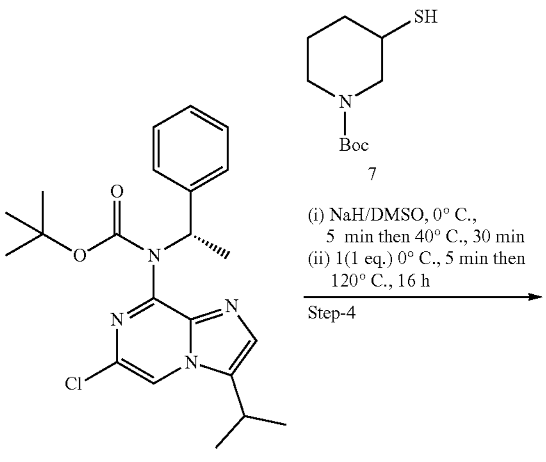

6

-continued

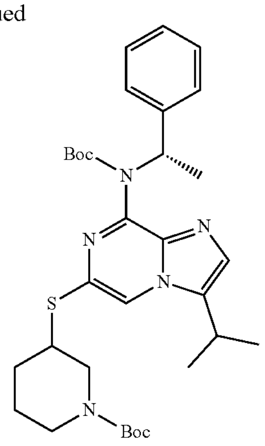

8

To a solution of tert-butyl 3-mercaptopiperidine-1-carboxylate (7) (0.393 g, 1.811 mmol, 3 eq.) in DMSO (3 mL) at 0 °C was added NaH (60% in mineral oil,) (0.072 g, 1.81 mmol, 3 eq.). Reaction mixture was heated at 40 °C for 30 min. After this time, reaction mixture was cool to 0 °C and added tert-butyl (S)-(3-isopropylimidazo [1, 2-a]pyrazin-8-yl) (1-phenylethyl) carbamate (7) (0.250 g, 0.603 mmol, 1 eq.) in DMSO (2 mL). Finally, reaction mixture was heated at 120 °C for 16 h. Progress of the reaction was monitored on TLC. Reaction mixture was cooled, quenched with ice cold water (10 mL) and extracted with ethyl acetate (3×15 mL). The combined organic layer was washed with brine solution (10 mL), dried over sodium sulphate, filtered and evaporated under reduced pressure to get crude compound as brown oil. Crude compound was purified by silica phase column chromatography (with a gradient elution of 15-20% of EtOAc/Hexane), to afford the title compound tert-butyl 3-((8-((tert-butoxycarbonyl)((S)-1-phenylethyl)amino)-3-isopropylimidazo[1,2-a]pyrazin-6-yl)thio)piperidine-1-carboxylate as a yellow oil. (0.090 g, 25.06%), $R_f$=0.3(4:1 Hexane/EtOAc). Note: Observed Cpd-8 59.21% and 10% of di de-boc of cpd-8 on TLC & LCMS. LCMS (m/z): 596.2 $(M+H)^+$.

Step-5: Synthesis of 3-isopropyl-N—((S)-1-phenylethyl)-6-(piperidin-3-ylthio) imidazo [1, 2-a] pyrazin-8-amine hydrochloride

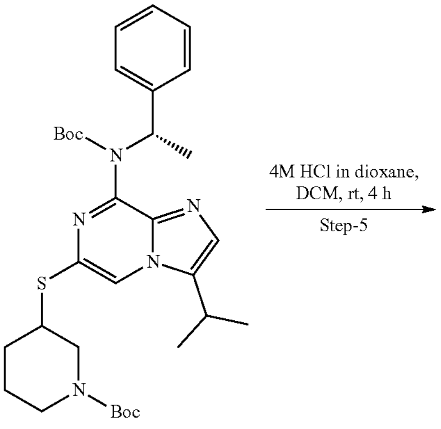

-continued

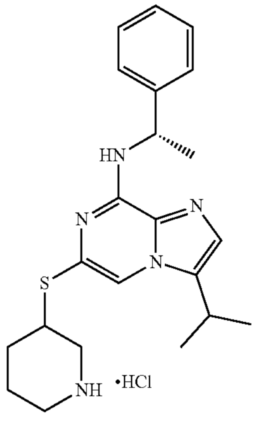

34

To a solution of tert-butyl 3-((8-((tert-butoxycarbonyl)((S)-1-phenylethyl)amino)-3-isopropylimidazo[1,2-a]pyrazin-6-yl)thio)piperidine-1-carboxylate (8) (0.090 g, 0.151 mmol, 1 eq.) in DCM (4 mL) at 0 °C was added 4M HCl in dioxane (2 mL) and stirred at RT for 4 h. After completion of conversion by TLC, volatiles portion was evaporated under reduced pressure to get crude compound. The crude compound was purified by Prep-HPLC using formic acid buffer to afford the title compound as 3-isopropyl-N—((S)-1-phenylethyl)-6-(piperidin-3-ylthio)imidazo [1,2-a]pyrazin-8-amine formate salt (34) as an off white solid. Formate salt was dissolved in acetonitrile (1 mL) and cooled to 0 °C and added 2N HCl (2 mL) at 0 °C and lyophilized for 24 h to afford the title compound as 3-isopropyl-N—((S)-1-phenylethyl)-6-(piperidin-3-ylthio)imidazo[1,2-a]pyrazin-8-amine hydrochloride (34) as an off white solid. Yield: (0.015 g, quantitative). $R_f$=0.1 (1:1Hexane/EtOAc). LCMS (m/z): 396.24 $(M+H)^+$. $^1$HNMR (400 MHz, DMSO) δ: 9.06 (s, 1H), 8.88 (s, 1H), 8.56 (s, 1H), 7.85 (d, J=5.6 Hz, 1H), 7.70 (s, 1H), 7.52-7.47 (m, 2H), 7.40-7.30 (m, 2H), 7.25-7.21 (m, 1H), 5.43-5.38 (m, 1H), 3.71-3.42 (m, 1H), 3.32-3.25 (m, 1H), 3.19 (s, 1H), 2.92-2.78 (m, 3H), 2.04 (s, 1H), 1.87-1.79 (m, 2H), 1.58-1.56 (m, 4H), 1.30-1.24 (m, 6H).

Example 95

Synthetic Scheme for 3-isopropyl-N-(2-methoxybenzyl)-6-(piperidin-4-ylthio) imidazo [1,2-a] pyrazin-8-amine formate

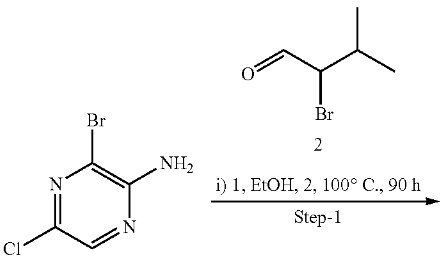

-continued

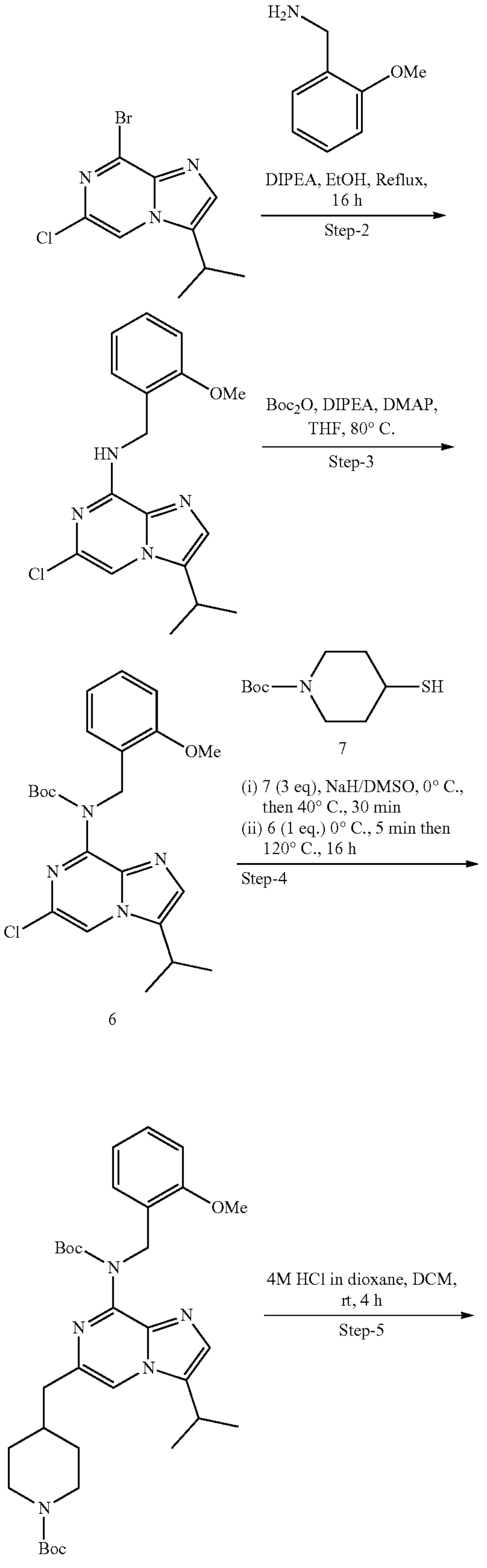

-continued

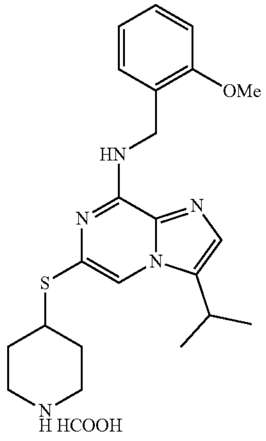

51

Step-1: Synthesis of 8-bromo-6-chloro-3-isopropylimidazo [1,2-a]pyrazine

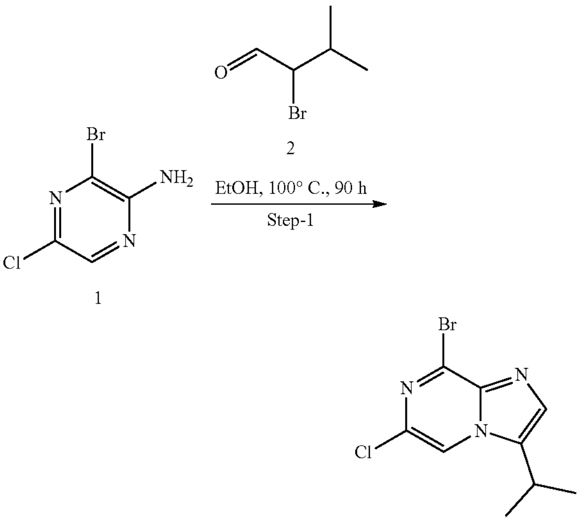

To a stirred solution of 3-bromo-5-chloropyrazin-2-amine (1) (4 g, 19.23 mmol, 1 eq.) in EtOH (40 mL) was added 2-bromo-3-methylbutanal (2) (31.73 g, 192.30 mmol, 10 eq.) at room temperature. The reaction mixture was heated at 100 °C for 90 h. After complete conversion by TLC, the reaction mixture was cooled to room temperature. Ethanol was evaporated under reduced pressure, diluted with water (200 mL), extracted with ethyl acetate (3×200 mL), washed with saturated sodium bicarbonate solution (100 mL), brine (100 mL), dried over sodium sulphate, filtered and evaporated under reduced pressure to get the crude residue. Crude residue was purified by column chromatography on silica column (100-200) mesh (EtOAc/hexane, gradient elution of 15-20% EtOAc) to afford the title compound as 8-bromo-6-chloro-3-isopropylimidazo [1, 2-a]pyrazine (3) as brown solid. (Yield: 2.6 g, 49%). $R_f$=0.4 (4:1 Hexane/EtOAc).

LCMS (m/z): 273.9 $(M+H)^+$. $^1H$ NMR (400 MHz, $CDCl_3$): δ=7.96 (m, 1H), 7.70 (m, 1H), 3.26-3.16 (m, 1H), 1.63-1.44 (m, 6H).

Step-2: Synthesis of 6-chloro-3-isopropyl-N-(2-methoxybenzyl) imidazo [1, 2-a]pyrazin-8-amine

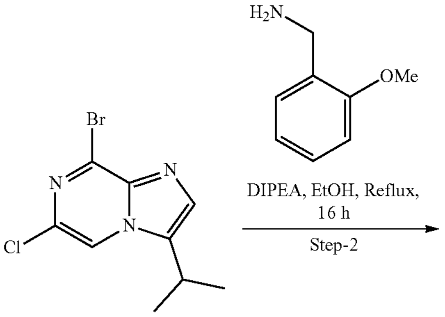

3

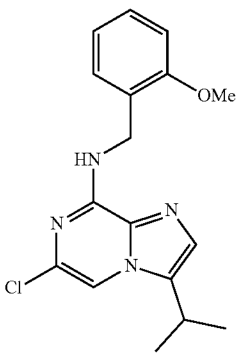

5

To a stirred solution 8-bromo-6-chloro-3-isopropylimidazo [1,2-a]pyrazine (3) (1 g, 3.64 mmol, 1 eq.) in EtOH (10 mL) was added DIPEA (1.27 mL, 7.29 mmol, 2 eq.) and (2-methoxyphenyl)methanamine (0.714 mL, 5.47 mmol, 1.5 eq.) at room temperature. Reaction mixture was heated at 80 °C for 16 h. After complete conversion by TLC, the reaction mixture was allowed to cool to room temperature, ethanol was evaporated under reduced pressure, diluted with water (100 mL), extracted with ethyl acetate (3×50 mL). The combined organic layer washed with brine (100 mL), dried over sodium sulphate, filtered and evaporated under reduced pressure to get crude residue. The crude residue was purified by combiflash on silica column (EtOAc/hexane, gradient elution of 0-20% EtOAc) to afford the title compound as 6-chloro-3-isopropyl-N-(2-methoxybenzyl) imidazo [1, 2-a] pyrazin-8-amine (5) as yellow solid. (Yield: 1 g, 83%). $R_f$=0.4 (4:1 Hexane/EtOAc). LCMS (m/z): 331.0 $(M+H)^+$. $^1H$ NMR (400 MHz, $CDCl_3$): δ=7.45-7.39 (m, 1H), 7.32-7.21 (m, 3H), 6.97-6.87 (m, 2H), 6.49 (m, 1H), 4.83-4.77 (m, 2H), 3.91-3.87 (m, 3H), 3.10-3.04 (m, 1H), 1.43-1.34 (m, 6H).

Step-3: Synthesis of tert-butyl (6-chloro-3-isopropylimidazo [1, 2-a]pyrazin-8-yl)(2-methoxybenzyl) carbamate

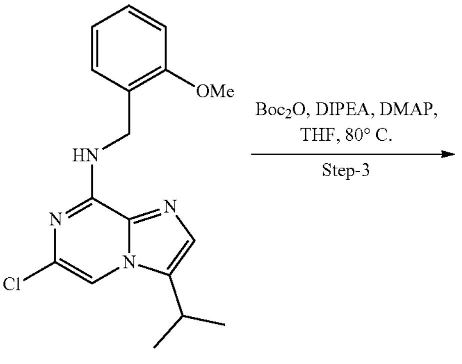

5

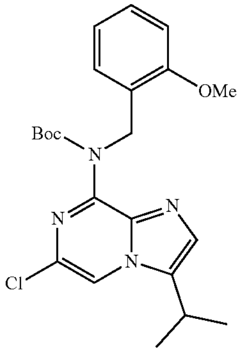

6

To a stirred solution of 6-chloro-3-isopropyl-N-(2-methoxybenzyl) imidazo [1, 2-a]pyrazin-8-amine (5) (1 g, 3.03 mmol, 1 eq.), in THF (10 mL) was added DIPEA (5.27 mL, 30.30 mmol, 10 eq.), Boc anhydride (6.95 mL, 30.30 mmol, 10 eq.) and DMAP (0.036 g, 0.303 mmol, 0.1 eq.) at room temperature. Reaction mixture was heated at 80 °C. 16 h. After complete conversion by TLC, the reaction mixture was cooled, THF was evaporated under reduced pressure to get the crude residue. To the crude residue water (100 mL) was added, extracted with ethyl acetate (3×100 mL). The combined organic layer washed with brine (50 mL), dried over sodium sulphate, evaporated under reduced pressure to get the crude residue. The crude residue was purified by column chromatography using silica gel (100-200) mesh (EtOAc/hexane, gradient elution of 15-20% EtOAc) to afford title compound as tert-butyl (6-chloro-3-isopropylimidazo[1,2-a]pyrazin-8-yl)(2-methoxybenzyl)carbamate (6) as yellow solid. (Yield: 1 g, 76%). $R_f$=0.6 (4:1 Hexane/EtOAc). LCMS (m/z): 431.01 $(M+H)^+$. $^1H$ NMR (400 MHz, $CDCl_3$,): δ=7.82 (d, J=8 Hz, 1H), 7.65-7.60 (m, 2H), 7.20-7.18 (m, 1H), 6.93-6.91 (q, J=8 Hz, 1H), 6.78 (t, J=8 Hz, 1H), 5.22 (d, J=12 Hz, 2H), 3.64 (d, J=8 Hz, 3H), 3.22-2.91 (m, 1H), 1.73-1.68 (m, 1H), 1.43-1.40 (s, 14H).

Step-4: Synthesis of tert-butyl 4-((8-((tert-butoxycarbonyl)(2-methoxybenzyl)amino)-3-isopropylimidazo[1,2-a]pyrazin-6-yl)thio)piperidine-1-carboxylate

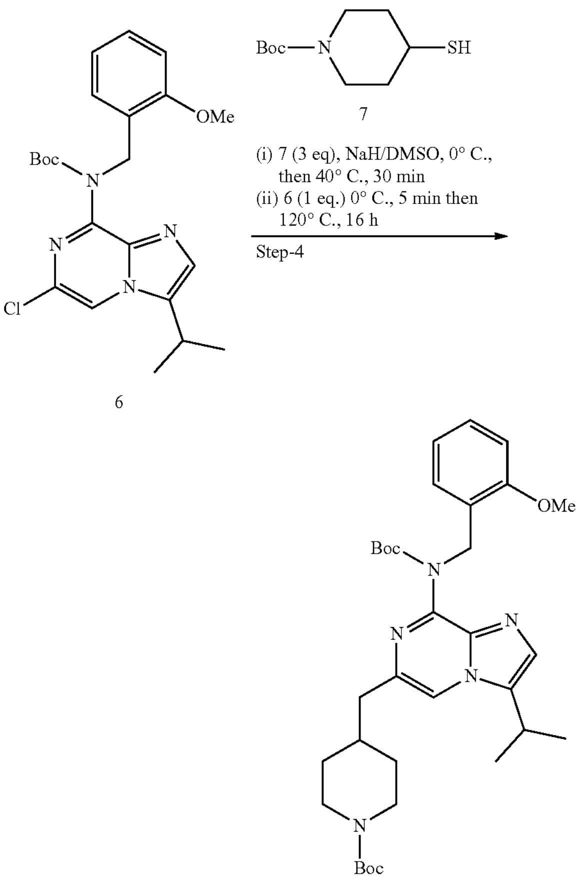

8

To a stirred solution of tert-butyl 4-mercaptopiperidine-1-carboxylate (7) (0.337 g, 1.55 mmol, 3 eq.) in DMSO (3 mL) at 0 °C was added NaH (60% in mineral oil,) (0.062 g, 1.55 mmol, 3 eq.). Reaction mixture was heated at 40 °C for 30 minutes. Reaction mixture was cooled to 0 °C. Then addition tert-butyl (6-chloro-3-isopropylimidazo [1, 2-a] pyrazin-8-yl)(2-methoxybenzyl)carbamate (6) (0.300 g, 1.55 mmol, 1 eq.) in DMSO (3 mL) was done at 0 °C. Reaction mixture was heated at 120 °C for 16 h. After complete conversion by TLC, reaction mixture was cooled, water (100 mL) was added, extracted with ethyl acetate (3×50 mL) and organic layer washed with brine (30 mL), dried over sodium sulfate, evaporated under reduced pressure to get the crude residue as yellow oil. Crude residue was purified by silica phase column chromatography using silica gel (100-200) mesh and (EtOAc/hexane, gradient elution of 15-20% EtOAc), to afford the title compound as tert-butyl 4-((8-((tert-butoxycarbonyl)(2-methoxybenzyl)amino)-3-isopropylimidazo[1,2-a]pyrazin-6-yl)thio)piperidine-1-carboxylate (8) as a yellow oil. Yield:(0.075 g, 23.65%), $R_f$=0.4 (4:1 Hexane/EtOAc). Note: Observed Cpd-8 (57%) along with 19% of de-boc of Cpd-8. LCMS (m/z): 612.2 $(M+H)^+$; LCMS (m/z): 512.1 $(M+H)^+$.

Step-5: Synthesis of 3-isopropyl-N-(2-methoxybenzyl)-6-(piperidin-4-ylthio) imidazo [1, 2-a]pyrazin-8-amine formate

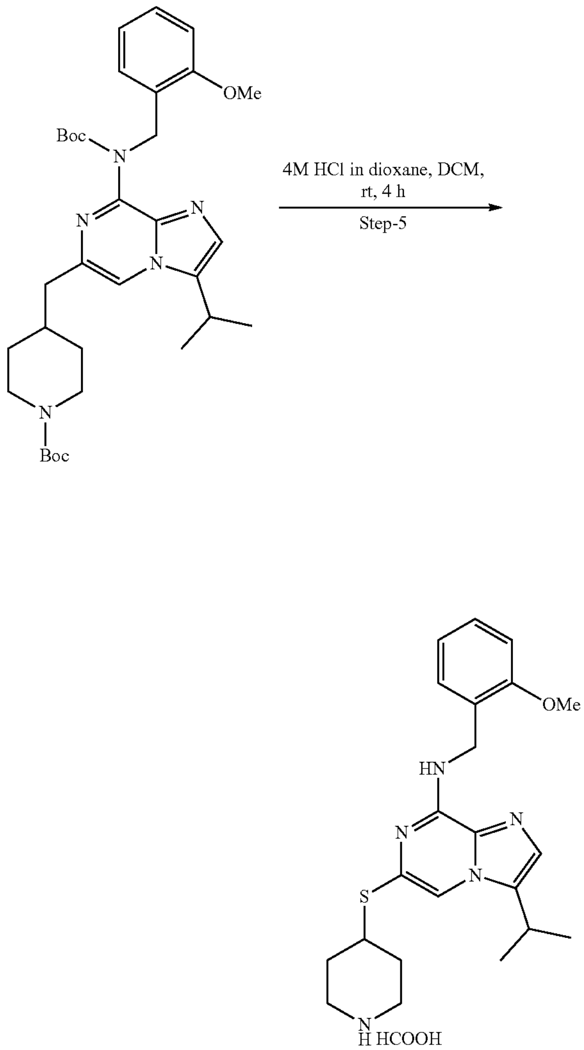

51

To a stirred solution of tert-butyl 4-((8-((tert-butoxycarbonyl)(2-methoxybenzyl)amino)-3-isopropylimidazo[1,2-a] pyrazin-6-yl)thio)piperidine-1-carboxylate (8) (0.075 g, 0.122 mmol, 1 eq.) in DCM (4 mL) at 0 °C was added 4M HCl in dioxane (1 mL) and stirred at room temperature for 4 h. After completion of conversion by TLC, volatiles were evaporated under reduced pressure to get crude residue. Crude residue was purified by Prep-HPLC using formic acid as a buffer to get title compound as 3-isopropyl-N-(2-methoxybenzyl)-6-(piperidin-4-ylthio)imidazo[1,2-a] pyrazin-8-amine formate as white solid. (51). (Yield: 0.025 g, quantitative). $R_f$=0.1 (1:1Hexane/EtOAc). LCMS (m/z): 412.1 $(M+H)^+$. $^1$HNMR (400 MHz, DMSO-$d_6$) δ:−8.34 (s, 1H), 7.95 (t, J=8.0 Hz, 1H), 7.63 (s, 1H), 7.31 (s, 1H), 7.19 (t, J=8.0 Hz, 1H), 7.08 (d, J=4.0 Hz, 1H), 6.98 (d, J=8.0 Hz, 1H), 6.82 (t, J=8.0 Hz, 1H), 4.61 (d, J=4 Hz, 2H), 3.85 (s, 3H), 3.37-3.20 (m, 2H), 2.90 (d, J=12.0 Hz, 2H), 2.42-2.39 (m, 2H), 1.76 (d, J=12 Hz, 2H), 1.43-1.343 (m, 2H), 1.28-1.26 (m, 6H).

Example 96

Synthetic Scheme for N-(2-(1H-pyrazol-1-yl)benzyl)-3-isopropyl-6-(piperidin-3-ylthio)imidazo[1,2-a]pyrazin-8-amine hydrochloride

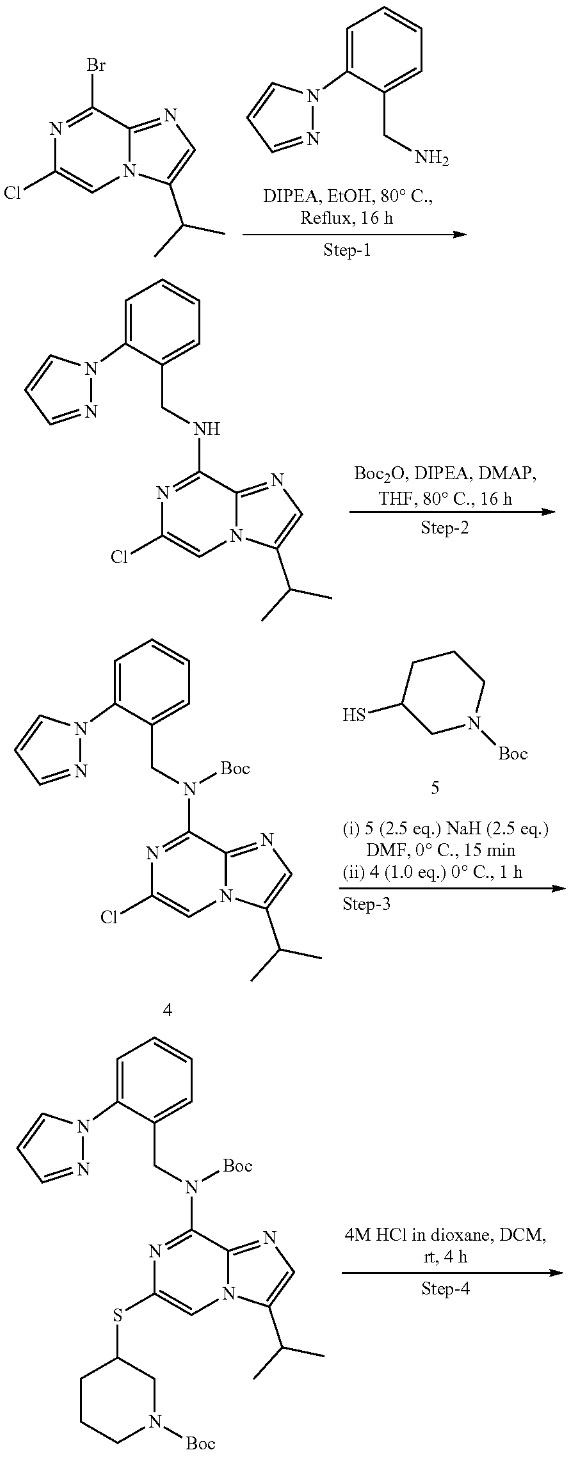

5

4

-continued

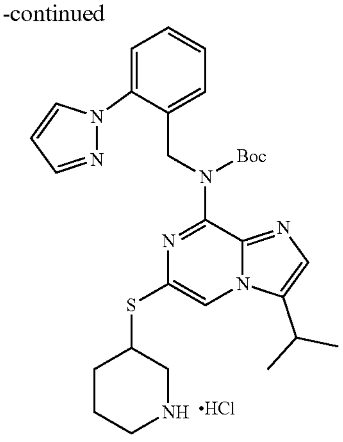

68

Step-1: Synthesis of N-(2-(1H-pyrazol-1-yl)benzyl)-6-chloro-3-isopropylimidazo[1,2-α]pyrazin-8-amine

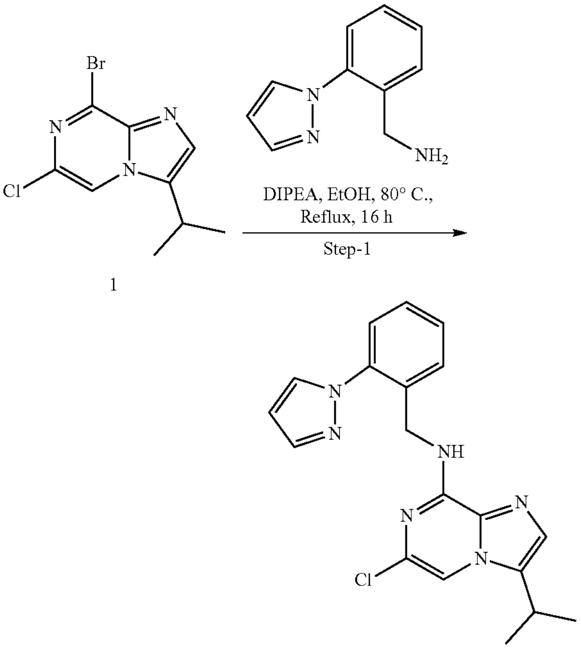

1

3

To a stirred solution of 8-bromo-6-chloro-3-isopropylimidazo[1,2-a]pyrazine (1) (0.25 g, 0.915 mmol, 1.0 eq.) in ethanol (10 mL) was added DIPEA (0.478 mL, 2.75 mmol, 3.0 eq.) and (2-(1H-pyrazol-1-yl)phenyl)methanamine (2) (0.31 g, 1.83 mmol, 2.0 eq.) at room temperature. The reaction mixture was heated to reflux at 80 °C for 12 h. After complete conversion by TLC, the reaction mixture was allowed to cool to room temperature, ethanol was evaporated under reduced pressure, obtained crude wad diluted with water (25 mL) and product was extracted with EtOAc (2×25 mL). The combined organic layer was washed with brine (25 mL), dried over $Na_2SO_4$, filtered and evaporated to get the crude residue. The crude residue was purified by silica gel column chromatography using silica gel (100-200)

mesh (EtOAc/hexane, gradient 25-28% EtOAc) to afford the title compound N-(2-(1H-pyrazol-1-yl)benzyl)-6-chloro-3-isopropylimidazo[1,2-a]pyrazin-8-amine (3) as brown solid. (Yield: 0.24 g, 72%). $R_f$=0.3 (7:3 Hexane/EtOAc). LCMS (m/z): 367.37M+H)$^+$; $^1$H NMR (400 MHz, DMSO-$d_6$): δ8.313 (t, J=6.4, 6.0 Hz 1H), 8.228 (d, J=2.4, 1H), 7.89-7.78 (m, 2H), 7.53-7.43 (m, 1H), 7.42-7.32 (m, 4H), 6.60-6.53 (m, 1H), 4.61 (d, J=6.0 Hz, 2H), 3.33-3.22 (m, 1H), 1.28 (d, J=6.8 Hz, 6H).

Step-2: Synthesis of tert-butyl (2-(1H-pyrazol-1-yl)benzyl)(6-chloro-3-isopropylimidazo[1,2-a]pyrazin-8-yl)carbamate

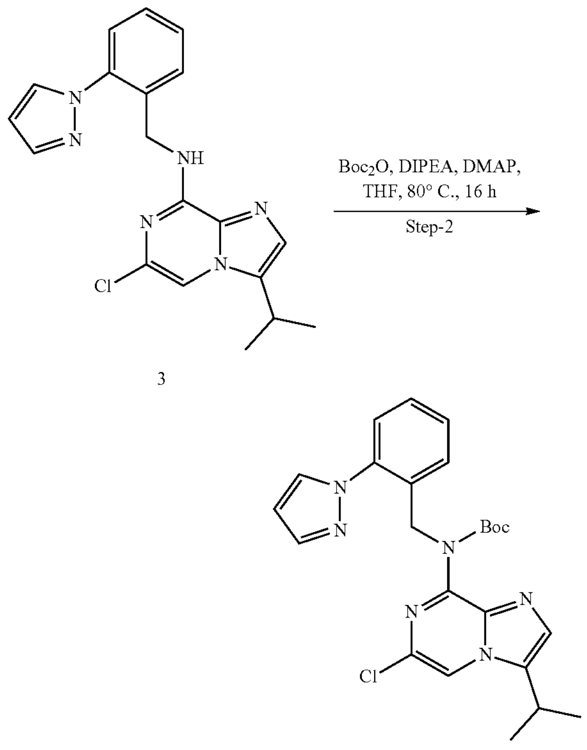

3

4

To a stirred solution of N-(2-(1H-pyrazol-1-yl)benzyl)-6-chloro-3-isopropylimidazo[1,2-a]pyrazin-8-amine (3) (0.240 g, 0.656 mmol, 1.0 eq.) in THF (5 mL) was added DIPEA (1.14 mL, 6.56 mmol, 10 eq.), $(Boc)_2O$ (1.50 mL, 6.56 mmol, 10 eq.) and DMAP (0.008 g, 0.065 mmol, 0.1 eq.) at ambient temperature. Reaction mixture was stirred at 80 °C for 16 h. The reaction mixture was allowed to cool to room temperature, THF was evaporated, water (25 mL) was added and product was extracted with EtOAc (3×25 mL). The combined organic layer washed with brine (25 mL) dried over sodium sulphate, filtered and evaporated under reduced pressure to get the crude residue. The residue was purified by column chromatography using silica gel (100-200) mesh (EtOAc/hexane, gradient 24-26% EtOAc) to afford the title compound as tert-butyl (2-(1H-pyrazol-1-yl)benzyl)(6-chloro-3-isopropylimidazo[1,2-a]pyrazin-8-yl)carbamate (4) as brown solid. (Yield: 0.260 g, 85%). $R_f$=0.6 (7:3 Hexane/EtOAc). LCMS (m/z): 467.17 (M+H)f; $^1$H NMR (400 MHz, DMSO-$d_6$): δ 8.637 (s, 1H), 7.91 (t, J=1.6, 0.8 Hz, 1H), 7.82 (d, J=7.6 Hz, 1H), 7.72 (s, 1H), 7.61 (m, 1H), 7.48-7.25 (m, 3H), 6.38 (t, J=2.0, 2.0 Hz, 1H), 5.03 (s, 2H), 3.48-3.32 (m, 1H), 1.32 (d, J=6.8 Hz, 6H), 1.24 (s, 9H).

Step-3: Synthesis of tert-butyl 3-((8-((2-(1H-pyrazol-1-yl)benzyl)(tert-butoxycarbonyl)amino)-3-isopropylimidazo[1,2-a]pyrazin-6-yl)thio)piperidine-1-carboxylate

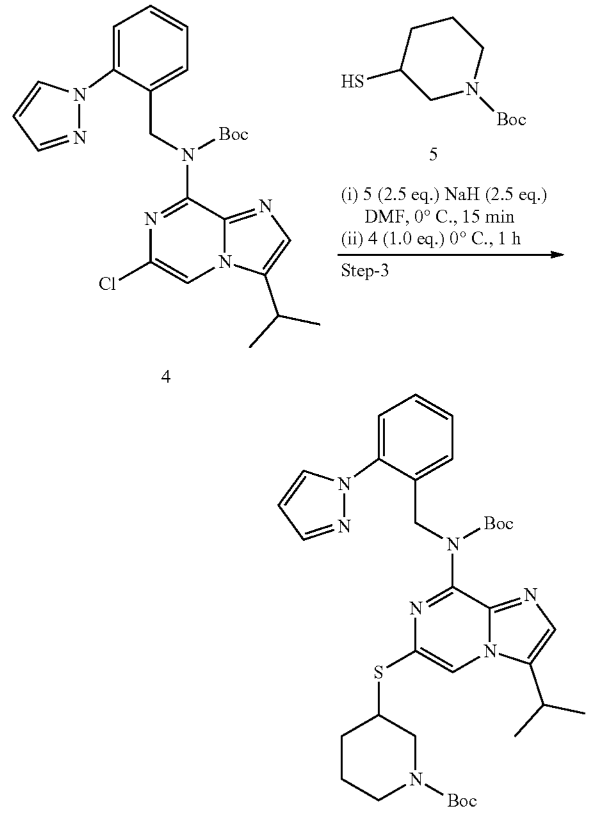

5

4

6

To a stirred solution tert-butyl 3-mercaptopiperidine-1-carboxylate (5) (0.304 g, 1.41 mmol, 2.5 eq.) in DMSO (4 mL) at 0 °C was added NaH (60% in mineral oil), (0.067 g, 1.40 mmol, 2.5 eq.). Reaction mixture was stirred at 40 °C for 30 minutes. Then reaction mixture was cooled to 0 °C and addition of tert-butyl (2-(1H-pyrazol-1-yl)benzyl)(6-chloro-3-isopropylimidazo[1,2-a]pyrazin-8-yl)carbamate (4) (0.260 g, 0.56 mmol, 1.0 eq.) in DMSO (2 mL) was added. The resulting reaction mixture was stirred at 120 °C for 16 h. After complete conversion by TLC, the reaction mixture was diluted with ice cold water (15 mL) was added, extracted with EtOAc (3×25 mL). The combined organic layer was washed with brine (15 mL) and dried over sodium sulphate, filtered and concentrated under reduced pressure to get the crude residue. Obtained crude product was purified by column chromatography using silica gel to get a brown liquid. The product was eluted in 28-32% EtOAc in hexane, to afford the title compound as (6) tert-butyl 3-((8-((2-(1H-pyrazol-1-yl)benzyl)(tert-butoxycarbonyl)amino)-3-isopropylimidazo[1,2-a]pyrazin-6-yl)thio)piperidine-1-carboxylate as an brown liquid. (Yield: 0.040 g, 11%). $R_f$=0.4(3:2 Hexane/EtOAc). LCMS (m/z): 548.28 (M+H)$^+$. Note: After purification, mono BOC product was confirmed by LCMS.

Step-4: Synthesis of N-(2-(1H-pyrazol-1-yl)benzyl)-3-isopropyl-6-(piperidin-3-ylthio)imidazo[1, 2-a] pyrazin-8-amine hydrochloride

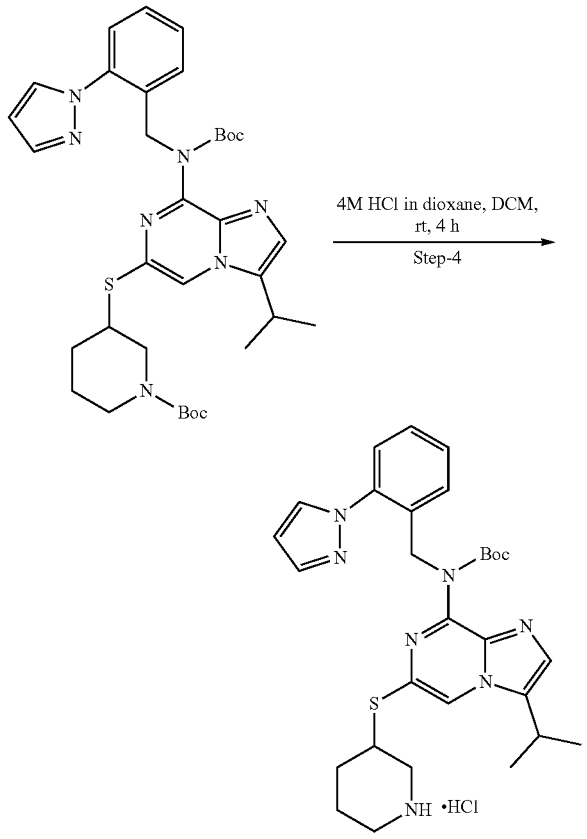

68

To a stirred solution of tert-butyl 3-((8-((2-(1H-pyrazol-1-yl)benzyl)(tert-butoxycarbonyl)amino)-3-isopropylimidazo[1,2-a]pyrazin-6-yl)thio)piperidine-1-carboxylate (6) (0.040 g, 0.062 mmol, 1.0 eq.) in DCM (5 mL) at 0 °C was added 4M HCl in 1,4-dioxane (1.0 mL) drop-wise and stirred at 0 °C. The reaction mixture was allowed to come to room temperature and stirred for 5 h. After completion of reaction by TLC, volatiles were evaporated by reduced pressure from the reaction mixture to get crude residue. The resulting crude compound was purified by Prep-HPLC (Trifluoroacetic acid buffer was used) to afford N-(2-(1H-pyrazol-1-yl)benzyl)-3-isopropyl-6-(piperidin-3-ylthio)imidazo [1,2-a]pyrazin-8-amine 2,2,2-trifluoroacetate. To get compound as a HCl salt, obtained 2,2,2-trifluoroacetate salt was dissolved in ACN: water and treated with 2N aq. HCl at 0 °C and lyophilized to afford N-(2-(1H-pyrazol-1-yl) benzyl)-3-isopropyl-6-(piperidin-3-ylthio)imidazo[1,2-a] pyrazin-8-amine hydrochloride (68) as a off white solid (0.010 g, 33% yield). $R_f$=0.1 (9:1 DCM/MeOH). LCMS (m/z): 448.46 $(M+H)^+$; $^1H$ NMR (400 MHz, DMSO-$d_6$,): δ=8.91 (br. s, 1H), 8.79 (br. s, 1H), 8.41 (s, 1H), 8.23 (d, J=2.4 Hz 1H), 7.88-7.79 (m, 2H), 7.62-7.49 (m, 2H), 7.48-7.37 (m, 3H) 6.56 (t, J=2.0 Hz, 1H), 4.78-4.53 (m, 2H), 3.62-3.56 (m, 1H), 3.39-3.23 (m, 2H), 3.19-3.08 (m, 1H), 2.92-2.83 (m, 1H), 2.80-2.71 (m, 1H), 2.02-1.91 (m, 1H), 1.81-1.63 (m, 2H) 1.59-1.48 (m, 1H), 1.28 (d, J=6.8 Hz, 6H).

Example 97

Biochemical Assay 1

Kinase Glo Assay

Materials:

- Assay Buffer: 50 mM HEPES, 3 mM $MgCl_2$, 3 mM $MnCl_2$, 1 mM DTT, 3 μM $Na_3VO_4$, pH 7.5
- Substrate RB
- CTF Peptide (ProQinase #: 0040-0000-6)
- Enzymes
- CDK7/CycH/MAT1 (ProQinase #: 0366-0360-4)
- ADP-Glo™ Assay (Promega #: V9101)
- ATP: 10 mM
- ADP-Glo™ Reagent
- Kinase Detection Reagent
- 384-well white assay plates Method:

A ten point serial dilution of compound was prepared at 5× concentration in assay buffer with the final assay concentrations starting at 30 μM, 10 μM, 3 μM, 1 μM . . . 0 μM. Enzyme, substrate, and ATP were used at 40 ng, 200 ng (or 400 ng)* and 1 μM, respectively. The assay plate was set up by mixing the components in a total reaction volume of 10 μL per well. The plate was centrifuged gently for 10 seconds and incubated at room temperature (RT) for 60 minutes in the dark. The ADP-Glo Reagent and kinase detection reagent were added and incubated as recommended. The reaction was quantified by measuring luminescence on the Perkin Elmer Envision plate reader.

Results for exemplary compounds of structure (I) are provided in Table 6 below.

TABLE 6

List of compounds and $IC_{50}$* values in nM for CDK7

| Compound | CDK7 |
|---|---|
| 2 | ++ |
| 3 | ++ |
| 4 | + |
| 5 | ++ |
| 6 | +++ |
| 7 | + |
| 8 | ++ |
| 9 | ++ |
| 10 | ++ |
| 11 | ++ |
| 12 | ++ |
| 13 | ++ |
| 14 | ++ |
| 15 | ++ |
| 16 | ++ |
| 17 | ++ |
| 18 | +++ |
| 19 | ++ |
| 20 | + |
| 21 | ++ |
| 22 | +++ |
| 23 | +++ |
| 24 | +++ |
| 25 | +++ |
| 26 | +++ |
| 27 | ++ |
| 28 | +++ |
| 29 | ++ |
| 30 | ++ |
| 31 | + |
| 32 | +++ |
| 33 | +++ |
| 34 | +++ |
| 35 | +++ |
| 36 | +++ |
| 37 | +++ |

TABLE 6-continued

| List of compounds and $IC_{50}$* values in nM for CDK7 | |
|---|---|
| Compound | CDK7 |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | ++ |
| 48 | +++ |
| 49 | ++ |
| 50 | ++ |
| 51 | +++ |
| 52 | +++ |
| 53 | +++ |
| 54 | +++ |
| 55 | +++ |
| 56 | +++ |
| 57 | ++ |
| 58 | ++ |
| 59 | +++ |
| 60 | ++ |
| 61 | ++ |
| 62 | +++ |
| 63 | +++ |
| 64 | +++ |
| 65 | +++ |
| 66 | +++ |
| 67 | +++ |
| 68 | +++ |
| 69 | ++ |
| 70 | +++ |
| 71 | + |
| 72 | +++ |
| 73 | +++ |
| 74 | ++ |
| 75 | ++ |
| 76 | ++ |
| 77 | +++ |
| 78 | +++ |
| 79 | ++ |
| 80 | ++ |
| 81 | ++ |
| 82 | +++ |
| I-1 | +++ |
| I-2 | ++ |
| I-3 | +++ |
| I-4 | ++ |

+++ indicates an $IC_{50}$ value up to 100 nM
++ indicates an $IC_{50}$ value from 100 to 1,000 nM
+ indicates an $IC_{50}$ value greater than 1,000 nM
*Kinase-Glo Assay was used

Example 98

Cell Viability Assay

Materials:

Cell Lines (Treated according to ATCC guidelines)

Cell Titer Glo (Promega Cat #G7572)

DMSO 96-well White Tissue Culture Treated Plates (Perkin Elmer Cat #60005680)

Method:

Cells were seeded in a white 96-well tissue culture treated plate at a density of 1500 cells in 90 μL of media per well and allowed to settle overnight. A ten point serial dilution of drugs was prepared at 10×concentration in media with the final assay concentrations starting at 30 μM, 10 μM, 3 μM, 1 μM, 0.3 μM . . . 0 μM. A dilution of DMSO was included as a control. The assay was set up by adding 10 μL of the corresponding drug to each well in duplicate, followed by a 72 hour incubation at 37 °C, 5% CO2. Cell viability was quantified by adding 90 μL of Cell Titer Glo to each well and incubating at room temperature for 10 minutes. The reaction was quantified by measuring luminescence using the Envision Plate Reader. Data was analyzed using Graphpad Prism 7 software.

Results for exemplary compounds of structure (I) are provided in Tables 7a-7b below.

TABLE 7a

| List of compounds and $IC_{50}$ values in μM for CDK7 expressed cancer cell lines | | | | | | |
|---|---|---|---|---|---|---|
| No. | MiaPaCa2[a] | HPAC[b] | Kasumi1[c] | MDA-MB-231[d] | A2780[e] | A673[f] |
| 6 | ++ | +++ | ++ | ND | ++ | ND |
| 22 | ++ | ++ | ++ | ++ | ++ | ++ |
| 23 | ++ | ++ | ++ | ++ | ++ | ++ |
| 24 | ++ | ++ | ++ | ++ | +++ | ++ |
| 26 | + | ++ | ++ | + | ++ | ++ |
| 32 | ++ | ++ | ++ | + | ++ | ++ |
| 33 | +++ | +++ | ++ | ++ | +++ | +++ |
| 34 | ++ | ++ | ++ | + | ++ | + |
| 35 | +++ | +++ | ++ | ++ | +++ | +++ |
| 36 | ++ | ++ | ++ | ++ | +++ | ++ |
| 37 | ++ | ++ | ++ | ++ | ++ | ++ |
| 38 | ++ | ++ | ++ | ++ | ++ | ++ |
| 39 | ++ | ++ | ++ | ++ | ++ | ++ |
| 40 | ++ | ++ | + | ++ | ++ | ++ |
| 41 | ++ | ++ | ND | ++ | ++ | ++ |
| 43 | ++ | ++ | ++ | ++ | ++ | ++ |
| 44 | +++ | +++ | +++ | +++ | +++ | +++ |
| 45 | +++ | ++ | ++ | ++ | ++ | ++ |
| 46 | ++ | ++ | + | ++ | ++ | ++ |
| 48 | ++ | ++ | + | ++ | ++ | ++ |
| 51 | ++ | ++ | ND | + | ++ | ND |
| 53 | +++ | +++ | ND | ++ | +++ | ND |
| 56 | +++ | +++ | ++ | ND | +++ | ND |
| 62 | +++ | ++ | +++ | ND | ND | ++ |
| 63 | +++ | +++ | +++ | ND | ND | ++ |
| 64 | +++ | ++ | +++ | ND | ND | +++ |
| 66 | +++ | +++ | ++ | ND | ND | +++ |
| 70 | ++ | ++ | ++ | ND | ++ | ND |
| 73 | ++ | ++ | ++ | ND | ++ | ND |
| 77 | ++ | ++ | ++ | ND | ++ | ND |

TABLE 7b

| List of compounds and $IC_{50}$ values in μM for CDK7 expressed cancer cell lines | | | | | |
|---|---|---|---|---|---|
| No. | MDA-MB436 | MDA-MB468 | MDA-MB231 | MIA PaCa2 | HPAC |
| I-1 | ++ | ++ | ++ | +++ | ++ |

+++ indicates an $IC_{50}$ value up to 1 μM
++ indicates an $IC_{50}$ value from 1 to 5 μM
+ indicates an $IC_{50}$ value greater than 5 μM
[a] Pancreatic cancer cell line
[b] Pancreatic cancer cell line
[c] Leukemia cancer cell line
[d] Breast cancer cell line
[e] Ovarian cancer cell line
[f] Ewingsarcoma cell line All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

U.S. Provisional Application 63/079,951, filed Sep. 17, 2020 and U.S. Provisional Application 63/079,954, filed Sep. 17, 2020 is incorporated herein by reference, in its entirety.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

The invention claimed is:

1. A compound having structure (I):

(I)

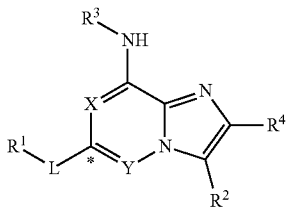

or a pharmaceutically acceptable salt, stereoisomer, or prodrug thereof, wherein:

X and Y are each independently N or $CR_5$, wherein one of X and Y is N, and the other of X and Y is $CR_5$;

$R^1$ is $C_3$-$C_8$ heterocyclyl or C(O)O—$C_{1-6}$ alkyl, each of which is optionally substituted with one or more substituents, or $R^1$ has one of the following structures:

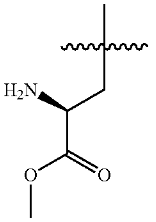 or 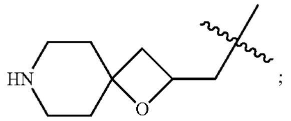 ;

$R^2$ is halo, —$CF_3$, $C_3$-$C_8$ cycloalkyl or $C_1$-$C_6$ alkyl, each of which optionally substituted with one or more substituents;

$R^3$ is $C_7$-$C_{12}$ arylalkyl, each of which is optionally substituted with one or more substituents;

$R^4$ and $R^5$ are independently H or $C_{1-6}$ alkyl;

L is —$(CHR^6)_n$—$NR^6$~, —$(CHR^6)_n$—O~, —$C(R^6)_2$~ or —$(CHR^6)_n$—S~, wherein $R^6$ is, at each occurrence, independently H, $C_{1-6}$ alkyl or amino, and ~ represents a covalent bond to the carbon with an *; and n is 0, 1, 2, or 3.

2. The compound of claim 1 having structure (Ia):

(Ia)

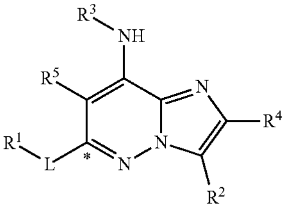

or a pharmaceutically acceptable salt, stereoisomer, or prodrug thereof.

3. The compound of claim 2, wherein -L-$R^1$ has one of the following structures:

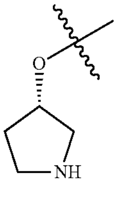 , 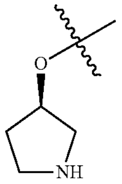 , 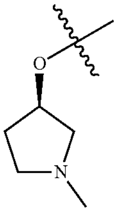 , 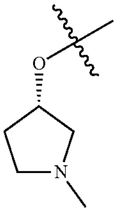 ,

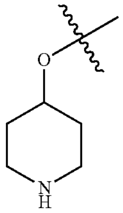 , 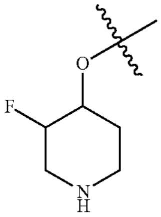 , 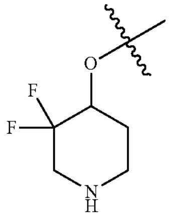 ,

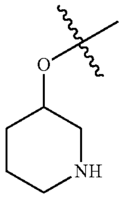 , 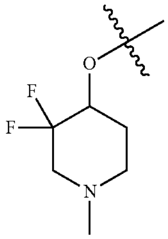 , 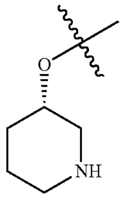 ,

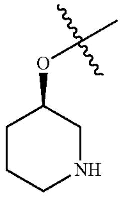 , 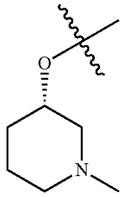 , 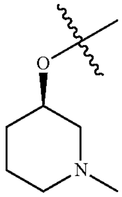 ,

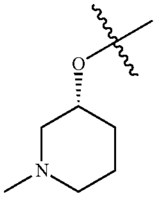 , 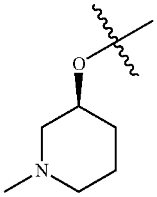 , 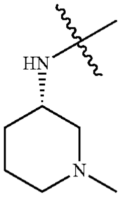 ,

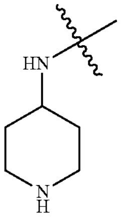 , 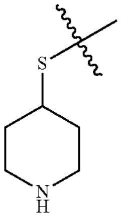 , 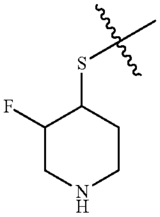 ,

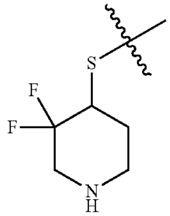 , 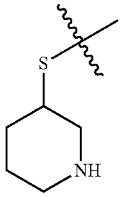 , 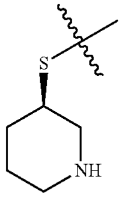 ,

-continued

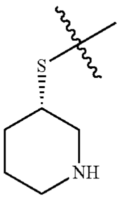,
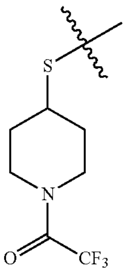,
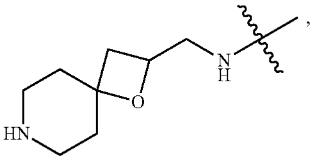,
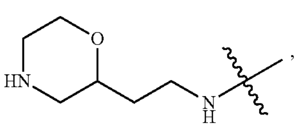,
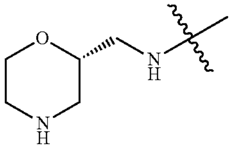,
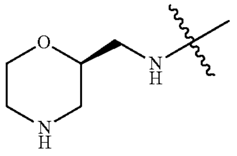,
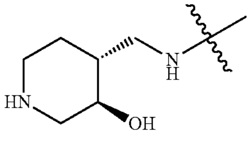, or
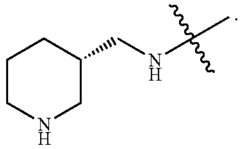.

4. The compound of claim 2, wherein $R^2$ is cyclopropyl, isopropyl, or $-CF_3$.

5. The compound of claim 2, wherein $R^3$ has one of the following structures:

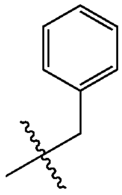,
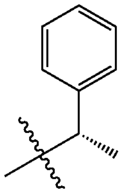,
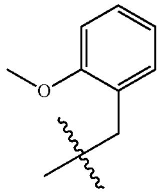,
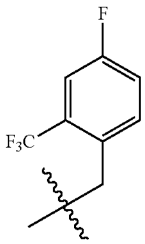,
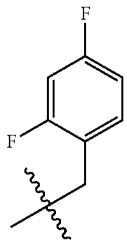,
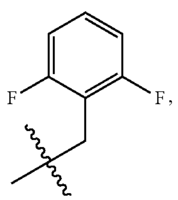, -continued

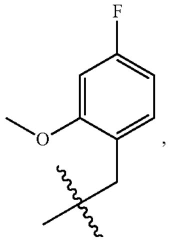,
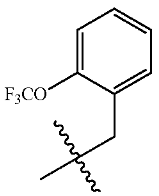,
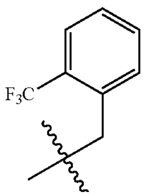,
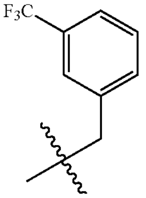,
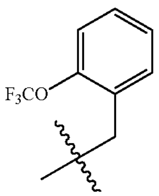,
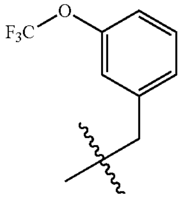,
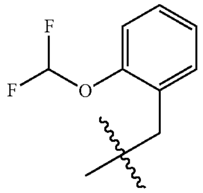,
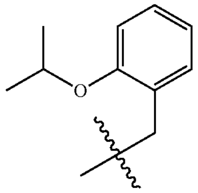,
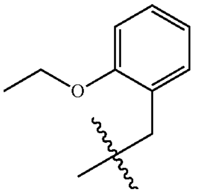,
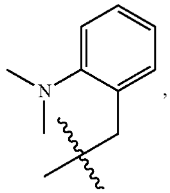, or
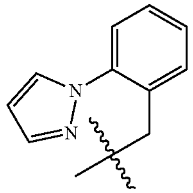.

6. The compound of claim 1 having structure (Ib):

(Ib)

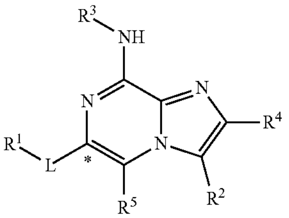

or a pharmaceutically acceptable salt, stereoisomer, or prodrug thereof.

7. The compound of claim 1, wherein $R^1$ is $C_3$-$C_8$ heterocyclyl.

8. The compound of claim 1, wherein $R^1$ is unsubstituted.

9. The compound of claim 1, wherein $R^1$ is substituted with substituents are selected from $C_{1-6}$ alkyl, $C_{1-6}$ haloalkyl, hydroxyl, halogen, and —CN.

10. The compound of claim 1, wherein $R^1$ has one of the following structures:

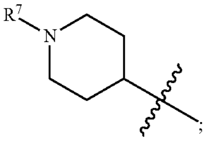
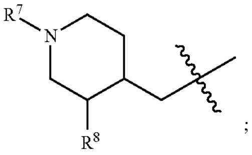
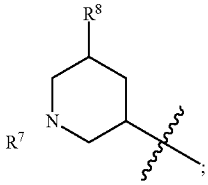
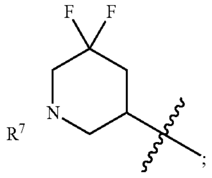
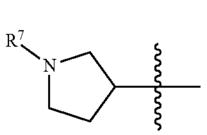
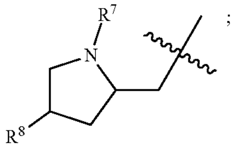
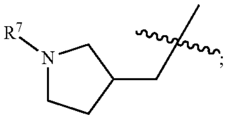
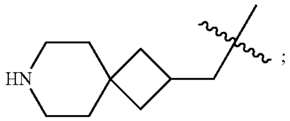
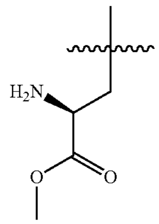
or
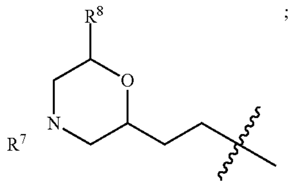
wherein: $R^7$ is H, —$CH_2CH_2OH$, —C(O) $CF_3$, or $C_{1-3}$ alkyl; and $R^8$ is H, OH, CN or F.
11. The compound of claim 1, wherein $R^2$ is $C_1$-$C_6$ alkyl, halo, $CF_3$, cyclopropyl, or isopropyl.
12. The compound of claim 1, wherein $R^3$ has one of the following structures:
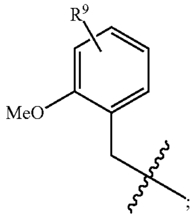
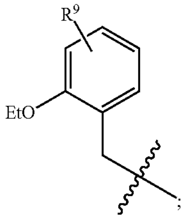
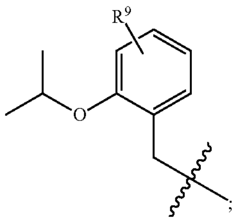
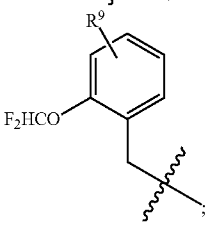
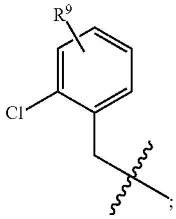
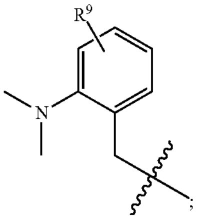
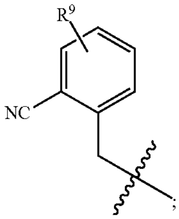
-continued
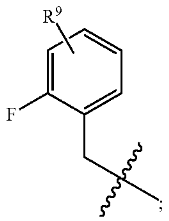
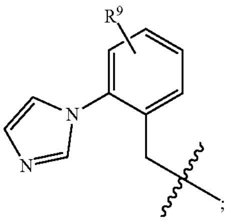
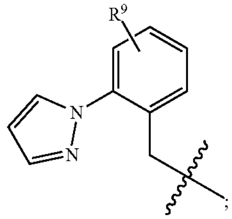
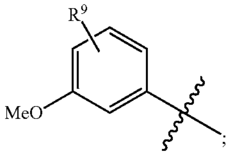
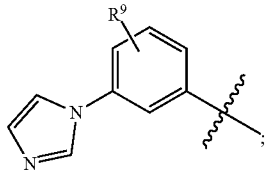
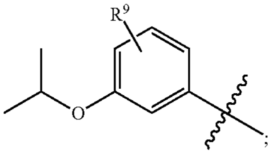
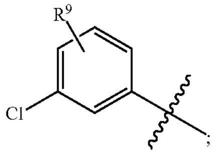
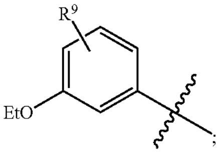
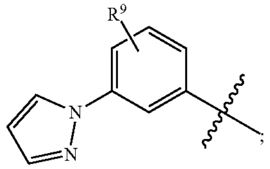
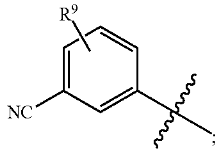
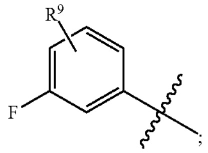
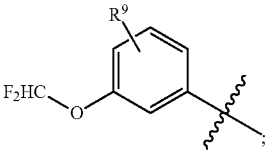
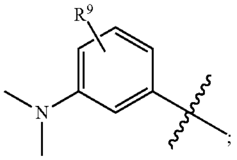
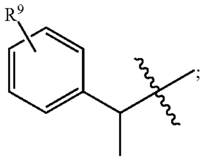
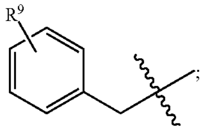
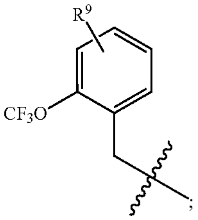
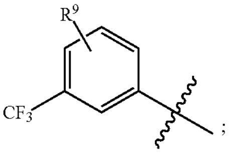

-continued

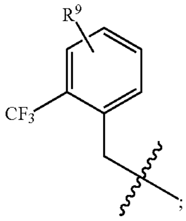

;

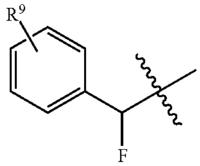

;

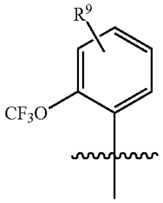

;

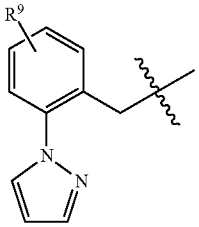

; or

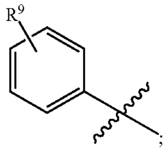

;

wherein $R^9$ is H, F, Cl, Me, CN, $CF_3$, $-OC_{1-6}$ alkyl, or $OCF_3$.

13. The compound of claim 1, wherein $R^4$ is H.

14. The compound of claim 1, wherein $R^5$ is H.

15. A pharmaceutical composition comprising the compound of claim 1, or a pharmaceutically acceptable salt, stereoisomer, or prodrug thereof, and at least one pharmaceutically acceptable excipient.

16. A compound having one of the following structures:

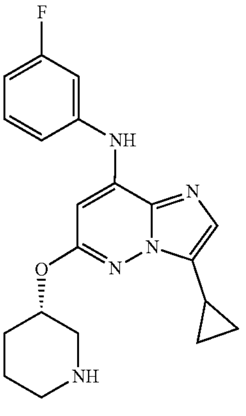

,

-continued

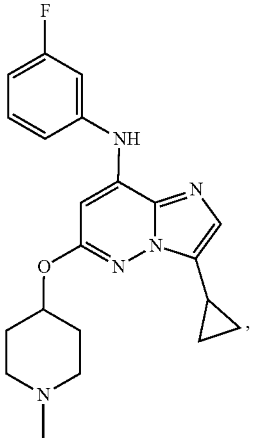

,

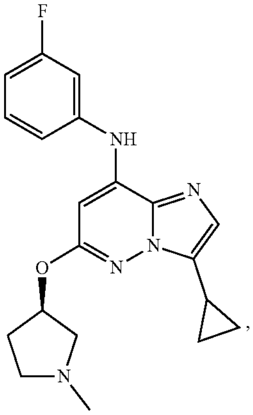

,

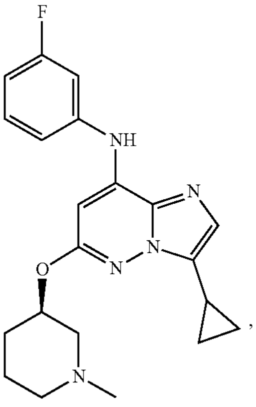

,

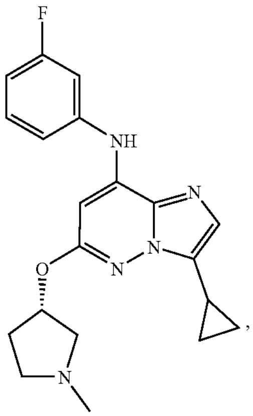

,

-continued
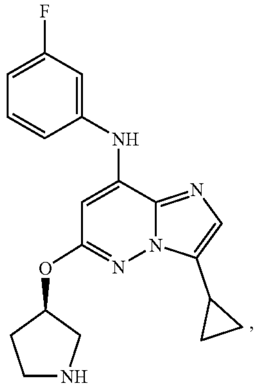
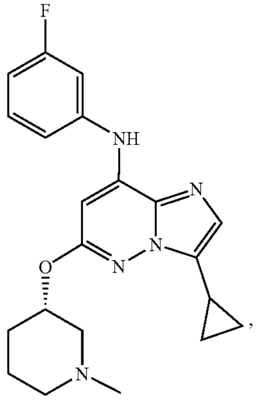
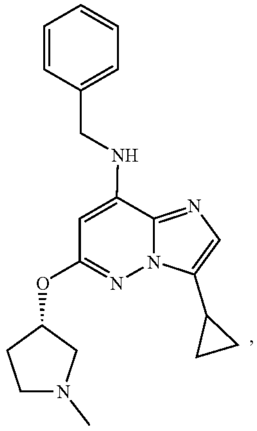
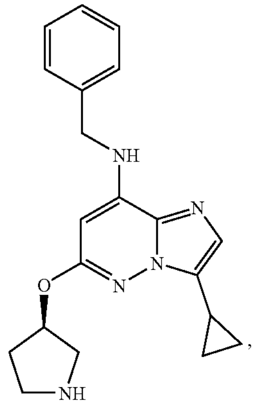
-continued
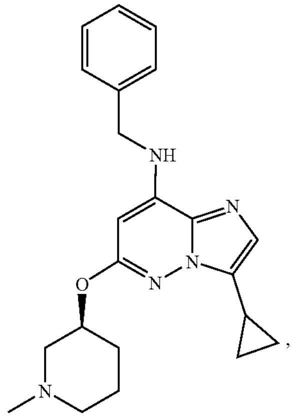
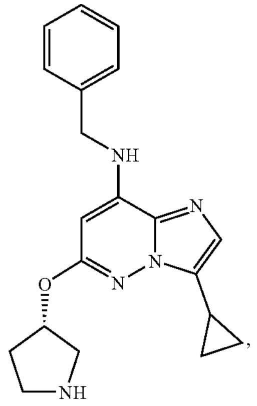
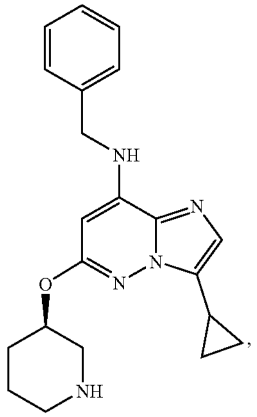
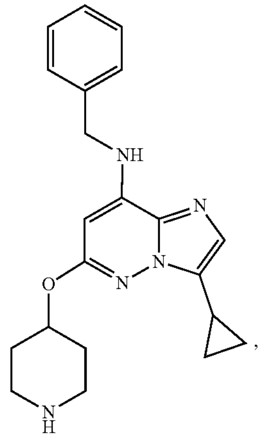

-continued
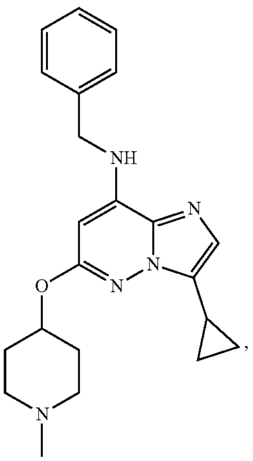
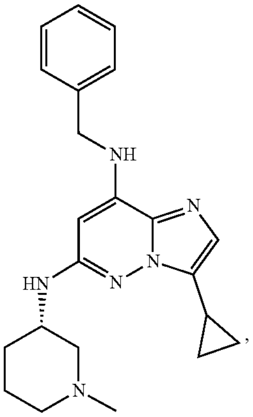
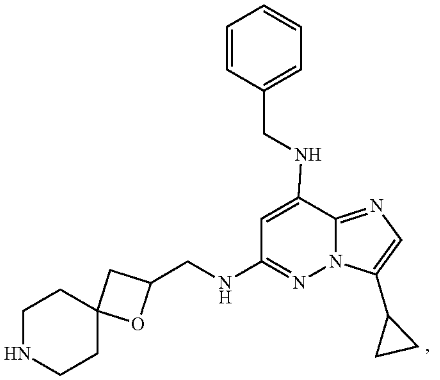
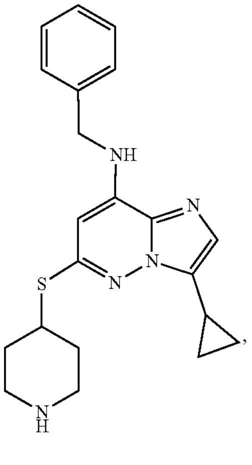
-continued
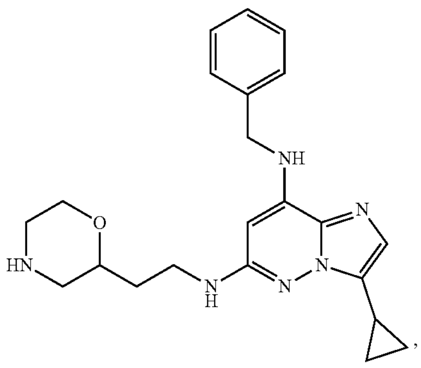
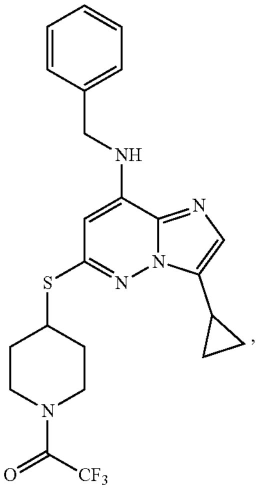
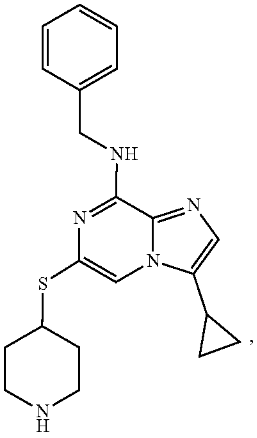
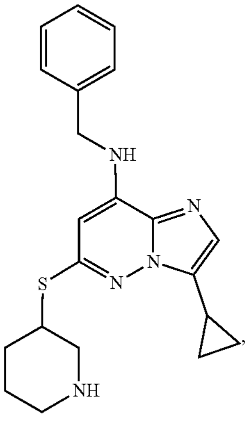

-continued
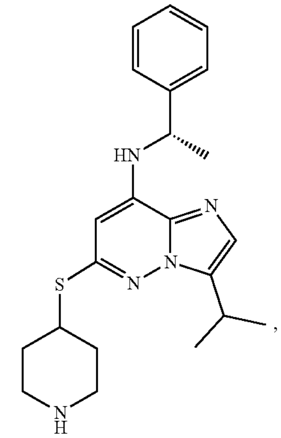
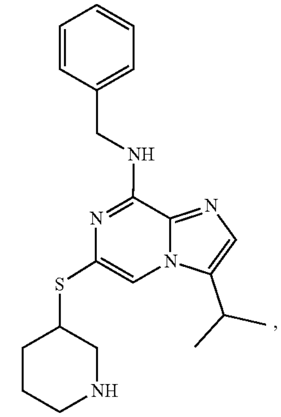
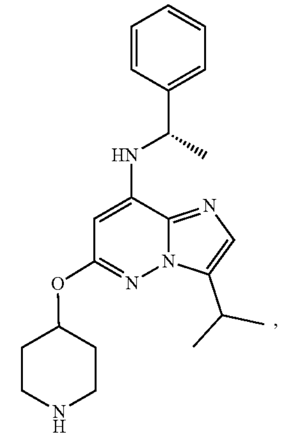
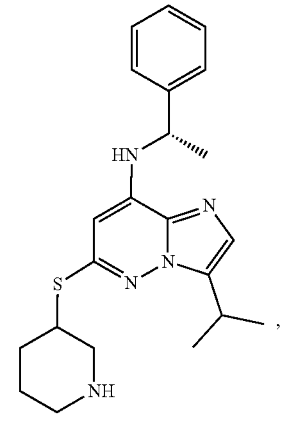
-continued
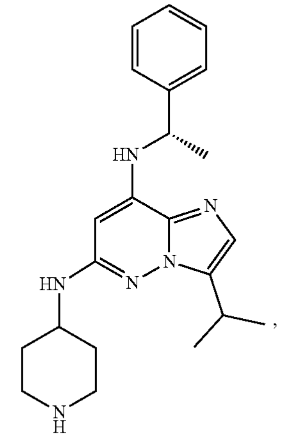
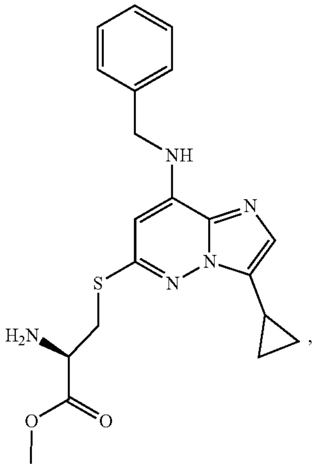
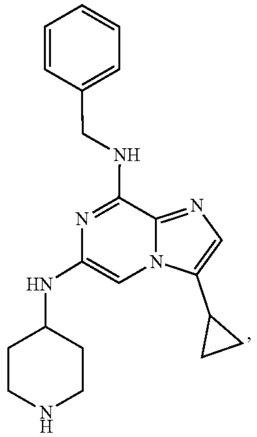

-continued
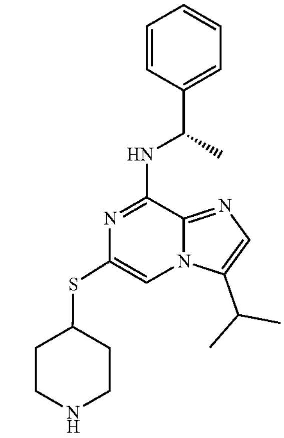
,
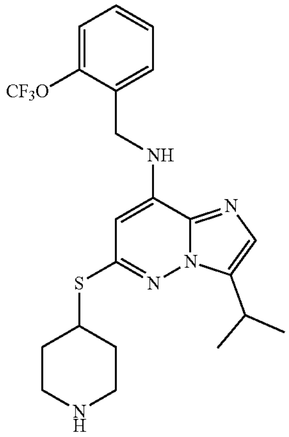
,
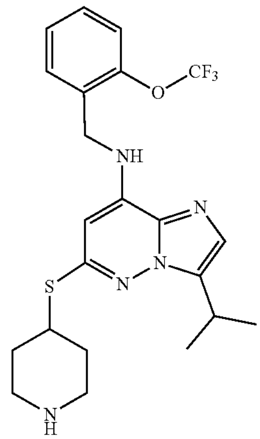
,
-continued
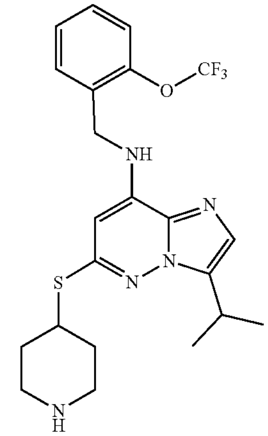
,
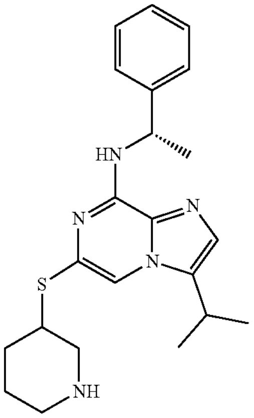
,
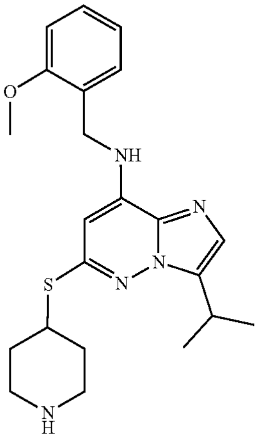
,
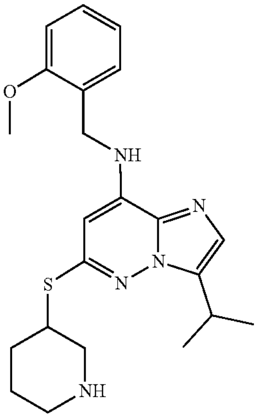
, -continued
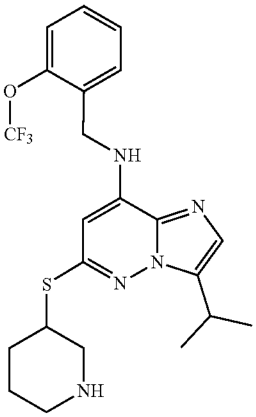
,
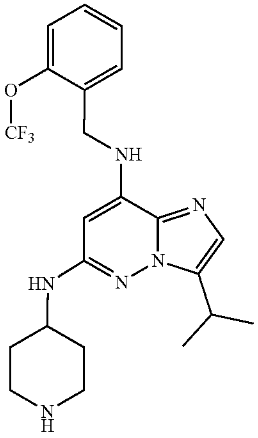
,
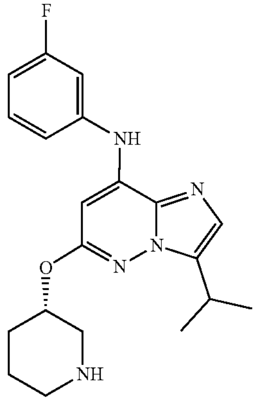
,
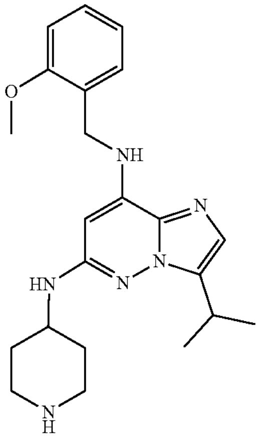
,
-continued
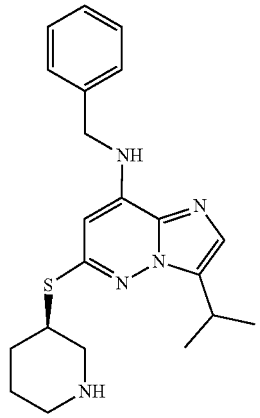
,
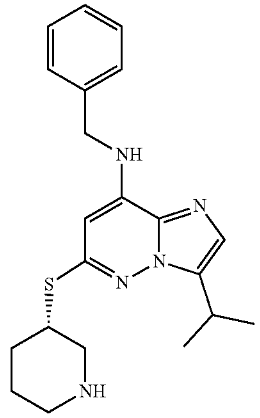
,
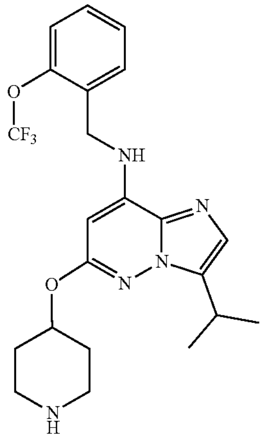
,
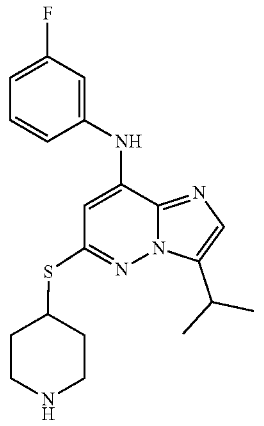
, -continued
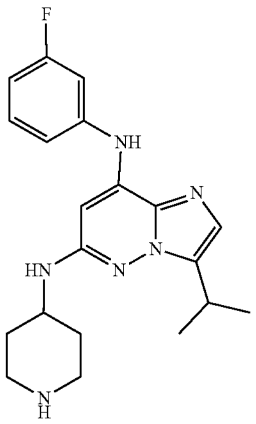
,
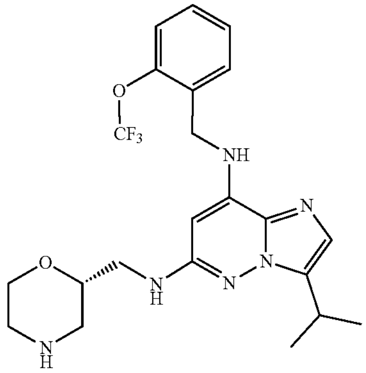
,
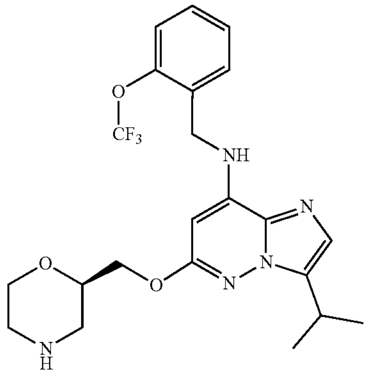
,
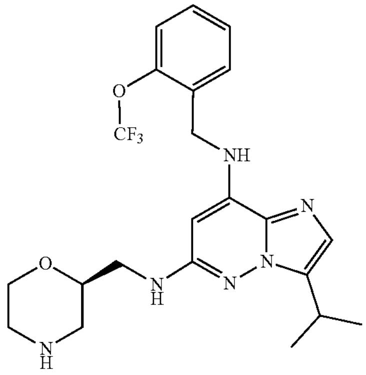
,
-continued
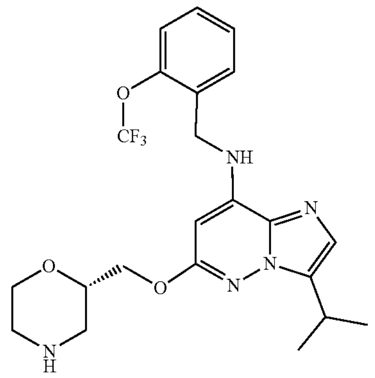
,
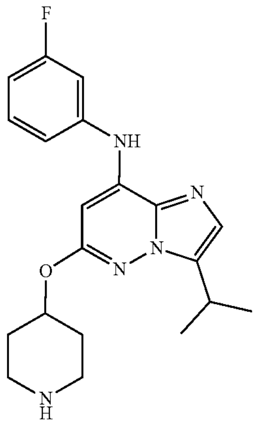
,
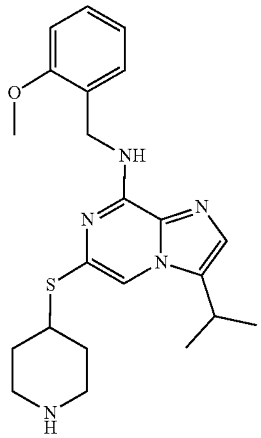
,
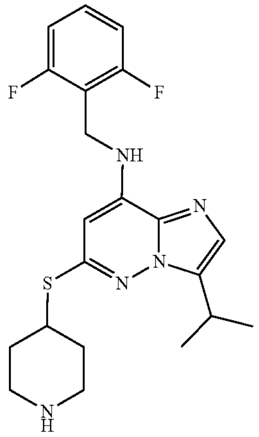
, -continued
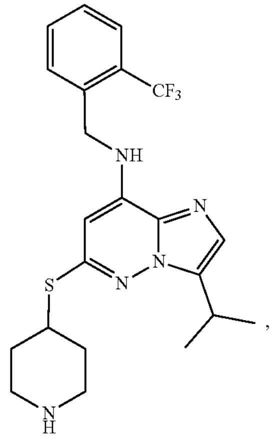
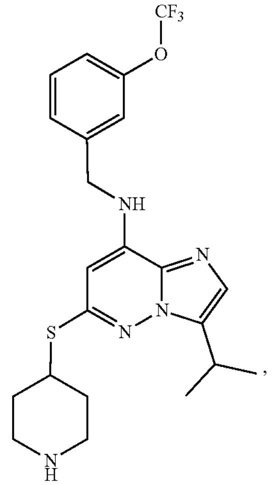
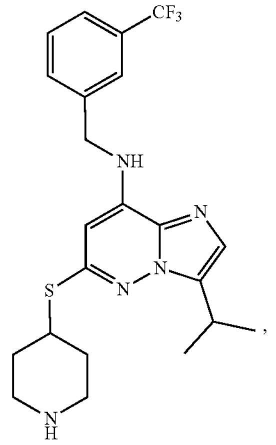
-continued
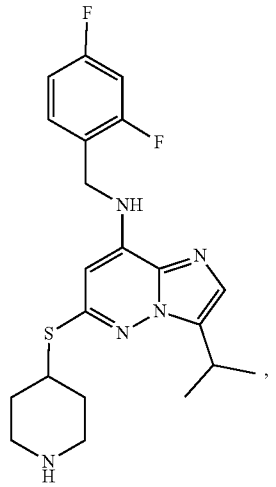
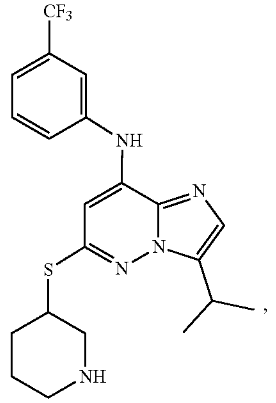
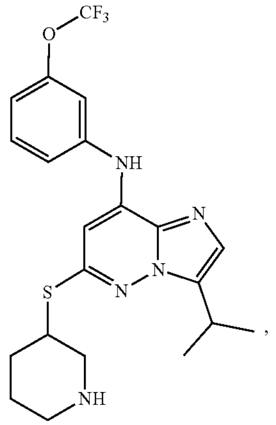
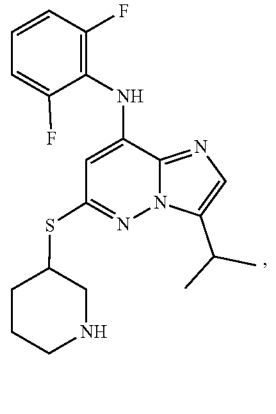

-continued
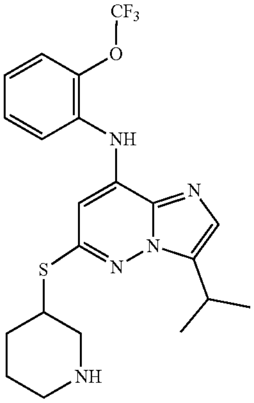
,
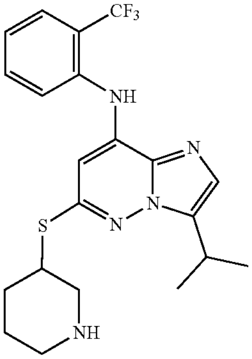
,
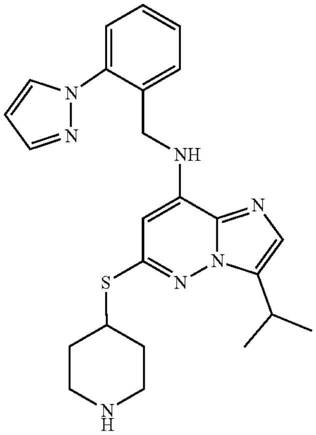
,
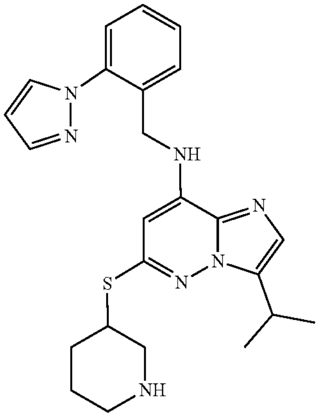
,
-continued
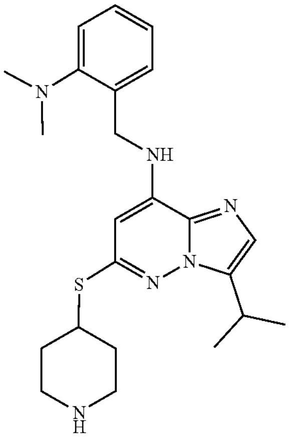
,
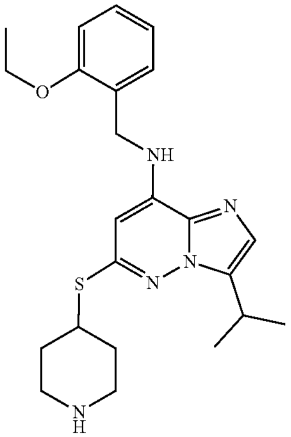
,
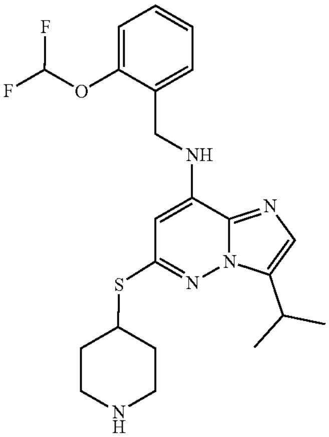
, -continued
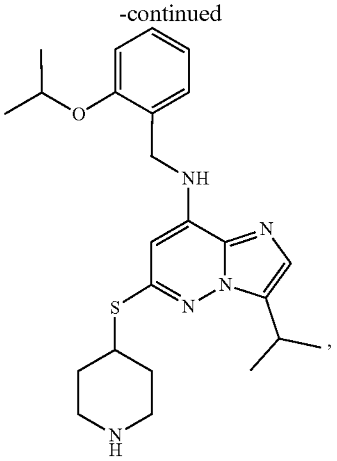
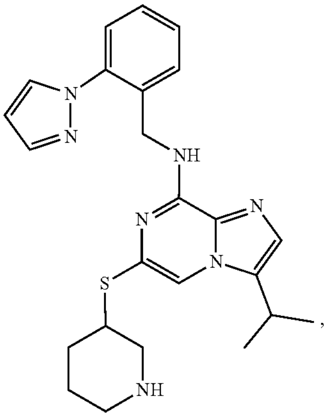
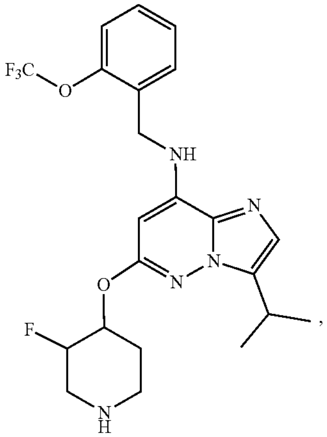
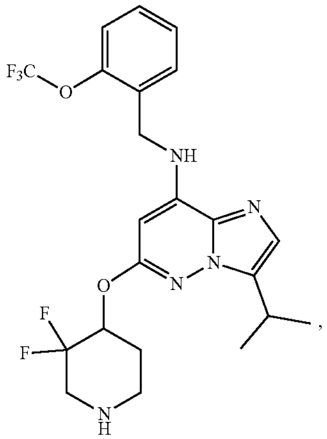
-continued
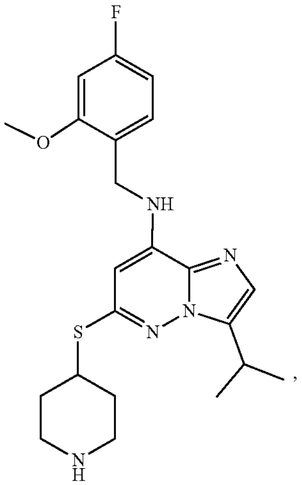
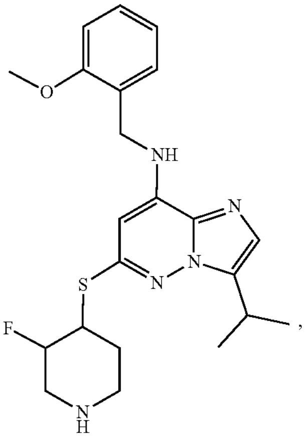
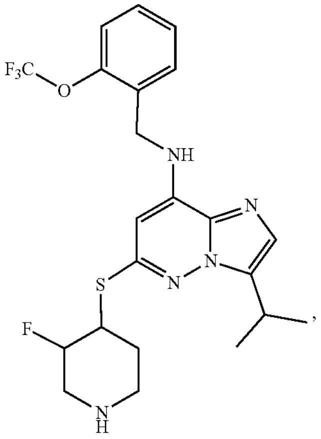

-continued
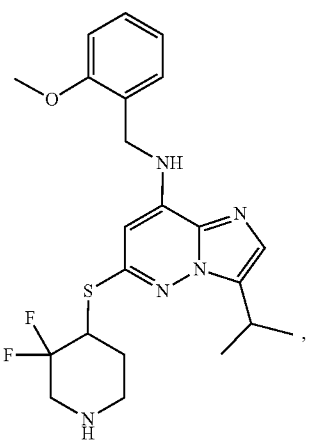
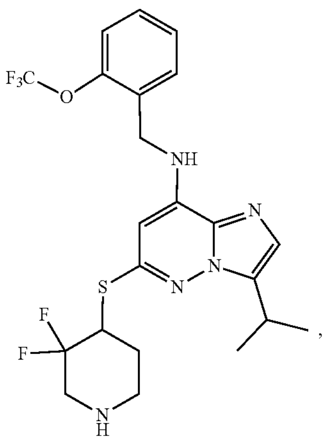
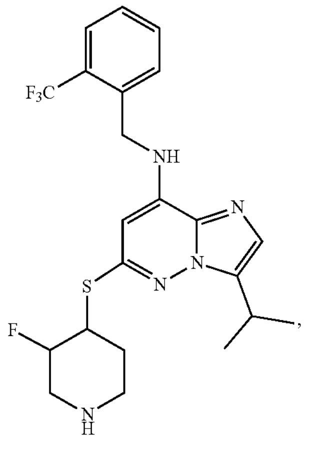
-continued
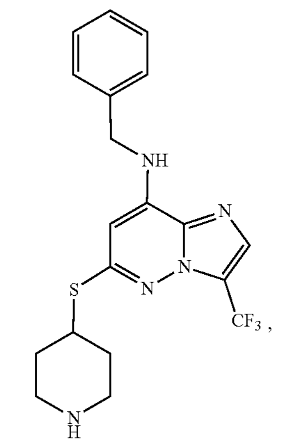
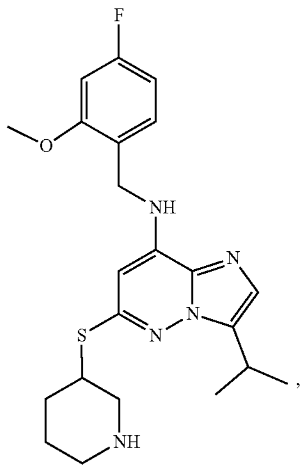
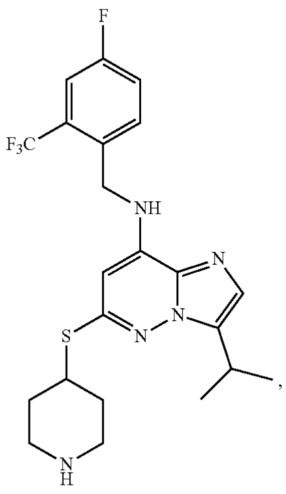

-continued
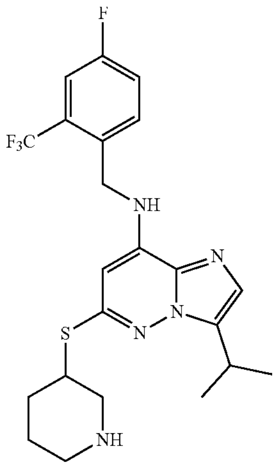
,
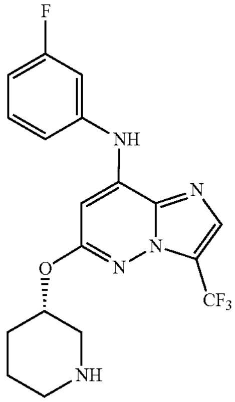
,
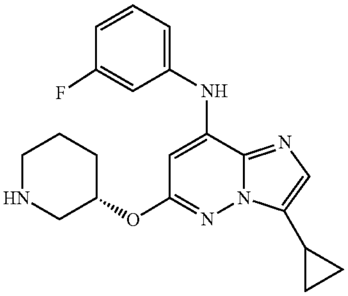
,
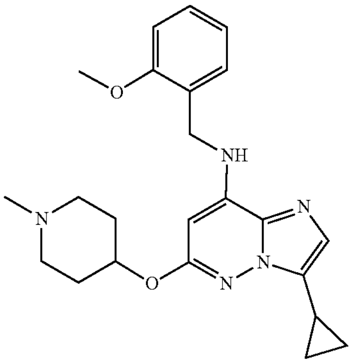
,
-continued
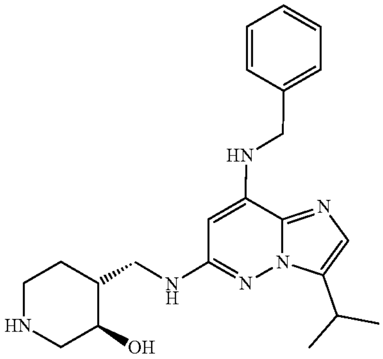
,
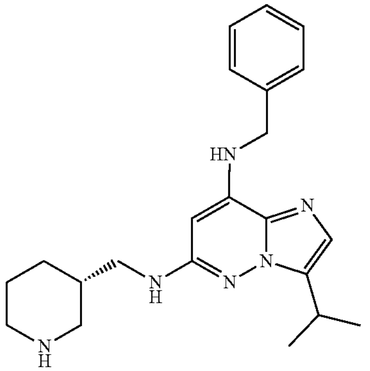
,
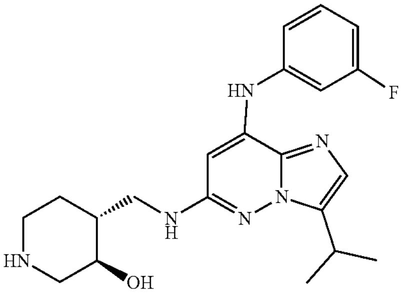
,
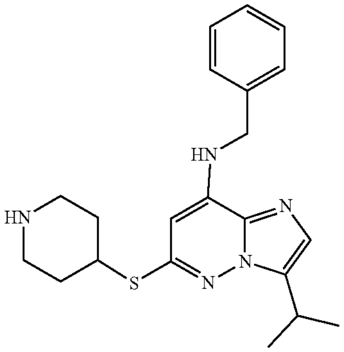
,
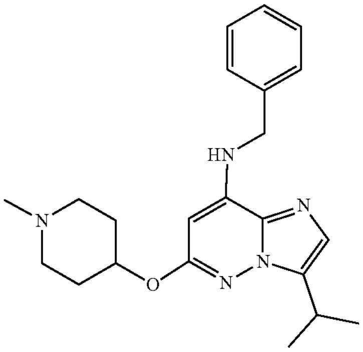
, -continued
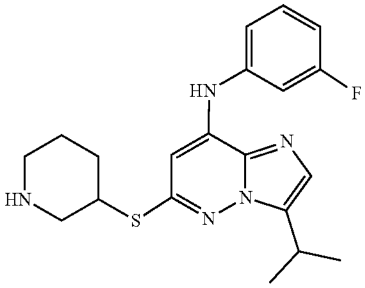,
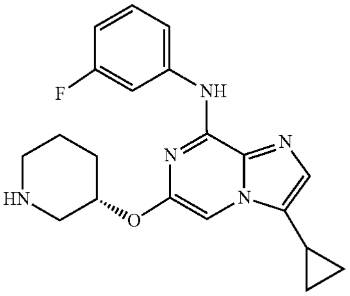,
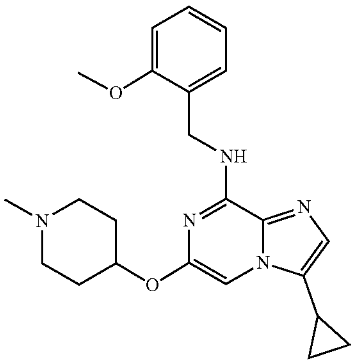,
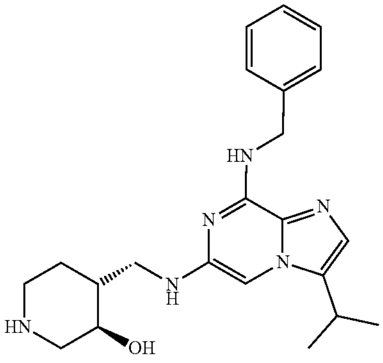,
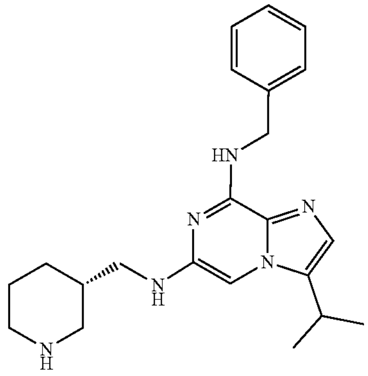,
-continued
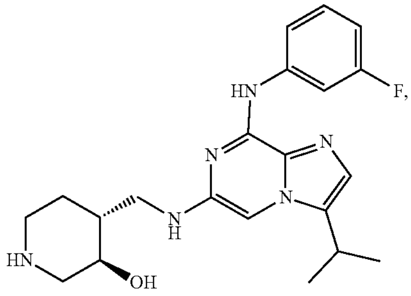,
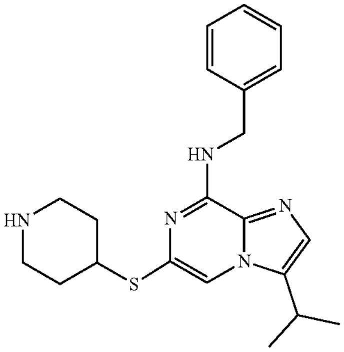,
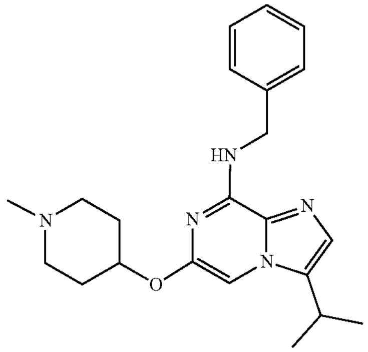,
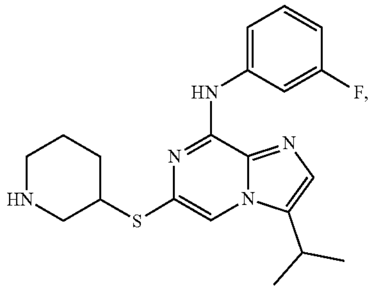,
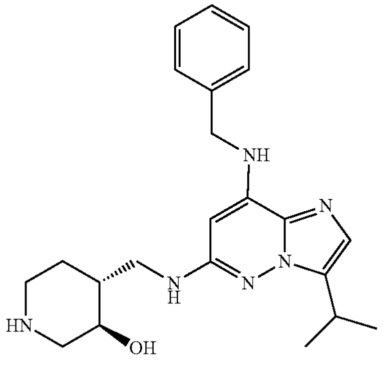, -continued
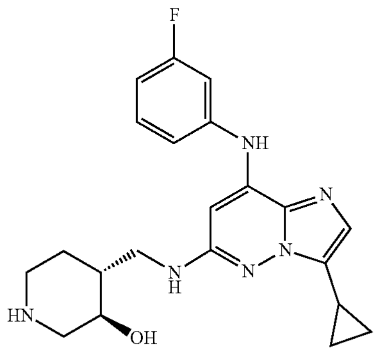
,
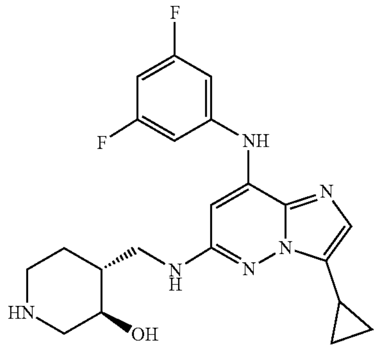
,
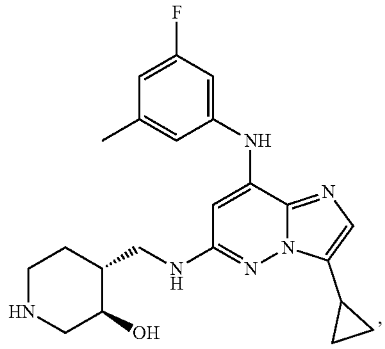
,
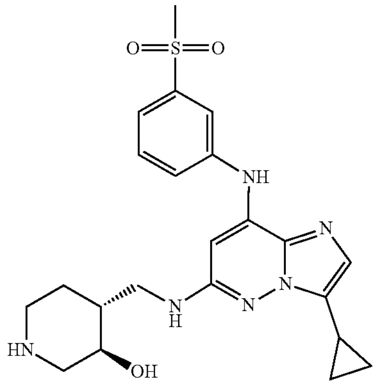
,
-continued
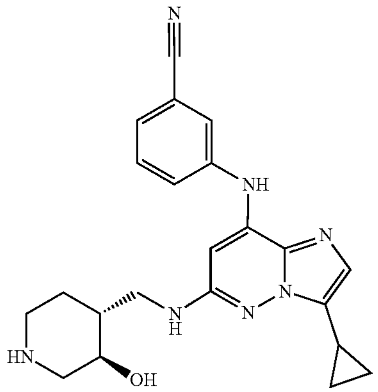
,
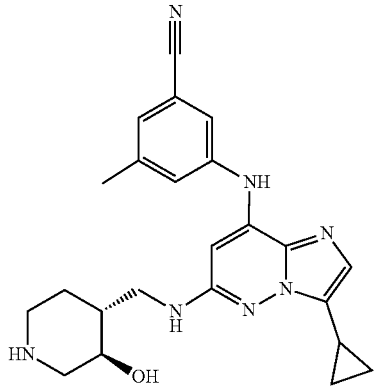
,
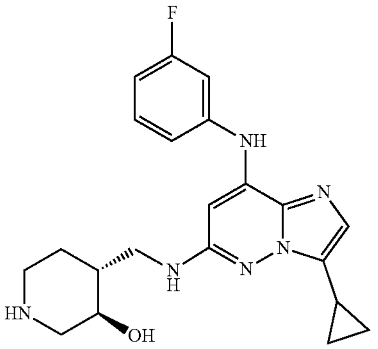
,
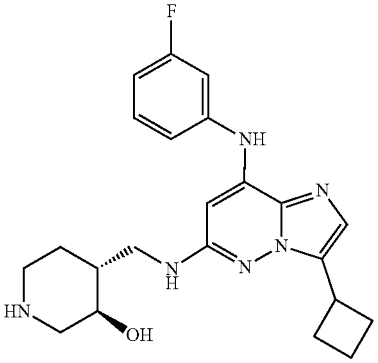
, -continued
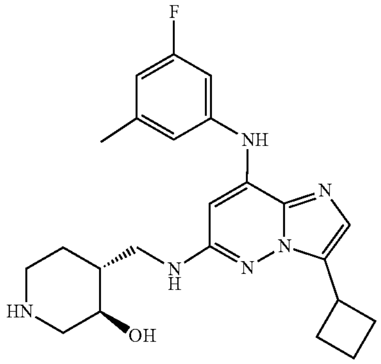
,
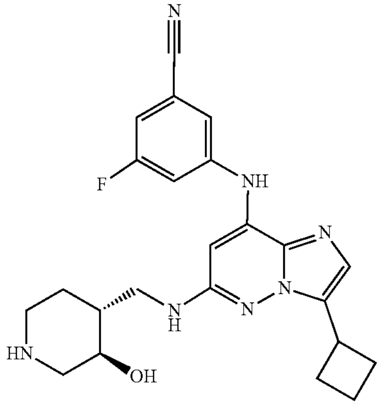
,
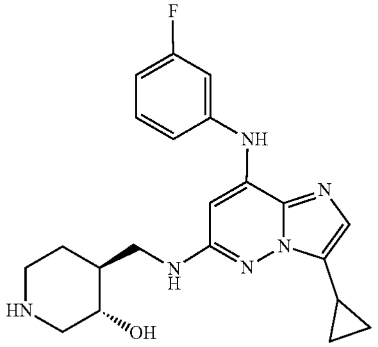
,
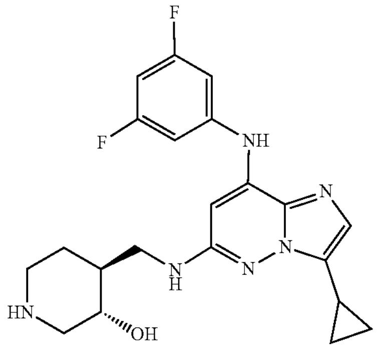
,
-continued
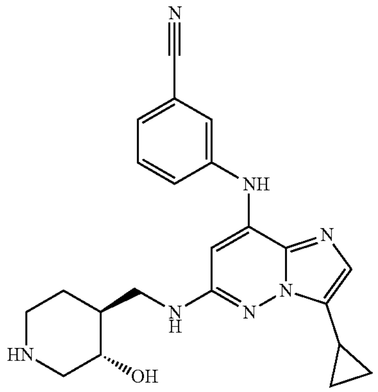
,
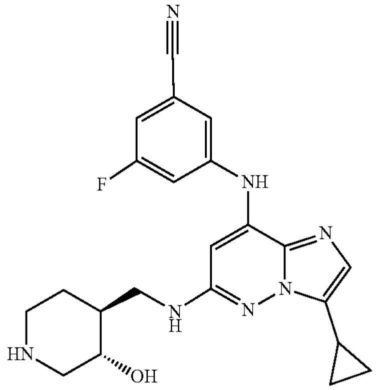
,
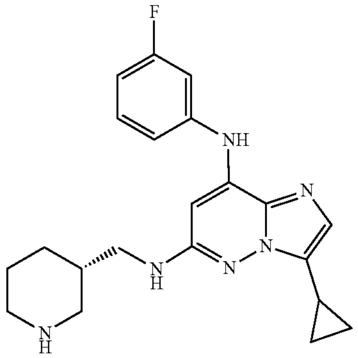
,
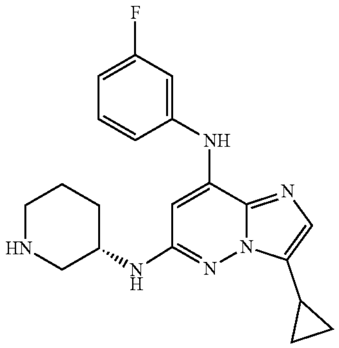
, -continued
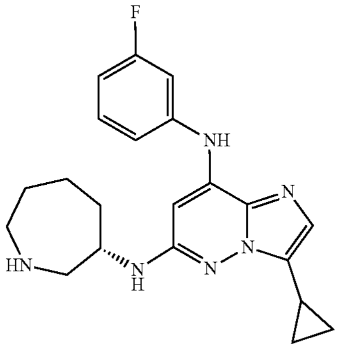
,
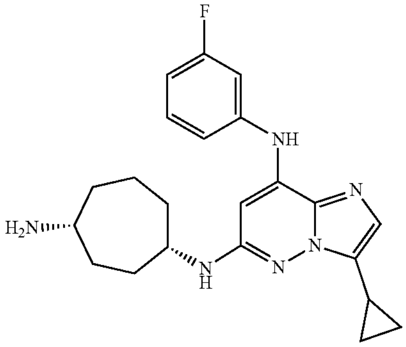
,
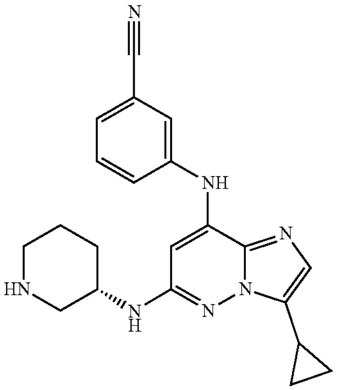
,
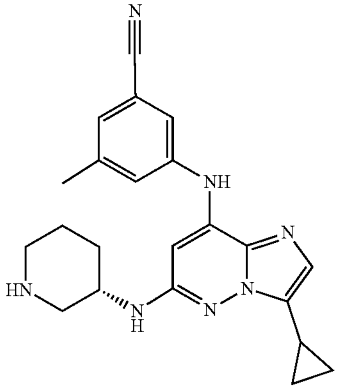
,
-continued
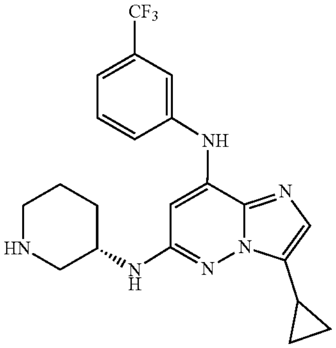
,
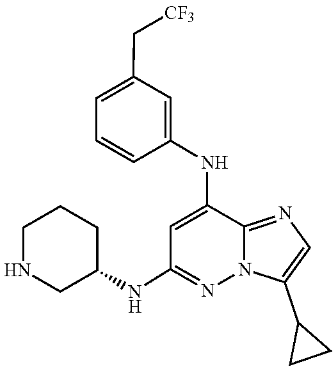
,
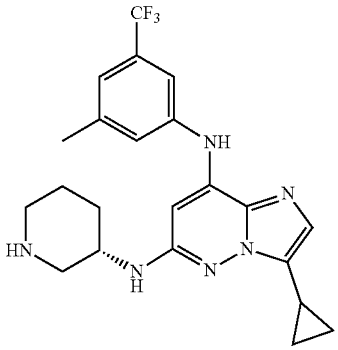
,
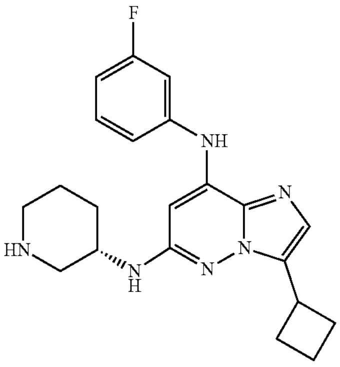
, -continued
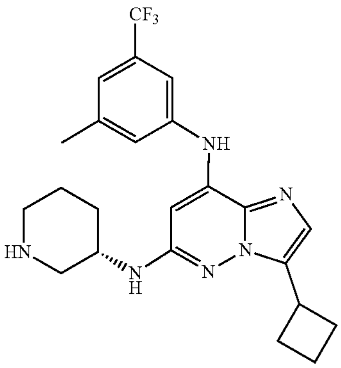
,
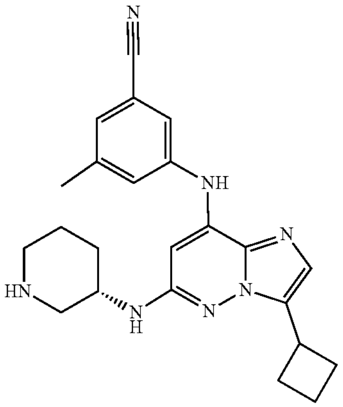
,
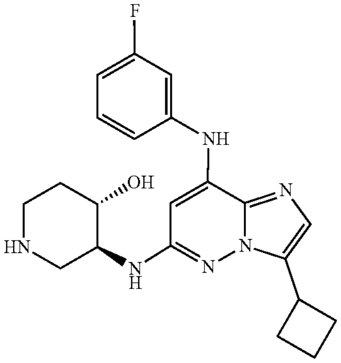
,
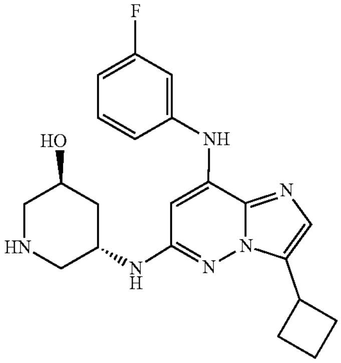
,
-continued
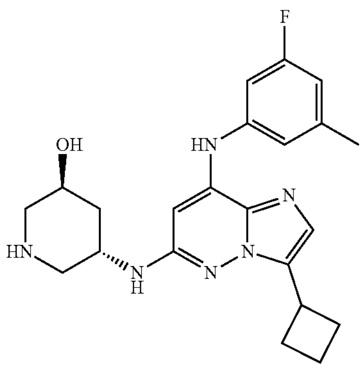
,
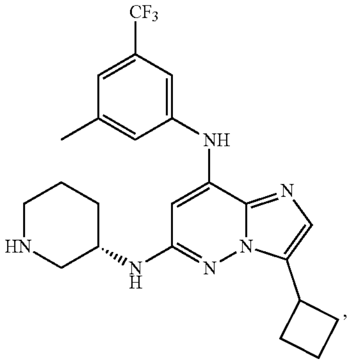
,
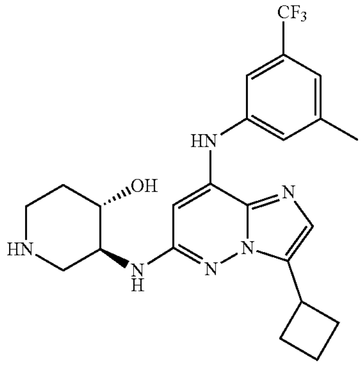
,
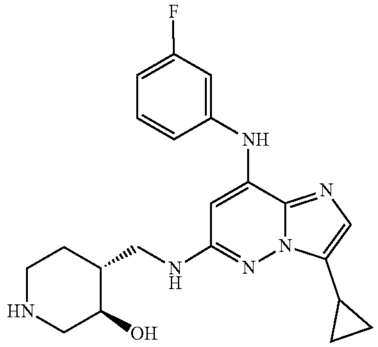
, -continued
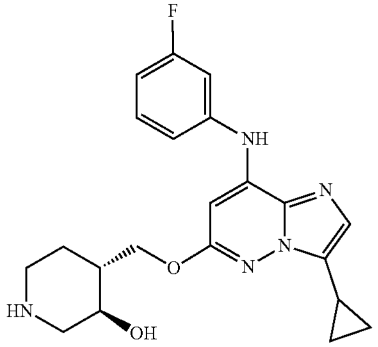
,
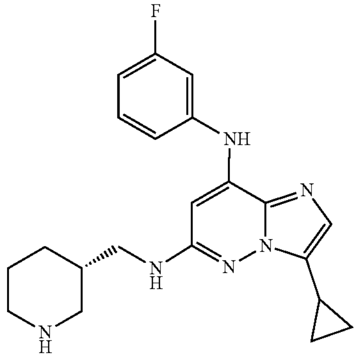
,
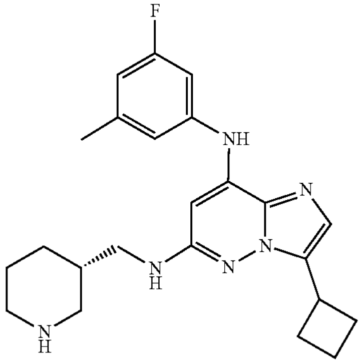
,
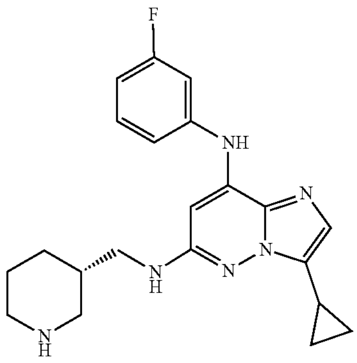
,
-continued
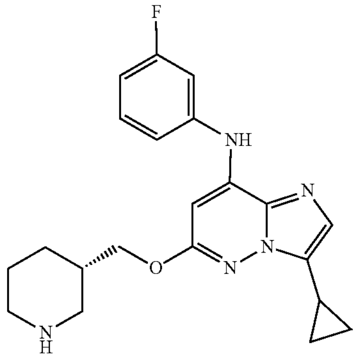
,
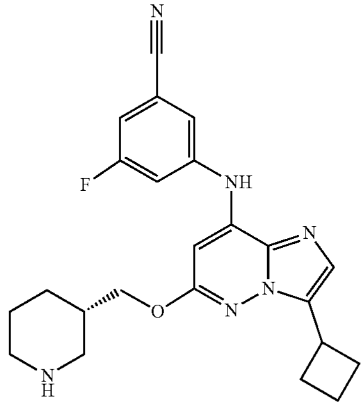
,
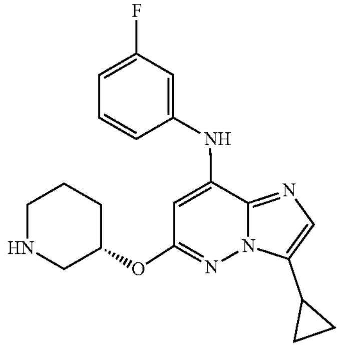
,
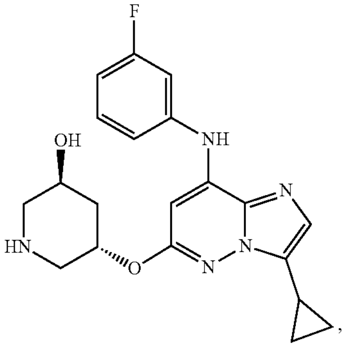
, -continued
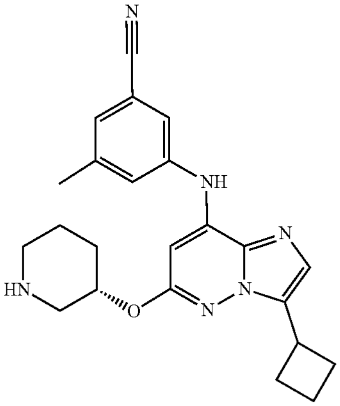
,
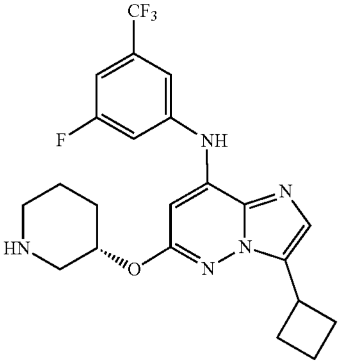
,
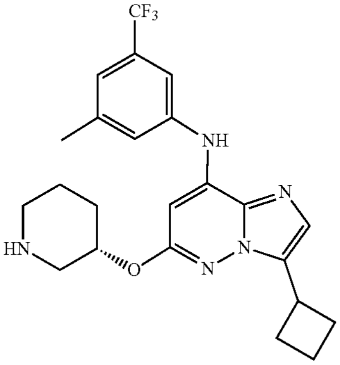
,
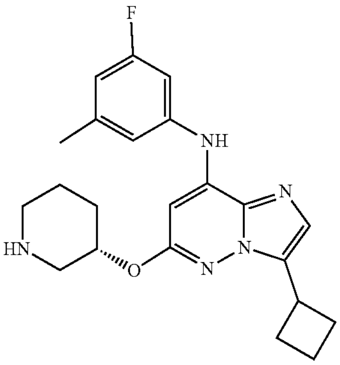
,
-continued
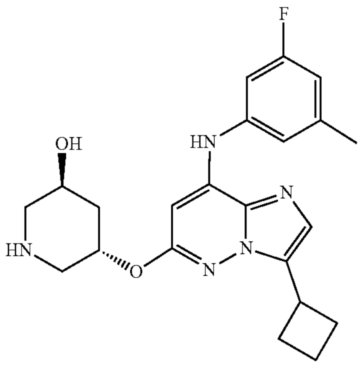
,
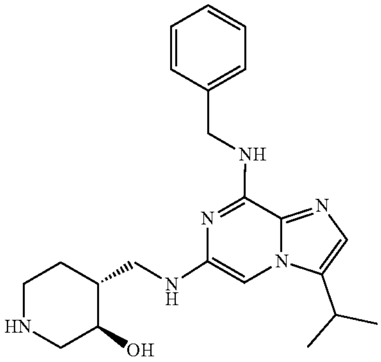
,
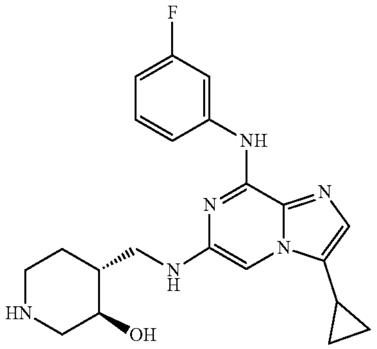
,
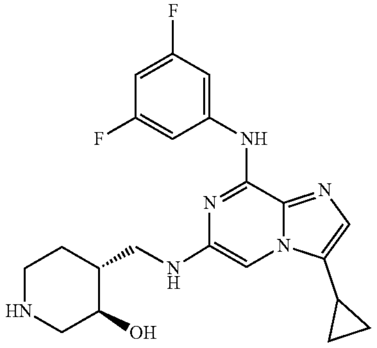
, -continued
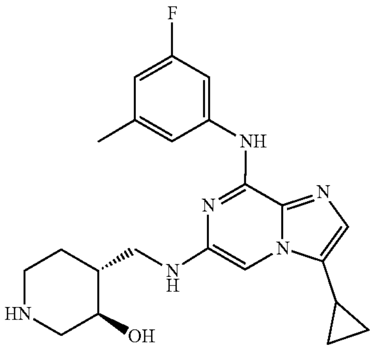
,
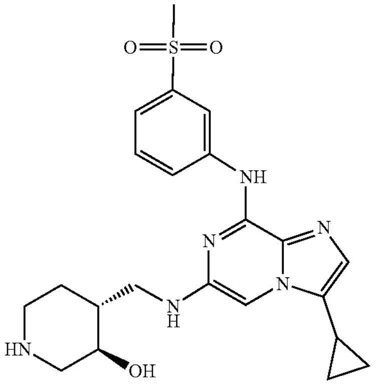
,
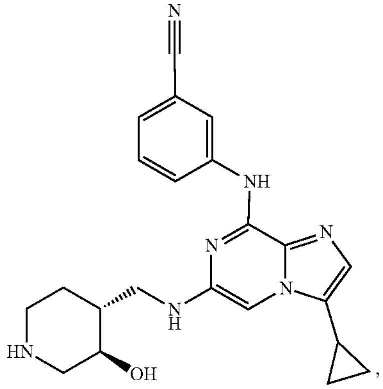
,
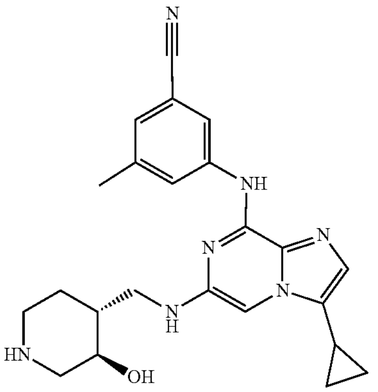
,
-continued
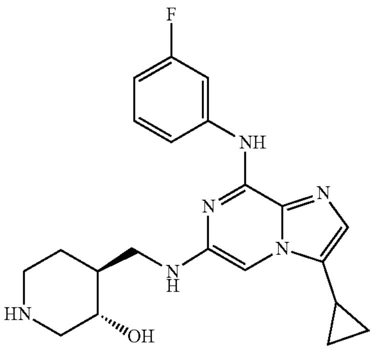
,
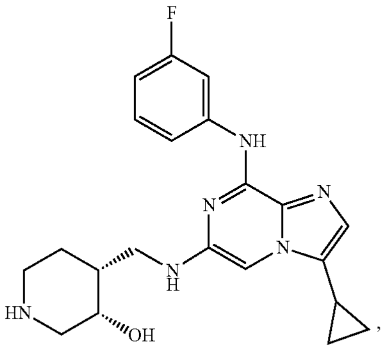
,
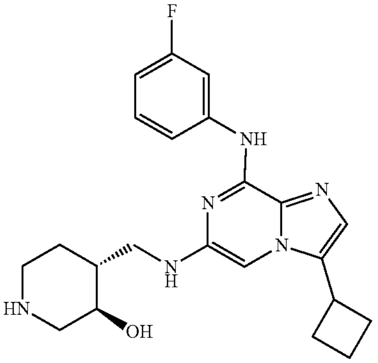
,
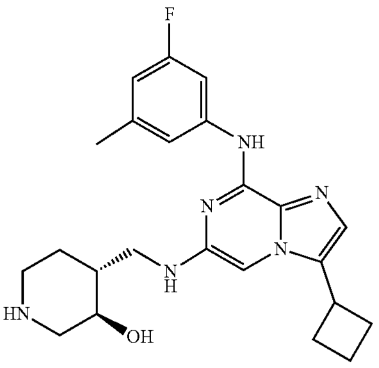
, -continued
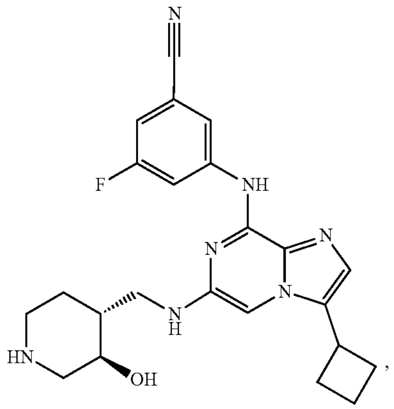
,
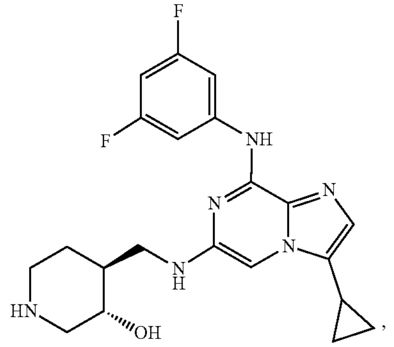
,
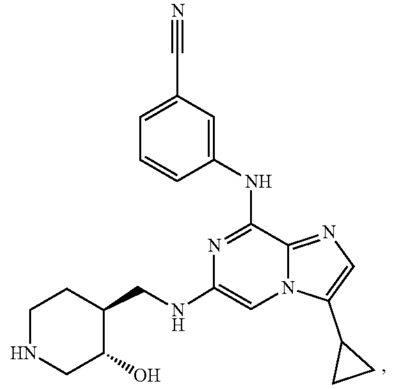
,
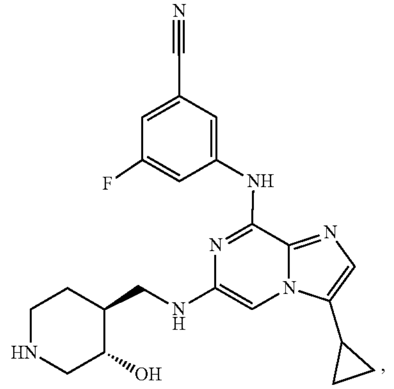
,
-continued
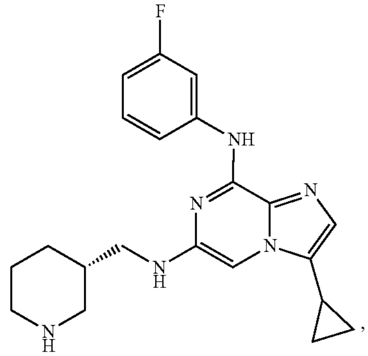
,
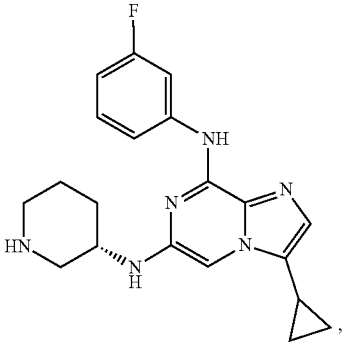
,
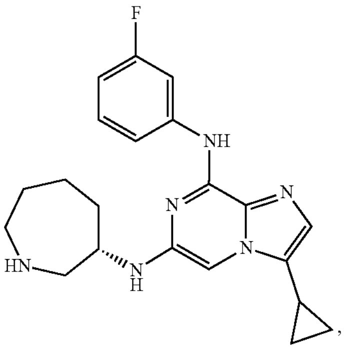
,
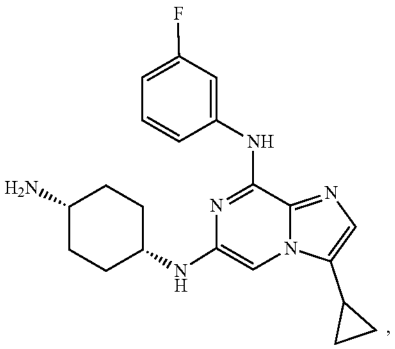
, -continued
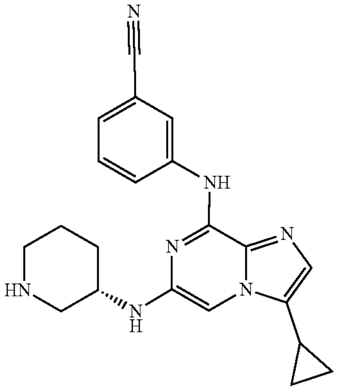
,
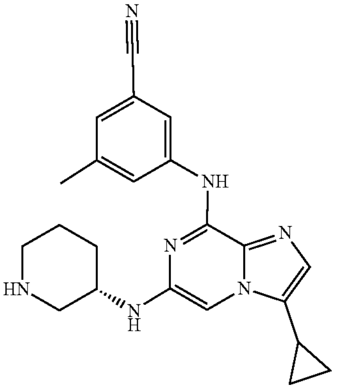
,
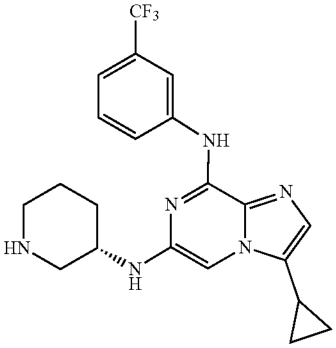
,
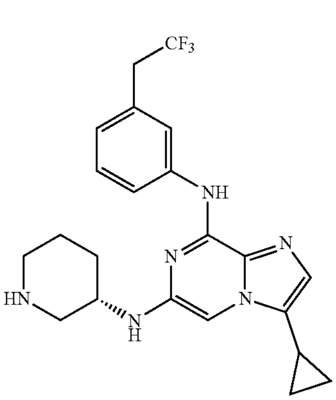
,
-continued
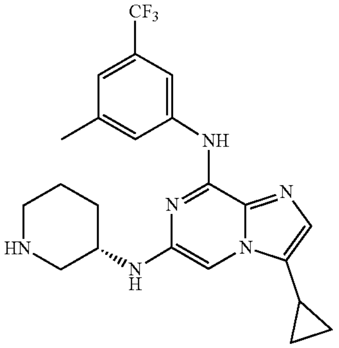
,
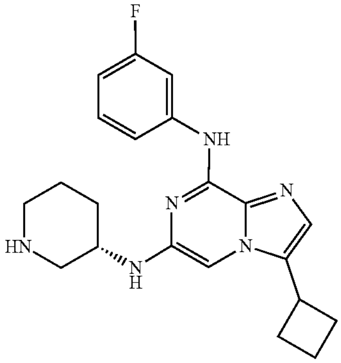
,
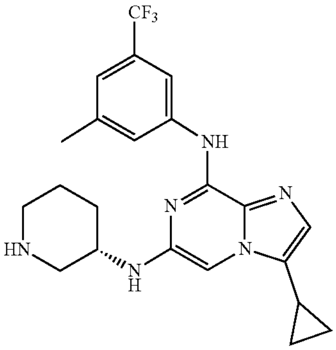
, -continued

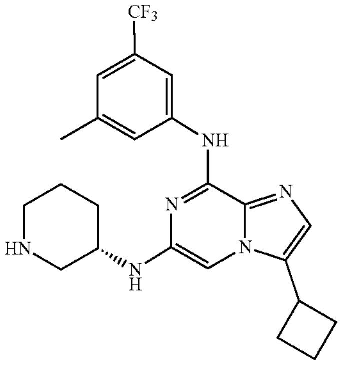

,

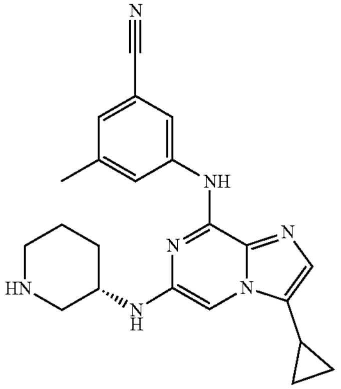

, or

-continued

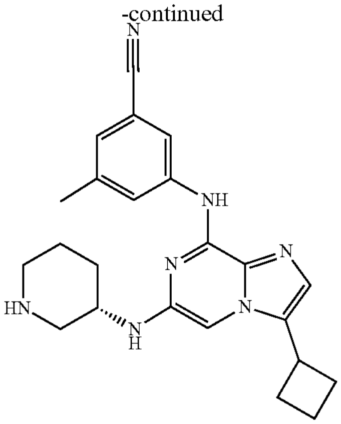

or a pharmaceutically acceptable salt, stereoisomer, or prodrug thereof.

17. A method of modulating CDK7, comprising contacting a cell with an effective amount of the compound of claim 1.

18. A method of treating a CDK7-dependent disease, comprising administering to a subject in need thereof an effective amount of the compound of claim 1.

19. The method of claim 18, wherein the CDK7-dependent disease is pancreatic cancer, breast cancer, neuroblastoma, medulloblastoma, Ewing sarcoma, chordoma, or combinations thereof.

20. The method or use of claim 19, wherein the breast cancer is triple negative breast cancer.

21. The method of claim 19, wherein the method further comprises administering an additional therapeutic agent selected from the group consisting of chemotherapeutic drugs, radiation therapy, HDAC inhibitors, PARP inhibitors, and checkpoint inhibitors.

* * * * *